(12) United States Patent
Collette et al.

(10) Patent No.: US 8,239,142 B2
(45) Date of Patent: Aug. 7, 2012

(54) SYSTEM, METHOD, DEVICE, AND COMPUTER PROGRAM PRODUCT FOR EXTRACTION, GATHERING, MANIPULATION, AND ANALYSIS OF PEAK DATA FROM AN AUTOMATED SEQUENCER

(75) Inventors: Alexis Collette, Paris (FR); Adrien Six, Arcueil (FR); Sylviane Bernadette Pied, Paris (FR); Pierre-Andre Cazenave, Paris (FR)

(73) Assignees: Université Pierre et Marie Curie (Paris VI), Paris (FR); Centre National de la Recherche Scientifique (CNRS), Paris (FR)

( * ) Notice: Subject to any disclaimer, the term of this patent is extended or adjusted under 35 U.S.C. 154(b) by 169 days.

(21) Appl. No.: 12/500,497

(22) Filed: Jul. 9, 2009

(65) Prior Publication Data

US 2010/0130371 A1   May 27, 2010

Related U.S. Application Data

(63) Continuation of application No. 10/519,950, filed as application No. PCT/IB03/03339 on Jul. 1, 2003, now abandoned.

(60) Provisional application No. 60/392,352, filed on Jul. 1, 2002, provisional application No. 60/392,373, filed on Jul. 1, 2002.

(51) Int. Cl.
*G01N 33/48* (2006.01)
*G01N 33/50* (2006.01)
*G01N 31/00* (2006.01)
*C12Q 1/68* (2006.01)

(52) U.S. Cl. ............... 702/20; 702/19; 702/22; 435/6.1

(58) Field of Classification Search ........................ None
See application file for complete search history.

(56) References Cited

U.S. PATENT DOCUMENTS

| 5,945,283 A * | 8/1999 | Kwok et al. ...................... 435/6 |
| 6,195,449 B1 * | 2/2001 | Bogden et al. ................. 382/129 |
| 2006/0085139 A1 | 4/2006 | Collette et al. |

OTHER PUBLICATIONS

Foley JP. Equations for chromatographic peak modeling and calculation of peak area. Analytical Chemistry, vol. 59, 1987, pp. 1984-1987.*

Aggerholm et al. Extensive intra- and interindividual heterogeneity of p15INK4B methylation in acute myeloid leukemia. Cancer Research, vol. 59, 1999, pp. 436-441.*

U.S. Appl. No. 12/940,657, filed Nov. 5, 2010, Collette, et al.

Collette, A. et al. "ISEApeaks: an Excel platform for GeneScan and Immunoscope data retrieval, management and analysis", Bioinformatics, vol. 18, No. 2, pp. 329-330, XP002310162 2002.

Sotak, et al., Software for quantitative analysis by carbon-13 Fourier Transform Nuclear Magnetic Resonance Spectrometry. Analytical Chemistry, 1983, vol. 55, pp. 782-787.

Faure et al. Tolerance to maternal immunoglobulins: resilience of the specific-T cell repertoire in spite of long-lasting perturbations. The Journal of Immunology, 1999, vol. 163, pp. 6511-6519.

U.S. Appl. No. 10/609,521, filed Jul. 1, 2003, Collette, et al.

\* cited by examiner

*Primary Examiner* — Russell S Negin

(74) *Attorney, Agent, or Firm* — Oblon, Spivak, McClelland, Maier & Neustadt, L.L.P.

(57) ABSTRACT

A system, method, device, and computer program product to extract and gather peak information from an automated sequencer of bioinformatics into a peak database, and to manipulate and analyze the peak information within the database.

24 Claims, 356 Drawing Sheets

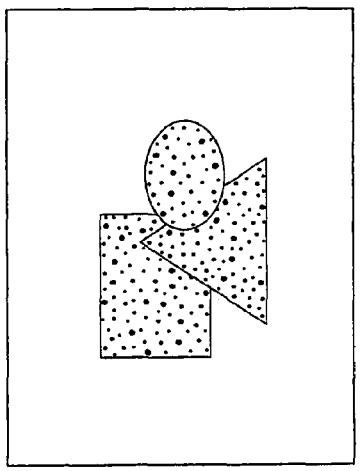
FIG. 7A
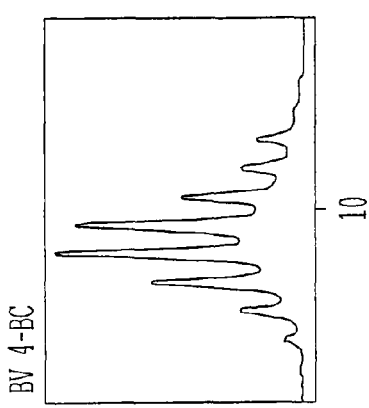
FIG. 7B
FIG. 7C
| | | | | | | | | | | | | | | |
|---|---|---|---|---|---|---|---|---|---|---|---|---|---|---|
| IMMUNOSCOPE RAW DATA | mLENGTH | | 178 | 182 | 184 | 187 | 190 | 192 | 193 | 196 | 198 | 199 | 201 | 202 | 202 |
| | mAREA | 100019 | 2008 | 6133 | 14418 | 23540 | 24664 | 751 | 13318 | 7082 | 789 | 4727 | 864 | 522 | 1203 |
| | misCONSIDERED | | 1 | 1 | 1 | 1 | 1 | 1 | 1 | 1 | 1 | 1 | 1 | 1 | 1 |
| FIRST FILTER | mLENGTH | | 178 | 182 | 184 | 187 | 190 | 192 | 193 | 196 | 198 | 199 | 201 | 202 | |
| | mAREA | 100019 | 2008 | 6133 | 14418 | 23540 | 24664 | 751 | 13318 | 7082 | 789 | 4727 | 864 | 1725 | |
| | misCONSIDERED | | 1 | 1 | 1 | 1 | 1 | 1 | 1 | 1 | 1 | 1 | 1 | 1 | |
| SECOND FILTER | mLENGTH | | 178 | 182 | 184 | 187 | 190 | 193 | 196 | 199 | 202 | | | | |
| | mAREA | 100019 | 2008 | 6133 | 14418 | 23540 | 24664 | 14069 | 7082 | 5516 | 2589 | | | | |
| | misCONSIDERED | | 1 | 1 | 1 | 1 | 1 | 1 | 1 | 1 | 1 | | | | |
| THIRD FILTER | mLENGTH | 0 | 178 | 181 | 183 | 186 | 189 | 192 | 195 | 198 | 201 | | | | |
| | mAREA | 100019 | 2008 | 6133 | 14418 | 23540 | 14418 | 14069 | 7082 | 5516 | 2589 | | | | |
| | misCONSIDERED | | 1 | 1 | 1 | 1 | 1 | 1 | 1 | 1 | 1 | | | | |

FIG. 10A
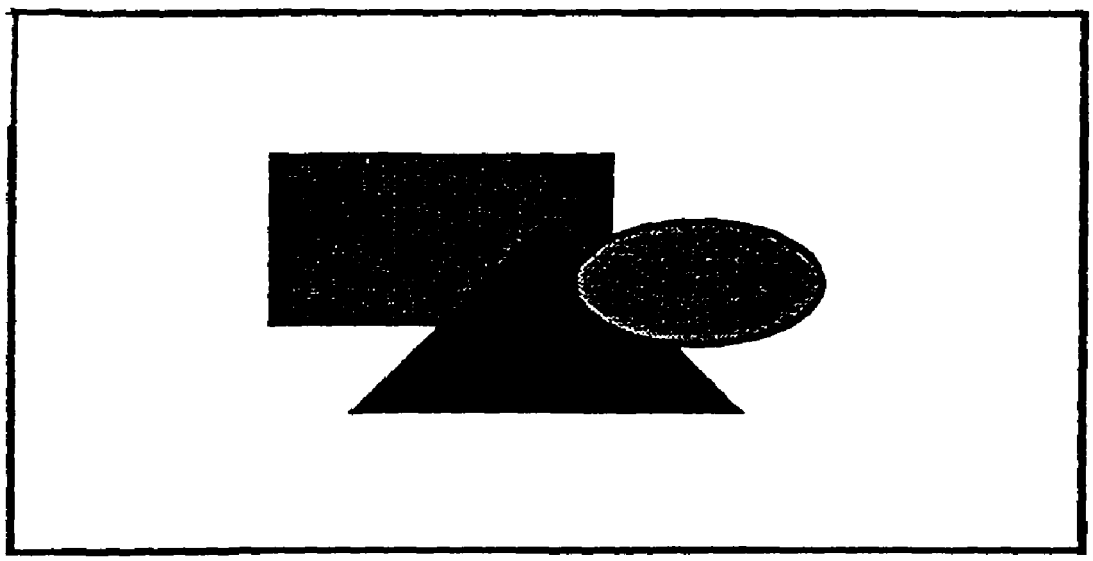
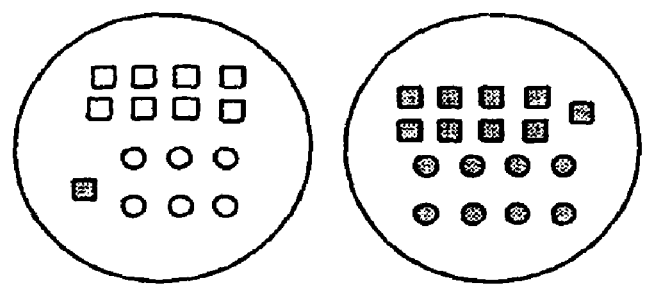
FIG 10B

FIG. 11A
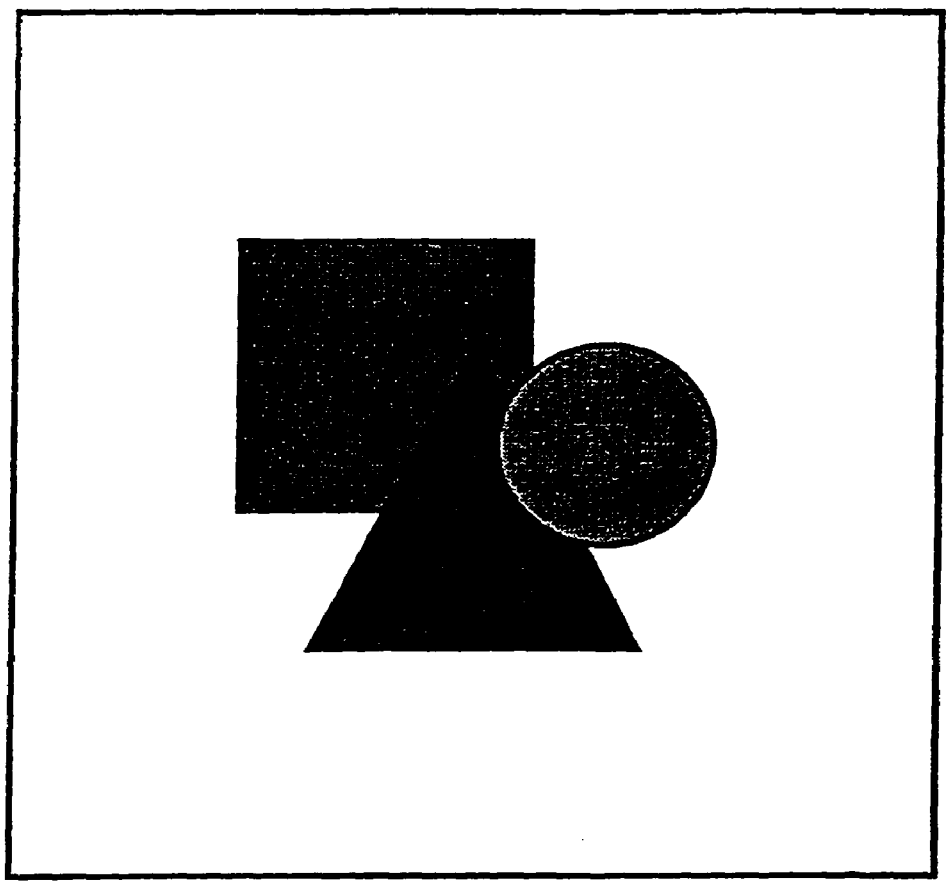
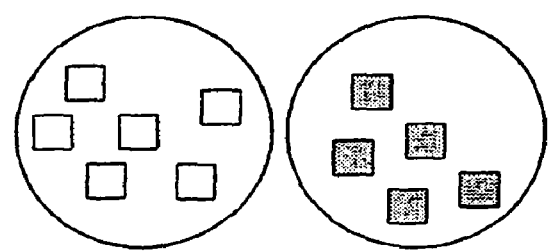
☐ CTR PBL　▨ HP PBL
FIG 11B

| | A | B 2,1 | C 2,2 | D 2,3 | E 2,4 | F 1,1 | G 1,2 | H 1,3 | I 1,4 | J 1,5 |
|---|---|---|---|---|---|---|---|---|---|---|
| 2 | Yb08.1-Jb1.1 | 8,78 | 8,99 | 11,27 | 10,99 | 12,23 | 10,74 | 4,72 | 17,59 | 13,46 |
| 3 | Yb08.1-Jb1.2 | 7,44 | 8,49 | 7,90 | 9,95 | 16,36 | 12,13 | 8,04 | 7,46 | 5,28 |
| 4 | Yb08.1-Jb1.3 | 4,04 | 6,02 | 4,68 | 4,76 | 1,90 | 6,17 | excluded | 5,09 | 1,42 |
| 5 | Yb08.1-Jb1.4 | 7,99 | 10,68 | 8,39 | 10,61 | 5,56 | 8,05 | 8,85 | 3,06 | 7,17 |
| 6 | Yb08.1-Jb1.5 | 4,89 | 4,15 | 5,41 | 4,03 | 5,21 | 4,91 | 5,12 | 2,57 | 4,65 |
| 7 | Yb08.1-Jb1.6 | 2,73 | 1,50 | 2,26 | 1,38 | 2,63 | 2,97 | 2,91 | 1,65 | 1,34 |
| 8 | Yb08.1-Jb2.1 | 12,30 | 17,24 | 13,74 | 11,81 | 10,39 | 13,33 | 22,61 | 19,70 | 12,94 |
| 9 | Yb08.1-Jb2.2 | 6,93 | 6,47 | 6,07 | 6,95 | 5,38 | 3,14 | 11,28 | 9,65 | 8,51 |
| 10 | Yb08.1-Jb2.3 | 10,98 | 4,81 | 9,63 | 9,27 | 6,71 | 5,41 | 5,14 | 8,05 | 13,52 |
| 11 | Yb08.1-Jb2.4 | 12,46 | 8,90 | 9,68 | 10,17 | 10,31 | 12,75 | 8,32 | 8,11 | 9,17 |
| 12 | Yb08.1-Jb2.5 | 9,05 | 10,14 | 11,15 | 8,97 | 9,78 | 12,35 | 11,97 | 7,75 | 5,84 |
| 13 | Yb08.1-Jb2.7 | 12,42 | 12,62 | 9,82 | 11,12 | 13,55 | 8,05 | 11,05 | 9,31 | 16,70 |

| | A | B 2,1 | C 2,2 | D 2,3 | E 2,4 | F 1,1 | G 1,2 | H 1,3 | I 1,4 | J 1,5 |
|---|---|---|---|---|---|---|---|---|---|---|
| 16 | Yb08.1-Jb1.1 | 39144 | 39387 | 45864 | 249425 | 36087 | 119154 | 16663 | 156203 | 285994 |
| 17 | Yb08.1-Jb1.2 | 33165 | 37208 | 102266 | 225983 | 48280 | 134508 | 28366 | 66293 | 112294 |
| 18 | Yb08.1-Jb1.3 | 18002 | 26363 | 60653 | 108024 | 5593 | 68404 | excluded | 45164 | 30231 |
| 19 | Yb08.1-Jb1.4 | 35641 | 46797 | 108585 | 240973 | 16392 | 89268 | 31214 | 27163 | 152436 |
| 20 | Yb08.1-Jb1.5 | 21802 | 18174 | 70107 | 91572 | 15359 | 54481 | 18056 | 22833 | 98859 |
| 21 | Yb08.1-Jb1.6 | 12185 | 6567 | 29306 | 31277 | 7754 | 32974 | 10283 | 14622 | 28401 |
| 22 | Yb08.1-Jb2.1 | 54850 | 75547 | 177878 | 268231 | 30660 | 147812 | 79788 | 174998 | 274977 |
| 23 | Yb08.1-Jb2.2 | 30917 | 28358 | 78625 | 157702 | 15884 | 34825 | 39808 | 85689 | 180862 |
| 24 | Yb08.1-Jb2.3 | 48970 | 21081 | 124696 | 210396 | 19807 | 59996 | 18150 | 71517 | 287295 |
| 25 | Yb08.1-Jb2.4 | 55571 | 38987 | 125304 | 230803 | 30422 | 141434 | 29346 | 72069 | 194977 |
| 26 | Yb08.1-Jb2.5 | 40354 | 44418 | 144331 | 203621 | 28853 | 137020 | 42234 | 68872 | 124007 |
| 27 | Yb08.1-Jb2.7 | 55382 | 55310 | 127157 | 252387 | 39974 | 89281 | 38982 | 82712 | 354859 |

DrawArray parameters

| when < | color |
|---|---|
| excluded | |
| 5 | |
| 10 | |
| 20 | |
| 25 | |
| 30 | |
| 50 | |
| 100 | |

Depiction of overall disturbance

| Gorochov | TCRAV02 | TCRAV08 | TCRAV15 | TCRBV04 | TCRBV08.1 |
|---|---|---|---|---|---|
| CTR01 | 1,94 | 5,17 | 16,38 | 7,82 | excluded |
| CTR02 | 0,63 | 3,77 | 19,38 | 5,23 | 2,82 |
| CTR03 | 2,02 | 2,32 | 11,74 | 4,74 | 3,22 |
| CTR04 | 2,81 | 7,01 | 11,51 | 2,80 | 5,55 |
| CTR05 | 0,82 | 7,29 | 11,99 | 5,03 | 7,24 |
| LACKC06 | 2,44 | 14,70 | 17,39 | excluded | 43,90 |
| LACKC07 | 2,23 | excluded | 17,82 | 4,25 | 8,94 |
| LACKC08 | 2,12 | 7,71 | 18,51 | excluded | 5,66 |
| LACKC09 | 0,79 | 11,32 | 18,32 | 6,00 | 5,46 |
| LACKC10 | excluded | 11,38 | 15,27 | 5,60 | 9,13 |
| LACKp11 | 2,15 | 8,99 | 16,37 | 9,01 | 5,81 |
| LACKp12 | 2,34 | 9,68 | 20,34 | 6,97 | 10,19 |
| LACKp13 | 4,27 | excluded | 16,72 | 12,33 | 9,34 |
| LACKp14 | 10,36 | 7,12 | 16,63 | 6,22 | 6,59 |
| LACKp15 | 2,79 | 3,09 | 20,18 | 8,52 | 3,89 |
| L+IL-2 16 | 5,17 | 6,09 | 19,78 | 5,63 | 8,77 |
| L+IL-2 17 | 4,51 | 2,94 | 16,81 | 6,25 | 8,94 |
| L+IL-2 18 | 2,29 | 5,91 | 19,72 | 4,14 | 10,65 |
| L+IL-2 19 | 2,52 | 9,62 | 18,48 | 4,89 | 8,58 |
| L+IL-2 20 | 4,53 | 7,69 | 20,02 | 4,76 | 6,80 |
| Lp+IL-2 21 | 2,55 | 4,89 | 19,57 | 5,47 | 8,78 |
| Lp+IL-2 22 | 5,50 | 4,15 | 14,00 | 6,33 | 7,12 |
| Lp+IL-2 23 | 2,33 | 3,19 | 18,08 | 4,43 | 9,80 |
| Lp+IL-2 24 | 3,27 | 4,84 | 20,00 | 7,23 | 10,53 |
| Lp+IL-2 25 | 4,83 | 5,70 | 19,00 | 36,51 | 35,78 |

| DrawArray parameters | |
|---|---|
| when < | color |
| excluded | |
| 5 | |
| 10 | |
| 20 | |
| 25 | |
| 30 | |
| 50 | |
| 100 | |

Depiction of overall disturbance versus oligoclonality

| G vs O | TCRAV02 | TCRAV08 | TCRAV15 | TCRBV04 | TCRBV08.1 |
|---|---|---|---|---|---|
| CTR01 | 1,94 | 5,17 | 16,38 | 7,82 | excluded |
| CTR02 | 0,63 | 3,77 | 19,38 | 5,23 | 2,82 |
| CTR03 | 2,02 | 2,32 | 11,74 | 4,74 | 3,22 |
| CTR04 | 2,81 | 7,01 | 11,51 | 2,80 | 5,55 |
| CTR05 | 0,82 | 7,29 | 11,99 | 5,03 | 7,24 |
| LACKC06 | 2,44 | 14,70 | 17,39 | excluded | 43,90 |
| LACKC07 | 2,23 | excluded | 17,82 | 4,25 | 8,94 |
| LACKC08 | 2,12 | 7,71 | 18,51 | excluded | 5,66 |
| LACKC09 | 0,79 | 11,32 | 18,32 | 6,00 | 5,46 |
| LACKC10 | excluded | 11,38 | 15,27 | 5,60 | 9,13 |
| LACKp11 | 2,15 | 8,99 | 16,37 | 9,01 | 5,81 |
| LACKp12 | 2,34 | 9,68 | 20,34 | 6,97 | 10,19 |
| LACKp13 | 4,27 | excluded | 16,72 | 12,33 | 9,34 |
| LACKp14 | 10,36 | 7,12 | 16,63 | 6,22 | 6,59 |
| LACKp15 | 2,79 | 3,09 | 20,18 | 8,52 | 3,89 |
| L+IL-2 16 | 5,17 | 6,09 | 19,78 | 5,63 | 8,77 |
| L+IL-2 17 | 4,51 | 2,94 | 16,81 | 6,25 | 8,94 |
| L+IL-2 18 | 2,29 | 5,91 | 19,72 | 4,14 | 10,65 |
| L+IL-2 19 | 2,52 | 9,62 | 18,48 | 4,89 | 8,58 |
| L+IL-2 20 | 4,53 | 7,69 | 20,02 | 4,76 | 6,80 |
| Lp+IL-2 21 | 2,55 | 4,89 | 19,57 | 5,47 | 8,78 |
| Lp+IL-2 22 | 5,50 | 4,15 | 14,00 | 6,33 | 7,12 |
| Lp+IL-2 23 | 2,33 | 3,19 | 18,08 | 4,43 | 9,80 |
| Lp+IL-2 24 | 3,27 | 4,84 | 20,00 | 7,23 | 10,53 |
| Lp+IL-2 25 | 4,83 | 5,70 | 19,00 | 36,51 | 35,78 |

DrawArray parameters

| when < | color |
|---|---|
| excluded | |
| 5 | |
| 10 | |
| 20 | |
| 25 | |
| 30 | |
| 50 | |
| 100 | |

Parameters of file to use

| | Workbook | Sheet | Group | Nature | Remarks |
|---|---|---|---|---|---|
| 1 | DF CC/281 AC by EF Delta1 | Data.1 | 1 | CTR01 | |
| 2 | DF CC/281 AC by EF Delta1 | Data.2 | 1 | CTR02 | |
| 3 | DF CC/281 AC by EF Delta1 | Data.3 | 1 | CTR03 | |
| 4 | DF CC/281 AC by EF Delta1 | Data.4 | 1 | CTR04 | |
| 5 | DF CC/281 AC by EF Delta1 | Data.5 | 1 | CTR05 | |
| 6 | DF CC/281 AC by EF Delta1 | Data.6 | 2 | LACKC06 | |
| 7 | DF CC/281 AC by EF Delta1 | Data.7 | 2 | LACKC07 | |
| 8 | DF CC/281 AC by EF Delta1 | Data.8 | 2 | LACKC08 | |
| 9 | DF CC/281 AC by EF Delta1 | Data.9 | 2 | LACKC09 | |
| 10 | DF CC/281 AC by EF Delta1 | Data.10 | 2 | LACKC10 | |
| 11 | DF CC/281 AC by EF Delta1 | Data.11 | 3 | LACKp11 | |
| 12 | DF CC/281 AC by EF Delta1 | Data.12 | 3 | LACKp12 | |
| 13 | DF CC/282 AC by EF Delta1 | Data.1 | 3 | LACKp13 | |
| 14 | DF CC/282 AC by EF Delta1 | Data.2 | 3 | LACKp14 | |
| 15 | DF CC/282 AC by EF Delta1 | Data.3 | 3 | LACKp15 | |
| 16 | DF CC/282 AC by EF Delta1 | Data.4 | 4 | +IL-2 16 | |
| 17 | DF CC/282 AC by EF Delta1 | Data.5 | 4 | +IL-2 17 | |
| 18 | DF CC/282 AC by EF Delta1 | Data.6 | 4 | +IL-2 18 | |
| 19 | DF CC/282 AC by EF Delta1 | Data.7 | 4 | +IL-2 19 | |
| 20 | DF CC/282 AC by EF Delta1 | Data.8 | 4 | +IL-2 20 | |
| 21 | DF CC/282 AC by EF Delta1 | Data.9 | 5 | p+IL-2 21 | |
| 22 | DF CC/282 AC by EF Delta1 | Data.10 | 5 | p+IL-2 22 | |
| 23 | DF CC/282 AC by EF Delta1 | Data.11 | 5 | p+IL-2 23 | |
| 24 | DF CC/282 AC by EF Delta1 | Data.12 | 5 | p+IL-2 24 | |
| 25 | DF CC/283 AC by EF Delta1 | Data.1 | 5 | p+IL-2 25 | |

*FIG. 29*

Depiction of overall disturbance versus oligoclonality

FIG. 31

DrawArray parameters

| when < | color |
|---|---|
| excluded | |
| 5 | |
| 10 | |
| 20 | |
| 25 | |
| 30 | |
| 50 | |
| 100 | |

Parameters of file to use

| | Workbook | Sheet | Group | Nature | Remark |
|---|---|---|---|---|---|
| 1 | EF/06 DF | Data.1 | 1 | CTR02 | CTR02 |
| 2 | EF/06 DF | Data.2 | 1 | CTR03 | CTR03 |
| 3 | EF/06 DF | Data.3 | 1 | CTR04 | CTR04 |
| 4 | EF/06 DF | Data.4 | 2 | L07 | Lack 07 |
| 5 | EF/06 DF | Data.5 | 2 | L08 | Lack 08 |
| 6 | EF/06 DF | Data.6 | 2 | L09 | Lack 09 |
| 7 | EF/06 DF | Data.7 | 3 | Lp12 | Lackp12 |
| 8 | EF/06 DF | Data.8 | 3 | Lp13 | Lackp13 |
| 9 | EF/06 DF | Data.9 | 3 | Lp14 | Lackp14 |
| 10 | EF/06 DF | Data.10 | 4 | L+IL2-17 | Lack+IL2-17 |
| 11 | EF/06 DF | Data.11 | 4 | L+IL2-18 | Lack+IL2-18 |
| 12 | EF/06 DF | Data.12 | 4 | L+IL2-19 | Lack+IL2-19 |
| 13 | EF/06 DF | Data.13 | 5 | Lp+IL2-22 | Lackp+IL2-22 |
| 14 | EF/06 DF | Data.14 | 5 | Lp+IL2-23 | Lackp+IL2-23 |
| 15 | EF/06 DF | Data.15 | 5 | Lp+IL2-24 | Lackp+IL2-24 |

Depiction of overall disturbance versus oligoclonality

| | Vb04-Jb1.1 | Vb04-Jb1.2 | Vb04-Jb1.3 | Vb04-Jb1.4 | Vb04-Jb1.5 | Vb04-Jb1.6 | Vb04-Jb2.1 | Vb04-Jb2.2 | Vb04-Jb2.3 | Vb04-Jb2.4 | Vb04-Jb2.5 | Vb04-Jb2.7 |
|---|---|---|---|---|---|---|---|---|---|---|---|---|
| CTR02 | 3,73 | 3,35 | 9,51 | 5,71 | 8,96 | 5,76 | 4,33 | 4,19 | 6,10 | 4,02 | 2,96 | 1,96 |
| CTR03 | 5,05 | 5,44 | 7,60 | 4,39 | 13,10 | 12,42 | 3,57 | 6,04 | 2,08 | 5,17 | 3,25 | 2,75 |
| CTR04 | 4,24 | 5,03 | 8,97 | 4,93 | 8,57 | 13,31 | 4,60 | 7,71 | 6,75 | 5,23 | 2,85 | 3,48 |
| L07 | 5,30 | 5,71 | 11,55 | 6,52 | 9,23 | 20,00 | 3,99 | 7,00 | 7,00 | 4,83 | 14,72 | 4,38 |
| L08 | 7,86 | 7,73 | excluded | 7,10 | 9,74 | 12,12 | 9,55 | 8,61 | 8,83 | 8,66 | 3,72 | 3,51 |
| L09 | 8,95 | 6,90 | 11,77 | 11,78 | 24,19 | 19,05 | 7,24 | 13,33 | 5,06 | 10,42 | 5,55 | 3,76 |
| Lp12 | 15,89 | 19,08 | 10,26 | 11,05 | 23,35 | 22,64 | 14,00 | 7,07 | 6,75 | 9,20 | 9,44 | 9,20 |
| Lp13 | 3,57 | 26,66 | 12,26 | 7,75 | 13,14 | 9,44 | 4,63 | 11,38 | 7,82 | 7,13 | 3,94 | 6,00 |
| Lp14 | 12,24 | 14,09 | 6,25 | 7,13 | 18,10 | 16,54 | 7,66 | 4,32 | 11,52 | 5,21 | 14,17 | 6,59 |
| L+IL2-17 | 7,54 | 10,06 | 11,95 | 6,84 | 7,39 | 20,34 | 5,32 | 11,28 | 9,57 | 11,98 | 10,44 | 6,03 |
| L+IL2-18 | 4,81 | 6,37 | 11,39 | 11,07 | 10,56 | 17,58 | 5,86 | 7,10 | 5,76 | 7,22 | 5,76 | 4,68 |
| L+IL2-19 | 6,26 | 6,08 | 10,11 | 8,41 | 6,95 | 10,36 | 5,14 | 3,97 | 7,99 | 3,46 | 4,29 | 7,95 |
| Lp+IL2-22 | 8,07 | 6,73 | 11,43 | 6,91 | 10,61 | 7,36 | 3,14 | 7,05 | 11,70 | 8,65 | 4,91 | 6,21 |
| Lp+IL2-23 | 6,13 | 6,70 | 14,28 | 8,67 | 11,02 | 7,44 | 8,56 | 4,33 | 6,21 | 9,21 | 3,58 | 4,65 |
| Lp+IL2-24 | 13,00 | 6,98 | 6,43 | 7,17 | 10,51 | 20,21 | 7,17 | 6,60 | 6,74 | 6,14 | 12,37 | 7,86 |

FIG. 32A

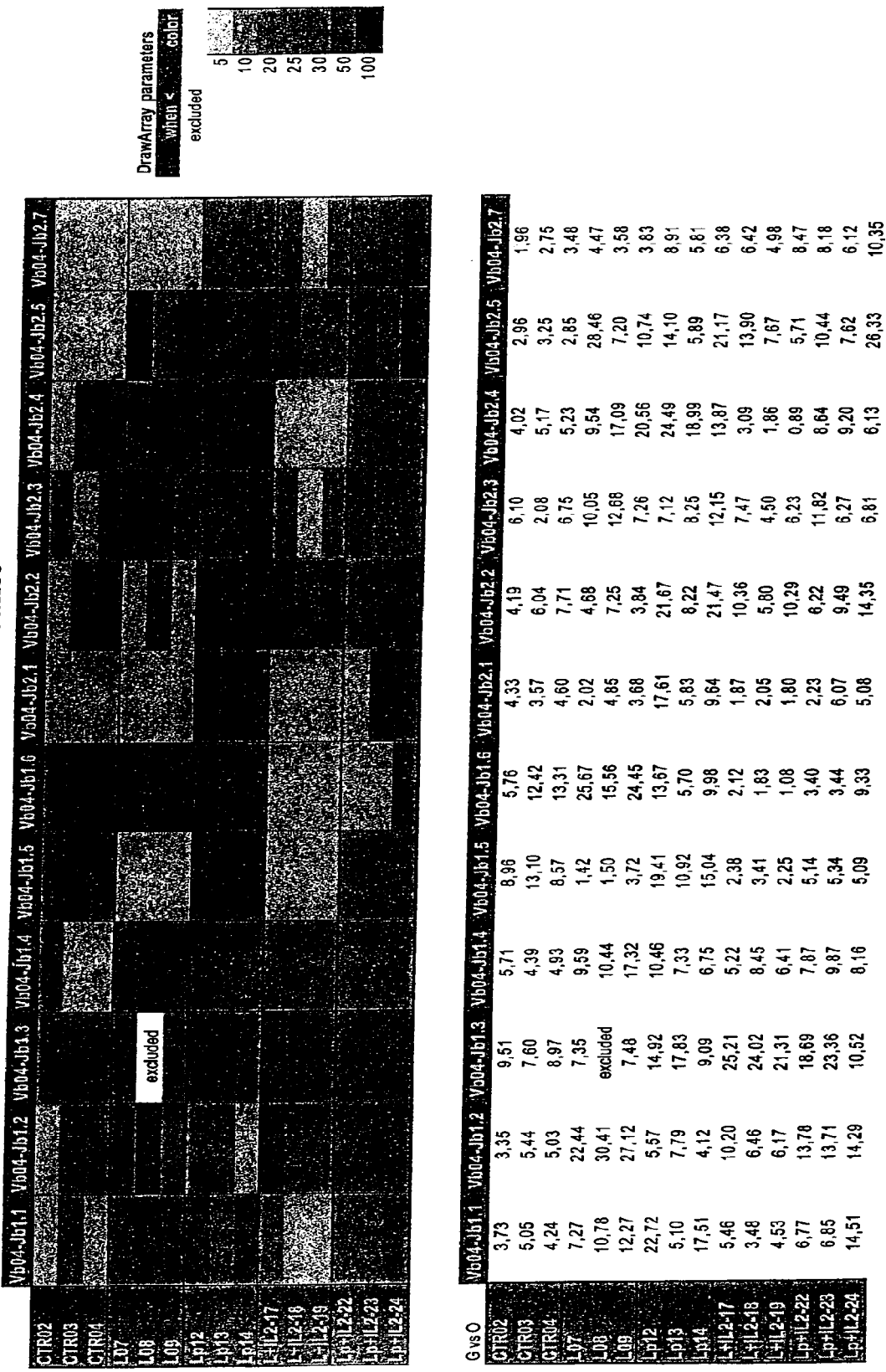
FIG. 32B Depiction of overall disturbance

DrawArray parameters

| when < | color |
|---|---|
| excluded | |
| 5 | |
| 10 | |
| 20 | |
| 25 | |
| 30 | |
| 50 | |
| 100 | |

Parameters of file to use

| | Workbook | Sheet | Group | Nature | Remark |
|---|---|---|---|---|---|
| 1 | EF/04 DF | Data.1 | 1 | CTR02 | CTR02 |
| 2 | EF/05-07-009b DF | Data.3 | 1 | CTR03 | CTR03 |
| 3 | EF/01-009b DF | Data.1 | 1 | CTR04 | CTR04 |
| 4 | EF/02-07 DF | Data.1 | 2 | L07 | Lack 07 |
| 5 | EF/04 DF | Data.5 | 2 | L08 | Lack 08 |
| 6 | EF/05-07-009b DF | Data.5 | 2 | L09 | Lack 09 |
| 7 | EF/04 DF | Data.3 | 3 | Lp12 | Lackp12 |
| 8 | EF/05-07-009b DF | Data.1 | 3 | Lp13 | Lackp13 |
| 9 | EF/01-009b DF | Data.5 | 3 | Lp14 | Lackp14 |
| 10 | EF/03 DF | Data.1 | 4 | L+IL2-17 | Lack+IL2-17 |
| 11 | EF/03 DF | Data.5 | 4 | L+IL2-18 | Lack+IL2-18 |
| 12 | EF/02-07 DF | Data.3 | 4 | L+IL2-19 | Lack+IL2-19 |
| 13 | EF/01-009b DF | Data.3 | 5 | Lp+IL2-22 | Lackp+IL2-22 |
| 14 | EF/02-07 DF | Data.5 | 5 | Lp+IL2-23 | Lackp+IL2-23 |
| 15 | EF/03 DF | Data.3 | 5 | Lp+IL2-24 | Lackp+IL2-24 |

*FIG. 33*

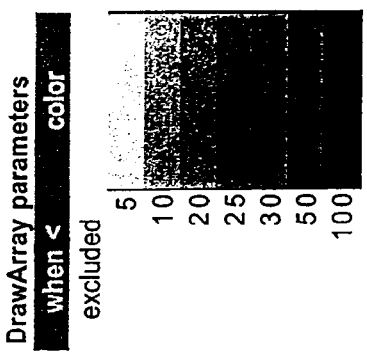

Parameters of file to use

| | Workbook | Sheet | Group | Nature | Remark |
|---|---|---|---|---|---|
| 1 | EF/04 DF | Data.2 | 1 | CTR02 | CTR02 |
| 2 | EF/05-07-009b DF | Data.4 | 1 | CTR03 | CTR03 |
| 3 | EF/01-009b DF | Data.2 | 1 | CTR04 | CTR04 |
| 4 | EF/02-07 DF | Data.2 | 2 | L07 | Lack 07 |
| 5 | EF/04 DF | Data.6 | 2 | L08 | Lack 08 |
| 6 | EF/05-07-009b DF | Data.6 | 2 | L09 | Lack 09 |
| 7 | EF/04 DF | Data.4 | 3 | Lp12 | Lackp12 |
| 8 | EF/05-07-009b DF | Data.2 | 3 | Lp13 | Lackp13 |
| 9 | EF/01-009b DF | Data.6 | 3 | Lp14 | Lackp14 |
| 10 | EF/03 DF | Data.2 | 4 | L+IL2-17 | Lack+IL2-17 |
| 11 | EF/03 DF | Data.6 | 4 | L+IL2-18 | Lack+IL2-18 |
| 12 | EF/02-07 DF | Data.4 | 4 | L+IL2-19 | Lack+IL2-19 |
| 13 | EF/01-009b DF | Data.4 | 5 | Lp+IL2-22 | Lackp+IL2-22 |
| 14 | EF/02-07 DF | Data.6 | 5 | Lp+IL2-23 | Lackp+IL2-23 |
| 15 | EF/03 DF | Data.4 | 5 | Lp+IL2-24 | Lackp+IL2-24 |

*FIG. 35*

| Parameters of file to use | | DA PWK/R-CD4+ | | | |
|---|---|---|---|---|---|
| | Workbook | Sheet | Group | Nature | Remark |
| 1 | DF BB/013 | Data.3 | 1 | RJ0a | 1 |
| 2 | DF BB/013 | Data.1 | 1 | RJ0b | 2 |
| 3 | DF BB/013 | Data.2 | 1 | RJ0c | 3 |
| 4 | DF BB/014 | Data.1 | 1 | RJ0d | 4 |
| 5 | DF BB/017 | Data.1 | 1 | RJ0e | 5 |
| 6 | DF BB/017 | Data.2 | 1 | RJ0f | 6 |
| 7 | DF BB/005 | Data.1 | 2 | R7sa | 7 |
| 8 | DF BB/005 | Data.2 | 2 | R7sb | 8 |
| 9 | DF BB/005 | Data.3 | 2 | R7sc | 9 |
| 10 | DF BB/006 | Data.2 | 2 | R7sd | 10 |
| 11 | DF BB/006 | Data.2 | 2 | R7se | 11 |
| 12 | DF BB/006 | Data.3 | 2 | R7sf | 12 |
| 13 | DF BB/023 | Data.1 | 3 | R20sa | 13 |
| 14 | DF BB/023 | Data.2 | 3 | R20sb | 14 |
| 15 | DF BB/023 | Data.3 | 3 | R20sc | 15 |
| 16 | DF BB/024 | Data.1 | 3 | R20sd | 16 |
| 17 | DF BB/024 | Data.2 | 3 | R20se | 17 |
| 18 | DF BB/024 | Data.3 | 3 | R20sf | 18 |
| 19 | DF BB/031 | Data.1 | 4 | R27sa | 19 |
| 20 | DF BB/031 | Data.2 | 4 | R27sb | 20 |
| 21 | DF BB/031 | Data.3 | 4 | R27sc | 21 |
| 22 | DF BB/032 | Data.1 | 4 | R27sd | 22 |
| 23 | DF BB/032 | Data.2 | 4 | R27se | 23 |
| 24 | DF BB/032 | Data.3 | 4 | R27sf | 24 |

| Oligoclonality Score βV: PWK/Rate-CD4+ ||
|---|---|
| 7 weeks post-infection | 27 weeks post-infection |
| βV01 (9-10-11 aa) | βV5.2 (9 aa) |
| βV09 (10-11 aa) | βV8.3 (8-9-10 aa) |
| βV16 (10 aa) | βV09 (7-9-10-12-13 aa) |
| βV19 (12 aa) | βV10 (9 aa) |
|  | βV11 (9-10-11 aa) |

*FIG. 39*

| Oligoclonality Score βV: PWK/GG-CD4+ ||
|---|---|
| 7 weeks post-infection | 27 weeks post-infection |
| βV01 (9-10-11 aa) | βV5.2 (8-9 aa) |
| βV03 (10 aa) | βV10 (9 aa) |
| βV8.1 (10 aa) | βV14 (10 aa) |
| βV8.2 (9-10-11 aa) | βV15 (9-10-11 aa) |
| βV09 (9-10-11 aa) |  |
| βV16 (10 aa) |  |
| βV19 (10-12 aa) |  |

*FIG. 44*

| Oligoclonality Score βV: PWK/GG-CD8+ ||
|---|---|
| 7 weeks post-infection | 27 weeks post-infection |
| βV12 (9-10 aa) | βV03 (10 aa) |
| βV15 (8-9 aa) | βV04 (11 aa) |

*FIG. 49*

| Oligoclonality Score βV: PWK/Rate-CD8+ ||
|---|---|
| 7 weeks post-infection | 27 weeks post-infection |
| βV01 (10-11-12 aa) | βV03 (10 aa) |
|  | βV13 (11 aa) |

*FIG. 54*

| Parameters of file to use | | DA PWK/GG-CD4+ | | | |
|---|---|---|---|---|---|
| | Workbook | Sheet | Group | Nature | Remark |
| 1 | DF BB/009 | Data.2 | 1 | GGJ0b | 1 |
| 2 | DF BB/009 | Data.3 | 1 | GGJ0c | 2 |
| 3 | DF BB/009 | Data.1 | 1 | GGJ0a | 3 |
| 4 | DF BB/010 | Data.1 | 1 | GGJ0d | 4 |
| 5 | DF BB/010 | Data.2 | 1 | GGJ0e | 5 |
| 6 | DF BB/010 | Data.3 | 1 | GGJ0f | 6 |
| 7 | DF BB/002 | Data.1 | 2 | GG7sa | 7 |
| 8 | DF BB/002 | Data.2 | 2 | GG7sb | 8 |
| 9 | DF BB/002 | Data.3 | 2 | GG7sc | 9 |
| 10 | DF BB/003 | Data.1 | 2 | GG7sd | 10 |
| 11 | DF BB/003 | Data.2 | 2 | GG7se | 11 |
| 12 | DF BB/007 | Data.3 | 2 | GG7sf | 12 |
| 13 | DF BB/019 | Data.1 | 3 | GG20sa | 13 |
| 14 | DF BB/019 | Data.2 | 3 | GG20sb | 14 |
| 15 | DF BB/019 | Data.3 | 3 | GG20sc | 15 |
| 16 | DF BB/020 | Data.1 | 3 | GG20sd | 16 |
| 17 | DF BB/020 | Data.2 | 3 | GG20se | 17 |
| 18 | DF BB/020 | Data.3 | 3 | GG20sf | 18 |
| 19 | DF BB/027 | Data.1 | 4 | GG27sa | 19 |
| 20 | DF BB/027 | Data.2 | 4 | GG27sb | 20 |
| 21 | DF BB/027 | Data.3 | 4 | GG27sc | 21 |
| 22 | DF BB/028 | Data.1 | 4 | GG27sd | 22 |
| 23 | DF BB/028 | Data.2 | 4 | GG27se | 23 |
| 24 | DF BB/028 | Data.3 | 4 | GG27sf | 24 |

*FIG. 41*

| Parameters of file to use | | DA PWK/GG-CD8+ | | | |
|---|---|---|---|---|---|
| | Workbook | Sheet | Group | Nature | Remark |
| 1 | DF BB/001 | Data.2 | 2 | GG7sb | 7 |
| 2 | DF BB/001 | Data.1 | 2 | GG7sa | 8 |
| 3 | DF BB/001 | Data.3 | 2 | GG7sc | 9 |
| 4 | DF BB/004 | Data.1 | 2 | GG7sd | 10 |
| 5 | DF BB/004 | Data.2 | 2 | GG7se | 11 |
| 6 | DF BB/004 | Data.3 | 2 | GG7sf | 12 |
| 7 | DF BB/011 | Data.1 | 1 | GGJOa | 1 |
| 8 | DF BB/011 | Data.2 | 1 | GGJOb | 2 |
| 9 | DF BB/011 | Data.3 | 1 | GGJOc | 3 |
| 10 | DF BB/012 | Data.1 | 1 | GGJOd | 4 |
| 11 | DF BB/012 | Data.2 | 1 | GGJOe | 5 |
| 12 | DF BB/012 | Data.3 | 1 | GGJOf | 6 |
| 13 | DF BB/021 | Data.1 | 3 | GG20sa | 13 |
| 14 | DF BB/021 | Data.2 | 3 | GG20sb | 14 |
| 15 | DF BB/021 | Data.3 | 3 | GG20sc | 15 |
| 16 | DF BB/022 | Data.1 | 3 | GG20sd | 16 |
| 17 | DF BB/022 | Data.2 | 3 | GG20se | 17 |
| 18 | DF BB/022 | Data.3 | 3 | GG20sf | 18 |
| 19 | DF BB/029 | Data.1 | 4 | GG27sa | 19 |
| 20 | DF BB/029 | Data.2 | 4 | GG27sb | 20 |
| 21 | DF BB/029 | Data.3 | 4 | GG27sc | 21 |
| 22 | DF BB/030 | Data.1 | 4 | GG27sd | 22 |
| 23 | DF BB/030 | Data.2 | 4 | GG27se | 23 |
| 24 | DF BB/030 | Data.3 | 4 | GG27sf | 24 |

*FIG. 46*

| Parameters of file to use | | DA | PWK/R-CD8+ | | |
|---|---|---|---|---|---|
| | Workbook | Sheet | Group | Nature | Remark |
| 1 | DF BB/017 | Data.3 | 1 | RJOa | 1 |
| 2 | DF BB/018 | Data.1 | 1 | RJOb | 2 |
| 3 | DF BB/015 | Data.3 | 1 | RJOc | 3 |
| 4 | DF BB/016 | Data.1 | 1 | RJOd | 4 |
| 5 | DF BB/016 | Data.2 | 1 | RJOe | 5 |
| 6 | DF BB/016 | Data.3 | 1 | RJOf | 6 |
| 7 | DF BB/007 | Data.1 | 2 | R7sa | 7 |
| 8 | DF BB/007 | Data.2 | 2 | R7sb | 8 |
| 9 | DF BB/008 | Data.1 | 2 | R7sc | 9 |
| 10 | DF BB/008 | Data.2 | 2 | R7sd | 10 |
| 11 | DF BB/008 | Data.3 | 2 | R7se | 11 |
| 12 | DF BB/018 | Data.2 | 2 | R7sf | 12 |
| 13 | DF BB/025 | Data.1 | 3 | R20sa | 13 |
| 14 | DF BB/025 | Data.2 | 3 | R20sb | 14 |
| 15 | DF BB/025 | Data.3 | 3 | R20sc | 15 |
| 16 | DF BB/026 | Data.1 | 3 | R20sd | 16 |
| 17 | DF BB/026 | Data.2 | 3 | R20se | 17 |
| 18 | DF BB/026 | Data.3 | 3 | R20sf | 18 |
| 19 | DF BB/033 | Data.1 | 4 | R27sa | 19 |
| 20 | DF BB/033 | Data.2 | 4 | R27sb | 20 |
| 21 | DF BB/033 | Data.3 | 4 | R27sc | 21 |
| 22 | DF BB/034 | Data.1 | 4 | R27sd | 22 |
| 23 | DF BB/034 | Data.2 | 4 | R27se | 23 |
| 24 | DF BB/034 | Data.3 | 4 | R27sf | 24 |

Parameters of file to use

|  | Workbook | Sheet | Group | Nature | Remarks |
|---|---|---|---|---|---|
| 1 | EF/043 DF | Data.2 | 1 | TN01 spleen | |
| 2 | EF/022 DF | Data.1 | 1 | TN02 spleen | |
| 3 | EF/018 DF | Data.1 | 1 | TN03 spleen | |
| 4 | EF/038 DF | Data.3 | 1 | TN04 spleen | |
| 5 | EF/039 DF | Data.1 | 2 | J3-01 spleen | |
| 6 | EF/016 DF | Data.1 | 2 | J3-02 spleen | |
| 7 | EF/034 DF | Data.1 | 2 | J3-03 spleen | |
| 8 | EF/046 DF | Data.2 | 2 | J3-04 spleen | |
| 9 | EF/023 DF | Data.2 | 2 | J3-05 spleen | |
| 10 | EF/029 DF | Data.3 | 3 | J4-01 spleen | |
| 11 | EF/026 DF | Data.1 | 3 | J4-02 spleen | |
| 12 | EF/029 DF | Data.1 | 3 | J4-03 spleen | |
| 13 | EF/036 DF | Data.2 | 3 | J4-04 spleen | |
| 14 | EF/019 DF | Data.2 | 3 | J4-06 spleen | |
| 15 | EF/038 DF | Data.1 | 3 | J4-07 spleen | |
| 16 | EF/045 DF | Data.1 | 3 | J4-08 spleen | |
| 17 | EF/042 DF | Data.3 | 3 | J4-09 spleen | |
| 18 | EF/042 DF | Data.1 | 3 | J4-10 spleen | |
| 19 | EF/016 DF | Data.3 | 4 | J5-01 spleen | |
| 20 | EF/026 DF | Data.3 | 4 | J5-02 spleen | |
| 21 | EF/031 DF | Data.1 | 4 | J5-03 spleen | |
| 22 | EF/021 DF | Data.1 | 4 | J5-04 spleen | |
| 23 | EF/021 DF | Data.3 | 4 | J5-05 spleen | |
| 24 | EF/028 DF | Data.2 | 4 | J5-06 spleen | |
| 25 | EF/043 DF | Data.3 | 4 | J5-07 spleen | |
| 26 | EF/041 DF | Data.2 | 4 | J5-08 spleen | |
| 27 | EF/012 DF | Data.3 | 4 | J5-09 spleen | |
| 28 | EF/046 DF | Data.3 | 4 | J5-10 spleen | |
| 29 | EF/024 DF | Data.1 | 5 | J6-01 spleen | |
| 30 | EF/017 DF | Data.1 | 5 | J6-02 spleen | |
| 31 | EF/025 DF | Data.1 | 5 | J6-03 spleen | |
| 32 | EF/040 DF | Data.1 | 5 | J6-04 spleen | |
| 33 | EF/014 DF | Data.2 | 5 | J6-05 spleen | |
| 34 | EF/020 DF | Data.1 | 5 | J6-06 spleen | |
| 35 | EF/033 DF | Data.1 | 5 | J6-07 spleen | |
| 36 | EF/030 DF | Data.1 | 5 | J6-08 spleen | |
| 37 | EF/013 DF | Data.2 | 5 | J6-09 spleen | |
| 38 | EF/027 DF | Data.1 | 5 | J6-10 spleen | |
| 39 | EF/031 DF | Data.3 | 6 | TSP01 CM+spleen | |
| 40 | EF/032 DF | Data.1 | 6 | TSP06 CM+spleen | |
| 41 | EF/034 DF | Data.3 | 6 | TSP09 CM+spleen | |
| 42 | EF/010 DF | Data.2 | 6 | TSP10 CM+++ spleen | |
| 43 | EF/044 DF | Data.1 | 6 | TSP18 CM+++ spleen | |
| 44 | EF/037 DF | Data.1 | 6 | TSP19 CM+++ spleen | |
| 45 | EF/011 DF | Data.2 | 6 | TSP20 CM+++ spleen | |

*FIG. 56A*

| | | | | |
|---|---|---|---|---|
| 46 | EF/022 DF | Data.2 | 7 | TN02 PBL |
| 47 | EF/018 DF | Data.2 | 7 | TN03 PBL |
| 48 | EF/039 DF | Data.2 | 8 | J3-01 PBL |
| 49 | EF/016 DF | Data.2 | 8 | J3-02 PBL |
| 50 | EF/034 DF | Data.2 | 8 | J3-03 PBL |
| 51 | EF/039 DF | Data.3 | 8 | J3-04 PBL |
| 52 | EF/023 DF | Data.3 | 8 | J3-05 PBL |
| 53 | EF/031 DF | Data.2 | 9 | J4-01 PBL |
| 54 | EF/026 DF | Data.2 | 9 | J4-02 PBL |
| 55 | EF/029 DF | Data.2 | 9 | J4-03 PBL |
| 56 | EF/036 DF | Data.3 | 9 | J4-04 PBL |
| 57 | EF/012 DF | Data.1 | 9 | J4-05 PBL |
| 58 | EF/019 DF | Data.3 | 9 | J4-06 PBL |
| 59 | EF/038 DF | Data.2 | 9 | J4-07 PBL |
| 60 | EF/045 DF | Data.2 | 9 | J4-08 PBL |
| 61 | EF/043 DF | Data.1 | 9 | J4-09 PBL |
| 62 | EF/042 DF | Data.2 | 9 | J4-10 PBL |
| 63 | EF/019 DF | Data.1 | 10 | J5-01 PBL |
| 64 | EF/028 DF | Data.1 | 10 | J5-02 PBL |
| 65 | EF/035 DF | Data.1 | 10 | J5-03 PBL |
| 66 | EF/021 DF | Data.2 | 10 | J5-04 PBL |
| 67 | EF/023 DF | Data.1 | 10 | J5-05 PBL |
| 68 | EF/028 DF | Data.3 | 10 | J5-06 PBL |
| 69 | EF/041 DF | Data.3 | 10 | J5-08 PBL |
| 70 | EF/012 DF | Data.2 | 10 | J5-09 PBL |
| 71 | EF/041 DF | Data.1 | 10 | J5-10 PBL |
| 72 | EF/024 DF | Data.2 | 11 | J6-01 PBL |
| 73 | EF/017 DF | Data.2 | 11 | J6-02 PBL |
| 74 | EF/025 DF | Data.2 | 11 | J6-03 PBL |
| 75 | EF/040 DF | Data.2 | 11 | J6-04 PBL |
| 76 | EF/014 DF | Data.1 | 11 | J6-05 PBL |
| 77 | EF/020 DF | Data.2 | 11 | J6-06 PBL |
| 78 | EF/033 DF | Data.2 | 11 | J6-07 PBL |
| 79 | EF/030 DF | Data.2 | 11 | J6-08 PBL |
| 80 | EF/013 DF | Data.1 | 11 | J6-09 PBL |
| 81 | EF/027 DF | Data.2 | 11 | J6-10 PBL |
| 82 | EF/032 DF | Data.2 | 12 | TSP06 CM+PBL |
| 83 | EF/035 DF | Data.3 | 12 | TSP09 CM+PBL |
| 84 | EF/010 DF | Data.1 | 12 | TSP10 CM+++ PBL |
| 85 | EF/044 DF | Data.2 | 12 | TSP18 CM+++ PBL |
| 86 | EF/037 DF | Data.2 | 12 | TSP19 CM+++ PBL |
| 87 | EF/011 DF | Data.1 | 12 | TSP20 CM+++ PBL |

Figure 58A:
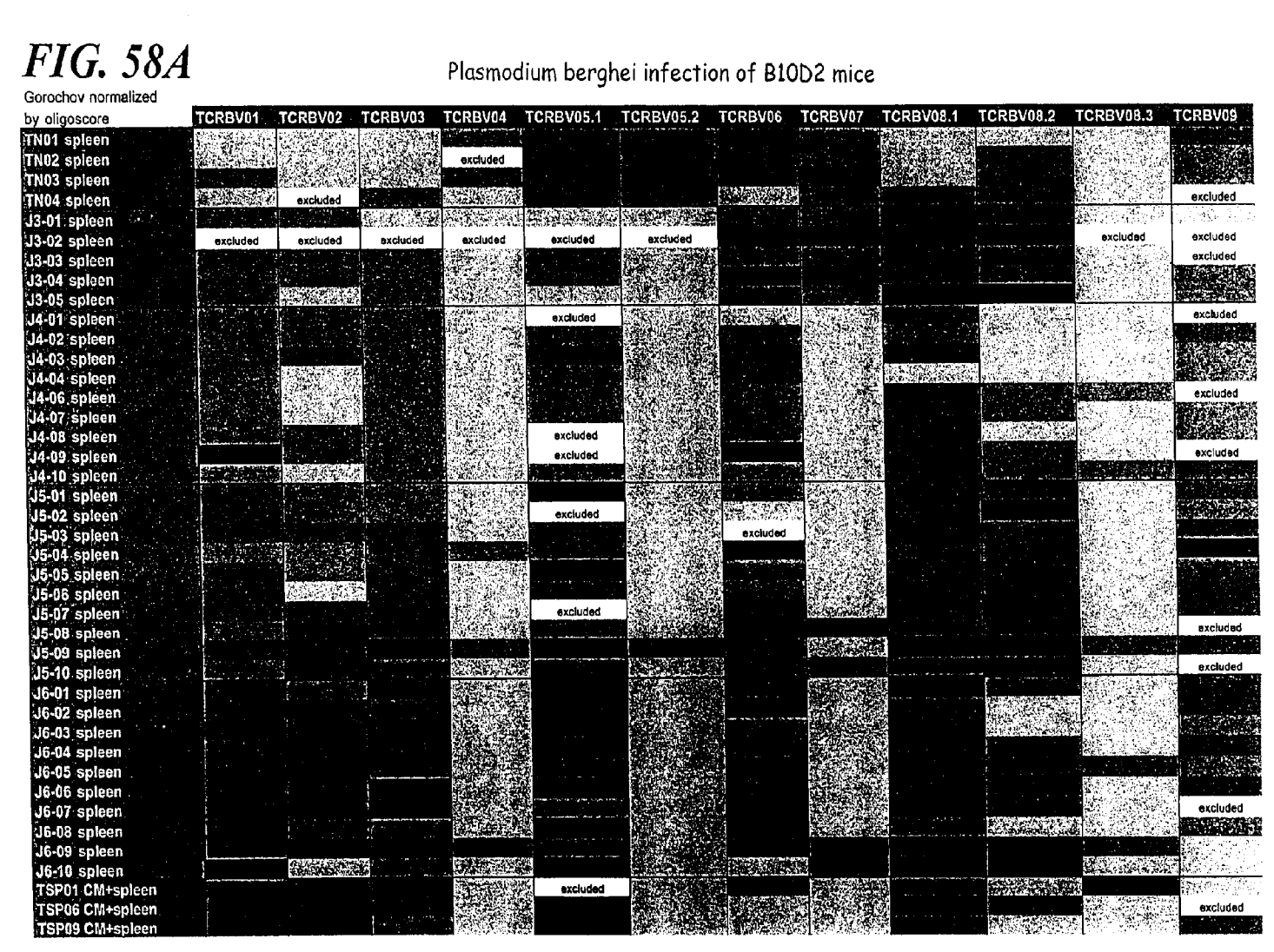
Figure 58B:
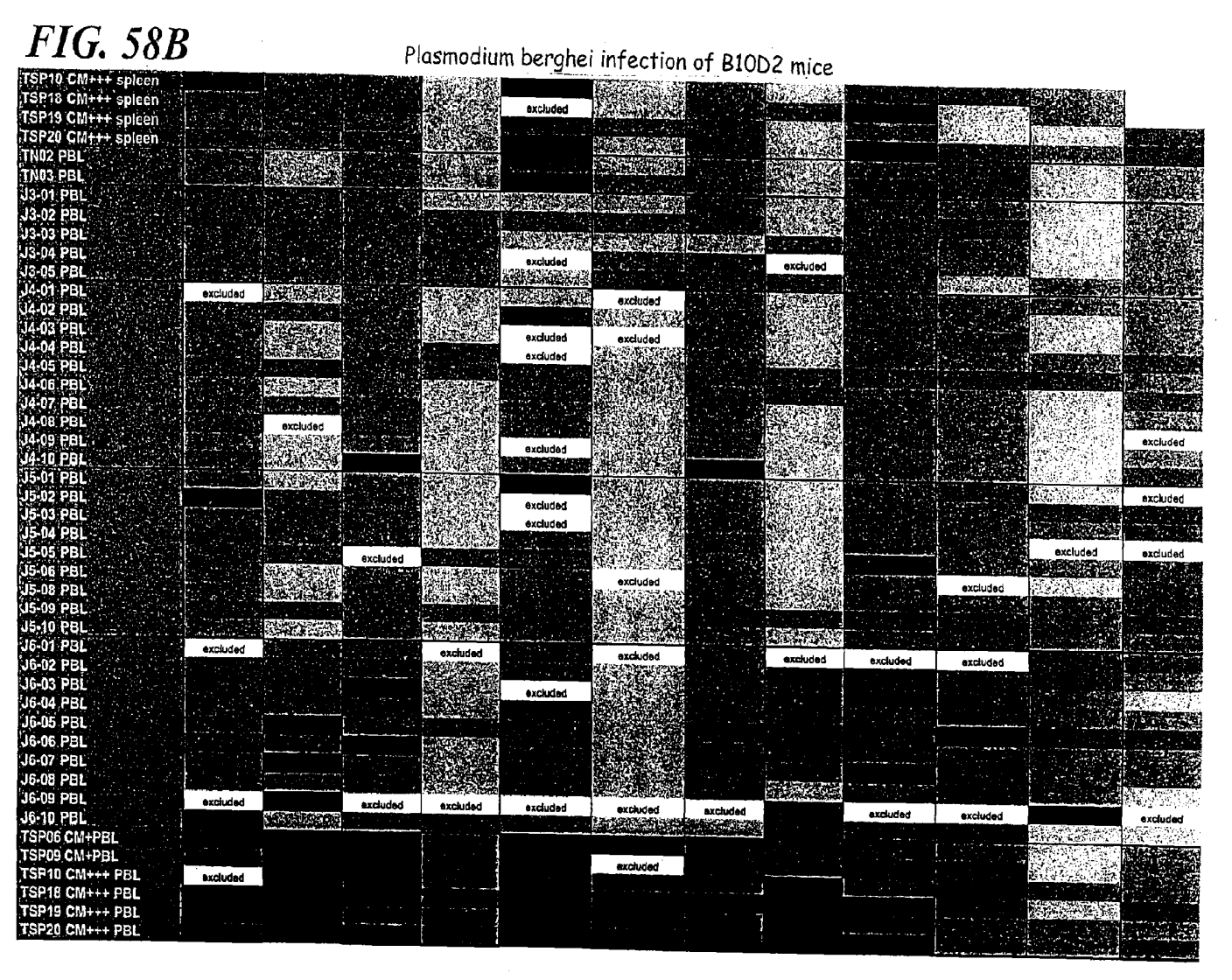

FIG. 58B  Plasmodium berghei infection of B10D2 mice

FIG. 59A

ANOVA (Analysis of Variance) Table for TCRBV01

|  | d.f. | Sum of Squares | Mean Square | F Value | p Value | Lambda | Power |
|---|---|---|---|---|---|---|---|
| Group | 11 | 487,099 | 44,282 | .963 | .4876 | 10,593 | .481 |
| Residue | 70 | 3218,716 | 45,982 | | | | |

Means Table for TCRBV01
Effect: Group

|  | Number | Mean | Standard Deviation (Dev.) | Standard Error (Err.) |
|---|---|---|---|---|
| CM+P | 5 | 12,655 | 6,248 | 2,794 |
| CM+S | 7 | 11,770 | 8,471 | 3,202 |
| J3P | 5 | 5,210 | 1,421 | .636 |
| J3S | 4 | 5,197 | 1,317 | .659 |
| J4P | 9 | 5,749 | 2,066 | .689 |
| J4S | 9 | 8,000 | 8,378 | 2,793 |
| J5P | 9 | 7,802 | 9,117 | 3,039 |
| J5S | 10 | 6,450 | 1,743 | .551 |
| J6P | 8 | 10,107 | 9,711 | 3,433 |
| J6S | 10 | 10,615 | 8,486 | 2,683 |
| TNP | 2 | 4,928 | 1,360 | .961 |
| TNS | 4 | 5,823 | 2,616 | 1,308 |

PLSD Fisher's Test for TCRBV01
Group effect
Significance level: 5%

| | Mean diff. | Critical diff. | p Value |
|---|---|---|---|
| CM+P, CM+S | .885 | 7.919 | .8242 |
| CM+P, J3P | 7.445 | 8.553 | .0870 |
| CM+P, J3S | 7.458 | 9.072 | .1056 |
| CM+P, J4P | 6.906 | 7.543 | .0721 |
| CM+P, J4S | 4.655 | 7.543 | .2225 |
| CM+P, J5P | 4.852 | 7.543 | .2037 |
| CM+P, J5S | 6.205 | 7.408 | .0993 |
| CM+P, J6P | 2.548 | 7.710 | .5120 |
| CM+P, J6S | 2.040 | 7.408 | .5846 |
| CM+P, TNP | 7.727 | 11.315 | .1776 |
| CM+P, TNS | 6.832 | 9.072 | .1376 |
| CM+S, J3P | 6.560 | 7.919 | .1030 |
| CM+S, J3S | 6.573 | 8.477 | .1265 |
| CM+S, J4P | 6.021 | 6.816 | .0825 |
| CM+S, J4S | 3.770 | 6.816 | .2738 |
| CM+S, J5P | 3.967 | 6.816 | .2496 |
| CM+S, J5S | 5.320 | 6.665 | .1159 |
| CM+S, J6P | 1.662 | 6.999 | .6372 |
| CM+S, J6S | 1.155 | 6.665 | .7308 |
| CM+S, TNP | 6.842 | 10.844 | .2124 |
| CM+S, TNS | 5.947 | 8.477 | .1662 |
| J3P, J3S | .013 | 9.072 | .9977 |
| J3P, J4P | -.539 | 7.543 | .8870 |
| J3P, J4S | -2.790 | 7.543 | .4632 |
| J3P, J5P | -2.593 | 7.543 | .4953 |
| J3P, J5S | -1.240 | 7.408 | .7395 |
| J3P, J6P | -4.897 | 7.710 | .2094 |
| J3P, J6S | -5.405 | 7.408 | .1500 |
| J3P, TNP | .282 | 11.315 | .9605 |

| | Mean diff. | Critical diff. | p Value |
|---|---|---|---|
| J3P, TNS | -.613 | 9.072 | .8932 |
| J3S, J4P | -.552 | 8.127 | .8926 |
| J3S, J4S | -2.803 | 8.127 | .4938 |
| J3S, J5P | -2.605 | 8.127 | .5247 |
| J3S, J5S | -1.253 | 8.001 | .7557 |
| J3S, J6P | -4.910 | 8.282 | .2410 |
| J3S, J6S | -5.418 | 8.001 | .1812 |
| J3S, TNP | .269 | 11.712 | .9636 |
| J3S, TNS | -.626 | 9.563 | .8965 |
| J4P, J4S | -2.251 | 6.375 | .4837 |
| J4P, J5P | -2.053 | 6.375 | .5228 |
| J4P, J5S | -.701 | 6.214 | .8227 |
| J4P, J6P | -4.358 | 6.572 | .1902 |
| J4P, J6S | -4.866 | 6.214 | .1228 |
| J4P, TNP | .821 | 10.572 | .8773 |
| J4P, TNS | -.074 | 8.127 | .9856 |
| J4S, J5P | .198 | 6.375 | .9509 |
| J4S, J5S | 1.550 | 6.214 | .6204 |
| J4S, J6P | -2.107 | 6.572 | .5246 |
| J4S, J6S | -2.615 | 6.214 | .4041 |
| J4S, TNP | 3.072 | 10.572 | .5641 |
| J4S, TNS | 2.177 | 8.127 | .5948 |
| J5P, J5S | 1.352 | 6.214 | .6656 |
| J5P, J6P | -2.305 | 6.572 | .4865 |
| J5P, J6S | -2.813 | 6.214 | .3697 |
| J5P, TNP | 2.874 | 10.572 | .5894 |
| J5P, TNS | 1.980 | 8.127 | .6286 |
| J5S, J6P | -3.657 | 6.415 | .2594 |
| J5S, J6S | -4.165 | 6.048 | .1740 |
| J5S, TNP | 1.522 | 10.476 | .7729 |
| J5S, TNS | .627 | 8.001 | .8762 |
| J6P, J6S | -.508 | 6.415 | .8750 |
| J6P, TNP | 5.179 | 10.692 | .3373 |
| J6P, TNS | 4.284 | 8.282 | .3057 |
| J6S, TNP | 5.687 | 10.476 | .2826 |
| J6S, TNS | 4.792 | 8.001 | .2363 |
| TNP, TNS | -.895 | 11.712 | .8793 |

FIG.59E

ANOVA (Analysis of Variance) Table for TCRBV02

| | d.f. | Sum of Squares | Mean Square | F Value | p Value | Lambda | Power |
|---|---|---|---|---|---|---|---|
| Group | 11 | 2669,319 | 242,665 | 7,138 | <,0001 | 78,523 | 1,000 |
| Residue | 72 | 2447,564 | 33,994 | | | | |

Means Table for TCRBV02
Effect: Group

| | Number | Mean | Standard Deviation (Dev.) | Standard Error (Err.) |
|---|---|---|---|---|
| CM+P | 6 | 24,950 | 9,665 | 3,946 |
| CM+S | 7 | 13,764 | 4,939 | 1,867 |
| J3P | 5 | 5,477 | ,881 | ,394 |
| J3S | 4 | 4,920 | 1,670 | ,835 |
| J4P | 9 | 5,462 | 3,842 | 1,281 |
| J4S | 9 | 4,352 | 2,535 | ,845 |
| J5P | 9 | 6,816 | 3,816 | 1,272 |
| J5S | 10 | 8,401 | 4,782 | 1,512 |
| J6P | 10 | 14,921 | 11,227 | 3,550 |
| J6S | 10 | 11,333 | 4,562 | 1,443 |
| TNP | 2 | 5,715 | 2,955 | 2,089 |
| TNS | 3 | 2,963 | ,461 | ,266 |

PLSD Fisher's Test for TCRBV02
Effect: Group
Significance level: 5%

FIG. 59H(2)

| | Mean diff. | Critical diff. | p Value | |
|---|---|---|---|---|
| CM+P, CM+S | 11.186 | 6.466 | .0009 | S |
| CM+P, J3P | 19.473 | 7.038 | <.0001 | S |
| CM+P, J3S | 20.031 | 7.502 | <.0001 | S |
| CM+P, J4P | 19.489 | 6.126 | <.0001 | S |
| CM+P, J4S | 20.598 | 6.126 | <.0001 | S |
| CM+P, J5P | 18.135 | 6.126 | <.0001 | S |
| CM+P, J5S | 16.550 | 6.002 | <.0001 | S |
| CM+P, J6P | 10.029 | 6.002 | .0014 | S |
| CM+P, J6S | 13.618 | 6.002 | <.0001 | S |
| CM+P, TNP | 19.235 | 9.490 | .0001 | S |
| CM+P, TNS | 21.987 | 8.219 | <.0001 | S |
| CM+S, J3P | 8.287 | 6.806 | .0177 | S |
| CM+S, J3S | 8.845 | 7.265 | .0180 | S |
| CM+S, J4P | 8.303 | 5.857 | .0061 | S |
| CM+S, J4S | 9.412 | 5.857 | .0020 | S |
| CM+S, J5P | 6.949 | 5.857 | .0207 | S |
| CM+S, J5S | 5.364 | 5.728 | .0660 | |
| CM+S, J6P | -1.157 | 5.728 | .6884 | |
| CM+S, J6S | 2.432 | 5.728 | .4002 | |
| CM+S, TNP | 8.049 | 9.319 | .0894 | |
| CM+S, TNS | 10.801 | 8.020 | .0090 | S |
| J3P, J3S | .558 | 7.797 | .8870 | |
| J3P, J4P | .016 | 6.483 | .9962 | |
| J3P, J4S | 1.125 | 6.483 | .7304 | |
| J3P, J5P | -1.339 | 6.483 | .6818 | |
| J3P, J5S | -2.923 | 6.366 | .3630 | |
| J3P, J6P | -9.444 | 6.366 | .0042 | S |
| J3P, J6S | -5.855 | 6.366 | .0709 | |
| J3P, TNP | -.238 | 9.724 | .9612 | |
| J3P, TNS | 2.514 | 8.488 | .5568 | |

FIG. 59H(1)

| | Mean diff. | Critical diff. | p Value | |
|---|---|---|---|---|
| J3S, J4P | -.542 | 6.984 | .8775 | |
| J3S, J4S | .567 | 6.984 | .8718 | |
| J3S, J5P | -1.896 | 6.984 | .5900 | |
| J3S, J5S | -3.481 | 6.876 | .3163 | |
| J3S, J6P | -10.002 | 6.876 | .0049 | S |
| J3S, J6S | -6.413 | 6.876 | .0671 | |
| J3S, TNP | -.796 | 10.066 | .8752 | |
| J3S, TNS | 1.956 | 8.877 | .6618 | |
| J4P, J4S | 1.109 | 5.479 | .6877 | |
| J4P, J5P | -1.354 | 5.479 | .6237 | |
| J4P, J5S | -2.939 | 5.340 | .2762 | |
| J4P, J6P | -9.460 | 5.340 | .0007 | S |
| J4P, J6S | -5.871 | 5.340 | .0316 | S |
| J4P, TNP | -.254 | 9.086 | .9557 | |
| J4P, TNS | 2.498 | 7.749 | .5225 | |
| J4S, J5P | -2.463 | 5.479 | .3731 | |
| J4S, J5S | -4.048 | 5.340 | .1351 | |
| J4S, J6P | -10.569 | 5.340 | .0002 | S |
| J4S, J6S | -6.980 | 5.340 | .0111 | S |
| J4S, TNP | -1.363 | 9.086 | .7658 | |
| J4S, TNS | 1.389 | 7.749 | .7219 | |
| J5P, J5S | -1.585 | 5.340 | .5560 | |
| J5P, J6P | -8.106 | 5.340 | .0034 | S |
| J5P, J6S | -4.517 | 5.340 | .0961 | |
| J5P, TNP | 1.100 | 9.086 | .8099 | |
| J5P, TNS | 3.852 | 7.749 | .3250 | |
| J5S, J6P | -6.521 | 5.198 | .0147 | S |
| J5S, J6S | -2.932 | 5.198 | .2646 | |
| J5S, TNP | 2.685 | 9.003 | .5540 | |
| J5S, TNS | 5.437 | 7.651 | .1609 | |
| J6P, J6S | 3.589 | 5.198 | .1730 | |
| J6P, TNP | 9.206 | 9.003 | .0452 | S |
| J6P, TNS | 11.958 | 7.651 | .0026 | S |
| J6S, TNP | 5.617 | 9.003 | .2176 | |
| J6S, TNS | 8.369 | 7.651 | .0325 | S |
| TNP, TNS | 2.752 | 10.610 | .6067 | |

FIG. 60A

| | d.f. | Sum of Squares | Mean Square | F Value | p Value | Lambda | Power |
|---|---|---|---|---|---|---|---|
| Group | 11 | 1734.159 | 157.651 | 4.890 | <.0001 | 53.795 | 1.000 |
| Residue | 72 | 2321.022 | 32.236 | | | | |

Means Table for TCRBV03
Effect: Group

| | Number | Mean | Standard Deviation (Dev.) | Standard Error (Err.) |
|---|---|---|---|---|
| CM+P | 6 | 18,836 | 3,623 | 1,479 |
| CM+S | 7 | 10,820 | 2,765 | 1,045 |
| J3P | 5 | 5,331 | 1,231 | .551 |
| J3S | 4 | 5,430 | 1,650 | .825 |
| J4P | 10 | 7,461 | 8,978 | 2,839 |
| J4S | 9 | 4,415 | .982 | .327 |
| J5P | 8 | 5,793 | 1,245 | .440 |
| J5S | 10 | 10,189 | 5,355 | 1,693 |
| J6P | 9 | 13,548 | 6,523 | 2,174 |
| J6S | 10 | 15,192 | 9,694 | 3,066 |
| TNP | 2 | 5,383 | 1,319 | .933 |
| TNS | 4 | 3,344 | 1,322 | .661 |

Chart of Interactions for TCRBV03
Effect: Group
Error bars: ± 1.96 Standard error(s)

FIG. 60D(1)

| | Mean diff. | Critical diff. | p Value | |
|---|---|---|---|---|
| CM+P, CM+S | 8.015 | 6.297 | .0133 | S |
| CM+P, J3P | 13.505 | 6.854 | .0002 | S |
| CM+P, J3S | 13.406 | 7.306 | .0005 | S |
| CM+P, J4P | 11.374 | 5.845 | .0002 | S |
| CM+P, J4S | 14.421 | 5.965 | <.0001 | S |
| CM+P, J5P | 13.043 | 6.113 | <.0001 | S |
| CM+P, J5S | 8.647 | 5.845 | .0043 | S |
| CM+P, J6P | 5.288 | 5.965 | .0815 | |
| CM+P, J6S | 3.644 | 5.845 | .2180 | |
| CM+P, TNP | 13.452 | 9.241 | .0049 | S |
| CM+P, TNS | 15.491 | 7.306 | <.0001 | S |
| CM+S, J3P | 5.489 | 6.627 | .1031 | |
| CM+S, J3S | 5.391 | 7.094 | .1342 | |
| CM+S, J4P | 3.359 | 5.578 | .2339 | |
| CM+S, J4S | 6.405 | 5.704 | .0283 | S |
| CM+S, J5P | 5.027 | 5.858 | .0914 | |
| CM+S, J5S | .632 | 5.578 | .8221 | |
| CM+S, J6P | -2.728 | 5.704 | .3436 | |
| CM+S, J6S | -4.372 | 5.578 | .1226 | |
| CM+S, TNP | 5.437 | 9.075 | .2363 | |
| CM+S, TNS | 7.476 | 7.094 | .0392 | S |
| J3P, J3S | -.099 | 7.593 | .9794 | |
| J3P, J4P | -2.130 | 6.199 | .4955 | |
| J3P, J4S | .916 | 6.313 | .7732 | |
| J3P, J5P | -.462 | 6.452 | .8869 | |
| J3P, J5S | -4.858 | 6.199 | .1227 | |
| J3P, J6P | -8.217 | 6.313 | .0115 | S |
| J3P, J6S | -9.861 | 6.199 | .0022 | S |
| J3P, TNP | -.052 | 9.470 | .9912 | |
| J3P, TNS | 1.987 | 7.593 | .6035 | |

FIG. 60D(2)

| | Mean diff. | Critical diff. | p Value | |
|---|---|---|---|---|
| J3S, J4P | -2.032 | 6.696 | .5472 | |
| J3S, J4S | 1.015 | 6.801 | .7670 | |
| J3S, J5P | -.363 | 6.931 | .9171 | |
| J3S, J5S | -4.759 | 6.696 | .1609 | |
| J3S, J6P | -8.118 | 6.801 | .0200 | S |
| J3S, J6S | -9.762 | 6.696 | .0049 | S |
| J3S, TNP | .046 | 9.802 | .9925 | |
| J3S, TNS | 2.086 | 8.003 | .6050 | |
| J4P, J4S | 3.046 | 5.200 | .2468 | |
| J4P, J5P | 1.668 | 5.369 | .5376 | |
| J4P, J5S | -2.727 | 5.062 | .2863 | |
| J4P, J6P | -6.087 | 5.200 | .0224 | S |
| J4P, J6S | -7.731 | 5.062 | .0033 | S |
| J4P, TNP | 2.078 | 8.767 | .6380 | |
| J4P, TNS | 4.117 | 6.696 | .2243 | |
| J4S, J5P | -1.378 | 5.500 | .6190 | |
| J4S, J5S | -5.774 | 5.200 | .0301 | S |
| J4S, J6P | -9.133 | 5.336 | .0011 | S |
| J4S, J6S | -10.777 | 5.200 | <.0001 | S |
| J4S, TNP | -.968 | 8.848 | .8270 | |
| J4S, TNS | 1.071 | 6.801 | .7545 | |
| J5P, J5S | -4.396 | 5.369 | .1070 | |
| J5P, J6P | -7.755 | 5.500 | .0064 | S |
| J5P, J6S | -9.399 | 5.369 | .0008 | S |
| J5P, TNP | .410 | 8.948 | .9275 | |
| J5P, TNS | 2.449 | 6.931 | .4835 | |
| J5S, J6P | -3.359 | 5.200 | .2020 | |
| J5S, J6S | -5.003 | 5.062 | .0526 | |
| J5S, TNP | 4.805 | 8.767 | .2782 | |
| J5S, TNS | 6.845 | 6.696 | .0453 | S |
| J6P, J6S | -1.644 | 5.200 | .5306 | |
| J6P, TNP | 8.165 | 8.848 | .0700 | |
| J6P, TNS | 10.204 | 6.801 | .0038 | S |
| J6S, TNP | 9.808 | 8.767 | .0288 | S |
| J6S, TNS | 11.848 | 6.696 | .0007 | S |
| TNP, TNS | 2.039 | 9.802 | .6796 | |

FIG.60E

ANOVA (Analysis of Variance) Table for TCRBV04

| | d.f. | Sum of Squares | Mean Square | F Value | p Value | Lambda | Power |
|---|---|---|---|---|---|---|---|
| Group | 11 | 480.614 | 43.692 | .929 | .5183 | 10.216 | .465 |
| Residue | 71 | 3340.055 | 47.043 | | | | |

Means Table for TCRBV04
Effect: Group

| | Number | Mean | Standard Deviation (Dev.) | Standard Error (Err.) |
|---|---|---|---|---|
| CM+P | 6 | 12,811 | 8,847 | 3,612 |
| CM+S | 7 | 8,619 | 3,258 | 1,231 |
| J3P | 5 | 7,932 | 2,114 | ,945 |
| J3S | 4 | 5,369 | 1,230 | ,615 |
| J4P | 10 | 9,371 | 10,068 | 3,184 |
| J4S | 9 | 5,627 | 2,092 | ,697 |
| J5P | 9 | 10,016 | 10,982 | 3,661 |
| J5S | 10 | 5,395 | 2,913 | ,921 |
| J6P | 8 | 10,734 | 10,645 | 3,764 |
| J6S | 10 | 6,812 | 2,906 | ,919 |
| TNP | 2 | 3,313 | ,404 | ,286 |
| TNS | 3 | 5,444 | 1,555 | ,898 |

Chart of Interactions for TCRBV04
Effect: Group
Error bars: ± 1.96 Standard error(s)

FIG. 60H(1)

| | Mean diff. | Critical diff. | p Value |
|---|---|---|---|
| CM+P, CM+S | 4.193 | 7.609 | .2756 |
| CM+P, J3P | 4.879 | 8.281 | .2440 |
| CM+P, J3S | 7.442 | 8.828 | .0972 |
| CM+P, J4P | 3.440 | 7.062 | .3347 |
| CM+P, J4S | 7.184 | 7.208 | .0507 |
| CM+P, J5P | 2.795 | 7.208 | .4419 |
| CM+P, J5S | 7.416 | 7.062 | .0398 |
| CM+P, J6P | 2.077 | 7.386 | .5767 |
| CM+P, J6S | 5.999 | 7.062 | .0947 |
| CM+P, TNP | 9.498 | 11.166 | .0943 |
| CM+P, TNS | 7.368 | 9.670 | .1332 |
| CM+S, J3P | .687 | 8.008 | .8648 |
| CM+S, J3S | 3.249 | 8.572 | .4522 |
| CM+S, J4P | -.753 | 6.740 | .8244 |
| CM+S, J4S | 2.992 | 6.892 | .3897 |
| CM+S, J5P | -1.397 | 6.892 | .6873 |
| CM+S, J5S | 3.223 | 6.740 | .3435 |
| CM+S, J6P | -2.115 | 7.078 | .5532 |
| CM+S, J6S | 1.806 | 6.740 | .5947 |
| CM+S, TNP | 5.305 | 10.965 | .3379 |
| CM+S, TNS | 3.175 | 9.437 | .5045 |
| J3P, J3S | 2.563 | 9.174 | .5793 |
| J3P, J4P | -1.439 | 7.491 | .7028 |
| J3P, J4S | 2.305 | 7.628 | .5487 |
| J3P, J5P | -2.084 | 7.628 | .5877 |
| J3P, J5S | 2.537 | 7.491 | .5017 |
| J3P, J6P | -2.802 | 7.797 | .4760 |
| J3P, J6S | 1.120 | 7.491 | .7665 |
| J3P, TNP | 4.619 | 11.442 | .4236 |
| J3P, TNS | 2.489 | 9.988 | .6209 |
| J3S, J4P | -4.002 | 8.091 | .3273 |
| J3S, J4S | -.258 | 8.218 | .9503 |

FIG. 60H(2)

| | Mean diff. | Critical diff. | p Value |
|---|---|---|---|
| J3S, J5P | -4.647 | 8.218 | .2634 |
| J3S, J5S | -.026 | 8.091 | .9949 |
| J3S, J6P | -5.364 | 8.375 | .2057 |
| J3S, J6S | -1.443 | 8.091 | .7232 |
| J3S, TNP | 2.056 | 11.844 | .7303 |
| J3S, TNS | -.074 | 10.445 | .9887 |
| J4P, J4S | 3.744 | 6.284 | .2387 |
| J4P, J5P | -.645 | 6.284 | .8385 |
| J4P, J5S | 3.976 | 6.116 | .1991 |
| J4P, J6P | -1.362 | 6.487 | .6766 |
| J4P, J6S | 2.559 | 6.116 | .4069 |
| J4P, TNP | 6.058 | 10.593 | .2580 |
| J4P, TNS | 3.928 | 9.003 | .3873 |
| J4S, J5P | -4.389 | 6.447 | .1790 |
| J4S, J5S | .232 | 6.284 | .9416 |
| J4S, J6P | -5.107 | 6.645 | .1299 |
| J4S, J6S | -1.185 | 6.284 | .7080 |
| J4S, TNP | 2.314 | 10.691 | .6674 |
| J4S, TNS | .183 | 9.117 | .9681 |
| J5P, J5S | 4.621 | 6.284 | .1470 |
| J5P, J6P | -.718 | 6.645 | .8301 |
| J5P, J6S | 3.204 | 6.284 | .3128 |
| J5P, TNP | 6.703 | 10.691 | .2154 |
| J5P, TNS | 4.572 | 9.117 | .3207 |
| J5S, J6P | -5.339 | 6.487 | .1052 |
| J5S, J6S | -1.417 | 6.116 | .6455 |
| J5S, TNP | 2.082 | 10.593 | .6963 |
| J5S, TNS | -.048 | 9.003 | .9915 |
| J6P, J6S | 3.922 | 6.487 | .2321 |
| J6P, TNP | 7.421 | 10.812 | .1755 |
| J6P, TNS | 5.290 | 9.259 | .2584 |
| J6S, TNP | 3.499 | 10.593 | .5123 |
| J6S, TNS | 1.369 | 9.003 | .7627 |
| TNP, TNS | -2.130 | 12.484 | .7347 |

| | d.f. | Sum of Squares | Mean Square | F Value | p Value | Lambda | Power |
|---|---|---|---|---|---|---|---|
| Group | 11 | 1661.862 | 151.078 | 1.949 | .0508 | 21.436 | .842 |
| Residue | 59 | 4574.151 | 77.528 | | | | |

Means Table for TCRBV05.1
Effect: Group

| | Number | Mean | Standard Deviation (Dev.) | Standard Error (Err.) |
|---|---|---|---|---|
| CM+P | 6 | 26,657 | 8,159 | 3,331 |
| CM+S | 5 | 13,877 | 4,933 | 2,206 |
| J3P | 4 | 19,960 | 14,417 | 7,208 |
| J3S | 4 | 10,518 | 3,153 | 1,577 |
| J4P | 7 | 19,651 | 14,109 | 5,333 |
| J4S | 6 | 8,088 | 1,826 | .746 |
| J5P | 7 | 20,393 | 9,875 | 3,733 |
| J5S | 8 | 15,429 | 8,348 | 2,952 |
| J6P | 8 | 19,805 | 7,737 | 2,735 |
| J6S | 10 | 19,787 | 8,877 | 2,807 |
| TNP | 2 | 11,334 | 1,795 | 1,269 |
| TNS | 4 | 14,094 | 5,006 | 2,503 |

FIG. 61D(1)

| | Mean diff. | Critical diff. | p Value | |
|---|---|---|---|---|
| CM+P, CM+S | 12.780 | 10.669 | .0197 | S |
| CM+P, J3P | 6.697 | 11.373 | .2434 | |
| CM+P, J3S | 16.139 | 11.373 | .0062 | S |
| CM+P, J4P | 7.006 | 9.802 | .1579 | |
| CM+P, J4S | 18.569 | 10.172 | .0006 | S |
| CM+P, J5P | 6.264 | 9.802 | .2060 | |
| CM+P, J5S | 11.228 | 9.515 | .0215 | S |
| CM+P, J6P | 6.852 | 9.515 | .1549 | |
| CM+P, J6S | 5.870 | 9.098 | .1362 | |
| CM+P, TNP | 15.323 | 14.386 | .0372 | S |
| CM+P, TNS | 12.563 | 11.373 | .0310 | S |
| CM+S, J3P | -6.083 | 11.819 | .3073 | |
| CM+S, J3S | 3.359 | 11.819 | .5717 | |
| CM+S, J4P | -5.774 | 10.316 | .2673 | |
| CM+S, J4S | 5.789 | 10.669 | .2820 | |
| CM+S, J5P | -6.516 | 10.316 | .2112 | |
| CM+S, J5S | -1.552 | 10.044 | .7582 | |
| CM+S, J6P | -5.928 | 10.044 | .2423 | |
| CM+S, J6S | -5.910 | 9.650 | .2252 | |
| CM+S, TNP | 2.543 | 14.741 | .7312 | |
| CM+S, TNS | -.217 | 11.819 | .9709 | |
| J3P, J3S | 9.442 | 12.458 | .1347 | |
| J3P, J4P | .310 | 11.043 | .9554 | |
| J3P, J4S | 11.872 | 11.373 | .0410 | S |
| J3P, J5P | -.433 | 11.043 | .9378 | |
| J3P, J5S | 4.531 | 10.789 | .4041 | |
| J3P, J6P | .155 | 10.789 | .9771 | |
| J3P, J6S | .173 | 10.423 | .9736 | |
| J3P, TNP | 8.626 | 15.258 | .2625 | |
| J3P, TNS | 5.867 | 12.458 | .3499 | |
| J3S, J4P | -9.133 | 11.043 | .1033 | |
| J3S, J4S | 2.430 | 11.373 | .6705 | |

FIG. 61D(2)

| | | | | |
|---|---|---|---|---|
| J3S, J5P | -9.875 | 11.043 | .0787 | |
| J3S, J5S | -4.911 | 10.789 | .3661 | |
| J3S, J6P | -9.287 | 10.789 | .0902 | |
| J3S, J6S | -9.269 | 10.423 | .0803 | |
| J3S, TNP | -.816 | 15.258 | .9151 | |
| J3S, TNS | -3.576 | 12.458 | .5679 | |
| J4P, J4S | 11.563 | 9.802 | .0216 | S |
| J4P, J5P | -.742 | 9.418 | .8752 | |
| J4P, J5S | 4.221 | 9.119 | .3580 | |
| J4P, J6P | -.155 | 9.119 | .9731 | |
| J4P, J6S | -.137 | 8.683 | .9750 | |
| J4P, TNP | 8.317 | 14.126 | .2435 | |
| J4P, TNS | 5.557 | 11.043 | .3181 | |
| J4S, J5P | -12.305 | 9.802 | .0148 | S |
| J4S, J5S | -7.341 | 9.515 | .1280 | |
| J4S, J6P | -11.717 | 9.515 | .0167 | S |
| J4S, J6S | -11.700 | 9.098 | .0126 | S |
| J4S, TNP | -3.246 | 14.386 | .6533 | |
| J4S, TNS | -6.006 | 11.373 | .2950 | |
| J5P, J5S | 4.964 | 9.119 | .2805 | |
| J5P, J6P | .588 | 9.119 | .8978 | |
| J5P, J6S | .606 | 8.683 | .8894 | |
| J5P, TNP | 9.059 | 14.126 | .2044 | |
| J5P, TNS | 6.299 | 11.043 | .2583 | |
| J5S, J6P | -4.376 | 8.809 | .3243 | |
| J5S, J6S | -4.358 | 8.357 | .3010 | |
| J5S, TNP | 4.095 | 13.929 | .5586 | |
| J5S, TNS | 1.336 | 10.789 | .8052 | |
| J6P, J6S | .018 | 8.357 | .9966 | |
| J6P, TNP | 8.471 | 13.929 | .2285 | |
| J6P, TNS | 5.712 | 10.789 | .2938 | |
| J6S, TNP | 8.453 | 13.647 | .2201 | |
| J6S, TNS | 5.694 | 10.423 | .2788 | |
| TNP, TNS | -2.760 | 15.258 | .7187 | |

FIG.61E

| | d.f. | Sum of Squares | Mean Square | F Value | p Value | Lambda | Power |
|---|---|---|---|---|---|---|---|
| Group | 11 | 1350.634 | 122.785 | 6.040 | <.0001 | 66.443 | 1.000 |
| Residue | 68 | 1382.288 | 20.328 | | | | |

Means Table for TCRBV05.2
Effect: Group

| | Number | Mean | Standard Deviation (Dev.) | Standard Error (Err.) |
|---|---|---|---|---|
| CM+P | 5 | 23.300 | 7.151 | 3.198 |
| CM+S | 7 | 9.868 | 4.811 | 1.818 |
| J3P | 5 | 14.277 | 8.343 | 3.731 |
| J3S | 4 | 6.390 | 1.693 | .847 |
| J4P | 8 | 10.889 | 1.436 | .508 |
| J4S | 9 | 8.759 | 2.111 | .704 |
| J5P | 8 | 17.091 | 3.750 | 1.326 |
| J5S | 10 | 8.415 | 6.726 | 2.127 |
| J6P | 8 | 12.346 | 3.849 | 1.361 |
| J6S | 10 | 9.966 | 2.723 | .861 |
| TNP | 2 | 9.361 | 4.477 | 3.165 |
| TNS | 4 | 8.400 | 1.384 | .692 |

FIG. 61H(1)

|  | Mean diff. | Critical diff. | p Value |  |
|---|---|---|---|---|
| CM+P, CM+S | 13.432 | 5.268 | <.0001 | S |
| CM+P, J3P | 9.024 | 5.690 | .0023 | S |
| CM+P, J3S | 16.910 | 6.035 | <.0001 | S |
| CM+P, J4P | 12.411 | 5.129 | <.0001 | S |
| CM+P, J4S | 14.541 | 5.018 | <.0001 | S |
| CM+P, J5P | 6.209 | 5.129 | .0184 | S |
| CM+P, J5S | 14.886 | 4.928 | <.0001 | S |
| CM+P, J6P | 10.955 | 5.129 | <.0001 | S |
| CM+P, J6S | 13.335 | 4.928 | <.0001 | S |
| CM+P, TNP | 13.939 | 7.527 | .0004 | S |
| CM+P, TNS | 14.901 | 6.035 | <.0001 | S |
| CM+S, J3P | -4.409 | 5.268 | .0995 |  |
| CM+S, J3S | 3.478 | 5.639 | .2227 |  |
| CM+S, J4P | -1.021 | 4.656 | .6632 |  |
| CM+S, J4S | 1.109 | 4.534 | .6271 |  |
| CM+S, J5P | -7.223 | 4.656 | .0029 | S |
| CM+S, J5S | 1.454 | 4.434 | .5152 |  |
| CM+S, J6P | -2.477 | 4.656 | .2921 |  |
| CM+S, J6S | -.098 | 4.434 | .9651 |  |
| CM+S, TNP | .507 | 7.214 | .8888 |  |
| CM+S, TNS | 1.469 | 5.639 | .6050 |  |
| J3P, J3S | 7.887 | 6.035 | .0112 | S |
| J3P, J4P | 3.388 | 5.129 | .1919 |  |
| J3P, J4S | 5.518 | 5.018 | .0317 | S |
| J3P, J5P | -2.815 | 5.129 | .2774 |  |
| J3P, J5S | 5.862 | 4.928 | .0204 | S |
| J3P, J6P | 1.931 | 5.129 | .4550 |  |
| J3P, J6S | 4.311 | 4.928 | .0854 |  |
| J3P, TNP | 4.916 | 7.527 | .1969 |  |
| J3P, TNS | 5.877 | 6.035 | .0561 |  |
| J3S, J4P | -4.499 | 5.509 | .1078 |  |
| J3S, J4S | -2.369 | 5.406 | .3850 |  |

FIG. 61H(2)

|  | Mean diff. | Critical diff. | p Value |  |
|---|---|---|---|---|
| J3S, J5P | -10.701 | 5.509 | .0002 | S |
| J3S, J5S | -2.025 | 5.323 | .4505 |  |
| J3S, J6P | -5.956 | 5.509 | .0345 | S |
| J3S, J6S | -3.576 | 5.323 | .1845 |  |
| J3S, TNP | -2.971 | 7.791 | .4494 |  |
| J3S, TNS | -2.009 | 6.362 | .5306 |  |
| J4P, J4S | 2.130 | 4.372 | .3344 |  |
| J4P, J5P | -6.202 | 4.498 | .0076 | S |
| J4P, J5S | 2.474 | 4.268 | .2513 |  |
| J4P, J6P | -1.457 | 4.498 | .5203 |  |
| J4P, J6S | .923 | 4.268 | .6674 |  |
| J4P, TNP | 1.528 | 7.113 | .6695 |  |
| J4P, TNS | 2.489 | 5.509 | .3704 |  |
| J4S, J5P | -8.332 | 4.372 | .0003 | S |
| J4S, J5S | .345 | 4.134 | .8684 |  |
| J4S, J6P | -3.586 | 4.372 | .1062 |  |
| J4S, J6S | -1.207 | 4.134 | .5622 |  |
| J4S, TNP | -.602 | 7.033 | .8649 |  |
| J4S, TNS | .360 | 5.406 | .8948 |  |
| J5P, J5S | 8.677 | 4.268 | .0001 | S |
| J5P, J6P | 4.746 | 4.498 | .0390 | S |
| J5P, J6S | 7.126 | 4.268 | .0014 | S |
| J5P, TNP | 7.730 | 7.113 | .0336 | S |
| J5P, TNS | 8.692 | 5.509 | .0024 | S |
| J5S, J6P | -3.931 | 4.268 | .0704 |  |
| J5S, J6S | -1.551 | 4.024 | .4444 |  |
| J5S, TNP | -.946 | 6.969 | .7872 |  |
| J5S, TNS | .015 | 5.323 | .9955 |  |
| J6P, J6S | 2.380 | 4.268 | .2697 |  |
| J6P, TNP | 2.985 | 7.113 | .4053 |  |
| J6P, TNS | 3.946 | 5.509 | .1575 |  |
| J6S, TNP | .605 | 6.969 | .8630 |  |
| J6S, TNS | 1.566 | 5.323 | .5590 |  |
| TNP, TNS | .961 | 7.791 | .8062 |  |

FIG. 62A

| | d.f. | Sum of Squares | Mean Square | F Value | p Value | Lambda | Power |
|---|---|---|---|---|---|---|---|
| Group | 11 | 1291.943 | 117.449 | 1.870 | .0575 | 20.575 | .837 |
| Residue | 73 | 4583.735 | 62.791 | | | | |

Means Table for TCRBV06
Effect: Group

| | Number | Mean | Standard Deviation (Dev.) | Standard Error (Err.) |
|---|---|---|---|---|
| CM+P | 6 | 15.125 | 7.023 | 2.867 |
| CM+S | 7 | 10.994 | 7.245 | 2.739 |
| J3P | 5 | 7.344 | 2.440 | 1.091 |
| J3S | 5 | 17.100 | 10.958 | 4.901 |
| J4P | 10 | 11.019 | 8.113 | 2.566 |
| J4S | 9 | 8.340 | 8.466 | 2.822 |
| J5P | 9 | 7.467 | 2.436 | .812 |
| J5S | 9 | 10.375 | 8.168 | 2.723 |
| J6P | 9 | 18.262 | 9.736 | 3.245 |
| J6S | 10 | 15.564 | 10.507 | 3.322 |
| TNP | 2 | 6.084 | .261 | .185 |
| TNS | 4 | 6.845 | 2.526 | 1.263 |

|  | Mean diff. | Critical diff. | p Value |
|---|---|---|---|
| CM+P, CM+S | 4.131 | 8.786 | .3518 |
| CM+P, J3P | 7.781 | 9.563 | .1092 |
| CM+P, J3S | -1.975 | 9.563 | .6818 |
| CM+P, J4P | 4.106 | 8.155 | .3190 |
| CM+P, J4S | 6.784 | 8.323 | .1086 |
| CM+P, J5P | 7.657 | 8.323 | .0708 |
| CM+P, J5S | 4.749 | 8.323 | .2592 |
| CM+P, J6P | -3.137 | 8.323 | .4550 |
| CM+P, J6S | -.440 | 8.155 | .9148 |
| CM+P, TNP | 9.041 | 12.895 | .1665 |
| CM+P, TNS | 8.280 | 10.194 | .1098 |
| CM+S, J3P | 3.650 | 9.247 | .4341 |
| CM+S, J3S | -6.106 | 9.247 | .1923 |
| CM+S, J4P | -.025 | 7.783 | .9949 |
| CM+S, J4S | 2.653 | 7.959 | .5085 |
| CM+S, J5P | 3.526 | 7.959 | .3801 |
| CM+S, J5S | .618 | 7.959 | .8774 |
| CM+S, J6P | -7.268 | 7.959 | .0728 |
| CM+S, J6S | -4.571 | 7.783 | .2456 |
| CM+S, TNP | 4.910 | 12.662 | .4421 |
| CM+S, TNS | 4.148 | 9.899 | .4063 |
| J3P, J3S | -9.756 | 9.988 | .0554 |
| J3P, J4P | -3.675 | 8.650 | .3999 |
| J3P, J4S | -.996 | 8.809 | .8223 |
| J3P, J5P | -.124 | 8.809 | .9778 |
| J3P, J5S | -3.032 | 8.809 | .4949 |
| J3P, J6P | -10.918 | 8.809 | .0158 S |
| J3P, J6S | -8.220 | 8.650 | .0622 |
| J3P, TNP | 1.260 | 13.213 | .8498 |
| J3P, TNS | .499 | 10.594 | .9255 |
| J3S, J4P | 6.081 | 8.650 | .1654 |
| J3S, J4S | 8.759 | 8.809 | .0513 |

|  | Mean diff. | Critical diff. | p Value | |
|---|---|---|---|---|
| J3S, J5P | 9.632 | 8.809 | .0325 | S |
| J3S, J5S | 6.724 | 8.809 | .1325 | |
| J3S, J6P | -1.162 | 8.809 | .7933 | |
| J3S, J6S | 1.536 | 8.650 | .7245 | |
| J3S, TNP | 11.016 | 13.213 | .1009 | |
| J3S, TNS | 10.255 | 10.594 | .0576 | |
| J4P, J4S | 2.678 | 7.256 | .4643 | |
| J4P, J5P | 3.551 | 7.256 | .3326 | |
| J4P, J5S | .643 | 7.256 | .8603 | |
| J4P, J6P | -7.243 | 7.256 | .0504 | |
| J4P, J6S | -4.545 | 7.063 | .2037 | |
| J4P, TNP | 4.935 | 12.233 | .4240 | |
| J4P, TNS | 4.174 | 9.343 | .3762 | |
| J4S, J5P | .873 | 7.445 | .8159 | |
| J4S, J5S | -2.035 | 7.445 | .5875 | |
| J4S, J6P | -9.921 | 7.445 | .0097 | S |
| J4S, J6S | -7.224 | 7.256 | .0510 | |
| J4S, TNP | 2.257 | 12.346 | .7167 | |
| J4S, TNS | 1.495 | 9.490 | .7544 | |
| J5P, J5S | -2.908 | 7.445 | .4388 | |
| J5P, J6P | -10.794 | 7.445 | .0051 | S |
| J5P, J6S | -8.097 | 7.256 | .0293 | S |
| J5P, TNP | 1.384 | 12.346 | .8239 | |
| J5P, TNS | .622 | 9.490 | .8964 | |
| J5S, J6P | -7.886 | 7.445 | .0382 | S |
| J5S, J6S | -5.189 | 7.256 | .1584 | |
| J5S, TNP | 4.292 | 12.346 | .4906 | |
| J5S, TNS | 3.530 | 9.490 | .4608 | |
| J6P, J6S | 2.698 | 7.256 | .4611 | |
| J6P, TNP | 12.178 | 12.346 | .0531 | |
| J6P, TNS | 11.417 | 9.490 | .0191 | S |
| J6S, TNP | 9.480 | 12.233 | .1268 | |
| J6S, TNS | 8.719 | 9.343 | .0669 | |
| TNP, TNS | -.761 | 13.677 | .9120 | |

FIG. 62E

| | d.f. | Sum of Squares | Mean Square | F Value | p Value | Lambda | Power |
|---|---|---|---|---|---|---|---|
| Group | 11 | 1662.073 | 151.098 | 2.273 | .0190 | 24.999 | .916 |
| Residue | 73 | 4853.374 | 66.485 | | | | |

Means Table for TCRBV07
Effect: Group

| | Number | Mean | Standard Deviation (Dev.) | Standard Error (Err.) |
|---|---|---|---|---|
| CM+P | 6 | 22,571 | 12,580 | 5,136 |
| CM+S | 7 | 12,394 | 5,957 | 2,251 |
| J3P | 4 | 8,192 | 3,515 | 1,758 |
| J3S | 5 | 18,202 | 12,455 | 5,570 |
| J4P | 10 | 9,671 | 7,238 | 2,289 |
| J4S | 9 | 7,380 | 1,678 | .559 |
| J5P | 9 | 7,781 | 3,973 | 1,324 |
| J5S | 10 | 11,235 | 7,477 | 2,365 |
| J6P | 9 | 17,036 | 11,325 | 3,775 |
| J6S | 10 | 13,534 | 9,840 | 3,112 |
| TNP | 2 | 5,798 | 1,335 | .944 |
| TNS | 4 | 11,232 | 7,499 | 3,749 |

Chart of Interactions for TCRBV07
Effect: Group
Error bars: ± 1.96 Standard error(s)

FIG. 62H(1)

|  | Mean diff. | Critical diff. | p Value |  |
|---|---|---|---|---|
| CM+P, CM+S | 10.177 | 9.041 | .0279 | S |
| CM+P, J3P | 14.380 | 10.490 | .0079 | S |
| CM+P, J3S | 4.369 | 9.840 | .3791 | |
| CM+P, J4P | 12.900 | 8.392 | .0031 | S |
| CM+P, J4S | 15.191 | 8.565 | .0007 | S |
| CM+P, J5P | 14.790 | 8.565 | .0010 | S |
| CM+P, J5S | 11.336 | 8.392 | .0088 | S |
| CM+P, J6P | 5.535 | 8.565 | .2018 | |
| CM+P, J6S | 9.037 | 8.392 | .0352 | S |
| CM+P, TNP | 16.773 | 13.268 | .0139 | S |
| CM+P, TNS | 11.339 | 10.490 | .0345 | S |
| CM+S, J3P | 4.202 | 10.186 | .4136 | |
| CM+S, J3S | -5.808 | 9.515 | .2277 | |
| CM+S, J4P | 2.723 | 8.008 | .5002 | |
| CM+S, J4S | 5.014 | 8.189 | .2263 | |
| CM+S, J5P | 4.612 | 8.189 | .2653 | |
| CM+S, J5S | 1.159 | 8.008 | .7739 | |
| CM+S, J6P | -4.642 | 8.189 | .2623 | |
| CM+S, J6S | -1.140 | 8.008 | .7775 | |
| CM+S, TNP | 6.596 | 13.029 | .3163 | |
| CM+S, TNS | 1.162 | 10.186 | .8208 | |
| J3P, J3S | -10.011 | 10.901 | .0713 | |
| J3P, J4P | -1.480 | 9.614 | .7599 | |
| J3P, J4S | .811 | 9.765 | .8689 | |
| J3P, J5P | .410 | 9.765 | .9335 | |
| J3P, J5S | -3.044 | 9.614 | .5301 | |
| J3P, J6P | -8.845 | 9.765 | .0752 | |
| J3P, J6S | -5.342 | 9.614 | .2717 | |
| J3P, TNP | 2.394 | 14.073 | .7356 | |
| J3P, TNS | -3.041 | 11.491 | .5995 | |
| J3S, J4P | 8.531 | 8.901 | .0600 | |
| J3S, J4S | 10.822 | 9.064 | .0200 | S |

FIG. 62H(2)

| | Mean diff. | Critical diff. | p Value | |
|---|---|---|---|---|
| J3S, J5P | 10.421 | 9.064 | .0248 | S |
| J3S, J5S | 6.967 | 8.901 | .1231 | |
| J3S, J6P | 1.166 | 9.064 | .7984 | |
| J3S, J6S | 4.668 | 8.901 | .2993 | |
| J3S, TNP | 12.404 | 13.596 | .0731 | |
| J3S, TNS | 6.970 | 10.901 | .2066 | |
| J4P, J4S | 2.291 | 7.467 | .5428 | |
| J4P, J5P | 1.890 | 7.467 | .6155 | |
| J4P, J5S | -1.564 | 7.267 | .6693 | |
| J4P, J6P | -7.365 | 7.467 | .0531 | |
| J4P, J6S | -3.863 | 7.267 | .2930 | |
| J4P, TNP | 3.873 | 12.588 | .5416 | |
| J4P, TNS | -1.561 | 9.614 | .7472 | |
| J4S, J5P | -.401 | 7.661 | .9171 | |
| J4S, J5S | -3.855 | 7.467 | .3069 | |
| J4S, J6P | -9.656 | 7.661 | .0142 | S |
| J4S, J6S | -6.154 | 7.467 | .1048 | |
| J4S, TNP | 1.582 | 12.704 | .8046 | |
| J4S, TNS | -3.852 | 9.765 | .4343 | |
| J5P, J5S | -3.454 | 7.467 | .3596 | |
| J5P, J6P | -9.255 | 7.661 | .0186 | S |
| J5P, J6S | -5.752 | 7.467 | .1290 | |
| J5P, TNP | 1.984 | 12.704 | .7565 | |
| J5P, TNS | -3.451 | 9.765 | .4835 | |
| J5S, J6P | -5.801 | 7.467 | .1258 | |
| J5S, J6S | -2.299 | 7.267 | .5304 | |
| J5S, TNP | 5.437 | 12.588 | .3921 | |
| J5S, TNS | .003 | 9.614 | .9995 | |
| J6P, J6S | 3.502 | 7.467 | .3530 | |
| J6P, TNP | 11.238 | 12.704 | .0821 | |
| J6P, TNS | 5.804 | 9.765 | .2401 | |
| J6S, TNP | 7.736 | 12.588 | .2246 | |
| J6S, TNS | 2.302 | 9.614 | .6347 | |
| TNP, TNS | -5.435 | 14.073 | .4440 | |

FIG. 63A

| | d.f. | Sum of Squares | Mean Square | F Value | p Value | Lambda | Power |
|---|---|---|---|---|---|---|---|
| Group | 11 | 460.326 | 41.848 | 2.870 | .0035 | 31.573 | .973 |
| Residue | 73 | 1064.330 | 14.580 | | | | |

Means Table for TCRBV08.1
Effect: Group

| | Number | Mean | Standard Deviation (Dev.) | Standard Error (Err.) |
|---|---|---|---|---|
| CM+P | 6 | 11,623 | 5,609 | 2,290 |
| CM+S | 7 | 8,948 | 2,515 | .950 |
| J3P | 5 | 7,514 | 1,811 | .810 |
| J3S | 5 | 7,790 | 3,225 | 1,442 |
| J4P | 10 | 6,330 | 1,351 | .427 |
| J4S | 9 | 4,583 | 1,739 | .580 |
| J5P | 9 | 6,969 | 1,629 | .543 |
| J5S | 10 | 6,622 | 2,787 | .881 |
| J6P | 8 | 9,385 | 3,428 | 1,212 |
| J6S | 10 | 11,825 | 8,039 | 2,542 |
| TNP | 2 | 6,355 | 2,775 | 1,963 |
| TNS | 4 | 4,560 | 1,918 | .959 |

Chart of Interactions for TCRBV08.1
Effect: Group
Error bars: ± 1.96 Standard error(s)

FIG. 63D(1)

| | Mean diff. | Critical diff. | p Value | |
|---|---|---|---|---|
| CM+P, CM+S | 2,675 | 4,234 | .2119 | |
| CM+P, J3P | 4,109 | 4,608 | .0797 | |
| CM+P, J3S | 3,833 | 4,608 | .1017 | |
| CM+P, J4P | 5,293 | 3,930 | .0090 | S |
| CM+P, J4S | 7,040 | 4,011 | .0008 | S |
| CM+P, J5P | 4,654 | 4,011 | .0236 | S |
| CM+P, J5S | 5,001 | 3,930 | .0133 | S |
| CM+P, J6P | 2,238 | 4,110 | .2813 | |
| CM+P, J6S | -.202 | 3,930 | .9185 | |
| CM+P, TNP | 5,267 | 6,214 | .0954 | |
| CM+P, TNS | 7,063 | 4,912 | .0054 | S |
| CM+S, J3P | 1,434 | 4,456 | .5234 | |
| CM+S, J3S | 1,157 | 4,456 | .6063 | |
| CM+S, J4P | 2,618 | 3,750 | .1684 | |
| CM+S, J4S | 4,365 | 3,835 | .0263 | S |
| CM+S, J5P | 1,979 | 3,835 | .3072 | |
| CM+S, J5S | 2,325 | 3,750 | .2205 | |
| CM+S, J6P | -.437 | 3,939 | .8256 | |
| CM+S, J6S | -2,878 | 3,750 | .1305 | |
| CM+S, TNP | 2,592 | 6,102 | .3999 | |
| CM+S, TNS | 4,388 | 4,770 | .0708 | |
| J3P, J3S | -.276 | 4,813 | .9092 | |
| J3P, J4P | 1,184 | 4,168 | .5730 | |
| J3P, J4S | 2,931 | 4,245 | .1729 | |
| J3P, J5P | .545 | 4,245 | .7988 | |
| J3P, J5S | .892 | 4,168 | .6711 | |
| J3P, J6P | -1,871 | 4,338 | .3930 | |
| J3P, J6S | -4,311 | 4,168 | .0428 | S |
| J3P, TNP | 1,158 | 6,367 | .7179 | |
| J3P, TNS | 2,954 | 5,105 | .2525 | |
| J3S, J4P | 1,461 | 4,168 | .4872 | |
| J3S, J4S | 3,208 | 4,245 | .1363 | |
| J3S, J5P | .821 | 4,245 | .7008 | |
| J3S, J5S | 1,168 | 4,168 | .5781 | |

FIG. 63D(2)

| | | | | |
|---|---|---|---|---|
| J3S, J6P | -1,594 | 4,338 | .4663 | |
| J3S, J6S | -4,035 | 4,168 | .0576 | |
| J3S, TNP | 1,435 | 6,367 | .6547 | |
| J3S, TNS | 3,231 | 5,105 | .2112 | |
| J4P, J4S | 1,747 | 3,497 | .3226 | |
| J4P, J5P | -.639 | 3,497 | .7167 | |
| J4P, J5S | -.292 | 3,403 | .8645 | |
| J4P, J6P | -3,055 | 3,610 | .0960 | |
| J4P, J6S | -5,496 | 3,403 | .0019 | S |
| J4P, TNP | -.026 | 5,895 | .9931 | |
| J4P, TNS | 1,770 | 4,502 | .4358 | |
| J4S, J5P | -2,386 | 3,587 | .1890 | |
| J4S, J5S | -2,040 | 3,497 | .2488 | |
| J4S, J6P | -4,802 | 3,698 | .0116 | S |
| J4S, J6S | -7,243 | 3,497 | <.0001 | S |
| J4S, TNP | -1,773 | 5,949 | .5544 | |
| J4S, TNS | .023 | 4,573 | .9921 | |
| J5P, J5S | .347 | 3,497 | .8439 | |
| J5P, J6P | -2,416 | 3,698 | .1970 | |
| J5P, J6S | -4,856 | 3,497 | .0071 | S |
| J5P, TNP | .613 | 5,949 | .8377 | |
| J5P, TNS | 2,409 | 4,573 | .2972 | |
| J5S, J6P | -2,762 | 3,610 | .1315 | |
| J5S, J6S | -5,203 | 3,403 | .0032 | S |
| J5S, TNP | .267 | 5,895 | .9284 | |
| J5S, TNS | 2,063 | 4,502 | .3642 | |
| J6P, J6S | -2,441 | 3,610 | .1820 | |
| J6P, TNP | 3,029 | 6,016 | .3190 | |
| J6P, TNS | 4,825 | 4,660 | .0426 | S |
| J6S, TNP | 5,470 | 5,895 | .0695 | |
| J6S, TNS | 7,266 | 4,502 | .0019 | S |
| TNP, TNS | 1,796 | 6,590 | .5887 | |

FIG. 63E

| | d.f. | Sum of Squares | Mean Square | F Value | p Value | Lambda | Power |
|---|---|---|---|---|---|---|---|
| Group | 11 | 261.752 | 23.796 | .845 | .5966 | 9.294 | .423 |
| Residue | 72 | 2027.752 | 28.163 | | | | |

Means Table for TCRBV08.2
Effect: Group

| | Number | Mean | Standard Deviation (Dev.) | Standard Error (Err.) |
|---|---|---|---|---|
| CM+P | 6 | 9,424 | 4,193 | 1,712 |
| CM+S | 7 | 9,822 | 8,175 | 3,090 |
| J3P | 5 | 7,368 | 3,371 | 1,508 |
| J3S | 5 | 11,440 | 8,893 | 3,977 |
| J4P | 10 | 7,015 | 3,452 | 1,092 |
| J4S | 9 | 5,927 | 2,128 | .709 |
| J5P | 8 | 7,913 | 2,982 | 1,054 |
| J5S | 10 | 7,678 | 4,199 | 1,328 |
| J6P | 8 | 9,707 | 5,289 | 1,870 |
| J6S | 10 | 11,101 | 8,149 | 2,577 |
| TNP | 2 | 6,014 | 1,405 | .993 |
| TNS | 4 | 6,761 | 2,393 | 1,197 |

Chart of Interactions for TCRBV08.2
Effect: Group
Error bars: ± 1.96 Standard error(s)

FIG. 63H(1)

| | Mean diff. | Critical diff. | p Value |
|---|---|---|---|
| CM+P, CM+S | -.398 | 5.886 | .8933 |
| CM+P, J3P | 2.056 | 6.406 | .5243 |
| CM+P, J3S | -2.016 | 6.406 | .5325 |
| CM+P, J4P | 2.409 | 5.463 | .3822 |
| CM+P, J4S | 3.497 | 5.576 | .2152 |
| CM+P, J5P | 1.511 | 5.713 | .5996 |
| CM+P, J5S | 1.746 | 5.463 | .5261 |
| CM+P, J6P | -.283 | 5.713 | .9217 |
| CM+P, J6S | -1.677 | 5.463 | .5425 |
| CM+P, TNP | 3.410 | 8.638 | .4339 |
| CM+P, TNS | 2.663 | 6.829 | .4395 |
| CM+S, J3P | 2.454 | 6.194 | .4323 |
| CM+S, J3S | -1.618 | 6.194 | .6042 |
| CM+S, J4P | 2.807 | 5.213 | .2867 |
| CM+S, J4S | 3.895 | 5.331 | .1497 |
| CM+S, J5P | 1.909 | 5.475 | .4893 |
| CM+S, J5S | 2.143 | 5.213 | .4152 |
| CM+S, J6P | .115 | 5.475 | .9667 |
| CM+S, J6S | -1.280 | 5.213 | .6262 |
| CM+S, TNP | 3.807 | 8.482 | .3739 |
| CM+S, TNS | 3.060 | 6.631 | .3606 |
| J3P, J3S | -4.072 | 6.691 | .2290 |
| J3P, J4P | .353 | 5.794 | .9036 |
| J3P, J4S | 1.441 | 5.901 | .6279 |
| J3P, J5P | -.545 | 6.031 | .8576 |
| J3P, J5S | -.310 | 5.794 | .9153 |
| J3P, J6P | -2.339 | 6.031 | .4420 |
| J3P, J6S | -3.733 | 5.794 | .2031 |
| J3P, TNP | 1.353 | 8.851 | .7614 |
| J3P, TNS | .606 | 7.097 | .8652 |
| J3S, J4P | 4.425 | 5.794 | .1323 |
| J3S, J4S | 5.513 | 5.901 | .0666 |
| J3S, J5P | 3.527 | 6.031 | .2475 |

FIG. 63H(2)

| | Mean diff. | Critical diff. | p Value |
|---|---|---|---|
| J3S, J5S | 3.761 | 5.794 | .1998 |
| J3S, J6P | 1.733 | 6.031 | .5686 |
| J3S, J6S | .338 | 5.794 | .9076 |
| J3S, TNP | 5.425 | 8.851 | .2257 |
| J3S, TNS | 4.678 | 7.097 | .1930 |
| J4P, J4S | 1.088 | 4.861 | .6569 |
| J4P, J5P | -.898 | 5.018 | .7223 |
| J4P, J5S | -.664 | 4.731 | .7806 |
| J4P, J6P | -2.692 | 5.018 | .2884 |
| J4P, J6S | -4.087 | 4.731 | .0894 |
| J4P, TNP | 1.000 | 8.195 | .8085 |
| J4P, TNS | .253 | 6.259 | .9360 |
| J4S, J5P | -1.986 | 5.141 | .4438 |
| J4S, J5S | -1.751 | 4.861 | .4750 |
| J4S, J6P | -3.780 | 5.141 | .1471 |
| J4S, J6S | -5.174 | 4.861 | .0373 S |
| J4S, TNP | -.087 | 8.270 | .9832 |
| J4S, TNS | -.835 | 6.357 | .7943 |
| J5P, J5S | .234 | 5.018 | .9260 |
| J5P, J6P | -1.794 | 5.290 | .5011 |
| J5P, J6S | -3.189 | 5.018 | .2094 |
| J5P, TNP | 1.898 | 8.364 | .6523 |
| J5P, TNS | 1.151 | 6.478 | .7242 |
| J5S, J6P | -2.028 | 5.018 | .4230 |
| J5S, J6S | -3.423 | 4.731 | .1536 |
| J5S, TNP | 1.664 | 8.195 | .6869 |
| J5S, TNS | .917 | 6.259 | .7711 |
| J6P, J6S | -1.394 | 5.018 | .5813 |
| J6P, TNP | 3.692 | 8.364 | .3819 |
| J6P, TNS | 2.945 | 6.478 | .3678 |
| J6S, TNP | 5.087 | 8.195 | .2199 |
| J6S, TNS | 4.340 | 6.259 | .1712 |
| TNP, TNS | -.747 | 9.162 | .8713 |

FIG. 64A

| | d.f. | Sum of Squares | Mean Square | F Value | p Value | Lambda | Power |
|---|---|---|---|---|---|---|---|
| Group | 11 | 564.311 | 51.301 | 1.738 | .0817 | 19.121 | .801 |
| Residue | 73 | 2154.478 | 29.513 | | | | |

Means Table for TCRBV08.3
Effect: Group

| | Number | Mean | Standard Deviation (Dev.) | Standard Error (Err.) |
|---|---|---|---|---|
| CM+P | 6 | 8,649 | 3,431 | 1,401 |
| CM+S | 7 | 10,400 | 7,544 | 2,851 |
| J3P | 5 | 4,319 | 1,074 | .480 |
| J3S | 4 | 5,041 | 1,346 | .673 |
| J4P | 10 | 5,428 | 3,063 | .969 |
| J4S | 9 | 3,465 | 1,420 | .473 |
| J5P | 8 | 6,072 | 2,450 | .866 |
| J5S | 10 | 3,777 | 1,722 | .545 |
| J6P | 10 | 10,578 | 12,746 | 4,031 |
| J6S | 10 | 7,271 | 3,527 | 1,115 |
| TNP | 2 | 4,127 | .033 | .023 |
| TNS | 4 | 3,071 | .500 | .250 |

FIG. 64D(1)

| | Mean diff. | Critical diff. | p Value | |
|---|---|---|---|---|
| CM+P, CM+S | -1.751 | 6.024 | .5641 | |
| CM+P, J3P | 4.330 | 6.556 | .1922 | |
| CM+P, J3S | 3.608 | 6.989 | .3070 | |
| CM+P, J4P | 3.221 | 5.591 | .2547 | |
| CM+P, J4S | 5.183 | 5.706 | .0744 | |
| CM+P, J5P | 2.577 | 6.847 | .3827 | |
| CM+P, J5S | 4.872 | 5.591 | .0867 | |
| CM+P, J6P | -1.930 | 5.591 | .4938 | |
| CM+P, J6S | 1.377 | 5.591 | .6249 | |
| CM+P, TNP | 4.522 | 8.840 | .3114 | |
| CM+P, TNS | 5.578 | 6.989 | .1160 | |
| CM+S, J3P | 6.081 | 6.340 | .0598 | |
| CM+S, J3S | 5.359 | 6.786 | .1199 | |
| CM+S, J4P | 4.972 | 5.336 | .0673 | |
| CM+S, J4S | 6.935 | 5.456 | .0135 | S |
| CM+S, J5P | 4.328 | 5.604 | .1281 | |
| CM+S, J5S | 6.623 | 5.336 | .0157 | S |
| CM+S, J6P | -.178 | 5.336 | .9471 | |
| CM+S, J6S | 3.129 | 5.336 | .2463 | |
| CM+S, TNP | 6.273 | 8.681 | .1541 | |
| CM+S, TNS | 7.329 | 6.786 | .0347 | S |
| J3P, J3S | -.723 | 7.263 | .8434 | |
| J3P, J4P | -1.109 | 5.930 | .7104 | |
| J3P, J4S | .853 | 6.039 | .7790 | |
| J3P, J5P | -1.753 | 6.172 | .5730 | |
| J3P, J5S | .541 | 5.930 | .8561 | |
| J3P, J6P | -6.260 | 5.930 | .0388 | S |
| J3P, J6S | -2.953 | 5.930 | .3243 | |
| J3P, TNP | .192 | 9.059 | .9664 | |
| J3P, TNS | 1.248 | 7.263 | .7331 | |
| J3S, J4P | -.387 | 6.405 | .9046 | |
| J3S, J4S | 1.576 | 6.506 | .6307 | |
| J3S, J5P | -1.031 | 6.630 | .7575 | |

FIG. 64D(2)

| | Mean diff. | Critical diff. | p Value | |
|---|---|---|---|---|
| J3S, J5S | 1.264 | 6.405 | .6952 | |
| J3S, J6P | -5.537 | 6.405 | .0892 | |
| J3S, J6S | -2.230 | 6.405 | .4900 | |
| J3S, TNP | .915 | 9.377 | .8464 | |
| J3S, TNS | 1.970 | 7.656 | .6096 | |
| J4P, J4S | 1.963 | 4.975 | .4342 | |
| J4P, J5P | -.644 | 5.136 | .8033 | |
| J4P, J5S | 1.651 | 4.842 | .4990 | |
| J4P, J6P | -5.150 | 4.842 | .0374 | S |
| J4P, J6S | -1.843 | 4.842 | .4505 | |
| J4P, TNP | 1.301 | 8.387 | .7580 | |
| J4P, TNS | 2.357 | 6.405 | .4657 | |
| J4S, J5P | -2.607 | 5.261 | .3267 | |
| J4S, J5S | -.312 | 4.975 | .9009 | |
| J4S, J6P | -7.113 | 4.975 | .0057 | S |
| J4S, J6S | -3.806 | 4.975 | .1316 | |
| J4S, TNP | -.661 | 8.464 | .8767 | |
| J4S, TNS | .394 | 6.506 | .9042 | |
| J5P, J5S | 2.295 | 5.136 | .3761 | |
| J5P, J6P | -4.506 | 5.136 | .0846 | |
| J5P, J6S | -1.199 | 5.136 | .6431 | |
| J5P, TNP | 1.945 | 8.560 | .6519 | |
| J5P, TNS | 3.001 | 6.630 | .3700 | |
| J5S, J6P | -6.801 | 4.842 | .0065 | S |
| J5S, J6S | -3.494 | 4.842 | .1547 | |
| J5S, TNP | -.350 | 8.387 | .9340 | |
| J5S, TNS | .706 | 6.405 | .8267 | |
| J6P, J6S | 3.307 | 4.842 | .1776 | |
| J6P, TNP | 6.452 | 8.387 | .1296 | |
| J6P, TNS | 7.507 | 6.405 | .0223 | S |
| J6S, TNP | 3.145 | 8.387 | .4573 | |
| J6S, TNS | 4.200 | 6.405 | .1954 | |
| TNP, TNS | 1.056 | 9.377 | .8231 | |

FIG.64E

| | d.f. | Sum of Squares | Mean Square | F Value | p Value | Lambda | Power |
|---|---|---|---|---|---|---|---|
| Group | 11 | 2082.438 | 189.313 | 2.237 | .0239 | 24.605 | .900 |
| Residue | 59 | 4993.532 | 84.636 | | | | |

Means Table for TCRBV09
Effect: Group

| | Number | Mean | Standard Deviation (Dev.) | Standard Error (Err.) |
|---|---|---|---|---|
| CM+P | 6 | 32,449 | 11,856 | 4,840 |
| CM+S | 4 | 18,668 | 12,314 | 6,157 |
| J3P | 5 | 15,347 | 3,162 | 1,414 |
| J3S | 3 | 13,712 | 6,283 | 3,628 |
| J4P | 9 | 16,677 | 7,101 | 2,367 |
| J4S | 6 | 17,918 | 9,498 | 3,878 |
| J5P | 7 | 20,567 | 6,361 | 2,404 |
| J5S | 8 | 12,019 | 10,703 | 3,784 |
| J6P | 9 | 16,190 | 10,703 | 3,568 |
| J6S | 9 | 19,402 | 10,490 | 3,497 |
| TNP | 2 | 15,419 | .537 | .380 |
| TNS | 3 | 7,443 | 3,207 | 1,852 |

Chart of Interactions for TCRBV09
Effect: Group
Error bars: ± 1.96 Standard error(s)

FIG. 64H(1)

| | Mean diff. | Critical diff. | p Value |
|---|---|---|---|
| CM+P, CM+S | 13,782 | 11,883 | .0238 |
| CM+P, J3P | 17,102 | 11,147 | .0032 |
| CM+P, J3S | 18,737 | 13,017 | .0055 |
| CM+P, J4P | 15,773 | 9,702 | .0019 |
| CM+P, J4S | 14,532 | 10,628 | .0082 |
| CM+P, J5P | 11,882 | 10,242 | .0237 |
| CM+P, J5S | 20,431 | 9,942 | .0001 |
| CM+P, J6P | 16,260 | 9,702 | .0014 |
| CM+P, J6S | 13,047 | 9,702 | .0093 |
| CM+P, TNP | 17,030 | 15,031 | .0271 |
| CM+P, TNS | 25,006 | 13,017 | .0003 |
| CM+S, J3P | 3,321 | 12,349 | .5926 |
| CM+S, J3S | 4,956 | 14,060 | .4834 |
| CM+S, J4P | 1,991 | 11,062 | .7200 |
| CM+S, J4S | .750 | 11,883 | .8999 |
| CM+S, J5P | -1,899 | 11,538 | .7430 |
| CM+S, J5S | 6,649 | 11,273 | .2426 |
| CM+S, J6P | 2,478 | 11,062 | .6556 |
| CM+S, J6S | -.734 | 11,062 | .8948 |
| CM+S, TNP | 3,248 | 15,942 | .6850 |
| CM+S, TNS | 11,224 | 14,060 | .1155 |
| J3P, J3S | 1,635 | 13,444 | .8086 |
| J3P, J4P | -1,329 | 10,268 | .7965 |
| J3P, J4S | -2,570 | 11,147 | .6462 |
| J3P, J5P | -5,220 | 10,779 | .3365 |
| J3P, J5S | 3,329 | 10,495 | .5281 |
| J3P, J6P | -.842 | 10,268 | .8702 |
| J3P, J6S | -4,055 | 10,268 | .4326 |
| J3P, TNP | -.072 | 15,402 | .9925 |
| J3P, TNS | 7,904 | 13,444 | .2442 |
| J3S, J4P | -2,965 | 12,272 | .6306 |
| J3S, J4S | -4,206 | 13,017 | .5205 |

FIG. 64H(2)

| | Mean diff. | Critical diff. | p Value |
|---|---|---|---|
| J3S, J5P | -6,855 | 12,703 | .2846 |
| J3S, J5S | 1,694 | 12,463 | .7866 |
| J3S, J6P | -2,478 | 12,272 | .6877 |
| J3S, J6S | -5,690 | 12,272 | .3573 |
| J3S, TNP | -1,707 | 16,805 | .8396 |
| J3S, TNS | 6,269 | 15,031 | .4073 |
| J4P, J4S | -1,241 | 9,702 | .7989 |
| J4P, J5P | -3,890 | 9,277 | .4048 |
| J4P, J5S | 4,658 | 8,945 | .3017 |
| J4P, J6P | .487 | 8,678 | .9110 |
| J4P, J6S | -2,726 | 8,678 | .5321 |
| J4P, TNP | 1,257 | 14,391 | .8618 |
| J4P, TNS | 9,233 | 12,272 | .1375 |
| J4S, J5P | -2,649 | 10,242 | .6067 |
| J4S, J5S | 5,899 | 9,942 | .2399 |
| J4S, J6P | 1,728 | 9,702 | .7228 |
| J4S, J6S | -1,484 | 9,702 | .7606 |
| J4S, TNP | 2,498 | 15,031 | .7406 |
| J4S, TNS | 10,474 | 13,017 | .1127 |
| J5P, J5S | 8,549 | 9,527 | .0777 |
| J5P, J6P | 4,377 | 9,277 | .3489 |
| J5P, J6S | 1,165 | 9,277 | .8025 |
| J5P, TNP | 5,148 | 14,760 | .4880 |
| J5P, TNS | 13,124 | 12,703 | .0431 |
| J5S, J6P | -4,171 | 8,945 | .3546 |
| J5S, J6S | -7,384 | 8,945 | .1039 |
| J5S, TNP | -3,401 | 14,553 | .6418 |
| J5S, TNS | 4,575 | 12,463 | .4655 |
| J6P, J6S | -3,213 | 8,678 | .4618 |
| J6P, TNP | .770 | 14,391 | .9151 |
| J6P, TNS | 8,746 | 12,272 | .1591 |
| J6S, TNP | 3,983 | 14,391 | .5818 |
| J6S, TNS | 11,959 | 12,272 | .0560 |
| TNP, TNS | 7,976 | 16,805 | .3461 |

FIG. 65A

| | d.f. | Sum of Squares | Mean Square | F Value | p Value | Lambda | Power |
|---|---|---|---|---|---|---|---|
| Group | 11 | 490.945 | 44.631 | .454 | .9251 | 4.991 | .223 |
| Residue | 71 | 6984.585 | 98.374 | | | | |

Means Table for TCRBV10
Effect: Group

| | Number | Mean | Standard Deviation (Dev.) | Standard Error (Err.) |
|---|---|---|---|---|
| CM+P | 6 | 10,175 | 3,320 | 1,355 |
| CM+S | 7 | 7,994 | 3,656 | 1,382 |
| J3P | 5 | 9,884 | 9,834 | 4,398 |
| J3S | 5 | 8,409 | 7,889 | 3,528 |
| J4P | 9 | 8,062 | 7,645 | 2,548 |
| J4S | 9 | 5,909 | 1,975 | .658 |
| J5P | 9 | 7,336 | 6,956 | 2,319 |
| J5S | 9 | 9,596 | 8,867 | 2,956 |
| J6P | 10 | 14,088 | 22,489 | 7,112 |
| J6S | 9 | 9,281 | 4,212 | 1,404 |
| TNP | 2 | 6,434 | 1,017 | .719 |
| TNS | 3 | 3,943 | 1,407 | .812 |

Chart of Interactions for TCRBV10
Effect: Group
Error bars: ± 1.96 Standard error(s)

FIG. 65D(1)

| | Mean diff. | Critical diff. | p Value |
|---|---|---|---|
| CM+P, CM+S | 2.180 | 11.003 | .6939 |
| CM+P, J3P | .291 | 11.975 | .9615 |
| CM+P, J3S | 1.766 | 11.975 | .7696 |
| CM+P, J4P | 2.113 | 10.423 | .6873 |
| CM+P, J4S | 4.266 | 10.423 | .4172 |
| CM+P, J5P | 2.838 | 10.423 | .5888 |
| CM+P, J5S | .579 | 10.423 | .9122 |
| CM+P, J6P | -3.913 | 10.213 | .4474 |
| CM+P, J6S | .894 | 10.423 | .8647 |
| CM+P, TNP | 3.741 | 16.146 | .6456 |
| CM+P, TNS | 6.232 | 13.984 | .3772 |
| CM+S, J3P | -1.890 | 11.580 | .7459 |
| CM+S, J3S | -.415 | 11.580 | .9433 |
| CM+S, J4P | -.067 | 9.967 | .9893 |
| CM+S, J4S | 2.086 | 9.967 | .6778 |
| CM+S, J5P | .658 | 9.967 | .8956 |
| CM+S, J5S | -1.602 | 9.967 | .7496 |
| CM+S, J6P | -6.093 | 9.746 | .2166 |
| CM+S, J6S | -1.286 | 9.967 | .7977 |
| CM+S, TNP | 1.560 | 15.857 | .8450 |
| CM+S, TNS | 4.052 | 13.647 | .5557 |
| J3P, J3S | 1.475 | 12.508 | .8148 |
| J3P, J4P | 1.822 | 11.031 | .7428 |
| J3P, J4S | 3.975 | 11.031 | .4748 |
| J3P, J5P | 2.548 | 11.031 | .6465 |
| J3P, J5S | .288 | 11.031 | .9586 |
| J3P, J6P | -4.204 | 10.832 | .4416 |
| J3P, J6S | .603 | 11.031 | .9135 |
| J3P, TNP | 3.450 | 16.546 | .6789 |
| J3P, TNS | 5.941 | 14.443 | .4148 |
| J3S, J4P | .347 | 11.031 | .9501 |
| J3S, J4S | 2.500 | 11.031 | .6527 |

FIG. 65D(2)

| | | | |
|---|---|---|---|
| J3S, J5P | 1.073 | 11.031 | .8468 |
| J3S, J5S | -1.187 | 11.031 | .8307 |
| J3S, J6P | -5.679 | 10.832 | .2994 |
| J3S, J6S | -.872 | 11.031 | .8752 |
| J3S, TNP | 1.975 | 16.546 | .8126 |
| J3S, TNS | 4.466 | 14.443 | .5395 |
| J4P, J4S | 2.153 | 9.323 | .6466 |
| J4P, J5P | .726 | 9.323 | .8771 |
| J4P, J5S | -1.534 | 9.323 | .7438 |
| J4P, J6P | -6.026 | 9.087 | .1903 |
| J4P, J6S | -1.219 | 9.323 | .7951 |
| J4P, TNP | 1.628 | 15.460 | .8343 |
| J4P, TNS | 4.119 | 13.184 | .5353 |
| J4S, J5P | -1.427 | 9.323 | .7610 |
| J4S, J5S | -3.687 | 9.323 | .4330 |
| J4S, J6P | -8.179 | 9.087 | .0770 |
| J4S, J6S | -3.372 | 9.323 | .4732 |
| J4S, TNP | -.525 | 15.460 | .9462 |
| J4S, TNS | 1.966 | 13.184 | .7671 |
| J5P, J5S | -2.260 | 9.323 | .6304 |
| J5P, J6P | -6.751 | 9.087 | .1429 |
| J5P, J6S | -1.944 | 9.323 | .6788 |
| J5P, TNP | .902 | 15.460 | .9077 |
| J5P, TNS | 3.394 | 13.184 | .6094 |
| J5S, J6P | -4.492 | 9.087 | .3277 |
| J5S, J6S | .315 | 9.323 | .9464 |
| J5S, TNP | 3.162 | 15.460 | .6847 |
| J5S, TNS | 5.653 | 13.184 | .3954 |
| J6P, J6S | 4.807 | 9.087 | .2951 |
| J6P, TNP | 7.653 | 15.319 | .3225 |
| J6P, TNS | 10.145 | 13.019 | .1247 |
| J6S, TNP | 2.847 | 15.460 | .7146 |
| J6S, TNS | 5.338 | 13.184 | .4222 |
| TNP, TNS | 2.492 | 18.054 | .7840 |

FIG.65E

| | d.f. | Sum of Squares | Mean Square | F Value | p Value | Lambda | Power |
|---|---|---|---|---|---|---|---|
| Group | 11 | 417.530 | 37.957 | 1.770 | .0767 | 19.473 | .806 |
| Residue | 68 | 1458.032 | 21.442 | | | | |

Means Table for TCRBV11
Effect: Group

|  | Number | Mean | Standard Deviation (Dev.) | Standard Error (Err.) |
|---|---|---|---|---|
| CM+P | 6 | 16,209 | 6,803 | 2,777 |
| CM+S | 7 | 11,705 | 4,930 | 1,863 |
| J3P | 5 | 8,778 | 4,081 | 1,825 |
| J3S | 5 | 10,993 | 6,723 | 3,007 |
| J4P | 9 | 9,435 | 5,363 | 1,788 |
| J4S | 8 | 9,870 | 4,441 | 1,570 |
| J5P | 8 | 8,500 | 2,323 | .821 |
| J5S | 9 | 10,472 | 3,326 | 1,109 |
| J6P | 9 | 13,144 | 4,194 | 1,398 |
| J6S | 9 | 11,466 | 4,765 | 1,588 |
| TNP | 2 | 7,048 | 3,828 | 2,707 |
| TNS | 3 | 6,057 | 1,005 | .580 |

FIG. 65H(1)

| | Mean diff. | Critical diff. | p Value | |
|---|---|---|---|---|
| CM+P, CM+S | 4.504 | 5.141 | .0849 | |
| CM+P, J3P | 7.432 | 5.595 | .0100 | S |
| CM+P, J3S | 5.216 | 5.595 | .0672 | |
| CM+P, J4P | 6.775 | 4.870 | .0071 | S |
| CM+P, J4S | 6.339 | 4.990 | .0136 | S |
| CM+P, J5P | 7.709 | 4.990 | .0030 | S |
| CM+P, J5S | 5.737 | 4.870 | .0216 | S |
| CM+P, J6P | 3.066 | 4.870 | .2134 | |
| CM+P, J6S | 4.743 | 4.870 | .0561 | |
| CM+P, TNP | 9.162 | 7.544 | .0181 | S |
| CM+P, TNS | 10.152 | 6.534 | .0026 | S |
| CM+S, J3P | 2.927 | 5.410 | .2841 | |
| CM+S, J3S | .712 | 5.410 | .7937 | |
| CM+S, J4P | 2.270 | 4.657 | .3340 | |
| CM+S, J4S | 1.835 | 4.782 | .4466 | |
| CM+S, J5P | 3.205 | 4.782 | .1855 | |
| CM+S, J5S | 1.233 | 4.657 | .5990 | |
| CM+S, J6P | -1.439 | 4.657 | .5396 | |
| CM+S, J6S | .239 | 4.657 | .9187 | |
| CM+S, TNP | 4.657 | 7.409 | .2140 | |
| CM+S, TNS | 5.648 | 6.376 | .0816 | |
| J3P, J3S | -2.216 | 5.844 | .4519 | |
| J3P, J4P | -.657 | 5.154 | .8000 | |
| J3P, J4S | -1.093 | 5.268 | .6802 | |
| J3P, J5P | .278 | 5.268 | .9165 | |
| J3P, J5S | -1.695 | 5.154 | .5139 | |
| J3P, J6P | -4.366 | 5.154 | .0955 | |
| J3P, J6S | -2.688 | 5.154 | .3016 | |
| J3P, TNP | 1.730 | 7.731 | .6566 | |
| J3P, TNS | 2.720 | 6.748 | .4239 | |
| J3S, J4P | 1.559 | 5.154 | .5482 | |
| J3S, J4S | 1.123 | 5.268 | .6719 | |

FIG. 65H(2)

| | | | | |
|---|---|---|---|---|
| J3S, J5P | 2.493 | 5.268 | .3483 | |
| J3S, J5S | .521 | 5.154 | .8407 | |
| J3S, J6P | -2.150 | 5.154 | .4080 | |
| J3S, J6S | -.473 | 5.154 | .8553 | |
| J3S, TNP | 3.946 | 7.731 | .3121 | |
| J3S, TNS | 4.936 | 6.748 | .1490 | |
| J4P, J4S | -.436 | 4.490 | .8470 | |
| J4P, J5P | .935 | 4.490 | .6792 | |
| J4P, J5S | -1.038 | 4.356 | .6360 | |
| J4P, J6P | -3.709 | 4.356 | .0938 | |
| J4P, J6S | -2.031 | 4.356 | .3554 | |
| J4P, TNP | 2.387 | 7.223 | .5119 | |
| J4P, TNS | 3.377 | 6.160 | .2778 | |
| J4S, J5P | 1.370 | 4.620 | .5559 | |
| J4S, J5S | -.602 | 4.490 | .7899 | |
| J4S, J6P | -3.273 | 4.490 | .1503 | |
| J4S, J6S | -1.596 | 4.490 | .4807 | |
| J4S, TNP | 2.823 | 7.305 | .4433 | |
| J4S, TNS | 3.813 | 6.256 | .2280 | |
| J5P, J5S | -1.972 | 4.490 | .3838 | |
| J5P, J6P | -4.644 | 4.490 | .0428 | S |
| J5P, J6S | -2.966 | 4.490 | .1919 | |
| J5P, TNP | 1.452 | 7.305 | .6928 | |
| J5P, TNS | 2.443 | 6.256 | .4385 | |
| J5S, J6P | -2.671 | 4.356 | .2252 | |
| J5S, J6S | -.994 | 4.356 | .6504 | |
| J5S, TNP | 3.425 | 7.223 | .3475 | |
| J5S, TNS | 4.415 | 6.160 | .1572 | |
| J6P, J6S | 1.678 | 4.356 | .4448 | |
| J6P, TNP | 6.096 | 7.223 | .0968 | |
| J6P, TNS | 7.087 | 6.160 | .0248 | S |
| J6S, TNP | 4.418 | 7.223 | .2265 | |
| J6S, TNS | 5.409 | 6.160 | .0843 | |
| TNP, TNS | .990 | 8.435 | .8154 | |

FIG. 66A

| | d.f. | Sum of Squares | Mean Square | F Value | p Value | Lambda | Power |
|---|---|---|---|---|---|---|---|
| Group | 11 | 847.506 | 77.046 | 1.734 | .0835 | 19.078 | .797 |
| Residue | 70 | 3109.660 | 44.424 | | | | |

Means Table for TCRBV12
Effect: Group

| | Number | Mean | Standard Deviation (Dev.) | Standard Error (Err.) |
|---|---|---|---|---|
| CM+P | 5 | 31,373 | 13,011 | 5,819 |
| CM+S | 7 | 23,583 | 6,355 | 2,402 |
| J3P | 5 | 16,521 | 4,564 | 2,041 |
| J3S | 5 | 22,474 | 7,502 | 3,355 |
| J4P | 10 | 20,547 | 4,914 | 1,554 |
| J4S | 8 | 20,444 | 3,354 | 1,186 |
| J5P | 9 | 21,202 | 7,031 | 2,344 |
| J5S | 10 | 20,410 | 3,361 | 1,063 |
| J6P | 8 | 23,789 | 7,661 | 2,709 |
| J6S | 9 | 19,862 | 4,989 | 1,663 |
| TNP | 2 | 21,202 | 1,749 | 1,237 |
| TNS | 4 | 27,005 | 12,590 | 6,295 |

Chart of Interactions for TCRBV12
Effect: Group
Error bars: ± 1.96 Standard error(s)

FIG. 66D(1)

| | Mean diff. | Critical diff. | p Value | |
|---|---|---|---|---|
| CM+P, CM+S | 7.790 | 7.784 | .0498 | S |
| CM+P, J3P | 14.851 | 8.407 | .0008 | S |
| CM+P, J3S | 8.899 | 8.407 | .0383 | S |
| CM+P, J4P | 10.825 | 7.281 | .0041 | S |
| CM+P, J4S | 10.928 | 7.578 | .0053 | S |
| CM+P, J5P | 10.170 | 7.415 | .0079 | S |
| CM+P, J5S | 10.963 | 7.281 | .0037 | S |
| CM+P, J6P | 7.584 | 7.578 | .0498 | S |
| CM+P, J6S | 11.511 | 7.415 | .0028 | S |
| CM+P, TNP | 10.171 | 11.122 | .0724 | |
| CM+P, TNS | 4.368 | 8.917 | .3320 | |
| CM+S, J3P | 7.062 | 7.784 | .0747 | |
| CM+S, J3S | 1.109 | 7.784 | .7770 | |
| CM+S, J4P | 3.036 | 6.551 | .3586 | |
| CM+S, J4S | 3.139 | 6.880 | .3660 | |
| CM+S, J5P | 2.381 | 6.699 | .4808 | |
| CM+S, J5S | 3.173 | 6.551 | .3374 | |
| CM+S, J6P | -.206 | 6.880 | .9525 | |
| CM+S, J6S | 3.721 | 6.699 | .2718 | |
| CM+S, TNP | 2.381 | 10.658 | .6573 | |
| CM+S, TNS | -3.422 | 8.332 | .4155 | |
| J3P, J3S | -5.952 | 8.407 | .1624 | |
| J3P, J4P | -4.026 | 7.281 | .2739 | |
| J3P, J4S | -3.923 | 7.578 | .3054 | |
| J3P, J5P | -4.681 | 7.415 | .2122 | |
| J3P, J5S | -3.889 | 7.281 | .2904 | |
| J3P, J6P | -7.268 | 7.578 | .0599 | |
| J3P, J6S | -3.341 | 7.415 | .3719 | |
| J3P, TNP | -4.680 | 11.122 | .4041 | |
| J3P, TNS | -10.484 | 8.917 | .0219 | S |
| J3S, J4P | 1.926 | 7.281 | .5994 | |
| J3S, J4S | 2.029 | 7.578 | .5950 | |

FIG. 66D(2)

| | Mean diff. | Critical diff. | p Value |
|---|---|---|---|
| J3S, J5P | 1.271 | 7.415 | .7334 |
| J3S, J5S | 2.063 | 7.281 | .5737 |
| J3S, J6P | -1.316 | 7.578 | .7302 |
| J3S, J6S | 2.611 | 7.415 | .4847 |
| J3S, TNP | 1.272 | 11.122 | .8203 |
| J3S, TNS | -4.532 | 8.917 | .3143 |
| J4P, J4S | .103 | 6.305 | .9741 |
| J4P, J5P | -.655 | 6.108 | .8313 |
| J4P, J5S | .137 | 5.945 | .9634 |
| J4P, J6P | -3.242 | 6.305 | .3087 |
| J4P, J6S | .685 | 6.108 | .8236 |
| J4P, TNP | -.654 | 10.297 | .8995 |
| J4P, TNS | -6.458 | 7.864 | .1060 |
| J4S, J5P | -.758 | 6.459 | .8156 |
| J4S, J5S | .034 | 6.305 | .9914 |
| J4S, J6P | -3.345 | 6.647 | .3190 |
| J4S, J6S | .582 | 6.459 | .8579 |
| J4S, TNP | -.757 | 10.509 | .8861 |
| J4S, TNS | -6.561 | 8.140 | .1125 |
| J5P, J5S | .792 | 6.108 | .7966 |
| J5P, J6P | -2.587 | 6.459 | .4271 |
| J5P, J6S | 1.340 | 6.266 | .6710 |
| J5P, TNP | .001 | 10.392 | >.9999 |
| J5P, TNS | -5.803 | 7.988 | .1519 |
| J5S, J6P | -3.379 | 6.305 | .2888 |
| J5S, J6S | .548 | 6.108 | .8585 |
| J5S, TNP | -.792 | 10.297 | .8786 |
| J5S, TNS | -6.595 | 7.864 | .0989 |
| J6P, J6S | 3.927 | 6.459 | .2294 | S |
| J6P, TNP | 2.587 | 10.509 | .6249 |
| J6P, TNS | -3.216 | 8.140 | .4334 |
| J6S, TNP | -1.340 | 10.392 | .7979 |
| J6S, TNS | -7.143 | 7.988 | .0789 |
| TNP, TNS | -5.803 | 11.512 | .3182 |

FIG.66E

| | d.f. | Sum of Squares | Mean Square | F Value | p Value | Lambda | Power |
|---|---|---|---|---|---|---|---|
| Group | 11 | 569.770 | 51.797 | 1.658 | .1019 | 18.243 | .773 |
| Residue | 69 | 2155.053 | 31.233 | | | | |

Means Table for TCRBV13
Effect: Group

| | Number | Mean | Standard Deviation (Dev.) | Standard Error (Err.) |
|---|---|---|---|---|
| CM+P | 6 | 16,053 | 8,177 | 3,338 |
| CM+S | 7 | 9,454 | 2,239 | ,846 |
| J3P | 5 | 12,093 | 11,473 | 5,131 |
| J3S | 4 | 7,463 | 2,623 | 1,312 |
| J4P | 9 | 8,545 | 3,606 | 1,202 |
| J4S | 9 | 8,837 | 4,734 | 1,578 |
| J5P | 9 | 12,000 | 6,015 | 2,005 |
| J5S | 8 | 11,132 | 5,742 | 2,030 |
| J6P | 8 | 10,075 | 3,850 | 1,361 |
| J6S | 10 | 9,057 | 3,207 | 1,014 |
| TNP | 2 | 16,242 | 15,161 | 10,720 |
| TNS | 4 | 4,103 | 2,133 | 1,067 |

Chart of Interactions for TCRB13
Effect: Group
Error bars: ± 1.96 Standard error(s)

*FIG. 66H(1)*

|  | Mean diff. | Critical diff. | p Value |
|---|---|---|---|
| CM+P, CM+S | 6.600 | 6.203 | .0374 |
| CM+P, J3P | 3.960 | 6.751 | .2459 |
| CM+P, J3S | 8.590 | 7.197 | .0200 |
| CM+P, J4P | 7.508 | 5.876 | .0130 |
| CM+P, J4S | 7.216 | 5.876 | .0168 |
| CM+P, J5P | 4.053 | 5.876 | .1733 |
| CM+P, J5S | 4.921 | 6.021 | .1076 |
| CM+P, J6P | 5.978 | 6.021 | .0516 |
| CM+P, J6S | 6.996 | 5.757 | .0180 |
| CM+P, TNP | -.189 | 9.103 | .9670 |
| CM+P, TNS | 11.951 | 7.197 | .0015 |
| CM+S, J3P | -2.640 | 6.528 | .4227 |
| CM+S, J3S | 1.991 | 6.988 | .5717 |
| CM+S, J4P | .909 | 5.619 | .7479 |
| CM+S, J4S | .616 | 5.619 | .8274 |
| CM+S, J5P | -2.547 | 5.619 | .3690 |
| CM+S, J5S | -1.679 | 5.770 | .5635 |
| CM+S, J6P | -.621 | 5.770 | .8305 |
| CM+S, J6S | .396 | 5.494 | .8860 |
| CM+S, TNP | -6.789 | 8.939 | .1343 |
| CM+S, TNS | 5.351 | 6.988 | .1312 |
| J3P, J3S | 4.630 | 7.479 | .2210 |
| J3P, J4P | 3.548 | 6.219 | .2589 |
| J3P, J4S | 3.256 | 6.219 | .2999 |
| J3P, J5P | .093 | 6.219 | .9763 |
| J3P, J5S | .961 | 6.356 | .7639 |
| J3P, J6P | 2.018 | 6.356 | .5286 |
| J3P, J6S | 3.036 | 6.107 | .3247 |
| J3P, TNP | -4.149 | 9.328 | .3779 |
| J3P, TNS | 7.991 | 7.479 | .0366 |
| J3S, J4P | -1.082 | 6.700 | .7483 |

*FIG. 66H(2)*

|  |  | Mean diff. | Critical diff. | p Value |  |
|---|---|---|---|---|---|
|  | J3S, J4S | -1.374 | 6.700 | .6837 |  |
| S | J3S, J5P | -4.537 | 6.700 | .1811 |  |
|  | J3S, J5S | -3.669 | 6.827 | .2874 |  |
| S | J3S, J6P | -2.612 | 6.827 | .4479 |  |
| S | J3S, J6S | -1.594 | 6.596 | .6312 |  |
| S | J3S, TNP | -8.779 | 9.655 | .0740 |  |
|  | J3S, TNS | 3.360 | 7.884 | .3981 |  |
|  | J4P, J4S | -.292 | 5.256 | .9120 |  |
|  | J4P, J5P | -3.456 | 5.256 | .1940 |  |
|  | J4P, J5S | -2.588 | 5.417 | .3440 |  |
|  | J4P, J6P | -1.530 | 5.417 | .5749 |  |
| S | J4P, J6S | -.512 | 5.123 | .8425 |  |
|  | J4P, TNP | -7.698 | 8.716 | .0825 |  |
|  | J4P, TNS | 4.442 | 6.700 | .1903 |  |
|  | J4S, J5P | -3.163 | 5.256 | .2340 |  |
|  | J4S, J5S | -2.295 | 5.417 | .4009 |  |
|  | J4S, J6P | -1.238 | 5.417 | .6499 |  |
|  | J4S, J6S | -.220 | 5.123 | .9320 |  |
|  | J4S, TNP | -7.405 | 8.716 | .0946 |  |
|  | J4S, TNS | 4.735 | 6.700 | .1631 |  |
|  | J5P, J5S | .868 | 5.417 | .7502 |  |
|  | J5P, J6P | 1.925 | 5.417 | .4807 |  |
|  | J5P, J6S | 2.943 | 5.123 | .2557 |  |
|  | J5P, TNP | -4.242 | 8.716 | .3349 |  |
|  | J5P, TNS | 7.898 | 6.700 | .0215 | S |
|  | J5S, J6P | 1.057 | 5.574 | .7063 |  |
|  | J5S, J6S | 2.075 | 5.288 | .4364 |  |
|  | J5S, TNP | -5.110 | 8.814 | .2514 |  |
|  | J5S, TNS | 7.030 | 6.827 | .0438 | S |
|  | J6P, J6S | 1.018 | 5.288 | .7022 |  |
| S | J6P, TNP | -6.167 | 8.814 | .1672 |  |
|  | J6P, TNS | 5.973 | 6.827 | .0854 |  |
|  | J6S, TNP | -7.185 | 8.636 | .1015 |  |
|  | J6S, TNS | 4.955 | 6.596 | .1386 |  |
|  | TNP, TNS | 12.140 | 9.655 | .0145 | S |

FIG. 67A

| | d.f. | Sum of Squares | Mean Square | F Value | p Value | Lambda | Power |
|---|---|---|---|---|---|---|---|
| Group | 11 | 231.107 | 21.010 | 1.322 | .2319 | 14.537 | .647 |
| Residue | 68 | 1081.036 | 15.898 | | | | |

Means Table for TCRBV14
Effect: Group

| | Number | Mean | Standard Deviation (Dev.) | Standard Error (Err.) |
|---|---|---|---|---|
| CM+P | 6 | 10,551 | 5,149 | 2,102 |
| CM+S | 7 | 7,043 | 1,990 | ,752 |
| J3P | 5 | 4,884 | 1,269 | ,567 |
| J3S | 4 | 4,908 | 2,004 | 1,002 |
| J4P | 9 | 6,371 | 3,227 | 1,076 |
| J4S | 9 | 5,163 | 2,562 | ,854 |
| J5P | 8 | 6,045 | 1,246 | ,440 |
| J5S | 9 | 5,140 | 1,601 | ,534 |
| J6P | 9 | 8,980 | 8,696 | 2,899 |
| J6S | 8 | 7,619 | 4,177 | 1,477 |
| TNP | 2 | 5,030 | ,384 | ,271 |
| TNS | 4 | 5,486 | 1,990 | ,995 |

Chart of Interactions for TCRBV14
Effect: Group
Error bars: ± 1.96 Standard error(s)

FIG. 67D(1)

|  | Mean diff. | Critical diff. | p Value |
|---|---|---|---|
| CM+P, CM+S | 3.508 | 4.426 | .1184 |
| CM+P, J3P | 5.668 | 4.818 | .0218 |
| CM+P, J3S | 5.843 | 5.136 | .0318 |
| CM+P, J4P | 4.180 | 4.193 | .0507 |
| CM+P, J4S | 5.388 | 4.193 | .0126 |
| CM+P, J5P | 4.506 | 4.297 | .0401 |
| CM+P, J5S | 5.411 | 4.193 | .0122 |
| CM+P, J6P | 1.571 | 4.193 | .4573 |
| CM+P, J6S | 2.932 | 4.297 | .1778 |
| CM+P, TNP | 5.521 | 6.496 | .0945 |
| CM+P, TNS | 5.066 | 5.136 | .0631 |
| CM+S, J3P | 2.160 | 4.659 | .3582 |
| CM+S, J3S | 2.135 | 4.987 | .3959 |
| CM+S, J4P | .673 | 4.010 | .7389 |
| CM+S, J4S | 1.880 | 4.010 | .3527 |
| CM+S, J5P | .998 | 4.118 | .6300 |
| CM+S, J5S | 1.903 | 4.010 | .3469 |
| CM+S, J6P | -1.937 | 4.010 | .3385 |
| CM+S, J6S | -.576 | 4.118 | .7810 |
| CM+S, TNP | 2.013 | 6.379 | .5310 |
| CM+S, TNS | 1.558 | 4.987 | .5351 |
| J3P, J3S | -.025 | 5.337 | .9926 |
| J3P, J4P | -1.487 | 4.438 | .5059 |
| J3P, J4S | -.280 | 4.438 | .9003 |
| J3P, J5P | -1.161 | 4.536 | .6111 |
| J3P, J5S | -.256 | 4.438 | .9085 |
| J3P, J6P | -4.097 | 4.438 | .0698 |
| J3P, J6S | -2.736 | 4.536 | .2329 |
| J3P, TNP | -.147 | 6.657 | .9651 |
| J3P, TNS | -.602 | 5.337 | .8226 |
| J3S, J4P | -1.462 | 4.781 | .5436 |
| J3S, J4S | -.255 | 4.781 | .9156 |
| J3S, J5P | -1.137 | 4.872 | .6431 |

FIG. 67D(2)

|  | Mean diff. | Critical diff. | p Value |  |
|---|---|---|---|---|
| J3S, J5S | -.232 | 4.781 | .9233 |  |
| J3S, J6P | -4.072 | 4.781 | .0938 |  |
| J3S, J6S | -2.711 | 4.872 | .2708 |  |
| J3S, TNP | -.122 | 6.890 | .9720 |  |
| J3S, TNS | -.577 | 5.626 | .8384 |  |
| J4P, J4S | 1.208 | 3.751 | .5227 |  |
| J4P, J5P | .326 | 3.866 | .8669 |  |
| J4P, J5S | 1.231 | 3.751 | .5148 |  |
| J4P, J6P | -2.609 | 3.751 | .1696 |  |
| J4P, J6S | -1.248 | 3.866 | .5215 |  |
| J4P, TNP | 1.341 | 6.220 | .6685 |  |
| J4P, TNS | .885 | 4.781 | .7129 |  |
| J4S, J5P | -.882 | 3.866 | .6505 |  |
| J4S, J5S | .023 | 3.751 | .9902 |  |
| J4S, J6P | -3.817 | 3.751 | .0462 | S |
| J4S, J6S | -2.456 | 3.866 | .2092 |  |
| J4S, TNP | .133 | 6.220 | .9661 |  |
| J4S, TNS | -.322 | 4.781 | .8934 |  |
| J5P, J5S | .905 | 3.866 | .6420 |  |
| J5P, J6P | -2.935 | 3.866 | .1344 |  |
| J5P, J6S | -1.574 | 3.978 | .4324 |  |
| J5P, TNP | 1.015 | 6.290 | .7485 |  |
| J5P, TNS | .559 | 4.872 | .8194 |  |
| J5S, J6P | -3.840 | 3.751 | .0449 | S |
| J5S, J6S | -2.479 | 3.866 | .2050 |  |
| J5S, TNP | .110 | 6.220 | .9720 |  |
| J5S, TNS | -.345 | 4.781 | .8858 |  |
| J6P, J6S | 1.361 | 3.866 | .4848 |  |
| J6P, TNP | 3.950 | 6.220 | .2094 |  |
| J6P, TNS | 3.495 | 4.781 | .1493 |  |
| J6S, TNP | 2.589 | 6.290 | .4143 |  |
| J6S, TNS | 2.134 | 4.872 | .3852 |  |
| TNP, TNS | -.455 | 6.890 | .8955 |  |

S markers on left table: CM+P, J3P; CM+P, J3S; CM+P, J4S; CM+P, J5P; CM+P, J5S (marked S)

FIG. 67E

| | d.f. | Sum of Squares | Mean Square | F Value | p Value | Lambda | Power |
|---|---|---|---|---|---|---|---|
| Group | 11 | 475.725 | 43.248 | 2.120 | .0299 | 23.320 | .888 |
| Residue | 69 | 1407.598 | 20.400 | | | | |

Means Table for TCRBV15
Effect: Group

| | Number | Mean | Standard Deviation (Dev.) | Standard Error (Err.) |
|---|---|---|---|---|
| CM+P | 6 | 12.587 | 5.913 | 2.414 |
| CM+S | 7 | 6.161 | 3.839 | 1.451 |
| J3P | 5 | 6.724 | 2.971 | 1.328 |
| J3S | 4 | 3.964 | .921 | .460 |
| J4P | 10 | 5.431 | 1.557 | .492 |
| J4S | 9 | 5.088 | 2.335 | .778 |
| J5P | 7 | 5.730 | 1.647 | .622 |
| J5S | 10 | 5.626 | 1.858 | .587 |
| J6P | 7 | 9.920 | 8.566 | 3.238 |
| J6S | 10 | 9.571 | 7.765 | 2.456 |
| TNP | 2 | 4.499 | 1.572 | 1.112 |
| TNS | 4 | 4.683 | 1.664 | .832 |

Chart of Interactions for TCRBV15
Effect: Group
Error bars: ± 1.96 Standard error(s)

FIG. 67H(1)

| | Mean diff. | Critical diff. | p Value | |
|---|---|---|---|---|
| CM+P, CM+S | 6.426 | 5.013 | .0128 | S |
| CM+P, J3P | 5.863 | 5.456 | .0356 | S |
| CM+P, J3S | 8.623 | 5.816 | .0042 | S |
| CM+P, J4P | 7.156 | 4.653 | .0031 | S |
| CM+P, J4S | 7.498 | 4.749 | .0024 | S |
| CM+P, J5P | 6.857 | 5.013 | .0061 | S |
| CM+P, J5S | 6.961 | 4.653 | .0039 | S |
| CM+P, J6P | 2.667 | 5.013 | .2922 | |
| CM+P, J6S | 3.018 | 4.653 | .2003 | |
| CM+P, TNP | 8.088 | 7.357 | .0317 | S |
| CM+P, TNS | 7.904 | 5.816 | .0085 | S |
| CM+S, J3P | -.562 | 5.276 | .8322 | |
| CM+S, J3S | 2.198 | 5.648 | .4403 | |
| CM+S, J4P | .730 | 4.440 | .7439 | |
| CM+S, J4S | 1.073 | 4.541 | .6388 | |
| CM+S, J5P | .431 | 4.816 | .8587 | |
| CM+S, J5S | .535 | 4.440 | .8107 | |
| CM+S, J6P | -3.758 | 4.816 | .1241 | |
| CM+S, J6S | -3.409 | 4.440 | .1302 | |
| CM+S, TNP | 1.662 | 7.224 | .6477 | |
| CM+S, TNS | 1.478 | 5.648 | .6033 | |
| J3P, J3S | 2.760 | 6.044 | .3655 | |
| J3P, J4P | 1.292 | 4.935 | .6030 | |
| J3P, J4S | 1.635 | 5.026 | .5184 | |
| J3P, J5P | .994 | 5.276 | .7082 | |
| J3P, J5S | 1.098 | 4.935 | .6587 | |
| J3P, J6P | -3.196 | 5.276 | .2310 | |
| J3P, J6S | -2.847 | 4.935 | .2538 | |
| J3P, TNP | 2.225 | 7.539 | .5580 | |
| J3P, TNS | 2.041 | 6.044 | .5029 | |
| J3S, J4P | -1.468 | 5.331 | .5846 | |
| J3S, J4S | -1.125 | 5.415 | .6799 | |

FIG. 67H(2)

| | Mean diff. | Critical diff. | p Value | |
|---|---|---|---|---|
| J3S, J5P | -1.766 | 5.648 | .5348 | |
| J3S, J5S | -1.662 | 5.331 | .5359 | |
| J3S, J6P | -5.956 | 5.648 | .0390 | S |
| J3S, J6S | -5.607 | 5.331 | .0395 | S |
| J3S, TNP | -.535 | 7.803 | .8915 | |
| J3S, TNS | -.719 | 6.371 | .8224 | |
| J4P, J4S | .343 | 4.140 | .8692 | |
| J4P, J5P | -.299 | 4.440 | .8937 | |
| J4P, J5S | -.195 | 4.030 | .9234 | |
| J4P, J6P | -4.488 | 4.440 | .0476 | S |
| J4P, J6S | -4.139 | 4.030 | .0442 | S |
| J4P, TNP | .932 | 6.979 | .7907 | |
| J4P, TNS | .748 | 5.331 | .7803 | |
| J4S, J5P | -.642 | 4.541 | .7789 | |
| J4S, J5S | -.538 | 4.140 | .7963 | |
| J4S, J6P | -4.831 | 4.541 | .0374 | S |
| J4S, J6S | -4.482 | 4.140 | .0343 | S |
| J4S, TNP | .589 | 7.044 | .8680 | |
| J4S, TNS | .405 | 5.415 | .8818 | |
| J5P, J5S | .104 | 4.440 | .9630 | |
| J5P, J6P | -4.190 | 4.816 | .0871 | |
| J5P, J6S | -3.841 | 4.440 | .0889 | |
| J5P, TNP | 1.231 | 7.224 | .7350 | |
| J5P, TNS | 1.047 | 5.648 | .7127 | |
| J5S, J6P | -4.293 | 4.440 | .0579 | |
| J5S, J6S | -3.944 | 4.030 | .0549 | |
| J5S, TNP | 1.127 | 6.979 | .7463 | |
| J5S, TNS | .943 | 5.331 | .7252 | |
| J6P, J6S | .349 | 4.440 | .8759 | |
| J6P, TNP | 5.420 | 7.224 | .1390 | |
| J6P, TNS | 5.236 | 5.648 | .0685 | |
| J6S, TNP | 5.071 | 6.979 | .1517 | |
| J6S, TNS | 4.887 | 5.331 | .0717 | |
| TNP, TNS | -.184 | 7.803 | .9625 | |

FIG. 68A

| d.f. | Sum of Squares | Mean Square | F Value | p Value | Lambda | Power |
|---|---|---|---|---|---|---|
| Group | 11 | 1108.367 | 100.761 | 2.419 | .0129 | 26.609 | .934 |
| Residue | 71 | 2957.431 | 41.654 | | | | |

Means Table for TCRBV16
Effect: Group

| | Number | Mean | Standard Deviation (Dev.) | Standard Error (Err.) |
|---|---|---|---|---|
| CM+P | 6 | 17.638 | 6.182 | 2.524 |
| CM+S | 7 | 9.511 | 1.933 | .731 |
| J3P | 5 | 6.405 | 2.491 | 1.114 |
| J3S | 4 | 6.253 | 1.812 | .906 |
| J4P | 9 | 6.565 | 1.382 | .461 |
| J4S | 9 | 5.835 | 1.449 | .483 |
| J5P | 9 | 8.828 | 4.243 | 1.414 |
| J5S | 10 | 11.179 | 11.924 | 3.771 |
| J6P | 9 | 13.766 | 7.046 | 2.349 |
| J6S | 10 | 13.173 | 9.708 | 3.070 |
| TNP | 2 | 5.439 | 1.203 | .851 |
| TNS | 3 | 4.811 | 1.861 | 1.075 |

FIG. 68D(2)

| | Mean diff. | Critical diff. | p Value | |
|---|---|---|---|---|
| CM+P, CM+S | 8.127 | 7.160 | .0267 | S |
| CM+P, J3P | 11.232 | 7.792 | .0053 | S |
| CM+P, J3S | 11.384 | 8.307 | .0079 | S |
| CM+P, J4P | 11.073 | 6.782 | .0017 | S |
| CM+P, J4S | 11.803 | 6.782 | .0009 | S |
| CM+P, J5P | 8.810 | 6.782 | .0116 | S |
| CM+P, J5S | 6.459 | 6.645 | .0566 | |
| CM+P, J6P | 3.872 | 6.782 | .2589 | |
| CM+P, J6S | 4.465 | 6.645 | .1846 | |
| CM+P, TNP | 12.199 | 10.507 | .0235 | S |
| CM+P, TNS | 12.826 | 9.100 | .0064 | S |
| CM+S, J3P | 3.105 | 7.535 | .4140 | |
| CM+S, J3S | 3.257 | 8.066 | .4234 | |
| CM+S, J4P | 2.946 | 6.485 | .3682 | |
| CM+S, J4S | 3.676 | 6.485 | .2622 | |
| CM+S, J5P | .683 | 6.485 | .8343 | |
| CM+S, J5S | -1.669 | 6.342 | .6015 | |
| CM+S, J6P | -4.256 | 6.485 | .1950 | |
| CM+S, J6S | -3.662 | 6.342 | .2534 | |
| CM+S, TNP | 4.072 | 10.318 | .4340 | |
| CM+S, TNS | 4.699 | 8.880 | .2949 | |
| J3P, J3S | .152 | 8.633 | .9721 | |
| J3P, J4P | -.160 | 7.178 | .9647 | |
| J3P, J4S | .571 | 7.178 | .8745 | |
| J3P, J5P | -2.422 | 7.178 | .5032 | |
| J3P, J5S | -4.774 | 7.049 | .1812 | |
| J3P, J6P | -7.361 | 7.178 | .0446 | S |
| J3P, J6S | -6.768 | 7.049 | .0596 | |
| J3P, TNP | .966 | 10.767 | .8585 | |
| J3P, TNS | 1.594 | 9.398 | .7362 | |
| J3S, J4P | -.312 | 7.733 | .9362 | |
| J3S, J4S | .419 | 7.733 | .9143 | |
| J3S, J5P | -2.574 | 7.733 | .5090 | |

| | Mean diff. | Critical diff. | p Value | |
|---|---|---|---|---|
| J3S, J5S | -4.926 | 7.613 | .2012 | |
| J3S, J6P | -7.513 | 7.733 | .0567 | |
| J3S, J6S | -6.920 | 7.613 | .0742 | |
| J3S, TNP | .814 | 11.145 | .8846 | |
| J3S, TNS | 1.442 | 9.829 | .7708 | |
| J4P, J4S | .730 | 6.066 | .8110 | |
| J4P, J5P | -2.263 | 6.066 | .4595 | |
| J4P, J5S | -4.614 | 5.913 | .1242 | |
| J4P, J6P | -7.201 | 6.066 | .0207 | S |
| J4P, J6S | -6.608 | 5.913 | .0290 | S |
| J4P, TNP | 1.126 | 10.060 | .8240 | |
| J4P, TNS | 1.754 | 8.579 | .6848 | |
| J4S, J5P | -2.993 | 6.066 | .3286 | |
| J4S, J5S | -5.345 | 5.913 | .0757 | |
| J4S, J6P | -7.932 | 6.066 | .0111 | S |
| J4S, J6S | -7.338 | 5.913 | .0157 | S |
| J4S, TNP | .396 | 10.060 | .9377 | |
| J4S, TNS | 1.023 | 8.579 | .8127 | |
| J5P, J5S | -2.351 | 5.913 | .4304 | |
| J5P, J6P | -4.938 | 6.066 | .1090 | |
| J5P, J6S | -4.345 | 5.913 | .1473 | |
| J5P, TNP | 3.389 | 10.060 | .5040 | |
| J5P, TNS | 4.016 | 8.579 | .3538 | |
| J5S, J6P | -2.587 | 5.913 | .3859 | |
| J5S, J6S | -1.994 | 5.755 | .4920 | |
| J5S, TNP | 6.740 | 9.968 | .2547 | |
| J5S, TNS | 6.368 | 8.471 | .1384 | |
| J6P, J6S | .593 | 5.913 | .8420 | |
| J6P, TNP | 8.327 | 10.060 | .1033 | |
| J6P, TNS | 8.955 | 8.579 | .0410 | S |
| J6S, TNP | 7.734 | 9.968 | .1263 | |
| J6S, TNS | 8.361 | 8.471 | .0530 | |
| TNP, TNS | .628 | 11.748 | .9155 | |

| | d.f. | Sum of Squares | Mean Square | F Value | p Value | Lambda | Power |
|---|---|---|---|---|---|---|---|
| Group | 11 | 1366.839 | 124.258 | 2.439 | .0125 | 26.832 | .935 |
| Residue | 68 | 3463.904 | 50.940 | | | | |

Means Table for TCRBV18
Effect: Group

| | Number | Mean | Standard Deviation (Dev.) | Standard Error (Err.) |
|---|---|---|---|---|
| CM+P | 5 | 20,923 | 14,298 | 6,394 |
| CM+S | 7 | 12,460 | 4,456 | 1,684 |
| J3P | 4 | 10,425 | 4,718 | 2,359 |
| J3S | 4 | 11,167 | 3,982 | 1,991 |
| J4P | 8 | 9,540 | 3,210 | 1,135 |
| J4S | 9 | 8,739 | 3,488 | 1,163 |
| J5P | 9 | 12,342 | 4,375 | 1,458 |
| J5S | 10 | 13,509 | 9,823 | 3,106 |
| J6P | 8 | 20,235 | 9,202 | 3,253 |
| J6S | 10 | 17,530 | 7,806 | 2,468 |
| TNP | 2 | 8,387 | 2,214 | 1,566 |
| TNS | 4 | 8,319 | 5,022 | 2,511 |

Chart of Interactions for TCRBV18
Effect: Group
Error bars: ± 1.96 Standard error(s)

|  | Mean diff. | Critical diff. | p Value |  |
|---|---|---|---|---|
| CM+P, CM+S | 8.463 | 8.339 | .0468 | S |
| CM+P, J3P | 10.498 | 9.554 | .0318 | S |
| CM+P, J3S | 9.756 | 9.554 | .0455 | S |
| CM+P, J4P | 11.383 | 8.119 | .0067 | S |
| CM+P, J4S | 12.184 | 7.944 | .0032 | S |
| CM+P, J5P | 8.582 | 7.944 | .0346 | S |
| CM+P, J5S | 7.414 | 7.801 | .0621 |  |
| CM+P, J6P | .689 | 8.119 | .8661 |  |
| CM+P, J6S | 3.393 | 7.801 | .3884 |  |
| CM+P, TNP | 12.536 | 11.916 | .0395 | S |
| CM+P, TNS | 12.604 | 9.554 | .0105 | S |
| CM+S, J3P | 2.035 | 8.927 | .6506 |  |
| CM+S, J3S | 1.293 | 8.927 | .7734 |  |
| CM+S, J4P | 2.920 | 7.371 | .4320 |  |
| CM+S, J4S | 3.721 | 7.177 | .3045 |  |
| CM+S, J5P | .119 | 7.177 | .9738 |  |
| CM+S, J5S | -1.049 | 7.019 | .7665 |  |
| CM+S, J6P | -7.775 | 7.371 | .0390 | S |
| CM+S, J6S | -5.070 | 7.019 | .1541 |  |
| CM+S, TNP | 4.073 | 11.419 | .4790 |  |
| CM+S, TNS | 4.141 | 8.927 | .3579 |  |
| J3P, J3S | -.742 | 10.071 | .8836 |  |
| J3P, J4P | .884 | 8.721 | .8402 |  |
| J3P, J4S | 1.686 | 8.558 | .6955 |  |
| J3P, J5P | -1.917 | 8.558 | .6564 |  |
| J3P, J5S | -3.084 | 8.426 | .4677 |  |
| J3P, J6P | -9.810 | 8.721 | .0281 | S |
| J3P, J6S | -7.105 | 8.426 | .0970 |  |
| J3P, TNP | 2.038 | 12.334 | .7426 |  |
| J3P, TNS | 2.106 | 10.071 | .6778 |  |
| J3S, J4P | 1.626 | 8.721 | .7110 |  |
| J3S, J4S | 2.428 | 8.558 | .5732 |  |

|  | Mean diff. | Critical diff. | p Value |  |
|---|---|---|---|---|
| J3S, J5P | -1.175 | 8.558 | .7850 |  |
| J3S, J5S | -2.342 | 8.426 | .5810 |  |
| J3S, J6P | -9.068 | 8.721 | .0418 | S |
| J3S, J6S | -6.363 | 8.426 | .1365 |  |
| J3S, TNP | 2.780 | 12.334 | .6543 |  |
| J3S, TNS | 2.848 | 10.071 | .5744 |  |
| J4P, J4S | .801 | 6.920 | .8180 |  |
| J4P, J5P | -2.801 | 6.920 | .4221 |  |
| J4P, J5S | -3.968 | 6.756 | .2452 |  |
| J4P, J6P | -10.694 | 7.121 | .0038 | S |
| J4P, J6S | -7.989 | 6.756 | .0212 | S |
| J4P, TNP | 1.153 | 11.259 | .8386 |  |
| J4P, TNS | 1.221 | 8.721 | .7807 |  |
| J4S, J5P | -3.602 | 6.714 | .2881 |  |
| J4S, J5S | -4.770 | 6.544 | .1504 |  |
| J4S, J6P | -11.496 | 6.920 | .0015 | S |
| J4S, J6S | -8.791 | 6.544 | .0092 | S |
| J4S, TNP | .352 | 11.134 | .9499 |  |
| J4S, TNS | .420 | 8.558 | .9223 |  |
| J5P, J5S | -1.167 | 6.544 | .7230 |  |
| J5P, J6P | -7.893 | 6.920 | .0260 | S |
| J5P, J6S | -5.188 | 6.544 | .1183 |  |
| J5P, TNP | 3.955 | 11.134 | .4809 |  |
| J5P, TNS | 4.023 | 8.558 | .3516 |  |
| J5S, J6P | -6.726 | 6.756 | .0510 |  |
| J5S, J6S | -4.021 | 6.369 | .2121 |  |
| J5S, TNP | 5.122 | 11.032 | .3575 |  |
| J5S, TNS | 5.190 | 8.426 | .2233 |  |
| J6P, J6S | 2.705 | 6.756 | .4271 |  |
| J6P, TNP | 11.848 | 11.259 | .0395 | S |
| J6P, TNS | 11.916 | 8.721 | .0081 | S |
| J6S, TNP | 9.143 | 11.032 | .1028 |  |
| J6S, TNS | 9.211 | 8.426 | .0326 | S |
| TNP, TNS | .068 | 12.334 | .9913 |  |

FIG. 69A

| | d.f. | Sum of Squares | Mean Square | F Value | p Value | Lambda | Power |
|---|---|---|---|---|---|---|---|
| Group | 11 | 1340.545 | 121.868 | 2.791 | .0044 | 30.703 | .968 |
| Residue | 72 | 3143.624 | 43.661 | | | | |

Means Table for TCRBV20
Effect: Group

| | Number | Mean | Standard Deviation (Dev.) | Standard Error (Err.) |
|---|---|---|---|---|
| CM+P | 5 | 27.772 | 16.719 | 7.477 |
| CM+S | 7 | 11.353 | 4.473 | 1.690 |
| J3P | 5 | 10.625 | .982 | .439 |
| J3S | 4 | 11.679 | 3.970 | 1.985 |
| J4P | 10 | 13.862 | 5.854 | 1.851 |
| J4S | 9 | 11.847 | 3.898 | 1.299 |
| J5P | 9 | 10.533 | 4.189 | 1.396 |
| J5S | 10 | 11.711 | 5.365 | 1.697 |
| J6P | 9 | 15.138 | 7.611 | 2.537 |
| J6S | 10 | 13.643 | 7.756 | 2.453 |
| TNP | 2 | 11.871 | 2.021 | 1.429 |
| TNS | 4 | 9.130 | 2.304 | 1.152 |

Chart of Interactions for TCRBV20
Effect: Group
Error bars: ± 1.96 Standard error(s)

FIG. 69D(1)

|  | Mean diff. | Critical diff. | p Value |
|---|---|---|---|
| CM+P, CM+S | 16.419 | 7.713 | <.0001 |
| CM+P, J3P | 17.147 | 8.331 | .0001 |
| CM+P, J3S | 16.092 | 8.836 | .0005 |
| CM+P, J4P | 13.910 | 7.215 | .0003 |
| CM+P, J4S | 15.924 | 7.347 | <.0001 |
| CM+P, J5P | 17.238 | 7.347 | <.0001 |
| CM+P, J5S | 16.061 | 7.215 | <.0001 |
| CM+P, J6P | 12.634 | 7.347 | .0010 |
| CM+P, J6S | 14.128 | 7.215 | .0002 |
| CM+P, TNP | 15.901 | 11.021 | .0053 |
| CM+P, TNS | 18.642 | 8.836 | <.0001 |
| CM+S, J3P | .728 | 7.713 | .8513 |
| CM+S, J3S | -.326 | 8.256 | .9374 |
| CM+S, J4P | -2.509 | 6.491 | .4436 |
| CM+S, J4S | -.495 | 6.638 | .8823 |
| CM+S, J5P | .819 | 6.638 | .8063 |
| CM+S, J5S | -.358 | 6.491 | .9128 |
| CM+S, J6P | -3.785 | 6.638 | .2594 |
| CM+S, J6S | -2.291 | 6.491 | .4840 |
| CM+S, TNP | -.518 | 10.561 | .9224 |
| CM+S, TNS | 2.223 | 8.256 | .5931 |
| J3P, J3S | -1.054 | 8.836 | .8126 |
| J3P, J4P | -3.237 | 7.215 | .3741 |
| J3P, J4S | -1.223 | 7.347 | .7410 |
| J3P, J5P | .091 | 7.347 | .9803 |
| J3P, J5S | -1.086 | 7.215 | .7650 |
| J3P, J6P | -4.513 | 7.347 | .2247 |
| J3P, J6S | -3.019 | 7.215 | .4070 |
| J3P, TNP | -1.246 | 11.021 | .8223 |
| J3P, TNS | 1.495 | 8.836 | .7369 |
| J3S, J4P | -2.183 | 7.793 | .5783 |
| J3S, J4S | -.168 | 7.915 | .9663 |
| J3S, J5P | 1.146 | 7.915 | .7738 |

FIG. 69D(2)

|  | Mean diff. | Critical diff. | p Value |
|---|---|---|---|
| J3S, J5S | -.032 | 7.793 | .9936 |
| J3S, J6P | -3.459 | 7.915 | .3866 |
| J3S, J6S | -1.964 | 7.793 | .6169 |
| J3S, TNP | -.192 | 11.407 | .9734 |
| J3S, TNS | 2.550 | 9.314 | .5870 |
| J4P, J4S | 2.014 | 6.052 | .5091 |
| J4P, J5P | 3.328 | 6.052 | .2766 |
| J4P, J5S | 2.151 | 5.891 | .4690 |
| J4P, J6P | -1.276 | 6.052 | .6755 |
| J4P, J6S | .218 | 5.891 | .9413 |
| J4P, TNP | 1.991 | 10.203 | .6984 |
| J4P, TNS | 4.732 | 7.793 | .2300 |
| J4S, J5P | 1.314 | 6.209 | .6744 |
| J4S, J5S | .137 | 6.052 | .9642 |
| J4S, J6P | -3.290 | 6.209 | .2943 |
| J4S, J6S | -1.796 | 6.052 | .5560 |
| J4S, TNP | -.023 | 10.297 | .9964 |
| J4S, TNS | 2.718 | 7.915 | .4959 |
| J5P, J5S | -1.177 | 6.052 | .6993 |
| J5P, J6P | -4.604 | 6.209 | .1437 |
| J5P, J6S | -3.110 | 6.052 | .3091 |
| J5P, TNP | -1.337 | 10.297 | .7964 |
| J5P, TNS | 1.404 | 7.915 | .7247 |
| J5S, J6P | -3.427 | 6.052 | .2627 |
| J5S, J6S | -1.933 | 5.891 | .5152 |
| J5S, TNP | -.160 | 10.203 | .9751 |
| J5S, TNS | 2.581 | 7.793 | .5112 |
| J6P, J6S | 1.494 | 6.052 | .6241 |
| J6P, TNP | 3.267 | 10.297 | .5291 |
| J6P, TNS | 6.008 | 7.915 | .1346 |
| J6S, TNP | 1.773 | 10.203 | .7301 |
| J6S, TNS | 4.514 | 7.793 | .2520 |
| TNP, TNS | 2.741 | 11.407 | .6334 |

FIG. 70A

| | d.f. | Sum of Squares | Mean Square | F Value | p Value | Lambda | Power |
|---|---|---|---|---|---|---|---|
| Group | 5 | 432.969 | 86.594 | 2.011 | .0866 | 10.054 | .640 |
| Residue | 78 | 3272.848 | 43.064 | | | | |

Means Table for TCRBV01
Effect: Group

| | Number | Mean | Standard Deviation (Dev.) | Standard Error (Err.) |
|---|---|---|---|---|
| CM+P | 13 | 11,087 | 8,348 | 2,315 |
| CM+S | 17 | 11,091 | 8,232 | 1,996 |
| J5P | 9 | 7,802 | 9,117 | 3,039 |
| J5S | 10 | 6,450 | 1,743 | .551 |
| TNP | 16 | 5,478 | 1,746 | .436 |
| TNS | 17 | 6,828 | 6,196 | 1,503 |

Chart of Interactions for TCRBV01
Effect: Group
Error bars: ± 1.96 Standard error(s)

FIG. 70D

|  | Mean diff. | Critical diff. | p Value |  |
|---|---|---|---|---|
| CM+P, CM+S | -.003 | 4.815 | .9989 |  |
| CM+P, J5P | 3.285 | 5.668 | .2520 |  |
| CM+P, J5S | 4.637 | 5.498 | .0971 |  |
| CM+P, TNP | 5.609 | 4.880 | .0248 | S |
| CM+P, TNS | 4.259 | 4.815 | .0822 |  |
| CM+S, J5P | 3.288 | 5.388 | .2279 |  |
| CM+S, J5S | 4.641 | 5.209 | .0800 |  |
| CM+S, TNP | 5.613 | 4.552 | .0164 | S |
| CM+S, TNS | 4.262 | 4.483 | .0621 |  |
| J5P, J5S | 1.352 | 6.005 | .6550 |  |
| J5P, TNP | 2.324 | 5.446 | .3979 |  |
| J5P, TNS | .974 | 5.388 | .7197 |  |
| J5S, TNP | .972 | 5.269 | .7143 |  |
| J5S, TNS | -.378 | 5.209 | .8854 |  |
| TNP, TNS | -1.350 | 4.552 | .5565 |  |

FIG. 70E

ANOVA (Analysis of Variance) Table for TCRBV02

| | d.f. | Sum of Squares | Mean Square | F Value | p Value | Lambda | Power |
|---|---|---|---|---|---|---|---|
| Group | 5 | 2280.845 | 452.169 | 12.349 | <.0001 | 61.745 | 1.000 |
| Residue | 78 | 2856.039 | 36.616 | | | | |

Means Table for TCRBV02
Effect: Group

|  | Number | Mean | Standard Deviation (Dev.) | Standard Error (Err.) |
|---|---|---|---|---|
| CM+P | 16 | 18,682 | 11,485 | 2,871 |
| CM+S | 17 | 12,334 | 4,730 | 1,147 |
| J5P | 9 | 6,816 | 3,816 | 1,272 |
| J5S | 10 | 8,401 | 4,782 | 1,512 |
| TNP | 16 | 5,498 | 2,944 | .736 |
| TNS | 16 | 4,234 | 2,115 | .529 |

$CM^+$ contains J6

TN contains J3, J4

PLSD Fisher's Test for TCRBV02
Group effect
Significance level: 5%

|  | Mean diff. | Critical diff. | p Value | |
|---|---|---|---|---|
| CM+P, CM+S | 6.348 | 4.196 | .0035 | S |
| CM+P, J5P | 11.866 | 5.020 | <.0001 | S |
| CM+P, J5S | 10.282 | 4.856 | <.0001 | S |
| CM+P, TNP | 13.184 | 4.259 | <.0001 | S |
| CM+P, TNS | 14.449 | 4.259 | <.0001 | S |
| CM+S, J5P | 5.518 | 4.966 | .0299 | S |
| CM+S, J5S | 3.933 | 4.801 | .1069 | |
| CM+S, TNP | 6.836 | 4.196 | .0017 | S |
| CM+S, TNS | 8.100 | 4.196 | .0002 | S |
| J5P, J5S | -1.585 | 5.535 | .5703 | |
| J5P, TNP | 1.318 | 5.020 | .6027 | |
| J5P, TNS | 2.582 | 5.020 | .3090 | |
| J5S, TNP | 2.903 | 4.856 | .2377 | |
| J5S, TNS | 4.167 | 4.856 | .0916 | |
| TNP, TNS | 1.264 | 4.259 | .5562 | |

| | d.f. | Sum of Squares | Mean Square | F Value | p Value | Lambda | Power |
|---|---|---|---|---|---|---|---|
| Group | 5 | 1527.689 | 305.538 | 9.429 | <.0001 | 47.145 | 1.000 |
| Residue | 78 | 2527.492 | 32.404 | | | | |

Means Table for TCRBV03
Effect: Group

| | Number | Mean | Standard Deviation (Dev.) | Standard Error (Err.) |
|---|---|---|---|---|
| CM+P | 15 | 15,663 | 6,018 | 1,553 |
| CM+S | 17 | 13,392 | 7,788 | 1,889 |
| J5P | 8 | 5,793 | 1,245 | .440 |
| J5S | 10 | 10,189 | 5,355 | 1,693 |
| TNP | 17 | 6,590 | 6,854 | 1,662 |
| TNS | 17 | 4,402 | 1,366 | .331 |

|  | Mean diff. | Critical diff. | p Value |  |
|---|---|---|---|---|
| CM+P, CM+S | 2.271 | 4.015 | .2635 |  |
| CM+P, J5P | 9.870 | 4.961 | .0002 | S |
| CM+P, J5S | 5.474 | 4.627 | .0210 | S |
| CM+P, TNP | 9.073 | 4.015 | <.0001 | S |
| CM+P, TNS | 11.261 | 4.015 | <.0001 | S |
| CM+S, J5P | 7.599 | 4.859 | .0026 | S |
| CM+S, J5S | 3.203 | 4.516 | .1620 |  |
| CM+S, TNP | 6.802 | 3.887 | .0008 | S |
| CM+S, TNS | 8.990 | 3.887 | <.0001 | S |
| J5P, J5S | -4.396 | 5.376 | .1076 |  |
| J5P, TNP | -.797 | 4.859 | .7448 |  |
| J5P, TNS | 1.391 | 4.859 | .5703 |  |
| J5S, TNP | 3.599 | 4.516 | .1167 |  |
| J5S, TNS | 5.787 | 4.516 | .0127 | S |
| TNP, TNS | 2.188 | 3.887 | .2658 |  |

| | d.f. | Sum of Squares | Mean Square | F Value | p Value | Lambda | Power |
|---|---|---|---|---|---|---|---|
| Group | 5 | 390,352 | 78,070 | 1,752 | .1328 | 8.762 | .569 |
| Residue | 77 | 3430,317 | 44,550 | | | | |

|      | Number | Mean   | Standard Deviation (Dev.) | Standard Error (Err.) |
|------|--------|--------|---------------------------|----------------------|
| CM+P | 14     | 11,624 | 9,605                     | 2,567                |
| CM+S | 17     | 7,556  | 3,093                     | .750                 |
| J5P  | 9      | 10,016 | 10,982                    | 3,661                |
| J5S  | 10     | 5,395  | 2,913                     | .921                 |
| TNP  | 17     | 8,235  | 7,874                     | 1,910                |
| TNS  | 16     | 5,528  | 1,724                     | .431                 |

|  | Mean diff. | Critical diff. | p Value |  |
|---|---|---|---|---|
| CM+P, CM+S | 4.068 | 4.797 | .0953 |  |
| CM+P, J5P | 1.608 | 5.678 | .5744 |  |
| CM+P, J5S | 6.229 | 5.503 | .0270 | S |
| CM+P, TNP | 3.389 | 4.797 | .1635 |  |
| CM+P, TNS | 6.096 | 4.864 | .0147 | S |
| CM+S, J5P | -2.460 | 5.479 | .3741 |  |
| CM+S, J5S | 2.161 | 5.297 | .4191 |  |
| CM+S, TNP | -.679 | 4.559 | .7675 |  |
| CM+S, TNS | 2.028 | 4.629 | .3858 |  |
| J5P, J5S | 4.621 | 6.107 | .1360 |  |
| J5P, TNP | 1.781 | 5.479 | .5195 |  |
| J5P, TNS | 4.488 | 5.538 | .1107 |  |
| J5S, TNP | -2.840 | 5.297 | .2890 |  |
| J5S, TNS | -.133 | 5.358 | .9607 |  |
| TNP, TNS | 2.707 | 4.629 | .2478 |  |

| | d.f. | Sum of Squares | Mean Square | F Value | p Value | Lambda | Power |
|---|---|---|---|---|---|---|---|
| Group | 5 | 1177.396 | 235.479 | 3.026 | .0162 | 15.129 | .840 |
| Residue | 65 | 5058.617 | 77.825 | | | | |

| | Number | Mean | Standard Deviation (Dev.) | Standard Error (Err.) |
|---|---|---|---|---|
| CM+P | 14 | 22,742 | 8,379 | 2,239 |
| CM+S | 15 | 17,817 | 8,119 | 2,096 |
| J5P | 7 | 20,393 | 9,875 | 3,733 |
| J5S | 8 | 15,429 | 8,348 | 2,852 |
| TNP | 13 | 18,467 | 12,720 | 3,528 |
| TNS | 14 | 10,498 | 4,002 | 1,070 |

|  | Mean diff. | Critical diff. | p Value |  |
|---|---|---|---|---|
| CM+P, CM+S | 4.925 | 6.547 | .1379 |  |
| CM+P, J5P | 2.349 | 8.156 | .5672 |  |
| CM+P, J5S | 7.312 | 7.809 | .0660 |  |
| CM+P, TNP | 4.275 | 6.786 | .2128 |  |
| CM+P, TNS | 12.244 | 6.659 | .0005 | S |
| CM+S, J5P | -2.576 | 8.065 | .5258 |  |
| CM+S, J5S | 2.388 | 7.713 | .5385 |  |
| CM+S, TNP | -.649 | 6.676 | .8466 |  |
| CM+S, TNS | 7.319 | 6.547 | .0290 | S |
| J5P, J5S | 4.964 | 9.118 | .2810 |  |
| J5P, TNP | 1.927 | 8.260 | .6429 |  |
| J5P, TNS | 9.895 | 8.156 | .0182 | S |
| J5S, TNP | -3.037 | 7.917 | .4464 |  |
| J5S, TNS | 4.931 | 7.809 | .2117 |  |
| TNP, TNS | 7.968 | 6.786 | .0221 | S |

| | d.f. | Sum of Squares | Mean Square | F Value | p Value | Lambda | Power |
|---|---|---|---|---|---|---|---|
| Group | 5 | 916.180 | 183.236 | 7.484 | <.0001 | 37.318 | .999 |
| Residue | 74 | 1818.741 | 24.551 | | | | |

|      | Number | Mean   | Standard Deviation (Dev.) | Standard Error (Err.) |
|------|--------|--------|---------------------------|-----------------------|
| CM+P | 13     | 16,559 | 7,514                     | 2,084                 |
| CM+S | 17     | 9,926  | 3,585                     | .869                  |
| J5P  | 8      | 17,091 | 3,750                     | 1,326                 |
| J5S  | 10     | 8,415  | 6,726                     | 2,127                 |
| TNP  | 15     | 11,815 | 5,086                     | 1,313                 |
| TNS  | 17     | 8,117  | 2,031                     | .492                  |

FIG. 72H

|  | Mean diff. | Critical diff. | p Value | |
|---|---|---|---|---|
| CM+P, CM+S | 6.633 | 3.637 | .0005 | S |
| CM+P, J5P | -.532 | 4.436 | .8117 | |
| CM+P, J5S | 8.144 | 4.153 | .0002 | S |
| CM+P, TNP | 4.745 | 3.741 | .0138 | S |
| CM+P, TNS | 8.442 | 3.637 | <.0001 | S |
| CM+S, J5P | -7.166 | 4.233 | .0012 | S |
| CM+S, J5S | 1.511 | 3.935 | .4466 | |
| CM+S, TNP | -1.889 | 3.497 | .2854 | |
| CM+S, TNS | 1.808 | 3.386 | .2907 | |
| J5P, J5S | 8.677 | 4.683 | .0004 | S |
| J5P, TNP | 5.277 | 4.322 | .0174 | S |
| J5P, TNS | 8.974 | 4.233 | <.0001 | S |
| J5S, TNP | -3.400 | 4.031 | .0970 | |
| J5S, TNS | .298 | 3.935 | .8806 | |
| TNP, TNS | 3.697 | 3.497 | .0386 | S |

FIG. 73A

| | d.f. | Sum of Squares | Mean Square | F Value | p Value | Lambda | Power |
|---|---|---|---|---|---|---|---|
| Group | 5 | 788.066 | 157.613 | 2.447 | .0409 | 12.237 | .745 |
| Residue | 79 | 5087.612 | 64.400 | | | | |

|      | Number | Mean   | Standard Deviation (Dev.) | Standard Error (Err.) |
|------|--------|--------|---------------------------|-----------------------|
| CM+P | 15     | 17,007 | 8,620                     | 2,226                 |
| CM+S | 17     | 13,682 | 9,336                     | 2,264                 |
| J5P  | 9      | 7,467  | 2,436                     | ,812                  |
| J5S  | 9      | 10,375 | 8,168                     | 2,723                 |
| TNP  | 17     | 9,357  | 6,546                     | 1,588                 |
| TNS  | 18     | 10,441 | 9,029                     | 2,128                 |

|  | Mean diff. | Critical diff. | p Value | |
|---|---|---|---|---|
| CM+P, CM+S | 3.325 | 5.658 | .2457 | |
| CM+P, J5P | 9.539 | 6.735 | .0061 | S |
| CM+P, J5S | 6.631 | 6.735 | .0535 | |
| CM+P, TNP | 7.650 | 5.658 | .0087 | S |
| CM+P, TNS | 6.566 | 5.584 | .0218 | S |
| CM+S, J5P | 6.215 | 6.585 | .0640 | |
| CM+S, J5S | 3.307 | 6.585 | .3206 | |
| CM+S, TNP | 4.325 | 5.479 | .1201 | |
| CM+S, TNS | 3.241 | 5.402 | .2360 | |
| J5P, J5S | -2.908 | 7.530 | .4444 | |
| J5P, TNP | -1.890 | 6.585 | .5694 | |
| J5P, TNS | -2.974 | 6.521 | .3668 | |
| J5S, TNP | 1.018 | 6.585 | .7590 | |
| J5S, TNS | -.066 | 6.521 | .9841 | |
| TNP, TNS | -1.084 | 5.402 | .6907 | |

| | d.f. | Sum of Squares | Mean Square | F Value | p Value | Lambda | Power |
|---|---|---|---|---|---|---|---|
| Group | 5 | 1142.901 | 228.580 | 3.361 | .0084 | 16.806 | .889 |
| Residue | 79 | 5372.547 | 68.007 | | | | |

|      | Number | Mean   | Standard Deviation (Dev.) | Standard Error (Err.) |
|------|--------|--------|---------------------------|------------------------|
| CM+P | 15     | 19,250 | 11,734                    | 3,030                  |
| CM+S | 17     | 13,065 | 8,253                     | 2,002                  |
| J5P  | 9      | 7,781  | 3,973                     | 1,324                  |
| J5S  | 10     | 11,235 | 7,477                     | 2,365                  |
| TNP  | 16     | 8,817  | 5,986                     | 1,496                  |
| TNS  | 18     | 11,242 | 8,360                     | 1,971                  |

|  | Mean diff. | Critical diff. | p Value |  |
|---|---|---|---|---|
| CM+P, CM+S | 6.186 | 5.815 | .0374 | S |
| CM+P, J5P | 11.469 | 6.921 | .0015 | S |
| CM+P, J5S | 8.015 | 6.701 | .0197 | S |
| CM+P, TNP | 10.433 | 5.899 | .0007 | S |
| CM+P, TNS | 8.008 | 5.739 | .0068 | S |
| CM+S, J5P | 5.283 | 6.767 | .1242 |  |
| CM+S, J5S | 1.829 | 6.542 | .5794 |  |
| CM+S, TNP | 4.247 | 5.717 | .1432 |  |
| CM+S, TNS | 1.822 | 5.551 | .5154 |  |
| J5P, J5S | -3.454 | 7.542 | .3648 |  |
| J5P, TNP | -1.036 | 6.839 | .7639 |  |
| J5P, TNS | -3.461 | 6.701 | .3071 |  |
| J5S, TNP | 2.418 | 6.617 | .4691 |  |
| J5S, TNS | -.007 | 6.474 | .9982 |  |
| TNP, TNS | -2.425 | 5.640 | .3946 |  |

| | d.f. | Sum of Squares | Mean Square | F Value | p Value | Lambda | Power |
|---|---|---|---|---|---|---|---|
| Group | 5 | 368,810 | 73,362 | 5,005 | .0005 | 25,027 | .983 |
| Residue | 79 | 1157,847 | 14,656 | | | | |

| | Number | Mean | Standard Deviation (Dev.) | Standard Error (Err.) |
|---|---|---|---|---|
| CM+P | 14 | 10,344 | 4,444 | 1,158 |
| CM+S | 17 | 10,640 | 6,391 | 1,550 |
| J5P | 9 | 6,969 | 1,629 | ,543 |
| J5S | 10 | 6,622 | 2,787 | ,881 |
| TNP | 17 | 6,681 | 1,623 | ,394 |
| TNS | 18 | 5,469 | 2,592 | ,611 |

|  | Mean diff. | Critical diff. | p Value | |
|---|---|---|---|---|
| CM+P, CM+S | -.297 | 2.750 | .8306 | |
| CM+P, J5P | 3.375 | 3.256 | .0424 | S |
| CM+P, J5S | 3.722 | 3.155 | .0214 | S |
| CM+P, TNP | 3.663 | 2.750 | .0097 | S |
| CM+P, TNS | 4.875 | 2.715 | .0006 | S |
| CM+S, J5P | 3.671 | 3.141 | .0226 | S |
| CM+S, J5S | 4.018 | 3.037 | .0102 | S |
| CM+S, TNP | 3.959 | 2.614 | .0035 | S |
| CM+S, TNS | 5.172 | 2.577 | .0001 | S |
| J5P, J5S | .347 | 3.501 | .8442 | |
| J5P, TNP | .288 | 3.141 | .8558 | |
| J5P, TNS | 1.500 | 3.111 | .3400 | |
| J5S, TNP | -.059 | 3.037 | .9693 | |
| J5S, TNS | 1.154 | 3.005 | .4471 | |
| TNP, TNS | 1.213 | 2.577 | .3519 | |

ANOVA (Analysis of Variance) Table for TCRBV08.2

| | d.f. | Sum of Squares | Mean Square | F Value | p Value | Lambda | Power |
|---|---|---|---|---|---|---|---|
| Group | 5 | 150.431 | 30.086 | 1.097 | .3688 | 5.485 | .364 |
| Residue | 78 | 2139.073 | 27.424 | | | | |

Means Table for TCRBV08.2
Effect: Group

| | Number | Mean | Standard Deviation (Dev.) | Standard Error (Err.) |
|---|---|---|---|---|
| CM+P | 14 | 9.586 | 4.874 | 1.249 |
| CM+S | 17 | 10.574 | 7.927 | 1.923 |
| J5P | 8 | 7.913 | 2.982 | 1.054 |
| J5S | 10 | 7.678 | 4.199 | 1.328 |
| TNP | 17 | 7.001 | 3.136 | .760 |
| TNS | 18 | 7.644 | 5.266 | 1.241 |

PLSD Fisher's Test for TCRBV08.2
Effect: Group
Significance level: 5%

|  | Mean diff. | Critical diff. | p Value |
|---|---|---|---|
| CM+P, CM+S | -.989 | 3.763 | .6023 |
| CM+P, J5P | 1.673 | 4.621 | .4732 |
| CM+P, J5S | 1.907 | 4.317 | .3817 |
| CM+P, TNP | 2.585 | 3.763 | .1754 |
| CM+P, TNS | 1.942 | 3.715 | .3013 |
| CM+S, J5P | 2.662 | 4.470 | .2394 |
| CM+S, J5S | 2.896 | 4.155 | .1692 |
| CM+S, TNP | 3.573 | 3.576 | .0502 |
| CM+S, TNS | 2.931 | 3.526 | .1020 |
| J5P, J5S | .234 | 4.945 | .9250 |
| J5P, TNP | .912 | 4.470 | .6858 |
| J5P, TNS | .269 | 4.430 | .9041 |
| J5S, TNP | .677 | 4.155 | .7464 |
| J5S, TNS | .034 | 4.112 | .9867 |
| TNP, TNS | -.643 | 3.526 | .7176 |

| | d.f. | Sum of Squares | Mean Square | F Value | p Value | Lambda | Power |
|---|---|---|---|---|---|---|---|
| Group | 5 | 495.165 | 99.033 | 3.518 | .0064 | 17.592 | .906 |
| Residue | 79 | 2223.623 | 28.147 | | | | |

|  | Number | Mean | Standard Deviation (Dev.) | Standard Error (Err.) |
|---|---|---|---|---|
| CM+P | 16 | 9,855 | 10,116 | 2,529 |
| CM+S | 17 | 8,560 | 5,555 | 1,347 |
| J5P | 8 | 6,072 | 2,450 | ,866 |
| J5S | 10 | 3,777 | 1,722 | ,545 |
| TNP | 17 | 4,949 | 2,433 | ,590 |
| TNS | 17 | 3,743 | 1,405 | ,341 |

|  | Mean diff. | Critical diff. | p Value | |
|---|---|---|---|---|
| CM+P, CM+S | 1.295 | 3.678 | .4854 | |
| CM+P, J5P | 3.783 | 4.573 | .1036 | |
| CM+P, J5S | 6.078 | 4.257 | .0057 | S |
| CM+P, TNP | 4.906 | 3.678 | .0096 | S |
| CM+P, TNS | 6.111 | 3.678 | .0014 | S |
| CM+S, J5P | 2.487 | 4.528 | .2775 | |
| CM+S, J5S | 4.782 | 4.208 | .0265 | S |
| CM+S, TNP | 3.611 | 3.622 | .0507 | |
| CM+S, TNS | 4.816 | 3.622 | .0098 | S |
| J5P, J5S | 2.295 | 5.009 | .3646 | |
| J5P, TNP | 1.123 | 4.528 | .6227 | |
| J5P, TNS | 2.329 | 4.528 | .3091 | |
| J5S, TNP | -1.171 | 4.208 | .5811 | |
| J5S, TNS | .034 | 4.208 | .9873 | |
| TNP, TNS | 1.205 | 3.622 | .5097 | |

ANOVA (Analysis of Variance) Table for TCRBV09

| | d.f. | Sum of Squares | Mean Square | F Value | p Value | Lambda | Power |
|---|---|---|---|---|---|---|---|
| Group | 5 | 901.856 | 180.371 | 1.899 | .1066 | 9.495 | .603 |
| Residue | 65 | 6174.114 | 94.986 | | | | |

| | Number | Mean | Standard Deviation (Dev.) | Standard Error (Err.) |
|---|---|---|---|---|
| CM+P | 15 | 22,693 | 13,552 | 3,499 |
| CM+S | 13 | 19,176 | 10,554 | 2,927 |
| J5P | 7 | 20,567 | 6,361 | 2,404 |
| J5S | 8 | 12,019 | 10,703 | 3,784 |
| TNP | 16 | 16,104 | 5,480 | 1,370 |
| TNS | 12 | 14,248 | 8,373 | 2,417 |

|            | Mean diff. | Critical diff. | p Value |   |
|------------|------------|----------------|---------|---|
| CM+P, CM+S | 3.517      | 7.376          | .3444   |   |
| CM+P, J5P  | 2.126      | 8.910          | .6352   |   |
| CM+P, J5S  | 10.875     | 8.521          | .0149   | S |
| CM+P, TNP  | 6.589      | 6.995          | .0644   |   |
| CM+P, TNS  | 8.446      | 7.538          | .0287   | S |
| CM+S, J5P  | -1.391     | 9.125          | .7618   |   |
| CM+S, J5S  | 7.158      | 8.746          | .1070   |   |
| CM+S, TNP  | 3.072      | 7.268          | .4017   |   |
| CM+S, TNS  | 4.928      | 7.792          | .2110   |   |
| J5P, J5S   | 8.549      | 10.074         | .0949   |   |
| J5P, TNP   | 4.463      | 8.821          | .3160   |   |
| J5P, TNS   | 6.319      | 9.257          | .1775   |   |
| J5S, TNP   | -4.085     | 8.428          | .3366   |   |
| J5S, TNS   | -2.229     | 8.884          | .6180   |   |
| TNP, TNS   | 1.856      | 7.433          | .6195   |   |

| | d.f. | Sum of Squares | Mean Square | F Value | p Value | Lambda | Power |
|---|---|---|---|---|---|---|---|
| Group | 5 | 366.970 | 73.394 | .795 | .5566 | 3.975 | .266 |
| Residue | 77 | 7108.560 | 92.319 | | | | |

|     | Number | Mean   | Standard Deviation (Dev.) | Standard Error (Err.) |
|-----|--------|--------|---------------------------|-----------------------|
| CM+P | 16 | 12,620 | 17,634 | 4,408 |
| CM+S | 16 | 8,718  | 3,904  | .976  |
| J5P  | 9  | 7,336  | 6,956  | 2,319 |
| J5S  | 9  | 9,596  | 8,867  | 2,956 |
| TNP  | 16 | 8,428  | 7,638  | 1,910 |
| TNS  | 17 | 6,297  | 4,503  | 1,092 |

|  | Mean diff. | Critical diff. | p Value |
|---|---|---|---|
| CM+P, CM+S | 3.902 | 6.764 | .2542 |
| CM+P, J5P | 5.284 | 7.972 | .1908 |
| CM+P, J5S | 3.024 | 7.972 | .4523 |
| CM+P, TNP | 4.193 | 6.764 | .2209 |
| CM+P, TNS | 6.323 | 6.664 | .0628 |
| CM+S, J5P | 1.382 | 7.972 | .7309 |
| CM+S, J5S | -.878 | 7.972 | .8270 |
| CM+S, TNP | .290 | 6.764 | .9322 |
| CM+S, TNS | 2.421 | 6.664 | .4717 |
| J5P, J5S | -2.260 | 9.019 | .6193 |
| J5P, TNP | -1.092 | 7.972 | .7859 |
| J5P, TNS | 1.039 | 7.887 | .7938 |
| J5S, TNP | 1.168 | 7.972 | .7712 |
| J5S, TNS | 3.299 | 7.887 | .4075 |
| TNP, TNS | 2.131 | 6.664 | .5263 |

| | d.f. | Sum of Squares | Mean Square | F Value | p Value | Lambda | Power |
|---|---|---|---|---|---|---|---|
| Group | 5 | 326,172 | 65,234 | 3,116 | .0132 | 15,578 | .857 |
| Residue | 74 | 1549,389 | 20,938 | | | | |

|     | Number | Mean | Standard Deviation (Dev.) | Standard Error (Err.) |
|-----|--------|------|---------------------------|-----------------------|
| CM+P | 15 | 14,370 | 5,385 | 1,390 |
| CM+S | 16 | 11,571 | 4,674 | 1,168 |
| J5P | 8 | 8,500 | 2,323 | .821 |
| J5S | 9 | 10,472 | 3,326 | 1,109 |
| TNP | 16 | 8,931 | 4,625 | 1,156 |
| TNS | 16 | 9,506 | 4,958 | 1,239 |

|  | Mean diff. | Critical diff. | p Value | |
|---|---|---|---|---|
| CM+P, CM+S | 2.799 | 3.277 | .0929 | |
| CM+P, J5P | 5.870 | 3.992 | .0045 | S |
| CM+P, J5S | 3.898 | 3.844 | .0470 | S |
| CM+P, TNP | 5.439 | 3.277 | .0015 | S |
| CM+P, TNS | 4.864 | 3.277 | .0042 | S |
| CM+S, J5P | 3.071 | 3.948 | .1255 | |
| CM+S, J5S | 1.098 | 3.799 | .5663 | |
| CM+S, TNP | 2.640 | 3.223 | .1070 | |
| CM+S, TNS | 2.064 | 3.223 | .2059 | |
| J5P, J5S | -1.972 | 4.430 | .3779 | |
| J5P, TNP | -.431 | 3.948 | .8284 | |
| J5P, TNS | -1.006 | 3.948 | .6130 | |
| J5S, TNP | 1.541 | 3.799 | .4214 | |
| J5S, TNS | .966 | 3.799 | .6139 | |
| TNP, TNS | -.575 | 3.223 | .7231 | |

| | d.f. | Sum of Squares | Mean Square | F Value | p Value | Lambda | Power |
|---|---|---|---|---|---|---|---|
| Group | 5 | 440.110 | 88.022 | 1.902 | .1038 | 9.510 | .610 |
| Residue | 76 | 3517.057 | 46.277 | | | | |

| | Number | Mean | Standard Deviation (Dev.) | Standard Error (Err.) |
|---|---|---|---|---|
| CM+P | 13 | 26,706 | 10,267 | 2,848 |
| CM+S | 16 | 21,490 | 5,750 | 1,438 |
| J5P | 9 | 21,202 | 7,031 | 2,344 |
| J5S | 10 | 20,410 | 3,361 | 1,063 |
| TNP | 17 | 19,440 | 4,775 | 1,158 |
| TNS | 17 | 22,585 | 7,476 | 1,813 |

|  | Mean diff. | Critical diff. | p Value |  |
|---|---|---|---|---|
| CM+P, CM+S | 5,216 | 5,059 | ,0435 | S |
| CM+P, J5P | 5,504 | 5,875 | ,0659 |  |
| CM+P, J5S | 6,296 | 5,699 | ,0308 | S |
| CM+P, TNP | 7,266 | 4,992 | ,0049 | S |
| CM+P, TNS | 4,121 | 4,992 | ,1043 |  |
| CM+S, J5P | ,288 | 5,645 | ,9194 |  |
| CM+S, J5S | 1,080 | 5,462 | ,6948 |  |
| CM+S, TNP | 2,050 | 4,719 | ,3897 |  |
| CM+S, TNS | -1,095 | 4,719 | ,6454 |  |
| J5P, J5S | ,792 | 6,225 | ,8006 |  |
| J5P, TNP | 1,762 | 5,585 | ,5316 |  |
| J5P, TNS | -1,383 | 5,585 | ,6234 |  |
| J5S, TNP | ,970 | 5,400 | ,7215 |  |
| J5S, TNS | -2,175 | 5,400 | ,4249 |  |
| TNP, TNS | -3,145 | 4,647 | ,1817 |  |

| | d.f. | Sum of Squares | Mean Square | F Value | p Value | Lambda | Power |
|---|---|---|---|---|---|---|---|
| Group | 5 | 271.666 | 54.333 | 1.661 | .1545 | 8.306 | .541 |
| Residue | 75 | 2453.157 | 32.709 | | | | |

|  | Number | Mean | Standard Deviation (Dev.) | Standard Error (Err.) |
|---|---|---|---|---|
| CM+P | 14 | 12,637 | 6,567 | 1,755 |
| CM+S | 17 | 9,220 | 2,776 | .673 |
| J5P | 9 | 12,000 | 6,015 | 2,005 |
| J5S | 8 | 11,132 | 5,742 | 2,030 |
| TNP | 16 | 10,618 | 8,055 | 2,014 |
| TNS | 17 | 7,400 | 4,151 | 1,007 |

|  | Mean diff. | Critical diff. | p Value | |
|---|---|---|---|---|
| CM+P, CM+S | 3.417 | 4.112 | .1020 | |
| CM+P, J5P | .637 | 4.868 | .7951 | |
| CM+P, J5S | 1.505 | 5.049 | .5545 | |
| CM+P, TNP | 2.021 | 4.169 | .3373 | |
| CM+P, TNS | 5.237 | 4.112 | .0132 | S |
| CM+S, J5P | -2.780 | 4.697 | .2421 | |
| CM+S, J5S | -1.912 | 4.885 | .4380 | |
| CM+S, TNP | -1.396 | 3.968 | .4858 | |
| CM+S, TNS | 1.821 | 3.908 | .3563 | |
| J5P, J5S | .868 | 5.536 | .7557 | |
| J5P, TNP | 1.384 | 4.747 | .5630 | |
| J5P, TNS | 4.601 | 4.697 | .0547 | |
| J5S, TNP | .517 | 4.933 | .8353 | |
| J5S, TNS | 3.733 | 4.885 | .1321 | |
| TNP, TNS | 3.216 | 3.968 | .1106 | |

| | d.f. | Sum of Squares | Mean Square | F Value | p Value | Lambda | Power |
|---|---|---|---|---|---|---|---|
| Group | 5 | 212.057 | 42.411 | 2.853 | .0207 | 14.265 | .818 |
| Residue | 74 | 1100.086 | 14.866 | | | | |

|  | Number | Mean | Standard Deviation (Dev.) | Standard Error (Err.) |
|---|---|---|---|---|
| CM+P | 15 | 9,609 | 7,302 | 1,885 |
| CM+S | 15 | 7,351 | 3,241 | .837 |
| J5P | 8 | 6,045 | 1,246 | .440 |
| J5S | 9 | 5,140 | 1,601 | .534 |
| TNP | 16 | 5,739 | 2,558 | .639 |
| TNS | 17 | 5,179 | 2,195 | .532 |

|  | Mean diff. | Critical diff. | p Value | |
|---|---|---|---|---|
| CM+P, CM+S | 2.258 | 2.805 | .1130 | |
| CM+P, J5P | 3.564 | 3.363 | .0381 | S |
| CM+P, J5S | 4.468 | 3.239 | .0075 | S |
| CM+P, TNP | 3.870 | 2.761 | .0066 | S |
| CM+P, TNS | 4.429 | 2.722 | .0018 | S |
| CM+S, J5P | 1.306 | 3.363 | .4417 | |
| CM+S, J5S | 2.210 | 3.239 | .1781 | |
| CM+S, TNP | 1.612 | 2.761 | .2484 | |
| CM+S, TNS | 2.171 | 2.722 | .1161 | |
| J5P, J5S | .905 | 3.733 | .6305 | |
| J5P, TNP | .306 | 3.327 | .8549 | |
| J5P, TNS | .866 | 3.294 | .6020 | |
| J5S, TNP | -.598 | 3.201 | .7106 | |
| J5S, TNS | -.039 | 3.167 | .9805 | |
| TNP, TNS | .559 | 2.678 | .6782 | |

| | d.f. | Sum of Squares | Mean Square | F Value | p Value | Lambda | Power |
|---|---|---|---|---|---|---|---|
| Group | 5 | 392,519 | 78,504 | 3.949 | .0031 | 19.747 | .939 |
| Residue | 75 | 1490,804 | 19,877 | | | | |

| | Number | Mean | Standard Deviation (Dev.) | Standard Error (Err.) |
|---|---|---|---|---|
| CM+P | 13 | 11,151 | 7,292 | 2,022 |
| CM+S | 17 | 8,167 | 6,514 | 1,580 |
| J5P | 7 | 5,730 | 1,647 | .622 |
| J5S | 10 | 5,626 | 1,858 | .587 |
| TNP | 17 | 5,702 | 2,068 | .502 |
| TNS | 17 | 4,728 | 1,904 | .462 |

|  | Mean diff. | Critical diff. | p Value | |
|---|---|---|---|---|
| CM+P, CM+S | 2.984 | 3.272 | .0733 | |
| CM+P, J5P | 5.421 | 4.164 | .0114 | S |
| CM+P, J5S | 5.524 | 3.736 | .0043 | S |
| CM+P, TNP | 5.449 | 3.272 | .0014 | S |
| CM+P, TNS | 6.422 | 3.272 | .0002 | S |
| CM+S, J5P | 2.437 | 3.989 | .2274 | |
| CM+S, J5S | 2.541 | 3.540 | .1569 | |
| CM+S, TNP | 2.465 | 3.046 | .1112 | |
| CM+S, TNS | 3.438 | 3.046 | .0275 | S |
| J5P, J5S | .104 | 4.377 | .9625 | |
| J5P, TNP | .028 | 3.989 | .9888 | |
| J5P, TNS | 1.001 | 3.989 | .6184 | |
| J5S, TNP | -.076 | 3.540 | .9662 | |
| J5S, TNS | .898 | 3.540 | .6148 | |
| TNP, TNS | .973 | 3.046 | .5264 | |

| | d.f. | Sum of Squares | Mean Square | F Value | p Value | Lambda | Power |
|---|---|---|---|---|---|---|---|
| Group | 5 | 993.378 | 198.676 | 4.979 | .0005 | 24.896 | .982 |
| Residue | 77 | 3072.420 | 39.902 | | | | |

|  | Number | Mean | Standard Deviation (Dev.) | Standard Error (Err.) |
|---|---|---|---|---|
| CM+P | 15 | 15,315 | 6,773 | 1,749 |
| CM+S | 17 | 11,665 | 7,607 | 1,845 |
| J5P | 9 | 8,828 | 4,243 | 1,414 |
| J5S | 10 | 11,179 | 11,924 | 3,771 |
| TNP | 16 | 6,374 | 1,705 | .426 |
| TNS | 16 | 5,747 | 1,577 | .394 |

|  | Mean diff. | Critical diff. | p Value | |
|---|---|---|---|---|
| CM+P, CM+S | 3.650 | 4.456 | .1070 | |
| CM+P, J5P | 6.487 | 5.303 | .0172 | S |
| CM+P, J5S | 4.136 | 5.135 | .1129 | |
| CM+P, TNP | 8.940 | 4.521 | .0002 | S |
| CM+P, TNS | 9.567 | 4.521 | <.0001 | S |
| CM+S, J5P | 2.837 | 5.185 | .2793 | |
| CM+S, J5S | .486 | 5.013 | .8475 | |
| CM+S, TNP | 5.291 | 4.381 | .0186 | S |
| CM+S, TNS | 5.917 | 4.381 | .0088 | S |
| J5P, J5S | -2.351 | 5.779 | .4203 | |
| J5P, TNP | 2.453 | 5.241 | .3542 | |
| J5P, TNS | 3.080 | 5.241 | .2455 | |
| J5S, TNP | 4.805 | 5.070 | .0629 | |
| J5S, TNS | 5.432 | 5.070 | .0361 | S |
| TNP, TNS | .627 | 4.447 | .7797 | |

| | d.f. | Sum of Squares | Mean Square | F Value | p Value | Lambda | Power |
|---|---|---|---|---|---|---|---|
| Group | 5 | 1233.374 | 246.675 | 5.074 | .0005 | 25.371 | .984 |
| Residue | 74 | 3597.369 | 48.613 | | | | |

| | Number | Mean | Standard Deviation (Dev.) | Standard Error (Err.) |
|---|---|---|---|---|
| CM+P | 13 | 20,499 | 10,847 | 3,008 |
| CM+S | 17 | 15,442 | 6,952 | 1,686 |
| J5P | 9 | 12,342 | 4,375 | 1,458 |
| J5S | 10 | 13,509 | 9,823 | 3,106 |
| TNP | 14 | 9,628 | 3,391 | .906 |
| TNS | 17 | 9,211 | 3,882 | .941 |

|  | Mean diff. | Critical diff. | p Value | |
|---|---|---|---|---|
| CM+P, CM+S | 5.057 | 5.119 | .0527 | |
| CM+P, J5P | 8.158 | 6.024 | .0086 | S |
| CM+P, J5S | 6.991 | 5.844 | .0197 | S |
| CM+P, TNP | 10.871 | 5.351 | .0001 | S |
| CM+P, TNS | 11.288 | 5.119 | <.0001 | S |
| CM+S, J5P | 3.101 | 5.727 | .2842 | |
| CM+S, J5S | 1.934 | 5.537 | .4887 | |
| CM+S, TNP | 5.814 | 5.014 | .0236 | S |
| CM+S, TNS | 6.231 | 4.765 | .0111 | S |
| J5P, J5S | -1.167 | 6.383 | .7166 | |
| J5P, TNP | 2.713 | 5.936 | .3654 | |
| J5P, TNS | 3.130 | 5.727 | .2797 | |
| J5S, TNP | 3.880 | 5.752 | .1830 | |
| J5S, TNS | 4.297 | 5.537 | .1262 | |
| TNP, TNS | .417 | 5.014 | .8689 | |

*FIG. 79H*

ANOVA TABLE FOR TCRBV20

| | DEGREE OF FREEDOM | SQUARE SUM | MEAN SQUARE | F VALUE | P VALUE | LAMBDA | TWO WAY ANOVA POWER CALCULATION |
|---|---|---|---|---|---|---|---|
| GROUP | 5 | 747,683 | 149,537 | 3,122 | ,0128 | 15,608 | ,860 |
| RESIDUAL | 78 | 3736,485 | 47,904 | | | | |

FISCHER'S PLSD TEST FOR TCRBV20
EFFECT: GROUP
SIGNIFICANCE UNDER: 5%

| | MEAN DIFFERENCE | CRITICAL DIFFERENCE | P VALUE | |
|---|---|---|---|---|
| CM+P, CM+S | 6,950 | 4,973 | ,0068 | S |
| CM+P, J5P | 9,116 | 5,887 | ,0028 | S |
| CM+P, J5S | 7,939 | 5,705 | ,0070 | S |
| CM+P, TNP | 6,974 | 4,973 | ,0066 | S |
| CM+P, TNS | 8,482 | 4,973 | ,0011 | S |
| CM+S, J5P | 2,167 | 5,680 | ,4499 | |
| CM+S, J5S | ,990 | 5,491 | ,7208 | |
| CM+S, TNP | ,025 | 4,726 | ,9917 | |
| CM+S, TNS | 1,532 | 4,726 | ,5206 | |
| J5P, J5S | -1,177 | 6,331 | ,7122 | |
| J5P, TNP | -2,142 | 5,680 | ,4551 | |
| J5P, TNS | -,635 | 5,680 | ,8245 | |
| J5S, TNP | -,965 | 5,491 | ,7275 | |
| J5S, TNS | ,542 | 5,491 | ,8446 | |
| TNP, TNS | 1,507 | 4,726 | ,5274 | |

*FIG. 80A*

MEAN TABLE FOR TCRBV20
EFFECT: GROUP

|      | NUMBER | MEAN   | STANDARD DEVIATION | STANDARD ERROR OF THE MEAN |
|------|--------|--------|--------------------|----------------------------|
| CM+P | 14     | 19,650 | 12,693             | 3,392                      |
| CM+S | 17     | 12,700 | 6,534              | 1,585                      |
| J5P  | 9      | 10,533 | 4,189              | 1,396                      |
| J5S  | 10     | 11,711 | 5,365              | 1,697                      |
| TNP  | 17     | 12,675 | 4,696              | 1,139                      |
| TNS  | 17     | 11,168 | 3,593              | ,871                       |

Peak Parameters to be recovered
Size        216
            | TCRBV 5.2 |
            13

Parameter of the files to be used

|    | Folder                  | Page   | Group | Type   | Comment |
|----|-------------------------|--------|-------|--------|---------|
| 1  | DataFormater OG/009 v1.01 | Data.1 | 1 | RT11 | |
| 2  | DataFormater OG/008 v1.03 | Data.2 | 1 | RT12 | |
| 3  | DataFormater OG/007 v1.04 | Data.3 | 1 | RT13 | |
| 4  | DataFormater OG/009 v1.01 | Data.2 | 1 | RT14 | |
| 5  | DataFormater OG/008 v1.03 | Data.3 | 1 | RT15 | |
| 6  | DataFormater OG/005.4 v1.01 | Data.3 | 1 | RT28 | |
| 7  | DataFormater OG/009 v1.01 | Data.3 | 1 | RT29 | |
| 8  | DataFormater OG/003 v1.01 | Data.2 | 1 | RT30 | |
| 9  | DataFormater OG/003 v1.01 | Data.3 | 1 | RT31 | |
| 29 | DataFormater OG/019 v1.04 | Data.3 | 2 | RS21 | |
| 30 | DataFormater OG/020 v1.01 | Data.2 | 2 | RS22 | |
| 31 | DataFormater OG/022 v1.04 | Data.1 | 2 | RS23 | |
| 32 | DataFormater OG/021 v1.04 | Data.2 | 2 | RS24 | |
| 33 | DataFormater OG/022 v1.04 | Data.2 | 2 | RS25 | |
| 19 | DataFormater OG/015 v1.04 | Data.2 | 3 | R3*16 | |
| 20 | DataFormater OG/019 v1.04 | Data.1 | 3 | R3*17 | |
| 21 | DataFormater OG/016 v1.01 | Data.2 | 3 | R3*18 | |
| 22 | DataFormater OG/019 v1.04 | Data.2 | 3 | R3*19 | |
| 23 | DataFormater OG/017 v1.01 | Data.2 | 3 | R3*20 | |
| 39 | DataFormater OG/010 v1.04 | Data.2 | 4 | R3*S06 | |
| 40 | DataFormater OG/013 v1.04 | Data.1 | 4 | R3*S07 | |
| 41 | DataFormater OG/011 v1.04 | Data.2 | 4 | R3*S08 | |
| 42 | DataFormater OG/013 v1.04 | Data.2 | 4 | R3*S09 | |
| 43 | DataFormater OG/012 v1.04 | Data.2 | 4 | R3*S10 | |

*Fig.81*

AC :DA v1.05 F without Vb19

Oligoclonality Score    16/05/00

|              | Score RT |
|--------------|----------|
| TCRBV15 :174 | 0.16     |
| TCRBV15 :177 | 0.15     |
| TCRBV10 :167 | 0.14     |
| TCRBV16 :148 | 0.11     |
| TCRBV15 :171 | 0.10     |
| TCRBV05.2 :216 | 0.10   |
| TCRBV16 :151 | 0.09     |
| TCRBV14 :158 | 0.09     |

|                | Score RS |
|----------------|----------|
| TCRBV08.1 :231 | 0.32     |
| TCRBV15 :174   | 0.19     |
| TCRBV05.2 :216 | 0.18     |
| TCRBV10 :138   | 0.15     |
| TCRBV15 :177   | 0.14     |
| TCRBV05.1 :225 | 0.14     |
| TCRBV05.1 :222 | 0.13     |
| TCRBV05.2 :219 | 0.13     |

|              | Score R3* |
|--------------|-----------|
| TCRBV15 :174 | 0.14      |
| TCRBV16 :148 | 0.13      |
| TCRBV15 :177 | 0.12      |
| TCRBV03 :153 | 0.10      |
| TCRBV09 :150 | 0.09      |
| TCRBV13 :168 | 0.09      |
| TCRBV15 :171 | 0.09      |
| TCRBV10 :138 | 0.09      |

|                | Score R3*S |
|----------------|------------|
| TCRBV15 :174   | 0.15       |
| TCRBV15 :177   | 0.13       |
| TCRBV05.2 :216 | 0.12       |
| TCRBV05.2 :213 | 0.10       |
| TCRBV05.1 :228 | 0.09       |
| TCRBV08.1 :231 | 0.08       |
| TCRBV15 :171   | 0.08       |
| TCRBV05.1 :225 | 0.08       |

*Fig.82A*

µDVb 15/06/00

| | µDVbRT | µDVbRS | µDVbR3* | µDVbR3*S |
|---|---|---|---|---|
| TCRBV01 | 7.22 | 5.99 | 9.87 | 6 |
| TCRBV02 | 3.49 | 6.01 | 6.13 | 6 |
| TCRBV03 | 15.85 | 16.58 | 16.28 | 16 |
| TCRBV04 | 13.12 | 18.02 | 17.95 | 18 |
| TCRBV05.1 | 9.42 | 23.63 | 24.96 | 27 |
| TCRBV05.2 | 7.40 | 12.10 | 12.44 | 12 |
| TCRBV06 | 13.04 | 12.37 | 6.61 | 8 |
| TCRBV07 | 3.81 | 6.49 | 4.57 | 9 |
| TCRBV08.1 | 2.40 | 18.20 | 5.98 | 12 |
| TCRBV08.2 | 13.38 | 21.83 | 14.72 | 16 |
| TCRBV08.3 | 4.50 | 8.26 | 5.98 | 5 |
| TCRBV09 | 15.74 | 18.39 | 23.49 | 28 |
| TCRBV10 | 6.93 | 11.33 | 11.69 | 8 |
| TCRBV11 | 7.35 | 7.88 | 5.97 | 9 |
| TCRBV12 | 14.78 | 14.66 | 8.34 | 13 |
| TCRBV13 | 11.25 | 10.17 | 12.27 | 9 |
| TCRBV14 | 3.28 | 8.20 | 5.43 | 7 |
| TCRBV15 | 7.85 | 8.52 | 9.27 | 9 |
| TCRBV16 | 17.11 | 15.19 | 13.97 | 12 |
| TCRBV18 | 15.28 | 11.24 | 15.53 | 19 |
| TCRBV20 | 11.82 | 16.43 | 11.61 | 11 |

*Fig. 82B*

AC: DA v1.05 F without Vb19 para

AC → OG
Liver Analysis

Peak Parameters to be recovered
Size    216
         | TCRBV 5.2 |
          13

Parameter of the files to be used

|    | Folder | Page | Group | Type | Comment |
|----|--------|------|-------|------|---------|
| 10 | DataFormater OG/006 v1.01 | Data.1 | 1 | FT11 | |
| 11 | DataFormater OG/006 v1.01 | Data.2 | 1 | FT12 | |
| 12 | DataFormater OG/007 v1.04 | Data.1 | 1 | FT13 | |
| 13 | DataFormater OG/007 v1.04 | Data.2 | 1 | FT14 | |
| 14 | DataFormater OG/008 v1.03 | Data.1 | 1 | FT15 | |
| 15 | DataFormater OG/003 v1.01 | Data.1 | 1 | FT26 | |
| 16 | DataFormater OG/005.4 v1.01 | Data.1 | 1 | FT27 | |
| 17 | DataFormater OG/005.4 v1.01 | Data.2 | 1 | FT28 | |
| 18 | DataFormater OG/006 v1.01 | Data.3 | 1 | FT29 | |
| 24 | DataFormater OG/015 v1.04 | Data.1 | 2 | F3*16 | |
| 25 | DataFormater OG/015 v1.04 | Data.3 | 2 | F3*17 | |
| 26 | DataFormater OG/016 v1.04 | Data.1 | 2 | F3*18 | |
| 27 | DataFormater OG/016 v1.04 | Data.3 | 2 | F3*19 | |
| 28 | DataFormater OG/017 v1.04 | Data.1 | 2 | F3*20 | |
| 34 | DataFormater OG/017 v1.01 | Data.3 | 3 | FS21 | |
| 35 | DataFormater OG/020 v1.01 | Data.1 | 3 | FS22 | |
| 36 | DataFormater OG/020 v1.01 | Data.3 | 3 | FS23 | |
| 37 | DataFormater OG/021 v1.04 | Data.1 | 3 | FS24 | |
| 38 | DataFormater OG/021 v1.04 | Data.3 | 3 | FS25 | |
| 44 | DataFormater OG/012 v1.04 | Data.3 | 4 | F3*S01 | |
| 45 | DataFormater OG/033 v1.04 | Data.3 | 4 | F3*S02 | |
| 46 | DataFormater OG/014 v1.01 | Data.1 | 4 | F3*S03 | |
| 47 | DataFormater OG/014 v1.01 | Data.2 | 4 | F3*S04 | |
| 48 | DataFormater OG/014 v1.01 | Data.3 | 4 | F3*S05 | |
| 49 | DataFormater OG/010 v1.04 | Data.1 | 4 | F3*S06 | |
| 50 | DataFormater OG/010 v1.04 | Data.3 | 4 | F3*S07 | |
| 51 | DataFormater OG/011 v1.04 | Data.1 | 4 | F3*S08 | |
| 52 | DataFormater OG/011 v1.04 | Data.3 | 4 | F3*S09 | |
| 53 | DataFormater OG/012 v1.04 | Data.1 | 4 | F3*S10 | |

*Fig. 83*

Ranging according to oligoclonality score for each of the groups

| | Score FT | | Score F3* |
|---|---|---|---|
| TCRBV19 :161 | 0.61 | TCRBV05.1 :222 | 0.52 |
| TCRBV19 :161 | 0.29 | TCRBV05.1 :225 | 0.31 |
| TCRBV08.1 :231 | 0.17 | TCRBV19 :167 | 0.25 |
| TCRBV16 :151 | 0.14 | TCRBV09 :144 | 0.21 |
| TCRBV08.1 :234 | 0.12 | TCRBV09 :147 | 0.20 |
| TCRBV05.1 :225 | 0.12 | TCRBV09 :150 | 0.20 |
| TCRBV05.2 :219 | 0.10 | TCRBV09 :153 | 0.19 |
| TCRBV08.1 :228 | 0.10 | TCRBV05.2 :213 | 0.18 |
| TCRBV05.1 :228 | 0.10 | TCRBV19 :104 | 0.17 |
| TCRBV05.2 :216 | 0.09 | TCRBV05.2 :219 | 0.14 |
| TCRBV10 :138 | 0.09 | TCRBV05.1 :228 | 0.13 |
| TCRBV05.1 :222 | 0.08 | TCRBV14 :158 | 0.13 |
| TCRBV10 :141 | 0.08 | TCRBV13 :168 | 0.12 |
| TCRBV05.2 :222 | 0.07 | TCRBV05.2 :222 | 0.11 |
| TCRBV18 :166 | 0.06 | TCRBV01 :173 | 0.11 |
| TCRBV18 :169 | 0.06 | TCRBV12 :204 | 0.10 |
| TCRBV04 :198 | 0.06 | TCRBV10 :138 | 0.10 |
| TCRBV12 :204 | 0.06 | TCRBV01 :176 | 0.10 |
| TCRBV13 :168 | 0.06 | TCRBV12 :210 | 0.10 |
| TCRBV01 :176 | 0.05 | TCRBV15 :174 | 0.10 |
| TCRBV03 :163 | 0.05 | TCRBV10 :141 | 0.10 |
| TCRBV10 :135 | 0.05 | TCRBV12 :201 | 0.10 |
| TCRBV02 :158 | 0.05 | TCRBV15 :177 | 0.09 |
| TCRBV12 :207 | 0.05 | TCRBV20 :155 | 0.09 |
| TCRBV02 :161 | 0.05 | TCRBV14 :155 | 0.08 |
| TCRBV14 :158 | 0.05 | TCRBV20 :152 | 0.08 |
| TCRBV13 :165 | 0.05 | TCRBV13 :165 | 0.08 |
| TCRBV15 :177 | 0.04 | TCRBV16 :151 | 0.08 |
| TCRBV04 :195 | 0.04 | TCRBV08.1 :231 | 0.07 |
| TCRBV05.1 :231 | 0.04 | TCRBV02 :158 | 0.07 |
| TCRBV20 :152 | 0.04 | TCRBV14 :161 | 0.07 |
| TCRBV20 :155 | 0.04 | TCRBV20 :149 | 0.07 |
| TCRBV08.2 :228 | 0.04 | TCRBV01 :179 | 0.07 |
| TCRBV01 :173 | 0.04 | TCRBV08.1 :228 | 0.07 |
| TCRBV06 :146 | 0.04 | TCRBV12 :207 | 0.07 |

*Fig. 84A*

Ranging according to oligoclonality score for each of the groups

| | Score FS | | Score F3*S |
|---|---|---|---|
| TCRBV05.1 :222 | 1.23 | TCRBV10 :138 | 0.22 |
| TCRBV05.1 :225 | 0.62 | TCRBV15 :177 | 0.21 |
| TCRBV08.1 :231 | 0.39 | TCRBV13 :168 | 0.20 |
| TCRBV08.1 :234 | 0.33 | TCRBV09 :153 | 0.20 |
| TCRBV05.1 :228 | 0.29 | TCRBV05.2 :216 | 0.20 |
| TCRBV05.2 :216 | 0.21 | TCRBV05.1 :225 | 0.17 |
| TCRBV08.1 :228 | 0.20 | TCRBV01 :176 | 0.16 |
| TCRBV05.2 :219 | 0.18 | TCRBV10 :141 | 0.15 |
| TCRBV16 :148 | 0.17 | TCRBV09 :147 | 0.15 |
| TCRBV10 :138 | 0.14 | TCRBV05.2 :213 | 0.14 |
| TCRBV20 :152 | 0.12 | TCRBV15 :174 | 0.13 |
| TCRBV10 :141 | 0.11 | TCRBV05.2 :219 | 0.12 |
| TCRBV05.2 :213 | 0.10 | TCRBV01 :173 | 0.11 |
| TCRBV13 :168 | 0.10 | TCRBV06 :146 | 0.11 |
| TCRBV15 :174 | 0.09 | TCRBV08.1 :231 | 0.11 |
| TCRBV10 :135 | 0.09 | TCRBV05.1 :228 | 0.11 |
| TCRBV16 :145 | 0.09 | TCRBV05.1 :231 | 0.11 |
| TCRBV14 :158 | 0.09 | TCRBV13 :165 | 0.10 |
| TCRBV09 :147 | 0.08 | TCRBV09 :150 | 0.10 |
| TCRBV05.2 :222 | 0.08 | TCRBV10 :135 | 0.10 |
| TCRBV16 :151 | 0.08 | TCRBV06 :149 | 0.09 |
| TCRBV20 :155 | 0.08 | TCRBV09 :144 | 0.08 |
| TCRBV15 :177 | 0.08 | TCRBV15 :171 | 0.08 |
| TCRBV08.2 :228 | 0.08 | TCRBV11 :154 | 0.08 |
| TCRBV03 :153 | 0.08 | TCRBV14 :158 | 0.08 |
| TCRBV13 :165 | 0.07 | TCRBV01 :170 | 0.08 |
| TCRBV20 :149 | 0.07 | TCRBV08.1 :228 | 0.07 |
| TCRBV07 :180 | 0.07 | TCRBV07 :180 | 0.07 |
| TCRBV14 :165 | 0.06 | TCRBV08.1 :234 | 0.07 |
| TCRBV19 :167 | 0.06 | TCRBV06 :143 | 0.07 |
| TCRBV15 :171 | 0.06 | TCRBV05.1 :222 | 0.07 |
| TCRBV08.3 :217 | 0.06 | TCRBV14 :161 | 0.06 |
| TCRBV16 :142 | 0.06 | TCRBV03 :156 | 0.06 |
| TCRBV09 :150 | 0.06 | TCRBV08.2 :228 | 0.06 |
| TCRBV06 :146 | 0.06 | TCRBV07 :183 | 0.06 |

*Fig. 84B*

| CaseS | GroupsS | TCRE |
|---|---|---|
| RT3 | 1 | 0.00 |
| RT4 | 1 | 0.00 |
| RT5 | 1 | 0.00 |
| RT6 | 1 | 0.00 |
| R11 | 1 | 0.00 |
| R12 | 1 | 0.00 |
| R13 | 1 | 0.00 |
| R14 | 1 | 0.00 |
| R15 | 1 | 0.00 |
| RS21 | 2 | 0.00 |
| RS22 | 2 | 0.00 |
| RS23 | 2 | 0.00 |
| RS24 | 2 | 0.00 |
| RS25 | 2 | 0.00 |
| R3*16 | 3 | 0.00 |
| R3*17 | 3 | 0.00 |
| R3*18 | 3 | 0.00 |
| R3*19 | 3 | 0.00 |
| R3*17 | 3 | 0.00 |
| R3*S6 | 4 | 0.00 |
| R3*S7 | 4 | 0.00 |
| R3*S8 | 4 | 0.00 |
| R3*S9 | 4 | 0.00 |
| R3*S10 | 4 | 0.00 |
| FT26 | 5 | 0.00 |
| FT27 | 5 | 0.00 |
| FT28 | 5 | 0.00 |
| FT11 | 5 | 0.00 |
| FT29 | 5 | 0.00 |
| FT12 | 5 | 0.87 |
| FT13 | 5 | 0.00 |
| FT14 | 5 | 2.61 |

Organ $\begin{cases} F=\text{liver} \\ R=\text{rate} \end{cases}$

Experimental Group $\begin{cases} T=\text{control} \\ S=\text{directly infected} \\ 3*=\text{immunized 3 times} \\ 3*S=\text{immunized 3 times, then infected!} \end{cases}$

*Fig. 85A*

| | | |
|---|---|---|
| FT15 | 5 | 0.00 |
| FS21 | 6 | 2.16 |
| FS22 | 6 | 0.00 |
| FS23 | 6 | 3.29 |
| FS24 | 6 | 0.00 |
| FS25 | 6 | 0.00 |
| F3*16 | 7 | 0.00 |
| F3*17 | 7 | 0.00 |
| F3*18 | 7 | 0.00 |
| F3*19 | 7 | 0.00 |
| F3*20 | 7 | 0.00 |
| F3*S1 | 8 | 0.00 |
| F3*S2 | 8 | 0.00 |
| F3*S3 | 8 | 0.00 |
| F3*S4 | 8 | 0.00 |
| F3*S5 | 8 | 0.00 |
| F3*S6 | 8 | 0.00 |
| F3*S7 | 8 | 0.00 |
| F3*S8 | 8 | 0.00 |
| F3*S9 | 8 | 0.00 |
| F3*S10 | 8 | 0.00 |

*Fig. 85B*

ANOVA Table for TCRBV10

| | d.f. | Sum of Squares | Mean Square | F Value | p Value | Lambda | Power |
|---|---|---|---|---|---|---|---|
| Group | 3 | 301.294 | 301.294 | 1.000 | .3734 | 3.197 | .262 |
| Organ | 1 | 345.472 | 345.472 | 3.558 | .0021 | 3.600 | .451 |
| Group + Organ | 3 | 277.666 | 277.666 | .982 | .4099 | 2.946 | .243 |
| Residue | 44 | 4146.899 | 4146.899 | | | | |

*Fig. 89A*

Means Table for TCRBV01
Effect: Group + Organ

|  | Number | Mean | Standard Dev. | Standard Err |
|---|---|---|---|---|
| T.R | 9 | 7.222 | 8.452 | 2.817 |
| T.F | 8 | 8.872 | 8.703 | 3.077 |
| S.R | 5 | 5.996 | 1.404 | .655 |
| S.F | 5 | 7.907 | .810 | .362 |
| 13*, R | 5 | 9.871 | 9.730 | 4.352 |
| 13*, F | 5 | 14.696 | 11.264 | 6.046 |
| 13*S, R | 5 | 6.113 | 3.748 | 1.676 |
| 13*S, F | 10 | 19.010 | 15.238 | 4.819 |

*Fig. 89B*

PLSD Fisher's Test for TCRBV02
Effect: Group
Significance Level: 5%

|  | Mean Diff. | Critical Diff. | p Value |
|---|---|---|---|
| T, S | 1.047 | 7.797 | .7879 |
| T, 13* | -4.385 | 7.797 | .2631 |
| T, 13*S | -6.713 | 6.931 | .0573 |
| S, 13* | -5.433 | 8.750 | .2174 |
| S, 13*S | -7.750 | 7.966 | .0565 |
| 13*, 13*S | -2.228 | 7.988 | .5600 |

*Fig. 89C*

ANOVA Table for TCRBV02

| | d.f. | Sum of Squares | Mean Square | F Value | p Value | Lambda | Power |
|---|---|---|---|---|---|---|---|
| Group | 3 | 59.308 | 19.769 | 1.781 | .1647 | 5.343 | .422 |
| Organ | 1 | 113.912 | 113.912 | 10.262 | .0025 | 10.262 | .897 |
| Group + Organ | 3 | 55.871 | 18.957 | 1.708 | .1792 | 5.123 | .406 |
| Residue | 44 | 488.432 | 11.101 | | | | |

*Fig. 89E*

Means Table for TCRBV02
Effect: Group + Organ

|  | Number | Mean | Standard Dev. | Standard Err |
|---|---|---|---|---|
| T.R | 9 | 3.490 | 2.263 | .751 |
| T.F | 8 | 6.657 | 5.551 | 1.963 |
| S.R | 5 | 6.006 | 2.337 | 1.045 |
| S.F | 5 | 5.307 | 1.494 | .864 |
| 13*, R | 5 | 3.135 | 1.630 | .729 |
| 13*, F | 5 | 10.072 | 3.968 | 1.775 |
| 13*S, R | 5 | 6.000 | 2.025 | .906 |
| 13*S, F | 10 | 10.022 | 3.518 | 1.113 |

*Fig. 89F*

PLSD Fisher's Test for TCRBV02
Effect: Group
Significance Level: 5%

|  | Mean Diff. | Critical Diff. | p Value |  |
|---|---|---|---|---|
| T, S | .265 | 2.676 | .8426 |  |
| T, 13* | -2.181 | 2.676 | .1075 |  |
| T, 13*S | -2.790 | 2.379 | .0226 | S |
| S, 13* | -2.447 | 3.003 | .1077 |  |
| S, 13*S | -3.055 | 2.471 | .0298 | S |
| 13*, 13*S | -.608 | 2.741 | .6570 |  |

*Fig. 89G*

ANOVA Table for TCRBV05.1

| | d.f. | Sum of Squares | Mean Square | F Value | p Value | Lambda | Power |
|---|---|---|---|---|---|---|---|
| Group | 3 | 2329.744 | 776.581 | 12.458 | <.0001 | 37.374 | 1.000 |
| Organ | 1 | 292.959 | 292.959 | 4.700 | .0356 | 4.700 | .555 |
| Group + Organ | 3 | 157.990 | 52.663 | .845 | .4768 | 2.535 | .213 |
| Residue | 44 | 2742.750 | 52.335 | | | | |

*Fig. 90A*

Means Table for TCRBV05.1
Effect: Group + Organ

|  | Number | Mean | Standard Dev. | Standard Err |
|---|---|---|---|---|
| T.R | 9 | 9.418 | 9.307 | 3.102 |
| T.F | 8 | 18.356 | 10.547 | 3.729 |
| S.R | 5 | 23.630 | 4.860 | 2.174 |
| S.F | 5 | 32.058 | 4.573 | 2.045 |
| 13*, R | 5 | 24.959 | 7.009 | 3.136 |
| 13*, F | 5 | 30.198 | 6.922 | 3.096 |
| 13*S, R | 5 | 20.963 | 5.018 | 2.512 |
| 13*S, F | 10 | 20.163 | 6.016 | 2.535 |

*Fig. 90B*

PLSD Fisher's Test for TCRBV05.1
Effect: Group
Significance Level: 5%

|  | Mean Diff. | Critical Diff. | p Value |  |
|---|---|---|---|---|
| T, S | -15.161 | 6.341 | <.0001 | S |
| T, 13* | -14.895 | 6.341 | <.0001 | S |
| T, 13*S | -13.753 | 5.637 | <.0001 | S |
| S, 13* | .265 | 7.116 | .9405 |  |
| S, 13*S | 1.408 | 6.496 | .6644 |  |
| 13*, 13*S | 1.143 | 6.496 | .7247 |  |

*Fig. 90C*

ANOVA Table for TCRBV05.2

| | d.f. | Sum of Squares | Mean Square | F Value | p Value | Lambda | Power |
|---|---|---|---|---|---|---|---|
| Group | 3 | 1180.456 | 395.152 | 4.395 | .0086 | 13.185 | .849 |
| Organ | 1 | 2230.335 | 2230.335 | 24.743 | <.0001 | 24.743 | 1.000 |
| Group + Organ | 3 | 453.445 | 151.148 | 1.677 | .1858 | 5.030 | .399 |
| Residue | 44 | 3966.148 | 90.140 | | | | |

*Fig. 90E*

Means Table for TCRBV05.2
Effect: Group + Organ

|       | Number | Mean   | Standard Dev. | Standard Err |
|-------|--------|--------|---------------|--------------|
| T,R   | 9      | 7.397  | 8.310         | 2.770        |
| T,F   | 8      | 14.408 | 6.948         | 2.456        |
| S,R   | 5      | 12.099 | 9.083         | 4.062        |
| S,F   | 5      | 20.831 | 9.563         | 4.277        |
| 13*, R | 5     | 12.444 | 7.334         | 3.280        |
| 13*, F | 5     | 34.650 | 11.084        | 4.957        |
| 13*S, R | 5    | 11.768 | 6.884         | 3.078        |
| 13*S, F | 10   | 28.408 | 12.840        | 4.060        |

*Fig. 90F*

PLSD Fisher's Test for TCRBV05.1
Effect: Group
Significance Level: 5%

|            | Mean Diff. | Critical Diff. | p Value |    |
|------------|------------|----------------|---------|----|
| T,S        | -5.769     | 7.626          | .1345   |    |
| T, 13*     | -12.851    | 7.626          | .0015   | S  |
| T, 13*S    | -12.165    | 6.778          | .0008   | S  |
| S, 13*     | -7.082     | 8.557          | .1024   |    |
| S, 13*S    | -8.397     | 7.812          | .1060   |    |
| 13*, 13*S  | .686       | 7.812          | .8604   |    |

*Fig. 90G*

ANOVA Table for TCRBV06.1

|  | d.f. | Sum of Squares | Mean Square | F Value | p Value | Lambda | Power |
|---|---|---|---|---|---|---|---|
| Group | 3 | 1122.158 | 374.053 | 4.322 | .0092 | 12.965 | .843 |
| Organ | 1 | 693.580 | 603.580 | 8.013 | .0069 | 8.013 | .803 |
| Group + Organ | 3 | 163.846 | 54.815 | .631 | .5988 | 1.893 | .168 |
| Residue | 45 | 3894.843 | 86.552 | | | | |

*Fig. 91A*

Means Table for TCRBV06.1
Effect: Group + Organ

|  | Number | Mean | Standard Dev. | Standard Err |
|---|---|---|---|---|
| T,R | 0 | 2.401 | 1.210 | .403 |
| T,F | 9 | 15.375 | 11.966 | 3.989 |
| S,R | 5 | 18.203 | 3.900 | 1.744 |
| S,F | 5 | 24.239 | 13.526 | 6.049 |
| 13*, R | 5 | 5.982 | 2.530 | 1.134 |
| 13*, F | 5 | 12.689 | 7.068 | 3.161 |
| 13*S, R | 5 | 11.682 | 15.563 | 6.955 |
| 13*S, F | 10 | 16.248 | 9.140 | 2.890 |

*Fig. 91B*

PLSD Fisher's Test for TCRBV06.1
Effect: Group
Significance Level: 5%

|  | Mean Diff. | Critical Diff. | p Value | |
|---|---|---|---|---|
| T, S | -12.333 | 7.390 | .0016 | S |
| T, 13* | -.448 | 7.390 | .9034 | |
| T, 13*S | -5.838 | 6.551 | .0794 | |
| S, 13* | 11.385 | 6.380 | .0065 | S |
| S, 13*S | 6.495 | 7.650 | .0941 | |
| 13*, 13*S | -5.390 | 7.650 | .1627 | |

*Fig. 91C*

ANOVA Table for TCRBV06.2

| | d.f. | Sum of Squares | Mean Square | F Value | p Value | Lambda | Power |
|---|---|---|---|---|---|---|---|
| Group | 3 | 61.854 | 20.618 | .422 | .7382 | 1.265 | .126 |
| Organ | 1 | 6.469 | 6.469 | .132 | .7177 | .132 | .064 |
| Group + Organ | 3 | 254.375 | 84.792 | 1.735 | .1734 | 5.204 | .413 |
| Residue | 44 | 2199.528 | 48.876 | | | | |

*Fig. 91E*

Means Table for TCRBV06.2  
Effect: Group + Organ

|       | Number | Mean   | Standard Dev. | Standard Err |
|-------|--------|--------|---------------|--------------|
| T.R   | 9      | 13.383 | 4.882         | 1.627        |
| T.F   | 9      | 15.148 | 6.011         | 2.004        |
| S.R   | 5      | 21.828 | 10.936        | 4.891        |
| S.F   | 5      | 12.804 | 9.454         | 4.228        |
| 13*, R | 5     | 14.720 | 7.593         | 3.396        |
| 13*, F | 5     | 16.326 | 6.149         | 2.750        |
| 13*S, R | 5    | 16.190 | 8.697         | 3.889        |
| 13*S, F | 10   | 17.919 | 4.708         | 1.489        |

*Fig. 91F*

PLSD Fisher's Test for TCRBV06.2  
Effect: Group  
Significance Level: 5%

|           | Mean Diff. | Critical Diff. | p Value |
|-----------|------------|----------------|---------|
| T, S      | -2.550     | 5.554          | .3599   |
| T, 13*    | -.758      | 5.554          | .7848   |
| T, 13*S   | -2.577     | 4.923          | .2973   |
| S, 13*    | 1.793      | 6.297          | .5692   |
| S, 13*S   | -.027      | 5.749          | .9925   |
| 13*, 13*S | -1.820     | 5.749          | .5270   |

*Fig. 91G*

ANOVA Table for TCRBV10

| | d.f. | Sum of Squares | Mean Square | F Value | p Value | Lambda | Power |
|---|---|---|---|---|---|---|---|
| Group | 3 | 27.050 | 9.017 | .181 | .9085 | .544 | .081 |
| Organ | 1 | 682.292 | 682.292 | 13.724 | .0006 | 13.724 | .967 |
| Group + Organ | 3 | 115.402 | 38.467 | .774 | .5148 | 2.321 | .198 |
| Residue | 45 | 2237.141 | 49.714 | | | | |

*Fig. 92A*

Means Table for TCRBV10
Effect: Group + Organ

|       | Number | Mean   | Standard Dev. | Standard Err |
|-------|--------|--------|---------------|--------------|
| T.R   | 9      | 8.928  | 7.974         | 2.658        |
| T.F   | 9      | 17.147 | 6.608         | 2.202        |
| S.R   | 5      | 11.331 | 5.743         | 2.506        |
| S.F   | 5      | 16.039 | 3.604         | 1.612        |
| 13*, R | 5     | 11.694 | 7.590         | 3.394        |
| 13*, F | 5     | 16.835 | 8.778         | 3.920        |
| 13*S, R | 5    | 7.509  | 2.533         | 1.133        |
| 13*S, F | 10   | 18.473 | 8.375         | 2.648        |

*Fig. 92B*

PLSD Fisher's Test for TCRBV10
Effect: Group
Significance Level: 5%

|            | Mean Diff. | Critical Diff. | p Value |
|------------|-----------|----------------|---------|
| T,S        | -1.647    | 5.601          | .5507   |
| T, 13*     | -1.728    | 5.601          | .5375   |
| T, 13*S    | -2.780    | 4.965          | .2653   |
| S, 13*     | -.081     | 6.351          | .9796   |
| S, 13*S    | -1.134    | 5.798          | .6956   |
| 13*, 13*S  | -1.053    | 5.798          | .7163   |

*Fig. 92C*

ANOVA Table for TCRBV11

| | d.f. | Sum of Squares | Mean Square | F Value | p Value | Lambda | Power |
|---|---|---|---|---|---|---|---|
| Group | 3 | 233.690 | 77.897 | 2.572 | .0661 | 7.715 | .588 |
| Organ | 1 | 2349.255 | 2349.255 | 77.562 | <.0001 | 77.562 | 1.000 |
| Group + Organ | 3 | 127.530 | 42.510 | 1.403 | .2544 | 4.210 | .338 |
| Residue | 44 | 1332.711 | 30.289 | | | | |

*Fig. 92E*

Means Table for TCRBV11
Effect: Group + Organ

|  | Number | Mean | Standard Dev. | Standard Err |
|---|---|---|---|---|
| T.R | 9 | 7.353 | 8.354 | 2.785 |
| T.F | 8 | 16.802 | 4.023 | 1.422 |
| S.R | 5 | 7.865 | 3.081 | 1.780 |
| S.F | 5 | 21.184 | 2.702 | 1.208 |
| 13*, R | 5 | 5.966 | 1.813 | .811 |
| 13*, F | 5 | 22.526 | 6.417 | 2.870 |
| 13*S, R | 5 | 9.306 | 3.977 | 1.778 |
| 13*S, F | 10 | 26.025 | 6.032 | 1.908 |

*Fig. 92F*

PLSD Fisher's Test for TCRBV11
Effect: Group
Significance Level: 5%

|  | Mean Diff. | Critical Diff. | p Value | |
|---|---|---|---|---|
| T, S | -2.735 | 4.420 | .2191 | |
| T, 13* | -2.446 | 4.420 | .2708 | |
| T, 13*S | -8.653 | 3.929 | <.0001 | S |
| S, 13* | .288 | 4.960 | .9073 | |
| S, 13*S | -5.918 | 4.528 | .0116 | S |
| 13*, 13*S | -6.206 | 4.528 | .0083 | S |

*Fig. 92G*

ANOVA Table for TCRBV14

| | d.f. | Sum of Squares | Mean Square | F Value | p Value | Lambda | Power |
|---|---|---|---|---|---|---|---|
| Group | 3 | 335.494 | 111.831 | 7.070 | .0005 | 21.210 | .978 |
| Organ | 1 | 411.359 | 411.359 | 26.006 | <.0001 | 26.006 | 1.000 |
| Group + Organ | 3 | 231.272 | 77.091 | 4.874 | .0051 | 14.621 | .890 |
| Residue | 45 | 711.807 | 15.818 | | | | |

*Fig. 93A*

Means Table for TCRBV14
Effect: Group + Organ

|       | Number | Mean   | Standard Dev. | Standard Err |
|-------|--------|--------|---------------|--------------|
| T,R   | 9      | 3.275  | 3.363         | 1.121        |
| T,F   | 8      | 8.150  | 2.423         | .808         |
| S,R   | 5      | 8.196  | 2.726         | 1.219        |
| S,F   | 5      | 6.830  | 1.772         | .792         |
| 13*, R | 5     | 5.434  | 2.510         | 1.123        |
| 13*, F | 5     | 16.608 | 7.417         | 3.317        |
| 13*S, R | 5    | 7.217  | 2.411         | 1.078        |
| 13*S, F | 10   | 15.857 | 5.412         | 1.711        |

*Fig.93B*

PLSD Fisher's Test for TCRBV14
Effect: Group
Significance Level: 5%

|            | Mean Diff. | Critical Diff. | p Value |   |
|------------|------------|----------------|---------|---|
| T,S        | -1.801     | 3.159          | .2571   |   |
| T, 13*     | -5.309     | 3.159          | .0015   | S |
| T, 13*S    | -7.264     | 2.800          | <.0001  | S |
| S, 13*     | -3.508     | 3.582          | .0547   |   |
| S, 13*S    | -5.454     | 3.270          | .0016   | S |
| 13*, 13*S  | -1.956     | 3.270          | .2347   | S |

*Fig.93C*

ANOVA Table for TCRBV15

| | d.f. | Sum of Squares | Mean Square | F Value | p Value | Lambda | Power |
|---|---|---|---|---|---|---|---|
| Group | 3 | 153.813 | 51.271 | 1.141 | .3429 | 3.424 | .279 |
| Organ | 1 | 1226.163 | 1226.163 | 27.299 | <.0001 | 27.299 | 1.000 |
| Group + Organ | 3 | 87.328 | 29.109 | .648 | .5884 | 1.944 | .171 |
| Residue | 44 | 1976.302 | 44.916 | | | | |

*Fig. 93E*

Means Table for TCRBV15
Effect: Group + Organ

|  | Number | Mean | Standard Dev. | Standard Err |
|---|---|---|---|---|
| T.R | 9 | 7.854 | 6.273 | 2.758 |
| T.F | 8 | 16.668 | 6.044 | 2.137 |
| S.R | 5 | 8.158 | 2.137 | 9.56 |
| S.F | 5 | 16.244 | 3.618 | 1.618 |
| 13*, R | 5 | 9.270 | 2.657 | 1.188 |
| 13*, F | 5 | 20.150 | 11.492 | 5.140 |
| 13*S, R | 5 | 9.082 | 4.892 | 2.188 |
| 13*S, F | 10 | 23.098 | 7.072 | 2.236 |

*Fig. 93F*

PLSD Fisher's Test for TCRBV15
Effect: Group
Significance Level: 5%

|  | Mean Diff. | Critical Diff. | p Value |  |
|---|---|---|---|---|
| T, S | .101 | 5.383 | .9700 |  |
| T, 13* | -2.708 | 5.383 | .3161 |  |
| T, 13*S | -6.424 | 4.785 | .0097 | S |
| S, 13* | -2.809 | 6.040 | .3537 |  |
| S, 13*S | -6.525 | 5.514 | .0215 | S |
| 13*, 13*S | -3.716 | 5.514 | .1814 |  |

*Fig. 93G*

ANOVA Table for TCRBV20

| | d.f. | Sum of Squares | Mean Square | F Value | p Value | Lambda | Power |
|---|---|---|---|---|---|---|---|
| Group | 3 | 326.663 | 108.888 | 1.907 | .1423 | 5.722 | .450 |
| Organ | 1 | 588.101 | 588.101 | 10.301 | .0025 | 10.301 | .888 |
| Group + Organ | 3 | 262.286 | 87.429 | 1.531 | .2197 | 4.594 | .366 |
| Residue | 44 | 2512.080 | 57.093 | | | | |

*Fig. 94A*

Means Table for TCRBV20
Effect: Group + Organ

|       | Number | Mean   | Standard Dev. | Standard Err |
|-------|--------|--------|---------------|--------------|
| T.R   | 9      | 11.820 | 7.851         | 2.617        |
| T.F   | 8      | 14.773 | 7.748         | 2.739        |
| S.R   | 5      | 16.432 | 4.136         | 1.850        |
| S.F   | 5      | 20.553 | 4.370         | 1.954        |
| 13*, R | 5     | 11.612 | 3.093         | 1.383        |
| 13*, F | 5     | 26.895 | 13.297        | 5.947        |
| 13*S, R | 5    | 11.495 | 4.683         | 2.094        |
| 13*S, F | 10   | 17.170 | 8.304         | 2.626        |

*Fig. 94B*

PLSD Fisher's Test for TCRBV20
Effect: Group
Significance Level: 5%

|            | Mean Diff. | Critical Diff. | p Value |   |
|------------|------------|----------------|---------|---|
| T, S       | -5.283     | 6.069          | .0863   |   |
| T, 13*     | -6.044     | 6.069          | .0509   |   |
| T, 13*S    | -2.068     | 5.394          | .4438   | S |
| S, 13*     | -.761      | 6.810          | .8228   |   |
| S, 13*S    | 3.214      | 6.217          | .3031   | S |
| 13*, 13*S  | 3.976      | 6.217          | .2042   |   |

*Fig. 94C*

- Only the results concerning the Gorochov index shall be detailed here. The other indices do not provide any relevant result in this study (multi-modal nature of the profiles of certain experimental units).
- ❖ The type of infection affecting the Gorochov index on average observed for the various Vb studied.
- ❖ The organ affecting the Gorochov index on average observed for various Vb studied.
- ❖ The Gorochov index observed, on average, in the various groups is not the same depending on the organ under consideration.

Results of the corresponding ANOVA: (@: with effect of interaction)

|  | Group Effect OUI | Group Effect NON |
|---|---|---|
| Group Effect OUI | 5.1{F3* (222,225) FS (222,225,228)}<br>5.2 {RS (216) F3* (213) FS (216,219) F3*S (216)}<br>7<br>8.1 {RS (231) FS (231,228)}<br>8.3 @F>>P for group 13* 13*S<br>14 @ F>>R for groups 13* and 13*S | 2<br>6<br>10 {F3*S (138)}<br>11<br>12 @ F>>R for group 13* and 13*S<br>13 {F3*S (168)}<br>15 {RS (174), F3*S(177)}<br>16<br>20 |
| Group Effect NON | 3 @ F>>R for group 13*S<br>9 {F3*(144,147,150,153) F3*S(153)}<br>18 | 1<br>4<br>8.2 |

Comment: The Vb, for which the oligoclonality index of certain peaks is greater than that of the control group, are followed by the groups in parentheses.

Fig. 95A

SYSTAT Rectangular file C:\Utilisateurs\OGp8586\Pr81OG290802.SYD,
created Thu Aug 29, 2002 at 15:24:34, contains variables:

| CASE$ | GROUPS$ | TCRBV01_ | TCRBV01_ | TCRBV01_ |
|---|---|---|---|---|
| TCRBV01_ | TCRBV01_ | TCRBV01_ | TCRBV01_ | TCRBV01_ |
| TCRBV02_ | TCRBV02_ | TCRBV02_ | TCRBV02_ | TCRBV02_ |
| TCRBV02_ | TCRBV03_ | TCRBV03_ | TCRBV03_ | TCRBV03_ |
| TCRBV03_ | TCRBV03_ | TCRBV03_ | TCRBV03_ | TCRBV03_ |
| TCRBV04_ | TCRBV04_ | TCRBV04_ | TCRBV04_ | TCRBV04_ |
| TCRBV04_ | TCRBV04_ | TCRBV04_ | TCRBV051_ | TCRBV051_ |
| TCRBV051_ | TCRBV051_ | TCRBV051_ | TCRBV051_ | TCRBV051_ |
| TCRBV052_ | TCRBV052_ | TCRBV052_ | TCRBV052_ | TCRBV052_ |
| TCRBV052_ | TCRBV052_ | TCRBV06_ | TCRBV06_ | TCRBV06_ |
| TCRBV06_ | TCRBV06_ | TCRBV06_ | TCRBV06_ | TCRBV06_ |
| TCRBV07_ | TCRBV07_ | TCRBV07_ | TCRBV07_ | TCRBV07_ |
| TCRBV07_ | TCRBV07_ | TCRBV081_ | TCRBV081_ | TCRBV081_ |
| TCRBV081_ | TCRBV081_ | TCRBV081_ | TCRBV081_ | TCRBV081_ |
| TCRBV082_ | TCRBV082_ | TCRBV082_ | TCRBV082_ | TCRBV082_ |
| TCRBV083_ | TCRBV083_ | TCRBV083_ | TCRBV083_ | TCRBV083_ |
| TCRBV083_ | TCRBV083_ | TCRBV083_ | TCRBV09_ | TCRBV09_ |
| TCRBV09_ | TCRBV09_ | TCRBV09_ | TCRBV09_ | TCRBV09_ |
| TCRBV09_ | TCRBV09_ | TCRBV10_ | TCRBV10_ | TCRBV10_ |
| TCRBV10_ | TCRBV10_ | TCRBV10_ | TCRBV10_ | TCRBV11_ |
| TCRBV11_ | TCRBV11_ | TCRBV11_ | TCRBV11_ | TCRBV11_ |
| TCRBV11_ | TCRBV11_ | TCRBV11_ | TCRBV12_ | TCRBV12_ |
| TCRBV12_ | TCRBV12_ | TCRBV12_ | TCRBV12_ | TCRBV12_ |
| TCRBV13_ | TCRBV13_ | TCRBV13_ | TCRBV13_ | TCRBV13_ |
| TCRBV13_ | TCRBV13_ | TCRBV13_ | TCRBV14_ | TCRBV14_ |
| TCRBV14_ | TCRBV14_ | TCRBV14_ | TCRBV14_ | TCRBV14_ |
| TCRBV15_ | TCRBV15_ | TCRBV15_ | TCRBV15_ | TCRBV15_ |
| TCRBV15_ | TCRBV15_ | TCRBV15_ | TCRBV16_ | TCRBV16_ |
| TCRBV16_ | TCRBV16_ | TCRBV16_ | TCRBV16_ | TCRBV16_ |
| TCRBV18_ | TCRBV18_ | TCRBV18_ | TCRBV18_ | TCRBV18_ |
| TCRBV18_ | TCRBV18_ | TCRBV18_ | TCRBV18_ | TCRBV18_ |
| TCRBV20_ | TCRBV20_ | TCRBV20_ | TCRBV20_ | TCRBV20_ |
| TCRBV20_ | TCRBV20_ | TCRBV20_ | | |

Latent Roots (Eigenvalues)

| 1 | 2 | 3 | 4 | 5 |
|---|---|---|---|---|
| 806.097 | 574.767 | 525.021 | 474.758 | 360.278 |
| 6 | 7 | 8 | 9 | 10 |
| 326.711 | 312.488 | 234.426 | 220.247 | 205.757 |
| 11 | 12 | 13 | 14 | 15 |
| 197.164 | 187.097 | 166.789 | 160.829 | 147.404 |
| 16 | 17 | 18 | 19 | 20 |
| 130.104 | 128.438 | 120.749 | 108.967 | 98.134 |
| 21 | 22 | 23 | 24 | 25 |

| | | | | |
|---|---|---|---|---|
| 90.690 | 78.013 | 76.711 | 61.271 | 59.256 |
| 26 | 27 | 28 | 29 | 30 |
| 50.362 | 48.663 | 39.763 | 37.130 | 32.355 |
| 31 | 32 | 33 | 34 | 35 |
| 29.161 | 26.169 | 24.054 | 21.550 | 20.080 |
| 36 | 37 | 38 | 39 | 40 |
| 18.509 | 17.875 | 15.007 | 13.936 | 12.903 |
| 41 | 42 | 43 | 44 | 45 |
| 11.317 | 9.508 | 8.822 | 8.187 | 7.641 |
| 46 | 47 | 48 | 49 | 50 |
| 6.640 | 5.734 | 4.707 | 4.103 | 3.624 |
| 51 | 52 | 53 | 54 | 55 |
| 3.345 | 2.374 | 0.000 | 0.000 | 0.000 |
| 56 | 57 | 58 | 59 | 60 |
| 0.000 | 0.000 | 0.000 | 0.000 | 0.000 |
| 61 | 62 | 63 | 64 | 65 |
| 0.000 | 0.000 | 0.000 | 0.000 | 0.000 |
| 66 | 67 | 68 | 69 | 70 |
| 0.000 | 0.000 | 0.000 | 0.000 | 0.000 |
| 71 | 72 | 73 | 74 | 75 |
| 0.000 | 0.000 | 0.000 | 0.000 | 0.000 |
| 76 | 77 | 78 | 79 | 80 |
| 0.000 | 0.000 | 0.000 | 0.000 | 0.000 |
| 81 | 82 | 83 | 84 | 85 |
| 0.000 | 0.000 | 0.000 | 0.000 | 0.000 |
| 86 | 87 | 88 | 89 | 90 |
| 0.000 | 0.000 | 0.000 | 0.000 | 0.000 |
| 91 | 92 | 93 | 94 | 95 |
| 0.000 | 0.000 | 0.000 | 0.000 | 0.000 |
| 96 | 97 | 98 | 99 | 100 |
| 0.000 | 0.000 | 0.000 | 0.000 | 0.000 |
| 101 | 102 | 103 | 104 | 105 |

FIG. 98C

| | | | | |
|---|---|---|---|---|
| 0.000 | 0.000 | 0.000 | 0.000 | 0.000 |
| 106 | 107 | 108 | 109 | 110 |
| 0.000 | 0.000 | 0.000 | 0.000 | 0.000 |
| 111 | 112 | 113 | 114 | 115 |
| 0.000 | 0.000 | 0.000 | 0.000 | 0.000 |
| 116 | 117 | 118 | 119 | 120 |
| 0.000 | 0.000 | 0.000 | 0.000 | 0.000 |
| 121 | 122 | 123 | 124 | 125 |
| 0.000 | 0.000 | 0.000 | 0.000 | 0.000 |
| 126 | 127 | 128 | 129 | 130 |
| 0.000 | 0.000 | 0.000 | 0.000 | 0.000 |
| 131 | 132 | 133 | 134 | 135 |
| 0.000 | 0.000 | 0.000 | 0.000 | 0.000 |
| 136 | 137 | 138 | 139 | 140 |
| 0.000 | 0.000 | 0.000 | 0.000 | 0.000 |
| 141 | 142 | 143 | 144 | 145 |
| 0.000 | 0.000 | 0.000 | 0.000 | 0.000 |
| 146 | 147 | 148 | 149 | 150 |
| 0.000 | 0.000 | 0.000 | 0.000 | 0.000 |
| 151 | 152 | 153 | 154 | 155 |
| 0.000 | 0.000 | 0.000 | 0.000 | 0.000 |
| 156 | 157 | 158 | 159 | 160 |
| 0.000 | 0.000 | 0.000 | 0.000 | 0.000 |
| 161 | 162 | 163 | 164 | 165 |
| 0.000 | 0.000 | 0.000 | 0.000 | 0.000 |
| 166 | 167 | 168 | 169 | 170 |
| 0.000 | 0.000 | 0.000 | 0.000 | 0.000 |
| 171 | 172 | 173 | 174 | 175 |
| 0.000 | 0.000 | 0.000 | 0.000 | 0.000 |
| 176 | 177 | 178 | 179 | 180 |
| 0.000 | 0.000 | 0.000 | 0.000 | 0.000 |
| 181 | 182 | 183 | 184 | 185 |

FIG. 98D

|  | | | | | |
|---|---:|---:|---:|---:|---:|
|  | 0.000 | 0.000 | 0.000 | 0.000 | 0.000 |
|  | 186 | 187 | 188 | 189 | 190 |
|  | 0.000 | 0.000 | 0.000 | 0.000 | 0.000 |
|  | 191 | 192 | 193 | | |
|  | 0.000 | 0.000 | 0.000 | | |

Component loadings

|  | 1 | 2 | 3 | 4 | 5 |
|---|---:|---:|---:|---:|---:|
| TCRBV01_6 | -0.075 | -0.020 | -0.031 | 0.142 | 0.070 |
| TCRBV01_7 | 0.586 | 0.776 | -0.084 | 0.178 | 0.101 |
| TCRBV01_8 | -2.381 | -1.196 | 4.073 | -4.774 | 2.594 |
| TCRBV01_9 | 1.202 | 2.269 | 1.717 | 2.764 | 1.996 |
| TCRBV01_10 | 3.454 | 2.257 | 2.246 | 1.329 | 1.040 |
| TCRBV01_11 | 0.055 | 2.659 | -0.708 | 1.386 | -0.059 |
| TCRBV01_12 | -0.258 | 1.305 | -0.889 | 0.074 | 0.185 |
| TCRBV01_13 | -0.223 | 0.178 | -0.392 | 0.102 | -0.044 |
| TCRBV01_14 | -0.021 | 0.016 | -0.050 | 0.010 | -0.016 |
| TCRBV02_6 | 0.750 | -0.283 | -0.629 | -0.090 | -0.108 |
| TCRBV02_7 | 0.480 | 0.642 | 0.637 | -0.136 | -0.988 |
| TCRBV02_8 | 0.059 | 0.586 | 0.088 | 0.089 | 0.736 |
| TCRBV02_9 | 1.130 | 0.110 | 0.203 | 0.181 | -1.461 |
| TCRBV02_10 | -0.113 | -0.187 | 0.290 | -0.738 | 0.606 |
| TCRBV02_11 | -0.724 | -0.097 | 1.786 | -0.013 | 0.307 |
| TCRBV02_12 | -0.450 | -0.019 | 0.601 | -0.160 | 0.175 |
| TCRBV02_13 | -0.236 | -0.160 | 0.201 | -0.296 | 0.196 |
| TCRBV03_4 | -0.023 | -0.015 | -0.082 | 0.030 | 0.014 |
| TCRBV03_5 | -0.120 | -0.002 | -0.121 | -0.003 | 0.061 |
| TCRBV03_6 | 2.225 | 0.178 | -0.733 | -1.112 | 0.066 |
| TCRBV03_7 | 2.053 | 1.677 | -0.686 | -0.785 | 0.612 |
| TCRBV03_8 | 3.224 | 2.522 | -0.052 | -1.015 | 1.279 |
| TCRBV03_9 | 4.341 | 2.926 | -1.482 | -0.044 | 1.981 |
| TCRBV03_10 | -3.235 | 0.499 | 3.479 | -1.136 | 4.894 |
| TCRBV03_11 | -5.143 | 0.869 | 1.720 | 2.027 | 0.546 |
| TCRBV03_12 | -0.448 | 0.066 | 1.408 | 1.085 | -1.392 |
| TCRBV03_13 | -0.536 | -0.476 | 2.430 | 2.163 | -2.194 |
| TCRBV04_6 | 0.012 | -0.001 | -0.019 | -0.011 | 0.005 |
| TCRBV04_7 | 1.152 | -0.155 | -0.030 | -0.668 | 0.049 |
| TCRBV04_8 | 1.873 | 0.011 | 0.527 | -0.928 | 0.155 |
| TCRBV04_9 | 4.587 | -1.410 | 0.450 | -1.396 | 0.161 |
| TCRBV04_10 | 5.214 | -0.729 | -0.519 | -0.539 | 1.093 |
| TCRBV04_11 | -2.756 | 0.589 | -1.756 | 1.854 | -0.619 |
| TCRBV04_12 | -3.817 | 0.894 | -0.456 | 1.589 | 1.304 |
| TCRBV04_13 | -3.121 | 1.805 | 0.381 | 2.556 | -2.504 |
| TCRBV04_14 | -3.131 | -1.158 | 1.410 | -2.431 | 0.426 |
| TCRBV04_15 | -0.012 | 0.154 | 0.012 | -0.025 | -0.070 |
| TCRBV051_5 | 0.174 | 0.196 | -0.112 | -0.095 | 0.048 |
| TCRBV051_6 | 0.215 | -0.029 | 0.032 | 0.178 | 0.642 |
| TCRBV051_7 | -0.042 | -0.512 | -0.317 | -0.818 | 1.006 |
| TCRBV051_8 | 5.708 | -11.263 | 7.492 | 6.584 | 0.181 |
| TCRBV051_9 | 0.294 | 1.095 | -1.810 | 3.037 | -1.682 |
| TCRBV051_10 | -0.617 | 5.252 | -3.907 | -2.022 | -1.555 |
| TCRBV051_11 | -2.015 | 2.799 | 2.297 | -6.363 | -1.086 |
| TCRBV051_12 | -0.959 | 3.191 | -0.695 | -1.023 | -0.729 |
| TCRBV051_13 | 0.084 | 0.240 | -0.060 | -0.185 | -0.127 |
| TCRBV052_6 | 0.340 | 0.857 | -0.295 | -0.436 | -0.045 |
| TCRBV052_7 | 0.742 | 2.607 | 0.258 | 0.375 | -0.707 |
| TCRBV052_8 | -2.966 | 5.924 | 6.078 | 3.420 | -3.444 |
| TCRBV052_9 | 1.864 | -0.893 | 1.072 | -0.675 | 0.061 |

| | | | | | |
|---|---|---|---|---|---|
| TCRBV052_10 | 1.482 | -2.328 | -2.449 | -0.869 | -0.364 |
| TCRBV052_11 | 1.183 | -2.592 | -0.353 | -1.828 | 1.509 |
| TCRBV052_12 | 0.184 | -2.206 | -1.170 | -0.621 | 0.008 |
| TCRBV052_13 | 0.013 | -0.400 | -0.221 | -0.073 | -0.320 |
| TCRBV06_5 | 0.028 | 0.045 | -0.011 | -0.063 | -0.023 |
| TCRBV06_6 | 0.893 | 0.443 | -0.309 | 0.021 | 0.249 |
| TCRBV06_7 | 2.017 | 1.415 | 0.546 | 0.161 | -0.133 |
| TCRBV06_8 | 2.766 | 1.952 | 1.966 | 0.511 | 0.512 |
| TCRBV06_9 | 3.375 | 1.408 | 2.821 | -3.418 | 2.216 |
| TCRBV06_10 | -2.099 | 2.397 | -0.216 | 1.039 | 1.658 |
| TCRBV06_11 | -2.924 | 1.046 | 1.312 | 1.670 | 0.587 |
| TCRBV06_12 | -1.604 | -0.326 | -0.042 | 1.137 | 0.619 |
| TCRBV06_13 | -0.114 | -0.137 | -0.185 | 0.152 | 0.181 |
| TCRBV07_5 | 0.008 | 0.028 | -0.008 | -0.007 | -0.006 |
| TCRBV07_6 | 0.837 | 0.060 | 1.858 | 1.278 | -1.079 |
| TCRBV07_7 | 1.214 | -0.479 | 3.067 | -1.119 | -0.853 |
| TCRBV07_8 | 1.397 | 2.345 | 0.393 | 0.465 | 1.264 |
| TCRBV07_9 | 4.717 | 2.550 | 2.366 | -0.826 | 1.030 |
| TCRBV07_10 | -0.442 | 2.391 | -0.665 | 0.761 | 3.003 |
| TCRBV07_11 | -3.185 | 0.834 | -0.280 | 0.043 | 1.876 |
| TCRBV07_12 | -1.960 | 0.518 | -0.716 | 0.657 | 0.453 |
| TCRBV07_13 | -0.246 | -0.005 | -0.134 | -0.042 | 0.180 |
| TCRBV081_5 | -0.014 | -0.039 | 0.066 | 0.071 | 0.088 |
| TCRBV081_6 | -0.233 | 0.804 | -0.102 | -0.341 | 0.688 |
| TCRBV081_7 | 0.704 | -0.501 | 0.138 | -0.835 | 2.223 |
| TCRBV081_8 | 0.540 | -0.086 | 1.200 | 0.121 | 0.646 |
| TCRBV081_9 | 3.830 | -4.333 | -0.332 | -1.541 | -0.526 |
| TCRBV081_10 | -1.574 | 1.153 | -1.559 | 2.277 | -1.302 |
| TCRBV081_11 | -2.194 | 2.038 | 0.379 | 0.551 | -0.926 |
| TCRBV081_12 | -1.059 | 0.963 | 0.211 | -0.303 | -0.892 |
| TCRBV082_4 | 0.424 | -0.358 | -0.028 | -0.768 | -0.292 |
| TCRBV082_5 | 1.519 | -1.085 | -0.387 | -2.354 | -0.715 |
| TCRBV082_6 | 1.924 | -0.687 | 0.185 | -1.745 | -0.622 |
| TCRBV082_7 | 4.198 | -2.368 | 1.356 | -4.012 | -2.978 |
| TCRBV082_8 | -1.227 | 1.076 | -0.107 | 1.819 | -0.476 |
| TCRBV082_9 | -3.201 | 2.555 | -0.558 | 3.505 | 2.871 |
| TCRBV082_10 | -2.699 | 0.852 | -0.631 | 2.618 | 1.452 |
| TCRBV082_11 | -0.938 | 0.015 | 0.169 | 0.937 | 0.760 |
| TCRBV083_4 | -0.014 | -0.041 | 0.169 | 0.163 | -0.147 |
| TCRBV083_5 | -0.068 | 0.075 | 0.105 | -0.232 | -0.108 |
| TCRBV083_6 | 0.507 | -0.204 | -0.849 | -0.544 | -0.608 |
| TCRBV083_7 | -0.108 | -0.302 | 1.102 | -0.398 | 1.583 |
| TCRBV083_8 | 0.297 | 0.863 | 0.017 | -1.155 | 1.218 |
| TCRBV083_9 | 0.473 | 0.115 | -1.272 | 0.152 | 0.523 |
| TCRBV083_10 | -0.565 | 0.494 | -0.172 | 0.803 | -0.014 |
| TCRBV083_11 | -0.472 | -0.205 | 1.392 | 0.772 | -1.418 |
| TCRBV083_12 | -0.050 | -0.797 | -0.492 | 0.439 | -1.028 |
| TCRBV09_5 | -0.130 | -0.039 | 0.139 | 0.133 | 0.079 |
| TCRBV09_6 | 0.040 | -0.080 | -0.402 | 0.148 | 0.444 |
| TCRBV09_7 | 0.934 | -0.535 | -0.164 | -0.246 | 2.171 |
| TCRBV09_8 | 0.369 | -0.995 | 2.707 | 4.763 | 4.320 |
| TCRBV09_9 | 2.212 | -0.760 | 4.327 | 2.838 | 3.010 |
| TCRBV09_10 | 2.774 | 3.177 | 0.449 | -2.120 | 3.543 |
| TCRBV09_11 | -1.487 | 2.603 | 6.703 | -3.932 | -5.167 |
| TCRBV09_12 | -0.264 | 3.204 | -0.360 | -1.573 | -1.144 |
| TCRBV09_13 | 0.317 | 0.847 | -0.183 | -0.596 | -0.481 |
| TCRBV09_14 | 0.100 | 0.111 | -0.013 | -0.204 | -0.066 |
| TCRBV09_15 | 0.090 | -0.012 | 0.013 | -0.019 | -0.014 |
| TCRBV10_6 | 0.486 | 0.626 | -0.103 | -0.518 | -0.360 |
| TCRBV10_7 | 0.830 | 1.733 | 1.173 | 1.028 | -1.646 |
| TCRBV10_8 | 1.789 | 1.616 | -0.162 | 0.700 | -0.176 |
| TCRBV10_9 | -3.735 | -1.632 | 0.512 | -2.124 | 0.498 |
| TCRBV10_10 | -0.813 | -1.518 | 0.188 | 0.424 | 0.368 |
| TCRBV10_11 | 1.331 | -0.607 | -0.813 | 0.275 | 0.931 |

*FIG. 99A*

| | | | | | |
|---|---|---|---|---|---|
| TCRBV10_12 | 0.123 | -0.210 | -0.756 | 0.200 | 0.378 |
| TCRBV10_13 | -0.011 | -0.007 | -0.040 | 0.015 | 0.007 |
| TCRBV11_5 | 0.054 | -0.171 | -0.024 | 0.112 | 0.227 |
| TCRBV11_6 | 0.645 | 0.491 | 0.188 | -0.714 | 0.376 |
| TCRBV11_7 | 1.025 | 1.292 | 1.255 | 0.194 | -0.196 |
| TCRBV11_8 | 0.761 | 1.916 | 2.296 | -1.473 | -0.143 |
| TCRBV11_9 | 3.448 | 1.820 | 5.538 | -0.829 | 0.968 |
| TCRBV11_10 | -0.317 | 1.741 | 0.140 | 1.767 | 1.806 |
| TCRBV11_11 | -1.405 | 1.169 | -1.376 | 0.594 | 1.496 |
| TCRBV11_12 | -1.177 | 0.105 | -1.167 | 1.265 | 0.817 |
| TCRBV11_13 | -0.626 | -0.073 | -0.722 | 0.205 | 0.474 |
| TCRBV11_14 | -0.051 | -0.033 | -0.180 | 0.066 | 0.030 |
| TCRBV11_15 | -0.019 | -0.012 | -0.067 | 0.024 | 0.011 |
| TCRBV12_4 | -0.057 | 0.257 | 0.160 | 0.162 | -0.221 |
| TCRBV12_5 | 1.293 | 0.663 | 2.995 | 0.630 | -3.022 |
| TCRBV12_6 | 2.748 | 1.366 | 1.113 | -1.987 | 1.080 |
| TCRBV12_7 | 3.631 | 0.361 | 0.059 | -2.201 | 1.916 |
| TCRBV12_8 | 1.486 | -0.394 | -3.294 | -0.997 | 0.698 |
| TCRBV12_9 | -4.150 | -1.433 | -2.887 | 2.225 | -0.539 |
| TCRBV12_10 | -1.210 | -0.525 | 1.600 | 1.272 | -0.263 |
| TCRBV12_11 | -3.118 | -0.274 | 0.050 | 0.649 | 0.371 |
| TCRBV12_12 | -0.622 | -0.022 | 0.204 | 0.248 | -0.021 |
| TCRBV13_5 | -0.020 | -0.007 | -0.107 | 0.019 | 0.053 |
| TCRBV13_6 | 0.236 | 0.737 | 0.059 | -1.254 | -0.553 |
| TCRBV13_7 | 1.220 | -0.566 | -1.444 | -1.137 | 2.591 |
| TCRBV13_8 | 1.117 | -0.003 | -1.307 | 0.057 | 1.241 |
| TCRBV13_9 | 0.093 | 0.101 | 4.513 | 4.666 | -4.488 |
| TCRBV13_10 | -2.026 | 0.461 | -0.842 | -1.267 | 1.472 |
| TCRBV13_11 | -0.556 | -0.611 | -0.561 | -1.254 | -0.605 |
| TCRBV13_12 | -0.312 | -0.035 | -0.263 | 0.081 | 0.148 |
| TCRBV13_13 | 0.248 | -0.076 | -0.048 | 0.088 | 0.140 |
| TCRBV14_5 | 0.002 | 0.043 | 0.128 | -0.072 | -0.191 |
| TCRBV14_6 | 0.560 | -0.013 | -0.866 | -0.723 | 0.361 |
| TCRBV14_7 | -0.886 | 0.111 | 0.110 | -0.734 | -0.876 |
| TCRBV14_8 | 2.788 | -0.379 | -0.601 | -0.066 | -0.369 |
| TCRBV14_9 | 0.982 | -0.783 | -0.866 | 3.516 | 0.367 |
| TCRBV14_10 | -1.647 | 0.192 | 1.058 | -1.735 | 0.565 |
| TCRBV14_11 | -1.420 | 0.784 | 1.203 | -0.363 | -0.069 |
| TCRBV14_12 | -0.314 | 0.072 | -0.065 | 0.145 | 0.144 |
| TCRBV14_13 | -0.064 | -0.026 | -0.101 | 0.031 | 0.067 |
| TCRBV15_4 | -0.048 | 0.005 | -0.098 | 0.069 | 0.058 |
| TCRBV15_5 | 0.876 | -1.126 | -0.311 | 0.027 | 1.451 |
| TCRBV15_6 | 1.635 | 0.164 | 0.742 | -0.557 | 1.197 |
| TCRBV15_7 | 2.958 | 1.462 | 1.759 | 0.217 | 1.348 |
| TCRBV15_8 | 4.711 | 2.103 | 2.764 | 0.244 | 1.387 |
| TCRBV15_9 | -1.609 | 3.526 | 3.496 | 0.975 | -0.027 |
| TCRBV15_10 | -3.220 | 1.441 | -1.397 | 0.340 | 0.671 |
| TCRBV15_11 | -2.089 | 0.535 | -1.100 | 0.108 | -0.046 |
| TCRBV15_12 | -0.876 | 0.132 | 0.026 | -0.212 | -0.172 |
| TCRBV16_5 | -0.004 | 0.063 | 0.143 | 0.057 | -0.221 |
| TCRBV16_6 | 0.740 | -0.458 | 0.685 | 0.961 | 0.315 |
| TCRBV16_7 | 4.029 | 0.612 | 0.870 | 0.467 | 0.419 |
| TCRBV16_8 | 5.524 | 3.170 | -1.084 | 0.257 | -1.066 |
| TCRBV16_9 | 6.852 | 5.592 | -1.963 | 1.947 | -1.891 |
| TCRBV16_10 | 0.165 | 3.517 | 0.669 | 2.334 | -1.033 |
| TCRBV16_11 | -3.812 | -1.117 | 3.607 | 1.146 | 4.580 |
| TCRBV16_12 | -8.256 | -2.143 | 5.834 | -6.750 | 1.526 |
| TCRBV16_13 | -0.058 | -0.024 | 0.040 | 0.085 | -0.063 |
| TCRBV18_3 | 0.030 | -0.017 | -0.003 | -0.005 | 0.009 |
| TCRBV18_4 | 0.043 | -0.147 | 0.188 | -0.730 | 0.278 |
| TCRBV18_5 | 0.125 | 0.793 | 1.558 | -0.021 | -0.578 |
| TCRBV18_6 | -1.454 | 1.826 | 3.098 | -1.120 | -0.762 |
| TCRBV18_7 | -0.152 | 3.168 | 2.247 | 1.449 | 1.188 |

*FIG. 99B*

|          |        |        |        |        |        |
|----------|--------|--------|--------|--------|--------|
| TCRBV18_8 | 1.814 | 5.078 | -0.855 | -0.154 | 3.140 |
| TCRBV18_9 | -1.031 | 1.918 | 0.229 | 1.614 | 3.512 |
| TCRBV18_10 | -0.094 | 1.019 | -0.043 | 1.279 | 1.501 |
| TCRBV18_11 | -0.786 | -0.011 | -0.531 | 0.647 | 1.080 |
| TCRBV18_12 | -0.061 | 0.022 | 0.078 | 0.163 | -0.112 |
| TCRBV18_13 | 0.049 | -0.009 | -0.017 | -0.010 | 0.025 |
| TCRBV20_5 | 0.006 | -0.081 | 0.103 | 0.066 | 0.252 |
| TCRBV20_6 | 0.820 | -0.019 | 0.545 | 0.203 | -0.182 |
| TCRBV20_7 | 1.733 | 0.721 | 0.380 | 0.515 | -0.112 |
| TCRBV20_8 | 3.344 | 1.243 | 1.094 | -0.664 | 0.208 |
| TCRBV20_9 | 3.148 | 2.159 | 1.851 | 1.730 | 1.856 |
| TCRBV20_10 | -0.717 | 3.433 | 1.768 | -1.723 | 0.168 |
| TCRBV20_11 | -3.744 | 1.517 | 1.836 | 0.103 | 0.433 |
| TCRBV20_12 | -1.968 | 0.750 | -0.669 | 0.580 | 0.447 |
| TCRBV20_13 | -0.245 | -1.482 | -0.948 | 0.345 | 2.751 |
| TCRBV20_14 | -0.039 | 0.004 | -0.079 | 0.056 | 0.047 |
|  | 6 | 7 | 8 | 9 | 10 |
| TCRBV01_6 | 0.021 | -0.137 | -0.052 | -0.005 | -0.092 |
| TCRBV01_7 | -0.643 | 0.055 | 0.055 | 0.226 | 0.238 |
| TCRBV01_8 | 0.786 | -2.649 | 0.542 | 2.361 | -0.491 |
| TCRBV01_9 | 0.085 | 0.952 | -0.612 | 2.294 | 0.205 |
| TCRBV01_10 | -0.117 | 1.597 | -0.377 | -1.762 | -0.096 |
| TCRBV01_11 | 2.327 | 0.810 | 0.368 | -1.797 | 1.295 |
| TCRBV01_12 | 0.734 | 0.415 | -0.371 | -0.381 | 0.648 |
| TCRBV01_13 | 0.489 | -0.254 | 0.165 | -0.219 | 0.124 |
| TCRBV01_14 | 0.075 | -0.054 | 0.026 | -0.037 | -0.002 |
| TCRBV02_6 | -0.411 | -0.685 | -0.233 | 0.366 | 0.110 |
| TCRBV02_7 | -0.375 | -0.363 | 0.367 | 0.450 | -0.673 |
| TCRBV02_8 | -1.359 | -0.407 | -0.058 | -0.717 | 0.158 |
| TCRBV02_9 | -0.206 | 0.488 | -2.104 | 0.418 | 0.067 |
| TCRBV02_10 | -1.294 | -0.476 | -0.688 | -0.459 | 0.204 |
| TCRBV02_11 | -0.075 | 0.083 | 0.450 | 0.138 | -0.089 |
| TCRBV02_12 | 0.488 | 0.385 | -0.049 | 0.021 | -0.524 |
| TCRBV02_13 | 0.142 | -0.078 | 0.275 | 0.192 | 0.082 |
| TCRBV03_4 | 0.080 | 0.027 | 0.053 | -0.011 | 0.017 |
| TCRBV03_5 | 0.060 | 0.097 | 0.112 | -0.004 | -0.062 |
| TCRBV03_6 | -0.107 | 1.055 | -0.342 | 0.821 | -0.548 |
| TCRBV03_7 | 0.146 | 1.148 | -0.772 | 0.402 | -0.358 |
| TCRBV03_8 | 0.035 | 1.190 | -1.144 | 2.683 | -0.290 |
| TCRBV03_9 | 0.647 | 1.593 | -1.654 | 1.464 | 0.050 |
| TCRBV03_10 | 2.574 | -2.731 | 1.180 | -0.028 | -0.095 |
| TCRBV03_11 | 1.653 | -1.677 | -2.411 | -1.695 | 2.068 |
| TCRBV03_12 | 0.457 | 0.061 | 1.460 | -1.841 | 0.257 |
| TCRBV03_13 | -1.787 | -0.027 | 3.263 | -1.111 | 0.788 |
| TCRBV04_6 | 0.037 | 0.015 | 0.031 | 0.040 | 0.044 |
| TCRBV04_7 | -0.299 | 0.208 | -0.066 | 0.153 | 0.939 |
| TCRBV04_8 | 0.213 | 0.582 | -0.761 | -0.070 | 1.250 |
| TCRBV04_9 | -0.141 | 1.267 | -0.328 | -1.489 | 1.663 |
| TCRBV04_10 | -0.590 | 0.912 | -0.715 | -1.192 | 0.128 |
| TCRBV04_11 | 0.112 | -0.805 | 0.930 | -0.875 | -1.657 |
| TCRBV04_12 | 0.160 | 0.155 | 0.849 | 0.034 | -2.181 |
| TCRBV04_13 | 0.079 | -0.716 | -0.245 | 3.168 | -0.196 |
| TCRBV04_14 | 0.515 | -1.584 | 0.155 | 0.054 | 0.211 |
| TCRBV04_15 | -0.087 | -0.034 | 0.150 | 0.177 | -0.200 |
| TCRBV051_5 | -0.106 | 0.048 | 0.089 | -0.068 | 0.171 |
| TCRBV051_6 | 0.029 | 0.318 | 0.252 | -0.142 | 0.301 |
| TCRBV051_7 | -0.159 | 0.221 | 0.309 | 0.500 | 1.070 |
| TCRBV051_8 | 2.572 | -2.042 | -2.164 | 0.044 | -0.762 |
| TCRBV051_9 | 4.444 | -1.496 | -0.137 | 2.643 | -0.465 |
| TCRBV051_10 | -1.104 | -0.084 | 0.969 | 1.300 | -1.749 |
| TCRBV051_11 | -0.987 | 0.698 | 2.606 | -1.346 | -0.209 |
| TCRBV051_12 | -1.048 | 0.469 | -0.142 | 0.044 | -1.542 |

*FIG. 99C*

| | | | | | |
|---|---|---|---|---|---|
| TCRBV051_13 | -0.111 | 0.030 | 0.013 | -0.028 | 0.073 |
| TCRBV052_6 | -0.429 | -0.125 | 0.159 | 0.032 | -0.196 |
| TCRBV052_7 | -1.586 | -1.674 | -0.624 | 0.571 | -0.045 |
| TCRBV052_8 | -4.403 | -0.485 | -3.190 | 0.378 | 0.467 |
| TCRBV052_9 | 1.889 | -2.483 | -0.890 | 2.997 | -5.603 |
| TCRBV052_10 | 2.085 | -1.036 | 1.997 | 0.374 | 0.520 |
| TCRBV052_11 | 3.685 | 2.322 | 3.163 | -1.554 | 1.262 |
| TCRBV052_12 | 2.094 | 1.373 | 1.268 | 0.039 | 0.557 |
| TCRBV052_13 | 0.194 | 0.267 | -0.089 | 0.109 | -0.072 |
| TCRBV06_5 | -0.028 | 0.012 | -0.015 | -0.010 | 0.028 |
| TCRBV06_6 | -0.054 | -0.562 | 0.235 | 0.175 | -0.085 |
| TCRBV06_7 | -0.102 | -0.502 | 0.664 | 0.892 | -0.794 |
| TCRBV06_8 | -1.117 | 0.072 | 1.946 | -0.955 | 0.019 |
| TCRBV06_9 | 3.021 | -2.951 | 1.747 | -1.565 | -0.637 |
| TCRBV06_10 | 2.419 | 1.433 | -1.640 | -0.765 | 1.583 |
| TCRBV06_11 | -0.259 | 1.838 | -1.574 | 1.468 | 1.021 |
| TCRBV06_12 | -0.036 | 1.358 | -1.405 | 1.428 | 0.635 |
| TCRBV06_13 | -0.086 | 0.037 | -0.213 | 0.012 | 0.059 |
| TCRBV07_5 | -0.005 | -0.002 | 0.019 | 0.017 | -0.024 |
| TCRBV07_6 | -0.827 | -0.235 | 1.877 | -0.943 | 1.078 |
| TCRBV07_7 | 3.084 | 0.756 | -0.478 | -1.146 | 0.282 |
| TCRBV07_8 | -1.780 | -0.387 | -1.115 | 2.083 | 1.386 |
| TCRBV07_9 | 0.335 | -2.246 | -0.097 | 0.479 | -1.363 |
| TCRBV07_10 | 1.901 | 1.229 | -1.259 | -0.785 | 0.280 |
| TCRBV07_11 | 1.186 | 0.419 | 0.927 | 0.775 | 0.062 |
| TCRBV07_12 | 0.030 | 1.034 | -0.156 | 0.279 | 0.165 |
| TCRBV07_13 | -0.167 | 0.167 | 0.027 | -0.079 | -0.040 |
| TCRBV081_5 | -0.009 | 0.090 | 0.005 | -0.140 | 0.041 |
| TCRBV081_6 | -0.289 | 0.625 | 1.094 | -0.524 | 0.273 |
| TCRBV081_7 | -1.016 | 2.906 | 1.137 | -0.857 | -0.546 |
| TCRBV081_8 | -1.066 | 2.816 | 0.724 | -0.342 | -0.803 |
| TCRBV081_9 | -2.867 | 0.115 | -1.058 | -0.081 | -0.371 |
| TCRBV081_10 | 3.775 | -5.061 | -0.414 | 0.308 | 0.164 |
| TCRBV081_11 | 1.486 | -1.138 | -0.736 | 0.953 | 0.983 |
| TCRBV081_12 | -0.015 | -0.355 | -0.752 | 0.683 | 0.259 |
| TCRBV082_4 | 0.055 | -0.029 | 0.046 | -0.051 | 0.638 |
| TCRBV082_5 | -0.344 | -0.203 | -0.521 | 0.137 | 1.641 |
| TCRBV082_6 | -0.074 | -0.440 | -0.570 | 0.468 | 1.114 |
| TCRBV082_7 | 0.263 | -0.594 | -0.517 | -0.195 | 2.755 |
| TCRBV082_8 | 0.554 | -0.492 | -0.254 | 0.195 | -1.583 |
| TCRBV082_9 | 0.305 | 0.673 | 0.717 | -0.634 | -2.363 |
| TCRBV082_10 | -0.735 | 0.388 | 0.784 | 0.019 | -1.785 |
| TCRBV082_11 | -0.024 | 0.696 | 0.315 | 0.061 | -0.418 |
| TCRBV083_4 | -0.131 | 0.003 | 0.257 | -0.085 | 0.044 |
| TCRBV083_5 | -0.025 | -0.087 | -0.036 | 0.450 | 0.165 |
| TCRBV083_6 | 0.327 | -0.057 | 0.164 | 0.304 | -0.026 |
| TCRBV083_7 | 0.946 | 0.272 | 1.107 | -1.423 | -0.272 |
| TCRBV083_8 | 0.428 | -0.485 | -0.866 | -0.517 | -0.317 |
| TCRBV083_9 | -0.913 | -0.250 | 0.379 | 0.158 | -1.019 |
| TCRBV083_10 | -1.367 | -0.538 | -0.083 | 0.389 | 0.819 |
| TCRBV083_11 | 0.537 | 1.008 | -0.303 | 0.126 | 0.443 |
| TCRBV083_12 | 0.197 | 0.136 | -0.619 | 0.598 | 0.164 |
| TCRBV09_5 | -0.047 | 0.092 | -0.073 | -0.194 | -0.105 |
| TCRBV09_6 | 0.079 | 0.096 | 0.119 | 0.218 | 0.618 |
| TCRBV09_7 | -0.426 | -0.792 | -0.658 | 0.464 | 1.475 |
| TCRBV09_8 | -1.150 | 0.751 | -0.059 | 2.114 | 2.512 |
| TCRBV09_9 | -1.427 | -1.220 | 0.603 | 0.310 | 1.771 |
| TCRBV09_10 | -3.653 | 0.761 | -1.931 | -0.265 | -0.570 |
| TCRBV09_11 | 2.346 | 4.886 | -2.610 | -0.817 | -1.496 |
| TCRBV09_12 | -0.794 | -0.147 | 0.193 | 1.915 | -2.329 |
| TCRBV09_13 | -0.370 | -0.153 | 0.008 | 0.403 | -0.513 |
| TCRBV09_14 | -0.142 | -0.044 | -0.045 | 0.034 | -0.044 |
| TCRBV09_15 | -0.033 | -0.053 | -0.031 | 0.006 | 0.036 |
| TCRBV10_6 | -0.011 | -0.025 | 0.240 | -0.378 | -0.486 |

*FIG. 99D*

| | | | | | |
|---|---|---|---|---|---|
| TCRBV10_7 | -0.846 | -0.571 | -0.083 | -0.103 | -0.801 |
| TCRBV10_8 | -1.940 | -1.965 | 0.318 | 0.191 | -1.208 |
| TCRBV10_9 | -3.228 | -2.858 | -3.466 | -3.201 | -0.140 |
| TCRBV10_10 | 0.905 | 1.209 | 1.031 | 1.595 | 0.029 |
| TCRBV10_11 | 3.868 | 3.072 | 1.212 | 0.989 | 1.470 |
| TCRBV10_12 | 1.212 | 1.125 | 0.722 | 0.912 | 1.126 |
| TCRBV10_13 | 0.039 | 0.013 | 0.026 | -0.005 | 0.008 |
| TCRBV11_5 | -0.050 | -0.045 | -0.156 | 0.081 | -0.219 |
| TCRBV11_6 | -0.178 | -0.975 | -0.254 | 0.425 | 0.322 |
| TCRBV11_7 | -0.707 | -0.515 | -0.275 | 0.313 | 0.285 |
| TCRBV11_8 | 0.365 | -1.932 | -0.336 | 1.796 | 0.859 |
| TCRBV11_9 | 1.232 | 1.065 | -2.009 | -1.357 | -1.209 |
| TCRBV11_10 | 0.552 | 0.504 | 1.077 | 0.352 | 0.806 |
| TCRBV11_11 | 1.134 | 0.543 | 1.004 | -0.589 | 0.380 |
| TCRBV11_12 | 1.027 | 1.424 | 0.213 | -0.171 | 0.292 |
| TCRBV11_13 | 0.143 | 0.584 | 0.324 | -0.137 | 0.260 |
| TCRBV11_14 | 0.175 | 0.060 | 0.115 | -0.023 | 0.038 |
| TCRBV11_15 | 0.065 | 0.022 | 0.043 | -0.009 | 0.014 |
| TCRBV12_4 | -0.150 | 0.055 | -0.102 | 0.270 | -0.033 |
| TCRBV12_5 | -1.571 | 0.588 | 3.528 | -0.107 | 1.233 |
| TCRBV12_6 | -0.568 | 1.431 | 0.523 | 0.279 | 0.579 |
| TCRBV12_7 | -0.956 | 1.053 | 0.361 | 2.507 | -0.079 |
| TCRBV12_8 | -0.159 | 0.382 | -0.103 | 1.866 | 0.641 |
| TCRBV12_9 | -0.056 | -3.527 | -0.407 | -0.837 | 0.557 |
| TCRBV12_10 | 2.350 | 1.956 | -2.592 | -4.345 | -3.795 |
| TCRBV12_11 | 0.881 | -1.674 | -0.794 | 0.260 | 0.800 |
| TCRBV12_12 | 0.230 | -0.264 | -0.413 | 0.107 | 0.098 |
| TCRBV13_5 | 0.076 | 0.008 | 0.067 | 0.044 | 0.033 |
| TCRBV13_6 | 2.347 | 1.421 | -1.265 | -0.081 | -0.483 |
| TCRBV13_7 | 0.890 | -1.644 | -0.824 | 0.685 | -1.078 |
| TCRBV13_8 | -2.806 | -0.933 | 0.717 | 0.080 | 0.151 |
| TCRBV13_9 | -1.570 | 0.847 | 2.456 | 1.181 | 0.257 |
| TCRBV13_10 | 0.410 | -0.242 | -1.887 | -1.004 | 0.312 |
| TCRBV13_11 | 0.428 | 0.590 | 0.728 | -0.956 | 0.598 |
| TCRBV13_12 | 0.300 | 0.096 | 0.012 | 0.015 | 0.275 |
| TCRBV13_13 | -0.074 | -0.145 | -0.005 | 0.036 | -0.065 |
| TCRBV14_5 | 0.143 | 0.091 | 0.098 | -0.168 | 0.061 |
| TCRBV14_6 | -0.006 | -0.451 | 0.205 | -0.471 | -0.095 |
| TCRBV14_7 | 0.196 | -0.358 | -1.411 | -0.055 | 1.201 |
| TCRBV14_8 | 0.723 | 0.278 | -1.039 | -0.522 | -0.216 |
| TCRBV14_9 | -0.986 | -0.709 | 0.892 | 1.919 | -0.163 |
| TCRBV14_10 | -0.069 | 0.383 | 0.959 | -0.075 | 0.459 |
| TCRBV14_11 | 0.144 | 0.249 | 0.290 | -0.350 | -1.433 |
| TCRBV14_12 | -0.131 | 0.468 | 0.006 | -0.219 | 0.121 |
| TCRBV14_13 | -0.014 | 0.049 | 0.000 | -0.058 | 0.065 |
| TCRBV15_4 | 0.085 | 0.146 | 0.111 | 0.076 | 0.114 |
| TCRBV15_5 | -0.014 | 0.965 | -0.858 | 0.796 | -2.141 |
| TCRBV15_6 | -0.782 | 0.032 | 0.709 | 0.119 | 0.178 |
| TCRBV15_7 | -0.568 | -0.412 | 1.741 | 0.356 | -0.017 |
| TCRBV15_8 | 0.590 | -0.164 | 0.529 | 1.953 | 0.471 |
| TCRBV15_9 | 2.449 | 0.557 | -1.023 | -1.399 | 0.259 |
| TCRBV15_10 | 1.173 | 0.101 | -0.702 | -0.744 | 1.992 |
| TCRBV15_11 | 0.787 | -0.388 | -0.279 | -0.434 | 0.660 |
| TCRBV15_12 | 0.037 | -0.102 | -0.482 | -0.042 | 0.311 |
| TCRBV16_5 | -0.149 | -0.080 | 0.366 | -0.042 | -0.038 |
| TCRBV16_6 | -1.187 | -0.135 | 0.822 | -0.106 | -0.203 |
| TCRBV16_7 | -0.990 | -2.100 | -0.183 | -2.733 | -1.300 |
| TCRBV16_8 | 0.923 | -2.155 | -0.251 | 0.053 | 0.684 |
| TCRBV16_9 | 6.027 | -2.138 | -0.724 | 0.202 | 0.053 |
| TCRBV16_10 | 1.533 | 4.222 | 0.883 | 1.462 | 1.876 |
| TCRBV16_11 | 0.283 | 3.477 | 1.545 | 0.794 | -3.877 |
| TCRBV16_12 | 0.862 | -2.339 | -0.839 | 3.805 | 1.543 |
| TCRBV16_13 | -0.014 | 0.144 | -0.078 | 0.191 | -0.021 |

*FIG. 100A*

| | | | | | |
|---|---|---|---|---|---|
| TCRBV18_3 | 0.010 | -0.005 | 0.011 | 0.004 | 0.026 |
| TCRBV18_4 | 0.376 | -0.071 | 0.845 | 0.676 | -0.408 |
| TCRBV18_5 | 0.044 | -0.234 | 1.934 | 0.669 | -0.082 |
| TCRBV18_6 | 1.002 | -2.737 | 2.759 | 0.137 | -0.167 |
| TCRBV18_7 | -0.923 | -2.518 | 4.985 | -2.402 | -0.768 |
| TCRBV18_8 | 0.355 | -3.888 | -0.600 | -3.218 | 0.983 |
| TCRBV18_9 | -1.719 | 0.752 | -1.847 | -1.847 | 2.425 |
| TCRBV18_10 | -0.495 | 0.068 | -1.102 | 0.650 | 0.739 |
| TCRBV18_11 | -0.631 | 0.660 | -0.391 | 0.157 | 0.008 |
| TCRBV18_12 | 0.019 | 0.095 | -0.038 | 0.137 | 0.035 |
| TCRBV18_13 | 0.015 | 0.021 | 0.036 | -0.010 | 0.075 |
| TCRBV20_5 | 0.091 | 0.012 | -0.065 | -0.190 | -0.227 |
| TCRBV20_6 | -0.052 | -0.617 | -0.670 | -0.484 | -0.213 |
| TCRBV20_7 | 0.660 | -0.862 | 0.571 | 0.475 | -0.101 |
| TCRBV20_8 | 1.607 | 0.279 | -0.753 | 0.098 | -1.345 |
| TCRBV20_9 | -1.161 | -1.488 | -0.001 | -0.149 | 1.441 |
| TCRBV20_10 | 0.864 | 0.735 | 0.117 | 0.790 | 1.829 |
| TCRBV20_11 | 1.879 | 0.292 | 0.966 | -0.001 | 1.358 |
| TCRBV20_12 | 0.598 | 0.964 | 0.263 | -0.659 | 0.373 |
| TCRBV20_13 | -0.797 | 1.301 | -0.772 | 0.738 | -1.378 |
| TCRBV20_14 | 0.069 | 0.118 | 0.090 | 0.062 | 0.092 |
| | 11 | 12 | 13 | 14 | 15 |
| TCRBV01_6 | -0.078 | 0.174 | 0.009 | -0.004 | 0.123 |
| TCRBV01_7 | -0.512 | 0.096 | 0.280 | 0.259 | -0.011 |
| TCRBV01_8 | -1.333 | 0.323 | 0.740 | -0.141 | -1.727 |
| TCRBV01_9 | 0.102 | -0.588 | -2.611 | -0.115 | -1.011 |
| TCRBV01_10 | -0.980 | 0.909 | 3.932 | -0.993 | -0.110 |
| TCRBV01_11 | 0.693 | 0.718 | -0.735 | 1.775 | 1.186 |
| TCRBV01_12 | 1.174 | 0.599 | 0.497 | 0.846 | 0.433 |
| TCRBV01_13 | 0.033 | 0.051 | 0.068 | 0.129 | 0.190 |
| TCRBV01_14 | -0.021 | 0.027 | 0.006 | -0.006 | 0.009 |
| TCRBV02_6 | 0.154 | -0.275 | -0.102 | 0.043 | -0.365 |
| TCRBV02_7 | 0.127 | -0.905 | 0.185 | 0.111 | 0.538 |
| TCRBV02_8 | -1.231 | -0.227 | -0.822 | 0.347 | 0.338 |
| TCRBV02_9 | -1.144 | 0.417 | -0.684 | 0.218 | -0.451 |
| TCRBV02_10 | -0.414 | -0.026 | -0.231 | 0.930 | 0.281 |
| TCRBV02_11 | 0.541 | -1.179 | 0.125 | 0.634 | 0.701 |
| TCRBV02_12 | 0.220 | -0.146 | -0.256 | 0.435 | 0.421 |
| TCRBV02_13 | -0.051 | 0.004 | 0.124 | -0.055 | -0.160 |
| TCRBV03_4 | 0.047 | 0.061 | 0.043 | -0.069 | -0.034 |
| TCRBV03_5 | 0.094 | 0.128 | 0.070 | -0.063 | -0.009 |
| TCRBV03_6 | -0.130 | 0.799 | 0.618 | 0.029 | -0.061 |
| TCRBV03_7 | 0.615 | 0.934 | 0.470 | -0.218 | 0.970 |
| TCRBV03_8 | -0.486 | 2.181 | 0.323 | -1.628 | 1.389 |
| TCRBV03_9 | -0.872 | 2.185 | 0.844 | 0.028 | -0.153 |
| TCRBV03_10 | 0.055 | -1.247 | -0.165 | -1.776 | -0.932 |
| TCRBV03_11 | 1.977 | -1.766 | -0.699 | 2.395 | -1.069 |
| TCRBV03_12 | 0.074 | -0.246 | -0.413 | 1.289 | -0.247 |
| TCRBV03_13 | -2.295 | -0.721 | 1.094 | 1.764 | -0.772 |
| TCRBV04_6 | 0.020 | 0.001 | 0.001 | 0.002 | 0.012 |
| TCRBV04_7 | 0.136 | -0.017 | -0.107 | 0.240 | 0.248 |
| TCRBV04_8 | -0.292 | -0.174 | -0.504 | 0.658 | 0.212 |
| TCRBV04_9 | -1.217 | -0.900 | -1.231 | 0.313 | 1.284 |
| TCRBV04_10 | -0.374 | -0.005 | 0.463 | 1.101 | -0.221 |
| TCRBV04_11 | 1.439 | 0.706 | 0.508 | 1.235 | -0.646 |
| TCRBV04_12 | 0.914 | 0.618 | 0.450 | 0.448 | -0.682 |
| TCRBV04_13 | -0.411 | 0.451 | 1.487 | -3.362 | 1.290 |
| TCRBV04_14 | -0.468 | -0.813 | -0.881 | -0.561 | -1.477 |
| TCRBV04_15 | 0.252 | 0.134 | -0.187 | -0.076 | -0.019 |
| TCRBV051_5 | 0.037 | 0.085 | -0.165 | 0.011 | -0.021 |
| TCRBV051_6 | 0.984 | 0.372 | -0.124 | 0.178 | -0.348 |
| TCRBV051_7 | 0.266 | -1.065 | -0.286 | 0.797 | 0.201 |

*FIG. 100B*

| | | | | | |
|---|---|---|---|---|---|
| TCRBV051_8 | 1.067 | -0.727 | 1.573 | 0.059 | 1.657 |
| TCRBV051_9 | 0.749 | -1.256 | 1.719 | 1.549 | 0.140 |
| TCRBV051_10 | 1.252 | -2.882 | -0.338 | 0.221 | -0.562 |
| TCRBV051_11 | 1.331 | 0.911 | -0.892 | 0.305 | 1.625 |
| TCRBV051_12 | -0.100 | -1.198 | -0.412 | -0.321 | -0.780 |
| TCRBV051_13 | -0.026 | 0.003 | -0.199 | -0.045 | -0.040 |
| TCRBV052_6 | -0.018 | 0.036 | -0.400 | 0.167 | -0.219 |
| TCRBV052_7 | 0.832 | -0.605 | -0.637 | 0.979 | -0.694 |
| TCRBV052_8 | 2.655 | 0.253 | 0.421 | 0.442 | -1.192 |
| TCRBV052_9 | -1.275 | -1.512 | -2.308 | 2.217 | 1.751 |
| TCRBV052_10 | 2.679 | -1.899 | 1.344 | 0.242 | -0.080 |
| TCRBV052_11 | 0.694 | -1.580 | 1.672 | -0.806 | 1.779 |
| TCRBV052_12 | 0.052 | -0.423 | 0.878 | -0.484 | 0.659 |
| TCRBV052_13 | -0.059 | -0.027 | -0.092 | -0.004 | -0.132 |
| TCRBV06_5 | 0.015 | -0.002 | -0.078 | 0.045 | 0.027 |
| TCRBV06_6 | 0.873 | 0.757 | -0.508 | 0.284 | 0.106 |
| TCRBV06_7 | 0.419 | 0.450 | -0.304 | -0.381 | 0.385 |
| TCRBV06_8 | 0.174 | -0.321 | -0.052 | 0.291 | 0.033 |
| TCRBV06_9 | -0.676 | 2.490 | -0.582 | 0.293 | -1.469 |
| TCRBV06_10 | -0.778 | 0.460 | 0.997 | 0.924 | -0.431 |
| TCRBV06_11 | -0.564 | -1.128 | 1.080 | -0.398 | 0.380 |
| TCRBV06_12 | -0.224 | -0.449 | 1.517 | 0.698 | 0.343 |
| TCRBV06_13 | -0.160 | 0.051 | 0.115 | -0.005 | -0.292 |
| TCRBV07_5 | 0.000 | -0.002 | 0.007 | 0.013 | -0.004 |
| TCRBV07_6 | -0.073 | 0.647 | -0.249 | 1.430 | -0.438 |
| TCRBV07_7 | 0.061 | 2.148 | -1.865 | 2.078 | -2.463 |
| TCRBV07_8 | 0.610 | 0.469 | 0.846 | 0.991 | 0.191 |
| TCRBV07_9 | 3.442 | -1.141 | 2.762 | 1.322 | 1.160 |
| TCRBV07_10 | -2.361 | -1.803 | 0.384 | -2.036 | 0.444 |
| TCRBV07_11 | -1.323 | 1.075 | -0.452 | -1.209 | -0.014 |
| TCRBV07_12 | -1.169 | 0.638 | 0.747 | -0.781 | 0.214 |
| TCRBV07_13 | -0.109 | 0.278 | 0.005 | -0.058 | -0.009 |
| TCRBV081_5 | 0.197 | 0.148 | -0.058 | 0.048 | -0.062 |
| TCRBV081_6 | 0.170 | -0.052 | -0.968 | 0.605 | -0.198 |
| TCRBV081_7 | -0.839 | -0.620 | -1.479 | 0.460 | -0.679 |
| TCRBV081_8 | 0.396 | 0.900 | -0.862 | 0.605 | -0.973 |
| TCRBV081_9 | 2.751 | -2.471 | 2.729 | -1.778 | -2.626 |
| TCRBV081_10 | -1.599 | 1.636 | 0.241 | 0.148 | 1.929 |
| TCRBV081_11 | -0.824 | 0.565 | -0.030 | 0.057 | 1.747 |
| TCRBV081_12 | -0.252 | -0.106 | 0.427 | -0.145 | 0.861 |
| TCRBV082_4 | 0.306 | 0.138 | -0.257 | -0.115 | 0.042 |
| TCRBV082_5 | 0.898 | 0.162 | -0.632 | 0.113 | 0.380 |
| TCRBV082_6 | 0.468 | 0.356 | -0.328 | 0.318 | 0.175 |
| TCRBV082_7 | 1.392 | 0.760 | -1.129 | -0.025 | 0.290 |
| TCRBV082_8 | -0.942 | 0.537 | 0.677 | 0.358 | -0.111 |
| TCRBV082_9 | -1.243 | -1.178 | 0.933 | -0.276 | -0.903 |
| TCRBV082_10 | -0.635 | -0.447 | 0.845 | -0.179 | 0.033 |
| TCRBV082_11 | -0.244 | -0.328 | -0.109 | -0.193 | 0.095 |
| TCRBV083_4 | -0.164 | -0.052 | 0.069 | 0.119 | -0.066 |
| TCRBV083_5 | -0.099 | -0.045 | 0.280 | -0.196 | 0.004 |
| TCRBV083_6 | 0.242 | -0.026 | -0.030 | 0.469 | -0.242 |
| TCRBV083_7 | -0.947 | -2.132 | -0.733 | -0.681 | -0.412 |
| TCRBV083_8 | -0.394 | -0.908 | -0.263 | -0.506 | 0.589 |
| TCRBV083_9 | 0.540 | 1.475 | 0.937 | 1.007 | 0.280 |
| TCRBV083_10 | 0.306 | 0.961 | 0.788 | 0.869 | -0.446 |
| TCRBV083_11 | 0.672 | 1.016 | -1.164 | -0.405 | 0.471 |
| TCRBV083_12 | -0.156 | -0.289 | 0.116 | -0.677 | -0.178 |
| TCRBV09_5 | 0.266 | 0.179 | -0.059 | 0.078 | -0.128 |
| TCRBV09_6 | -0.111 | 0.146 | 0.128 | 0.116 | -0.105 |
| TCRBV09_7 | -0.594 | -0.490 | 0.412 | 0.140 | -0.174 |
| TCRBV09_8 | 2.326 | 1.296 | -4.307 | -0.116 | -0.213 |
| TCRBV09_9 | -4.105 | -2.611 | 1.735 | 2.524 | -0.563 |
| TCRBV09_10 | 1.694 | -0.367 | 2.112 | 2.090 | -0.820 |
| TCRBV09_11 | -1.337 | -0.362 | -0.255 | 1.706 | 1.682 |

*FIG. 100C*

| | | | | | |
|---|---|---|---|---|---|
| TCRBV09_12 | 0.541 | -0.364 | 0.534 | -1.227 | -0.188 |
| TCRBV09_13 | 0.211 | 0.151 | -0.133 | -0.311 | 0.074 |
| TCRBV09_14 | 0.125 | 0.130 | -0.114 | -0.045 | 0.051 |
| TCRBV09_15 | 0.009 | 0.002 | -0.025 | -0.027 | 0.013 |
| TCRBV10_6 | -0.012 | 0.368 | -0.653 | 0.868 | 0.090 |
| TCRBV10_7 | -0.912 | 0.002 | -0.393 | 0.171 | -0.084 |
| TCRBV10_8 | 0.355 | 0.095 | -0.061 | 0.674 | -0.364 |
| TCRBV10_9 | -1.991 | -2.010 | -0.427 | 0.144 | 1.149 |
| TCRBV10_10 | 1.567 | 0.473 | 0.279 | -1.791 | 0.670 |
| TCRBV10_11 | 0.695 | 1.273 | 0.407 | -0.031 | -1.730 |
| TCRBV10_12 | 0.275 | -0.231 | 0.827 | -0.000 | 0.285 |
| TCRBV10_13 | 0.023 | 0.029 | 0.021 | -0.033 | -0.016 |
| TCRBV11_5 | -0.193 | -0.014 | 0.031 | 0.315 | 0.141 |
| TCRBV11_6 | 0.376 | -0.396 | 0.466 | 0.083 | 0.262 |
| TCRBV11_7 | -1.021 | -0.708 | -0.515 | 0.206 | -0.530 |
| TCRBV11_8 | -0.618 | -0.189 | -0.437 | 0.867 | -0.265 |
| TCRBV11_9 | -0.559 | 0.011 | 0.206 | -2.024 | 1.101 |
| TCRBV11_10 | 0.684 | 1.088 | 0.268 | 0.829 | -0.592 |
| TCRBV11_11 | -0.032 | 0.970 | 1.096 | 0.727 | 0.166 |
| TCRBV11_12 | 0.295 | 0.819 | 0.576 | 1.136 | -0.948 |
| TCRBV11_13 | 0.007 | 0.547 | 0.366 | -0.183 | -0.153 |
| TCRBV11_14 | 0.102 | 0.132 | 0.094 | -0.150 | -0.074 |
| TCRBV11_15 | 0.038 | 0.049 | 0.035 | -0.056 | -0.027 |
| TCRBV12_4 | -0.091 | 0.082 | -0.005 | -0.348 | 0.187 |
| TCRBV12_5 | -1.887 | -0.275 | -0.056 | 0.520 | 0.450 |
| TCRBV12_6 | -1.370 | -1.728 | -0.007 | -1.965 | 1.374 |
| TCRBV12_7 | -0.900 | -1.145 | 0.008 | 0.832 | 0.147 |
| TCRBV12_8 | -0.161 | -0.736 | 0.491 | 0.882 | -0.985 |
| TCRBV12_9 | 1.034 | 1.046 | -0.573 | 0.630 | 0.530 |
| TCRBV12_10 | 2.665 | 2.278 | 0.950 | -0.544 | -1.339 |
| TCRBV12_11 | 0.437 | 0.418 | -0.469 | -0.049 | -0.546 |
| TCRBV12_12 | 0.273 | 0.061 | -0.338 | 0.042 | 0.183 |
| TCRBV13_5 | 0.028 | 0.098 | 0.045 | -0.072 | -0.086 |
| TCRBV13_6 | -0.577 | 0.100 | -0.288 | -0.483 | -2.301 |
| TCRBV13_7 | -0.692 | 1.404 | 0.701 | 0.790 | -0.563 |
| TCRBV13_8 | -1.035 | 1.378 | 1.371 | 1.368 | -0.324 |
| TCRBV13_9 | -1.463 | 0.973 | -0.447 | -2.218 | 0.425 |
| TCRBV13_10 | 2.114 | -2.950 | -0.854 | -0.823 | 1.730 |
| TCRBV13_11 | 1.287 | -0.497 | -1.093 | 1.108 | 1.210 |
| TCRBV13_12 | 0.316 | -0.348 | 0.284 | 0.370 | 0.021 |
| TCRBV13_13 | 0.021 | -0.157 | 0.282 | -0.039 | -0.113 |
| TCRBV14_5 | -0.049 | -0.091 | -0.288 | 0.112 | 0.008 |
| TCRBV14_6 | 0.008 | -0.564 | 0.211 | -0.628 | 0.052 |
| TCRBV14_7 | -0.276 | -0.354 | -0.163 | 1.050 | 0.214 |
| TCRBV14_8 | -0.362 | 0.764 | 1.069 | 1.242 | -1.025 |
| TCRBV14_9 | 0.786 | -0.529 | -1.315 | -0.640 | 0.109 |
| TCRBV14_10 | -0.477 | -0.907 | 0.267 | -0.782 | 0.454 |
| TCRBV14_11 | 0.316 | 1.092 | 0.004 | 0.011 | 0.132 |
| TCRBV14_12 | 0.124 | 0.451 | 0.204 | -0.275 | 0.110 |
| TCRBV14_13 | -0.070 | 0.138 | 0.010 | -0.090 | -0.053 |
| TCRBV15_4 | 0.012 | -0.078 | 0.138 | 0.067 | 0.001 |
| TCRBV15_5 | -1.850 | 0.707 | 0.205 | 2.402 | 1.265 |
| TCRBV15_6 | 0.065 | 1.000 | 0.117 | -0.358 | -0.624 |
| TCRBV15_7 | 1.385 | -0.331 | -0.309 | 0.726 | -0.696 |
| TCRBV15_8 | 1.706 | -0.015 | -1.181 | -0.679 | -0.295 |
| TCRBV15_9 | -1.423 | -2.321 | 0.532 | -2.150 | -2.565 |
| TCRBV15_10 | -0.206 | 2.095 | 1.694 | 1.098 | 1.240 |
| TCRBV15_11 | -0.457 | 1.007 | 0.755 | 0.430 | 0.465 |
| TCRBV15_12 | -0.154 | 0.244 | 0.236 | 0.214 | 0.289 |
| TCRBV16_5 | -0.091 | 0.009 | 0.033 | 0.184 | -0.132 |
| TCRBV16_6 | -0.820 | 0.114 | -0.049 | 1.644 | 0.804 |
| TCRBV16_7 | 1.402 | 0.547 | 2.353 | -1.251 | 0.165 |
| TCRBV16_8 | -0.242 | -1.401 | 0.563 | 0.608 | -1.375 |

*FIG. 100D*

|           |        |        |        |        |        |
|-----------|--------|--------|--------|--------|--------|
| TCRBV16_9  | -0.508 | -1.945 | -2.137 |  0.262 | -1.293 |
| TCRBV16_10 |  1.217 | -1.664 |  2.018 |  1.802 |  1.830 |
| TCRBV16_11 |  3.340 | -0.994 | -1.906 |  1.049 |  1.875 |
| TCRBV16_12 |  0.410 |  1.889 |  2.087 |  0.325 | -0.894 |
| TCRBV16_13 | -0.071 | -0.004 |  0.100 | -0.119 | -0.026 |
| TCRBV18_3  |  0.008 | -0.001 |  0.009 | -0.021 |  0.004 |
| TCRBV18_4  |  0.464 | -0.011 |  0.314 |  0.352 |  0.224 |
| TCRBV18_5  |  0.602 | -0.431 |  0.536 |  0.388 |  0.572 |
| TCRBV18_6  |  1.182 | -0.288 |  1.124 |  1.667 |  2.070 |
| TCRBV18_7  | -0.701 |  1.554 |  0.514 | -0.669 | -0.124 |
| TCRBV18_8  |  0.382 | -0.273 | -0.817 | -1.371 |  3.707 |
| TCRBV18_9  |  0.826 |  0.369 | -1.522 | -0.119 |  0.722 |
| TCRBV18_10 |  0.431 | -0.395 | -0.410 | -0.265 |  1.129 |
| TCRBV18_11 | -1.118 |  1.089 | -0.078 | -0.216 |  0.141 |
| TCRBV18_12 | -0.017 |  0.102 |  0.061 | -0.269 |  0.059 |
| TCRBV18_13 |  0.017 |  0.022 | -0.014 | -0.002 |  0.015 |
| TCRBV20_5  | -0.139 | -0.344 | -0.040 | -0.216 |  0.167 |
| TCRBV20_6  | -0.136 |  0.001 |  0.388 |  0.103 |  0.193 |
| TCRBV20_7  |  0.527 |  0.900 | -0.383 | -0.072 | -0.663 |
| TCRBV20_8  | -0.893 |  2.152 | -0.642 | -0.108 | -0.774 |
| TCRBV20_9  |  0.793 |  2.037 | -0.021 | -2.053 |  0.144 |
| TCRBV20_10 |  1.088 |  0.647 |  1.517 |  0.033 |  1.514 |
| TCRBV20_11 |  0.094 | -2.801 |  0.007 |  0.559 | -2.299 |
| TCRBV20_12 |  0.625 | -0.993 |  1.211 |  0.927 | -0.801 |
| TCRBV20_13 | -2.891 |  0.774 |  0.037 |  2.526 |  1.599 |
| TCRBV20_14 |  0.010 | -0.063 |  0.112 |  0.054 |  0.001 |
|           | 16     | 17     | 18     | 19     | 20     |
| TCRBV01_6  |  0.124 | -0.157 |  0.071 |  0.040 | -0.061 |
| TCRBV01_7  | -0.062 | -0.845 |  0.717 |  0.465 | -0.518 |
| TCRBV01_8  | -1.057 | -0.575 |  0.555 |  0.526 |  0.206 |
| TCRBV01_9  |  0.722 | -1.905 |  1.473 |  1.528 |  1.108 |
| TCRBV01_10 |  1.325 |  2.409 | -0.095 | -0.398 | -0.287 |
| TCRBV01_11 | -0.453 |  0.570 |  0.135 | -0.873 | -0.276 |
| TCRBV01_12 | -0.420 | -0.005 | -1.074 | -1.012 |  0.120 |
| TCRBV01_13 |  0.157 |  0.356 | -0.377 | -0.476 |  0.195 |
| TCRBV01_14 |  0.023 |  0.007 | -0.040 | -0.029 |  0.054 |
| TCRBV02_6  |  0.124 | -0.487 |  0.092 |  0.060 | -0.427 |
| TCRBV02_7  |  0.137 | -0.177 | -0.015 | -0.403 |  0.425 |
| TCRBV02_8  |  0.898 | -0.608 |  0.935 | -0.899 |  0.276 |
| TCRBV02_9  |  0.891 | -0.608 |  0.180 | -2.825 | -0.066 |
| TCRBV02_10 |  0.563 | -0.344 |  1.209 | -2.132 |  1.038 |
| TCRBV02_11 |  0.535 | -0.072 |  0.086 | -0.848 |  0.656 |
| TCRBV02_12 |  0.057 | -0.164 | -0.255 |  0.113 |  0.913 |
| TCRBV02_13 | -0.119 |  0.038 | -0.124 | -0.115 |  0.028 |
| TCRBV03_4  | -0.080 |  0.063 | -0.055 |  0.183 | -0.074 |
| TCRBV03_5  |  0.017 |  0.072 | -0.042 |  0.251 | -0.093 |
| TCRBV03_6  | -0.049 | -0.981 |  0.734 |  0.182 |  0.651 |
| TCRBV03_7  | -0.240 | -1.014 |  0.022 |  0.530 |  0.368 |
| TCRBV03_8  | -1.294 | -0.648 | -0.327 | -0.074 | -0.214 |
| TCRBV03_9  |  0.695 |  0.387 |  1.157 | -0.263 | -0.296 |
| TCRBV03_10 |  1.129 |  0.715 | -1.522 | -2.032 | -0.622 |
| TCRBV03_11 | -0.592 |  0.692 |  0.946 |  0.613 |  0.755 |
| TCRBV03_12 | -0.058 |  0.619 |  0.307 | -1.371 | -0.138 |
| TCRBV03_13 |  0.829 | -0.050 |  0.147 |  1.753 |  0.204 |
| TCRBV04_6  | -0.032 | -0.039 |  0.043 |  0.035 | -0.003 |
| TCRBV04_7  |  0.086 | -0.052 | -0.209 | -0.021 |  0.669 |
| TCRBV04_8  |  0.498 |  0.595 | -0.175 |  0.273 |  0.735 |
| TCRBV04_9  |  1.633 |  0.667 | -0.553 |  0.853 |  0.758 |
| TCRBV04_10 |  1.406 |  1.839 | -1.796 |  0.574 |  0.575 |
| TCRBV04_11 | -0.894 | -2.797 |  0.324 | -0.295 | -1.388 |
| TCRBV04_12 |  0.243 | -1.215 |  0.951 | -0.001 | -1.222 |
| TCRBV04_13 | -1.891 |  0.962 |  0.844 | -1.124 | -1.209 |

*FIG. 101A*

| | | | | | |
|---|---|---|---|---|---|
| TCRBV04_14 | -1.180 | 0.062 | 0.229 | -0.274 | 1.002 |
| TCRBV04_15 | 0.133 | -0.022 | 0.342 | -0.019 | 0.082 |
| TCRBV051_5 | 0.049 | 0.126 | 0.001 | 0.049 | -0.038 |
| TCRBV051_6 | -0.172 | 0.329 | -0.255 | 0.342 | -0.356 |
| TCRBV051_7 | 0.564 | 0.652 | -0.237 | 0.532 | -2.308 |
| TCRBV051_8 | -0.607 | -1.852 | -1.027 | 0.178 | 0.088 |
| TCRBV051_9 | 0.505 | 2.708 | -1.401 | 0.296 | 0.629 |
| TCRBV051_10 | 1.410 | 0.309 | -0.606 | 1.567 | 0.580 |
| TCRBV051_11 | 0.191 | -1.680 | -1.705 | -0.481 | 0.606 |
| TCRBV051_12 | -0.260 | -0.387 | 0.506 | 0.405 | 1.067 |
| TCRBV051_13 | 0.072 | 0.055 | 0.127 | 0.034 | 0.072 |
| TCRBV052_6 | -0.021 | -0.066 | 0.048 | 0.285 | -0.426 |
| TCRBV052_7 | 0.516 | 0.563 | 0.432 | 0.349 | -1.158 |
| TCRBV052_8 | 1.275 | 0.287 | -3.475 | 1.409 | 1.577 |
| TCRBV052_9 | 0.447 | 2.745 | -0.828 | -0.674 | -1.669 |
| TCRBV052_10 | 0.331 | 0.319 | 0.222 | 0.947 | 0.459 |
| TCRBV052_11 | -0.075 | -2.727 | -0.831 | 0.463 | 0.986 |
| TCRBV052_12 | -0.760 | -0.671 | -0.183 | 0.057 | 0.650 |
| TCRBV052_13 | 0.040 | -0.190 | 0.018 | 0.086 | -0.077 |
| TCRBV06_5 | 0.001 | 0.014 | -0.014 | 0.032 | 0.008 |
| TCRBV06_6 | 0.318 | -0.382 | -0.296 | 0.091 | 0.336 |
| TCRBV06_7 | -0.106 | -0.250 | 0.097 | 0.079 | -0.238 |
| TCRBV06_8 | 1.015 | -0.993 | 0.506 | 2.042 | 0.232 |
| TCRBV06_9 | 0.155 | 0.610 | -1.311 | -0.041 | 0.240 |
| TCRBV06_10 | 0.775 | 0.108 | -0.016 | -0.287 | -0.528 |
| TCRBV06_11 | -1.610 | 0.622 | 2.046 | -0.848 | -0.011 |
| TCRBV06_12 | -0.285 | 0.525 | 0.107 | -0.984 | 0.711 |
| TCRBV06_13 | 0.095 | -0.399 | 0.248 | -0.314 | -0.209 |
| TCRBV07_5 | 0.001 | -0.006 | 0.033 | 0.003 | -0.030 |
| TCRBV07_6 | -0.199 | 0.250 | -0.337 | 0.099 | -0.432 |
| TCRBV07_7 | -0.655 | -0.015 | -1.094 | -0.517 | -1.191 |
| TCRBV07_8 | -0.707 | 0.607 | 0.002 | -0.295 | -0.780 |
| TCRBV07_9 | -2.083 | 0.792 | 1.591 | 0.743 | 0.641 |
| TCRBV07_10 | 2.228 | -0.425 | 0.112 | 0.196 | -0.042 |
| TCRBV07_11 | 0.535 | -1.187 | 0.726 | -0.364 | 1.592 |
| TCRBV07_12 | 1.107 | -0.151 | 0.153 | -0.067 | 0.806 |
| TCRBV07_13 | 0.129 | -0.010 | 0.181 | -0.028 | -0.023 |
| TCRBV081_5 | 0.013 | 0.091 | -0.109 | 0.007 | 0.044 |
| TCRBV081_6 | -0.541 | 0.327 | 0.288 | 0.012 | -0.439 |
| TCRBV081_7 | -0.518 | 0.827 | -0.029 | 0.556 | -0.679 |
| TCRBV081_8 | -1.803 | 0.175 | -0.575 | 0.082 | -0.739 |
| TCRBV081_9 | 0.123 | 0.510 | 0.698 | -1.334 | 0.899 |
| TCRBV081_10 | 2.174 | -2.065 | -0.454 | -0.221 | 0.812 |
| TCRBV081_11 | 0.352 | -0.104 | 0.127 | 0.647 | -0.016 |
| TCRBV081_12 | 0.200 | 0.240 | 0.053 | 0.251 | 0.119 |
| TCRBV082_4 | 0.049 | 0.139 | 0.365 | 0.270 | 0.226 |
| TCRBV082_5 | 0.463 | 0.344 | 0.562 | 0.192 | 0.019 |
| TCRBV082_6 | 0.073 | 0.598 | 0.327 | -0.317 | 0.399 |
| TCRBV082_7 | 0.692 | 0.806 | 0.925 | -1.173 | 0.811 |
| TCRBV082_8 | 0.196 | -0.960 | -0.411 | 0.222 | 0.033 |
| TCRBV082_9 | -0.748 | -0.707 | -0.838 | 0.240 | -0.546 |
| TCRBV082_10 | -0.574 | -0.492 | -0.743 | 0.435 | -0.707 |
| TCRBV082_11 | -0.152 | 0.272 | -0.188 | 0.132 | -0.235 |
| TCRBV083_4 | 0.049 | -0.010 | 0.000 | 0.113 | 0.011 |
| TCRBV083_5 | 0.183 | -0.010 | -0.152 | -0.114 | 0.093 |
| TCRBV083_6 | -0.087 | -0.244 | 0.511 | -0.237 | -0.027 |
| TCRBV083_7 | 1.562 | -0.251 | 0.484 | 0.466 | 0.080 |
| TCRBV083_8 | 1.240 | 0.498 | 0.490 | 0.384 | -1.463 |
| TCRBV083_9 | -1.147 | -0.422 | -0.174 | 0.433 | 1.133 |
| TCRBV083_10 | -0.259 | 0.133 | 0.203 | 0.659 | 0.279 |
| TCRBV083_11 | -1.268 | 0.143 | -0.426 | -1.292 | -0.063 |
| TCRBV083_12 | -0.273 | 0.162 | -0.935 | -0.413 | -0.044 |
| TCRBV09_5 | -0.018 | -0.023 | -0.181 | -0.007 | -0.004 |
| TCRBV09_6 | -0.059 | -0.000 | 0.298 | -0.222 | -0.285 |

*FIG.101B*

| | | | | | |
|---|---|---|---|---|---|
| TCRBV09_7 | -0.299 | 0.014 | 0.683 | -0.647 | -0.585 |
| TCRBV09_8 | 0.845 | 0.325 | 1.078 | -1.432 | 1.841 |
| TCRBV09_9 | 0.057 | -1.447 | 1.129 | -0.144 | -1.919 |
| TCRBV09_10 | 0.091 | -2.132 | -0.403 | -2.030 | -0.489 |
| TCRBV09_11 | 0.168 | 0.086 | 2.772 | 0.247 | 0.091 |
| TCRBV09_12 | 0.049 | -0.331 | 1.005 | -0.468 | 0.093 |
| TCRBV09_13 | 0.331 | 0.113 | 0.254 | -0.124 | 0.043 |
| TCRBV09_14 | 0.311 | 0.178 | 0.149 | 0.026 | 0.069 |
| TCRBV09_15 | 0.042 | 0.067 | 0.015 | -0.008 | 0.029 |
| TCRBV10_6 | -0.048 | 0.040 | 0.139 | -0.675 | -0.522 |
| TCRBV10_7 | 0.311 | -0.534 | -1.023 | -1.924 | -0.602 |
| TCRBV10_8 | 1.288 | -0.821 | -0.583 | -1.239 | 0.429 |
| TCRBV10_9 | 0.178 | -0.709 | 0.306 | 1.088 | 0.276 |
| TCRBV10_10 | -0.732 | 0.220 | 0.837 | 0.390 | 1.168 |
| TCRBV10_11 | -0.260 | 1.184 | 0.179 | 1.810 | -0.676 |
| TCRBV10_12 | -0.699 | 0.588 | 0.171 | 0.461 | -0.036 |
| TCRBV10_13 | -0.039 | 0.030 | -0.026 | 0.088 | -0.036 |
| TCRBV11_5 | -0.187 | 0.121 | -0.022 | -0.054 | 0.064 |
| TCRBV11_6 | -0.403 | -0.962 | 0.567 | 0.149 | 0.162 |
| TCRBV11_7 | -0.099 | -0.881 | 0.560 | -0.106 | 0.368 |
| TCRBV11_8 | -0.061 | -0.851 | 0.280 | -0.539 | -0.037 |
| TCRBV11_9 | 1.009 | 0.080 | -0.135 | 0.004 | -0.111 |
| TCRBV11_10 | 0.417 | 0.408 | -0.147 | -0.359 | 0.545 |
| TCRBV11_11 | 0.105 | 0.837 | 0.107 | -0.425 | 0.336 |
| TCRBV11_12 | 0.065 | 0.524 | 0.250 | 0.166 | -0.212 |
| TCRBV11_13 | -0.249 | 0.392 | 0.070 | 0.387 | -0.355 |
| TCRBV11_14 | -0.174 | 0.137 | -0.119 | 0.398 | -0.161 |
| TCRBV11_15 | -0.065 | 0.051 | -0.044 | 0.148 | -0.060 |
| TCRBV12_4 | -0.244 | 0.064 | -0.262 | -0.166 | -0.207 |
| TCRBV12_5 | -1.143 | 0.239 | -0.599 | -0.243 | -0.526 |
| TCRBV12_6 | 0.699 | 0.772 | -0.679 | 0.103 | -0.365 |
| TCRBV12_7 | -1.397 | 0.324 | -1.048 | 0.097 | 1.693 |
| TCRBV12_8 | 1.237 | -0.944 | -0.089 | -0.817 | 0.050 |
| TCRBV12_9 | -0.144 | 0.008 | 1.166 | -0.049 | -1.230 |
| TCRBV12_10 | 0.229 | -0.337 | 0.371 | -0.210 | 0.230 |
| TCRBV12_11 | 0.655 | 0.039 | 0.818 | 0.658 | 0.117 |
| TCRBV12_12 | 0.109 | -0.166 | 0.321 | 0.629 | 0.238 |
| TCRBV13_5 | -0.120 | 0.101 | -0.151 | 0.302 | -0.156 |
| TCRBV13_6 | 0.219 | -0.180 | 0.339 | 1.069 | -0.024 |
| TCRBV13_7 | 0.336 | -0.753 | 0.308 | -0.422 | 1.965 |
| TCRBV13_8 | -0.253 | -0.434 | 0.583 | 0.931 | 0.916 |
| TCRBV13_9 | -0.136 | 0.253 | -0.955 | 0.323 | 0.098 |
| TCRBV13_10 | 0.615 | 0.796 | 0.191 | 0.492 | -1.495 |
| TCRBV13_11 | -0.627 | 0.030 | -0.067 | -1.998 | -1.172 |
| TCRBV13_12 | 0.155 | 0.326 | -0.308 | -0.711 | -0.234 |
| TCRBV13_13 | -0.189 | -0.140 | 0.061 | 0.013 | 0.101 |
| TCRBV14_5 | -0.199 | -0.049 | 0.061 | -0.224 | -0.008 |
| TCRBV14_6 | 0.772 | -0.000 | -0.173 | -0.210 | -0.758 |
| TCRBV14_7 | -0.673 | -0.330 | 1.015 | 0.553 | 0.062 |
| TCRBV14_8 | 0.312 | -0.529 | -0.133 | -0.306 | -0.777 |
| TCRBV14_9 | 2.124 | 0.026 | -0.375 | -0.035 | 1.647 |
| TCRBV14_10 | -1.006 | 0.793 | -0.506 | -0.449 | -0.709 |
| TCRBV14_11 | -0.945 | 0.163 | 0.354 | 0.464 | 0.697 |
| TCRBV14_12 | -0.307 | -0.108 | -0.291 | 0.149 | -0.104 |
| TCRBV14_13 | -0.079 | 0.033 | 0.048 | 0.059 | -0.050 |
| TCRBV15_4 | -0.069 | 0.047 | -0.002 | -0.041 | 0.038 |
| TCRBV15_5 | -1.626 | 0.821 | -0.612 | 0.508 | 1.755 |
| TCRBV15_6 | -0.294 | -0.803 | 0.108 | 0.105 | -0.695 |
| TCRBV15_7 | -0.310 | -1.202 | 0.567 | 0.897 | -1.000 |
| TCRBV15_8 | 0.473 | -0.798 | -0.195 | -0.387 | -2.128 |
| TCRBV15_9 | -1.754 | 0.153 | 0.793 | -1.055 | 2.012 |
| TCRBV15_10 | 2.513 | 0.699 | 0.264 | -0.576 | 0.071 |
| TCRBV15_11 | 1.052 | 0.811 | 0.078 | -0.046 | 0.332 |

*FIG.101C*

| | | | | | |
|---|---|---|---|---|---|
| TCRBV15_12 | 0.373 | 0.129 | 0.365 | 0.366 | 0.157 |
| TCRBV16_5 | 0.146 | -0.002 | 0.260 | 0.062 | -0.063 |
| TCRBV16_6 | -0.200 | -0.088 | -0.380 | 0.761 | 0.949 |
| TCRBV16_7 | -0.042 | 0.935 | 0.401 | 0.641 | -0.147 |
| TCRBV16_8 | 0.165 | 1.818 | -0.501 | -0.790 | 0.478 |
| TCRBV16_9 | -2.297 | -1.579 | -0.346 | 0.342 | 0.375 |
| TCRBV16_10 | 1.631 | -1.711 | -0.706 | 0.161 | -0.469 |
| TCRBV16_11 | 1.966 | 0.598 | 0.138 | -0.291 | 0.474 |
| TCRBV16_12 | 0.732 | 0.347 | -2.025 | 1.928 | -0.653 |
| TCRBV16_13 | 0.010 | -0.203 | -0.071 | -0.121 | -0.060 |
| TCRBV18_3 | 0.003 | 0.009 | 0.025 | 0.002 | 0.021 |
| TCRBV18_4 | -0.382 | 0.172 | 1.117 | -0.505 | -0.140 |
| TCRBV18_5 | -0.088 | 0.569 | 2.138 | -0.633 | -0.143 |
| TCRBV18_6 | 0.177 | 0.767 | 3.683 | 0.621 | 0.572 |
| TCRBV18_7 | 0.141 | 2.436 | 0.365 | -1.603 | 1.022 |
| TCRBV18_8 | -2.443 | -0.368 | -1.166 | 0.594 | 0.801 |
| TCRBV18_9 | -2.942 | 0.730 | -0.489 | 1.739 | -0.345 |
| TCRBV18_10 | -1.010 | 1.406 | -1.356 | 1.166 | -0.982 |
| TCRBV18_11 | -0.379 | 1.000 | -0.400 | 0.442 | -0.154 |
| TCRBV18_12 | -0.210 | 0.135 | -0.170 | 0.079 | -0.144 |
| TCRBV18_13 | 0.017 | 0.073 | 0.006 | 0.008 | 0.032 |
| TCRBV20_5 | 0.174 | 0.057 | 0.143 | 0.002 | -0.209 |
| TCRBV20_6 | 0.316 | -0.883 | 0.112 | 0.476 | -0.215 |
| TCRBV20_7 | 1.152 | -0.721 | -0.117 | 1.019 | -0.307 |
| TCRBV20_8 | 0.936 | 0.095 | 1.419 | 2.026 | -0.289 |
| TCRBV20_9 | 0.848 | 1.014 | 2.647 | 0.289 | -0.908 |
| TCRBV20_10 | -0.694 | -2.291 | -1.970 | -1.817 | -0.435 |
| TCRBV20_11 | -0.868 | 0.564 | -0.547 | -0.839 | 1.198 |
| TCRBV20_12 | 0.171 | 0.778 | -0.076 | -0.695 | 0.193 |
| TCRBV20_13 | -1.621 | 1.203 | -0.243 | -0.657 | 1.482 |
| TCRBV20_14 | -0.056 | 0.038 | -0.001 | -0.033 | 0.031 |
| | 21 | 22 | 23 | 24 | 25 |
| TCRBV01_6 | 0.176 | 0.112 | 0.092 | 0.019 | 0.220 |
| TCRBV01_7 | -0.025 | 0.204 | 0.115 | 0.784 | -0.249 |
| TCRBV01_8 | -0.548 | 0.610 | -0.567 | 0.525 | 0.793 |
| TCRBV01_9 | 0.806 | -0.919 | -1.334 | 0.404 | 0.220 |
| TCRBV01_10 | 1.758 | 1.350 | -0.293 | -1.577 | -1.049 |
| TCRBV01_11 | 0.213 | -0.948 | 0.690 | 0.516 | 0.032 |
| TCRBV01_12 | -0.628 | -0.167 | 1.157 | 0.782 | 0.126 |
| TCRBV01_13 | -0.014 | -0.154 | 0.417 | -0.050 | 0.203 |
| TCRBV01_14 | 0.007 | -0.030 | 0.022 | -0.007 | -0.025 |
| TCRBV02_6 | -0.154 | -0.144 | -0.062 | -0.182 | -0.046 |
| TCRBV02_7 | -0.300 | -0.612 | 0.634 | -0.200 | 0.247 |
| TCRBV02_8 | -0.753 | -0.138 | 0.397 | -0.490 | 0.138 |
| TCRBV02_9 | -0.882 | -1.559 | 1.175 | -0.541 | -0.216 |
| TCRBV02_10 | -0.241 | -0.310 | 0.858 | -1.293 | -0.075 |
| TCRBV02_11 | -0.595 | 0.219 | 0.346 | -0.399 | -0.503 |
| TCRBV02_12 | -0.223 | 0.216 | 0.268 | -0.271 | -0.172 |
| TCRBV02_13 | -0.083 | 0.054 | -0.072 | -0.051 | 0.146 |
| TCRBV03_4 | 0.084 | 0.059 | -0.092 | 0.089 | 0.012 |
| TCRBV03_5 | 0.260 | 0.057 | -0.045 | 0.149 | 0.083 |
| TCRBV03_6 | 0.805 | 0.524 | 0.640 | 0.081 | 0.446 |
| TCRBV03_7 | 0.367 | 0.132 | 1.060 | -0.101 | -0.038 |
| TCRBV03_8 | 0.560 | 0.177 | 0.901 | -0.332 | 0.677 |
| TCRBV03_9 | 1.092 | -0.183 | -0.343 | 0.379 | -0.169 |
| TCRBV03_10 | -2.127 | -0.655 | -1.703 | 0.653 | 0.548 |
| TCRBV03_11 | 0.172 | 0.102 | -0.182 | 0.237 | -1.295 |
| TCRBV03_12 | 0.681 | 0.039 | -0.892 | -0.369 | -0.379 |
| TCRBV03_13 | -0.149 | -0.193 | 0.955 | 0.609 | 0.385 |
| TCRBV04_6 | -0.011 | 0.031 | 0.032 | -0.044 | -0.079 |
| TCRBV04_7 | 0.125 | 0.106 | 0.112 | 0.430 | -0.034 |
| TCRBV04_8 | 0.159 | 0.143 | 0.492 | 0.417 | 0.131 |

*FIG.101D*

| | | | | | |
|---|---|---|---|---|---|
| TCRBV04_9 | -0.380 | -0.497 | 0.305 | 0.967 | 0.401 |
| TCRBV04_10 | 0.067 | 0.229 | -0.235 | -1.262 | 0.703 |
| TCRBV04_11 | 0.696 | 0.081 | -0.381 | -1.045 | -0.781 |
| TCRBV04_12 | 0.930 | -0.023 | 0.262 | 0.160 | -0.422 |
| TCRBV04_13 | -1.525 | -0.411 | -0.484 | 0.267 | -0.492 |
| TCRBV04_14 | 0.085 | 0.119 | -0.064 | -0.042 | 0.604 |
| TCRBV04_15 | -0.145 | 0.222 | -0.039 | 0.153 | -0.031 |
| TCRBV051_5 | -0.187 | 0.084 | 0.140 | -0.156 | -0.047 |
| TCRBV051_6 | -0.784 | 0.005 | 1.127 | -0.349 | -1.081 |
| TCRBV051_7 | -0.145 | 0.663 | 0.917 | -0.724 | -1.560 |
| TCRBV051_8 | 1.494 | 0.566 | -0.074 | 1.290 | 0.101 |
| TCRBV051_9 | -2.002 | -1.365 | 0.071 | -0.026 | -0.021 |
| TCRBV051_10 | 0.689 | 0.479 | -0.173 | -1.119 | 0.751 |
| TCRBV051_11 | 0.589 | 0.298 | -2.312 | -0.076 | 0.224 |
| TCRBV051_12 | 0.311 | 0.128 | -0.474 | 0.243 | 0.596 |
| TCRBV051_13 | -0.058 | 0.172 | -0.043 | 0.226 | 0.025 |
| TCRBV052_6 | -0.193 | 0.005 | 0.047 | -0.306 | -0.083 |
| TCRBV052_7 | 0.474 | 0.620 | 0.038 | 0.063 | 0.734 |
| TCRBV052_8 | -0.841 | 1.022 | 0.192 | 1.215 | -1.125 |
| TCRBV052_9 | 0.841 | 0.225 | -0.634 | 0.213 | 0.509 |
| TCRBV052_10 | 0.915 | -0.694 | 0.182 | -0.944 | -0.388 |
| TCRBV052_11 | -0.563 | -0.004 | -0.516 | -0.179 | -0.233 |
| TCRBV052_12 | -0.552 | -0.167 | -0.179 | -0.596 | -0.379 |
| TCRBV052_13 | -0.175 | 0.021 | 0.050 | -0.157 | -0.044 |
| TCRBV06_5 | 0.006 | 0.012 | -0.049 | -0.038 | 0.124 |
| TCRBV06_6 | 0.384 | -0.089 | 0.336 | 0.547 | -0.537 |
| TCRBV06_7 | 0.510 | 0.824 | 0.632 | 0.069 | -0.184 |
| TCRBV06_8 | 0.278 | 0.455 | 0.106 | 0.178 | 0.432 |
| TCRBV06_9 | 1.472 | -0.367 | -0.245 | -0.017 | -0.570 |
| TCRBV06_10 | -0.804 | -0.066 | 0.105 | 0.279 | 0.045 |
| TCRBV06_11 | -0.178 | -0.623 | 0.586 | 0.092 | 1.272 |
| TCRBV06_12 | 0.080 | -0.207 | -0.967 | 0.384 | -0.366 |
| TCRBV06_13 | -0.004 | 0.120 | -0.206 | -0.099 | 0.054 |
| TCRBV07_5 | 0.005 | -0.011 | 0.025 | 0.001 | -0.061 |
| TCRBV07_6 | 0.273 | -0.356 | 0.593 | -0.086 | -0.048 |
| TCRBV07_7 | -0.452 | -1.366 | 0.766 | 0.175 | -0.434 |
| TCRBV07_8 | -0.701 | 0.737 | -0.779 | 0.164 | -0.084 |
| TCRBV07_9 | 0.020 | -0.299 | 0.263 | -0.804 | 1.635 |
| TCRBV07_10 | 0.525 | 0.727 | -0.751 | 1.821 | -0.753 |
| TCRBV07_11 | 0.931 | 0.422 | 0.884 | 0.200 | 0.171 |
| TCRBV07_12 | 0.869 | 0.257 | -0.832 | -0.173 | -0.303 |
| TCRBV07_13 | 0.275 | -0.052 | 0.129 | 0.098 | 0.148 |
| TCRBV081_5 | -0.186 | 0.018 | 0.214 | -0.042 | -0.124 |
| TCRBV081_6 | -0.383 | 0.415 | -0.237 | -0.181 | 0.147 |
| TCRBV081_7 | -0.135 | 0.263 | -0.377 | 0.501 | -0.332 |
| TCRBV081_8 | -0.470 | 0.091 | 0.358 | 0.083 | -0.587 |
| TCRBV081_9 | 1.522 | -2.568 | -1.689 | 1.176 | 0.150 |
| TCRBV081_10 | 0.102 | 1.256 | 0.980 | -0.910 | 0.959 |
| TCRBV081_11 | -0.321 | 0.553 | 0.529 | -0.535 | -0.090 |
| TCRBV081_12 | -0.129 | -0.027 | 0.222 | -0.092 | -0.122 |
| TCRBV082_4 | -0.605 | 0.479 | 0.143 | -0.066 | 0.096 |
| TCRBV082_5 | -0.214 | 0.771 | 0.245 | 0.443 | 0.490 |
| TCRBV082_6 | -0.308 | 1.061 | 0.104 | 0.159 | 0.290 |
| TCRBV082_7 | 0.105 | 1.090 | 0.137 | 0.544 | 0.534 |
| TCRBV082_8 | -0.909 | -2.105 | -0.899 | -0.301 | -0.941 |
| TCRBV082_9 | 0.967 | -0.858 | -0.159 | -0.188 | -0.426 |
| TCRBV082_10 | 0.650 | -0.672 | -0.046 | -0.573 | -0.063 |
| TCRBV082_11 | 0.313 | 0.234 | 0.474 | -0.016 | 0.019 |
| TCRBV083_4 | -0.010 | -0.006 | 0.079 | 0.049 | 0.038 |
| TCRBV083_5 | -0.037 | -0.000 | -0.069 | 0.041 | 0.079 |
| TCRBV083_6 | -0.326 | -0.030 | -0.069 | 0.140 | -0.048 |
| TCRBV083_7 | -0.331 | 0.408 | -0.024 | 0.293 | -0.242 |
| TCRBV083_8 | -0.608 | 0.310 | -0.479 | 0.183 | -0.342 |
| TCRBV083_9 | -0.990 | -0.398 | 0.460 | -0.094 | 0.578 |

*FIG. 102A*

| | | | | | |
|---|---|---|---|---|---|
| TCRBV083_10 | 0.333 | 0.091 | 0.214 | -0.766 | 0.370 |
| TCRBV083_11 | 1.560 | -0.275 | -0.432 | 0.101 | -0.658 |
| TCRBV083_12 | 0.410 | -0.100 | 0.321 | 0.054 | 0.226 |
| TCRBV09_5 | -0.154 | -0.028 | 0.180 | 0.083 | -0.236 |
| TCRBV09_6 | -0.220 | 0.273 | 0.448 | -0.401 | 0.203 |
| TCRBV09_7 | 0.191 | 0.844 | 0.598 | -0.603 | -0.383 |
| TCRBV09_8 | -1.128 | -0.203 | -0.908 | -2.343 | 0.176 |
| TCRBV09_9 | -1.097 | -0.258 | 0.663 | -0.596 | 1.788 |
| TCRBV09_10 | -0.528 | 0.356 | 0.622 | -0.181 | -0.575 |
| TCRBV09_11 | 0.462 | -1.803 | -1.502 | -0.530 | 0.616 |
| TCRBV09_12 | 0.124 | 0.435 | 1.089 | 1.636 | 0.320 |
| TCRBV09_13 | 0.131 | 0.467 | 0.605 | 0.913 | -0.066 |
| TCRBV09_14 | 0.140 | 0.199 | 0.164 | 0.490 | 0.108 |
| TCRBV09_15 | 0.030 | -0.003 | 0.032 | 0.081 | -0.037 |
| TCRBV10_6 | 0.722 | 0.362 | -0.485 | -0.361 | -0.139 |
| TCRBV10_7 | 0.842 | 0.382 | -0.713 | 0.063 | 0.823 |
| TCRBV10_8 | 0.316 | -0.457 | -0.381 | -0.072 | 1.074 |
| TCRBV10_9 | 0.045 | -0.956 | 1.048 | 0.279 | -1.374 |
| TCRBV10_10 | -0.434 | -0.530 | 0.421 | -0.130 | -0.567 |
| TCRBV10_11 | -1.029 | 0.651 | 0.111 | 0.352 | 0.481 |
| TCRBV10_12 | -0.502 | 0.520 | 0.044 | -0.173 | -0.303 |
| TCRBV10_13 | 0.040 | 0.028 | -0.044 | 0.043 | 0.006 |
| TCRBV11_5 | -0.064 | 0.062 | -0.260 | 0.134 | -0.098 |
| TCRBV11_6 | -0.972 | 0.017 | -0.360 | 0.328 | 0.057 |
| TCRBV11_7 | -0.587 | 0.263 | 0.146 | 0.243 | 0.084 |
| TCRBV11_8 | 0.172 | -0.023 | -0.417 | -0.758 | -0.457 |
| TCRBV11_9 | -1.042 | 0.612 | -0.205 | -1.241 | -1.087 |
| TCRBV11_10 | 1.012 | -0.917 | 0.936 | 0.819 | -0.365 |
| TCRBV11_11 | 1.613 | 0.243 | 0.545 | 0.251 | 0.750 |
| TCRBV11_12 | 0.682 | -0.543 | 0.273 | 0.916 | 0.850 |
| TCRBV11_13 | 0.680 | 0.169 | -0.085 | 0.438 | 0.498 |
| TCRBV11_14 | 0.183 | 0.129 | -0.200 | 0.194 | 0.027 |
| TCRBV11_15 | 0.068 | 0.048 | -0.074 | 0.072 | 0.010 |
| TCRBV12_4 | 0.022 | 0.053 | 0.180 | -0.065 | -0.101 |
| TCRBV12_5 | 1.110 | -0.584 | 1.057 | -0.068 | -0.140 |
| TCRBV12_6 | -0.075 | -0.769 | 0.467 | 0.097 | -0.644 |
| TCRBV12_7 | -0.259 | -1.402 | 0.689 | -0.125 | -1.174 |
| TCRBV12_8 | 0.087 | -0.402 | 0.187 | -0.477 | -0.052 |
| TCRBV12_9 | 0.119 | 0.966 | -0.925 | 1.005 | 0.253 |
| TCRBV12_10 | -2.043 | 1.000 | -0.114 | -0.685 | 0.668 |
| TCRBV12_11 | 0.547 | 0.877 | -1.581 | 0.308 | 0.942 |
| TCRBV12_12 | 0.492 | 0.262 | 0.041 | 0.011 | 0.249 |
| TCRBV13_5 | 0.121 | 0.015 | -0.081 | -0.017 | 0.009 |
| TCRBV13_6 | -1.169 | 0.258 | 0.295 | 0.299 | 0.480 |
| TCRBV13_7 | 0.554 | 1.274 | 0.108 | -0.247 | -0.776 |
| TCRBV13_8 | -0.691 | -0.703 | -1.262 | 0.501 | -0.489 |
| TCRBV13_9 | 0.455 | 0.203 | 0.486 | -0.737 | 0.389 |
| TCRBV13_10 | -0.196 | -0.138 | 1.183 | 0.206 | -0.237 |
| TCRBV13_11 | 0.740 | -0.070 | -0.809 | -0.165 | 0.427 |
| TCRBV13_12 | 0.053 | -0.160 | 0.256 | 0.096 | 0.192 |
| TCRBV13_13 | 0.132 | -0.680 | -0.176 | 0.063 | 0.005 |
| TCRBV14_5 | 0.308 | 0.021 | -0.164 | -0.004 | -0.105 |
| TCRBV14_6 | 0.564 | 0.312 | -0.184 | -0.277 | 0.014 |
| TCRBV14_7 | 1.453 | -0.325 | 0.497 | -0.407 | -0.207 |
| TCRBV14_8 | 0.303 | -0.679 | -0.102 | 0.386 | 0.164 |
| TCRBV14_9 | -0.497 | -0.954 | -0.253 | -0.098 | -0.256 |
| TCRBV14_10 | -1.038 | 1.158 | -0.080 | -0.496 | -0.094 |
| TCRBV14_11 | -1.230 | 0.427 | 0.330 | 0.618 | 0.386 |
| TCRBV14_12 | 0.086 | 0.023 | -0.003 | 0.211 | 0.073 |
| TCRBV14_13 | 0.052 | 0.017 | -0.041 | 0.066 | 0.025 |
| TCRBV15_4 | -0.022 | 0.052 | 0.015 | -0.064 | 0.065 |
| TCRBV15_5 | -0.051 | 1.008 | -1.136 | 0.049 | -0.596 |
| TCRBV15_6 | -0.773 | -0.068 | 0.204 | 0.636 | -0.051 |
| TCRBV15_7 | -1.179 | -0.041 | -0.204 | 0.111 | -0.181 |

*FIG.102B*

|  |  |  |  |  |  |
|---|---|---|---|---|---|
| TCRBV15_8 | 0.828 | 0.729 | -0.001 | 0.308 | 0.060 |
| TCRBV15_9 | 1.208 | 0.830 | 1.383 | -0.416 | 0.418 |
| TCRBV15_10 | 0.580 | -1.442 | 0.006 | 0.863 | 0.370 |
| TCRBV15_11 | 0.879 | -0.697 | 0.040 | -0.025 | 0.349 |
| TCRBV15_12 | 0.276 | -0.312 | -0.008 | -0.065 | -0.163 |
| TCRBV16_5 | -0.131 | 0.237 | 0.055 | 0.198 | -0.079 |
| TCRBV16_6 | -0.499 | 0.666 | -0.886 | 1.169 | 0.117 |
| TCRBV16_7 | -0.295 | 0.423 | -0.001 | -1.066 | 0.136 |
| TCRBV16_8 | -0.055 | 0.742 | 0.373 | 1.006 | 0.007 |
| TCRBV16_9 | 0.553 | -0.298 | -0.533 | 0.181 | -1.618 |
| TCRBV16_10 | -0.445 | 0.654 | -2.438 | -0.383 | 0.453 |
| TCRBV16_11 | 1.179 | -0.232 | 2.576 | 0.828 | 0.555 |
| TCRBV16_12 | 1.234 | -1.220 | 0.280 | -1.105 | -0.258 |
| TCRBV16_13 | 0.110 | 0.115 | 0.051 | -0.121 | -0.053 |
| TCRBV18_3 | 0.002 | -0.007 | 0.012 | 0.016 | -0.028 |
| TCRBV18_4 | -0.345 | 0.670 | 0.183 | 0.552 | -0.536 |
| TCRBV18_5 | -0.407 | 0.864 | 0.120 | 0.568 | -0.878 |
| TCRBV18_6 | -0.245 | 0.101 | 0.120 | 0.372 | -2.058 |
| TCRBV18_7 | -1.112 | -0.788 | -0.503 | 0.752 | 0.228 |
| TCRBV18_8 | 0.099 | -1.862 | 0.205 | -0.204 | 1.216 |
| TCRBV18_9 | 0.612 | -0.109 | -0.765 | 0.095 | 0.892 |
| TCRBV18_10 | 0.873 | -0.445 | -0.474 | -0.505 | 0.795 |
| TCRBV18_11 | 0.327 | 0.278 | -0.587 | 0.179 | -0.186 |
| TCRBV18_12 | 0.117 | 0.057 | -0.029 | 0.069 | -0.053 |
| TCRBV18_13 | -0.060 | 0.025 | 0.067 | -0.066 | 0.020 |
| TCRBV20_5 | -0.155 | -0.149 | -0.129 | 0.106 | -0.029 |
| TCRBV20_6 | -0.480 | 0.164 | -0.032 | 0.041 | 0.879 |
| TCRBV20_7 | 0.101 | -0.950 | 0.416 | -0.827 | -0.719 |
| TCRBV20_8 | -0.927 | -1.448 | 0.547 | 0.407 | 1.055 |
| TCRBV20_9 | 1.665 | -0.690 | -0.903 | 0.222 | -1.122 |
| TCRBV20_10 | -0.152 | 0.082 | 0.733 | 1.987 | 0.025 |
| TCRBV20_11 | 1.612 | 1.397 | 0.181 | -0.414 | 0.622 |
| TCRBV20_12 | 0.094 | 0.274 | 0.268 | -0.489 | 0.438 |
| TCRBV20_13 | 0.006 | 1.336 | -0.794 | 0.415 | -0.930 |
| TCRBV20_14 | -0.018 | 0.042 | 0.012 | -0.052 | 0.052 |
|  | 26 | 27 | 28 | 29 | 30 |
| TCRBV01_6 | -0.202 | -0.173 | -0.047 | 0.033 | 0.145 |
| TCRBV01_7 | -0.078 | -0.189 | 0.155 | 0.172 | -0.121 |
| TCRBV01_8 | 0.777 | 0.327 | 0.297 | 0.175 | 0.398 |
| TCRBV01_9 | 0.358 | 0.670 | -0.505 | -1.099 | -1.170 |
| TCRBV01_10 | 0.181 | 0.121 | -0.041 | 0.488 | 0.052 |
| TCRBV01_11 | 0.142 | 0.104 | 0.155 | 0.100 | 0.322 |
| TCRBV01_12 | 0.180 | -0.363 | -0.174 | 0.290 | 0.364 |
| TCRBV01_13 | 0.092 | 0.227 | 0.053 | 0.046 | -0.015 |
| TCRBV01_14 | 0.021 | 0.030 | 0.018 | -0.007 | 0.004 |
| TCRBV02_6 | 0.003 | 0.027 | -0.094 | 0.174 | 0.716 |
| TCRBV02_7 | 0.504 | -0.302 | -0.266 | 0.158 | -0.047 |
| TCRBV02_8 | -0.324 | -0.440 | -0.028 | -0.282 | 0.282 |
| TCRBV02_9 | -1.091 | 0.926 | 0.506 | 0.292 | -0.324 |
| TCRBV02_10 | -0.999 | 0.221 | 0.548 | -0.144 | 0.010 |
| TCRBV02_11 | -0.992 | 0.143 | -0.135 | -0.056 | -0.027 |
| TCRBV02_12 | -0.464 | -0.114 | 0.553 | -0.206 | 0.057 |
| TCRBV02_13 | -0.078 | -0.051 | -0.008 | -0.158 | 0.002 |
| TCRBV03_4 | 0.089 | -0.011 | -0.028 | 0.006 | -0.017 |
| TCRBV03_5 | -0.011 | -0.028 | 0.016 | 0.096 | -0.002 |
| TCRBV03_6 | 0.558 | -0.170 | 0.019 | 0.282 | -0.220 |
| TCRBV03_7 | 0.303 | -0.272 | 0.535 | -0.055 | -0.301 |
| TCRBV03_8 | -0.346 | -0.173 | 1.131 | -0.456 | -0.218 |
| TCRBV03_9 | -0.599 | -0.208 | -0.268 | -0.890 | 0.365 |
| TCRBV03_10 | 0.111 | 0.363 | 0.357 | 0.032 | 0.553 |
| TCRBV03_11 | 0.539 | 0.257 | -0.549 | 0.608 | -0.206 |

*FIG.102C*

| | | | | | |
|---|---|---|---|---|---|
| TCRBV03_12 | 0.462 | -0.235 | -0.704 | 0.351 | 0.054 |
| TCRBV03_13 | 0.364 | 1.230 | -0.599 | 0.225 | -0.028 |
| TCRBV04_6 | -0.077 | 0.040 | 0.017 | 0.051 | 0.045 |
| TCRBV04_7 | 0.065 | -0.373 | 0.127 | 0.131 | 0.327 |
| TCRBV04_8 | 0.501 | -0.621 | -0.021 | 0.118 | -0.199 |
| TCRBV04_9 | 0.646 | -1.073 | 0.121 | 0.612 | -0.214 |
| TCRBV04_10 | -0.266 | 0.339 | -0.595 | -1.448 | -0.492 |
| TCRBV04_11 | -0.192 | 0.607 | -0.088 | 0.668 | -0.148 |
| TCRBV04_12 | -0.249 | 0.168 | 0.115 | 0.937 | 0.617 |
| TCRBV04_13 | -0.147 | 0.626 | -0.038 | -0.248 | 0.120 |
| TCRBV04_14 | -0.370 | 0.090 | 0.280 | -0.437 | -0.093 |
| TCRBV04_15 | 0.088 | 0.198 | 0.080 | -0.383 | 0.038 |
| TCRBV051_5 | 0.095 | -0.072 | -0.117 | 0.091 | 0.322 |
| TCRBV051_6 | 0.300 | -0.742 | -0.158 | 0.665 | -0.061 |
| TCRBV051_7 | 1.154 | 0.150 | 0.548 | -0.309 | 0.131 |
| TCRBV051_8 | -1.168 | -0.692 | -0.229 | -0.912 | 0.212 |
| TCRBV051_9 | 0.976 | 1.173 | 1.475 | 0.917 | -0.242 |
| TCRBV051_10 | -1.264 | 0.031 | -0.311 | 0.388 | -0.368 |
| TCRBV051_11 | 0.470 | 0.370 | 0.480 | -0.433 | 0.694 |
| TCRBV051_12 | -0.706 | -0.664 | -0.425 | 0.434 | 0.334 |
| TCRBV051_13 | -0.006 | 0.036 | -0.079 | -0.212 | 0.323 |
| TCRBV052_6 | -0.000 | -0.001 | 0.129 | -0.560 | 0.064 |
| TCRBV052_7 | -0.333 | 0.676 | 0.304 | -0.790 | 0.025 |
| TCRBV052_8 | -0.546 | -0.549 | 0.473 | -0.043 | 0.581 |
| TCRBV052_9 | 0.330 | -0.116 | -0.366 | 0.897 | -0.606 |
| TCRBV052_10 | -0.455 | -0.901 | 0.349 | 0.189 | 0.489 |
| TCRBV052_11 | 0.885 | 0.292 | 0.343 | 0.291 | 0.434 |
| TCRBV052_12 | 0.151 | 0.068 | -0.110 | 0.506 | 0.378 |
| TCRBV052_13 | -0.182 | 0.121 | 0.060 | 0.139 | -0.017 |
| TCRBV06_5 | 0.019 | -0.053 | 0.071 | 0.071 | 0.009 |
| TCRBV06_6 | -0.364 | -0.263 | 0.103 | 0.178 | -0.106 |
| TCRBV06_7 | 0.036 | -0.190 | 0.745 | 0.582 | -0.091 |
| TCRBV06_8 | -0.246 | -0.401 | 0.456 | -0.169 | -0.512 |
| TCRBV06_9 | -1.055 | 0.098 | 0.255 | 0.189 | -0.909 |
| TCRBV06_10 | 0.811 | 1.255 | -0.533 | -0.726 | 0.203 |
| TCRBV06_11 | 1.757 | 0.041 | -0.638 | -0.549 | 0.587 |
| TCRBV06_12 | 0.007 | -0.043 | -0.614 | 0.246 | 0.821 |
| TCRBV06_13 | 0.505 | 0.310 | 0.064 | 0.379 | -0.023 |
| TCRBV07_5 | -0.008 | -0.009 | 0.025 | -0.037 | -0.034 |
| TCRBV07_6 | 0.158 | 0.794 | -0.811 | -0.267 | 0.119 |
| TCRBV07_7 | 0.186 | 0.154 | -0.658 | -0.270 | 0.274 |
| TCRBV07_8 | -0.102 | -0.646 | -0.247 | 0.820 | -0.469 |
| TCRBV07_9 | 0.988 | 0.655 | 0.107 | -1.057 | -0.005 |
| TCRBV07_10 | -0.005 | -0.136 | 0.508 | 0.254 | 0.536 |
| TCRBV07_11 | 0.947 | 0.498 | 0.487 | 0.199 | -0.428 |
| TCRBV07_12 | -0.505 | -0.544 | 0.455 | 0.428 | -0.000 |
| TCRBV07_13 | -0.188 | -0.013 | 0.043 | 0.130 | -0.013 |
| TCRBV081_5 | 0.015 | -0.163 | -0.033 | 0.165 | 0.068 |
| TCRBV081_6 | 0.340 | -0.221 | 0.134 | -0.209 | 0.390 |
| TCRBV081_7 | 0.196 | 0.983 | 0.882 | -0.781 | 0.283 |
| TCRBV081_8 | 0.018 | 0.290 | 1.469 | -0.344 | 0.362 |
| TCRBV081_9 | -0.341 | 0.693 | 0.100 | 0.604 | -0.275 |
| TCRBV081_10 | -0.120 | -0.935 | -0.876 | -0.295 | 0.917 |
| TCRBV081_11 | -0.066 | -0.504 | -0.345 | 0.167 | -0.487 |
| TCRBV081_12 | -0.043 | -0.144 | -1.332 | 0.692 | -1.259 |
| TCRBV082_4 | -0.267 | 0.115 | 0.380 | 0.258 | 0.345 |
| TCRBV082_5 | -0.027 | 0.511 | -0.006 | 0.191 | 0.217 |
| TCRBV082_6 | -0.029 | 0.512 | 0.684 | 0.553 | 0.447 |
| TCRBV082_7 | -0.075 | 0.719 | -0.209 | 0.577 | 0.049 |
| TCRBV082_8 | -0.099 | -0.784 | -0.190 | -0.494 | -0.021 |
| TCRBV082_9 | 0.376 | -0.543 | -0.367 | -0.632 | -0.330 |
| TCRBV082_10 | -0.155 | -0.423 | -0.153 | -0.418 | -0.374 |
| TCRBV082_11 | 0.275 | -0.108 | -0.139 | -0.034 | -0.332 |
| TCRBV083_4 | 0.026 | 0.095 | -0.041 | 0.017 | -0.000 |

*FIG. 102D*

| | | | | | |
|---|---|---|---|---|---|
| TCRBV083_5 | -0.095 | -0.090 | -0.301 | 0.208 | -0.310 |
| TCRBV083_6 | -0.365 | 0.072 | -0.393 | 0.206 | -0.193 |
| TCRBV083_7 | -0.307 | 0.082 | -0.850 | 0.039 | -0.266 |
| TCRBV083_8 | -0.246 | 0.198 | -0.447 | 0.165 | 0.648 |
| TCRBV083_9 | 0.032 | -0.558 | 0.305 | -0.293 | -0.202 |
| TCRBV083_10 | 0.487 | 0.366 | 0.362 | -0.291 | -0.267 |
| TCRBV083_11 | 0.254 | -0.423 | 0.741 | 0.074 | 0.065 |
| TCRBV083_12 | 0.212 | 0.258 | 0.623 | -0.126 | 0.525 |
| TCRBV09_5 | -0.009 | -0.187 | -0.075 | 0.104 | 0.032 |
| TCRBV09_6 | -0.060 | -0.095 | 0.170 | -0.202 | 0.084 |
| TCRBV09_7 | -0.322 | -0.221 | 0.730 | 0.444 | -0.431 |
| TCRBV09_8 | -0.200 | -0.387 | -0.064 | -0.400 | -0.451 |
| TCRBV09_9 | -1.272 | -0.683 | 1.048 | 0.775 | -0.097 |
| TCRBV09_10 | -0.704 | 0.103 | -1.093 | 0.460 | 0.947 |
| TCRBV09_11 | 0.085 | -1.288 | 0.082 | 0.418 | 0.021 |
| TCRBV09_12 | -0.859 | 0.702 | -1.093 | -0.856 | 0.552 |
| TCRBV09_13 | -0.235 | 0.495 | -0.389 | -0.297 | -0.352 |
| TCRBV09_14 | -0.100 | 0.184 | 0.152 | 0.069 | 0.097 |
| TCRBV09_15 | -0.017 | 0.068 | 0.041 | 0.042 | -0.074 |
| TCRBV10_6 | 0.297 | 0.039 | 0.045 | -0.334 | 0.420 |
| TCRBV10_7 | 0.439 | -0.491 | 0.188 | 0.207 | 0.390 |
| TCRBV10_8 | 0.633 | 0.591 | 0.583 | -0.091 | 0.481 |
| TCRBV10_9 | 0.639 | 0.461 | 0.981 | -0.555 | -0.853 |
| TCRBV10_10 | 0.389 | -0.797 | -0.232 | -0.116 | -0.167 |
| TCRBV10_11 | -1.769 | 0.224 | -0.595 | 0.531 | -0.325 |
| TCRBV10_12 | -0.671 | -0.022 | -0.956 | 0.355 | 0.062 |
| TCRBV10_13 | 0.043 | -0.005 | -0.013 | 0.003 | -0.008 |
| TCRBV11_5 | 0.092 | 0.215 | -0.106 | 0.099 | 0.087 |
| TCRBV11_6 | 0.025 | -0.117 | 0.066 | 0.195 | 0.215 |
| TCRBV11_7 | 0.289 | 0.254 | -0.198 | 0.658 | -0.015 |
| TCRBV11_8 | 0.671 | -0.420 | 0.403 | 0.608 | 0.132 |
| TCRBV11_9 | 0.102 | 0.910 | 0.055 | -0.293 | -0.308 |
| TCRBV11_10 | 0.501 | 0.385 | -0.148 | -0.130 | -0.076 |
| TCRBV11_11 | 0.001 | 0.372 | -0.022 | -0.481 | 0.018 |
| TCRBV11_12 | -0.534 | -0.716 | -0.048 | -0.342 | 0.086 |
| TCRBV11_13 | 0.055 | -0.098 | -0.010 | -0.133 | -0.107 |
| TCRBV11_14 | 0.194 | -0.023 | -0.061 | 0.013 | -0.038 |
| TCRBV11_15 | 0.072 | -0.009 | -0.023 | 0.005 | -0.014 |
| TCRBV12_4 | 0.063 | 0.093 | -0.032 | 0.160 | 0.048 |
| TCRBV12_5 | 0.547 | 0.406 | -0.901 | 0.493 | -0.088 |
| TCRBV12_6 | 0.015 | -0.262 | -0.075 | -0.603 | 0.862 |
| TCRBV12_7 | -0.338 | -0.765 | -0.332 | -0.421 | 0.136 |
| TCRBV12_8 | -0.346 | 0.402 | 0.469 | 0.321 | -0.268 |
| TCRBV12_9 | 0.128 | -0.130 | 0.618 | 0.256 | -0.225 |
| TCRBV12_10 | -0.084 | 0.212 | -0.067 | 0.144 | -0.508 |
| TCRBV12_11 | 0.065 | -0.002 | 0.339 | -0.119 | -0.125 |
| TCRBV12_12 | -0.049 | 0.045 | -0.018 | -0.232 | 0.168 |
| TCRBV13_5 | 0.134 | -0.043 | -0.026 | -0.075 | -0.077 |
| TCRBV13_6 | -0.455 | 0.187 | -0.305 | 0.187 | -0.607 |
| TCRBV13_7 | 1.379 | 0.112 | -0.400 | 0.364 | 0.455 |
| TCRBV13_8 | -0.206 | -0.742 | 0.866 | 0.551 | -0.291 |
| TCRBV13_9 | -0.552 | -1.274 | 0.468 | 0.356 | 0.763 |
| TCRBV13_10 | -0.064 | -0.313 | 0.061 | -0.774 | -0.327 |
| TCRBV13_11 | -0.172 | -0.645 | -0.488 | -0.527 | -0.411 |
| TCRBV13_12 | 0.022 | 0.212 | -0.287 | -0.298 | 0.283 |
| TCRBV13_13 | -0.087 | -0.042 | 0.111 | 0.217 | 0.213 |
| TCRBV14_5 | 0.043 | -0.197 | -0.047 | 0.044 | -0.007 |
| TCRBV14_6 | 0.033 | -0.131 | 0.080 | 0.067 | -0.056 |
| TCRBV14_7 | 0.549 | 0.205 | 0.166 | -0.187 | 0.236 |
| TCRBV14_8 | -0.499 | 0.691 | 0.235 | 0.008 | -0.218 |
| TCRBV14_9 | 0.479 | 0.757 | -0.523 | 0.098 | 0.099 |
| TCRBV14_10 | -1.073 | -0.076 | -0.466 | -0.276 | -0.006 |
| TCRBV14_11 | 0.382 | -1.236 | 0.478 | 0.254 | -0.056 |
| TCRBV14_12 | 0.029 | -0.014 | 0.115 | -0.001 | 0.042 |

*FIG. 103A*

| | | | | | |
|---|---:|---:|---:|---:|---:|
| TCRBV14_13 | 0.056 | 0.001 | -0.038 | -0.008 | -0.034 |
| TCRBV15_4 | -0.012 | -0.074 | 0.008 | -0.185 | -0.024 |
| TCRBV15_5 | -0.333 | 0.810 | -0.200 | 0.363 | 0.228 |
| TCRBV15_6 | 0.096 | 0.049 | -0.169 | 0.347 | 0.092 |
| TCRBV15_7 | 1.306 | -0.907 | -0.742 | 0.105 | 0.265 |
| TCRBV15_8 | 0.958 | 0.577 | -0.079 | -0.265 | -0.664 |
| TCRBV15_9 | 0.368 | 0.137 | -0.007 | 0.657 | -0.303 |
| TCRBV15_10 | -0.563 | 0.401 | 0.636 | -0.747 | 0.476 |
| TCRBV15_11 | -0.275 | -0.223 | 0.463 | -0.132 | -0.037 |
| TCRBV15_12 | -0.074 | -0.016 | -0.002 | 0.057 | -0.056 |
| TCRBV16_5 | 0.002 | 0.162 | 0.110 | -0.150 | 0.038 |
| TCRBV16_6 | 0.245 | 1.253 | -0.268 | 0.049 | -0.097 |
| TCRBV16_7 | 1.056 | 0.195 | 0.512 | 0.207 | -0.292 |
| TCRBV16_8 | 1.032 | -1.770 | -0.134 | -0.369 | 0.366 |
| TCRBV16_9 | -0.786 | 0.057 | 0.661 | -0.379 | 0.802 |
| TCRBV16_10 | 0.052 | 0.426 | 0.296 | 0.136 | -0.490 |
| TCRBV16_11 | -0.134 | 0.080 | 0.459 | 1.341 | 0.655 |
| TCRBV16_12 | -0.373 | -0.169 | -0.732 | -0.136 | 0.291 |
| TCRBV16_13 | 0.227 | 0.109 | 0.187 | 0.131 | 0.054 |
| TCRBV18_3 | -0.011 | -0.018 | -0.005 | 0.012 | -0.006 |
| TCRBV18_4 | -0.385 | 0.155 | 0.296 | -0.584 | -0.075 |
| TCRBV18_5 | -1.028 | -0.527 | 0.357 | -0.442 | 0.315 |
| TCRBV18_6 | -1.260 | 0.842 | 0.617 | -0.909 | -0.125 |
| TCRBV18_7 | -0.193 | -1.547 | -0.017 | -0.470 | -0.537 |
| TCRBV18_8 | -1.171 | 1.573 | -0.965 | 1.106 | 0.010 |
| TCRBV18_9 | -0.879 | -0.272 | 0.121 | 0.609 | 1.186 |
| TCRBV18_10 | 0.039 | -0.131 | 0.680 | 0.363 | -0.174 |
| TCRBV18_11 | 0.204 | -0.378 | 0.270 | -0.017 | -0.215 |
| TCRBV18_12 | 0.103 | 0.052 | 0.174 | 0.010 | 0.103 |
| TCRBV18_13 | 0.014 | -0.029 | 0.011 | 0.067 | 0.033 |
| TCRBV20_5 | 0.280 | 0.036 | -0.046 | 0.038 | 0.125 |
| TCRBV20_6 | 0.542 | -0.193 | -0.693 | -0.806 | 0.759 |
| TCRBV20_7 | 0.607 | 0.076 | 0.128 | -0.035 | 0.560 |
| TCRBV20_8 | -0.045 | 0.321 | 0.621 | 0.470 | 0.751 |
| TCRBV20_9 | 0.289 | 0.033 | -0.723 | 1.306 | 0.168 |
| TCRBV20_10 | 0.205 | -0.131 | 0.222 | 0.118 | -2.418 |
| TCRBV20_11 | -0.540 | 0.134 | 0.724 | -0.342 | -0.123 |
| TCRBV20_12 | 0.086 | -0.456 | 0.225 | -0.390 | 0.227 |
| TCRBV20_13 | 0.054 | 0.993 | -0.555 | -0.010 | -0.050 |
| TCRBV20_14 | -0.009 | -0.060 | 0.007 | -0.150 | -0.019 |
| | 31 | 32 | 33 | 34 | 35 |
| TCRBV01_6 | -0.018 | 0.070 | 0.011 | 0.093 | 0.015 |
| TCRBV01_7 | 0.623 | 0.102 | 0.195 | 0.141 | 0.047 |
| TCRBV01_8 | 0.678 | -0.704 | 0.327 | -0.704 | 0.059 |
| TCRBV01_9 | 0.879 | 1.282 | 0.305 | 0.333 | 0.123 |
| TCRBV01_10 | -0.250 | 0.005 | -0.065 | -0.239 | -0.013 |
| TCRBV01_11 | -1.133 | -0.810 | -0.609 | 0.385 | -0.278 |
| TCRBV01_12 | -0.410 | 0.356 | -0.278 | -0.117 | -0.078 |
| TCRBV01_13 | -0.154 | -0.135 | -0.249 | -0.156 | -0.062 |
| TCRBV01_14 | 0.006 | -0.005 | 0.005 | 0.009 | -0.021 |
| TCRBV02_6 | 0.177 | 0.356 | -0.049 | 0.221 | 0.287 |
| TCRBV02_7 | -0.560 | 0.001 | -0.021 | -0.055 | 0.303 |
| TCRBV02_8 | 0.353 | -0.334 | 0.209 | -0.125 | 0.170 |
| TCRBV02_9 | 0.090 | -0.538 | -0.084 | 1.106 | 0.298 |
| TCRBV02_10 | 0.124 | 0.199 | 0.518 | 0.361 | -0.133 |
| TCRBV02_11 | 0.075 | 0.057 | 0.255 | 0.155 | -0.296 |
| TCRBV02_12 | -0.547 | -0.180 | 0.474 | -0.264 | -0.089 |
| TCRBV02_13 | -0.026 | -0.190 | 0.304 | -0.027 | 0.105 |
| TCRBV03_4 | 0.008 | 0.016 | -0.042 | -0.036 | -0.017 |
| TCRBV03_5 | -0.042 | 0.028 | -0.033 | 0.072 | 0.015 |
| TCRBV03_6 | 0.674 | -0.302 | -0.291 | -0.348 | 0.138 |

*FIG 103B*

| | | | | | |
|---|---|---|---|---|---|
| TCRBV03_7 | 0.077 | -0.182 | 0.433 | 0.105 | -0.334 |
| TCRBV03_8 | 0.153 | -0.595 | 0.393 | -0.247 | 0.172 |
| TCRBV03_9 | -0.075 | 0.146 | 0.024 | -0.469 | 0.315 |
| TCRBV03_10 | -0.903 | 0.337 | -0.269 | 0.435 | -0.141 |
| TCRBV03_11 | 0.134 | 0.223 | 0.046 | 0.759 | -0.637 |
| TCRBV03_12 | -0.009 | 0.547 | -0.302 | 0.033 | 0.410 |
| TCRBV03_13 | 0.203 | -0.056 | -0.318 | -0.559 | -0.130 |
| TCRBV04_6 | -0.079 | 0.050 | -0.030 | -0.049 | 0.007 |
| TCRBV04_7 | -0.166 | 0.108 | -0.211 | -0.025 | -0.197 |
| TCRBV04_8 | 0.598 | -0.612 | -0.079 | 0.431 | 0.285 |
| TCRBV04_9 | 0.604 | 0.005 | -0.715 | 0.115 | 0.306 |
| TCRBV04_10 | -0.869 | -0.510 | 0.181 | 0.371 | 0.542 |
| TCRBV04_11 | -0.614 | 0.128 | 0.423 | -0.830 | 0.603 |
| TCRBV04_12 | 0.461 | 0.316 | 1.297 | 0.276 | 0.287 |
| TCRBV04_13 | 0.010 | 0.803 | -0.832 | -0.224 | -0.893 |
| TCRBV04_14 | -0.101 | -0.435 | -0.146 | -0.098 | -0.736 |
| TCRBV04_15 | 0.156 | 0.146 | 0.111 | 0.032 | -0.204 |
| TCRBV051_5 | -0.354 | -0.499 | 0.016 | -0.014 | -0.017 |
| TCRBV051_6 | 0.230 | 0.114 | -0.261 | 0.300 | 0.279 |
| TCRBV051_7 | -0.467 | -0.417 | 0.229 | -0.036 | 0.325 |
| TCRBV051_8 | 0.200 | -0.266 | -0.052 | 0.210 | 0.148 |
| TCRBV051_9 | 0.160 | 0.982 | 0.835 | -0.258 | 0.613 |
| TCRBV051_10 | 0.310 | -0.280 | -0.588 | -0.172 | 0.265 |
| TCRBV051_11 | 0.081 | 0.011 | -0.039 | 0.675 | -0.050 |
| TCRBV051_12 | -0.019 | -0.744 | -0.175 | 0.560 | -0.864 |
| TCRBV051_13 | -0.153 | -0.109 | 0.157 | -0.028 | 0.013 |
| TCRBV052_6 | -0.062 | -0.094 | 0.049 | 0.262 | -0.220 |
| TCRBV052_7 | -0.403 | 0.096 | 0.157 | 0.340 | -0.075 |
| TCRBV052_8 | 0.253 | -0.176 | -0.081 | 0.102 | 0.196 |
| TCRBV052_9 | -0.459 | -0.266 | 0.223 | 0.438 | 0.427 |
| TCRBV052_10 | 0.864 | -1.009 | -0.094 | 0.035 | -0.119 |
| TCRBV052_11 | -0.329 | 0.277 | -0.042 | 0.137 | 0.406 |
| TCRBV052_12 | 0.216 | -0.078 | -0.036 | -0.036 | 0.116 |
| TCRBV052_13 | -0.092 | 0.043 | -0.054 | -0.041 | -0.019 |
| TCRBV06_5 | 0.114 | -0.034 | 0.034 | -0.001 | -0.124 |
| TCRBV06_6 | -0.184 | 0.180 | 0.164 | -0.162 | -0.180 |
| TCRBV06_7 | -0.416 | 0.498 | -0.096 | -0.261 | -0.044 |
| TCRBV06_8 | -0.696 | 0.805 | -0.729 | -0.191 | -0.012 |
| TCRBV06_9 | -0.263 | 0.019 | -0.086 | -0.087 | -0.739 |
| TCRBV06_10 | 1.044 | -0.719 | 0.273 | 0.282 | -0.062 |
| TCRBV06_11 | 0.154 | -0.814 | -0.162 | 0.123 | 0.634 |
| TCRBV06_12 | 0.398 | 0.386 | 0.232 | -0.107 | 0.023 |
| TCRBV06_13 | 0.068 | -0.158 | 0.011 | 0.150 | 0.296 |
| TCRBV07_5 | -0.014 | 0.008 | 0.026 | 0.010 | -0.045 |
| TCRBV07_6 | 0.266 | -0.215 | -0.050 | -0.478 | -0.042 |
| TCRBV07_7 | 0.565 | 0.110 | 0.458 | -0.355 | -0.371 |
| TCRBV07_8 | 0.355 | 0.039 | -0.635 | 0.109 | -0.063 |
| TCRBV07_9 | -0.133 | 0.051 | -0.807 | -0.165 | -0.325 |
| TCRBV07_10 | -0.434 | -0.074 | 0.342 | -0.064 | 0.125 |
| TCRBV07_11 | -0.193 | -0.166 | 0.054 | 0.216 | 0.109 |
| TCRBV07_12 | -0.105 | 0.356 | 0.230 | 0.322 | 0.368 |
| TCRBV07_13 | -0.085 | 0.053 | 0.023 | 0.150 | 0.035 |
| TCRBV081_5 | -0.043 | -0.155 | 0.061 | -0.013 | 0.023 |
| TCRBV081_6 | -0.521 | -0.078 | -0.159 | 0.379 | 0.099 |
| TCRBV081_7 | 0.071 | -0.461 | -0.553 | -0.047 | 0.469 |
| TCRBV081_8 | 0.097 | 0.174 | -0.233 | 0.237 | -0.259 |
| TCRBV081_9 | -0.131 | -0.053 | 0.365 | -0.281 | 0.149 |
| TCRBV081_10 | 0.496 | 0.811 | 0.419 | 0.083 | -0.839 |
| TCRBV081_11 | 0.105 | -0.036 | 0.002 | 0.278 | 0.130 |
| TCRBV081_12 | -0.075 | -0.202 | 0.097 | -0.636 | 0.228 |
| TCRBV082_4 | -0.097 | -0.014 | 0.054 | -0.097 | -0.018 |
| TCRBV082_5 | 0.278 | 0.205 | 0.313 | -0.058 | 0.042 |
| TCRBV082_6 | 0.236 | -0.162 | 0.086 | -0.188 | -0.378 |
| TCRBV082_7 | -0.109 | 0.677 | -0.027 | -0.006 | 0.737 |

*FIG. 103C*

| | | | | | |
|---|---|---|---|---|---|
| TCRBV082_8 | -0.328 | -1.074 | -0.302 | -0.826 | -0.273 |
| TCRBV082_9 | 0.182 | 0.031 | -0.251 | 0.364 | 0.188 |
| TCRBV082_10 | -0.042 | -0.133 | -0.021 | 0.497 | -0.293 |
| TCRBV082_11 | -0.120 | 0.470 | 0.148 | 0.315 | -0.005 |
| TCRBV083_4 | 0.011 | 0.001 | -0.022 | -0.035 | -0.012 |
| TCRBV083_5 | 0.241 | 0.045 | 0.267 | -0.033 | 0.232 |
| TCRBV083_6 | 0.132 | -0.060 | -0.261 | 0.134 | -0.110 |
| TCRBV083_7 | 0.253 | 0.005 | -0.075 | -0.952 | -0.102 |
| TCRBV083_8 | 0.120 | -0.907 | -0.038 | -0.766 | -0.009 |
| TCRBV083_9 | -0.464 | 0.315 | -0.667 | 0.101 | -0.169 |
| TCRBV083_10 | -0.447 | 0.596 | 0.062 | 0.659 | 0.167 |
| TCRBV083_11 | -0.067 | 0.051 | 0.413 | 0.476 | 0.093 |
| TCRBV083_12 | 0.220 | -0.046 | 0.321 | 0.416 | -0.089 |
| TCRBV09_5 | 0.128 | -0.013 | 0.123 | -0.036 | 0.038 |
| TCRBV09_6 | 0.167 | 0.254 | 0.074 | -0.044 | 0.353 |
| TCRBV09_7 | 0.397 | -0.556 | -0.991 | 0.735 | 0.063 |
| TCRBV09_8 | -0.781 | -0.127 | 0.403 | -0.989 | 0.418 |
| TCRBV09_9 | -0.324 | 0.277 | -0.097 | 0.104 | 0.126 |
| TCRBV09_10 | -0.403 | -0.411 | 0.159 | -0.153 | -0.023 |
| TCRBV09_11 | -0.187 | -0.146 | 0.805 | -0.018 | -0.623 |
| TCRBV09_12 | 0.036 | 0.309 | 0.061 | 0.566 | 0.809 |
| TCRBV09_13 | 0.162 | 0.200 | 0.169 | -0.007 | 0.519 |
| TCRBV09_14 | 0.083 | 0.131 | 0.191 | 0.146 | 0.384 |
| TCRBV09_15 | 0.085 | 0.039 | -0.055 | 0.056 | 0.118 |
| TCRBV10_6 | -0.113 | 0.027 | -0.019 | 0.123 | 0.386 |
| TCRBV10_7 | -0.171 | 0.507 | -0.384 | -0.329 | -0.007 |
| TCRBV10_8 | 0.490 | 0.194 | -0.171 | -0.715 | -0.123 |
| TCRBV10_9 | -0.034 | 0.230 | 0.320 | -0.004 | 0.281 |
| TCRBV10_10 | -0.116 | -0.723 | -0.345 | 0.160 | -0.111 |
| TCRBV10_11 | -0.172 | -0.027 | 0.380 | 0.802 | -0.495 |
| TCRBV10_12 | 0.112 | -0.217 | 0.238 | -0.020 | 0.077 |
| TCRBV10_13 | 0.004 | 0.008 | -0.020 | -0.017 | -0.008 |
| TCRBV11_5 | -0.079 | -0.146 | 0.011 | 0.258 | 0.144 |
| TCRBV11_6 | 0.003 | 0.344 | -0.289 | 0.575 | 0.199 |
| TCRBV11_7 | -0.201 | -0.186 | -0.099 | -0.030 | -0.017 |
| TCRBV11_8 | 0.635 | -0.145 | -0.442 | -0.239 | -0.470 |
| TCRBV11_9 | 0.743 | 0.179 | -0.476 | -0.048 | 0.143 |
| TCRBV11_10 | -0.094 | 0.223 | 0.044 | -0.495 | -0.530 |
| TCRBV11_11 | -0.303 | 0.099 | 0.288 | -0.166 | 0.087 |
| TCRBV11_12 | -0.373 | -0.268 | 0.534 | 0.036 | 0.127 |
| TCRBV11_13 | -0.135 | 0.014 | 0.195 | -0.038 | 0.157 |
| TCRBV11_14 | 0.018 | 0.036 | -0.091 | -0.078 | -0.036 |
| TCRBV11_15 | 0.007 | 0.013 | -0.034 | -0.029 | -0.013 |
| TCRBV12_4 | -0.099 | -0.217 | -0.014 | 0.035 | -0.128 |
| TCRBV12_5 | 0.146 | 0.283 | 0.133 | -0.088 | 0.231 |
| TCRBV12_6 | -0.572 | 0.562 | 0.620 | -0.135 | -0.459 |
| TCRBV12_7 | -0.110 | 0.756 | 0.188 | 0.522 | -0.425 |
| TCRBV12_8 | 0.998 | -0.035 | -0.218 | 0.107 | 0.043 |
| TCRBV12_9 | -0.411 | -0.734 | -0.346 | 0.297 | -0.174 |
| TCRBV12_10 | 0.350 | 0.160 | -0.358 | -0.199 | 0.532 |
| TCRBV12_11 | -0.478 | -0.797 | -0.041 | -0.376 | 0.322 |
| TCRBV12_12 | 0.177 | 0.022 | 0.035 | -0.163 | 0.059 |
| TCRBV13_5 | 0.017 | 0.160 | -0.027 | 0.060 | 0.074 |
| TCRBV13_6 | -0.872 | 0.024 | 0.039 | 0.464 | 0.107 |
| TCRBV13_7 | -0.199 | -0.169 | 0.253 | 0.467 | 0.249 |
| TCRBV13_8 | -0.088 | -0.105 | 0.282 | 0.132 | -0.070 |
| TCRBV13_9 | -0.083 | -1.220 | 0.259 | 0.033 | 0.152 |
| TCRBV13_10 | 0.578 | 0.035 | 0.060 | -0.578 | -0.353 |
| TCRBV13_11 | 0.477 | 0.749 | -0.481 | -0.104 | 0.251 |
| TCRBV13_12 | 0.133 | 0.295 | -0.610 | -0.119 | -0.314 |
| TCRBV13_13 | 0.037 | 0.231 | 0.226 | -0.355 | -0.098 |
| TCRBV14_5 | -0.013 | 0.073 | 0.025 | 0.045 | 0.085 |
| TCRBV14_6 | 0.097 | 0.038 | 0.240 | -0.049 | -0.053 |
| TCRBV14_7 | -0.070 | -0.196 | -0.172 | 0.238 | 0.203 |

*FIG. 103D*

| | | | | | |
|---|---|---|---|---|---|
| TCRBV14_8 | 0.034 | 0.097 | -0.329 | 0.191 | -0.224 |
| TCRBV14_9 | -0.249 | -0.531 | -0.014 | 0.168 | -0.416 |
| TCRBV14_10 | 0.260 | 0.504 | -0.177 | -0.209 | -0.169 |
| TCRBV14_11 | 0.022 | 0.008 | 0.245 | -0.484 | 0.642 |
| TCRBV14_12 | -0.087 | -0.024 | 0.209 | 0.144 | -0.046 |
| TCRBV14_13 | 0.005 | 0.031 | -0.027 | -0.043 | -0.023 |
| TCRBV15_4 | -0.028 | -0.129 | 0.355 | 0.011 | 0.126 |
| TCRBV15_5 | 0.215 | 0.049 | -0.463 | -0.431 | -0.207 |
| TCRBV15_6 | 0.127 | 0.098 | 0.479 | -0.055 | 0.071 |
| TCRBV15_7 | -0.173 | 0.226 | 0.370 | 0.105 | 0.203 |
| TCRBV15_8 | 0.674 | -0.573 | 0.558 | 0.429 | -0.784 |
| TCRBV15_9 | -0.963 | 0.331 | -0.454 | 0.042 | 0.252 |
| TCRBV15_10 | 0.137 | 0.252 | -0.874 | -0.452 | -0.020 |
| TCRBV15_11 | 0.204 | 0.038 | -0.347 | 0.101 | 0.098 |
| TCRBV15_12 | 0.029 | -0.129 | 0.019 | -0.005 | 0.053 |
| TCRBV16_5 | 0.028 | 0.102 | 0.061 | 0.021 | -0.190 |
| TCRBV16_6 | -0.263 | -0.318 | 0.050 | 0.486 | -0.358 |
| TCRBV16_7 | 0.632 | 0.089 | 0.880 | 0.459 | -0.717 |
| TCRBV16_8 | -0.921 | -0.349 | 0.855 | -0.423 | -0.181 |
| TCRBV16_9 | 0.530 | -0.300 | -0.991 | -0.228 | 1.081 |
| TCRBV16_10 | 0.002 | -0.277 | 0.147 | 0.423 | 0.007 |
| TCRBV16_11 | 0.253 | 0.024 | -0.740 | 0.006 | -0.182 |
| TCRBV16_12 | -0.177 | 0.070 | -0.478 | 0.198 | 1.037 |
| TCRBV16_13 | 0.124 | -0.088 | -0.019 | 0.040 | 0.008 |
| TCRBV18_3 | 0.029 | -0.024 | -0.038 | 0.032 | 0.011 |
| TCRBV18_4 | 0.086 | 0.210 | 0.155 | 0.049 | -0.296 |
| TCRBV18_5 | -0.019 | 0.319 | 0.319 | -0.147 | 0.718 |
| TCRBV18_6 | -0.666 | -0.215 | 0.426 | -0.088 | 0.177 |
| TCRBV18_7 | 1.820 | -0.588 | 0.247 | 0.764 | 0.904 |
| TCRBV18_8 | 0.018 | -0.401 | 0.714 | 0.179 | 0.365 |
| TCRBV18_9 | 0.381 | 0.330 | 0.507 | -0.398 | 0.234 |
| TCRBV18_10 | 0.151 | 0.406 | 0.369 | -0.072 | 0.259 |
| TCRBV18_11 | 0.216 | 0.575 | -0.400 | -0.179 | 0.029 |
| TCRBV18_12 | -0.002 | -0.025 | -0.043 | 0.052 | -0.086 |
| TCRBV18_13 | -0.087 | -0.101 | -0.013 | 0.007 | -0.001 |
| TCRBV20_5 | -0.131 | -0.110 | 0.019 | 0.173 | 0.201 |
| TCRBV20_6 | -0.637 | 0.239 | -0.235 | 0.837 | 0.197 |
| TCRBV20_7 | -0.381 | 0.078 | -0.016 | 0.078 | 0.143 |
| TCRBV20_8 | 0.211 | 0.227 | -0.198 | -0.297 | -0.068 |
| TCRBV20_9 | -0.155 | 0.173 | -0.877 | 0.386 | -0.219 |
| TCRBV20_10 | -0.412 | -0.519 | 0.084 | -0.685 | 0.109 |
| TCRBV20_11 | 0.588 | 0.092 | 0.394 | -0.291 | -0.454 |
| TCRBV20_12 | 0.857 | 0.133 | 0.160 | -0.181 | -0.046 |
| TCRBV20_13 | 0.304 | -0.047 | 0.025 | -0.284 | -0.174 |
| TCRBV20_14 | -0.023 | -0.104 | 0.287 | 0.009 | 0.102 |
| | 36 | 37 | 38 | 39 | 40 |
| TCRBV01_6 | -0.081 | -0.005 | -0.041 | -0.011 | 0.038 |
| TCRBV01_7 | -0.012 | -0.180 | 0.064 | 0.238 | 0.174 |
| TCRBV01_8 | -0.570 | 0.176 | -0.114 | 0.201 | 0.386 |
| TCRBV01_9 | 0.027 | -0.269 | -0.088 | 0.785 | 0.246 |
| TCRBV01_10 | -0.102 | -0.319 | 0.148 | -0.837 | 0.349 |
| TCRBV01_11 | 0.662 | 0.414 | -0.212 | -0.263 | -0.554 |
| TCRBV01_12 | 0.612 | 0.048 | 0.305 | -0.231 | -0.341 |
| TCRBV01_13 | 0.129 | 0.109 | 0.084 | -0.090 | -0.272 |
| TCRBV01_14 | 0.017 | -0.017 | -0.003 | 0.008 | 0.012 |
| TCRBV02_6 | 0.027 | 0.051 | 0.091 | 0.286 | -0.029 |
| TCRBV02_7 | 0.190 | -0.274 | 0.161 | 0.209 | -0.089 |
| TCRBV02_8 | 0.071 | -0.413 | 0.051 | -0.401 | -0.267 |
| TCRBV02_9 | -0.014 | 0.038 | 0.122 | -0.125 | 0.164 |
| TCRBV02_10 | -0.053 | -0.372 | 0.170 | 0.094 | 0.020 |
| TCRBV02_11 | 0.123 | -0.426 | -0.531 | 0.345 | 0.367 |

*FIG. 104A*

| | | | | | |
|---|---|---|---|---|---|
| TCRBV02_12 | -0.112 | 0.175 | 0.088 | 0.240 | -0.046 |
| TCRBV02_13 | -0.228 | 0.061 | 0.010 | -0.029 | 0.052 |
| TCRBV03_4 | -0.000 | 0.030 | -0.004 | -0.016 | -0.004 |
| TCRBV03_5 | -0.008 | -0.040 | -0.017 | 0.024 | 0.000 |
| TCRBV03_6 | 0.256 | 0.463 | -0.027 | -0.203 | -0.102 |
| TCRBV03_7 | 0.174 | 0.134 | -0.040 | -0.507 | -0.188 |
| TCRBV03_8 | 0.045 | 0.050 | -0.375 | 0.013 | -0.497 |
| TCRBV03_9 | -0.361 | -0.221 | -0.084 | 0.496 | -0.451 |
| TCRBV03_10 | 0.320 | 0.304 | 0.332 | -0.249 | 0.619 |
| TCRBV03_11 | -0.485 | -0.367 | 0.306 | 0.237 | 0.083 |
| TCRBV03_12 | 0.322 | -0.395 | 0.179 | 0.134 | 0.452 |
| TCRBV03_13 | 0.420 | 0.000 | -0.126 | -0.129 | 0.126 |
| TCRBV04_6 | -0.010 | -0.023 | 0.009 | -0.045 | 0.027 |
| TCRBV04_7 | 0.166 | -0.143 | 0.275 | -0.197 | 0.027 |
| TCRBV04_8 | -0.405 | -0.386 | 0.099 | 0.152 | -0.010 |
| TCRBV04_9 | -0.884 | 0.005 | -0.228 | 0.168 | 0.463 |
| TCRBV04_10 | 0.321 | -0.472 | -0.614 | -0.196 | 0.297 |
| TCRBV04_11 | 0.246 | 0.584 | -0.269 | -0.161 | 0.213 |
| TCRBV04_12 | 0.615 | -0.365 | 0.698 | 0.239 | 0.074 |
| TCRBV04_13 | 0.118 | -0.093 | -0.115 | 0.143 | -0.668 |
| TCRBV04_14 | -0.229 | 0.912 | -0.008 | -0.073 | -0.041 |
| TCRBV04_15 | 0.062 | -0.019 | 0.152 | -0.030 | -0.382 |
| TCRBV051_5 | 0.099 | 0.220 | -0.220 | 0.103 | -0.138 |
| TCRBV051_6 | 0.217 | 0.547 | -0.239 | -0.212 | 0.374 |
| TCRBV051_7 | 0.190 | 0.310 | -0.306 | 0.500 | 0.079 |
| TCRBV051_8 | 0.257 | 0.064 | 0.223 | 0.123 | -0.298 |
| TCRBV051_9 | -0.678 | -0.295 | -0.711 | 0.000 | -0.043 |
| TCRBV051_10 | -0.118 | -0.439 | 0.727 | 0.214 | 0.071 |
| TCRBV051_11 | -0.653 | -0.542 | 0.310 | 0.083 | -0.586 |
| TCRBV051_12 | 0.525 | 0.306 | 0.484 | -0.017 | -0.192 |
| TCRBV051_13 | 0.090 | -0.024 | 0.369 | 0.341 | 0.287 |
| TCRBV052_6 | 0.345 | 0.346 | 0.330 | 0.356 | 0.347 |
| TCRBV052_7 | 0.030 | -0.171 | -0.721 | -0.126 | -0.001 |
| TCRBV052_8 | 0.021 | -0.075 | 0.017 | 0.067 | -0.277 |
| TCRBV052_9 | -0.196 | 0.602 | 0.371 | 0.234 | -0.052 |
| TCRBV052_10 | 0.130 | -0.388 | 0.273 | 0.417 | 0.100 |
| TCRBV052_11 | -0.249 | 0.024 | 0.205 | 0.184 | -0.498 |
| TCRBV052_12 | -0.062 | -0.200 | 0.121 | 0.022 | -0.096 |
| TCRBV052_13 | -0.089 | 0.009 | 0.040 | -0.018 | 0.033 |
| TCRBV06_5 | 0.078 | -0.029 | 0.024 | -0.095 | 0.009 |
| TCRBV06_6 | 0.271 | -0.294 | 0.049 | -0.043 | -0.066 |
| TCRBV06_7 | 0.310 | -0.297 | -0.242 | 0.058 | -0.250 |
| TCRBV06_8 | 0.483 | 0.370 | -0.247 | 0.015 | 0.011 |
| TCRBV06_9 | -0.448 | 0.293 | 0.106 | 0.014 | 0.025 |
| TCRBV06_10 | -0.153 | 0.035 | 0.528 | 0.115 | -0.405 |
| TCRBV06_11 | -0.281 | -0.067 | -0.067 | 0.047 | 0.211 |
| TCRBV06_12 | 0.389 | -0.026 | -0.215 | -0.238 | 0.453 |
| TCRBV06_13 | 0.033 | -0.026 | 0.206 | -0.073 | 0.049 |
| TCRBV07_5 | -0.014 | 0.047 | -0.039 | 0.011 | 0.018 |
| TCRBV07_6 | 0.227 | 0.192 | 0.005 | 0.100 | -0.283 |
| TCRBV07_7 | -0.263 | -0.341 | 0.112 | 0.146 | -0.545 |
| TCRBV07_8 | 0.382 | 0.747 | 0.105 | -0.413 | 0.006 |
| TCRBV07_9 | -0.333 | 0.133 | 0.263 | -0.335 | 0.279 |
| TCRBV07_10 | 0.391 | -0.408 | 0.027 | 0.274 | 0.219 |
| TCRBV07_11 | -0.131 | -0.503 | 0.002 | 0.113 | 0.271 |
| TCRBV07_12 | 0.434 | 0.221 | -0.291 | -0.132 | 0.048 |
| TCRBV07_13 | -0.011 | -0.130 | -0.041 | 0.036 | 0.023 |
| TCRBV081_5 | 0.086 | 0.032 | 0.056 | -0.213 | -0.105 |
| TCRBV081_6 | 0.193 | -0.201 | 0.136 | -0.201 | -0.024 |
| TCRBV081_7 | -0.095 | -0.271 | -0.059 | -0.207 | 0.034 |
| TCRBV081_8 | 0.206 | -0.008 | 0.222 | 0.221 | 0.427 |
| TCRBV081_9 | 0.407 | -0.000 | -0.423 | 0.244 | -0.245 |
| TCRBV081_10 | -0.766 | 0.336 | -0.617 | -0.315 | 0.436 |
| TCRBV081_11 | 0.065 | 0.307 | 0.349 | 0.129 | 0.242 |

*FIG. 104B*

| | | | | | |
|---|---|---|---|---|---|
| TCRBV081_12 | -0.096 | -0.194 | 0.337 | 0.342 | -0.766 |
| TCRBV082_4 | 0.152 | -0.014 | 0.246 | 0.425 | 0.007 |
| TCRBV082_5 | 0.038 | 0.256 | 0.247 | -0.130 | -0.086 |
| TCRBV082_6 | 0.416 | -0.275 | 0.066 | 0.011 | -0.159 |
| TCRBV082_7 | -0.087 | 0.454 | 0.092 | -0.314 | 0.181 |
| TCRBV082_8 | 0.059 | -0.624 | -0.209 | 0.080 | 0.439 |
| TCRBV082_9 | -0.152 | 0.156 | -0.246 | -0.202 | -0.353 |
| TCRBV082_10 | -0.336 | -0.006 | -0.223 | 0.073 | -0.089 |
| TCRBV082_11 | -0.091 | 0.053 | 0.027 | 0.056 | 0.060 |
| TCRBV083_4 | 0.028 | -0.002 | -0.010 | -0.008 | 0.011 |
| TCRBV083_5 | 0.420 | 0.225 | 0.027 | -0.068 | 0.065 |
| TCRBV083_6 | 0.083 | 0.300 | -0.001 | -0.033 | 0.150 |
| TCRBV083_7 | 0.160 | 0.325 | 0.076 | -0.330 | 0.002 |
| TCRBV083_8 | -0.346 | -0.023 | 0.080 | -0.038 | -0.493 |
| TCRBV083_9 | -0.127 | -0.614 | 0.001 | 0.555 | 0.334 |
| TCRBV083_10 | 0.047 | -0.207 | -0.094 | 0.227 | -0.108 |
| TCRBV083_11 | -0.393 | -0.111 | 0.051 | -0.209 | 0.033 |
| TCRBV083_12 | 0.128 | 0.106 | -0.130 | -0.095 | 0.006 |
| TCRBV09_5 | 0.021 | 0.015 | 0.130 | -0.037 | 0.037 |
| TCRBV09_6 | 0.188 | 0.005 | -0.215 | 0.126 | -0.090 |
| TCRBV09_7 | -0.262 | 0.198 | -0.043 | 0.581 | -0.323 |
| TCRBV09_8 | 0.032 | 0.027 | 0.687 | -0.015 | -0.227 |
| TCRBV09_9 | 0.083 | -0.639 | 0.675 | -0.262 | -0.329 |
| TCRBV09_10 | -1.054 | 0.658 | -0.866 | 0.656 | 0.011 |
| TCRBV09_11 | 0.516 | 0.151 | -0.489 | -0.221 | 0.162 |
| TCRBV09_12 | -0.028 | -0.145 | 0.651 | -0.889 | 0.185 |
| TCRBV09_13 | -0.131 | -0.042 | 0.213 | -0.218 | -0.268 |
| TCRBV09_14 | -0.012 | -0.079 | -0.183 | 0.079 | 0.096 |
| TCRBV09_15 | -0.061 | 0.098 | -0.021 | -0.056 | -0.017 |
| TCRBV10_6 | 0.359 | 0.016 | 0.235 | 0.419 | 0.118 |
| TCRBV10_7 | -0.387 | 0.296 | 0.392 | 0.464 | -0.202 |
| TCRBV10_8 | 0.096 | -0.255 | -0.170 | -0.041 | -0.007 |
| TCRBV10_9 | -0.250 | 0.548 | 0.096 | -0.434 | -0.117 |
| TCRBV10_10 | 0.248 | -0.162 | -0.131 | -0.300 | 0.725 |
| TCRBV10_11 | 0.012 | -0.084 | -0.251 | 0.056 | -0.470 |
| TCRBV10_12 | -0.077 | -0.374 | -0.169 | -0.158 | -0.044 |
| TCRBV10_13 | -0.000 | 0.015 | -0.002 | -0.008 | -0.002 |
| TCRBV11_5 | 0.107 | -0.065 | 0.064 | -0.003 | -0.075 |
| TCRBV11_6 | 0.329 | -0.004 | -0.107 | 0.154 | -0.308 |
| TCRBV11_7 | 0.439 | -0.370 | -0.303 | 0.238 | -0.027 |
| TCRBV11_8 | 0.645 | -0.675 | -0.246 | -0.410 | 0.190 |
| TCRBV11_9 | 0.243 | 0.057 | -0.314 | -0.009 | -0.196 |
| TCRBV11_10 | 0.036 | 0.334 | 0.363 | -0.026 | 0.098 |
| TCRBV11_11 | -0.266 | 0.096 | 0.118 | 0.047 | 0.154 |
| TCRBV11_12 | -0.542 | 0.435 | 0.614 | -0.091 | 0.234 |
| TCRBV11_13 | -0.308 | 0.060 | -0.033 | -0.052 | -0.020 |
| TCRBV11_14 | -0.000 | 0.066 | -0.009 | -0.035 | -0.010 |
| TCRBV11_15 | -0.000 | 0.024 | -0.003 | -0.013 | -0.004 |
| TCRBV12_4 | -0.133 | 0.057 | -0.089 | 0.239 | -0.197 |
| TCRBV12_5 | 0.037 | -0.293 | 0.115 | 0.011 | -0.134 |
| TCRBV12_6 | -0.078 | 0.151 | 0.344 | -0.135 | -0.103 |
| TCRBV12_7 | -0.119 | 0.439 | 0.253 | 0.008 | 0.267 |
| TCRBV12_8 | 0.405 | 0.615 | 0.094 | 0.038 | 0.418 |
| TCRBV12_9 | -0.107 | -0.619 | -0.186 | -0.102 | -0.025 |
| TCRBV12_10 | -0.187 | -0.416 | 0.402 | -0.327 | 0.340 |
| TCRBV12_11 | 0.239 | 0.113 | -0.603 | 0.127 | -0.277 |
| TCRBV12_12 | -0.057 | -0.048 | -0.331 | 0.141 | -0.288 |
| TCRBV13_5 | 0.125 | 0.054 | -0.022 | -0.033 | -0.056 |
| TCRBV13_6 | 0.327 | 0.242 | -0.202 | 0.243 | 0.075 |
| TCRBV13_7 | 0.933 | 0.100 | -0.126 | 0.077 | -0.236 |
| TCRBV13_8 | -0.897 | -0.610 | 0.189 | -0.973 | -0.351 |
| TCRBV13_9 | -0.423 | 0.468 | 0.312 | 0.527 | 0.871 |
| TCRBV13_10 | 0.004 | 0.068 | 0.094 | 0.095 | 0.136 |
| TCRBV13_11 | -0.027 | -0.156 | -0.353 | -0.034 | -0.188 |

*FIG. 104C*

|  |  |  |  |  |  |
|---|---|---|---|---|---|
| TCRBV13_12 | 0.119 | -0.129 | -0.114 | 0.024 | 0.072 |
| TCRBV13_13 | -0.162 | -0.038 | 0.222 | 0.073 | -0.324 |
| TCRBV14_5 | 0.009 | -0.013 | -0.051 | -0.040 | -0.079 |
| TCRBV14_6 | 0.190 | -0.084 | 0.069 | -0.140 | 0.054 |
| TCRBV14_7 | 0.074 | 0.023 | -0.029 | 0.180 | -0.171 |
| TCRBV14_8 | -0.226 | -0.005 | -0.047 | -0.146 | 0.573 |
| TCRBV14_9 | -0.079 | 0.382 | 0.203 | -0.669 | -0.508 |
| TCRBV14_10 | 0.102 | -0.655 | -0.342 | 0.662 | 0.181 |
| TCRBV14_11 | 0.020 | 0.316 | 0.204 | 0.218 | -0.145 |
| TCRBV14_12 | -0.091 | 0.021 | 0.007 | -0.035 | 0.090 |
| TCRBV14_13 | 0.001 | 0.016 | -0.014 | -0.030 | 0.005 |
| TCRBV15_4 | -0.212 | -0.004 | 0.003 | -0.016 | 0.010 |
| TCRBV15_5 | 0.136 | -0.135 | 0.161 | 0.079 | -0.009 |
| TCRBV15_6 | -0.541 | -0.191 | -0.169 | -0.404 | -0.006 |
| TCRBV15_7 | 0.265 | 0.696 | -0.099 | -0.147 | 0.133 |
| TCRBV15_8 | 0.413 | -0.865 | -0.073 | -0.630 | 0.245 |
| TCRBV15_9 | -0.463 | 0.061 | -0.047 | 0.195 | -0.436 |
| TCRBV15_10 | 0.575 | 0.393 | 0.342 | 0.538 | 0.152 |
| TCRBV15_11 | 0.475 | 0.120 | 0.024 | 0.145 | -0.039 |
| TCRBV15_12 | 0.034 | -0.118 | 0.001 | 0.040 | -0.012 |
| TCRBV16_5 | 0.032 | 0.045 | 0.087 | 0.078 | -0.158 |
| TCRBV16_6 | 0.279 | 0.137 | -0.370 | -0.104 | -0.016 |
| TCRBV16_7 | 0.533 | 0.447 | 0.849 | 0.863 | -0.185 |
| TCRBV16_8 | 0.124 | -0.748 | 0.162 | 0.512 | 0.171 |
| TCRBV16_9 | 0.019 | 0.096 | 0.247 | -0.373 | 0.093 |
| TCRBV16_10 | -0.520 | 0.806 | 0.104 | 0.097 | -0.098 |
| TCRBV16_11 | -0.206 | -0.377 | -0.578 | 0.008 | -0.138 |
| TCRBV16_12 | 0.382 | -0.335 | 0.203 | -0.129 | -0.135 |
| TCRBV16_13 | -0.032 | 0.035 | 0.075 | -0.014 | 0.058 |
| TCRBV18_3 | -0.016 | 0.019 | 0.005 | 0.037 | -0.004 |
| TCRBV18_4 | 0.166 | -0.041 | -0.161 | 0.006 | 0.086 |
| TCRBV18_5 | 0.042 | 0.049 | -0.283 | 0.054 | -0.104 |
| TCRBV18_6 | -0.342 | 0.136 | 0.214 | -0.084 | 0.116 |
| TCRBV18_7 | 0.363 | 0.560 | -0.685 | 0.208 | -0.378 |
| TCRBV18_8 | 0.556 | -0.420 | -0.280 | 0.138 | 0.096 |
| TCRBV18_9 | 0.074 | 0.325 | -0.210 | -0.176 | 0.642 |
| TCRBV18_10 | 0.067 | 0.190 | 0.193 | -0.374 | -0.180 |
| TCRBV18_11 | 0.203 | 0.020 | 0.194 | 0.040 | 0.013 |
| TCRBV18_12 | -0.044 | -0.012 | 0.018 | -0.008 | 0.021 |
| TCRBV18_13 | 0.050 | 0.015 | -0.020 | -0.130 | -0.089 |
| TCRBV20_5 | 0.033 | -0.102 | 0.037 | -0.094 | -0.069 |
| TCRBV20_6 | 0.225 | -0.285 | 0.058 | 0.011 | 0.039 |
| TCRBV20_7 | 0.344 | 0.159 | -0.436 | -0.026 | -0.330 |
| TCRBV20_8 | 0.169 | 0.122 | 0.067 | 0.256 | -0.097 |
| TCRBV20_9 | -0.934 | -0.037 | 0.056 | 0.166 | 0.213 |
| TCRBV20_10 | 0.279 | -0.185 | 0.293 | 0.184 | 0.632 |
| TCRBV20_11 | 0.255 | 0.298 | -0.618 | -0.325 | -0.141 |
| TCRBV20_12 | 0.142 | -0.008 | 0.462 | -0.528 | -0.231 |
| TCRBV20_13 | 0.340 | 0.000 | 0.222 | 0.169 | 0.014 |
| TCRBV20_14 | -0.172 | -0.004 | 0.002 | -0.013 | 0.008 |
|  | 41 | 42 | 43 | 44 | 45 |
| TCRBV01_6 | -0.008 | 0.039 | -0.042 | 0.005 | 0.023 |
| TCRBV01_7 | 0.197 | -0.173 | -0.288 | -0.100 | 0.008 |
| TCRBV01_8 | -0.123 | -0.454 | -0.154 | 0.432 | -0.048 |
| TCRBV01_9 | 0.205 | 0.140 | 0.123 | -0.455 | -0.171 |
| TCRBV01_10 | -0.222 | 0.160 | 0.276 | 0.222 | -0.278 |
| TCRBV01_11 | 0.292 | 0.071 | -0.028 | -0.375 | -0.078 |
| TCRBV01_12 | 0.009 | 0.185 | -0.003 | 0.069 | 0.396 |
| TCRBV01_13 | -0.005 | 0.081 | 0.081 | 0.041 | 0.088 |
| TCRBV01_14 | 0.006 | 0.002 | 0.009 | -0.005 | -0.011 |
| TCRBV02_6 | 0.159 | -0.260 | 0.187 | 0.004 | -0.005 |
| TCRBV02_7 | -0.029 | -0.161 | 0.034 | -0.273 | 0.034 |

*FIG. 104D*

| | | | | | |
|---|---|---|---|---|---|
| TCRBV02_8 | 0.098 | 0.433 | -0.381 | -0.098 | -0.198 |
| TCRBV02_9 | 0.017 | -0.018 | -0.018 | 0.194 | 0.098 |
| TCRBV02_10 | -0.038 | -0.227 | -0.027 | 0.011 | 0.026 |
| TCRBV02_11 | -0.001 | -0.113 | 0.216 | -0.118 | -0.331 |
| TCRBV02_12 | 0.279 | 0.095 | -0.413 | 0.015 | -0.080 |
| TCRBV02_13 | 0.009 | -0.116 | -0.020 | 0.002 | -0.104 |
| TCRBV03_4 | -0.013 | 0.010 | 0.011 | 0.007 | 0.015 |
| TCRBV03_5 | -0.025 | 0.015 | 0.007 | -0.000 | 0.021 |
| TCRBV03_6 | 0.163 | -0.116 | 0.344 | 0.213 | 0.048 |
| TCRBV03_7 | 0.277 | -0.285 | 0.433 | -0.356 | 0.058 |
| TCRBV03_8 | 0.020 | 0.170 | 0.149 | 0.194 | -0.044 |
| TCRBV03_9 | -0.284 | -0.207 | -0.179 | 0.022 | -0.169 |
| TCRBV03_10 | 0.231 | 0.089 | -0.083 | -0.048 | 0.072 |
| TCRBV03_11 | -0.214 | 0.379 | -0.361 | 0.063 | 0.208 |
| TCRBV03_12 | -0.092 | 0.246 | -0.180 | -0.006 | 0.055 |
| TCRBV03_13 | 0.288 | -0.249 | -0.168 | -0.257 | -0.334 |
| TCRBV04_6 | 0.038 | 0.039 | 0.030 | 0.011 | -0.075 |
| TCRBV04_7 | 0.113 | 0.046 | 0.327 | 0.131 | -0.024 |
| TCRBV04_8 | -0.059 | 0.336 | -0.189 | -0.099 | 0.100 |
| TCRBV04_9 | -0.006 | 0.348 | 0.031 | 0.458 | -0.568 |
| TCRBV04_10 | -0.236 | -0.019 | -0.190 | -0.179 | 0.643 |
| TCRBV04_11 | 0.036 | -0.557 | 0.245 | -0.224 | 0.077 |
| TCRBV04_12 | -0.063 | -0.095 | -0.046 | -0.262 | 0.033 |
| TCRBV04_13 | 0.168 | -0.099 | -0.476 | -0.189 | -0.186 |
| TCRBV04_14 | 0.059 | -0.057 | 0.263 | 0.273 | 0.237 |
| TCRBV04_15 | -0.051 | 0.058 | 0.006 | 0.080 | -0.237 |
| TCRBV051_5 | -0.202 | 0.112 | 0.218 | -0.148 | 0.224 |
| TCRBV051_6 | -0.272 | 0.191 | 0.410 | 0.223 | 0.201 |
| TCRBV051_7 | -0.589 | 0.082 | -0.136 | 0.391 | -0.233 |
| TCRBV051_8 | -0.226 | -0.202 | 0.059 | -0.229 | 0.035 |
| TCRBV051_9 | 0.068 | -0.366 | -0.325 | 0.095 | -0.026 |
| TCRBV051_10 | 0.580 | 0.088 | 0.057 | -0.052 | 0.363 |
| TCRBV051_11 | 0.718 | -0.212 | 0.094 | 0.380 | -0.065 |
| TCRBV051_12 | -0.600 | 0.238 | -0.455 | -0.313 | -0.668 |
| TCRBV051_13 | -0.129 | 0.131 | 0.449 | -0.251 | 0.164 |
| TCRBV052_6 | -0.069 | -0.250 | 0.178 | 0.176 | 0.189 |
| TCRBV052_7 | -0.213 | -0.079 | -0.016 | 0.265 | -0.368 |
| TCRBV052_8 | 0.031 | -0.282 | 0.204 | 0.158 | -0.025 |
| TCRBV052_9 | 0.175 | 0.376 | 0.240 | -0.103 | -0.355 |
| TCRBV052_10 | -0.583 | -0.022 | -0.262 | -0.122 | 0.219 |
| TCRBV052_11 | 0.170 | 0.078 | -0.119 | -0.164 | 0.276 |
| TCRBV052_12 | -0.180 | 0.132 | 0.070 | -0.126 | 0.171 |
| TCRBV052_13 | 0.016 | 0.109 | 0.076 | 0.011 | -0.115 |
| TCRBV06_5 | 0.174 | -0.151 | 0.083 | -0.049 | 0.025 |
| TCRBV06_6 | 0.094 | -0.099 | -0.076 | 0.013 | 0.039 |
| TCRBV06_7 | 0.192 | 0.040 | -0.085 | -0.116 | -0.009 |
| TCRBV06_8 | 0.036 | 0.121 | -0.408 | 0.239 | -0.035 |
| TCRBV06_9 | -0.167 | -0.409 | -0.408 | -0.232 | 0.120 |
| TCRBV06_10 | 0.032 | -0.135 | 0.658 | 0.044 | -0.392 |
| TCRBV06_11 | -0.117 | 0.385 | 0.348 | -0.226 | 0.272 |
| TCRBV06_12 | 0.089 | 0.248 | -0.207 | 0.171 | -0.021 |
| TCRBV06_13 | 0.017 | 0.053 | 0.068 | -0.011 | -0.069 |
| TCRBV07_5 | -0.068 | -0.069 | 0.020 | 0.062 | 0.073 |
| TCRBV07_6 | 0.427 | -0.064 | -0.079 | 0.085 | -0.177 |
| TCRBV07_7 | 0.106 | -0.006 | -0.073 | 0.320 | -0.007 |
| TCRBV07_8 | -0.111 | -0.269 | 0.015 | -0.227 | 0.231 |
| TCRBV07_9 | -0.042 | -0.044 | -0.094 | 0.044 | -0.036 |
| TCRBV07_10 | 0.093 | 0.084 | 0.100 | -0.267 | 0.144 |
| TCRBV07_11 | 0.005 | 0.261 | 0.149 | -0.273 | -0.037 |
| TCRBV07_12 | -0.064 | 0.155 | -0.043 | 0.106 | -0.269 |
| TCRBV07_13 | 0.003 | 0.004 | -0.022 | -0.016 | 0.006 |
| TCRBV081_5 | -0.100 | 0.036 | 0.021 | 0.059 | 0.115 |
| TCRBV081_6 | -0.302 | 0.097 | 0.210 | 0.221 | -0.070 |

*FIG. 105A*

| | | | | | |
|---|---|---|---|---|---|
| TCRBV081_7 | 0.143 | -0.256 | -0.154 | -0.257 | -0.003 |
| TCRBV081_8 | -0.533 | -0.017 | -0.247 | -0.523 | -0.273 |
| TCRBV081_9 | 0.409 | 0.125 | 0.085 | 0.383 | -0.059 |
| TCRBV081_10 | 0.115 | 0.107 | -0.021 | -0.005 | 0.059 |
| TCRBV081_11 | 0.243 | -0.014 | -0.008 | -0.052 | 0.018 |
| TCRBV081_12 | 0.025 | -0.079 | 0.115 | 0.174 | 0.214 |
| TCRBV082_4 | 0.110 | -0.106 | 0.144 | 0.055 | -0.096 |
| TCRBV082_5 | -0.022 | 0.044 | -0.125 | 0.093 | 0.141 |
| TCRBV082_6 | -0.118 | 0.014 | 0.008 | -0.056 | -0.152 |
| TCRBV082_7 | -0.034 | 0.002 | -0.023 | -0.636 | -0.279 |
| TCRBV082_8 | -0.063 | 0.012 | 0.261 | -0.039 | -0.620 |
| TCRBV082_9 | -0.102 | 0.047 | -0.351 | 0.347 | 0.384 |
| TCRBV082_10 | 0.117 | 0.141 | 0.145 | 0.282 | 0.165 |
| TCRBV082_11 | 0.112 | -0.154 | -0.059 | -0.046 | 0.457 |
| TCRBV083_4 | 0.023 | -0.019 | -0.009 | -0.021 | -0.023 |
| TCRBV083_5 | 0.163 | 0.419 | -0.137 | 0.090 | 0.115 |
| TCRBV083_6 | -0.142 | -0.047 | -0.115 | 0.011 | 0.004 |
| TCRBV083_7 | -0.047 | 0.053 | -0.296 | 0.103 | -0.167 |
| TCRBV083_8 | -0.111 | -0.343 | 0.287 | -0.127 | 0.027 |
| TCRBV083_9 | -0.283 | -0.019 | 0.264 | -0.232 | 0.001 |
| TCRBV083_10 | -0.006 | -0.262 | 0.311 | -0.107 | -0.084 |
| TCRBV083_11 | -0.054 | -0.017 | -0.129 | 0.166 | 0.022 |
| TCRBV083_12 | 0.458 | 0.236 | -0.177 | 0.119 | 0.106 |
| TCRBV09_5 | 0.020 | 0.005 | 0.017 | 0.033 | -0.002 |
| TCRBV09_6 | 0.115 | 0.109 | -0.169 | 0.327 | 0.114 |
| TCRBV09_7 | 0.493 | -0.420 | -0.372 | -0.495 | -0.386 |
| TCRBV09_8 | 0.001 | -0.052 | -0.212 | 0.141 | -0.020 |
| TCRBV09_9 | 0.354 | -0.147 | 0.150 | 0.403 | 0.036 |
| TCRBV09_10 | 0.607 | 0.764 | -0.523 | -0.397 | 0.146 |
| TCRBV09_11 | 0.069 | -0.288 | -0.111 | -0.116 | 0.190 |
| TCRBV09_12 | -0.530 | -0.222 | -0.710 | 0.327 | 0.054 |
| TCRBV09_13 | -0.319 | -0.208 | 0.368 | -0.038 | 0.160 |
| TCRBV09_14 | -0.359 | 0.005 | 0.259 | -0.212 | 0.051 |
| TCRBV09_15 | -0.120 | -0.069 | 0.103 | -0.017 | -0.028 |
| TCRBV10_6 | -0.139 | -0.231 | -0.013 | 0.171 | 0.090 |
| TCRBV10_7 | -0.343 | 0.337 | 0.297 | -0.138 | 0.132 |
| TCRBV10_8 | -0.370 | 0.224 | 0.140 | -0.305 | -0.050 |
| TCRBV10_9 | -0.126 | -0.257 | -0.157 | -0.083 | 0.190 |
| TCRBV10_10 | 0.801 | -0.238 | -0.261 | 0.001 | -0.263 |
| TCRBV10_11 | 0.076 | 0.272 | 0.089 | 0.333 | 0.093 |
| TCRBV10_12 | 0.107 | -0.112 | -0.101 | 0.018 | -0.199 |
| TCRBV10_13 | -0.006 | 0.005 | 0.005 | 0.003 | 0.007 |
| TCRBV11_5 | 0.053 | 0.005 | 0.119 | 0.105 | -0.081 |
| TCRBV11_6 | -0.048 | -0.165 | 0.128 | -0.257 | 0.144 |
| TCRBV11_7 | -0.054 | 0.190 | 0.134 | 0.111 | 0.170 |
| TCRBV11_8 | -0.048 | -0.193 | 0.169 | 0.081 | 0.239 |
| TCRBV11_9 | -0.048 | 0.054 | -0.369 | -0.042 | 0.034 |
| TCRBV11_10 | -0.024 | 0.281 | -0.112 | 0.043 | 0.008 |
| TCRBV11_11 | 0.254 | -0.011 | 0.052 | 0.019 | -0.155 |
| TCRBV11_12 | 0.259 | -0.033 | -0.127 | -0.200 | -0.398 |
| TCRBV11_13 | 0.044 | -0.105 | -0.055 | -0.048 | -0.073 |
| TCRBV11_14 | -0.028 | 0.021 | 0.024 | 0.015 | 0.032 |
| TCRBV11_15 | -0.010 | 0.008 | 0.009 | 0.006 | 0.012 |
| TCRBV12_4 | 0.141 | 0.044 | 0.018 | -0.126 | 0.033 |
| TCRBV12_5 | 0.228 | 0.066 | -0.140 | -0.056 | -0.050 |
| TCRBV12_6 | -0.108 | -0.114 | 0.092 | -0.231 | 0.140 |
| TCRBV12_7 | -0.251 | -0.173 | 0.523 | 0.142 | -0.265 |
| TCRBV12_8 | 0.090 | -0.242 | -0.180 | 0.239 | 0.181 |
| TCRBV12_9 | -0.192 | 0.101 | -0.204 | -0.012 | -0.061 |
| TCRBV12_10 | 0.400 | 0.009 | 0.024 | -0.023 | -0.104 |
| TCRBV12_11 | -0.153 | 0.144 | -0.023 | -0.018 | 0.077 |
| TCRBV12_12 | -0.155 | 0.165 | -0.110 | 0.084 | 0.048 |
| TCRBV13_5 | 0.015 | 0.084 | 0.027 | -0.118 | 0.011 |
| TCRBV13_6 | 0.168 | -0.328 | 0.359 | 0.024 | -0.082 |

*FIG. 105B*

| | | | | | |
|---|---|---|---|---|---|
| TCRBV13_7 | 0.092 | -0.328 | -0.345 | 0.286 | -0.170 |
| TCRBV13_8 | -0.340 | 0.461 | -0.080 | -0.091 | -0.058 |
| TCRBV13_9 | 0.075 | 0.131 | -0.278 | 0.089 | 0.201 |
| TCRBV13_10 | 0.529 | 0.005 | 0.015 | -0.308 | -0.069 |
| TCRBV13_11 | -0.316 | 0.032 | 0.076 | 0.260 | -0.063 |
| TCRBV13_12 | -0.032 | -0.099 | 0.102 | -0.062 | 0.020 |
| TCRBV13_13 | -0.189 | 0.042 | 0.125 | -0.080 | 0.210 |
| TCRBV14_5 | -0.065 | 0.052 | -0.071 | 0.051 | -0.018 |
| TCRBV14_6 | 0.148 | -0.051 | 0.148 | 0.037 | -0.207 |
| TCRBV14_7 | 0.080 | -0.167 | -0.558 | 0.251 | 0.071 |
| TCRBV14_8 | 0.176 | 0.100 | 0.338 | -0.368 | 0.018 |
| TCRBV14_9 | -0.044 | -0.026 | 0.142 | -0.020 | 0.090 |
| TCRBV14_10 | -0.334 | 0.092 | 0.208 | -0.122 | 0.162 |
| TCRBV14_11 | 0.180 | 0.128 | 0.006 | 0.205 | -0.054 |
| TCRBV14_12 | -0.145 | -0.134 | -0.214 | -0.037 | -0.069 |
| TCRBV14_13 | 0.004 | 0.005 | 0.000 | 0.002 | 0.009 |
| TCRBV15_4 | 0.033 | -0.124 | -0.041 | -0.048 | -0.104 |
| TCRBV15_5 | 0.353 | 0.060 | 0.107 | 0.027 | 0.241 |
| TCRBV15_6 | -0.072 | -0.117 | 0.075 | -0.346 | -0.236 |
| TCRBV15_7 | -0.234 | -0.026 | -0.080 | -0.036 | -0.307 |
| TCRBV15_8 | 0.241 | 0.311 | -0.025 | 0.026 | 0.377 |
| TCRBV15_9 | -0.335 | -0.005 | 0.067 | -0.097 | -0.079 |
| TCRBV15_10 | -0.114 | -0.104 | 0.116 | 0.456 | 0.038 |
| TCRBV15_11 | 0.516 | 0.032 | -0.164 | -0.179 | 0.018 |
| TCRBV15_12 | -0.037 | 0.024 | -0.082 | 0.029 | -0.018 |
| TCRBV16_5 | 0.084 | 0.060 | 0.099 | -0.039 | 0.136 |
| TCRBV16_6 | 0.165 | 0.342 | 0.304 | -0.148 | 0.209 |
| TCRBV16_7 | 0.006 | 0.583 | 0.143 | 0.354 | -0.294 |
| TCRBV16_8 | 0.301 | -0.713 | -0.273 | -0.172 | 0.245 |
| TCRBV16_9 | 0.254 | 0.293 | 0.173 | 0.137 | -0.117 |
| TCRBV16_10 | -0.768 | -0.458 | -0.242 | -0.033 | -0.102 |
| TCRBV16_11 | -0.199 | -0.411 | 0.120 | 0.305 | -0.053 |
| TCRBV16_12 | -0.119 | 0.380 | 0.015 | -0.471 | -0.175 |
| TCRBV16_13 | -0.026 | 0.037 | 0.006 | -0.004 | 0.076 |
| TCRBV18_3 | 0.023 | -0.030 | -0.046 | -0.036 | -0.003 |
| TCRBV18_4 | 0.163 | 0.191 | -0.073 | 0.092 | -0.110 |
| TCRBV18_5 | 0.169 | 0.430 | 0.267 | 0.210 | -0.288 |
| TCRBV18_6 | 0.197 | 0.469 | 0.390 | 0.074 | 0.354 |
| TCRBV18_7 | 0.075 | -0.252 | 0.085 | -0.360 | 0.329 |
| TCRBV18_8 | -0.609 | -0.192 | -0.038 | 0.136 | -0.541 |
| TCRBV18_9 | 0.286 | -0.175 | 0.130 | 0.129 | 0.338 |
| TCRBV18_10 | 0.634 | 0.322 | -0.199 | -0.376 | -0.065 |
| TCRBV18_11 | -0.021 | 0.335 | -0.248 | 0.157 | -0.256 |
| TCRBV18_12 | 0.009 | 0.003 | -0.028 | -0.007 | 0.056 |
| TCRBV18_13 | -0.078 | 0.023 | 0.007 | 0.026 | 0.080 |
| TCRBV20_5 | 0.135 | 0.039 | 0.111 | 0.058 | -0.109 |
| TCRBV20_6 | 0.572 | -0.241 | -0.132 | 0.512 | -0.225 |
| TCRBV20_7 | 0.259 | 0.389 | 0.205 | -0.235 | -0.309 |
| TCRBV20_8 | -0.568 | 0.514 | -0.402 | -0.123 | 0.668 |
| TCRBV20_9 | 0.190 | -0.622 | 0.318 | 0.083 | 0.232 |
| TCRBV20_10 | -0.154 | 0.268 | -0.126 | 0.243 | 0.034 |
| TCRBV20_11 | -0.080 | 0.205 | 0.361 | -0.047 | -0.257 |
| TCRBV20_12 | -0.106 | -0.227 | -0.099 | -0.595 | -0.096 |
| TCRBV20_13 | 0.075 | -0.173 | -0.230 | -0.025 | 0.075 |
| TCRBV20_14 | 0.026 | -0.100 | -0.033 | -0.039 | -0.084 |
| | 46 | 47 | 48 | 49 | 50 |
| TCRBV01_6 | -0.094 | -0.019 | -0.109 | -0.013 | -0.073 |
| TCRBV01_7 | 0.014 | 0.212 | -0.055 | -0.017 | 0.014 |
| TCRBV01_8 | 0.056 | 0.090 | -0.072 | 0.048 | 0.034 |
| TCRBV01_9 | 0.068 | -0.044 | 0.100 | -0.198 | -0.050 |
| TCRBV01_10 | -0.258 | 0.237 | -0.029 | -0.367 | -0.009 |
| TCRBV01_11 | -0.110 | -0.140 | 0.044 | 0.336 | 0.034 |

*FIG. 105C*

| | | | | | |
|---|---|---|---|---|---|
| TCRBV01_12 | 0.159 | 0.002 | -0.125 | 0.152 | -0.053 |
| TCRBV01_13 | 0.102 | -0.126 | 0.078 | 0.066 | 0.002 |
| TCRBV01_14 | -0.007 | 0.009 | 0.004 | 0.001 | -0.001 |
| TCRBV02_6 | -0.031 | 0.204 | -0.019 | -0.316 | 0.276 |
| TCRBV02_7 | 0.109 | -0.019 | -0.011 | -0.097 | 0.167 |
| TCRBV02_8 | 0.281 | -0.141 | 0.150 | 0.408 | -0.069 |
| TCRBV02_9 | -0.286 | 0.030 | -0.174 | 0.038 | -0.303 |
| TCRBV02_10 | 0.192 | -0.164 | -0.161 | -0.066 | -0.093 |
| TCRBV02_11 | -0.338 | -0.040 | -0.252 | -0.136 | -0.029 |
| TCRBV02_12 | 0.021 | -0.169 | 0.204 | -0.042 | -0.002 |
| TCRBV02_13 | 0.026 | 0.060 | -0.059 | -0.005 | -0.002 |
| TCRBV03_4 | 0.001 | 0.006 | 0.008 | 0.006 | 0.001 |
| TCRBV03_5 | -0.069 | 0.006 | 0.005 | -0.009 | -0.004 |
| TCRBV03_6 | 0.100 | 0.046 | -0.447 | 0.194 | -0.271 |
| TCRBV03_7 | -0.060 | -0.022 | 0.007 | -0.122 | -0.055 |
| TCRBV03_8 | -0.143 | -0.036 | -0.064 | 0.035 | 0.103 |
| TCRBV03_9 | -0.020 | 0.009 | 0.023 | -0.056 | 0.289 |
| TCRBV03_10 | 0.297 | 0.246 | 0.266 | -0.166 | -0.115 |
| TCRBV03_11 | -0.196 | 0.167 | 0.157 | 0.091 | 0.038 |
| TCRBV03_12 | 0.065 | -0.072 | -0.010 | 0.084 | 0.105 |
| TCRBV03_13 | -0.045 | -0.128 | -0.110 | -0.047 | -0.194 |
| TCRBV04_6 | 0.082 | 0.035 | 0.012 | 0.007 | -0.039 |
| TCRBV04_7 | 0.008 | 0.259 | 0.142 | -0.115 | 0.027 |
| TCRBV04_8 | 0.162 | 0.092 | -0.010 | 0.131 | 0.000 |
| TCRBV04_9 | 0.114 | -0.324 | 0.036 | -0.122 | 0.068 |
| TCRBV04_10 | 0.366 | 0.090 | -0.088 | -0.049 | 0.112 |
| TCRBV04_11 | -0.055 | -0.161 | -0.064 | 0.022 | -0.144 |
| TCRBV04_12 | -0.139 | -0.093 | -0.181 | 0.428 | 0.080 |
| TCRBV04_13 | -0.510 | 0.153 | 0.132 | -0.270 | 0.035 |
| TCRBV04_14 | 0.009 | 0.119 | 0.039 | 0.045 | -0.258 |
| TCRBV04_15 | -0.036 | -0.169 | -0.018 | -0.078 | 0.118 |
| TCRBV051_5 | -0.142 | -0.230 | -0.047 | 0.164 | 0.051 |
| TCRBV051_6 | 0.031 | 0.039 | -0.233 | -0.315 | 0.022 |
| TCRBV051_7 | -0.317 | -0.028 | 0.328 | 0.079 | -0.235 |
| TCRBV051_8 | -0.036 | 0.029 | 0.394 | 0.013 | -0.065 |
| TCRBV051_9 | 0.313 | -0.371 | -0.116 | 0.090 | 0.029 |
| TCRBV051_10 | -0.400 | 0.166 | 0.043 | -0.051 | 0.027 |
| TCRBV051_11 | -0.185 | -0.056 | -0.146 | -0.120 | 0.158 |
| TCRBV051_12 | 0.242 | 0.176 | -0.147 | 0.103 | 0.190 |
| TCRBV051_13 | 0.148 | -0.206 | -0.092 | 0.100 | 0.089 |
| TCRBV052_6 | 0.117 | -0.030 | 0.065 | -0.251 | -0.007 |
| TCRBV052_7 | -0.120 | -0.137 | 0.255 | 0.094 | 0.104 |
| TCRBV052_8 | 0.042 | 0.040 | -0.246 | 0.084 | -0.036 |
| TCRBV052_9 | -0.258 | 0.016 | -0.169 | 0.018 | 0.166 |
| TCRBV052_10 | -0.054 | -0.203 | 0.129 | -0.267 | -0.060 |
| TCRBV052_11 | -0.208 | -0.155 | -0.089 | 0.201 | -0.094 |
| TCRBV052_12 | 0.004 | -0.018 | 0.034 | 0.156 | 0.243 |
| TCRBV052_13 | 0.132 | 0.005 | 0.005 | 0.030 | -0.049 |
| TCRBV06_5 | 0.057 | 0.041 | -0.017 | -0.034 | -0.080 |
| TCRBV06_6 | 0.040 | 0.038 | -0.146 | -0.090 | 0.022 |
| TCRBV06_7 | 0.290 | 0.121 | 0.013 | 0.064 | 0.088 |
| TCRBV06_8 | -0.119 | -0.038 | 0.030 | 0.013 | 0.001 |
| TCRBV06_9 | 0.051 | -0.117 | -0.103 | 0.113 | 0.131 |
| TCRBV06_10 | 0.353 | -0.158 | 0.200 | 0.057 | -0.100 |
| TCRBV06_11 | -0.067 | 0.067 | -0.146 | -0.070 | 0.135 |
| TCRBV06_12 | -0.561 | 0.259 | -0.113 | -0.092 | -0.072 |
| TCRBV06_13 | -0.114 | 0.006 | 0.117 | 0.047 | -0.228 |
| TCRBV07_5 | -0.003 | -0.030 | 0.077 | 0.092 | -0.148 |
| TCRBV07_6 | 0.045 | 0.184 | 0.000 | 0.076 | -0.069 |
| TCRBV07_7 | -0.081 | 0.100 | -0.038 | -0.276 | -0.058 |
| TCRBV07_8 | 0.334 | -0.083 | 0.141 | -0.182 | 0.238 |
| TCRBV07_9 | -0.152 | 0.034 | -0.184 | 0.371 | -0.039 |
| TCRBV07_10 | -0.005 | -0.047 | -0.242 | -0.022 | 0.043 |

*FIG. 105D*

| | | | | | |
|---|---|---|---|---|---|
| TCRBV07_11 | -0.100 | 0.018 | 0.005 | -0.117 | 0.116 |
| TCRBV07_12 | -0.004 | 0.032 | 0.085 | 0.095 | -0.168 |
| TCRBV07_13 | -0.106 | 0.012 | -0.007 | -0.028 | -0.017 |
| TCRBV081_5 | -0.041 | -0.089 | -0.063 | -0.025 | 0.020 |
| TCRBV081_6 | -0.119 | -0.006 | 0.061 | -0.235 | -0.281 |
| TCRBV081_7 | -0.140 | -0.080 | -0.004 | 0.018 | 0.024 |
| TCRBV081_8 | 0.159 | -0.219 | -0.120 | -0.007 | 0.048 |
| TCRBV081_9 | 0.093 | 0.200 | -0.247 | 0.106 | 0.147 |
| TCRBV081_10 | -0.136 | -0.137 | -0.111 | 0.069 | 0.097 |
| TCRBV081_11 | 0.025 | 0.236 | 0.104 | 0.098 | 0.072 |
| TCRBV081_12 | 0.158 | 0.096 | 0.380 | -0.025 | -0.127 |
| TCRBV082_4 | -0.060 | -0.361 | 0.341 | 0.085 | -0.004 |
| TCRBV082_5 | -0.219 | 0.128 | 0.042 | -0.060 | 0.123 |
| TCRBV082_6 | -0.085 | -0.150 | 0.327 | 0.075 | 0.364 |
| TCRBV082_7 | -0.219 | 0.150 | -0.305 | -0.219 | -0.305 |
| TCRBV082_8 | -0.195 | -0.015 | -0.194 | 0.263 | -0.147 |
| TCRBV082_9 | 0.371 | 0.014 | -0.077 | -0.062 | -0.018 |
| TCRBV082_10 | 0.190 | 0.173 | -0.157 | -0.194 | -0.050 |
| TCRBV082_11 | 0.217 | 0.062 | 0.022 | 0.112 | 0.037 |
| TCRBV083_4 | -0.002 | -0.009 | -0.010 | -0.004 | -0.019 |
| TCRBV083_5 | 0.042 | 0.073 | 0.324 | 0.204 | 0.112 |
| TCRBV083_6 | -0.154 | -0.021 | 0.041 | 0.021 | 0.276 |
| TCRBV083_7 | -0.065 | -0.154 | -0.219 | -0.027 | -0.135 |
| TCRBV083_8 | -0.077 | 0.033 | 0.189 | -0.171 | 0.023 |
| TCRBV083_9 | -0.103 | 0.037 | -0.096 | 0.040 | -0.201 |
| TCRBV083_10 | 0.231 | -0.167 | 0.210 | -0.153 | -0.144 |
| TCRBV083_11 | 0.083 | -0.156 | -0.167 | -0.175 | 0.197 |
| TCRBV083_12 | 0.045 | 0.364 | -0.272 | 0.265 | -0.109 |
| TCRBV09_5 | 0.066 | 0.031 | -0.028 | 0.002 | -0.018 |
| TCRBV09_6 | 0.294 | -0.010 | -0.068 | -0.224 | 0.112 |
| TCRBV09_7 | 0.362 | 0.295 | -0.238 | -0.103 | -0.191 |
| TCRBV09_8 | -0.228 | 0.185 | -0.183 | 0.216 | 0.030 |
| TCRBV09_9 | -0.213 | -0.273 | -0.309 | -0.218 | 0.227 |
| TCRBV09_10 | 0.033 | -0.354 | 0.222 | -0.147 | 0.034 |
| TCRBV09_11 | 0.137 | -0.168 | 0.179 | -0.043 | -0.165 |
| TCRBV09_12 | 0.027 | -0.706 | 0.063 | -0.020 | -0.256 |
| TCRBV09_13 | -0.170 | 0.004 | -0.032 | 0.059 | -0.019 |
| TCRBV09_14 | 0.119 | 0.063 | -0.215 | 0.082 | 0.118 |
| TCRBV09_15 | 0.022 | 0.182 | -0.209 | 0.092 | 0.044 |
| TCRBV10_6 | -0.024 | -0.097 | 0.226 | -0.236 | -0.050 |
| TCRBV10_7 | 0.094 | 0.025 | -0.184 | -0.020 | -0.310 |
| TCRBV10_8 | 0.261 | 0.252 | 0.308 | 0.122 | -0.093 |
| TCRBV10_9 | -0.443 | 0.090 | -0.022 | 0.150 | 0.356 |
| TCRBV10_10 | 0.020 | -0.452 | 0.064 | -0.243 | 0.097 |
| TCRBV10_11 | -0.026 | 0.083 | -0.245 | 0.121 | -0.043 |
| TCRBV10_12 | 0.116 | 0.095 | -0.150 | 0.103 | 0.043 |
| TCRBV10_13 | 0.000 | 0.003 | 0.004 | 0.003 | 0.001 |
| TCRBV11_5 | -0.032 | 0.031 | 0.073 | -0.073 | -0.188 |
| TCRBV11_6 | 0.014 | -0.101 | 0.013 | -0.160 | -0.153 |
| TCRBV11_7 | 0.026 | -0.095 | 0.063 | 0.013 | -0.193 |
| TCRBV11_8 | 0.154 | -0.046 | 0.049 | 0.026 | 0.307 |
| TCRBV11_9 | 0.176 | 0.062 | -0.284 | 0.256 | -0.062 |
| TCRBV11_10 | -0.308 | 0.023 | -0.191 | -0.155 | 0.118 |
| TCRBV11_11 | -0.248 | 0.330 | 0.097 | 0.155 | 0.157 |
| TCRBV11_12 | 0.140 | -0.124 | -0.002 | -0.078 | -0.102 |
| TCRBV11_13 | 0.004 | 0.123 | -0.006 | 0.007 | 0.009 |
| TCRBV11_14 | 0.001 | 0.014 | 0.018 | 0.012 | 0.003 |
| TCRBV11_15 | 0.001 | 0.005 | 0.007 | 0.005 | 0.001 |
| TCRBV12_4 | -0.075 | 0.100 | 0.066 | 0.006 | 0.094 |
| TCRBV12_5 | 0.233 | 0.034 | 0.101 | 0.012 | 0.035 |
| TCRBV12_6 | 0.107 | 0.038 | -0.088 | 0.073 | 0.026 |
| TCRBV12_7 | -0.081 | 0.088 | 0.119 | 0.191 | -0.084 |
| TCRBV12_8 | -0.003 | 0.093 | 0.350 | 0.278 | 0.005 |
| TCRBV12_9 | 0.107 | 0.007 | -0.488 | 0.051 | -0.149 |

*FIG. 106A*

| | | | | | |
|---|---|---|---|---|---|
| TCRBV12_10 | -0.016 | 0.048 | 0.237 | -0.142 | 0.207 |
| TCRBV12_11 | -0.090 | -0.388 | -0.127 | -0.193 | 0.108 |
| TCRBV12_12 | -0.183 | -0.019 | -0.171 | -0.275 | -0.243 |
| TCRBV13_5 | 0.044 | -0.033 | 0.014 | 0.017 | -0.012 |
| TCRBV13_6 | -0.271 | -0.059 | 0.035 | 0.203 | 0.209 |
| TCRBV13_7 | -0.030 | 0.250 | 0.077 | -0.161 | -0.196 |
| TCRBV13_8 | -0.160 | 0.156 | 0.398 | 0.084 | -0.160 |
| TCRBV13_9 | 0.137 | 0.118 | 0.070 | 0.023 | 0.158 |
| TCRBV13_10 | 0.164 | -0.032 | -0.287 | -0.074 | -0.152 |
| TCRBV13_11 | 0.127 | -0.228 | -0.211 | 0.086 | 0.066 |
| TCRBV13_12 | 0.009 | -0.035 | -0.054 | 0.065 | 0.008 |
| TCRBV13_13 | -0.020 | -0.136 | -0.042 | -0.243 | 0.078 |
| TCRBV14_5 | 0.004 | -0.033 | -0.009 | 0.002 | 0.036 |
| TCRBV14_6 | 0.185 | -0.045 | 0.216 | 0.046 | -0.146 |
| TCRBV14_7 | -0.272 | 0.160 | -0.134 | -0.059 | 0.053 |
| TCRBV14_8 | -0.308 | 0.053 | 0.100 | -0.057 | 0.089 |
| TCRBV14_9 | 0.054 | -0.639 | -0.201 | -0.271 | 0.040 |
| TCRBV14_10 | -0.316 | 0.026 | -0.028 | 0.343 | -0.065 |
| TCRBV14_11 | 0.564 | 0.282 | 0.078 | 0.100 | -0.028 |
| TCRBV14_12 | 0.084 | 0.183 | -0.028 | -0.108 | 0.024 |
| TCRBV14_13 | 0.006 | 0.012 | 0.005 | 0.002 | -0.004 |
| TCRBV15_4 | 0.018 | 0.085 | -0.051 | -0.025 | 0.026 |
| TCRBV15_5 | -0.042 | -0.167 | -0.165 | -0.102 | -0.247 |
| TCRBV15_6 | -0.059 | 0.224 | -0.017 | 0.096 | -0.169 |
| TCRBV15_7 | 0.054 | 0.265 | -0.259 | -0.083 | 0.285 |
| TCRBV15_8 | -0.097 | 0.013 | 0.078 | 0.146 | -0.113 |
| TCRBV15_9 | -0.133 | -0.227 | 0.184 | 0.039 | 0.053 |
| TCRBV15_10 | 0.068 | -0.079 | 0.066 | 0.147 | 0.153 |
| TCRBV15_11 | 0.274 | 0.090 | -0.031 | -0.191 | -0.183 |
| TCRBV15_12 | -0.155 | 0.018 | 0.031 | -0.020 | 0.091 |
| TCRBV16_5 | 0.036 | 0.104 | 0.034 | -0.229 | 0.176 |
| TCRBV16_6 | 0.142 | -0.036 | 0.005 | 0.102 | 0.301 |
| TCRBV16_7 | -0.134 | -0.585 | -0.273 | 0.005 | -0.060 |
| TCRBV16_8 | -0.189 | 0.060 | 0.007 | 0.025 | -0.232 |
| TCRBV16_9 | -0.051 | 0.020 | 0.006 | 0.007 | 0.051 |
| TCRBV16_10 | -0.131 | 0.268 | -0.036 | 0.047 | -0.116 |
| TCRBV16_11 | -0.172 | 0.251 | 0.222 | -0.016 | -0.005 |
| TCRBV16_12 | 0.037 | -0.280 | -0.150 | 0.103 | -0.017 |
| TCRBV16_13 | 0.044 | -0.063 | 0.005 | 0.029 | 0.065 |
| TCRBV18_3 | 0.029 | -0.042 | 0.002 | -0.023 | -0.023 |
| TCRBV18_4 | 0.318 | -0.139 | 0.208 | -0.178 | 0.000 |
| TCRBV18_5 | 0.329 | -0.013 | -0.063 | 0.201 | 0.163 |
| TCRBV18_6 | 0.299 | 0.392 | 0.038 | -0.194 | -0.116 |
| TCRBV18_7 | -0.813 | -0.105 | 0.141 | 0.029 | -0.013 |
| TCRBV18_8 | 0.313 | 0.305 | 0.063 | -0.275 | 0.014 |
| TCRBV18_9 | -0.229 | -0.283 | 0.005 | 0.047 | -0.084 |
| TCRBV18_10 | -0.205 | -0.198 | 0.318 | 0.048 | -0.313 |
| TCRBV18_11 | -0.155 | -0.036 | 0.150 | 0.090 | -0.068 |
| TCRBV18_12 | -0.013 | 0.008 | 0.008 | -0.003 | 0.035 |
| TCRBV18_13 | -0.057 | -0.076 | -0.031 | -0.018 | 0.022 |
| TCRBV20_5 | 0.001 | 0.172 | 0.110 | -0.027 | -0.213 |
| TCRBV20_6 | -0.161 | 0.200 | 0.001 | 0.219 | 0.053 |
| TCRBV20_7 | -0.277 | 0.053 | 0.085 | -0.109 | 0.113 |
| TCRBV20_8 | -0.077 | 0.280 | -0.130 | -0.204 | -0.219 |
| TCRBV20_9 | 0.312 | -0.332 | 0.028 | 0.436 | -0.109 |
| TCRBV20_10 | -0.214 | -0.152 | -0.028 | -0.169 | 0.013 |
| TCRBV20_11 | 0.151 | -0.090 | 0.053 | -0.048 | -0.151 |
| TCRBV20_12 | 0.152 | 0.226 | -0.058 | -0.109 | 0.329 |
| TCRBV20_13 | 0.027 | -0.203 | -0.184 | 0.039 | 0.059 |
| TCRBV20_14 | 0.015 | 0.069 | -0.041 | -0.020 | 0.021 |

| | 51 | 52 |
|---|---|---|
| TCRBV01_6 | 0.016 | 0.001 |

*FIG. 106B*

| | | |
|---|---|---|
| TCRBV01_7 | -0.020 | -0.075 |
| TCRBV01_8 | -0.138 | 0.225 |
| TCRBV01_9 | -0.111 | -0.177 |
| TCRBV01_10 | 0.077 | 0.009 |
| TCRBV01_11 | -0.103 | -0.006 |
| TCRBV01_12 | 0.204 | -0.057 |
| TCRBV01_13 | 0.045 | 0.035 |
| TCRBV01_14 | -0.004 | -0.002 |
| TCRBV02_6 | 0.155 | -0.115 |
| TCRBV02_7 | -0.123 | -0.062 |
| TCRBV02_8 | -0.486 | 0.108 |
| TCRBV02_9 | 0.044 | 0.010 |
| TCRBV02_10 | -0.018 | -0.073 |
| TCRBV02_11 | -0.030 | -0.039 |
| TCRBV02_12 | -0.053 | -0.132 |
| TCRBV02_13 | 0.004 | -0.038 |
| TCRBV03_4 | 0.013 | 0.009 |
| TCRBV03_5 | -0.013 | 0.017 |
| TCRBV03_6 | -0.052 | -0.094 |
| TCRBV03_7 | 0.096 | -0.156 |
| TCRBV03_8 | 0.103 | 0.047 |
| TCRBV03_9 | 0.047 | 0.087 |
| TCRBV03_10 | -0.035 | -0.112 |
| TCRBV03_11 | -0.110 | 0.052 |
| TCRBV03_12 | -0.035 | -0.024 |
| TCRBV03_13 | -0.046 | 0.128 |
| TCRBV04_6 | -0.036 | 0.015 |
| TCRBV04_7 | -0.061 | -0.174 |
| TCRBV04_8 | 0.157 | -0.086 |
| TCRBV04_9 | -0.013 | -0.501 |
| TCRBV04_10 | -0.157 | 0.379 |
| TCRBV04_11 | 0.170 | 0.114 |
| TCRBV04_12 | -0.081 | 0.102 |
| TCRBV04_13 | -0.178 | 0.053 |
| TCRBV04_14 | 0.221 | 0.006 |
| TCRBV04_15 | -0.022 | 0.093 |
| TCRBV051_5 | -0.218 | -0.117 |
| TCRBV051_6 | -0.130 | -0.082 |
| TCRBV051_7 | -0.092 | -0.197 |
| TCRBV051_8 | -0.016 | 0.098 |
| TCRBV051_9 | 0.115 | 0.071 |
| TCRBV051_10 | -0.193 | 0.118 |
| TCRBV051_11 | 0.184 | 0.174 |
| TCRBV051_12 | 0.140 | -0.014 |
| TCRBV051_13 | 0.193 | 0.064 |
| TCRBV052_6 | -0.046 | -0.243 |
| TCRBV052_7 | 0.062 | 0.085 |
| TCRBV052_8 | 0.001 | 0.106 |
| TCRBV052_9 | 0.140 | 0.107 |
| TCRBV052_10 | 0.067 | 0.130 |
| TCRBV052_11 | -0.041 | -0.072 |
| TCRBV052_12 | -0.120 | -0.036 |
| TCRBV052_13 | -0.079 | 0.038 |
| TCRBV06_5 | -0.084 | -0.030 |
| TCRBV06_6 | -0.046 | -0.081 |
| TCRBV06_7 | -0.200 | -0.093 |
| TCRBV06_8 | 0.281 | 0.003 |
| TCRBV06_9 | -0.182 | -0.116 |
| TCRBV06_10 | 0.037 | 0.149 |
| TCRBV06_11 | 0.050 | -0.020 |
| TCRBV06_12 | -0.010 | 0.049 |
| TCRBV06_13 | 0.121 | 0.093 |
| TCRBV07_5 | 0.004 | -0.075 |
| TCRBV07_6 | 0.025 | -0.118 |

*FIG. 106C*

| | | |
|---|---|---|
| TCRBV07_7 | -0.084 | -0.014 |
| TCRBV07_8 | 0.078 | 0.105 |
| TCRBV07_9 | -0.127 | -0.129 |
| TCRBV07_10 | 0.244 | 0.127 |
| TCRBV07_11 | -0.027 | 0.159 |
| TCRBV07_12 | -0.098 | -0.110 |
| TCRBV07_13 | -0.048 | 0.008 |
| TCRBV081_5 | 0.068 | 0.013 |
| TCRBV081_6 | -0.048 | 0.102 |
| TCRBV081_7 | 0.022 | 0.081 |
| TCRBV081_8 | -0.095 | -0.081 |
| TCRBV081_9 | -0.026 | -0.092 |
| TCRBV081_10 | 0.012 | 0.096 |
| TCRBV081_11 | -0.043 | 0.029 |
| TCRBV081_12 | 0.110 | -0.148 |
| TCRBV082_4 | 0.344 | -0.050 |
| TCRBV082_5 | -0.179 | -0.047 |
| TCRBV082_6 | 0.337 | -0.016 |
| TCRBV082_7 | -0.287 | 0.254 |
| TCRBV082_8 | 0.044 | -0.045 |
| TCRBV082_9 | -0.169 | 0.056 |
| TCRBV082_10 | -0.109 | -0.130 |
| TCRBV082_11 | 0.020 | -0.021 |
| TCRBV083_4 | -0.003 | 0.009 |
| TCRBV083_5 | -0.066 | -0.001 |
| TCRBV083_6 | -0.157 | -0.003 |
| TCRBV083_7 | 0.199 | 0.101 |
| TCRBV083_8 | -0.327 | 0.003 |
| TCRBV083_9 | 0.173 | 0.032 |
| TCRBV083_10 | 0.206 | -0.042 |
| TCRBV083_11 | -0.173 | 0.039 |
| TCRBV083_12 | 0.148 | -0.139 |
| TCRBV09_5 | 0.036 | 0.008 |
| TCRBV09_6 | 0.075 | 0.122 |
| TCRBV09_7 | -0.183 | 0.216 |
| TCRBV09_8 | 0.168 | -0.023 |
| TCRBV09_9 | 0.002 | -0.075 |
| TCRBV09_10 | 0.084 | -0.016 |
| TCRBV09_11 | 0.143 | 0.010 |
| TCRBV09_12 | 0.013 | -0.297 |
| TCRBV09_13 | -0.277 | -0.142 |
| TCRBV09_14 | -0.264 | 0.022 |
| TCRBV09_15 | -0.030 | -0.055 |
| TCRBV10_6 | -0.015 | -0.051 |
| TCRBV10_7 | -0.087 | -0.026 |
| TCRBV10_8 | 0.007 | -0.177 |
| TCRBV10_9 | 0.026 | 0.096 |
| TCRBV10_10 | -0.149 | 0.220 |
| TCRBV10_11 | 0.094 | -0.065 |
| TCRBV10_12 | 0.117 | -0.002 |
| TCRBV10_13 | 0.006 | 0.004 |
| TCRBV11_5 | 0.041 | 0.053 |
| TCRBV11_6 | 0.108 | 0.035 |
| TCRBV11_7 | -0.150 | 0.218 |
| TCRBV11_8 | -0.292 | -0.158 |
| TCRBV11_9 | 0.194 | -0.136 |
| TCRBV11_10 | -0.113 | 0.030 |
| TCRBV11_11 | 0.093 | -0.169 |
| TCRBV11_12 | 0.019 | 0.053 |
| TCRBV11_13 | 0.026 | -0.000 |
| TCRBV11_14 | 0.029 | 0.019 |
| TCRBV11_15 | 0.011 | 0.007 |
| TCRBV12_4 | -0.159 | -0.079 |

*FIG. 106D*

| | | |
|---|---|---|
| TCRBV12_5 | 0.077 | 0.128 |
| TCRBV12_6 | -0.113 | -0.017 |
| TCRBV12_7 | -0.022 | 0.280 |
| TCRBV12_8 | 0.151 | 0.020 |
| TCRBV12_9 | 0.132 | -0.241 |
| TCRBV12_10 | 0.001 | -0.051 |
| TCRBV12_11 | -0.136 | -0.088 |
| TCRBV12_12 | 0.069 | 0.049 |
| TCRBV13_5 | 0.074 | -0.037 |
| TCRBV13_6 | -0.307 | -0.069 |
| TCRBV13_7 | 0.086 | -0.060 |
| TCRBV13_8 | -0.001 | 0.140 |
| TCRBV13_9 | 0.061 | -0.077 |
| TCRBV13_10 | 0.175 | -0.011 |
| TCRBV13_11 | 0.064 | 0.225 |
| TCRBV13_12 | 0.014 | 0.036 |
| TCRBV13_13 | -0.165 | -0.147 |
| TCRBV14_5 | -0.002 | 0.019 |
| TCRBV14_6 | -0.189 | -0.020 |
| TCRBV14_7 | 0.083 | -0.062 |
| TCRBV14_8 | 0.103 | -0.023 |
| TCRBV14_9 | 0.028 | 0.026 |
| TCRBV14_10 | 0.080 | -0.040 |
| TCRBV14_11 | -0.259 | 0.123 |
| TCRBV14_12 | 0.148 | -0.026 |
| TCRBV14_13 | 0.008 | 0.003 |
| TCRBV15_4 | 0.029 | -0.052 |
| TCRBV15_5 | -0.116 | -0.158 |
| TCRBV15_6 | -0.006 | -0.061 |
| TCRBV15_7 | 0.240 | 0.066 |
| TCRBV15_8 | 0.057 | 0.031 |
| TCRBV15_9 | 0.076 | 0.015 |
| TCRBV15_10 | -0.095 | 0.189 |
| TCRBV15_11 | -0.164 | -0.094 |
| TCRBV15_12 | -0.053 | 0.018 |
| TCRBV16_5 | 0.264 | 0.038 |
| TCRBV16_6 | 0.025 | 0.032 |
| TCRBV16_7 | -0.235 | 0.165 |
| TCRBV16_8 | -0.007 | -0.071 |
| TCRBV16_9 | 0.099 | 0.058 |
| TCRBV16_10 | -0.263 | -0.097 |
| TCRBV16_11 | -0.055 | 0.105 |
| TCRBV16_12 | 0.113 | -0.166 |
| TCRBV16_13 | 0.008 | 0.003 |
| TCRBV18_3 | 0.010 | 0.022 |
| TCRBV18_4 | -0.061 | 0.036 |
| TCRBV18_5 | -0.064 | 0.023 |
| TCRBV18_6 | 0.039 | -0.065 |
| TCRBV18_7 | 0.121 | -0.108 |
| TCRBV18_8 | 0.036 | -0.001 |
| TCRBV18_9 | -0.230 | -0.031 |
| TCRBV18_10 | -0.010 | -0.013 |
| TCRBV18_11 | 0.078 | 0.235 |
| TCRBV18_12 | 0.007 | 0.001 |
| TCRBV18_13 | 0.031 | 0.006 |
| TCRBV20_5 | 0.092 | 0.080 |
| TCRBV20_6 | -0.210 | 0.024 |
| TCRBV20_7 | -0.208 | -0.132 |
| TCRBV20_8 | 0.075 | 0.200 |
| TCRBV20_9 | 0.136 | 0.064 |
| TCRBV20_10 | -0.026 | 0.105 |
| TCRBV20_11 | -0.060 | 0.007 |
| TCRBV20_12 | 0.170 | -0.154 |
| TCRBV20_13 | -0.025 | -0.197 |

*FIG. 107A*

| TCRBV20_14 | 0.023 | -0.042 |

Variance Explained by Components

| 1 | 2 | 3 | 4 | 5 |
|---|---|---|---|---|
| 806.097 | 574.767 | 525.021 | 474.758 | 360.278 |
| 6 | 7 | 8 | 9 | 10 |
| 326.711 | 312.488 | 234.426 | 220.247 | 205.757 |
| 11 | 12 | 13 | 14 | 15 |
| 197.164 | 187.097 | 166.789 | 160.829 | 147.404 |
| 16 | 17 | 18 | 19 | 20 |
| 130.104 | 128.438 | 120.749 | 108.967 | 98.134 |
| 21 | 22 | 23 | 24 | 25 |
| 90.690 | 78.013 | 76.711 | 61.271 | 59.256 |
| 26 | 27 | 28 | 29 | 30 |
| 50.362 | 48.663 | 39.763 | 37.130 | 32.355 |
| 31 | 32 | 33 | 34 | 35 |
| 29.161 | 26.169 | 24.054 | 21.550 | 20.080 |
| 36 | 37 | 38 | 39 | 40 |
| 18.509 | 17.875 | 15.007 | 13.936 | 12.903 |
| 41 | 42 | 43 | 44 | 45 |
| 11.317 | 9.508 | 8.822 | 8.187 | 7.641 |
| 46 | 47 | 48 | 49 | 50 |
| 6.640 | 5.734 | 4.707 | 4.103 | 3.624 |
| 51 | 52 | | | |
| 3.345 | 2.374 | | | |

Percent of Total Variance Explained

| 1 | 2 | 3 | 4 | 5 |
|---|---|---|---|---|
| 12.723 | 9.072 | 8.287 | 7.493 | 5.686 |
| 6 | 7 | 8 | 9 | 10 |
| 5.157 | 4.932 | 3.700 | 3.476 | 3.248 |
| 11 | 12 | 13 | 14 | 15 |
| 3.112 | 2.953 | 2.633 | 2.538 | 2.327 |
| 16 | 17 | 18 | 19 | 20 |

*FIG. 107B*

| | | | | |
|---|---|---|---|---|
| 2.054 | 2.027 | 1.906 | 1.720 | 1.549 |
| 21 | 22 | 23 | 24 | 25 |
| 1.431 | 1.231 | 1.211 | 0.967 | 0.935 |
| 26 | 27 | 28 | 29 | 30 |
| 0.795 | 0.768 | 0.628 | 0.586 | 0.511 |
| 31 | 32 | 33 | 34 | 35 |
| 0.460 | 0.413 | 0.380 | 0.340 | 0.317 |
| 36 | 37 | 38 | 39 | 40 |
| 0.292 | 0.282 | 0.237 | 0.220 | 0.204 |
| 41 | 42 | 43 | 44 | 45 |
| 0.179 | 0.150 | 0.139 | 0.129 | 0.121 |
| 46 | 47 | 48 | 49 | 50 |
| 0.105 | 0.090 | 0.074 | 0.065 | 0.057 |
| 51 | 52 | | | |
| 0.053 | 0.037 | | | |

Coefficients for Standardized Factor Scores

|  | 1 | 2 | 3 | 4 | 5 |
|---|---|---|---|---|---|
| TCRBV01_6 | -0.000 | -0.000 | -0.000 | 0.000 | 0.000 |
| TCRBV01_7 | 0.001 | 0.001 | -0.000 | 0.000 | 0.000 |
| TCRBV01_8 | -0.003 | -0.002 | 0.008 | -0.010 | 0.007 |
| TCRBV01_9 | 0.001 | 0.004 | 0.003 | 0.006 | 0.006 |
| TCRBV01_10 | 0.004 | 0.004 | 0.004 | 0.003 | 0.003 |
| TCRBV01_11 | 0.000 | 0.005 | -0.001 | 0.003 | -0.000 |
| TCRBV01_12 | -0.000 | 0.002 | -0.002 | 0.000 | 0.001 |
| TCRBV01_13 | -0.000 | 0.000 | -0.001 | 0.000 | -0.000 |
| TCRBV01_14 | -0.000 | 0.000 | -0.000 | 0.000 | -0.000 |
| TCRBV02_6 | 0.001 | -0.000 | -0.001 | -0.000 | -0.000 |
| TCRBV02_7 | 0.001 | 0.001 | 0.001 | -0.000 | -0.003 |
| TCRBV02_8 | 0.000 | 0.001 | 0.000 | 0.000 | 0.002 |
| TCRBV02_9 | 0.001 | 0.000 | 0.000 | 0.000 | -0.004 |
| TCRBV02_10 | -0.000 | -0.000 | 0.001 | -0.002 | 0.002 |
| TCRBV02_11 | -0.001 | -0.000 | 0.003 | -0.000 | 0.001 |
| TCRBV02_12 | -0.001 | -0.000 | 0.001 | -0.000 | 0.000 |
| TCRBV02_13 | -0.000 | -0.000 | 0.000 | -0.001 | 0.001 |
| TCRBV03_4 | -0.000 | -0.000 | -0.000 | 0.000 | 0.000 |
| TCRBV03_5 | -0.000 | -0.000 | -0.000 | -0.000 | 0.000 |
| TCRBV03_6 | 0.003 | 0.000 | -0.001 | -0.002 | 0.000 |
| TCRBV03_7 | 0.003 | 0.003 | -0.001 | -0.002 | 0.002 |
| TCRBV03_8 | 0.004 | 0.004 | -0.000 | -0.002 | 0.004 |
| TCRBV03_9 | 0.005 | 0.005 | -0.003 | -0.000 | 0.005 |
| TCRBV03_10 | -0.004 | 0.001 | 0.007 | -0.002 | 0.014 |
| TCRBV03_11 | -0.006 | 0.002 | 0.003 | 0.004 | 0.002 |
| TCRBV03_12 | -0.001 | 0.000 | 0.003 | 0.002 | -0.004 |
| TCRBV03_13 | -0.001 | -0.001 | 0.005 | 0.005 | -0.006 |
| TCRBV04_6 | 0.000 | -0.000 | -0.000 | -0.000 | 0.000 |
| TCRBV04_7 | 0.001 | -0.000 | -0.000 | -0.001 | 0.000 |
| TCRBV04_8 | 0.002 | 0.000 | 0.001 | -0.002 | 0.000 |
| TCRBV04_9 | 0.006 | -0.002 | 0.001 | -0.003 | 0.000 |
| TCRBV04_10 | 0.006 | -0.001 | -0.001 | -0.001 | 0.003 |
| TCRBV04_11 | -0.003 | 0.001 | -0.003 | 0.004 | -0.002 |
| TCRBV04_12 | -0.005 | 0.002 | -0.001 | 0.003 | 0.004 |
| TCRBV04_13 | -0.004 | 0.003 | 0.001 | 0.005 | -0.007 |
| TCRBV04_14 | -0.004 | -0.002 | 0.003 | -0.005 | 0.001 |
| TCRBV04_15 | -0.000 | 0.000 | 0.000 | -0.000 | -0.000 |
| TCRBV051_5 | 0.000 | 0.000 | -0.000 | -0.000 | 0.000 |
| TCRBV051_6 | 0.000 | -0.000 | 0.000 | 0.000 | 0.002 |
| TCRBV051_7 | -0.000 | -0.001 | -0.001 | -0.002 | 0.003 |
| TCRBV051_8 | 0.007 | -0.020 | 0.014 | 0.014 | 0.001 |
| TCRBV051_9 | 0.000 | 0.002 | -0.003 | 0.006 | -0.005 |
| TCRBV051_10 | -0.001 | 0.009 | -0.007 | -0.004 | -0.004 |
| TCRBV051_11 | -0.002 | 0.005 | 0.004 | -0.013 | -0.003 |
| TCRBV051_12 | -0.001 | 0.006 | -0.001 | -0.002 | -0.002 |
| TCRBV051_13 | 0.000 | 0.000 | -0.000 | -0.000 | -0.000 |
| TCRBV052_6 | 0.000 | 0.001 | -0.001 | -0.001 | -0.000 |
| TCRBV052_7 | 0.001 | 0.005 | 0.000 | 0.001 | -0.002 |
| TCRBV052_8 | -0.004 | 0.010 | 0.012 | 0.007 | -0.010 |
| TCRBV052_9 | 0.002 | -0.002 | 0.002 | -0.001 | 0.000 |
| TCRBV052_10 | 0.002 | -0.004 | -0.005 | -0.002 | -0.001 |
| TCRBV052_11 | 0.001 | -0.005 | -0.001 | -0.004 | 0.004 |
| TCRBV052_12 | 0.000 | -0.004 | -0.002 | -0.001 | 0.000 |
| TCRBV052_13 | 0.000 | -0.001 | -0.000 | -0.000 | -0.001 |
| TCRBV06_5 | 0.000 | 0.000 | -0.000 | -0.000 | -0.000 |
| TCRBV06_6 | 0.001 | 0.001 | -0.001 | 0.000 | 0.001 |
| TCRBV06_7 | 0.003 | 0.002 | 0.001 | 0.000 | -0.000 |
| TCRBV06_8 | 0.003 | 0.003 | 0.004 | 0.001 | 0.001 |

*FIG. 108A*

| | | | | | |
|---|---|---|---|---|---|
| TCRBV06_9 | 0.004 | 0.002 | 0.005 | -0.007 | 0.006 |
| TCRBV06_10 | -0.003 | 0.004 | -0.000 | 0.002 | 0.005 |
| TCRBV06_11 | -0.004 | 0.002 | 0.002 | 0.004 | 0.002 |
| TCRBV06_12 | -0.002 | -0.001 | -0.000 | 0.002 | 0.002 |
| TCRBV06_13 | -0.000 | -0.000 | -0.000 | 0.000 | 0.001 |
| TCRBV07_5 | 0.000 | 0.000 | -0.000 | -0.000 | -0.000 |
| TCRBV07_6 | 0.001 | 0.000 | 0.004 | 0.003 | -0.003 |
| TCRBV07_7 | 0.002 | -0.001 | 0.006 | -0.002 | -0.002 |
| TCRBV07_8 | 0.002 | 0.004 | 0.001 | 0.001 | 0.004 |
| TCRBV07_9 | 0.006 | 0.004 | 0.005 | -0.002 | 0.003 |
| TCRBV07_10 | -0.001 | 0.004 | -0.001 | 0.002 | 0.008 |
| TCRBV07_11 | -0.004 | 0.001 | -0.001 | 0.000 | 0.005 |
| TCRBV07_12 | -0.002 | 0.001 | -0.001 | 0.001 | 0.001 |
| TCRBV07_13 | -0.000 | -0.000 | -0.000 | -0.000 | 0.000 |
| TCRBV081_5 | -0.000 | -0.000 | 0.000 | 0.000 | 0.000 |
| TCRBV081_6 | -0.000 | 0.001 | -0.000 | -0.001 | 0.002 |
| TCRBV081_7 | 0.001 | -0.001 | 0.000 | -0.002 | 0.006 |
| TCRBV081_8 | 0.001 | -0.000 | 0.002 | 0.000 | 0.002 |
| TCRBV081_9 | 0.005 | -0.008 | -0.001 | -0.003 | -0.001 |
| TCRBV081_10 | -0.002 | 0.002 | -0.003 | 0.005 | -0.004 |
| TCRBV081_11 | -0.003 | 0.004 | 0.001 | 0.001 | -0.003 |
| TCRBV081_12 | -0.001 | 0.002 | 0.000 | -0.001 | -0.002 |
| TCRBV082_4 | 0.001 | -0.001 | -0.000 | -0.002 | -0.001 |
| TCRBV082_5 | 0.002 | -0.002 | -0.001 | -0.005 | -0.002 |
| TCRBV082_6 | 0.002 | -0.001 | 0.000 | -0.004 | -0.002 |
| TCRBV082_7 | 0.005 | -0.004 | 0.003 | -0.008 | -0.008 |
| TCRBV082_8 | -0.002 | 0.002 | -0.000 | 0.004 | -0.001 |
| TCRBV082_9 | -0.004 | 0.004 | -0.001 | 0.007 | 0.008 |
| TCRBV082_10 | -0.003 | 0.001 | -0.001 | 0.006 | 0.004 |
| TCRBV082_11 | -0.001 | 0.000 | 0.000 | 0.002 | 0.002 |
| TCRBV083_4 | -0.000 | -0.000 | 0.000 | 0.000 | -0.000 |
| TCRBV083_5 | -0.000 | 0.000 | 0.000 | -0.000 | -0.000 |
| TCRBV083_6 | 0.001 | -0.000 | -0.002 | -0.001 | -0.002 |
| TCRBV083_7 | -0.000 | -0.001 | 0.002 | -0.001 | 0.004 |
| TCRBV083_8 | 0.000 | 0.002 | 0.000 | -0.002 | 0.003 |
| TCRBV083_9 | 0.001 | 0.000 | -0.002 | 0.000 | 0.001 |
| TCRBV083_10 | -0.001 | 0.001 | -0.000 | 0.002 | -0.000 |
| TCRBV083_11 | -0.001 | -0.000 | 0.003 | 0.002 | -0.004 |
| TCRBV083_12 | -0.000 | -0.001 | -0.001 | 0.001 | -0.003 |
| TCRBV09_5 | -0.000 | -0.000 | 0.000 | 0.000 | 0.000 |
| TCRBV09_6 | 0.000 | -0.000 | -0.001 | 0.000 | 0.001 |
| TCRBV09_7 | 0.001 | -0.001 | -0.000 | -0.001 | 0.006 |
| TCRBV09_8 | 0.000 | -0.002 | 0.005 | 0.010 | 0.012 |
| TCRBV09_9 | 0.003 | -0.001 | 0.008 | 0.006 | 0.008 |
| TCRBV09_10 | 0.003 | 0.006 | 0.001 | -0.004 | 0.010 |
| TCRBV09_11 | -0.002 | 0.005 | 0.013 | -0.008 | -0.014 |
| TCRBV09_12 | -0.000 | 0.006 | -0.001 | -0.003 | -0.003 |
| TCRBV09_13 | 0.000 | 0.001 | -0.000 | -0.001 | -0.001 |
| TCRBV09_14 | 0.000 | 0.000 | -0.000 | -0.000 | -0.000 |
| TCRBV09_15 | 0.000 | -0.000 | 0.000 | -0.000 | -0.000 |
| TCRBV10_6 | 0.001 | 0.001 | -0.000 | -0.001 | -0.001 |
| TCRBV10_7 | 0.001 | 0.003 | 0.002 | 0.002 | -0.005 |
| TCRBV10_8 | 0.002 | 0.003 | -0.000 | 0.001 | -0.000 |
| TCRBV10_9 | -0.005 | -0.003 | 0.001 | -0.004 | 0.001 |
| TCRBV10_10 | -0.001 | -0.003 | 0.000 | 0.001 | 0.001 |
| TCRBV10_11 | 0.002 | -0.001 | -0.002 | 0.001 | 0.003 |
| TCRBV10_12 | 0.000 | -0.000 | -0.001 | 0.000 | 0.001 |
| TCRBV10_13 | -0.000 | -0.000 | -0.000 | 0.000 | 0.000 |
| TCRBV11_5 | 0.000 | -0.000 | -0.000 | 0.000 | 0.001 |
| TCRBV11_6 | 0.001 | 0.001 | 0.000 | -0.002 | 0.001 |
| TCRBV11_7 | 0.001 | 0.002 | 0.002 | 0.000 | -0.001 |
| TCRBV11_8 | 0.001 | 0.003 | 0.004 | -0.003 | -0.000 |
| TCRBV11_9 | 0.004 | 0.003 | 0.011 | -0.002 | 0.003 |
| TCRBV11_10 | -0.000 | 0.003 | 0.000 | 0.004 | 0.005 |

*FIG. 108B*

| | | | | | |
|---|---|---|---|---|---|
| TCRBV11_11 | -0.002 | 0.002 | -0.003 | 0.001 | 0.004 |
| TCRBV11_12 | -0.001 | 0.000 | -0.002 | 0.003 | 0.002 |
| TCRBV11_13 | -0.001 | -0.000 | -0.001 | 0.000 | 0.001 |
| TCRBV11_14 | -0.000 | -0.000 | -0.000 | 0.000 | 0.000 |
| TCRBV11_15 | -0.000 | -0.000 | -0.000 | 0.000 | 0.000 |
| TCRBV12_4 | -0.000 | 0.000 | 0.000 | 0.000 | -0.001 |
| TCRBV12_5 | 0.002 | 0.001 | 0.006 | 0.001 | -0.008 |
| TCRBV12_6 | 0.003 | 0.002 | 0.002 | -0.004 | 0.003 |
| TCRBV12_7 | 0.005 | 0.001 | 0.000 | -0.005 | 0.005 |
| TCRBV12_8 | 0.002 | -0.001 | -0.006 | -0.002 | 0.002 |
| TCRBV12_9 | -0.005 | -0.002 | -0.005 | 0.005 | -0.001 |
| TCRBV12_10 | -0.002 | -0.001 | 0.003 | 0.003 | -0.001 |
| TCRBV12_11 | -0.004 | -0.000 | 0.000 | 0.001 | 0.001 |
| TCRBV12_12 | -0.001 | -0.000 | 0.000 | 0.001 | -0.000 |
| TCRBV13_5 | -0.000 | -0.000 | -0.000 | 0.000 | 0.000 |
| TCRBV13_6 | 0.000 | 0.001 | 0.000 | -0.003 | -0.002 |
| TCRBV13_7 | 0.002 | -0.001 | -0.003 | -0.002 | 0.007 |
| TCRBV13_8 | 0.001 | -0.000 | -0.002 | 0.000 | 0.003 |
| TCRBV13_9 | 0.000 | 0.000 | 0.009 | 0.010 | -0.012 |
| TCRBV13_10 | -0.003 | 0.001 | -0.002 | -0.003 | 0.004 |
| TCRBV13_11 | -0.001 | -0.001 | -0.001 | -0.003 | -0.002 |
| TCRBV13_12 | -0.000 | -0.000 | -0.001 | 0.000 | 0.000 |
| TCRBV13_13 | 0.000 | -0.000 | -0.000 | 0.000 | 0.000 |
| TCRBV14_5 | 0.000 | 0.000 | 0.000 | -0.000 | -0.001 |
| TCRBV14_6 | 0.001 | -0.000 | -0.002 | -0.002 | 0.001 |
| TCRBV14_7 | -0.001 | 0.000 | 0.000 | -0.002 | -0.002 |
| TCRBV14_8 | 0.003 | -0.001 | -0.001 | -0.000 | -0.001 |
| TCRBV14_9 | 0.001 | -0.001 | -0.002 | 0.007 | 0.001 |
| TCRBV14_10 | -0.002 | 0.000 | 0.002 | -0.004 | 0.002 |
| TCRBV14_11 | -0.002 | 0.001 | 0.002 | -0.001 | -0.000 |
| TCRBV14_12 | -0.000 | 0.000 | -0.000 | 0.000 | 0.000 |
| TCRBV14_13 | -0.000 | -0.000 | -0.000 | 0.000 | 0.000 |
| TCRBV15_4 | -0.000 | 0.000 | -0.000 | 0.000 | 0.004 |
| TCRBV15_5 | 0.001 | -0.002 | -0.001 | 0.000 | 0.003 |
| TCRBV15_6 | 0.002 | 0.000 | 0.001 | -0.001 | 0.004 |
| TCRBV15_7 | 0.004 | 0.003 | 0.003 | 0.000 | 0.004 |
| TCRBV15_8 | 0.006 | 0.004 | 0.005 | 0.001 | -0.000 |
| TCRBV15_9 | -0.002 | 0.006 | 0.007 | 0.002 | 0.002 |
| TCRBV15_10 | -0.004 | 0.003 | -0.003 | 0.001 | -0.000 |
| TCRBV15_11 | -0.003 | 0.001 | -0.002 | 0.000 | -0.000 |
| TCRBV15_12 | -0.001 | 0.000 | 0.000 | -0.000 | -0.001 |
| TCRBV16_5 | -0.000 | 0.000 | 0.000 | 0.000 | 0.001 |
| TCRBV16_6 | 0.001 | -0.001 | 0.001 | 0.002 | 0.001 |
| TCRBV16_7 | 0.005 | 0.001 | 0.002 | 0.001 | -0.003 |
| TCRBV16_8 | 0.007 | 0.006 | -0.002 | 0.001 | -0.005 |
| TCRBV16_9 | 0.009 | 0.010 | -0.004 | 0.004 | -0.003 |
| TCRBV16_10 | 0.000 | 0.006 | 0.001 | 0.005 | 0.013 |
| TCRBV16_11 | -0.005 | -0.002 | 0.007 | 0.002 | 0.004 |
| TCRBV16_12 | -0.010 | -0.004 | 0.011 | -0.014 | -0.000 |
| TCRBV16_13 | -0.000 | -0.000 | 0.000 | 0.000 | 0.000 |
| TCRBV18_3 | 0.000 | -0.000 | -0.000 | -0.000 | 0.001 |
| TCRBV18_4 | 0.000 | -0.000 | 0.000 | -0.002 | -0.002 |
| TCRBV18_5 | 0.000 | 0.001 | 0.003 | -0.000 | -0.002 |
| TCRBV18_6 | -0.002 | 0.003 | 0.006 | -0.002 | 0.003 |
| TCRBV18_7 | -0.000 | 0.006 | 0.004 | 0.003 | 0.009 |
| TCRBV18_8 | 0.002 | 0.009 | -0.002 | -0.000 | 0.010 |
| TCRBV18_9 | -0.001 | 0.003 | 0.000 | 0.003 | 0.004 |
| TCRBV18_10 | -0.000 | 0.002 | -0.000 | 0.003 | 0.003 |
| TCRBV18_11 | -0.001 | -0.000 | -0.001 | 0.001 | -0.000 |
| TCRBV18_12 | -0.000 | 0.000 | 0.000 | 0.000 | 0.000 |
| TCRBV18_13 | 0.000 | -0.000 | -0.000 | -0.000 | 0.001 |
| TCRBV20_5 | 0.000 | -0.000 | 0.000 | 0.000 | -0.001 |
| TCRBV20_6 | 0.001 | -0.000 | 0.001 | 0.001 | -0.000 |
| TCRBV20_7 | 0.002 | 0.001 | 0.001 | 0.001 | -0.000 |

*FIG. 108C*

|            |        |        |        |        |        |
|------------|--------|--------|--------|--------|--------|
| TCRBV20_8  | 0.004  | 0.002  | 0.002  | -0.001 | 0.001  |
| TCRBV20_9  | 0.004  | 0.004  | 0.004  | 0.004  | 0.005  |
| TCRBV20_10 | -0.001 | 0.006  | 0.003  | -0.004 | 0.000  |
| TCRBV20_11 | -0.005 | 0.003  | 0.003  | 0.000  | 0.001  |
| TCRBV20_12 | -0.002 | 0.001  | -0.001 | 0.001  | 0.001  |
| TCRBV20_13 | -0.000 | -0.003 | -0.002 | 0.001  | 0.008  |
| TCRBV20_14 | -0.000 | 0.000  | -0.000 | 0.000  | 0.000  |
|            | 6      | 7      | 8      | 9      | 10     |
| TCRBV01_6  | 0.000  | -0.000 | -0.000 | -0.000 | -0.000 |
| TCRBV01_7  | -0.002 | 0.000  | 0.000  | 0.001  | 0.001  |
| TCRBV01_8  | 0.002  | -0.008 | 0.002  | 0.011  | -0.002 |
| TCRBV01_9  | 0.000  | 0.003  | -0.003 | 0.010  | 0.001  |
| TCRBV01_10 | -0.000 | 0.005  | -0.002 | -0.008 | -0.000 |
| TCRBV01_11 | 0.007  | 0.003  | 0.002  | -0.008 | 0.006  |
| TCRBV01_12 | 0.002  | 0.001  | -0.002 | -0.002 | 0.003  |
| TCRBV01_13 | 0.001  | -0.001 | 0.001  | -0.001 | 0.001  |
| TCRBV01_14 | 0.000  | -0.000 | 0.000  | -0.000 | -0.000 |
| TCRBV02_6  | -0.001 | -0.002 | -0.001 | 0.002  | 0.001  |
| TCRBV02_7  | -0.001 | -0.001 | 0.002  | 0.002  | -0.003 |
| TCRBV02_8  | -0.004 | -0.001 | -0.000 | -0.003 | 0.001  |
| TCRBV02_9  | -0.001 | 0.002  | -0.009 | 0.002  | 0.000  |
| TCRBV02_10 | -0.004 | -0.002 | -0.003 | -0.002 | 0.001  |
| TCRBV02_11 | -0.000 | 0.000  | 0.002  | 0.001  | -0.000 |
| TCRBV02_12 | 0.001  | 0.001  | -0.000 | 0.000  | -0.003 |
| TCRBV02_13 | 0.000  | -0.000 | 0.001  | 0.001  | 0.000  |
| TCRBV03_4  | 0.000  | 0.000  | 0.000  | -0.000 | 0.000  |
| TCRBV03_5  | 0.000  | 0.000  | 0.000  | -0.000 | -0.000 |
| TCRBV03_6  | -0.000 | 0.003  | -0.001 | 0.004  | -0.003 |
| TCRBV03_7  | 0.000  | 0.004  | -0.003 | 0.002  | -0.002 |
| TCRBV03_8  | 0.000  | 0.004  | -0.005 | 0.012  | -0.001 |
| TCRBV03_9  | 0.002  | 0.005  | -0.007 | 0.007  | 0.000  |
| TCRBV03_10 | 0.008  | -0.009 | 0.005  | -0.000 | -0.000 |
| TCRBV03_11 | 0.005  | -0.005 | -0.010 | -0.008 | 0.010  |
| TCRBV03_12 | 0.001  | 0.000  | 0.006  | -0.008 | 0.001  |
| TCRBV03_13 | -0.005 | -0.000 | 0.014  | -0.005 | 0.004  |
| TCRBV04_6  | 0.000  | 0.000  | 0.000  | 0.000  | 0.000  |
| TCRBV04_7  | -0.001 | 0.001  | -0.000 | 0.001  | 0.005  |
| TCRBV04_8  | 0.001  | 0.002  | -0.003 | -0.000 | 0.006  |
| TCRBV04_9  | -0.000 | 0.004  | -0.001 | -0.007 | 0.008  |
| TCRBV04_10 | -0.002 | 0.003  | -0.003 | -0.005 | 0.001  |
| TCRBV04_11 | 0.000  | -0.003 | 0.004  | -0.004 | -0.008 |
| TCRBV04_12 | 0.000  | 0.000  | 0.004  | 0.000  | -0.011 |
| TCRBV04_13 | 0.000  | -0.002 | -0.001 | 0.014  | -0.001 |
| TCRBV04_14 | 0.002  | -0.005 | 0.001  | 0.000  | 0.001  |
| TCRBV04_15 | -0.000 | -0.000 | 0.001  | 0.001  | -0.001 |
| TCRBV051_5 | -0.000 | 0.000  | 0.000  | -0.000 | 0.001  |
| TCRBV051_6 | 0.000  | 0.001  | 0.001  | -0.001 | 0.001  |
| TCRBV051_7 | -0.000 | 0.001  | 0.001  | 0.002  | 0.005  |
| TCRBV051_8 | 0.008  | -0.007 | -0.009 | 0.000  | -0.004 |
| TCRBV051_9 | 0.014  | -0.005 | -0.001 | 0.012  | -0.002 |
| TCRBV051_10| -0.003 | -0.000 | 0.004  | 0.006  | -0.008 |
| TCRBV051_11| -0.003 | 0.002  | 0.011  | -0.006 | -0.001 |
| TCRBV051_12| -0.003 | 0.001  | -0.001 | 0.000  | -0.007 |
| TCRBV051_13| -0.000 | 0.000  | 0.000  | -0.000 | 0.000  |
| TCRBV052_6 | -0.001 | -0.000 | 0.001  | 0.000  | -0.001 |
| TCRBV052_7 | -0.005 | -0.005 | -0.003 | 0.003  | -0.000 |
| TCRBV052_8 | -0.013 | -0.002 | -0.014 | 0.002  | 0.002  |
| TCRBV052_9 | 0.006  | -0.008 | -0.004 | 0.014  | -0.027 |
| TCRBV052_10| 0.006  | -0.003 | 0.009  | 0.002  | 0.003  |
| TCRBV052_11| 0.011  | 0.007  | 0.013  | -0.007 | 0.006  |
| TCRBV052_12| 0.006  | 0.004  | 0.005  | 0.000  | 0.003  |

*FIG. 109A*

| | | | | | |
|---|---|---|---|---|---|
| TCRBV052_13 | 0.001 | 0.001 | -0.000 | 0.000 | -0.000 |
| TCRBV06_5 | -0.000 | 0.000 | -0.000 | -0.000 | 0.000 |
| TCRBV06_6 | -0.000 | -0.002 | 0.001 | 0.001 | -0.000 |
| TCRBV06_7 | -0.000 | -0.002 | 0.003 | 0.004 | -0.004 |
| TCRBV06_8 | -0.003 | 0.000 | 0.008 | -0.004 | 0.000 |
| TCRBV06_9 | 0.009 | -0.009 | 0.007 | -0.007 | -0.003 |
| TCRBV06_10 | 0.007 | 0.005 | -0.007 | -0.003 | 0.008 |
| TCRBV06_11 | -0.001 | 0.006 | -0.007 | 0.007 | 0.005 |
| TCRBV06_12 | -0.000 | 0.004 | -0.006 | 0.006 | 0.003 |
| TCRBV06_13 | -0.000 | 0.000 | -0.001 | 0.000 | 0.000 |
| TCRBV07_5 | -0.000 | -0.000 | 0.000 | 0.000 | -0.000 |
| TCRBV07_6 | -0.003 | -0.001 | 0.008 | -0.004 | 0.005 |
| TCRBV07_7 | 0.009 | 0.002 | -0.002 | -0.005 | 0.001 |
| TCRBV07_8 | -0.005 | -0.001 | -0.005 | 0.009 | 0.007 |
| TCRBV07_9 | 0.001 | -0.007 | -0.000 | 0.002 | -0.007 |
| TCRBV07_10 | 0.006 | 0.004 | -0.005 | -0.004 | 0.001 |
| TCRBV07_11 | 0.004 | 0.001 | 0.004 | 0.004 | 0.000 |
| TCRBV07_12 | 0.000 | 0.003 | -0.001 | 0.001 | 0.001 |
| TCRBV07_13 | -0.001 | 0.001 | 0.000 | -0.000 | -0.000 |
| TCRBV081_5 | -0.000 | 0.000 | 0.000 | -0.001 | 0.000 |
| TCRBV081_6 | -0.001 | 0.002 | 0.005 | -0.002 | 0.001 |
| TCRBV081_7 | -0.003 | 0.009 | 0.005 | -0.004 | -0.003 |
| TCRBV081_8 | -0.003 | 0.009 | 0.003 | -0.002 | -0.004 |
| TCRBV081_9 | -0.009 | 0.000 | -0.005 | -0.000 | -0.002 |
| TCRBV081_10 | 0.012 | -0.016 | -0.002 | 0.001 | 0.001 |
| TCRBV081_11 | 0.005 | -0.004 | -0.003 | 0.004 | 0.005 |
| TCRBV081_12 | -0.000 | -0.001 | -0.003 | 0.003 | 0.001 |
| TCRBV082_4 | 0.000 | -0.000 | 0.000 | -0.000 | 0.003 |
| TCRBV082_5 | -0.001 | -0.001 | -0.002 | 0.001 | 0.008 |
| TCRBV082_6 | -0.000 | -0.001 | -0.002 | 0.002 | 0.005 |
| TCRBV082_7 | 0.001 | -0.002 | -0.002 | -0.001 | 0.013 |
| TCRBV082_8 | 0.002 | -0.002 | -0.001 | 0.001 | -0.008 |
| TCRBV082_9 | 0.001 | 0.002 | 0.003 | -0.003 | -0.011 |
| TCRBV082_10 | -0.002 | 0.001 | 0.003 | 0.000 | -0.009 |
| TCRBV082_11 | -0.000 | 0.002 | 0.001 | 0.000 | -0.002 |
| TCRBV083_4 | -0.000 | 0.000 | 0.001 | -0.000 | 0.000 |
| TCRBV083_5 | -0.000 | -0.000 | -0.000 | 0.002 | 0.001 |
| TCRBV083_6 | 0.001 | -0.000 | 0.001 | 0.001 | -0.000 |
| TCRBV083_7 | 0.003 | 0.001 | 0.005 | -0.006 | -0.001 |
| TCRBV083_8 | 0.001 | -0.002 | -0.004 | -0.002 | -0.002 |
| TCRBV083_9 | -0.003 | -0.001 | 0.002 | 0.001 | -0.005 |
| TCRBV083_10 | -0.004 | -0.002 | -0.000 | 0.002 | 0.004 |
| TCRBV083_11 | 0.002 | 0.003 | -0.001 | 0.001 | 0.002 |
| TCRBV083_12 | 0.001 | 0.000 | -0.003 | 0.003 | 0.001 |
| TCRBV09_5 | -0.000 | 0.000 | -0.000 | -0.001 | -0.001 |
| TCRBV09_6 | 0.000 | 0.000 | 0.001 | 0.001 | 0.003 |
| TCRBV09_7 | -0.001 | -0.003 | -0.003 | 0.002 | 0.007 |
| TCRBV09_8 | -0.004 | 0.002 | -0.000 | 0.010 | 0.012 |
| TCRBV09_9 | -0.004 | -0.004 | 0.003 | 0.001 | 0.009 |
| TCRBV09_10 | -0.011 | 0.002 | -0.008 | -0.001 | -0.003 |
| TCRBV09_11 | 0.007 | 0.016 | -0.011 | -0.004 | -0.007 |
| TCRBV09_12 | -0.002 | -0.000 | 0.001 | 0.009 | -0.011 |
| TCRBV09_13 | -0.001 | -0.000 | 0.000 | 0.002 | -0.002 |
| TCRBV09_14 | -0.000 | -0.000 | -0.000 | 0.000 | -0.000 |
| TCRBV09_15 | -0.000 | -0.000 | -0.000 | 0.000 | 0.000 |
| TCRBV10_6 | -0.000 | -0.000 | 0.001 | -0.002 | -0.002 |
| TCRBV10_7 | -0.003 | -0.002 | -0.000 | -0.000 | -0.004 |
| TCRBV10_8 | -0.006 | -0.006 | 0.001 | 0.001 | -0.006 |
| TCRBV10_9 | -0.010 | -0.009 | -0.015 | -0.015 | -0.001 |
| TCRBV10_10 | 0.003 | 0.004 | 0.004 | 0.007 | 0.000 |
| TCRBV10_11 | 0.012 | 0.010 | 0.005 | 0.004 | 0.007 |
| TCRBV10_12 | 0.004 | 0.004 | 0.003 | 0.004 | 0.005 |
| TCRBV10_13 | 0.000 | 0.000 | 0.000 | -0.000 | 0.000 |
| TCRBV11_5 | -0.000 | -0.000 | -0.001 | 0.000 | -0.001 |

*FIG. 109B*

| | | | | | |
|---|---|---|---|---|---|
| TCRBV11_6 | -0.001 | -0.003 | -0.001 | 0.002 | 0.002 |
| TCRBV11_7 | -0.002 | -0.002 | -0.001 | 0.001 | 0.001 |
| TCRBV11_8 | 0.001 | -0.006 | -0.001 | 0.008 | 0.004 |
| TCRBV11_9 | 0.004 | 0.003 | -0.009 | -0.006 | -0.006 |
| TCRBV11_10 | 0.002 | 0.002 | 0.005 | 0.002 | 0.004 |
| TCRBV11_11 | 0.003 | 0.002 | 0.004 | -0.003 | 0.002 |
| TCRBV11_12 | 0.003 | 0.005 | 0.001 | -0.001 | 0.001 |
| TCRBV11_13 | 0.000 | 0.002 | 0.001 | -0.001 | 0.001 |
| TCRBV11_14 | 0.001 | 0.000 | 0.000 | -0.000 | 0.000 |
| TCRBV11_15 | 0.000 | 0.000 | 0.000 | -0.000 | 0.000 |
| TCRBV12_4 | -0.000 | 0.000 | -0.000 | 0.001 | -0.000 |
| TCRBV12_5 | -0.005 | 0.002 | 0.015 | -0.000 | 0.006 |
| TCRBV12_6 | -0.002 | 0.005 | 0.002 | 0.001 | 0.003 |
| TCRBV12_7 | -0.003 | 0.003 | 0.002 | 0.011 | -0.000 |
| TCRBV12_8 | -0.000 | 0.001 | -0.000 | 0.008 | 0.003 |
| TCRBV12_9 | -0.000 | -0.011 | -0.002 | -0.004 | 0.003 |
| TCRBV12_10 | 0.007 | 0.006 | -0.011 | -0.020 | -0.018 |
| TCRBV12_11 | 0.003 | -0.005 | -0.003 | 0.001 | 0.004 |
| TCRBV12_12 | 0.001 | -0.001 | -0.002 | 0.000 | 0.000 |
| TCRBV13_5 | 0.000 | 0.000 | 0.000 | 0.000 | 0.000 |
| TCRBV13_6 | 0.007 | 0.005 | -0.005 | -0.000 | -0.002 |
| TCRBV13_7 | 0.003 | -0.005 | -0.004 | 0.003 | -0.005 |
| TCRBV13_8 | -0.009 | -0.003 | 0.003 | 0.000 | 0.001 |
| TCRBV13_9 | -0.005 | 0.003 | 0.010 | 0.005 | 0.001 |
| TCRBV13_10 | 0.001 | -0.001 | -0.008 | -0.005 | 0.002 |
| TCRBV13_11 | 0.001 | 0.002 | 0.003 | -0.004 | 0.003 |
| TCRBV13_12 | 0.001 | 0.000 | 0.000 | 0.000 | 0.001 |
| TCRBV13_13 | -0.000 | -0.000 | -0.000 | 0.000 | -0.000 |
| TCRBV14_5 | 0.000 | 0.000 | 0.000 | -0.001 | 0.000 |
| TCRBV14_6 | -0.000 | -0.001 | 0.001 | -0.002 | -0.000 |
| TCRBV14_7 | 0.001 | -0.001 | -0.006 | -0.000 | 0.006 |
| TCRBV14_8 | 0.002 | 0.001 | -0.004 | -0.002 | -0.001 |
| TCRBV14_9 | -0.003 | -0.002 | 0.004 | 0.009 | -0.001 |
| TCRBV14_10 | -0.000 | 0.001 | 0.004 | -0.000 | 0.002 |
| TCRBV14_11 | 0.000 | 0.001 | 0.001 | -0.002 | -0.007 |
| TCRBV14_12 | -0.000 | 0.001 | 0.000 | -0.001 | 0.001 |
| TCRBV14_13 | -0.000 | 0.000 | 0.000 | -0.000 | 0.000 |
| TCRBV15_4 | 0.000 | 0.000 | 0.000 | 0.000 | 0.001 |
| TCRBV15_5 | -0.000 | 0.003 | -0.004 | 0.004 | -0.010 |
| TCRBV15_6 | -0.002 | 0.000 | 0.003 | 0.001 | 0.001 |
| TCRBV15_7 | -0.002 | -0.001 | 0.007 | 0.002 | -0.000 |
| TCRBV15_8 | 0.002 | -0.001 | 0.002 | 0.009 | 0.002 |
| TCRBV15_9 | 0.007 | 0.002 | -0.004 | -0.006 | 0.001 |
| TCRBV15_10 | 0.004 | 0.000 | -0.003 | -0.003 | 0.010 |
| TCRBV15_11 | 0.002 | -0.001 | -0.001 | -0.002 | 0.003 |
| TCRBV15_12 | 0.000 | -0.000 | -0.002 | -0.000 | 0.002 |
| TCRBV16_5 | -0.000 | -0.000 | 0.002 | -0.000 | -0.000 |
| TCRBV16_6 | -0.004 | -0.000 | 0.004 | -0.000 | -0.001 |
| TCRBV16_7 | -0.003 | -0.007 | -0.001 | -0.012 | -0.006 |
| TCRBV16_8 | 0.003 | -0.007 | -0.001 | 0.000 | 0.003 |
| TCRBV16_9 | 0.018 | -0.007 | -0.003 | 0.001 | 0.000 |
| TCRBV16_10 | 0.005 | 0.014 | 0.004 | 0.007 | 0.009 |
| TCRBV16_11 | 0.001 | 0.011 | 0.007 | 0.004 | -0.019 |
| TCRBV16_12 | 0.003 | -0.007 | -0.004 | 0.017 | 0.008 |
| TCRBV16_13 | -0.000 | 0.000 | -0.000 | 0.001 | -0.000 |
| TCRBV18_3 | 0.000 | -0.000 | 0.000 | 0.000 | 0.000 |
| TCRBV18_4 | 0.001 | -0.000 | 0.004 | 0.003 | -0.002 |
| TCRBV18_5 | 0.000 | -0.001 | 0.008 | 0.003 | -0.000 |
| TCRBV18_6 | 0.003 | -0.009 | 0.012 | 0.001 | -0.001 |
| TCRBV18_7 | -0.003 | -0.008 | 0.021 | -0.011 | -0.004 |
| TCRBV18_8 | 0.001 | -0.012 | -0.003 | -0.015 | 0.005 |
| TCRBV18_9 | -0.005 | 0.002 | -0.008 | -0.008 | 0.012 |
| TCRBV18_10 | -0.002 | 0.002 | 0.000 | 0.003 | 0.004 |
| TCRBV18_11 | -0.002 | 0.002 | -0.002 | 0.001 | 0.000 |

*FIG. 109C*

| | | | | | |
|---|---|---|---|---|---|
| TCRBV18_12 | 0.000 | 0.000 | -0.000 | 0.001 | 0.000 |
| TCRBV18_13 | 0.000 | 0.000 | 0.000 | -0.000 | 0.000 |
| TCRBV20_5 | 0.000 | 0.000 | -0.000 | -0.001 | -0.001 |
| TCRBV20_6 | -0.000 | -0.002 | -0.003 | -0.002 | -0.001 |
| TCRBV20_7 | 0.002 | -0.003 | 0.002 | 0.002 | -0.000 |
| TCRBV20_8 | 0.005 | 0.001 | -0.003 | 0.000 | -0.007 |
| TCRBV20_9 | -0.004 | -0.005 | -0.000 | -0.001 | 0.007 |
| TCRBV20_10 | 0.003 | 0.002 | 0.000 | 0.004 | 0.009 |
| TCRBV20_11 | 0.006 | 0.001 | 0.004 | -0.000 | 0.007 |
| TCRBV20_12 | 0.002 | 0.003 | 0.001 | -0.003 | 0.002 |
| TCRBV20_13 | -0.002 | 0.004 | -0.003 | 0.003 | -0.007 |
| TCRBV20_14 | 0.000 | 0.000 | 0.000 | 0.000 | 0.000 |
| | 11 | 12 | 13 | 14 | 15 |
| TCRBV01_6 | -0.000 | 0.001 | 0.000 | -0.000 | 0.001 |
| TCRBV01_7 | -0.003 | 0.001 | 0.002 | 0.002 | -0.000 |
| TCRBV01_8 | -0.007 | 0.002 | 0.004 | -0.001 | -0.012 |
| TCRBV01_9 | 0.001 | -0.003 | -0.016 | -0.001 | -0.007 |
| TCRBV01_10 | -0.005 | 0.005 | 0.024 | -0.006 | -0.001 |
| TCRBV01_11 | 0.004 | 0.004 | -0.004 | 0.011 | 0.008 |
| TCRBV01_12 | 0.006 | 0.003 | 0.003 | 0.005 | 0.003 |
| TCRBV01_13 | 0.000 | 0.000 | 0.000 | 0.001 | 0.001 |
| TCRBV01_14 | -0.000 | 0.000 | 0.000 | -0.000 | 0.000 |
| TCRBV02_6 | 0.001 | -0.001 | -0.001 | 0.000 | -0.002 |
| TCRBV02_7 | 0.001 | -0.005 | 0.001 | 0.001 | 0.004 |
| TCRBV02_8 | -0.006 | -0.001 | -0.005 | 0.002 | 0.002 |
| TCRBV02_9 | -0.006 | 0.002 | -0.004 | 0.001 | -0.003 |
| TCRBV02_10 | -0.002 | -0.000 | -0.001 | 0.006 | 0.002 |
| TCRBV02_11 | 0.003 | -0.006 | 0.001 | 0.004 | 0.005 |
| TCRBV02_12 | 0.001 | -0.001 | -0.002 | 0.003 | 0.003 |
| TCRBV02_13 | -0.000 | 0.000 | 0.001 | -0.000 | -0.001 |
| TCRBV03_4 | 0.000 | 0.000 | 0.000 | -0.000 | -0.000 |
| TCRBV03_5 | 0.000 | 0.001 | 0.000 | -0.000 | -0.000 |
| TCRBV03_6 | -0.001 | 0.004 | 0.004 | 0.000 | -0.000 |
| TCRBV03_7 | 0.003 | 0.005 | 0.003 | -0.001 | 0.007 |
| TCRBV03_8 | -0.002 | 0.012 | 0.002 | -0.010 | 0.009 |
| TCRBV03_9 | -0.004 | 0.012 | 0.005 | 0.000 | -0.001 |
| TCRBV03_10 | 0.000 | -0.007 | -0.001 | -0.011 | -0.006 |
| TCRBV03_11 | 0.010 | -0.009 | -0.004 | 0.015 | -0.007 |
| TCRBV03_12 | 0.000 | -0.001 | -0.002 | 0.008 | -0.002 |
| TCRBV03_13 | -0.012 | -0.004 | 0.007 | 0.011 | -0.005 |
| TCRBV04_6 | 0.000 | 0.000 | 0.000 | 0.000 | 0.000 |
| TCRBV04_7 | 0.001 | -0.000 | -0.001 | 0.001 | 0.002 |
| TCRBV04_8 | -0.001 | -0.001 | -0.003 | 0.004 | 0.001 |
| TCRBV04_9 | -0.006 | -0.005 | -0.007 | 0.002 | 0.009 |
| TCRBV04_10 | -0.002 | -0.000 | 0.003 | 0.007 | -0.002 |
| TCRBV04_11 | 0.007 | 0.004 | 0.003 | 0.008 | -0.004 |
| TCRBV04_12 | 0.005 | 0.003 | 0.003 | 0.003 | -0.005 |
| TCRBV04_13 | -0.002 | 0.002 | 0.009 | -0.021 | 0.009 |
| TCRBV04_14 | -0.002 | -0.004 | -0.005 | -0.003 | -0.010 |
| TCRBV04_15 | 0.001 | 0.001 | -0.001 | -0.000 | -0.000 |
| TCRBV051_5 | 0.000 | 0.000 | -0.001 | 0.000 | -0.000 |
| TCRBV051_6 | 0.005 | 0.002 | -0.001 | 0.001 | -0.002 |
| TCRBV051_7 | 0.001 | -0.006 | -0.002 | 0.005 | 0.001 |
| TCRBV051_8 | 0.005 | -0.004 | 0.009 | 0.000 | 0.011 |
| TCRBV051_9 | 0.004 | -0.007 | 0.010 | 0.010 | 0.001 |
| TCRBV051_10 | 0.006 | -0.015 | -0.002 | 0.001 | -0.004 |
| TCRBV051_11 | 0.007 | 0.005 | -0.005 | 0.002 | 0.011 |
| TCRBV051_12 | -0.001 | -0.006 | -0.002 | -0.002 | -0.005 |
| TCRBV051_13 | -0.000 | 0.000 | 0.000 | -0.000 | -0.000 |
| TCRBV052_6 | -0.000 | 0.000 | -0.002 | 0.001 | -0.001 |
| TCRBV052_7 | 0.004 | -0.003 | -0.004 | 0.006 | -0.005 |

*FIG. 109D*

| | | | | | |
|---|---|---|---|---|---|
| TCRBV052_8 | 0.013 | 0.001 | 0.003 | 0.003 | -0.008 |
| TCRBV052_9 | -0.006 | -0.008 | -0.014 | 0.014 | 0.012 |
| TCRBV052_10 | 0.014 | -0.010 | 0.008 | 0.002 | -0.001 |
| TCRBV052_11 | 0.004 | -0.008 | 0.010 | -0.005 | 0.012 |
| TCRBV052_12 | 0.000 | -0.002 | 0.005 | -0.003 | 0.004 |
| TCRBV052_13 | -0.000 | -0.000 | -0.001 | -0.000 | -0.001 |
| TCRBV06_5 | 0.000 | -0.000 | -0.000 | 0.000 | 0.000 |
| TCRBV06_6 | 0.004 | 0.004 | -0.003 | 0.002 | 0.001 |
| TCRBV06_7 | 0.002 | 0.002 | -0.002 | -0.002 | 0.003 |
| TCRBV06_8 | 0.001 | -0.002 | -0.000 | 0.002 | 0.000 |
| TCRBV06_9 | -0.003 | 0.013 | -0.003 | 0.002 | -0.010 |
| TCRBV06_10 | -0.004 | 0.002 | 0.006 | 0.006 | -0.003 |
| TCRBV06_11 | -0.003 | -0.006 | 0.006 | -0.002 | 0.003 |
| TCRBV06_12 | -0.001 | -0.002 | 0.009 | 0.004 | 0.002 |
| TCRBV06_13 | -0.001 | 0.000 | 0.001 | -0.000 | -0.002 |
| TCRBV07_5 | 0.000 | -0.000 | 0.000 | 0.000 | -0.000 |
| TCRBV07_6 | -0.000 | 0.003 | -0.001 | 0.009 | -0.003 |
| TCRBV07_7 | 0.000 | 0.011 | -0.011 | 0.013 | -0.017 |
| TCRBV07_8 | 0.003 | 0.003 | 0.005 | 0.006 | 0.001 |
| TCRBV07_9 | 0.017 | -0.006 | 0.017 | 0.008 | 0.008 |
| TCRBV07_10 | -0.012 | -0.010 | 0.002 | -0.013 | 0.003 |
| TCRBV07_11 | -0.007 | 0.006 | -0.003 | -0.008 | -0.000 |
| TCRBV07_12 | -0.006 | 0.003 | 0.004 | -0.005 | 0.001 |
| TCRBV07_13 | -0.001 | 0.001 | 0.000 | -0.000 | -0.000 |
| TCRBV081_5 | 0.001 | 0.001 | -0.000 | 0.000 | -0.000 |
| TCRBV081_6 | 0.001 | -0.000 | -0.006 | 0.004 | -0.001 |
| TCRBV081_7 | -0.004 | -0.003 | -0.009 | 0.003 | -0.005 |
| TCRBV081_8 | 0.002 | 0.005 | -0.005 | 0.004 | -0.007 |
| TCRBV081_9 | 0.014 | -0.013 | 0.016 | -0.011 | -0.018 |
| TCRBV081_10 | -0.008 | 0.009 | 0.001 | 0.001 | 0.013 |
| TCRBV081_11 | -0.004 | 0.003 | -0.000 | 0.000 | 0.012 |
| TCRBV081_12 | -0.001 | -0.001 | 0.003 | -0.001 | 0.006 |
| TCRBV082_4 | 0.002 | 0.001 | -0.002 | -0.001 | 0.000 |
| TCRBV082_5 | 0.005 | 0.001 | -0.004 | 0.001 | 0.003 |
| TCRBV082_6 | 0.002 | 0.002 | -0.002 | 0.002 | 0.001 |
| TCRBV082_7 | 0.007 | 0.004 | -0.007 | -0.000 | 0.002 |
| TCRBV082_8 | -0.005 | 0.003 | 0.004 | 0.002 | -0.001 |
| TCRBV082_9 | -0.006 | -0.006 | 0.006 | -0.002 | -0.006 |
| TCRBV082_10 | -0.003 | -0.002 | 0.005 | -0.001 | 0.000 |
| TCRBV082_11 | -0.001 | -0.002 | -0.001 | -0.001 | 0.001 |
| TCRBV083_4 | -0.001 | -0.000 | 0.000 | 0.001 | -0.000 |
| TCRBV083_5 | -0.001 | -0.000 | 0.002 | -0.001 | 0.000 |
| TCRBV083_6 | 0.001 | -0.000 | -0.000 | 0.003 | -0.002 |
| TCRBV083_7 | -0.005 | -0.011 | -0.004 | -0.004 | -0.003 |
| TCRBV083_8 | -0.002 | -0.005 | -0.002 | -0.003 | 0.004 |
| TCRBV083_9 | 0.003 | 0.008 | 0.006 | 0.006 | 0.002 |
| TCRBV083_10 | 0.002 | 0.005 | 0.005 | 0.005 | -0.003 |
| TCRBV083_11 | 0.003 | 0.005 | -0.007 | -0.003 | 0.003 |
| TCRBV083_12 | -0.001 | -0.002 | 0.001 | -0.004 | -0.001 |
| TCRBV09_5 | 0.001 | 0.001 | -0.000 | 0.000 | -0.001 |
| TCRBV09_6 | -0.001 | 0.001 | 0.001 | 0.001 | -0.001 |
| TCRBV09_7 | -0.003 | -0.003 | 0.002 | 0.001 | -0.001 |
| TCRBV09_8 | 0.012 | 0.007 | -0.026 | -0.001 | -0.001 |
| TCRBV09_9 | -0.021 | -0.014 | 0.010 | 0.016 | -0.004 |
| TCRBV09_10 | 0.009 | -0.002 | 0.013 | 0.013 | -0.006 |
| TCRBV09_11 | -0.007 | -0.002 | -0.002 | 0.011 | 0.011 |
| TCRBV09_12 | 0.003 | -0.002 | 0.003 | -0.008 | -0.001 |
| TCRBV09_13 | 0.001 | 0.001 | -0.001 | -0.002 | 0.000 |
| TCRBV09_14 | 0.001 | 0.001 | -0.001 | -0.000 | 0.000 |
| TCRBV09_15 | 0.000 | 0.000 | -0.000 | -0.000 | 0.000 |
| TCRBV10_6 | -0.000 | 0.002 | -0.004 | 0.005 | 0.001 |
| TCRBV10_7 | -0.005 | 0.000 | -0.002 | 0.001 | -0.001 |
| TCRBV10_8 | 0.002 | 0.001 | -0.000 | 0.004 | -0.002 |
| TCRBV10_9 | -0.010 | -0.011 | -0.003 | 0.001 | 0.008 |

*FIG. 110A*

| | | | | | |
|---|---|---|---|---|---|
| TCRBV10_10 | 0.008 | 0.003 | 0.002 | -0.011 | 0.005 |
| TCRBV10_11 | 0.004 | 0.007 | 0.002 | -0.000 | -0.012 |
| TCRBV10_12 | 0.001 | -0.001 | 0.005 | -0.000 | 0.002 |
| TCRBV10_13 | 0.000 | 0.000 | 0.000 | -0.000 | -0.000 |
| TCRBV11_5 | -0.001 | -0.000 | 0.000 | 0.002 | 0.001 |
| TCRBV11_6 | 0.002 | -0.002 | 0.003 | 0.001 | 0.002 |
| TCRBV11_7 | -0.005 | -0.004 | -0.003 | 0.001 | -0.004 |
| TCRBV11_8 | -0.003 | -0.001 | -0.003 | 0.005 | -0.002 |
| TCRBV11_9 | -0.003 | 0.000 | 0.001 | -0.013 | 0.007 |
| TCRBV11_10 | 0.003 | 0.006 | 0.002 | 0.005 | -0.004 |
| TCRBV11_11 | -0.000 | 0.005 | 0.007 | 0.005 | 0.001 |
| TCRBV11_12 | 0.001 | 0.004 | 0.003 | 0.007 | -0.006 |
| TCRBV11_13 | 0.000 | 0.003 | 0.002 | -0.001 | -0.001 |
| TCRBV11_14 | 0.001 | 0.001 | 0.001 | -0.001 | -0.000 |
| TCRBV11_15 | 0.000 | 0.000 | 0.000 | -0.000 | -0.000 |
| TCRBV12_4 | -0.000 | 0.000 | -0.000 | -0.002 | 0.001 |
| TCRBV12_5 | -0.010 | -0.001 | -0.000 | 0.003 | 0.003 |
| TCRBV12_6 | -0.007 | -0.009 | -0.000 | -0.012 | 0.009 |
| TCRBV12_7 | -0.005 | -0.006 | 0.000 | 0.005 | 0.001 |
| TCRBV12_8 | -0.001 | -0.004 | 0.003 | 0.005 | -0.007 |
| TCRBV12_9 | 0.005 | 0.006 | -0.003 | 0.004 | 0.004 |
| TCRBV12_10 | 0.014 | 0.012 | 0.006 | -0.003 | -0.009 |
| TCRBV12_11 | 0.002 | 0.002 | -0.003 | -0.000 | -0.004 |
| TCRBV12_12 | 0.001 | 0.000 | -0.002 | 0.000 | 0.001 |
| TCRBV13_5 | 0.000 | 0.001 | 0.000 | -0.000 | -0.001 |
| TCRBV13_6 | -0.003 | 0.001 | -0.002 | -0.003 | -0.016 |
| TCRBV13_7 | -0.004 | 0.008 | 0.004 | 0.005 | -0.004 |
| TCRBV13_8 | -0.005 | 0.007 | 0.008 | 0.009 | -0.002 |
| TCRBV13_9 | -0.007 | 0.005 | -0.003 | -0.014 | 0.003 |
| TCRBV13_10 | 0.011 | -0.016 | -0.005 | -0.005 | 0.012 |
| TCRBV13_11 | 0.007 | -0.003 | -0.007 | 0.007 | 0.008 |
| TCRBV13_12 | 0.002 | -0.002 | 0.002 | 0.002 | 0.000 |
| TCRBV13_13 | 0.000 | -0.001 | 0.002 | -0.000 | -0.001 |
| TCRBV14_5 | -0.000 | -0.000 | -0.002 | 0.001 | 0.000 |
| TCRBV14_6 | 0.000 | -0.003 | 0.001 | -0.004 | 0.000 |
| TCRBV14_7 | -0.001 | -0.002 | -0.001 | 0.007 | 0.001 |
| TCRBV14_8 | -0.002 | 0.004 | 0.006 | 0.008 | -0.007 |
| TCRBV14_9 | 0.004 | -0.003 | -0.008 | -0.004 | 0.001 |
| TCRBV14_10 | -0.002 | -0.005 | 0.002 | -0.005 | 0.003 |
| TCRBV14_11 | 0.002 | 0.006 | 0.000 | 0.000 | 0.001 |
| TCRBV14_12 | 0.001 | 0.002 | 0.001 | -0.002 | 0.001 |
| TCRBV14_13 | -0.000 | 0.001 | 0.000 | -0.001 | -0.000 |
| TCRBV15_4 | 0.000 | -0.000 | 0.001 | 0.000 | 0.000 |
| TCRBV15_5 | -0.009 | 0.004 | 0.001 | 0.015 | 0.009 |
| TCRBV15_6 | 0.000 | 0.005 | 0.001 | -0.002 | -0.004 |
| TCRBV15_7 | 0.007 | -0.002 | -0.002 | 0.005 | -0.005 |
| TCRBV15_8 | 0.009 | -0.000 | -0.007 | -0.004 | -0.002 |
| TCRBV15_9 | -0.007 | -0.012 | 0.003 | -0.013 | -0.017 |
| TCRBV15_10 | -0.001 | 0.011 | 0.010 | 0.007 | 0.008 |
| TCRBV15_11 | -0.002 | 0.005 | 0.005 | 0.003 | 0.003 |
| TCRBV15_12 | -0.001 | 0.001 | 0.001 | 0.001 | 0.002 |
| TCRBV16_5 | -0.000 | 0.000 | 0.000 | 0.001 | -0.001 |
| TCRBV16_6 | -0.004 | 0.001 | -0.000 | 0.010 | 0.005 |
| TCRBV16_7 | 0.007 | 0.003 | 0.014 | -0.008 | 0.001 |
| TCRBV16_8 | -0.001 | -0.007 | 0.003 | 0.004 | -0.009 |
| TCRBV16_9 | -0.003 | -0.010 | -0.013 | 0.002 | -0.009 |
| TCRBV16_10 | 0.006 | -0.009 | 0.012 | 0.011 | 0.012 |
| TCRBV16_11 | 0.017 | -0.005 | -0.011 | 0.007 | 0.013 |
| TCRBV16_12 | 0.002 | 0.010 | 0.013 | 0.002 | -0.006 |
| TCRBV16_13 | -0.000 | -0.000 | 0.001 | -0.001 | -0.000 |
| TCRBV18_3 | 0.000 | -0.000 | 0.000 | -0.000 | 0.000 |
| TCRBV18_4 | 0.002 | -0.000 | 0.002 | 0.002 | 0.002 |
| TCRBV18_5 | 0.003 | -0.002 | 0.003 | 0.002 | 0.004 |
| TCRBV18_6 | 0.006 | -0.002 | 0.007 | 0.010 | 0.014 |

*FIG. 110B*

|  |  |  |  |  |  |
|---|---|---|---|---|---|
| TCRBV18_7 | -0.004 | 0.008 | 0.003 | -0.004 | -0.001 |
| TCRBV18_8 | 0.002 | -0.001 | -0.005 | -0.009 | 0.025 |
| TCRBV18_9 | 0.004 | 0.002 | -0.009 | -0.001 | 0.005 |
| TCRBV18_10 | 0.002 | -0.002 | -0.002 | -0.002 | 0.008 |
| TCRBV18_11 | -0.006 | 0.006 | -0.000 | -0.001 | 0.001 |
| TCRBV18_12 | -0.000 | 0.001 | 0.000 | -0.002 | 0.000 |
| TCRBV18_13 | 0.000 | 0.000 | -0.000 | -0.000 | 0.000 |
| TCRBV20_5 | -0.001 | -0.002 | -0.000 | -0.001 | 0.001 |
| TCRBV20_6 | -0.001 | 0.000 | 0.002 | 0.001 | 0.001 |
| TCRBV20_7 | 0.003 | 0.005 | -0.002 | -0.000 | -0.004 |
| TCRBV20_8 | -0.005 | 0.012 | -0.004 | -0.001 | -0.005 |
| TCRBV20_9 | 0.004 | 0.011 | -0.000 | -0.013 | 0.001 |
| TCRBV20_10 | 0.006 | 0.003 | 0.009 | 0.000 | 0.010 |
| TCRBV20_11 | 0.000 | -0.015 | 0.000 | 0.003 | -0.016 |
| TCRBV20_12 | 0.003 | -0.005 | 0.007 | 0.006 | -0.005 |
| TCRBV20_13 | -0.015 | 0.004 | 0.000 | 0.016 | 0.011 |
| TCRBV20_14 | 0.000 | -0.000 | 0.001 | 0.000 | 0.000 |
|  | 16 | 17 | 18 | 19 | 20 |
| TCRBV01_6 | 0.001 | -0.001 | 0.001 | 0.000 | -0.001 |
| TCRBV01_7 | -0.000 | -0.007 | 0.006 | 0.004 | -0.005 |
| TCRBV01_8 | -0.008 | -0.004 | 0.005 | 0.005 | 0.002 |
| TCRBV01_9 | 0.006 | -0.015 | 0.012 | 0.014 | 0.011 |
| TCRBV01_10 | 0.010 | 0.019 | -0.001 | -0.004 | -0.003 |
| TCRBV01_11 | -0.003 | 0.004 | 0.001 | -0.008 | -0.003 |
| TCRBV01_12 | -0.003 | -0.000 | -0.009 | -0.009 | 0.001 |
| TCRBV01_13 | 0.001 | 0.003 | -0.003 | -0.004 | 0.002 |
| TCRBV01_14 | 0.000 | 0.000 | -0.000 | -0.000 | 0.001 |
| TCRBV02_6 | 0.001 | -0.004 | 0.001 | 0.001 | -0.004 |
| TCRBV02_7 | 0.001 | -0.001 | -0.000 | -0.004 | 0.004 |
| TCRBV02_8 | 0.007 | -0.005 | 0.008 | -0.008 | 0.003 |
| TCRBV02_9 | 0.007 | -0.005 | 0.001 | -0.026 | -0.001 |
| TCRBV02_10 | 0.004 | -0.003 | 0.010 | -0.020 | 0.011 |
| TCRBV02_11 | 0.004 | -0.001 | 0.001 | -0.008 | 0.007 |
| TCRBV02_12 | 0.000 | -0.001 | -0.002 | 0.001 | 0.009 |
| TCRBV02_13 | -0.001 | 0.000 | -0.001 | -0.001 | 0.000 |
| TCRBV03_4 | -0.001 | 0.000 | -0.000 | 0.002 | -0.001 |
| TCRBV03_5 | 0.000 | 0.001 | -0.000 | 0.002 | -0.001 |
| TCRBV03_6 | -0.000 | -0.008 | 0.006 | 0.002 | 0.007 |
| TCRBV03_7 | -0.002 | -0.008 | 0.000 | 0.005 | 0.004 |
| TCRBV03_8 | -0.010 | -0.005 | -0.003 | -0.001 | -0.002 |
| TCRBV03_9 | 0.005 | 0.003 | 0.010 | -0.002 | -0.003 |
| TCRBV03_10 | 0.009 | 0.006 | -0.013 | -0.019 | -0.006 |
| TCRBV03_11 | -0.005 | 0.005 | 0.008 | 0.006 | 0.008 |
| TCRBV03_12 | -0.000 | 0.005 | 0.003 | -0.013 | -0.001 |
| TCRBV03_13 | 0.006 | -0.000 | 0.001 | 0.016 | 0.002 |
| TCRBV04_6 | -0.000 | -0.000 | 0.000 | 0.000 | -0.000 |
| TCRBV04_7 | 0.001 | -0.000 | -0.002 | -0.000 | 0.007 |
| TCRBV04_8 | 0.004 | 0.005 | -0.001 | 0.003 | 0.007 |
| TCRBV04_9 | 0.013 | -0.005 | -0.005 | 0.008 | 0.008 |
| TCRBV04_10 | 0.011 | 0.014 | -0.015 | 0.005 | 0.006 |
| TCRBV04_11 | -0.007 | -0.022 | 0.003 | -0.003 | -0.014 |
| TCRBV04_12 | 0.002 | -0.009 | 0.008 | -0.000 | -0.012 |
| TCRBV04_13 | -0.015 | 0.007 | 0.007 | -0.010 | -0.012 |
| TCRBV04_14 | -0.009 | 0.000 | 0.002 | -0.003 | 0.010 |
| TCRBV04_15 | 0.001 | -0.000 | 0.003 | -0.000 | 0.001 |
| TCRBV051_5 | 0.000 | 0.001 | 0.000 | 0.000 | -0.000 |
| TCRBV051_6 | -0.001 | 0.003 | -0.002 | 0.003 | -0.004 |
| TCRBV051_7 | 0.004 | 0.005 | -0.002 | 0.005 | -0.024 |
| TCRBV051_8 | -0.005 | -0.014 | -0.009 | 0.002 | 0.001 |
| TCRBV051_9 | 0.004 | 0.021 | -0.012 | 0.003 | 0.006 |
| TCRBV051_10 | 0.011 | 0.002 | -0.005 | 0.014 | 0.006 |

*FIG. 110C*

| | | | | | |
|---|---|---|---|---|---|
| TCRBV051_11 | 0.001 | -0.013 | -0.014 | -0.004 | 0.006 |
| TCRBV051_12 | -0.002 | -0.003 | 0.004 | 0.004 | 0.011 |
| TCRBV051_13 | 0.001 | 0.000 | 0.001 | 0.000 | 0.001 |
| TCRBV052_6 | -0.000 | -0.001 | 0.000 | 0.003 | -0.004 |
| TCRBV052_7 | 0.004 | 0.004 | 0.004 | 0.003 | -0.012 |
| TCRBV052_8 | 0.010 | 0.002 | -0.029 | 0.013 | 0.016 |
| TCRBV052_9 | 0.003 | 0.021 | -0.007 | -0.006 | -0.017 |
| TCRBV052_10 | 0.003 | 0.002 | 0.002 | 0.009 | 0.005 |
| TCRBV052_11 | -0.001 | -0.021 | -0.007 | 0.004 | 0.010 |
| TCRBV052_12 | -0.006 | -0.005 | -0.002 | 0.001 | 0.007 |
| TCRBV052_13 | 0.000 | -0.001 | 0.000 | 0.001 | -0.001 |
| TCRBV06_5 | 0.000 | 0.000 | -0.000 | 0.000 | 0.000 |
| TCRBV06_6 | 0.002 | -0.003 | -0.002 | 0.001 | 0.003 |
| TCRBV06_7 | -0.001 | -0.002 | 0.001 | 0.001 | -0.002 |
| TCRBV06_8 | 0.008 | -0.008 | 0.004 | 0.019 | 0.002 |
| TCRBV06_9 | 0.001 | 0.005 | -0.011 | -0.000 | 0.002 |
| TCRBV06_10 | 0.006 | 0.001 | -0.000 | -0.003 | -0.005 |
| TCRBV06_11 | -0.012 | 0.005 | 0.017 | -0.008 | -0.000 |
| TCRBV06_12 | -0.002 | 0.004 | 0.001 | -0.009 | 0.007 |
| TCRBV06_13 | 0.001 | -0.003 | 0.002 | -0.003 | -0.002 |
| TCRBV07_5 | 0.000 | -0.000 | 0.000 | 0.000 | -0.000 |
| TCRBV07_6 | -0.002 | 0.002 | -0.003 | 0.001 | -0.004 |
| TCRBV07_7 | -0.005 | -0.000 | -0.009 | -0.005 | -0.012 |
| TCRBV07_8 | -0.005 | 0.005 | 0.000 | -0.003 | -0.008 |
| TCRBV07_9 | -0.016 | 0.006 | 0.013 | 0.007 | 0.007 |
| TCRBV07_10 | 0.017 | -0.003 | 0.001 | 0.002 | -0.000 |
| TCRBV07_11 | 0.004 | -0.009 | 0.006 | -0.003 | 0.016 |
| TCRBV07_12 | 0.009 | -0.001 | 0.001 | -0.001 | 0.008 |
| TCRBV07_13 | 0.001 | -0.000 | 0.001 | -0.000 | -0.000 |
| TCRBV081_5 | 0.000 | 0.001 | -0.001 | 0.000 | 0.000 |
| TCRBV081_6 | -0.004 | 0.003 | 0.002 | 0.000 | -0.004 |
| TCRBV081_7 | -0.004 | 0.006 | -0.000 | 0.005 | -0.007 |
| TCRBV081_8 | -0.014 | 0.001 | -0.005 | 0.001 | -0.008 |
| TCRBV081_9 | 0.001 | 0.004 | 0.006 | -0.012 | 0.009 |
| TCRBV081_10 | 0.017 | -0.016 | -0.004 | -0.002 | 0.008 |
| TCRBV081_11 | 0.003 | -0.001 | 0.001 | 0.006 | -0.000 |
| TCRBV081_12 | 0.002 | 0.002 | 0.000 | 0.002 | 0.001 |
| TCRBV082_4 | 0.000 | 0.001 | 0.003 | 0.002 | 0.002 |
| TCRBV082_5 | 0.004 | 0.003 | 0.005 | 0.002 | 0.000 |
| TCRBV082_6 | 0.001 | 0.005 | 0.003 | -0.003 | 0.004 |
| TCRBV082_7 | 0.005 | 0.006 | 0.008 | -0.011 | 0.008 |
| TCRBV082_8 | 0.002 | -0.007 | -0.003 | 0.002 | 0.000 |
| TCRBV082_9 | -0.006 | -0.006 | -0.007 | 0.002 | -0.006 |
| TCRBV082_10 | -0.004 | -0.004 | -0.006 | 0.004 | -0.007 |
| TCRBV082_11 | -0.001 | 0.002 | -0.002 | 0.001 | -0.002 |
| TCRBV083_4 | 0.000 | -0.000 | 0.000 | 0.001 | 0.000 |
| TCRBV083_5 | 0.001 | -0.000 | -0.001 | -0.001 | 0.001 |
| TCRBV083_6 | -0.001 | -0.002 | 0.004 | -0.002 | -0.000 |
| TCRBV083_7 | 0.012 | -0.002 | 0.004 | 0.004 | 0.001 |
| TCRBV083_8 | 0.010 | 0.004 | 0.004 | 0.004 | -0.015 |
| TCRBV083_9 | -0.009 | -0.003 | -0.001 | 0.004 | 0.012 |
| TCRBV083_10 | -0.002 | 0.001 | 0.002 | 0.006 | 0.003 |
| TCRBV083_11 | -0.010 | 0.001 | -0.004 | -0.012 | -0.001 |
| TCRBV083_12 | -0.002 | 0.001 | -0.008 | -0.004 | -0.000 |
| TCRBV09_5 | -0.000 | -0.000 | -0.001 | -0.000 | -0.000 |
| TCRBV09_6 | -0.000 | -0.000 | 0.002 | -0.002 | -0.003 |
| TCRBV09_7 | -0.002 | 0.000 | 0.006 | -0.006 | -0.006 |
| TCRBV09_8 | 0.006 | 0.003 | 0.009 | -0.013 | 0.019 |
| TCRBV09_9 | 0.000 | -0.011 | 0.009 | -0.001 | -0.020 |
| TCRBV09_10 | 0.001 | -0.017 | -0.003 | -0.019 | -0.005 |
| TCRBV09_11 | 0.001 | 0.001 | 0.023 | 0.002 | 0.001 |
| TCRBV09_12 | 0.000 | -0.003 | 0.008 | -0.004 | 0.001 |
| TCRBV09_13 | 0.003 | 0.001 | 0.002 | -0.001 | 0.000 |
| TCRBV09_14 | 0.002 | 0.001 | 0.001 | 0.000 | 0.001 |

*FIG. 110D*

| | | | | | |
|---|---|---|---|---|---|
| TCRBV09_15 | 0.000 | 0.001 | 0.000 | -0.000 | 0.000 |
| TCRBV10_6 | -0.000 | 0.000 | 0.001 | -0.006 | -0.005 |
| TCRBV10_7 | 0.002 | -0.004 | -0.008 | -0.018 | -0.006 |
| TCRBV10_8 | 0.010 | -0.006 | -0.005 | -0.011 | 0.004 |
| TCRBV10_9 | 0.001 | -0.006 | 0.003 | 0.010 | 0.003 |
| TCRBV10_10 | -0.006 | 0.002 | 0.007 | 0.004 | 0.012 |
| TCRBV10_11 | -0.002 | 0.009 | 0.001 | 0.017 | -0.007 |
| TCRBV10_12 | -0.005 | 0.005 | 0.001 | 0.004 | -0.000 |
| TCRBV10_13 | -0.000 | 0.000 | -0.000 | 0.001 | -0.000 |
| TCRBV11_5 | -0.001 | 0.001 | -0.000 | -0.000 | 0.001 |
| TCRBV11_6 | -0.003 | -0.007 | 0.005 | 0.001 | 0.002 |
| TCRBV11_7 | -0.001 | -0.007 | 0.005 | -0.001 | 0.004 |
| TCRBV11_8 | -0.000 | -0.007 | 0.002 | -0.005 | -0.000 |
| TCRBV11_9 | 0.008 | 0.001 | -0.001 | 0.000 | -0.001 |
| TCRBV11_10 | 0.003 | 0.003 | -0.001 | -0.003 | 0.006 |
| TCRBV11_11 | 0.001 | 0.007 | 0.001 | -0.004 | 0.003 |
| TCRBV11_12 | 0.000 | 0.004 | 0.002 | 0.002 | -0.002 |
| TCRBV11_13 | -0.002 | 0.003 | 0.001 | 0.004 | -0.004 |
| TCRBV11_14 | -0.001 | 0.001 | -0.001 | 0.004 | -0.002 |
| TCRBV11_15 | -0.000 | 0.000 | -0.000 | 0.001 | -0.001 |
| TCRBV12_4 | -0.002 | 0.001 | -0.002 | -0.002 | -0.002 |
| TCRBV12_5 | -0.009 | 0.002 | -0.005 | -0.002 | -0.005 |
| TCRBV12_6 | 0.005 | 0.006 | -0.006 | 0.001 | -0.004 |
| TCRBV12_7 | -0.011 | 0.003 | -0.009 | 0.001 | 0.017 |
| TCRBV12_8 | 0.010 | -0.007 | -0.001 | -0.007 | 0.001 |
| TCRBV12_9 | -0.001 | 0.000 | 0.010 | -0.000 | -0.013 |
| TCRBV12_10 | 0.002 | -0.003 | 0.003 | -0.002 | 0.002 |
| TCRBV12_11 | 0.005 | 0.000 | 0.007 | 0.006 | 0.001 |
| TCRBV12_12 | 0.001 | -0.001 | 0.003 | 0.006 | 0.002 |
| TCRBV13_5 | -0.001 | 0.001 | -0.001 | 0.003 | -0.002 |
| TCRBV13_6 | 0.002 | -0.001 | 0.003 | 0.010 | -0.000 |
| TCRBV13_7 | 0.003 | -0.006 | 0.003 | -0.004 | 0.020 |
| TCRBV13_8 | -0.002 | -0.003 | 0.005 | 0.009 | 0.009 |
| TCRBV13_9 | -0.001 | 0.002 | -0.008 | 0.003 | 0.001 |
| TCRBV13_10 | 0.005 | 0.006 | 0.002 | 0.005 | -0.015 |
| TCRBV13_11 | -0.005 | 0.000 | -0.001 | -0.018 | -0.012 |
| TCRBV13_12 | 0.001 | 0.003 | -0.003 | -0.007 | -0.002 |
| TCRBV13_13 | -0.001 | -0.001 | 0.001 | 0.000 | 0.001 |
| TCRBV14_5 | -0.002 | -0.000 | 0.001 | -0.002 | -0.000 |
| TCRBV14_6 | 0.006 | -0.000 | -0.001 | -0.002 | -0.008 |
| TCRBV14_7 | -0.005 | -0.003 | 0.008 | 0.005 | 0.001 |
| TCRBV14_8 | 0.002 | -0.004 | -0.001 | -0.003 | -0.008 |
| TCRBV14_9 | 0.016 | 0.000 | -0.003 | -0.000 | 0.017 |
| TCRBV14_10 | -0.008 | 0.006 | -0.004 | -0.004 | -0.007 |
| TCRBV14_11 | -0.007 | 0.001 | 0.003 | 0.004 | 0.007 |
| TCRBV14_12 | -0.002 | -0.001 | -0.002 | 0.001 | -0.001 |
| TCRBV14_13 | -0.001 | 0.000 | 0.000 | 0.001 | -0.001 |
| TCRBV15_4 | -0.001 | 0.000 | -0.000 | -0.000 | 0.000 |
| TCRBV15_5 | -0.012 | 0.006 | -0.005 | 0.005 | 0.018 |
| TCRBV15_6 | -0.002 | -0.006 | 0.001 | 0.001 | -0.007 |
| TCRBV15_7 | -0.002 | -0.009 | 0.005 | 0.008 | -0.010 |
| TCRBV15_8 | 0.004 | -0.006 | -0.002 | -0.004 | -0.022 |
| TCRBV15_9 | -0.013 | 0.001 | 0.007 | -0.010 | 0.021 |
| TCRBV15_10 | 0.019 | 0.005 | 0.002 | -0.005 | 0.001 |
| TCRBV15_11 | 0.008 | 0.006 | 0.001 | -0.000 | 0.003 |
| TCRBV15_12 | 0.003 | 0.001 | 0.003 | 0.003 | 0.002 |
| TCRBV16_5 | 0.001 | -0.000 | 0.002 | 0.001 | -0.001 |
| TCRBV16_6 | -0.002 | -0.001 | -0.003 | 0.007 | 0.010 |
| TCRBV16_7 | -0.000 | 0.007 | 0.003 | 0.006 | -0.001 |
| TCRBV16_8 | 0.001 | 0.014 | -0.004 | -0.007 | 0.005 |
| TCRBV16_9 | -0.018 | -0.012 | -0.003 | 0.003 | 0.004 |
| TCRBV16_10 | 0.013 | -0.013 | -0.006 | 0.001 | -0.005 |
| TCRBV16_11 | 0.015 | 0.005 | 0.001 | -0.003 | 0.005 |
| TCRBV16_12 | 0.006 | 0.003 | -0.017 | 0.018 | -0.007 |

*FIG. 111A*

| | | | | | |
|---|---|---|---|---|---|
| TCRBV16_13 | 0.000 | -0.002 | -0.001 | -0.001 | -0.001 |
| TCRBV18_3 | 0.000 | 0.000 | 0.000 | 0.000 | 0.000 |
| TCRBV18_4 | -0.003 | 0.001 | 0.009 | -0.005 | -0.001 |
| TCRBV18_5 | -0.001 | 0.004 | 0.018 | -0.006 | -0.001 |
| TCRBV18_6 | 0.001 | 0.006 | 0.031 | 0.006 | 0.006 |
| TCRBV18_7 | 0.001 | 0.019 | 0.003 | -0.015 | 0.010 |
| TCRBV18_8 | -0.019 | -0.003 | -0.010 | 0.005 | 0.008 |
| TCRBV18_9 | -0.023 | 0.006 | -0.004 | 0.016 | -0.004 |
| TCRBV18_10 | -0.008 | 0.011 | -0.011 | 0.011 | -0.010 |
| TCRBV18_11 | -0.003 | 0.008 | -0.003 | 0.004 | -0.002 |
| TCRBV18_12 | -0.002 | 0.001 | -0.001 | 0.001 | -0.001 |
| TCRBV18_13 | 0.000 | 0.001 | 0.000 | 0.000 | 0.000 |
| TCRBV20_5 | 0.001 | 0.000 | 0.001 | 0.000 | -0.002 |
| TCRBV20_6 | 0.002 | -0.007 | 0.001 | 0.004 | -0.002 |
| TCRBV20_7 | 0.009 | -0.006 | -0.001 | 0.009 | -0.003 |
| TCRBV20_8 | 0.007 | 0.001 | 0.012 | 0.019 | -0.003 |
| TCRBV20_9 | 0.007 | 0.008 | 0.022 | 0.003 | -0.009 |
| TCRBV20_10 | -0.005 | -0.018 | -0.016 | -0.017 | -0.004 |
| TCRBV20_11 | -0.007 | 0.004 | -0.005 | -0.008 | 0.012 |
| TCRBV20_12 | 0.001 | 0.006 | -0.001 | -0.006 | 0.002 |
| TCRBV20_13 | -0.012 | 0.009 | -0.002 | -0.006 | 0.015 |
| TCRBV20_14 | -0.000 | 0.000 | -0.000 | -0.000 | 0.000 |
| | 21 | 22 | 23 | 24 | 25 |
| TCRBV01_6 | 0.002 | 0.001 | 0.001 | 0.000 | 0.004 |
| TCRBV01_7 | -0.000 | 0.003 | 0.001 | 0.013 | -0.004 |
| TCRBV01_8 | -0.006 | 0.008 | -0.007 | 0.009 | 0.013 |
| TCRBV01_9 | 0.009 | -0.012 | -0.017 | 0.007 | 0.004 |
| TCRBV01_10 | 0.019 | 0.017 | -0.004 | -0.026 | -0.018 |
| TCRBV01_11 | 0.002 | -0.012 | 0.009 | 0.008 | 0.001 |
| TCRBV01_12 | -0.007 | -0.002 | 0.015 | 0.013 | 0.002 |
| TCRBV01_13 | -0.000 | -0.002 | 0.005 | -0.001 | 0.003 |
| TCRBV01_14 | 0.000 | -0.000 | 0.000 | -0.000 | -0.000 |
| TCRBV02_6 | -0.002 | -0.002 | -0.001 | -0.003 | -0.001 |
| TCRBV02_7 | -0.003 | -0.008 | 0.008 | -0.003 | 0.004 |
| TCRBV02_8 | -0.008 | -0.002 | 0.005 | -0.008 | 0.002 |
| TCRBV02_9 | -0.010 | -0.020 | 0.015 | -0.009 | -0.004 |
| TCRBV02_10 | -0.003 | -0.004 | 0.011 | -0.021 | -0.001 |
| TCRBV02_11 | -0.007 | 0.003 | 0.005 | -0.007 | -0.008 |
| TCRBV02_12 | -0.002 | 0.003 | 0.003 | -0.004 | -0.003 |
| TCRBV02_13 | -0.001 | 0.001 | -0.001 | -0.001 | 0.002 |
| TCRBV03_4 | 0.001 | 0.001 | -0.001 | 0.001 | 0.000 |
| TCRBV03_5 | 0.003 | 0.001 | -0.001 | 0.002 | 0.001 |
| TCRBV03_6 | 0.009 | 0.007 | 0.008 | 0.001 | 0.008 |
| TCRBV03_7 | 0.004 | 0.002 | 0.014 | -0.002 | -0.001 |
| TCRBV03_8 | 0.006 | 0.002 | 0.012 | -0.005 | 0.011 |
| TCRBV03_9 | 0.012 | -0.002 | -0.004 | 0.006 | -0.003 |
| TCRBV03_10 | -0.023 | -0.008 | -0.022 | 0.011 | 0.009 |
| TCRBV03_11 | 0.002 | 0.001 | -0.002 | 0.004 | -0.022 |
| TCRBV03_12 | 0.008 | 0.000 | -0.012 | -0.006 | -0.006 |
| TCRBV03_13 | -0.002 | -0.002 | 0.012 | 0.010 | 0.006 |
| TCRBV04_6 | -0.000 | 0.000 | 0.000 | -0.001 | -0.001 |
| TCRBV04_7 | 0.001 | 0.001 | 0.001 | 0.007 | -0.001 |
| TCRBV04_8 | 0.002 | 0.002 | 0.006 | 0.007 | 0.002 |
| TCRBV04_9 | -0.004 | -0.006 | 0.004 | 0.016 | 0.007 |
| TCRBV04_10 | 0.001 | 0.003 | -0.003 | -0.021 | 0.012 |
| TCRBV04_11 | 0.008 | 0.001 | -0.005 | -0.017 | -0.013 |
| TCRBV04_12 | 0.010 | -0.000 | 0.003 | 0.003 | -0.007 |
| TCRBV04_13 | -0.017 | -0.005 | -0.006 | 0.004 | -0.008 |
| TCRBV04_14 | 0.001 | 0.002 | -0.001 | -0.001 | 0.010 |
| TCRBV04_15 | -0.002 | 0.003 | -0.001 | 0.002 | -0.001 |
| TCRBV051_5 | -0.002 | 0.001 | 0.002 | -0.003 | -0.001 |
| TCRBV051_6 | -0.009 | 0.000 | 0.015 | -0.006 | -0.018 |

*FIG. 111B*

| | | | | | |
|---|---|---|---|---|---|
| TCRBV051_7 | -0.002 | 0.008 | 0.012 | -0.012 | -0.026 |
| TCRBV051_8 | 0.016 | 0.007 | -0.001 | 0.021 | 0.002 |
| TCRBV051_9 | -0.022 | -0.018 | 0.001 | -0.000 | -0.000 |
| TCRBV051_10 | 0.008 | 0.006 | -0.002 | -0.018 | 0.013 |
| TCRBV051_11 | 0.006 | 0.004 | -0.030 | -0.001 | 0.004 |
| TCRBV051_12 | 0.003 | 0.002 | -0.006 | 0.004 | 0.010 |
| TCRBV051_13 | -0.001 | 0.002 | -0.001 | 0.004 | 0.000 |
| TCRBV052_6 | -0.002 | 0.000 | 0.001 | -0.005 | -0.001 |
| TCRBV052_7 | 0.005 | 0.008 | 0.000 | 0.001 | 0.012 |
| TCRBV052_8 | -0.009 | 0.013 | 0.002 | 0.020 | -0.019 |
| TCRBV052_9 | 0.009 | 0.003 | -0.008 | 0.003 | 0.009 |
| TCRBV052_10 | 0.010 | -0.009 | 0.002 | -0.015 | -0.007 |
| TCRBV052_11 | -0.006 | -0.000 | -0.007 | -0.003 | -0.004 |
| TCRBV052_12 | -0.006 | -0.002 | -0.002 | -0.010 | -0.006 |
| TCRBV052_13 | -0.002 | 0.000 | 0.001 | -0.003 | -0.001 |
| TCRBV06_5 | 0.000 | 0.000 | -0.001 | -0.001 | 0.002 |
| TCRBV06_6 | 0.004 | -0.001 | 0.004 | 0.009 | -0.009 |
| TCRBV06_7 | 0.006 | 0.011 | 0.008 | 0.001 | -0.003 |
| TCRBV06_8 | 0.003 | 0.006 | 0.001 | 0.003 | 0.007 |
| TCRBV06_9 | 0.016 | -0.005 | -0.003 | -0.000 | -0.010 |
| TCRBV06_10 | -0.009 | -0.001 | 0.001 | 0.005 | 0.001 |
| TCRBV06_11 | -0.002 | -0.008 | 0.008 | 0.002 | 0.021 |
| TCRBV06_12 | 0.001 | -0.003 | -0.013 | 0.006 | -0.006 |
| TCRBV06_13 | -0.000 | 0.002 | -0.003 | -0.002 | 0.001 |
| TCRBV07_5 | 0.000 | -0.000 | 0.000 | 0.000 | -0.001 |
| TCRBV07_6 | 0.003 | -0.005 | 0.008 | -0.001 | -0.001 |
| TCRBV07_7 | -0.005 | -0.018 | 0.010 | 0.003 | -0.007 |
| TCRBV07_8 | -0.008 | 0.009 | -0.010 | 0.003 | -0.001 |
| TCRBV07_9 | 0.000 | -0.004 | 0.003 | -0.013 | 0.028 |
| TCRBV07_10 | 0.006 | 0.009 | -0.010 | 0.030 | -0.013 |
| TCRBV07_11 | 0.010 | 0.005 | 0.012 | 0.003 | 0.003 |
| TCRBV07_12 | 0.010 | 0.003 | -0.011 | -0.003 | -0.005 |
| TCRBV07_13 | 0.003 | -0.001 | 0.002 | 0.002 | 0.002 |
| TCRBV081_5 | -0.002 | 0.000 | 0.003 | -0.001 | -0.002 |
| TCRBV081_6 | -0.004 | 0.005 | -0.003 | -0.003 | 0.002 |
| TCRBV081_7 | -0.001 | 0.003 | -0.005 | 0.008 | -0.006 |
| TCRBV081_8 | -0.005 | 0.001 | 0.005 | 0.001 | -0.010 |
| TCRBV081_9 | 0.017 | -0.033 | -0.022 | 0.019 | 0.003 |
| TCRBV081_10 | 0.001 | 0.016 | 0.013 | -0.015 | 0.016 |
| TCRBV081_11 | -0.004 | 0.007 | 0.007 | -0.009 | -0.002 |
| TCRBV081_12 | -0.001 | -0.000 | 0.003 | -0.002 | -0.002 |
| TCRBV082_4 | -0.007 | 0.006 | 0.002 | -0.001 | 0.002 |
| TCRBV082_5 | -0.002 | 0.010 | 0.003 | 0.007 | 0.008 |
| TCRBV082_6 | -0.003 | 0.014 | 0.001 | 0.003 | 0.005 |
| TCRBV082_7 | 0.001 | 0.014 | 0.002 | 0.009 | 0.009 |
| TCRBV082_8 | -0.010 | -0.027 | -0.012 | -0.005 | -0.016 |
| TCRBV082_9 | 0.011 | -0.011 | -0.002 | -0.003 | -0.007 |
| TCRBV082_10 | 0.007 | -0.009 | -0.001 | -0.009 | -0.001 |
| TCRBV082_11 | 0.003 | 0.003 | 0.006 | -0.000 | 0.000 |
| TCRBV083_4 | -0.000 | -0.000 | 0.001 | 0.001 | 0.001 |
| TCRBV083_5 | -0.000 | -0.000 | -0.001 | 0.001 | 0.001 |
| TCRBV083_6 | -0.004 | -0.000 | -0.001 | 0.002 | -0.001 |
| TCRBV083_7 | -0.004 | 0.005 | -0.000 | 0.005 | -0.004 |
| TCRBV083_8 | -0.007 | 0.004 | -0.006 | 0.003 | -0.006 |
| TCRBV083_9 | -0.011 | -0.005 | 0.006 | -0.002 | 0.010 |
| TCRBV083_10 | 0.004 | 0.001 | 0.003 | -0.013 | 0.006 |
| TCRBV083_11 | 0.017 | -0.004 | -0.006 | 0.002 | -0.011 |
| TCRBV083_12 | 0.005 | -0.001 | 0.004 | 0.001 | 0.004 |
| TCRBV09_5 | -0.002 | -0.000 | 0.002 | 0.001 | -0.004 |
| TCRBV09_6 | -0.002 | 0.004 | 0.006 | -0.007 | 0.003 |
| TCRBV09_7 | 0.002 | 0.011 | 0.008 | -0.010 | -0.006 |
| TCRBV09_8 | -0.012 | -0.003 | -0.012 | -0.038 | 0.003 |
| TCRBV09_9 | -0.012 | -0.003 | 0.009 | -0.010 | 0.030 |

*FIG. 111C*

| | | | | | |
|---|---|---|---|---|---|
| TCRBV09_10 | -0.006 | 0.005 | 0.008 | -0.003 | -0.010 |
| TCRBV09_11 | 0.005 | -0.023 | -0.020 | -0.009 | 0.010 |
| TCRBV09_12 | 0.001 | 0.006 | 0.014 | 0.027 | 0.005 |
| TCRBV09_13 | 0.001 | 0.006 | 0.008 | 0.015 | -0.001 |
| TCRBV09_14 | 0.002 | 0.003 | 0.002 | 0.008 | 0.002 |
| TCRBV09_15 | 0.000 | -0.000 | 0.000 | 0.001 | -0.001 |
| TCRBV10_6 | 0.008 | 0.005 | -0.006 | -0.006 | -0.002 |
| TCRBV10_7 | 0.009 | 0.005 | -0.009 | 0.001 | 0.014 |
| TCRBV10_8 | 0.003 | -0.006 | -0.005 | -0.001 | 0.018 |
| TCRBV10_9 | 0.000 | -0.012 | 0.014 | 0.005 | -0.023 |
| TCRBV10_10 | -0.005 | -0.007 | 0.005 | -0.002 | -0.010 |
| TCRBV10_11 | -0.011 | 0.008 | 0.001 | 0.006 | 0.008 |
| TCRBV10_12 | -0.006 | 0.007 | 0.001 | -0.003 | -0.005 |
| TCRBV10_13 | 0.000 | 0.000 | -0.001 | 0.001 | 0.000 |
| TCRBV11_5 | -0.001 | 0.001 | -0.003 | 0.002 | -0.002 |
| TCRBV11_6 | -0.011 | 0.000 | -0.005 | 0.005 | 0.001 |
| TCRBV11_7 | -0.006 | 0.003 | 0.002 | 0.004 | 0.001 |
| TCRBV11_8 | 0.002 | -0.000 | -0.005 | -0.012 | -0.008 |
| TCRBV11_9 | -0.011 | 0.008 | -0.003 | -0.020 | -0.018 |
| TCRBV11_10 | 0.011 | -0.012 | 0.012 | 0.013 | -0.006 |
| TCRBV11_11 | 0.018 | 0.003 | 0.007 | 0.004 | 0.013 |
| TCRBV11_12 | 0.008 | -0.007 | 0.004 | 0.015 | 0.014 |
| TCRBV11_13 | 0.007 | 0.002 | -0.001 | 0.007 | 0.008 |
| TCRBV11_14 | 0.002 | 0.002 | -0.003 | 0.003 | 0.000 |
| TCRBV11_15 | 0.001 | 0.001 | -0.001 | 0.001 | 0.000 |
| TCRBV12_4 | 0.000 | 0.001 | 0.002 | -0.001 | -0.002 |
| TCRBV12_5 | 0.012 | -0.007 | 0.014 | -0.001 | -0.002 |
| TCRBV12_6 | -0.001 | -0.010 | 0.006 | 0.002 | -0.011 |
| TCRBV12_7 | -0.003 | -0.018 | 0.009 | -0.002 | -0.020 |
| TCRBV12_8 | 0.001 | -0.005 | 0.002 | -0.008 | -0.001 |
| TCRBV12_9 | 0.001 | 0.012 | -0.012 | 0.016 | 0.004 |
| TCRBV12_10 | -0.023 | 0.013 | -0.001 | -0.011 | 0.011 |
| TCRBV12_11 | 0.006 | 0.011 | -0.021 | 0.005 | 0.016 |
| TCRBV12_12 | 0.005 | 0.003 | 0.001 | 0.000 | 0.004 |
| TCRBV13_5 | 0.001 | 0.000 | -0.001 | -0.000 | 0.000 |
| TCRBV13_6 | -0.013 | 0.003 | 0.004 | 0.005 | 0.008 |
| TCRBV13_7 | 0.006 | 0.016 | 0.001 | -0.004 | -0.013 |
| TCRBV13_8 | -0.008 | -0.009 | -0.016 | 0.008 | -0.008 |
| TCRBV13_9 | 0.005 | 0.003 | 0.006 | -0.012 | 0.007 |
| TCRBV13_10 | -0.002 | -0.002 | 0.015 | 0.003 | -0.004 |
| TCRBV13_11 | 0.008 | -0.001 | -0.011 | -0.003 | 0.007 |
| TCRBV13_12 | 0.001 | -0.002 | 0.003 | 0.002 | 0.003 |
| TCRBV13_13 | 0.001 | -0.009 | -0.002 | 0.001 | 0.000 |
| TCRBV14_5 | 0.003 | 0.000 | -0.002 | -0.000 | -0.002 |
| TCRBV14_6 | 0.006 | 0.004 | -0.002 | -0.005 | 0.000 |
| TCRBV14_7 | 0.016 | -0.004 | 0.006 | -0.007 | -0.003 |
| TCRBV14_8 | 0.003 | -0.009 | -0.001 | 0.006 | 0.003 |
| TCRBV14_9 | -0.005 | -0.012 | -0.003 | -0.002 | -0.004 |
| TCRBV14_10 | -0.011 | 0.015 | -0.001 | -0.008 | -0.002 |
| TCRBV14_11 | -0.014 | -0.005 | 0.004 | 0.010 | 0.007 |
| TCRBV14_12 | 0.001 | 0.000 | -0.000 | 0.003 | 0.001 |
| TCRBV14_13 | 0.001 | 0.000 | -0.001 | 0.001 | 0.000 |
| TCRBV15_4 | -0.000 | 0.001 | 0.000 | -0.001 | 0.001 |
| TCRBV15_5 | -0.001 | 0.013 | -0.015 | 0.001 | -0.010 |
| TCRBV15_6 | -0.009 | -0.001 | 0.003 | 0.010 | -0.001 |
| TCRBV15_7 | -0.013 | -0.001 | -0.003 | 0.002 | -0.003 |
| TCRBV15_8 | 0.009 | 0.009 | -0.000 | 0.005 | 0.001 |
| TCRBV15_9 | 0.013 | 0.011 | 0.018 | -0.007 | 0.007 |
| TCRBV15_10 | 0.006 | -0.018 | 0.000 | 0.014 | 0.006 |
| TCRBV15_11 | 0.010 | -0.009 | 0.001 | -0.000 | 0.006 |
| TCRBV15_12 | 0.003 | -0.004 | -0.000 | -0.001 | -0.003 |
| TCRBV16_5 | -0.001 | 0.003 | 0.001 | 0.003 | -0.001 |
| TCRBV16_6 | -0.006 | 0.009 | -0.012 | 0.019 | 0.002 |
| TCRBV16_7 | -0.003 | 0.005 | -0.000 | -0.017 | 0.002 |

*FIG. 111D*

|           |        |        |        |        |        |
|-----------|--------|--------|--------|--------|--------|
| TCRBV16_8 | -0.001 | 0.010  | 0.005  | 0.016  | 0.000  |
| TCRBV16_9 | 0.006  | -0.004 | -0.007 | 0.003  | -0.027 |
| TCRBV16_10 | -0.005 | 0.008 | -0.032 | -0.006 | 0.008  |
| TCRBV16_11 | 0.013 | -0.003 | 0.034  | 0.014  | 0.009  |
| TCRBV16_12 | 0.014 | -0.016 | 0.004  | -0.018 | -0.004 |
| TCRBV16_13 | 0.001 | 0.001  | 0.001  | -0.002 | -0.001 |
| TCRBV18_3 | 0.000  | -0.000 | 0.000  | 0.000  | -0.000 |
| TCRBV18_4 | -0.004 | 0.009 | 0.002  | 0.009  | -0.009 |
| TCRBV18_5 | -0.004 | 0.011 | 0.002  | 0.009  | -0.015 |
| TCRBV18_6 | -0.003 | 0.001 | 0.002  | 0.006  | -0.035 |
| TCRBV18_7 | -0.012 | -0.010 | -0.007 | 0.012 | 0.004  |
| TCRBV18_8 | 0.001  | -0.024 | 0.003  | -0.003 | 0.021 |
| TCRBV18_9 | 0.007  | -0.001 | -0.010 | 0.002  | 0.015 |
| TCRBV18_10 | 0.010 | -0.006 | -0.006 | -0.008 | 0.013 |
| TCRBV18_11 | 0.004 | 0.004  | -0.008 | 0.003  | -0.003 |
| TCRBV18_12 | 0.001 | 0.001  | -0.000 | 0.001  | -0.001 |
| TCRBV18_13 | -0.001 | 0.000 | 0.001  | -0.001 | 0.000 |
| TCRBV20_5 | -0.002 | -0.002 | -0.002 | 0.002  | -0.000 |
| TCRBV20_6 | -0.005 | 0.002  | -0.000 | 0.001  | 0.015 |
| TCRBV20_7 | 0.001  | -0.012 | 0.005  | -0.013 | -0.012 |
| TCRBV20_8 | -0.010 | -0.019 | 0.007 | 0.007  | 0.018 |
| TCRBV20_9 | 0.018  | -0.009 | -0.012 | 0.004  | -0.019 |
| TCRBV20_10 | -0.002 | 0.001 | 0.010  | 0.032  | 0.000 |
| TCRBV20_11 | 0.018 | 0.018  | 0.002  | -0.007 | 0.010 |
| TCRBV20_12 | 0.001 | 0.004  | 0.003  | -0.008 | 0.007 |
| TCRBV20_13 | 0.000 | 0.017  | -0.010 | 0.007  | -0.016 |
| TCRBV20_14 | -0.000 | 0.001 | 0.000  | -0.001 | 0.001 |
|           | 26     | 27     | 28     | 29     | 30     |
| TCRBV01_6 | -0.004 | -0.004 | -0.001 | 0.001  | 0.004 |
| TCRBV01_7 | -0.002 | -0.004 | 0.004  | 0.005  | -0.004 |
| TCRBV01_8 | 0.015  | 0.007  | 0.007  | 0.005  | 0.012 |
| TCRBV01_9 | 0.007  | 0.014  | -0.013 | -0.030 | -0.036 |
| TCRBV01_10 | 0.004 | 0.002  | -0.001 | 0.013  | 0.002 |
| TCRBV01_11 | 0.003 | 0.002  | 0.004  | 0.003  | 0.010 |
| TCRBV01_12 | 0.004 | -0.007 | -0.004 | 0.008  | 0.011 |
| TCRBV01_13 | 0.002 | 0.005  | 0.001  | 0.001  | -0.000 |
| TCRBV01_14 | 0.000 | 0.001  | 0.000  | -0.000 | 0.000 |
| TCRBV02_6 | 0.000  | 0.001  | -0.002 | 0.005  | 0.022 |
| TCRBV02_7 | 0.010  | -0.006 | -0.007 | 0.004  | -0.001 |
| TCRBV02_8 | -0.006 | -0.009 | -0.001 | -0.008 | 0.009 |
| TCRBV02_9 | -0.022 | 0.019  | 0.013  | 0.008  | -0.010 |
| TCRBV02_10 | -0.020 | 0.005 | 0.014  | -0.004 | 0.000 |
| TCRBV02_11 | -0.020 | 0.003 | -0.003 | -0.002 | -0.001 |
| TCRBV02_12 | -0.009 | -0.002 | 0.014 | -0.006 | 0.002 |
| TCRBV02_13 | -0.002 | -0.001 | -0.000 | -0.004 | 0.000 |
| TCRBV03_4 | 0.002  | -0.000 | -0.001 | 0.000  | -0.001 |
| TCRBV03_5 | -0.000 | -0.001 | 0.000  | 0.003  | -0.000 |
| TCRBV03_6 | 0.011  | -0.004 | 0.000  | 0.008  | -0.007 |
| TCRBV03_7 | 0.006  | -0.006 | 0.013  | -0.001 | -0.009 |
| TCRBV03_8 | -0.007 | -0.004 | 0.028 | -0.012 | -0.007 |
| TCRBV03_9 | -0.012 | -0.004 | -0.007 | -0.024 | 0.011 |
| TCRBV03_10 | 0.002 | 0.007  | 0.009  | 0.001  | 0.017 |
| TCRBV03_11 | 0.011 | 0.005  | -0.014 | 0.016  | -0.006 |
| TCRBV03_12 | 0.009 | -0.005 | -0.018 | 0.009  | 0.002 |
| TCRBV03_13 | 0.007 | 0.025  | -0.015 | 0.006  | -0.001 |
| TCRBV04_6 | -0.002 | 0.001  | 0.000  | 0.001  | 0.001 |
| TCRBV04_7 | 0.001  | -0.008 | 0.003  | 0.004  | 0.010 |
| TCRBV04_8 | 0.010  | -0.013 | -0.001 | 0.003  | -0.006 |
| TCRBV04_9 | 0.013  | -0.022 | 0.003  | 0.016  | -0.007 |
| TCRBV04_10 | -0.005 | 0.007 | -0.015 | -0.039 | -0.015 |
| TCRBV04_11 | -0.004 | 0.012 | -0.002 | 0.018  | -0.005 |
| TCRBV04_12 | -0.005 | 0.003 | 0.003  | 0.025  | 0.019 |

*FIG. 112A*

| | | | | | |
|---|---|---|---|---|---|
| TCRBV04_13 | -0.003 | 0.013 | -0.001 | -0.007 | 0.004 |
| TCRBV04_14 | -0.007 | 0.002 | 0.007 | -0.012 | -0.003 |
| TCRBV04_15 | 0.002 | 0.004 | 0.002 | -0.010 | 0.001 |
| TCRBV051_5 | 0.002 | -0.001 | -0.003 | 0.002 | 0.010 |
| TCRBV051_6 | 0.006 | -0.015 | -0.004 | 0.018 | -0.002 |
| TCRBV051_7 | 0.023 | 0.003 | 0.014 | -0.008 | 0.004 |
| TCRBV051_8 | -0.023 | -0.014 | -0.006 | -0.025 | 0.007 |
| TCRBV051_9 | 0.019 | 0.024 | 0.037 | 0.025 | -0.007 |
| TCRBV051_10 | -0.025 | 0.001 | -0.008 | 0.010 | -0.011 |
| TCRBV051_11 | 0.009 | 0.008 | 0.012 | -0.012 | 0.021 |
| TCRBV051_12 | -0.014 | -0.014 | -0.011 | 0.012 | 0.010 |
| TCRBV051_13 | -0.000 | 0.001 | -0.002 | -0.006 | 0.010 |
| TCRBV052_6 | -0.000 | -0.000 | 0.003 | -0.015 | 0.002 |
| TCRBV052_7 | -0.007 | 0.014 | 0.008 | -0.021 | 0.001 |
| TCRBV052_8 | -0.011 | -0.011 | 0.012 | -0.001 | 0.018 |
| TCRBV052_9 | 0.007 | -0.002 | -0.009 | 0.024 | -0.019 |
| TCRBV052_10 | -0.009 | -0.019 | 0.009 | 0.005 | 0.015 |
| TCRBV052_11 | 0.018 | 0.006 | 0.009 | 0.008 | 0.013 |
| TCRBV052_12 | 0.003 | 0.001 | -0.003 | 0.014 | 0.012 |
| TCRBV052_13 | -0.004 | 0.002 | 0.002 | 0.004 | -0.001 |
| TCRBV06_5 | 0.000 | -0.001 | 0.002 | 0.002 | 0.000 |
| TCRBV06_6 | -0.007 | -0.005 | 0.003 | 0.005 | -0.003 |
| TCRBV06_7 | 0.001 | -0.004 | 0.019 | 0.016 | -0.003 |
| TCRBV06_8 | -0.005 | -0.008 | 0.011 | -0.005 | -0.016 |
| TCRBV06_9 | -0.021 | 0.002 | 0.006 | 0.005 | -0.028 |
| TCRBV06_10 | 0.016 | 0.026 | -0.013 | -0.020 | 0.006 |
| TCRBV06_11 | 0.035 | 0.001 | -0.016 | -0.015 | 0.018 |
| TCRBV06_12 | 0.000 | -0.001 | -0.015 | 0.007 | 0.025 |
| TCRBV06_13 | 0.010 | 0.006 | 0.002 | 0.010 | -0.001 |
| TCRBV07_5 | -0.000 | -0.000 | 0.001 | -0.001 | -0.001 |
| TCRBV07_6 | 0.003 | 0.016 | -0.020 | -0.007 | 0.004 |
| TCRBV07_7 | 0.004 | 0.003 | -0.017 | -0.007 | 0.008 |
| TCRBV07_8 | -0.002 | -0.013 | -0.006 | 0.022 | -0.014 |
| TCRBV07_9 | 0.020 | 0.013 | 0.003 | -0.028 | -0.000 |
| TCRBV07_10 | -0.000 | -0.003 | 0.013 | 0.007 | 0.017 |
| TCRBV07_11 | 0.019 | 0.010 | 0.012 | 0.005 | -0.013 |
| TCRBV07_12 | -0.010 | -0.011 | 0.011 | 0.012 | -0.000 |
| TCRBV07_13 | -0.004 | -0.000 | 0.001 | 0.003 | -0.000 |
| TCRBV081_5 | 0.000 | -0.003 | -0.001 | 0.004 | 0.002 |
| TCRBV081_6 | 0.007 | -0.005 | 0.003 | -0.006 | 0.012 |
| TCRBV081_7 | 0.004 | 0.020 | 0.022 | -0.021 | 0.009 |
| TCRBV081_8 | 0.000 | 0.006 | 0.037 | -0.009 | 0.011 |
| TCRBV081_9 | -0.007 | 0.014 | 0.003 | 0.016 | -0.008 |
| TCRBV081_10 | -0.002 | -0.019 | -0.022 | -0.008 | 0.028 |
| TCRBV081_11 | -0.001 | -0.010 | -0.009 | 0.004 | -0.015 |
| TCRBV081_12 | -0.001 | -0.003 | -0.033 | 0.019 | -0.039 |
| TCRBV082_4 | -0.005 | 0.002 | 0.010 | 0.007 | 0.011 |
| TCRBV082_5 | -0.001 | 0.011 | -0.000 | 0.005 | 0.007 |
| TCRBV082_6 | -0.001 | 0.011 | 0.017 | 0.015 | 0.014 |
| TCRBV082_7 | -0.001 | 0.015 | -0.005 | 0.016 | 0.002 |
| TCRBV082_8 | -0.002 | -0.016 | -0.005 | -0.013 | -0.001 |
| TCRBV082_9 | 0.007 | -0.011 | -0.009 | -0.017 | -0.010 |
| TCRBV082_10 | -0.003 | -0.009 | -0.004 | -0.011 | -0.012 |
| TCRBV082_11 | 0.005 | -0.002 | -0.003 | -0.001 | -0.010 |
| TCRBV083_4 | 0.001 | 0.002 | -0.001 | 0.000 | -0.000 |
| TCRBV083_5 | -0.002 | -0.002 | -0.008 | 0.006 | -0.010 |
| TCRBV083_6 | -0.007 | 0.001 | -0.010 | 0.006 | -0.006 |
| TCRBV083_7 | -0.006 | 0.002 | -0.021 | 0.001 | -0.008 |
| TCRBV083_8 | -0.005 | 0.004 | -0.011 | 0.004 | 0.020 |
| TCRBV083_9 | 0.001 | -0.011 | 0.008 | -0.008 | -0.006 |
| TCRBV083_10 | 0.010 | 0.008 | 0.009 | -0.008 | -0.008 |
| TCRBV083_11 | 0.005 | -0.009 | 0.019 | 0.002 | 0.002 |
| TCRBV083_12 | 0.004 | 0.005 | 0.016 | -0.003 | 0.016 |

*FIG. 112B*

| | | | | | |
|---|---|---|---|---|---|
| TCRBV09_5 | -0.000 | -0.004 | -0.002 | 0.003 | 0.001 |
| TCRBV09_6 | -0.001 | -0.002 | 0.004 | -0.005 | 0.003 |
| TCRBV09_7 | -0.006 | -0.005 | 0.018 | 0.012 | -0.013 |
| TCRBV09_8 | -0.004 | -0.008 | -0.002 | -0.011 | -0.014 |
| TCRBV09_9 | -0.025 | -0.014 | 0.026 | 0.021 | -0.003 |
| TCRBV09_10 | -0.014 | 0.002 | -0.027 | 0.012 | 0.029 |
| TCRBV09_11 | 0.002 | -0.026 | 0.002 | 0.011 | 0.001 |
| TCRBV09_12 | -0.017 | 0.014 | -0.027 | -0.023 | 0.017 |
| TCRBV09_13 | -0.005 | 0.010 | -0.010 | -0.008 | -0.011 |
| TCRBV09_14 | -0.002 | 0.004 | 0.004 | 0.002 | 0.003 |
| TCRBV09_15 | -0.000 | 0.001 | 0.001 | 0.001 | -0.002 |
| TCRBV10_6 | 0.006 | 0.001 | 0.001 | -0.009 | 0.013 |
| TCRBV10_7 | 0.009 | -0.010 | 0.005 | 0.006 | 0.012 |
| TCRBV10_8 | 0.013 | 0.012 | 0.015 | -0.002 | 0.015 |
| TCRBV10_9 | 0.013 | 0.009 | 0.025 | -0.015 | -0.026 |
| TCRBV10_10 | 0.008 | -0.016 | -0.006 | -0.003 | -0.005 |
| TCRBV10_11 | -0.035 | 0.005 | -0.015 | 0.014 | -0.010 |
| TCRBV10_12 | -0.013 | -0.000 | -0.024 | 0.010 | 0.002 |
| TCRBV10_13 | 0.001 | -0.000 | -0.000 | 0.000 | -0.000 |
| TCRBV11_5 | 0.002 | 0.004 | -0.003 | 0.003 | 0.003 |
| TCRBV11_6 | 0.001 | -0.002 | 0.002 | 0.005 | 0.007 |
| TCRBV11_7 | 0.006 | 0.005 | -0.005 | 0.018 | -0.000 |
| TCRBV11_8 | 0.013 | -0.009 | 0.010 | 0.016 | 0.004 |
| TCRBV11_9 | 0.002 | 0.019 | 0.001 | -0.008 | -0.010 |
| TCRBV11_10 | 0.010 | 0.008 | -0.004 | -0.003 | -0.002 |
| TCRBV11_11 | 0.000 | 0.008 | -0.001 | -0.013 | 0.001 |
| TCRBV11_12 | -0.011 | -0.015 | -0.001 | -0.009 | 0.003 |
| TCRBV11_13 | 0.001 | -0.002 | -0.000 | -0.004 | -0.003 |
| TCRBV11_14 | 0.004 | -0.000 | -0.002 | 0.000 | -0.001 |
| TCRBV11_15 | 0.001 | -0.000 | -0.001 | 0.000 | -0.000 |
| TCRBV12_4 | 0.001 | 0.002 | -0.001 | 0.004 | 0.001 |
| TCRBV12_5 | 0.011 | 0.008 | -0.023 | 0.013 | -0.003 |
| TCRBV12_6 | 0.000 | -0.005 | -0.002 | -0.016 | 0.027 |
| TCRBV12_7 | -0.007 | -0.016 | -0.008 | -0.011 | 0.004 |
| TCRBV12_8 | -0.007 | 0.008 | 0.012 | 0.009 | -0.008 |
| TCRBV12_9 | 0.003 | -0.003 | 0.016 | 0.007 | -0.007 |
| TCRBV12_10 | -0.002 | 0.004 | -0.002 | 0.004 | -0.016 |
| TCRBV12_11 | 0.001 | -0.000 | 0.009 | -0.003 | -0.004 |
| TCRBV12_12 | -0.001 | 0.001 | -0.000 | -0.006 | 0.005 |
| TCRBV13_5 | 0.003 | -0.001 | -0.001 | -0.002 | -0.002 |
| TCRBV13_6 | -0.009 | 0.004 | -0.008 | 0.005 | -0.019 |
| TCRBV13_7 | 0.027 | 0.002 | -0.010 | 0.010 | 0.014 |
| TCRBV13_8 | -0.004 | -0.015 | 0.022 | 0.015 | -0.009 |
| TCRBV13_9 | -0.011 | 0.026 | 0.012 | 0.010 | 0.024 |
| TCRBV13_10 | -0.001 | -0.006 | 0.002 | -0.021 | -0.010 |
| TCRBV13_11 | -0.003 | -0.013 | -0.012 | -0.014 | -0.013 |
| TCRBV13_12 | 0.000 | 0.004 | -0.007 | -0.008 | 0.009 |
| TCRBV13_13 | -0.002 | -0.001 | 0.003 | 0.006 | 0.007 |
| TCRBV14_5 | 0.001 | -0.004 | -0.001 | 0.001 | -0.000 |
| TCRBV14_6 | 0.001 | -0.003 | 0.002 | 0.002 | -0.002 |
| TCRBV14_7 | 0.011 | 0.004 | 0.004 | -0.005 | 0.007 |
| TCRBV14_8 | -0.010 | 0.014 | 0.006 | 0.000 | -0.007 |
| TCRBV14_9 | 0.010 | 0.016 | -0.013 | 0.003 | 0.003 |
| TCRBV14_10 | -0.021 | -0.002 | -0.012 | -0.007 | -0.000 |
| TCRBV14_11 | 0.008 | -0.025 | 0.012 | 0.007 | -0.002 |
| TCRBV14_12 | 0.001 | -0.000 | 0.003 | -0.000 | 0.001 |
| TCRBV14_13 | 0.001 | 0.000 | -0.001 | -0.000 | -0.001 |
| TCRBV15_4 | -0.000 | -0.002 | 0.000 | -0.005 | -0.001 |
| TCRBV15_5 | -0.007 | 0.017 | -0.005 | 0.010 | 0.007 |
| TCRBV15_6 | 0.002 | 0.001 | -0.004 | 0.009 | 0.003 |
| TCRBV15_7 | 0.026 | -0.019 | -0.019 | 0.003 | 0.008 |
| TCRBV15_8 | 0.019 | 0.012 | -0.002 | -0.007 | -0.021 |
| TCRBV15_9 | 0.007 | 0.003 | -0.000 | 0.018 | -0.009 |
| TCRBV15_10 | -0.011 | 0.008 | 0.016 | -0.020 | 0.015 |

*FIG. 112C*

|  |  |  |  |  |  |
|---|---|---|---|---|---|
| TCRBV15_11 | -0.005 | -0.005 | 0.012 | -0.004 | -0.001 |
| TCRBV15_12 | -0.001 | -0.000 | -0.000 | 0.002 | -0.002 |
| TCRBV16_5 | 0.000 | 0.003 | 0.003 | -0.004 | 0.001 |
| TCRBV16_6 | 0.005 | 0.026 | -0.007 | 0.001 | -0.003 |
| TCRBV16_7 | 0.021 | 0.004 | 0.013 | 0.006 | -0.009 |
| TCRBV16_8 | 0.020 | -0.036 | -0.003 | -0.010 | 0.011 |
| TCRBV16_9 | -0.016 | 0.001 | 0.017 | -0.010 | 0.025 |
| TCRBV16_10 | 0.001 | 0.009 | 0.007 | 0.004 | -0.015 |
| TCRBV16_11 | -0.003 | 0.002 | 0.012 | 0.036 | 0.020 |
| TCRBV16_12 | -0.007 | -0.003 | -0.018 | -0.004 | 0.009 |
| TCRBV16_13 | 0.005 | 0.002 | 0.005 | 0.004 | 0.002 |
| TCRBV18_3 | -0.000 | -0.000 | -0.000 | 0.000 | -0.000 |
| TCRBV18_4 | -0.008 | 0.003 | 0.007 | -0.016 | -0.002 |
| TCRBV18_5 | -0.020 | -0.011 | 0.009 | -0.012 | 0.010 |
| TCRBV18_6 | -0.025 | 0.017 | 0.016 | -0.024 | -0.004 |
| TCRBV18_7 | -0.004 | -0.032 | -0.000 | -0.013 | -0.017 |
| TCRBV18_8 | -0.023 | 0.032 | -0.024 | 0.030 | 0.000 |
| TCRBV18_9 | -0.017 | -0.006 | 0.003 | 0.016 | 0.037 |
| TCRBV18_10 | 0.001 | -0.003 | 0.017 | 0.010 | -0.005 |
| TCRBV18_11 | 0.004 | -0.008 | 0.007 | -0.000 | -0.007 |
| TCRBV18_12 | 0.002 | 0.001 | 0.004 | 0.000 | 0.003 |
| TCRBV18_13 | 0.000 | -0.001 | 0.000 | 0.002 | 0.001 |
| TCRBV20_5 | 0.006 | 0.001 | -0.001 | 0.001 | 0.004 |
| TCRBV20_6 | 0.011 | -0.004 | -0.017 | -0.022 | 0.023 |
| TCRBV20_7 | 0.012 | 0.002 | 0.003 | -0.001 | 0.017 |
| TCRBV20_8 | -0.001 | 0.007 | 0.016 | 0.013 | 0.023 |
| TCRBV20_9 | 0.006 | 0.001 | -0.018 | 0.035 | 0.005 |
| TCRBV20_10 | 0.004 | -0.003 | 0.006 | 0.003 | -0.075 |
| TCRBV20_11 | -0.011 | 0.003 | 0.018 | -0.009 | -0.004 |
| TCRBV20_12 | 0.002 | -0.009 | 0.006 | -0.010 | 0.007 |
| TCRBV20_13 | 0.001 | 0.020 | -0.014 | -0.000 | -0.002 |
| TCRBV20_14 | -0.000 | -0.001 | 0.000 | -0.004 | -0.001 |
|  | 31 | 32 | 33 | 34 | 35 |
| TCRBV01_6 | -0.001 | 0.003 | 0.000 | 0.004 | 0.001 |
| TCRBV01_7 | 0.021 | 0.004 | 0.008 | 0.007 | 0.002 |
| TCRBV01_8 | 0.023 | -0.027 | 0.014 | -0.033 | 0.003 |
| TCRBV01_9 | 0.030 | 0.049 | 0.013 | 0.015 | 0.006 |
| TCRBV01_10 | -0.009 | 0.000 | -0.003 | -0.011 | -0.001 |
| TCRBV01_11 | -0.039 | -0.031 | -0.025 | 0.018 | -0.014 |
| TCRBV01_12 | -0.014 | 0.014 | -0.012 | -0.005 | -0.004 |
| TCRBV01_13 | -0.005 | -0.005 | -0.010 | -0.007 | -0.003 |
| TCRBV01_14 | 0.000 | -0.000 | 0.000 | 0.000 | -0.001 |
| TCRBV02_6 | 0.006 | 0.014 | -0.002 | 0.010 | 0.014 |
| TCRBV02_7 | -0.019 | 0.000 | -0.001 | -0.003 | 0.015 |
| TCRBV02_8 | 0.012 | -0.013 | 0.009 | -0.006 | 0.008 |
| TCRBV02_9 | 0.003 | -0.021 | -0.003 | 0.051 | 0.015 |
| TCRBV02_10 | 0.004 | 0.008 | 0.022 | 0.017 | -0.007 |
| TCRBV02_11 | 0.003 | 0.002 | 0.011 | 0.007 | -0.015 |
| TCRBV02_12 | -0.019 | -0.007 | 0.020 | -0.012 | -0.004 |
| TCRBV02_13 | -0.001 | -0.007 | 0.013 | -0.001 | 0.005 |
| TCRBV03_4 | 0.000 | 0.001 | -0.002 | -0.002 | -0.001 |
| TCRBV03_5 | -0.001 | 0.001 | -0.001 | 0.003 | 0.001 |
| TCRBV03_6 | 0.023 | -0.012 | -0.012 | -0.016 | 0.007 |
| TCRBV03_7 | 0.003 | -0.007 | 0.018 | 0.005 | -0.017 |
| TCRBV03_8 | 0.005 | -0.023 | 0.016 | -0.011 | 0.009 |
| TCRBV03_9 | -0.003 | 0.006 | 0.001 | -0.022 | 0.016 |
| TCRBV03_10 | -0.031 | 0.013 | -0.011 | 0.020 | -0.007 |
| TCRBV03_11 | 0.005 | 0.009 | 0.002 | 0.035 | -0.032 |
| TCRBV03_12 | -0.000 | 0.021 | -0.013 | 0.002 | 0.020 |
| TCRBV03_13 | 0.007 | -0.002 | -0.013 | -0.026 | -0.006 |
| TCRBV04_6 | -0.003 | 0.002 | -0.001 | -0.002 | 0.000 |
| TCRBV04_7 | -0.006 | 0.004 | -0.009 | -0.001 | -0.010 |

*FIG. 112D*

| | | | | | |
|---|---|---|---|---|---|
| TCRBV04_8 | 0.020 | -0.023 | -0.003 | 0.020 | 0.014 |
| TCRBV04_9 | 0.021 | 0.000 | -0.030 | 0.005 | 0.015 |
| TCRBV04_10 | -0.030 | -0.019 | 0.008 | 0.017 | 0.027 |
| TCRBV04_11 | -0.021 | 0.005 | 0.018 | -0.039 | 0.030 |
| TCRBV04_12 | 0.016 | 0.012 | 0.054 | 0.013 | 0.014 |
| TCRBV04_13 | 0.000 | 0.031 | -0.035 | -0.010 | -0.044 |
| TCRBV04_14 | -0.003 | -0.017 | -0.006 | -0.005 | -0.037 |
| TCRBV04_15 | 0.005 | 0.006 | 0.005 | 0.001 | -0.010 |
| TCRBV051_5 | -0.012 | -0.019 | 0.001 | -0.001 | -0.001 |
| TCRBV051_6 | 0.008 | 0.004 | -0.011 | 0.014 | 0.014 |
| TCRBV051_7 | -0.016 | -0.016 | 0.010 | -0.002 | 0.016 |
| TCRBV051_8 | 0.007 | -0.010 | -0.002 | 0.010 | 0.007 |
| TCRBV051_9 | 0.005 | 0.038 | 0.035 | -0.012 | 0.031 |
| TCRBV051_10 | 0.011 | -0.011 | -0.024 | -0.008 | 0.013 |
| TCRBV051_11 | 0.003 | 0.000 | -0.002 | 0.031 | -0.003 |
| TCRBV051_12 | -0.001 | -0.028 | -0.007 | 0.026 | -0.043 |
| TCRBV051_13 | -0.005 | -0.004 | 0.007 | -0.001 | 0.001 |
| TCRBV052_6 | -0.002 | -0.004 | 0.002 | 0.012 | -0.011 |
| TCRBV052_7 | -0.014 | 0.004 | 0.007 | 0.016 | -0.004 |
| TCRBV052_8 | 0.009 | -0.007 | -0.003 | 0.005 | 0.010 |
| TCRBV052_9 | -0.016 | -0.010 | 0.009 | 0.020 | 0.021 |
| TCRBV052_10 | 0.030 | -0.039 | -0.004 | 0.002 | -0.006 |
| TCRBV052_11 | -0.011 | 0.011 | -0.002 | 0.006 | 0.020 |
| TCRBV052_12 | 0.007 | -0.003 | -0.001 | -0.002 | 0.006 |
| TCRBV052_13 | -0.003 | 0.002 | -0.002 | -0.002 | -0.001 |
| TCRBV06_5 | 0.004 | -0.001 | 0.001 | -0.000 | -0.006 |
| TCRBV06_6 | -0.006 | 0.007 | 0.007 | -0.008 | -0.009 |
| TCRBV06_7 | -0.014 | 0.019 | -0.004 | -0.012 | -0.002 |
| TCRBV06_8 | -0.024 | 0.031 | -0.030 | -0.009 | -0.001 |
| TCRBV06_9 | -0.009 | 0.001 | -0.004 | -0.004 | -0.037 |
| TCRBV06_10 | 0.036 | -0.027 | 0.011 | 0.013 | -0.003 |
| TCRBV06_11 | 0.005 | -0.031 | -0.007 | 0.006 | 0.032 |
| TCRBV06_12 | 0.014 | 0.015 | 0.010 | -0.005 | 0.001 |
| TCRBV06_13 | 0.002 | -0.006 | 0.000 | 0.007 | 0.015 |
| TCRBV07_5 | -0.000 | 0.000 | 0.001 | 0.000 | -0.002 |
| TCRBV07_6 | 0.009 | -0.008 | -0.002 | -0.022 | -0.002 |
| TCRBV07_7 | 0.019 | 0.004 | 0.019 | -0.016 | -0.018 |
| TCRBV07_8 | 0.012 | 0.001 | -0.026 | 0.005 | -0.003 |
| TCRBV07_9 | -0.005 | 0.002 | -0.034 | -0.008 | -0.016 |
| TCRBV07_10 | -0.015 | -0.003 | 0.014 | -0.003 | 0.006 |
| TCRBV07_11 | -0.007 | -0.006 | 0.002 | 0.010 | 0.005 |
| TCRBV07_12 | -0.004 | 0.014 | 0.010 | 0.015 | 0.018 |
| TCRBV07_13 | -0.003 | 0.002 | 0.001 | 0.007 | 0.002 |
| TCRBV081_5 | -0.001 | -0.006 | 0.003 | -0.001 | 0.001 |
| TCRBV081_6 | -0.018 | -0.003 | -0.007 | 0.018 | 0.005 |
| TCRBV081_7 | 0.002 | -0.018 | -0.023 | -0.002 | 0.023 |
| TCRBV081_8 | 0.003 | 0.007 | -0.010 | 0.011 | -0.013 |
| TCRBV081_9 | -0.004 | -0.002 | 0.015 | -0.013 | 0.007 |
| TCRBV081_10 | 0.017 | 0.031 | 0.017 | 0.004 | -0.042 |
| TCRBV081_11 | 0.004 | -0.001 | 0.000 | 0.013 | 0.006 |
| TCRBV081_12 | -0.003 | -0.008 | 0.004 | -0.030 | 0.011 |
| TCRBV082_4 | -0.003 | -0.001 | 0.002 | -0.005 | -0.001 |
| TCRBV082_5 | 0.010 | 0.008 | 0.013 | -0.003 | 0.002 |
| TCRBV082_6 | 0.008 | -0.006 | 0.004 | -0.009 | -0.019 |
| TCRBV082_7 | -0.004 | 0.026 | -0.001 | -0.000 | 0.037 |
| TCRBV082_8 | -0.011 | -0.041 | -0.013 | -0.038 | -0.014 |
| TCRBV082_9 | 0.006 | 0.001 | -0.010 | 0.017 | 0.009 |
| TCRBV082_10 | -0.001 | -0.005 | -0.001 | 0.023 | -0.015 |
| TCRBV082_11 | -0.004 | 0.018 | 0.006 | 0.015 | -0.000 |
| TCRBV083_4 | 0.000 | 0.000 | -0.001 | -0.002 | -0.001 |
| TCRBV083_5 | 0.008 | 0.002 | 0.011 | -0.002 | 0.012 |
| TCRBV083_6 | 0.005 | -0.002 | -0.011 | 0.006 | -0.005 |
| TCRBV083_7 | 0.009 | 0.000 | -0.003 | -0.044 | -0.005 |

*FIG. 113A*

| | | | | | |
|---|---|---|---|---|---|
| TCRBV083_8 | 0.004 | -0.035 | -0.002 | -0.036 | -0.000 |
| TCRBV083_9 | -0.016 | 0.012 | -0.028 | 0.005 | -0.008 |
| TCRBV083_10 | -0.015 | 0.023 | 0.003 | 0.031 | 0.008 |
| TCRBV083_11 | -0.002 | 0.002 | 0.017 | 0.022 | 0.005 |
| TCRBV083_12 | 0.008 | -0.002 | 0.013 | 0.019 | -0.004 |
| TCRBV09_5 | 0.004 | -0.001 | 0.005 | -0.002 | 0.002 |
| TCRBV09_6 | 0.006 | 0.010 | 0.003 | -0.002 | 0.018 |
| TCRBV09_7 | 0.014 | -0.021 | -0.041 | 0.034 | 0.003 |
| TCRBV09_8 | -0.027 | -0.005 | 0.017 | -0.046 | 0.021 |
| TCRBV09_9 | -0.011 | 0.011 | -0.004 | 0.005 | 0.006 |
| TCRBV09_10 | -0.014 | -0.016 | 0.007 | -0.007 | -0.001 |
| TCRBV09_11 | -0.006 | -0.006 | 0.033 | -0.001 | -0.031 |
| TCRBV09_12 | 0.001 | 0.012 | 0.003 | 0.026 | 0.040 |
| TCRBV09_13 | 0.006 | 0.008 | 0.007 | -0.000 | 0.026 |
| TCRBV09_14 | 0.003 | 0.005 | 0.008 | 0.007 | 0.019 |
| TCRBV09_15 | 0.003 | 0.001 | -0.002 | 0.003 | 0.006 |
| TCRBV10_6 | -0.004 | 0.001 | -0.001 | 0.006 | 0.019 |
| TCRBV10_7 | -0.006 | 0.019 | -0.016 | -0.015 | -0.000 |
| TCRBV10_8 | 0.017 | 0.007 | -0.007 | -0.033 | -0.006 |
| TCRBV10_9 | -0.001 | 0.009 | 0.013 | -0.000 | 0.014 |
| TCRBV10_10 | -0.004 | -0.028 | -0.014 | 0.007 | -0.006 |
| TCRBV10_11 | -0.006 | -0.001 | 0.016 | 0.037 | -0.025 |
| TCRBV10_12 | 0.004 | -0.008 | 0.010 | -0.001 | 0.004 |
| TCRBV10_13 | 0.000 | 0.000 | -0.001 | -0.001 | -0.000 |
| TCRBV11_5 | -0.003 | -0.006 | 0.000 | 0.012 | 0.007 |
| TCRBV11_6 | 0.000 | 0.013 | -0.012 | 0.027 | 0.010 |
| TCRBV11_7 | -0.007 | -0.007 | -0.004 | -0.001 | -0.001 |
| TCRBV11_8 | 0.022 | -0.006 | -0.018 | -0.011 | -0.023 |
| TCRBV11_9 | 0.025 | 0.007 | -0.020 | -0.002 | 0.007 |
| TCRBV11_10 | -0.003 | 0.009 | 0.002 | -0.023 | -0.026 |
| TCRBV11_11 | -0.010 | 0.004 | 0.012 | -0.008 | 0.004 |
| TCRBV11_12 | -0.013 | -0.010 | 0.022 | 0.002 | 0.006 |
| TCRBV11_13 | -0.005 | 0.001 | 0.008 | -0.002 | 0.008 |
| TCRBV11_14 | 0.001 | 0.001 | -0.004 | -0.004 | -0.002 |
| TCRBV11_15 | 0.000 | 0.001 | -0.001 | -0.001 | -0.001 |
| TCRBV12_4 | -0.003 | -0.008 | -0.001 | 0.002 | -0.006 |
| TCRBV12_5 | 0.005 | 0.011 | 0.006 | -0.004 | 0.011 |
| TCRBV12_6 | -0.020 | 0.021 | 0.026 | -0.006 | -0.023 |
| TCRBV12_7 | -0.004 | 0.029 | 0.008 | 0.024 | -0.021 |
| TCRBV12_8 | 0.034 | -0.001 | -0.009 | 0.005 | 0.002 |
| TCRBV12_9 | -0.014 | -0.028 | -0.014 | 0.014 | -0.009 |
| TCRBV12_10 | 0.012 | 0.006 | -0.015 | -0.009 | 0.026 |
| TCRBV12_11 | -0.016 | -0.030 | -0.002 | -0.017 | 0.016 |
| TCRBV12_12 | 0.006 | 0.001 | 0.001 | -0.008 | 0.003 |
| TCRBV13_5 | 0.001 | 0.006 | -0.001 | 0.003 | 0.004 |
| TCRBV13_6 | -0.030 | 0.001 | 0.002 | 0.022 | 0.005 |
| TCRBV13_7 | -0.007 | -0.006 | 0.010 | 0.022 | 0.012 |
| TCRBV13_8 | -0.003 | -0.004 | 0.012 | 0.006 | -0.003 |
| TCRBV13_9 | -0.003 | -0.047 | 0.011 | 0.002 | 0.008 |
| TCRBV13_10 | 0.020 | 0.001 | 0.002 | -0.027 | -0.018 |
| TCRBV13_11 | 0.016 | 0.029 | -0.020 | -0.005 | 0.013 |
| TCRBV13_12 | 0.005 | 0.011 | -0.025 | -0.006 | -0.016 |
| TCRBV13_13 | 0.001 | 0.009 | 0.009 | -0.016 | -0.005 |
| TCRBV14_5 | -0.000 | 0.003 | 0.001 | 0.002 | 0.004 |
| TCRBV14_6 | 0.003 | 0.001 | 0.010 | -0.002 | -0.003 |
| TCRBV14_7 | -0.002 | -0.007 | -0.007 | 0.011 | 0.010 |
| TCRBV14_8 | 0.001 | 0.004 | -0.014 | 0.009 | -0.011 |
| TCRBV14_9 | -0.009 | -0.020 | -0.001 | 0.008 | -0.021 |
| TCRBV14_10 | 0.009 | 0.019 | -0.007 | -0.010 | -0.008 |
| TCRBV14_11 | 0.001 | 0.000 | 0.010 | -0.022 | 0.032 |
| TCRBV14_12 | -0.003 | -0.001 | 0.009 | 0.007 | -0.002 |
| TCRBV14_13 | 0.000 | 0.001 | -0.001 | -0.002 | -0.001 |
| TCRBV15_4 | -0.001 | -0.005 | 0.015 | 0.001 | 0.006 |
| TCRBV15_5 | 0.007 | 0.002 | -0.019 | -0.020 | -0.010 |

*FIG. 113B*

| | | | | | |
|---|---|---|---|---|---|
| TCRBV15_6 | 0.004 | 0.004 | 0.020 | -0.003 | 0.004 |
| TCRBV15_7 | -0.006 | 0.009 | 0.015 | 0.005 | 0.010 |
| TCRBV15_8 | 0.023 | -0.022 | 0.023 | 0.020 | -0.039 |
| TCRBV15_9 | -0.033 | 0.013 | -0.019 | 0.002 | 0.013 |
| TCRBV15_10 | 0.005 | 0.010 | -0.036 | -0.021 | -0.001 |
| TCRBV15_11 | 0.007 | 0.001 | -0.014 | 0.005 | 0.005 |
| TCRBV15_12 | 0.001 | -0.005 | 0.001 | -0.000 | 0.003 |
| TCRBV16_5 | 0.001 | 0.004 | 0.003 | 0.001 | -0.009 |
| TCRBV16_6 | -0.009 | -0.012 | 0.002 | 0.023 | -0.018 |
| TCRBV16_7 | 0.022 | 0.003 | 0.037 | 0.021 | -0.036 |
| TCRBV16_8 | -0.032 | -0.013 | 0.036 | -0.020 | -0.009 |
| TCRBV16_9 | 0.018 | -0.011 | -0.041 | -0.011 | 0.054 |
| TCRBV16_10 | 0.000 | -0.011 | 0.006 | 0.020 | 0.000 |
| TCRBV16_11 | 0.009 | 0.001 | -0.031 | 0.000 | -0.009 |
| TCRBV16_12 | -0.006 | 0.003 | -0.020 | 0.009 | 0.052 |
| TCRBV16_13 | 0.004 | -0.003 | -0.001 | 0.002 | 0.000 |
| TCRBV18_3 | 0.001 | -0.001 | -0.002 | 0.001 | 0.001 |
| TCRBV18_4 | 0.003 | 0.008 | 0.006 | 0.002 | -0.015 |
| TCRBV18_5 | -0.001 | 0.012 | 0.013 | -0.007 | 0.036 |
| TCRBV18_6 | -0.023 | -0.008 | 0.018 | -0.004 | 0.009 |
| TCRBV18_7 | 0.062 | -0.022 | 0.010 | 0.035 | 0.045 |
| TCRBV18_8 | 0.001 | -0.015 | 0.030 | 0.008 | 0.018 |
| TCRBV18_9 | 0.013 | 0.013 | 0.021 | -0.018 | 0.012 |
| TCRBV18_10 | 0.005 | 0.015 | 0.015 | -0.003 | 0.013 |
| TCRBV18_11 | 0.007 | 0.022 | -0.017 | -0.008 | 0.001 |
| TCRBV18_12 | -0.000 | -0.001 | -0.002 | 0.002 | -0.004 |
| TCRBV18_13 | -0.003 | -0.004 | -0.001 | 0.000 | -0.000 |
| TCRBV20_5 | -0.004 | -0.004 | 0.001 | 0.008 | 0.010 |
| TCRBV20_6 | -0.022 | 0.009 | -0.010 | 0.039 | 0.010 |
| TCRBV20_7 | -0.013 | 0.003 | -0.001 | 0.004 | 0.007 |
| TCRBV20_8 | 0.007 | 0.009 | -0.008 | -0.014 | -0.003 |
| TCRBV20_9 | -0.005 | 0.007 | -0.036 | 0.018 | -0.011 |
| TCRBV20_10 | -0.014 | -0.020 | 0.003 | -0.032 | 0.005 |
| TCRBV20_11 | 0.020 | 0.004 | 0.016 | -0.013 | -0.023 |
| TCRBV20_12 | 0.029 | 0.005 | 0.007 | -0.008 | -0.002 |
| TCRBV20_13 | 0.010 | -0.002 | 0.001 | -0.013 | -0.009 |
| TCRBV20_14 | -0.001 | -0.004 | 0.012 | 0.000 | 0.005 |
| | 36 | 37 | 38 | 39 | 40 |
| TCRBV01_6 | -0.004 | -0.000 | -0.003 | -0.001 | 0.003 |
| TCRBV01_7 | -0.001 | -0.010 | 0.004 | 0.017 | 0.013 |
| TCRBV01_8 | -0.031 | 0.010 | -0.008 | 0.014 | 0.030 |
| TCRBV01_9 | 0.001 | -0.015 | -0.006 | 0.056 | 0.019 |
| TCRBV01_10 | -0.006 | -0.018 | 0.010 | -0.060 | 0.027 |
| TCRBV01_11 | 0.036 | 0.023 | -0.014 | -0.019 | -0.043 |
| TCRBV01_12 | 0.033 | 0.003 | 0.020 | -0.017 | -0.026 |
| TCRBV01_13 | 0.007 | 0.006 | 0.006 | -0.006 | -0.021 |
| TCRBV01_14 | 0.001 | -0.001 | -0.000 | 0.001 | 0.001 |
| TCRBV02_6 | 0.001 | 0.003 | 0.006 | 0.021 | -0.002 |
| TCRBV02_7 | 0.010 | -0.015 | 0.011 | 0.015 | -0.007 |
| TCRBV02_8 | 0.004 | -0.023 | 0.003 | -0.029 | -0.021 |
| TCRBV02_9 | -0.001 | 0.002 | 0.008 | -0.009 | 0.013 |
| TCRBV02_10 | -0.003 | -0.021 | 0.011 | 0.007 | 0.002 |
| TCRBV02_11 | 0.007 | -0.024 | -0.035 | 0.025 | 0.028 |
| TCRBV02_12 | -0.006 | 0.010 | 0.006 | 0.017 | -0.004 |
| TCRBV02_13 | -0.012 | 0.003 | 0.001 | -0.002 | 0.004 |
| TCRBV03_4 | -0.000 | 0.002 | -0.000 | -0.001 | -0.000 |
| TCRBV03_5 | -0.000 | -0.002 | -0.001 | 0.002 | 0.000 |
| TCRBV03_6 | 0.014 | 0.026 | -0.002 | -0.015 | -0.008 |
| TCRBV03_7 | 0.009 | 0.007 | -0.003 | -0.036 | -0.015 |
| TCRBV03_8 | 0.002 | 0.003 | -0.025 | 0.001 | -0.038 |
| TCRBV03_9 | -0.020 | -0.012 | -0.006 | 0.036 | -0.035 |
| TCRBV03_10 | 0.017 | 0.017 | 0.022 | -0.018 | 0.048 |

*FIG. 113C*

| | | | | | |
|---|---|---|---|---|---|
| TCRBV03_11 | -0.026 | -0.021 | 0.020 | 0.017 | 0.006 |
| TCRBV03_12 | 0.017 | -0.022 | 0.012 | 0.010 | 0.035 |
| TCRBV03_13 | 0.023 | 0.000 | -0.008 | -0.009 | 0.010 |
| TCRBV04_6 | -0.001 | -0.001 | 0.001 | -0.003 | 0.002 |
| TCRBV04_7 | 0.009 | -0.008 | 0.018 | -0.014 | 0.002 |
| TCRBV04_8 | -0.022 | -0.022 | 0.007 | 0.011 | -0.001 |
| TCRBV04_9 | -0.048 | 0.000 | -0.015 | 0.012 | 0.036 |
| TCRBV04_10 | 0.017 | -0.026 | -0.041 | -0.014 | 0.023 |
| TCRBV04_11 | 0.013 | 0.033 | -0.018 | -0.012 | 0.017 |
| TCRBV04_12 | 0.033 | -0.020 | 0.047 | 0.017 | 0.006 |
| TCRBV04_13 | 0.006 | -0.005 | -0.008 | 0.010 | -0.052 |
| TCRBV04_14 | -0.012 | 0.051 | -0.001 | -0.005 | -0.003 |
| TCRBV04_15 | 0.003 | -0.001 | 0.010 | -0.002 | -0.030 |
| TCRBV051_5 | 0.005 | 0.012 | -0.015 | 0.007 | -0.011 |
| TCRBV051_6 | 0.012 | 0.031 | -0.016 | -0.015 | 0.029 |
| TCRBV051_7 | 0.010 | 0.017 | -0.020 | 0.036 | 0.006 |
| TCRBV051_8 | 0.014 | 0.004 | 0.015 | 0.009 | -0.023 |
| TCRBV051_9 | -0.037 | -0.017 | -0.047 | 0.000 | -0.003 |
| TCRBV051_10 | -0.006 | -0.025 | 0.048 | 0.015 | 0.005 |
| TCRBV051_11 | -0.035 | -0.030 | 0.021 | 0.006 | -0.045 |
| TCRBV051_12 | 0.028 | 0.017 | 0.032 | -0.001 | -0.015 |
| TCRBV051_13 | 0.005 | -0.001 | 0.025 | 0.024 | 0.022 |
| TCRBV052_6 | 0.019 | 0.019 | 0.022 | 0.026 | 0.027 |
| TCRBV052_7 | 0.002 | -0.010 | -0.048 | -0.009 | -0.000 |
| TCRBV052_8 | 0.001 | -0.004 | 0.001 | 0.005 | -0.021 |
| TCRBV052_9 | -0.011 | 0.034 | 0.025 | 0.017 | -0.004 |
| TCRBV052_10 | 0.007 | -0.022 | 0.018 | 0.030 | 0.008 |
| TCRBV052_11 | -0.013 | 0.001 | 0.014 | 0.013 | -0.039 |
| TCRBV052_12 | -0.003 | -0.011 | 0.008 | 0.002 | -0.007 |
| TCRBV052_13 | -0.005 | 0.001 | 0.003 | -0.001 | 0.003 |
| TCRBV06_5 | 0.004 | -0.002 | 0.002 | -0.007 | 0.001 |
| TCRBV06_6 | 0.015 | -0.016 | 0.003 | -0.003 | -0.005 |
| TCRBV06_7 | 0.017 | -0.017 | -0.016 | 0.004 | -0.019 |
| TCRBV06_8 | 0.026 | 0.021 | -0.016 | 0.001 | 0.001 |
| TCRBV06_9 | -0.024 | 0.016 | 0.007 | 0.001 | 0.002 |
| TCRBV06_10 | -0.008 | 0.002 | 0.035 | 0.008 | -0.031 |
| TCRBV06_11 | -0.015 | -0.004 | -0.004 | 0.003 | 0.016 |
| TCRBV06_12 | 0.021 | -0.001 | -0.014 | -0.017 | 0.035 |
| TCRBV06_13 | 0.002 | -0.001 | 0.014 | -0.005 | 0.004 |
| TCRBV07_5 | -0.001 | 0.003 | -0.003 | 0.001 | 0.001 |
| TCRBV07_6 | 0.012 | 0.011 | 0.000 | 0.007 | -0.022 |
| TCRBV07_7 | -0.014 | -0.019 | 0.007 | 0.010 | -0.042 |
| TCRBV07_8 | 0.021 | 0.042 | 0.007 | -0.030 | 0.000 |
| TCRBV07_9 | -0.018 | 0.007 | 0.018 | -0.024 | 0.022 |
| TCRBV07_10 | 0.021 | -0.023 | 0.002 | 0.020 | 0.017 |
| TCRBV07_11 | -0.007 | -0.028 | 0.000 | 0.008 | 0.021 |
| TCRBV07_12 | 0.023 | 0.012 | -0.019 | -0.010 | 0.004 |
| TCRBV07_13 | -0.001 | -0.007 | -0.003 | 0.003 | 0.002 |
| TCRBV081_5 | 0.005 | 0.002 | 0.004 | -0.015 | -0.008 |
| TCRBV081_6 | 0.010 | -0.011 | 0.009 | -0.014 | -0.002 |
| TCRBV081_7 | -0.005 | -0.015 | -0.004 | -0.015 | 0.003 |
| TCRBV081_8 | 0.011 | -0.000 | 0.015 | 0.016 | 0.033 |
| TCRBV081_9 | 0.022 | -0.000 | -0.028 | 0.017 | -0.019 |
| TCRBV081_10 | -0.041 | 0.019 | -0.041 | -0.023 | 0.034 |
| TCRBV081_11 | 0.004 | 0.017 | 0.023 | 0.009 | 0.019 |
| TCRBV081_12 | -0.005 | -0.011 | 0.022 | 0.025 | -0.059 |
| TCRBV082_4 | 0.008 | -0.001 | 0.016 | 0.030 | 0.001 |
| TCRBV082_5 | 0.002 | 0.014 | 0.016 | -0.009 | -0.007 |
| TCRBV082_6 | 0.022 | -0.015 | 0.004 | 0.001 | -0.012 |
| TCRBV082_7 | -0.005 | 0.025 | 0.006 | -0.023 | 0.014 |
| TCRBV082_8 | 0.003 | -0.035 | -0.014 | 0.006 | 0.034 |
| TCRBV082_9 | -0.008 | 0.009 | -0.016 | -0.014 | -0.027 |
| TCRBV082_10 | -0.018 | -0.000 | -0.015 | 0.005 | -0.007 |

*FIG. 113D*

| Label | | | | | |
|---|---|---|---|---|---|
| TCRBV082_11 | -0.005 | 0.003 | 0.002 | 0.004 | 0.005 |
| TCRBV083_4 | 0.002 | -0.000 | -0.001 | -0.001 | 0.001 |
| TCRBV083_5 | 0.023 | 0.013 | 0.002 | -0.005 | 0.005 |
| TCRBV083_6 | 0.005 | 0.017 | -0.000 | -0.002 | 0.012 |
| TCRBV083_7 | 0.009 | 0.018 | 0.005 | -0.024 | 0.000 |
| TCRBV083_8 | -0.019 | -0.001 | 0.005 | -0.003 | -0.038 |
| TCRBV083_9 | -0.007 | -0.034 | 0.000 | 0.040 | 0.026 |
| TCRBV083_10 | 0.003 | -0.012 | -0.006 | 0.016 | -0.008 |
| TCRBV083_11 | -0.021 | -0.006 | 0.003 | -0.015 | 0.003 |
| TCRBV083_12 | 0.007 | 0.006 | -0.009 | -0.007 | 0.000 |
| TCRBV09_5 | 0.001 | 0.001 | 0.009 | -0.003 | 0.003 |
| TCRBV09_6 | 0.010 | 0.000 | -0.014 | 0.009 | -0.007 |
| TCRBV09_7 | -0.014 | 0.011 | -0.003 | 0.042 | -0.025 |
| TCRBV09_8 | 0.002 | 0.002 | 0.046 | -0.001 | -0.018 |
| TCRBV09_9 | 0.005 | -0.036 | 0.045 | -0.019 | -0.025 |
| TCRBV09_10 | -0.057 | 0.037 | -0.058 | 0.047 | 0.001 |
| TCRBV09_11 | 0.028 | 0.008 | -0.033 | -0.016 | 0.013 |
| TCRBV09_12 | -0.001 | -0.008 | 0.043 | -0.064 | 0.014 |
| TCRBV09_13 | -0.007 | -0.002 | 0.014 | -0.016 | -0.021 |
| TCRBV09_14 | -0.001 | -0.004 | -0.012 | 0.006 | 0.007 |
| TCRBV09_15 | -0.003 | 0.005 | -0.001 | -0.004 | -0.001 |
| TCRBV10_6 | 0.019 | 0.001 | 0.016 | 0.030 | 0.009 |
| TCRBV10_7 | -0.021 | 0.017 | 0.026 | 0.033 | -0.016 |
| TCRBV10_8 | 0.005 | -0.014 | -0.011 | -0.003 | -0.001 |
| TCRBV10_9 | -0.014 | 0.031 | 0.006 | -0.031 | -0.009 |
| TCRBV10_10 | 0.013 | -0.009 | -0.009 | -0.021 | 0.056 |
| TCRBV10_11 | 0.001 | -0.005 | -0.017 | 0.004 | -0.036 |
| TCRBV10_12 | -0.004 | -0.021 | -0.011 | -0.011 | -0.003 |
| TCRBV10_13 | -0.000 | 0.001 | -0.000 | -0.001 | -0.000 |
| TCRBV11_5 | 0.006 | -0.004 | 0.004 | -0.000 | -0.006 |
| TCRBV11_6 | 0.018 | -0.000 | -0.007 | 0.011 | -0.024 |
| TCRBV11_7 | 0.024 | -0.021 | -0.020 | 0.017 | -0.002 |
| TCRBV11_8 | 0.035 | -0.038 | -0.016 | -0.029 | 0.015 |
| TCRBV11_9 | 0.013 | 0.003 | -0.021 | -0.001 | -0.015 |
| TCRBV11_10 | 0.002 | 0.019 | 0.024 | -0.002 | 0.008 |
| TCRBV11_11 | -0.014 | 0.005 | 0.008 | 0.003 | 0.012 |
| TCRBV11_12 | -0.029 | 0.024 | 0.041 | -0.007 | 0.018 |
| TCRBV11_13 | -0.017 | 0.003 | -0.002 | -0.004 | -0.002 |
| TCRBV11_14 | -0.000 | 0.004 | -0.001 | -0.003 | -0.001 |
| TCRBV11_15 | -0.000 | 0.001 | -0.000 | -0.001 | -0.000 |
| TCRBV12_4 | -0.007 | 0.003 | -0.006 | 0.017 | -0.015 |
| TCRBV12_5 | 0.002 | -0.016 | 0.008 | 0.001 | -0.010 |
| TCRBV12_6 | -0.004 | 0.008 | 0.023 | -0.010 | -0.008 |
| TCRBV12_7 | -0.006 | 0.025 | 0.017 | 0.001 | 0.021 |
| TCRBV12_8 | 0.022 | 0.034 | 0.006 | 0.003 | 0.032 |
| TCRBV12_9 | -0.006 | -0.035 | -0.012 | -0.007 | -0.002 |
| TCRBV12_10 | -0.010 | -0.023 | 0.027 | -0.023 | 0.026 |
| TCRBV12_11 | 0.013 | 0.006 | -0.040 | 0.009 | -0.021 |
| TCRBV12_12 | -0.003 | -0.003 | -0.022 | 0.010 | -0.022 |
| TCRBV13_5 | 0.007 | 0.003 | -0.001 | -0.002 | -0.004 |
| TCRBV13_6 | 0.018 | 0.014 | -0.013 | 0.017 | 0.006 |
| TCRBV13_7 | 0.050 | 0.006 | -0.008 | 0.006 | -0.018 |
| TCRBV13_8 | -0.048 | -0.034 | 0.013 | -0.070 | -0.027 |
| TCRBV13_9 | -0.023 | 0.026 | 0.021 | 0.038 | 0.068 |
| TCRBV13_10 | 0.000 | 0.004 | 0.006 | 0.007 | 0.011 |
| TCRBV13_11 | -0.001 | -0.009 | -0.024 | -0.002 | -0.015 |
| TCRBV13_12 | 0.006 | -0.007 | -0.008 | 0.002 | 0.006 |
| TCRBV13_13 | -0.009 | -0.002 | 0.015 | 0.005 | -0.025 |
| TCRBV14_5 | 0.000 | -0.001 | -0.003 | -0.003 | -0.006 |
| TCRBV14_6 | 0.010 | -0.005 | 0.005 | -0.010 | 0.004 |
| TCRBV14_7 | 0.004 | 0.001 | -0.002 | 0.013 | -0.013 |
| TCRBV14_8 | -0.012 | -0.000 | -0.003 | -0.010 | 0.044 |
| TCRBV14_9 | -0.004 | 0.021 | 0.014 | -0.048 | -0.039 |
| TCRBV14_10 | 0.006 | -0.037 | -0.023 | 0.047 | 0.014 |

*FIG. 114A*

|            |        |        |        |        |        |
|------------|--------|--------|--------|--------|--------|
| TCRBV14_11 |  0.001 |  0.018 |  0.014 |  0.016 | -0.011 |
| TCRBV14_12 | -0.005 |  0.001 |  0.000 | -0.003 |  0.007 |
| TCRBV14_13 |  0.000 |  0.001 | -0.001 | -0.002 |  0.000 |
| TCRBV15_4  | -0.011 | -0.000 |  0.000 | -0.001 |  0.001 |
| TCRBV15_5  |  0.007 | -0.008 |  0.011 |  0.006 | -0.001 |
| TCRBV15_6  | -0.029 | -0.011 | -0.011 | -0.029 | -0.000 |
| TCRBV15_7  |  0.014 |  0.039 | -0.007 | -0.011 |  0.010 |
| TCRBV15_8  |  0.022 | -0.048 | -0.005 | -0.045 |  0.019 |
| TCRBV15_9  | -0.025 |  0.003 | -0.003 |  0.014 | -0.034 |
| TCRBV15_10 |  0.031 |  0.022 |  0.023 |  0.039 |  0.012 |
| TCRBV15_11 |  0.026 |  0.007 |  0.002 |  0.010 | -0.003 |
| TCRBV15_12 |  0.002 | -0.007 |  0.000 |  0.003 | -0.001 |
| TCRBV16_5  |  0.002 |  0.002 |  0.006 |  0.006 | -0.012 |
| TCRBV16_6  |  0.015 |  0.008 | -0.025 | -0.007 | -0.001 |
| TCRBV16_7  |  0.029 |  0.025 |  0.057 |  0.062 | -0.014 |
| TCRBV16_8  |  0.007 | -0.042 |  0.011 |  0.037 |  0.013 |
| TCRBV16_9  |  0.001 |  0.005 |  0.016 | -0.027 |  0.007 |
| TCRBV16_10 | -0.028 |  0.045 |  0.007 |  0.007 | -0.008 |
| TCRBV16_11 | -0.011 | -0.021 | -0.039 |  0.001 | -0.011 |
| TCRBV16_12 |  0.021 | -0.019 |  0.014 | -0.009 | -0.010 |
| TCRBV16_13 | -0.002 |  0.002 |  0.005 | -0.001 |  0.004 |
| TCRBV18_3  | -0.001 |  0.001 |  0.000 |  0.003 | -0.000 |
| TCRBV18_4  |  0.009 | -0.002 | -0.011 |  0.000 |  0.007 |
| TCRBV18_5  |  0.002 |  0.003 | -0.019 |  0.004 | -0.008 |
| TCRBV18_6  | -0.018 |  0.008 |  0.014 | -0.006 |  0.009 |
| TCRBV18_7  |  0.020 |  0.031 | -0.046 |  0.015 | -0.029 |
| TCRBV18_8  |  0.030 | -0.024 | -0.019 |  0.010 |  0.007 |
| TCRBV18_9  |  0.004 |  0.018 | -0.014 | -0.013 |  0.050 |
| TCRBV18_10 |  0.004 |  0.011 |  0.013 | -0.027 | -0.014 |
| TCRBV18_11 |  0.011 |  0.001 |  0.013 |  0.003 |  0.001 |
| TCRBV18_12 | -0.002 | -0.001 |  0.001 | -0.001 |  0.002 |
| TCRBV18_13 |  0.003 |  0.001 | -0.001 | -0.009 | -0.007 |
| TCRBV20_5  |  0.002 | -0.006 |  0.002 | -0.007 | -0.005 |
| TCRBV20_6  |  0.012 | -0.016 |  0.004 |  0.001 |  0.003 |
| TCRBV20_7  |  0.019 |  0.009 | -0.029 | -0.002 | -0.026 |
| TCRBV20_8  |  0.009 |  0.007 |  0.004 |  0.018 | -0.008 |
| TCRBV20_9  | -0.050 | -0.002 |  0.004 |  0.012 |  0.017 |
| TCRBV20_10 |  0.015 | -0.010 |  0.020 |  0.013 |  0.049 |
| TCRBV20_11 |  0.014 |  0.017 | -0.041 | -0.023 | -0.011 |
| TCRBV20_12 |  0.008 | -0.000 |  0.031 | -0.038 | -0.018 |
| TCRBV20_13 |  0.018 |  0.000 |  0.015 |  0.012 |  0.001 |
| TCRBV20_14 | -0.009 | -0.000 |  0.000 | -0.001 |  0.001 |

|            | 41     | 42     | 43     | 44     | 45     |
|------------|--------|--------|--------|--------|--------|
| TCRBV01_6  | -0.001 |  0.004 | -0.005 |  0.001 |  0.003 |
| TCRBV01_7  |  0.017 | -0.018 | -0.033 | -0.012 |  0.001 |
| TCRBV01_8  | -0.011 | -0.048 | -0.017 |  0.053 | -0.006 |
| TCRBV01_9  |  0.018 |  0.015 |  0.014 | -0.056 | -0.022 |
| TCRBV01_10 | -0.020 |  0.017 |  0.031 |  0.027 | -0.036 |
| TCRBV01_11 |  0.026 |  0.007 | -0.003 | -0.046 | -0.010 |
| TCRBV01_12 |  0.001 |  0.019 | -0.000 |  0.008 |  0.052 |
| TCRBV01_13 | -0.000 |  0.009 |  0.009 |  0.005 |  0.011 |
| TCRBV01_14 |  0.001 |  0.000 |  0.001 | -0.001 | -0.001 |
| TCRBV02_6  |  0.014 | -0.027 |  0.021 |  0.000 | -0.001 |
| TCRBV02_7  | -0.003 | -0.017 |  0.004 | -0.033 |  0.004 |
| TCRBV02_8  |  0.009 |  0.046 | -0.043 | -0.012 | -0.026 |
| TCRBV02_9  |  0.002 | -0.002 | -0.002 |  0.024 |  0.013 |
| TCRBV02_10 | -0.003 | -0.024 | -0.003 |  0.001 |  0.003 |
| TCRBV02_11 | -0.000 | -0.012 |  0.024 | -0.014 | -0.043 |
| TCRBV02_12 |  0.025 |  0.010 | -0.047 |  0.002 | -0.010 |
| TCRBV02_13 |  0.001 | -0.012 | -0.002 |  0.000 | -0.014 |
| TCRBV03_4  | -0.001 |  0.001 |  0.001 |  0.001 |  0.002 |
| TCRBV03_5  | -0.002 |  0.002 |  0.001 | -0.000 |  0.003 |

*FIG. 114B*

| | | | | | |
|---|---|---|---|---|---|
| TCRBV03_6 | 0.014 | -0.012 | 0.039 | 0.026 | 0.006 |
| TCRBV03_7 | 0.024 | -0.030 | 0.049 | -0.043 | 0.008 |
| TCRBV03_8 | 0.002 | 0.018 | 0.017 | 0.024 | -0.006 |
| TCRBV03_9 | -0.025 | -0.022 | -0.020 | 0.003 | -0.022 |
| TCRBV03_10 | 0.020 | 0.009 | -0.009 | -0.006 | 0.009 |
| TCRBV03_11 | -0.019 | 0.040 | -0.041 | 0.008 | 0.027 |
| TCRBV03_12 | -0.008 | 0.026 | -0.020 | -0.001 | 0.007 |
| TCRBV03_13 | 0.025 | -0.026 | -0.019 | -0.031 | -0.044 |
| TCRBV04_6 | 0.003 | 0.004 | 0.003 | 0.001 | -0.010 |
| TCRBV04_7 | 0.010 | 0.005 | 0.037 | 0.016 | -0.003 |
| TCRBV04_8 | -0.005 | 0.035 | -0.021 | -0.012 | 0.013 |
| TCRBV04_9 | -0.001 | 0.037 | 0.004 | 0.056 | -0.074 |
| TCRBV04_10 | -0.021 | -0.002 | -0.022 | -0.022 | 0.084 |
| TCRBV04_11 | 0.003 | -0.059 | 0.028 | -0.027 | 0.010 |
| TCRBV04_12 | -0.006 | -0.010 | -0.005 | -0.032 | 0.004 |
| TCRBV04_13 | 0.015 | -0.010 | -0.054 | -0.023 | -0.024 |
| TCRBV04_14 | 0.005 | -0.006 | 0.030 | 0.033 | 0.031 |
| TCRBV04_15 | -0.005 | 0.006 | 0.001 | 0.010 | -0.031 |
| TCRBV051_5 | -0.018 | 0.012 | 0.025 | -0.018 | 0.029 |
| TCRBV051_6 | -0.024 | 0.020 | 0.047 | 0.027 | 0.026 |
| TCRBV051_7 | -0.052 | 0.009 | -0.015 | 0.048 | -0.031 |
| TCRBV051_8 | -0.020 | -0.021 | 0.007 | -0.028 | 0.005 |
| TCRBV051_9 | 0.006 | -0.038 | -0.037 | 0.012 | -0.003 |
| TCRBV051_10 | 0.051 | 0.009 | 0.007 | -0.006 | 0.047 |
| TCRBV051_11 | 0.063 | -0.022 | 0.011 | 0.046 | -0.009 |
| TCRBV051_12 | -0.053 | 0.025 | -0.052 | -0.038 | -0.087 |
| TCRBV051_13 | -0.011 | 0.014 | 0.051 | -0.031 | 0.021 |
| TCRBV052_6 | -0.006 | -0.026 | 0.020 | 0.022 | 0.025 |
| TCRBV052_7 | -0.019 | -0.008 | -0.002 | 0.032 | -0.048 |
| TCRBV052_8 | 0.003 | -0.030 | 0.023 | 0.019 | -0.003 |
| TCRBV052_9 | 0.015 | 0.040 | 0.027 | -0.013 | -0.046 |
| TCRBV052_10 | -0.052 | -0.002 | -0.030 | -0.015 | 0.029 |
| TCRBV052_11 | 0.015 | 0.008 | -0.014 | -0.020 | 0.036 |
| TCRBV052_12 | -0.016 | 0.014 | 0.008 | -0.015 | 0.022 |
| TCRBV052_13 | 0.001 | 0.011 | 0.009 | 0.001 | -0.015 |
| TCRBV06_5 | 0.015 | -0.016 | 0.009 | -0.006 | 0.003 |
| TCRBV06_6 | 0.008 | -0.010 | -0.009 | 0.002 | 0.005 |
| TCRBV06_7 | 0.017 | 0.004 | -0.010 | -0.014 | -0.001 |
| TCRBV06_8 | 0.003 | 0.013 | -0.046 | 0.029 | -0.005 |
| TCRBV06_9 | -0.015 | -0.043 | -0.046 | -0.028 | 0.016 |
| TCRBV06_10 | 0.003 | -0.014 | 0.075 | 0.005 | -0.051 |
| TCRBV06_11 | -0.010 | 0.040 | 0.039 | -0.028 | 0.036 |
| TCRBV06_12 | 0.008 | 0.026 | -0.024 | 0.021 | -0.003 |
| TCRBV06_13 | 0.002 | 0.006 | 0.008 | -0.001 | -0.009 |
| TCRBV07_5 | -0.006 | -0.007 | 0.002 | 0.008 | 0.010 |
| TCRBV07_6 | 0.038 | -0.007 | -0.009 | 0.010 | -0.023 |
| TCRBV07_7 | 0.009 | -0.001 | -0.008 | 0.039 | -0.001 |
| TCRBV07_8 | -0.010 | -0.028 | 0.002 | -0.028 | 0.030 |
| TCRBV07_9 | -0.004 | -0.005 | -0.011 | 0.005 | -0.005 |
| TCRBV07_10 | 0.008 | 0.009 | 0.011 | -0.033 | 0.019 |
| TCRBV07_11 | 0.000 | 0.027 | 0.017 | -0.033 | -0.005 |
| TCRBV07_12 | -0.006 | 0.016 | -0.005 | 0.013 | -0.035 |
| TCRBV07_13 | 0.000 | 0.000 | -0.002 | -0.002 | 0.001 |
| TCRBV081_5 | -0.009 | 0.004 | 0.002 | 0.007 | 0.015 |
| TCRBV081_6 | -0.027 | 0.010 | 0.024 | 0.027 | -0.009 |
| TCRBV081_7 | 0.013 | -0.027 | -0.018 | -0.031 | -0.000 |
| TCRBV081_8 | -0.047 | -0.002 | -0.028 | -0.064 | -0.036 |
| TCRBV081_9 | 0.036 | 0.013 | 0.010 | 0.047 | -0.008 |
| TCRBV081_10 | 0.010 | 0.011 | -0.002 | -0.001 | 0.008 |
| TCRBV081_11 | 0.021 | -0.002 | -0.001 | -0.006 | 0.002 |
| TCRBV081_12 | 0.002 | -0.008 | 0.013 | 0.021 | 0.028 |
| TCRBV082_4 | 0.010 | -0.011 | 0.016 | 0.007 | -0.013 |
| TCRBV082_5 | -0.002 | 0.005 | -0.014 | 0.011 | 0.018 |
| TCRBV082_6 | -0.010 | 0.001 | 0.001 | -0.007 | -0.020 |

*FIG. 114C*

| | | | | | |
|---|---|---|---|---|---|
| TCRBV082_7 | -0.003 | 0.000 | -0.003 | -0.078 | -0.037 |
| TCRBV082_8 | -0.006 | 0.001 | 0.030 | -0.005 | -0.081 |
| TCRBV082_9 | -0.009 | 0.005 | -0.040 | 0.042 | 0.050 |
| TCRBV082_10 | 0.010 | 0.015 | 0.016 | 0.035 | 0.022 |
| TCRBV082_11 | 0.010 | -0.016 | -0.007 | -0.006 | 0.060 |
| TCRBV083_4 | 0.002 | -0.002 | -0.001 | -0.003 | -0.003 |
| TCRBV083_5 | 0.014 | 0.044 | -0.015 | 0.011 | 0.015 |
| TCRBV083_6 | -0.013 | -0.005 | -0.013 | 0.001 | 0.001 |
| TCRBV083_7 | -0.004 | 0.006 | -0.034 | 0.013 | -0.022 |
| TCRBV083_8 | -0.010 | -0.036 | 0.033 | -0.016 | 0.003 |
| TCRBV083_9 | -0.025 | -0.002 | 0.030 | -0.028 | 0.000 |
| TCRBV083_10 | -0.001 | -0.028 | 0.035 | -0.013 | -0.011 |
| TCRBV083_11 | -0.005 | -0.002 | -0.015 | 0.020 | 0.003 |
| TCRBV083_12 | 0.040 | 0.025 | -0.020 | 0.015 | 0.014 |
| TCRBV09_5 | 0.002 | 0.001 | 0.002 | 0.004 | -0.000 |
| TCRBV09_6 | 0.010 | 0.012 | -0.019 | 0.040 | 0.015 |
| TCRBV09_7 | 0.044 | -0.044 | -0.042 | -0.060 | -0.051 |
| TCRBV09_8 | 0.000 | -0.005 | -0.024 | 0.017 | -0.003 |
| TCRBV09_9 | 0.031 | -0.015 | 0.017 | 0.049 | 0.005 |
| TCRBV09_10 | 0.054 | 0.080 | -0.059 | -0.049 | 0.019 |
| TCRBV09_11 | 0.006 | -0.030 | -0.013 | -0.014 | 0.025 |
| TCRBV09_12 | -0.047 | -0.023 | -0.080 | 0.040 | 0.007 |
| TCRBV09_13 | -0.028 | -0.022 | 0.042 | -0.005 | 0.021 |
| TCRBV09_14 | -0.032 | 0.000 | 0.029 | -0.026 | 0.007 |
| TCRBV09_15 | -0.011 | -0.007 | 0.012 | -0.002 | -0.004 |
| TCRBV10_6 | -0.012 | -0.024 | -0.001 | 0.021 | 0.012 |
| TCRBV10_7 | -0.030 | 0.035 | 0.034 | -0.017 | 0.017 |
| TCRBV10_8 | -0.033 | 0.024 | 0.016 | -0.037 | -0.007 |
| TCRBV10_9 | -0.011 | -0.027 | -0.018 | -0.010 | 0.025 |
| TCRBV10_10 | 0.071 | -0.025 | -0.030 | 0.000 | -0.034 |
| TCRBV10_11 | 0.007 | 0.029 | 0.010 | 0.041 | 0.012 |
| TCRBV10_12 | 0.009 | -0.012 | -0.011 | 0.002 | -0.026 |
| TCRBV10_13 | -0.001 | 0.000 | 0.001 | 0.000 | 0.001 |
| TCRBV11_5 | 0.005 | 0.001 | 0.014 | 0.013 | -0.011 |
| TCRBV11_6 | -0.004 | -0.017 | 0.015 | -0.031 | 0.019 |
| TCRBV11_7 | -0.005 | 0.020 | 0.015 | 0.014 | 0.022 |
| TCRBV11_8 | -0.004 | -0.020 | 0.019 | 0.010 | 0.031 |
| TCRBV11_9 | -0.004 | 0.006 | -0.042 | -0.005 | 0.004 |
| TCRBV11_10 | -0.002 | 0.030 | -0.013 | 0.005 | 0.001 |
| TCRBV11_11 | 0.022 | -0.001 | 0.006 | 0.002 | -0.020 |
| TCRBV11_12 | 0.023 | -0.003 | -0.014 | -0.024 | -0.052 |
| TCRBV11_13 | 0.004 | -0.011 | -0.006 | -0.006 | -0.010 |
| TCRBV11_14 | -0.002 | 0.002 | 0.003 | 0.002 | 0.004 |
| TCRBV11_15 | -0.001 | 0.001 | 0.001 | 0.001 | 0.002 |
| TCRBV12_4 | 0.012 | 0.005 | 0.002 | -0.015 | 0.004 |
| TCRBV12_5 | 0.020 | 0.007 | -0.016 | -0.007 | -0.006 |
| TCRBV12_6 | -0.010 | -0.012 | 0.010 | -0.028 | 0.018 |
| TCRBV12_7 | -0.022 | -0.018 | 0.059 | 0.017 | -0.035 |
| TCRBV12_8 | 0.008 | -0.025 | -0.020 | 0.029 | 0.024 |
| TCRBV12_9 | -0.017 | 0.011 | -0.023 | -0.001 | -0.008 |
| TCRBV12_10 | 0.035 | 0.001 | 0.003 | -0.003 | -0.014 |
| TCRBV12_11 | -0.014 | 0.015 | -0.003 | -0.002 | 0.010 |
| TCRBV12_12 | -0.014 | 0.017 | -0.012 | 0.010 | 0.006 |
| TCRBV13_5 | 0.001 | 0.009 | 0.003 | -0.014 | 0.001 |
| TCRBV13_6 | 0.015 | -0.034 | 0.041 | 0.003 | -0.011 |
| TCRBV13_7 | 0.008 | -0.034 | -0.039 | 0.035 | -0.022 |
| TCRBV13_8 | -0.030 | 0.048 | -0.009 | -0.011 | -0.008 |
| TCRBV13_9 | 0.007 | 0.014 | -0.032 | 0.011 | 0.026 |
| TCRBV13_10 | 0.047 | 0.001 | 0.002 | -0.038 | -0.009 |
| TCRBV13_11 | -0.028 | 0.003 | 0.009 | 0.032 | -0.008 |
| TCRBV13_12 | -0.003 | -0.010 | 0.012 | -0.008 | 0.003 |
| TCRBV13_13 | -0.017 | 0.004 | 0.014 | -0.010 | 0.027 |
| TCRBV14_5 | -0.006 | 0.006 | -0.008 | 0.006 | -0.002 |

*FIG. 114D*

| | | | | | |
|---|---|---|---|---|---|
| TCRBV14_6 | 0.013 | -0.005 | 0.017 | 0.004 | -0.027 |
| TCRBV14_7 | 0.007 | -0.018 | -0.063 | 0.031 | 0.009 |
| TCRBV14_8 | 0.016 | 0.011 | 0.038 | -0.045 | 0.002 |
| TCRBV14_9 | -0.004 | -0.003 | 0.016 | -0.002 | 0.012 |
| TCRBV14_10 | -0.030 | 0.010 | 0.024 | -0.015 | 0.021 |
| TCRBV14_11 | 0.016 | 0.013 | 0.001 | 0.025 | -0.007 |
| TCRBV14_12 | -0.013 | -0.014 | -0.024 | -0.005 | -0.009 |
| TCRBV14_13 | 0.000 | 0.000 | 0.000 | 0.000 | 0.001 |
| TCRBV15_4 | 0.003 | -0.013 | -0.005 | -0.006 | -0.014 |
| TCRBV15_5 | 0.031 | 0.006 | 0.012 | 0.003 | 0.032 |
| TCRBV15_6 | -0.006 | -0.012 | 0.009 | -0.042 | -0.031 |
| TCRBV15_7 | -0.021 | -0.003 | -0.009 | -0.004 | -0.040 |
| TCRBV15_8 | 0.021 | 0.033 | -0.003 | 0.003 | 0.049 |
| TCRBV15_9 | -0.030 | -0.001 | 0.008 | -0.012 | -0.010 |
| TCRBV15_10 | -0.010 | -0.011 | 0.013 | 0.056 | 0.005 |
| TCRBV15_11 | 0.046 | 0.003 | -0.019 | -0.022 | 0.002 |
| TCRBV15_12 | -0.003 | 0.003 | -0.009 | 0.004 | -0.002 |
| TCRBV16_5 | 0.007 | 0.006 | 0.011 | -0.005 | 0.018 |
| TCRBV16_6 | 0.015 | 0.036 | 0.034 | -0.018 | 0.027 |
| TCRBV16_7 | 0.001 | 0.061 | 0.016 | 0.043 | -0.038 |
| TCRBV16_8 | 0.027 | -0.075 | -0.031 | -0.021 | 0.032 |
| TCRBV16_9 | 0.022 | 0.031 | 0.020 | 0.017 | -0.015 |
| TCRBV16_10 | -0.068 | -0.048 | -0.027 | -0.004 | -0.013 |
| TCRBV16_11 | -0.018 | -0.043 | 0.014 | 0.037 | -0.007 |
| TCRBV16_12 | -0.011 | 0.040 | 0.002 | -0.058 | -0.023 |
| TCRBV16_13 | -0.002 | 0.004 | 0.001 | -0.000 | 0.010 |
| TCRBV18_3 | 0.002 | -0.003 | -0.005 | -0.004 | -0.000 |
| TCRBV18_4 | 0.014 | 0.020 | -0.008 | 0.011 | -0.014 |
| TCRBV18_5 | 0.015 | 0.045 | 0.030 | 0.026 | -0.038 |
| TCRBV18_6 | 0.017 | 0.049 | 0.044 | 0.009 | 0.046 |
| TCRBV18_7 | 0.007 | -0.026 | 0.010 | -0.044 | 0.043 |
| TCRBV18_8 | -0.054 | -0.020 | -0.004 | 0.017 | -0.071 |
| TCRBV18_9 | 0.025 | -0.018 | 0.015 | 0.016 | 0.044 |
| TCRBV18_10 | 0.056 | 0.034 | -0.023 | -0.046 | -0.009 |
| TCRBV18_11 | -0.002 | 0.035 | -0.028 | 0.019 | -0.034 |
| TCRBV18_12 | 0.001 | 0.000 | -0.003 | -0.001 | 0.007 |
| TCRBV18_13 | -0.007 | 0.002 | 0.001 | 0.003 | 0.010 |
| TCRBV20_5 | 0.012 | 0.004 | 0.013 | 0.007 | -0.014 |
| TCRBV20_6 | 0.051 | -0.025 | -0.015 | 0.063 | -0.029 |
| TCRBV20_7 | 0.023 | 0.041 | 0.023 | -0.029 | -0.041 |
| TCRBV20_8 | -0.050 | 0.054 | -0.046 | -0.015 | 0.087 |
| TCRBV20_9 | 0.017 | -0.065 | 0.036 | 0.010 | 0.030 |
| TCRBV20_10 | -0.014 | 0.028 | -0.014 | 0.030 | 0.004 |
| TCRBV20_11 | -0.007 | 0.022 | 0.041 | -0.006 | -0.034 |
| TCRBV20_12 | -0.009 | -0.024 | -0.011 | -0.073 | -0.013 |
| TCRBV20_13 | 0.007 | -0.018 | -0.026 | -0.003 | 0.010 |
| TCRBV20_14 | 0.002 | -0.011 | -0.004 | -0.005 | -0.011 |
| | 46 | 47 | 48 | 49 | 50 |
| TCRBV01_6 | -0.014 | -0.003 | -0.023 | -0.003 | -0.020 |
| TCRBV01_7 | 0.002 | 0.037 | -0.012 | -0.004 | 0.004 |
| TCRBV01_8 | 0.008 | 0.016 | -0.015 | 0.012 | 0.009 |
| TCRBV01_9 | 0.010 | -0.008 | 0.021 | -0.048 | -0.014 |
| TCRBV01_10 | -0.039 | 0.041 | -0.006 | -0.089 | -0.003 |
| TCRBV01_11 | -0.017 | -0.024 | 0.009 | 0.082 | 0.009 |
| TCRBV01_12 | 0.024 | 0.000 | -0.026 | 0.037 | -0.015 |
| TCRBV01_13 | 0.015 | -0.022 | 0.017 | 0.016 | 0.001 |
| TCRBV01_14 | -0.001 | 0.002 | 0.001 | 0.000 | -0.000 |
| TCRBV02_6 | -0.005 | 0.036 | -0.004 | -0.077 | 0.076 |
| TCRBV02_7 | 0.016 | -0.003 | -0.002 | -0.024 | 0.046 |
| TCRBV02_8 | 0.042 | -0.025 | 0.032 | 0.099 | -0.019 |
| TCRBV02_9 | -0.043 | 0.005 | -0.037 | 0.009 | -0.084 |
| TCRBV02_10 | 0.029 | -0.029 | -0.034 | -0.016 | -0.026 |

*FIG. 115A*

| | | | | | |
|---|---|---|---|---|---|
| TCRBV02_11 | -0.051 | -0.007 | -0.053 | -0.033 | -0.008 |
| TCRBV02_12 | 0.003 | -0.029 | 0.043 | -0.010 | -0.001 |
| TCRBV02_13 | 0.004 | 0.011 | -0.012 | -0.001 | -0.001 |
| TCRBV03_4 | 0.000 | 0.001 | 0.002 | 0.001 | 0.000 |
| TCRBV03_5 | -0.010 | 0.001 | 0.001 | -0.002 | -0.001 |
| TCRBV03_6 | 0.015 | 0.008 | -0.095 | 0.047 | -0.075 |
| TCRBV03_7 | -0.009 | -0.004 | 0.002 | -0.030 | -0.015 |
| TCRBV03_8 | -0.022 | -0.006 | -0.014 | 0.009 | 0.028 |
| TCRBV03_9 | -0.003 | 0.002 | 0.005 | -0.014 | 0.080 |
| TCRBV03_10 | 0.045 | 0.043 | 0.057 | -0.041 | -0.032 |
| TCRBV03_11 | -0.030 | 0.029 | 0.033 | 0.022 | 0.010 |
| TCRBV03_12 | 0.010 | -0.013 | -0.002 | 0.020 | 0.029 |
| TCRBV03_13 | -0.007 | -0.022 | -0.023 | -0.011 | -0.054 |
| TCRBV04_6 | 0.012 | 0.006 | 0.003 | 0.002 | -0.011 |
| TCRBV04_7 | 0.001 | 0.045 | 0.030 | -0.028 | 0.008 |
| TCRBV04_8 | 0.024 | 0.016 | -0.002 | 0.032 | 0.000 |
| TCRBV04_9 | 0.017 | -0.057 | 0.008 | -0.030 | 0.019 |
| TCRBV04_10 | 0.055 | 0.016 | -0.019 | -0.012 | 0.031 |
| TCRBV04_11 | -0.008 | -0.028 | -0.014 | 0.005 | -0.040 |
| TCRBV04_12 | -0.021 | -0.016 | -0.038 | 0.104 | 0.022 |
| TCRBV04_13 | -0.077 | 0.027 | 0.028 | -0.066 | 0.010 |
| TCRBV04_14 | 0.001 | 0.021 | 0.008 | 0.011 | -0.071 |
| TCRBV04_15 | -0.005 | -0.030 | -0.004 | -0.019 | 0.033 |
| TCRBV051_5 | -0.021 | -0.040 | -0.010 | 0.040 | 0.014 |
| TCRBV051_6 | 0.005 | 0.007 | -0.050 | -0.077 | 0.006 |
| TCRBV051_7 | -0.048 | -0.005 | 0.070 | 0.019 | -0.065 |
| TCRBV051_8 | -0.005 | 0.005 | 0.084 | 0.003 | -0.018 |
| TCRBV051_9 | 0.047 | -0.065 | -0.025 | 0.022 | 0.008 |
| TCRBV051_10 | -0.060 | 0.029 | 0.009 | -0.012 | 0.007 |
| TCRBV051_11 | -0.028 | -0.010 | -0.031 | -0.029 | 0.044 |
| TCRBV051_12 | 0.036 | 0.031 | -0.031 | 0.025 | 0.053 |
| TCRBV051_13 | 0.022 | -0.036 | -0.019 | 0.024 | 0.024 |
| TCRBV052_6 | 0.018 | -0.005 | 0.014 | -0.061 | -0.002 |
| TCRBV052_7 | -0.018 | -0.024 | 0.054 | 0.023 | 0.029 |
| TCRBV052_8 | 0.006 | 0.007 | -0.052 | 0.021 | -0.010 |
| TCRBV052_9 | -0.039 | 0.003 | -0.036 | 0.004 | 0.046 |
| TCRBV052_10 | -0.008 | -0.035 | 0.027 | -0.065 | -0.017 |
| TCRBV052_11 | -0.031 | -0.027 | -0.019 | 0.049 | -0.026 |
| TCRBV052_12 | 0.001 | -0.003 | 0.007 | 0.038 | 0.067 |
| TCRBV052_13 | 0.020 | 0.001 | 0.001 | 0.007 | -0.014 |
| TCRBV06_5 | 0.009 | 0.007 | -0.004 | -0.008 | -0.022 |
| TCRBV06_6 | 0.006 | 0.007 | -0.031 | -0.022 | 0.006 |
| TCRBV06_7 | 0.044 | 0.021 | 0.003 | 0.016 | 0.024 |
| TCRBV06_8 | -0.018 | -0.007 | 0.006 | 0.003 | 0.000 |
| TCRBV06_9 | 0.008 | -0.020 | -0.022 | 0.028 | 0.036 |
| TCRBV06_10 | 0.053 | -0.027 | 0.042 | 0.014 | -0.028 |
| TCRBV06_11 | -0.010 | 0.012 | -0.031 | -0.017 | 0.037 |
| TCRBV06_12 | -0.085 | 0.045 | -0.024 | -0.023 | -0.020 |
| TCRBV06_13 | -0.017 | 0.001 | 0.025 | 0.011 | -0.063 |
| TCRBV07_5 | -0.000 | -0.005 | 0.016 | 0.022 | -0.041 |
| TCRBV07_6 | 0.007 | 0.032 | 0.000 | 0.019 | -0.019 |
| TCRBV07_7 | -0.012 | 0.017 | -0.008 | -0.067 | -0.016 |
| TCRBV07_8 | 0.050 | -0.014 | 0.030 | -0.044 | 0.066 |
| TCRBV07_9 | -0.023 | 0.006 | -0.039 | 0.091 | -0.011 |
| TCRBV07_10 | -0.001 | -0.008 | -0.052 | -0.005 | 0.012 |
| TCRBV07_11 | -0.015 | 0.003 | 0.001 | -0.028 | 0.032 |
| TCRBV07_12 | -0.001 | 0.006 | 0.018 | 0.023 | -0.046 |
| TCRBV07_13 | -0.016 | 0.002 | -0.001 | -0.007 | -0.005 |
| TCRBV081_5 | -0.006 | -0.016 | -0.013 | -0.006 | 0.006 |
| TCRBV081_6 | -0.018 | -0.001 | 0.013 | -0.057 | -0.077 |
| TCRBV081_7 | -0.021 | -0.014 | -0.001 | 0.004 | 0.007 |
| TCRBV081_8 | 0.024 | -0.038 | -0.025 | -0.002 | 0.013 |
| TCRBV081_9 | 0.014 | 0.035 | -0.053 | 0.026 | 0.041 |
| TCRBV081_10 | -0.021 | -0.024 | -0.024 | 0.017 | 0.027 |

*FIG. 115B*

| | | | | | |
|---|---|---|---|---|---|
| TCRBV081_11 | 0.004 | 0.041 | 0.022 | 0.024 | 0.020 |
| TCRBV081_12 | 0.024 | 0.017 | 0.081 | -0.006 | -0.035 |
| TCRBV082_4 | -0.009 | -0.063 | 0.072 | 0.021 | -0.001 |
| TCRBV082_5 | -0.033 | 0.022 | 0.009 | -0.015 | 0.034 |
| TCRBV082_6 | -0.013 | -0.026 | 0.070 | 0.018 | 0.100 |
| TCRBV082_7 | -0.033 | 0.026 | -0.065 | -0.053 | -0.084 |
| TCRBV082_8 | -0.029 | -0.003 | -0.041 | 0.064 | -0.041 |
| TCRBV082_9 | 0.056 | 0.002 | -0.016 | -0.015 | -0.005 |
| TCRBV082_10 | 0.029 | 0.030 | -0.033 | -0.047 | -0.014 |
| TCRBV082_11 | 0.033 | 0.011 | 0.005 | 0.027 | 0.010 |
| TCRBV083_4 | -0.000 | -0.002 | -0.002 | -0.001 | -0.005 |
| TCRBV083_5 | 0.006 | 0.013 | 0.069 | 0.050 | 0.031 |
| TCRBV083_6 | -0.023 | -0.004 | 0.009 | 0.005 | 0.076 |
| TCRBV083_7 | -0.010 | -0.027 | -0.047 | -0.007 | -0.037 |
| TCRBV083_8 | -0.012 | 0.006 | 0.040 | -0.042 | 0.006 |
| TCRBV083_9 | -0.015 | 0.007 | -0.020 | 0.010 | -0.056 |
| TCRBV083_10 | 0.035 | -0.029 | 0.045 | -0.037 | -0.040 |
| TCRBV083_11 | 0.012 | -0.027 | -0.035 | -0.043 | 0.054 |
| TCRBV083_12 | 0.007 | 0.063 | -0.058 | 0.065 | -0.030 |
| TCRBV09_5 | 0.010 | 0.005 | -0.006 | 0.000 | -0.005 |
| TCRBV09_6 | 0.044 | -0.002 | -0.014 | -0.055 | 0.031 |
| TCRBV09_7 | 0.055 | 0.052 | -0.051 | -0.025 | -0.053 |
| TCRBV09_8 | -0.034 | 0.032 | -0.039 | 0.053 | 0.008 |
| TCRBV09_9 | -0.032 | -0.048 | -0.066 | -0.053 | 0.063 |
| TCRBV09_10 | 0.005 | -0.062 | 0.047 | -0.036 | 0.009 |
| TCRBV09_11 | 0.021 | -0.029 | 0.038 | -0.010 | -0.046 |
| TCRBV09_12 | 0.004 | -0.123 | 0.013 | -0.005 | -0.071 |
| TCRBV09_13 | -0.026 | 0.001 | -0.007 | 0.014 | -0.005 |
| TCRBV09_14 | 0.018 | 0.011 | -0.046 | 0.020 | 0.033 |
| TCRBV09_15 | 0.003 | 0.032 | -0.044 | 0.022 | 0.012 |
| TCRBV10_6 | -0.004 | -0.017 | 0.048 | -0.058 | -0.014 |
| TCRBV10_7 | 0.014 | 0.004 | -0.039 | -0.005 | -0.086 |
| TCRBV10_8 | 0.039 | 0.044 | 0.065 | 0.030 | -0.026 |
| TCRBV10_9 | -0.067 | 0.016 | -0.005 | 0.037 | 0.098 |
| TCRBV10_10 | 0.003 | -0.079 | 0.014 | -0.059 | 0.027 |
| TCRBV10_11 | -0.004 | 0.014 | -0.052 | 0.030 | -0.012 |
| TCRBV10_12 | 0.018 | 0.017 | -0.032 | 0.025 | 0.012 |
| TCRBV10_13 | 0.000 | 0.001 | 0.001 | 0.001 | 0.000 |
| TCRBV11_5 | -0.005 | 0.005 | 0.016 | -0.018 | -0.052 |
| TCRBV11_6 | 0.002 | -0.018 | 0.003 | -0.039 | -0.042 |
| TCRBV11_7 | 0.004 | -0.017 | 0.013 | 0.003 | -0.053 |
| TCRBV11_8 | 0.023 | -0.008 | 0.010 | 0.006 | 0.085 |
| TCRBV11_9 | 0.026 | 0.011 | -0.060 | 0.062 | -0.017 |
| TCRBV11_10 | -0.046 | 0.004 | -0.041 | -0.038 | 0.033 |
| TCRBV11_11 | -0.037 | 0.058 | 0.021 | 0.038 | 0.043 |
| TCRBV11_12 | 0.021 | -0.022 | -0.000 | -0.019 | -0.028 |
| TCRBV11_13 | 0.001 | 0.021 | -0.001 | 0.002 | 0.002 |
| TCRBV11_14 | 0.000 | 0.002 | 0.004 | 0.003 | 0.001 |
| TCRBV11_15 | 0.000 | 0.001 | 0.001 | 0.001 | 0.000 |
| TCRBV12_4 | -0.011 | 0.018 | 0.014 | 0.002 | 0.026 |
| TCRBV12_5 | 0.035 | 0.006 | 0.022 | 0.003 | 0.010 |
| TCRBV12_6 | 0.016 | 0.007 | -0.019 | 0.018 | 0.007 |
| TCRBV12_7 | -0.012 | 0.015 | 0.025 | 0.047 | -0.023 |
| TCRBV12_8 | -0.000 | 0.016 | 0.074 | 0.068 | 0.001 |
| TCRBV12_9 | 0.016 | 0.001 | -0.104 | 0.012 | -0.041 |
| TCRBV12_10 | -0.002 | 0.008 | 0.050 | -0.035 | 0.057 |
| TCRBV12_11 | -0.014 | -0.068 | -0.027 | -0.047 | 0.030 |
| TCRBV12_12 | -0.028 | -0.003 | -0.036 | -0.067 | -0.067 |
| TCRBV13_5 | 0.007 | -0.006 | 0.003 | 0.004 | -0.003 |
| TCRBV13_6 | -0.041 | -0.010 | 0.007 | 0.049 | 0.058 |
| TCRBV13_7 | -0.005 | 0.044 | 0.016 | -0.039 | -0.054 |
| TCRBV13_8 | -0.024 | 0.027 | 0.085 | 0.021 | -0.044 |
| TCRBV13_9 | 0.021 | 0.021 | 0.015 | 0.006 | 0.044 |

*FIG. 115C*

| | | | | | |
|---|---|---|---|---|---|
| TCRBV13_10 | 0.025 | -0.006 | -0.061 | -0.018 | -0.042 |
| TCRBV13_11 | 0.019 | -0.040 | -0.045 | 0.021 | 0.018 |
| TCRBV13_12 | 0.001 | -0.006 | -0.012 | 0.016 | 0.002 |
| TCRBV13_13 | -0.003 | -0.024 | -0.009 | -0.059 | 0.022 |
| TCRBV14_5 | 0.001 | -0.006 | -0.002 | 0.001 | 0.010 |
| TCRBV14_6 | 0.028 | -0.008 | 0.046 | 0.011 | -0.040 |
| TCRBV14_7 | -0.041 | 0.028 | -0.029 | -0.014 | 0.015 |
| TCRBV14_8 | -0.046 | 0.009 | 0.021 | -0.014 | 0.024 |
| TCRBV14_9 | 0.008 | -0.111 | -0.043 | -0.066 | 0.011 |
| TCRBV14_10 | -0.048 | 0.004 | -0.006 | 0.084 | -0.018 |
| TCRBV14_11 | 0.085 | 0.049 | 0.017 | 0.024 | -0.008 |
| TCRBV14_12 | 0.013 | 0.032 | -0.006 | -0.026 | 0.007 |
| TCRBV14_13 | 0.001 | 0.002 | 0.001 | 0.001 | -0.001 |
| TCRBV15_4 | 0.003 | 0.015 | -0.011 | -0.006 | 0.007 |
| TCRBV15_5 | -0.006 | -0.029 | -0.035 | -0.025 | -0.068 |
| TCRBV15_6 | -0.009 | 0.039 | -0.004 | 0.023 | -0.047 |
| TCRBV15_7 | 0.008 | 0.046 | -0.055 | -0.020 | 0.079 |
| TCRBV15_8 | -0.015 | 0.002 | 0.017 | 0.036 | -0.031 |
| TCRBV15_9 | -0.020 | -0.040 | 0.039 | 0.010 | 0.015 |
| TCRBV15_10 | 0.010 | -0.014 | 0.014 | 0.036 | 0.042 |
| TCRBV15_11 | 0.041 | 0.016 | -0.007 | -0.047 | -0.050 |
| TCRBV15_12 | -0.023 | 0.003 | 0.007 | -0.005 | 0.025 |
| TCRBV16_5 | 0.005 | 0.018 | 0.007 | -0.056 | 0.049 |
| TCRBV16_6 | 0.021 | -0.006 | 0.001 | 0.025 | 0.083 |
| TCRBV16_7 | -0.020 | -0.102 | -0.058 | 0.001 | -0.017 |
| TCRBV16_8 | -0.028 | 0.010 | 0.002 | 0.006 | -0.064 |
| TCRBV16_9 | -0.008 | 0.004 | 0.001 | 0.002 | 0.014 |
| TCRBV16_10 | -0.020 | 0.047 | -0.008 | 0.011 | -0.032 |
| TCRBV16_11 | -0.026 | 0.044 | 0.047 | -0.004 | -0.001 |
| TCRBV16_12 | 0.006 | -0.049 | -0.032 | 0.025 | -0.005 |
| TCRBV16_13 | 0.007 | -0.011 | 0.001 | 0.007 | 0.018 |
| TCRBV18_3 | 0.004 | -0.007 | 0.000 | -0.005 | -0.006 |
| TCRBV18_4 | 0.048 | -0.024 | 0.044 | -0.043 | 0.000 |
| TCRBV18_5 | 0.050 | -0.002 | -0.013 | 0.049 | 0.045 |
| TCRBV18_6 | 0.045 | 0.068 | 0.008 | -0.047 | -0.032 |
| TCRBV18_7 | -0.122 | -0.018 | 0.030 | 0.007 | -0.003 |
| TCRBV18_8 | 0.047 | 0.053 | 0.013 | -0.067 | 0.004 |
| TCRBV18_9 | -0.035 | -0.049 | 0.001 | 0.011 | -0.023 |
| TCRBV18_10 | -0.031 | -0.035 | 0.067 | 0.012 | -0.086 |
| TCRBV18_11 | -0.023 | -0.006 | 0.032 | 0.022 | -0.019 |
| TCRBV18_12 | -0.002 | 0.001 | 0.002 | -0.001 | 0.010 |
| TCRBV18_13 | -0.009 | -0.013 | -0.007 | -0.004 | 0.006 |
| TCRBV20_5 | 0.000 | 0.030 | 0.023 | -0.006 | -0.059 |
| TCRBV20_6 | -0.024 | 0.035 | 0.000 | 0.053 | 0.015 |
| TCRBV20_7 | -0.042 | 0.009 | 0.018 | -0.027 | 0.031 |
| TCRBV20_8 | -0.012 | 0.049 | -0.028 | -0.050 | -0.060 |
| TCRBV20_9 | 0.047 | -0.058 | 0.006 | 0.106 | -0.030 |
| TCRBV20_10 | -0.032 | -0.027 | -0.006 | -0.041 | 0.004 |
| TCRBV20_11 | 0.023 | -0.016 | 0.011 | -0.012 | -0.042 |
| TCRBV20_12 | 0.023 | 0.039 | -0.012 | -0.027 | 0.091 |
| TCRBV20_13 | 0.004 | -0.035 | -0.039 | 0.010 | 0.016 |
| TCRBV20_14 | 0.002 | 0.012 | -0.009 | -0.005 | 0.006 |

| | 51 | 52 |
|---|---|---|
| TCRBV01_6 | 0.005 | 0.001 |
| TCRBV01_7 | -0.006 | -0.031 |
| TCRBV01_8 | -0.041 | 0.095 |
| TCRBV01_9 | -0.033 | -0.074 |
| TCRBV01_10 | 0.023 | 0.004 |
| TCRBV01_11 | -0.031 | -0.003 |
| TCRBV01_12 | 0.061 | -0.024 |
| TCRBV01_13 | 0.013 | 0.015 |
| TCRBV01_14 | -0.001 | -0.001 |

*FIG. 115D*

| | | |
|---|---:|---:|
| TCRBV02_6 | 0.046 | -0.048 |
| TCRBV02_7 | -0.037 | -0.026 |
| TCRBV02_8 | -0.145 | 0.046 |
| TCRBV02_9 | 0.013 | 0.004 |
| TCRBV02_10 | -0.005 | -0.031 |
| TCRBV02_11 | -0.009 | -0.017 |
| TCRBV02_12 | -0.016 | -0.055 |
| TCRBV02_13 | 0.001 | -0.016 |
| TCRBV03_4 | 0.004 | 0.004 |
| TCRBV03_5 | -0.004 | 0.007 |
| TCRBV03_6 | -0.016 | -0.040 |
| TCRBV03_7 | 0.029 | -0.066 |
| TCRBV03_8 | 0.031 | 0.020 |
| TCRBV03_9 | 0.014 | 0.036 |
| TCRBV03_10 | -0.011 | -0.047 |
| TCRBV03_11 | -0.033 | 0.022 |
| TCRBV03_12 | -0.010 | -0.010 |
| TCRBV03_13 | -0.014 | 0.054 |
| TCRBV04_6 | -0.011 | 0.006 |
| TCRBV04_7 | -0.018 | -0.073 |
| TCRBV04_8 | 0.047 | -0.036 |
| TCRBV04_9 | -0.004 | -0.211 |
| TCRBV04_10 | -0.047 | 0.160 |
| TCRBV04_11 | 0.051 | 0.048 |
| TCRBV04_12 | -0.024 | 0.043 |
| TCRBV04_13 | -0.053 | 0.022 |
| TCRBV04_14 | 0.066 | 0.002 |
| TCRBV04_15 | -0.007 | 0.039 |
| TCRBV051_5 | -0.065 | -0.049 |
| TCRBV051_6 | -0.039 | -0.035 |
| TCRBV051_7 | -0.027 | -0.083 |
| TCRBV051_8 | -0.005 | 0.041 |
| TCRBV051_9 | 0.034 | 0.030 |
| TCRBV051_10 | -0.058 | 0.050 |
| TCRBV051_11 | 0.055 | 0.073 |
| TCRBV051_12 | 0.042 | -0.006 |
| TCRBV051_13 | 0.058 | 0.027 |
| TCRBV052_6 | -0.014 | -0.102 |
| TCRBV052_7 | 0.018 | 0.036 |
| TCRBV052_8 | 0.000 | 0.045 |
| TCRBV052_9 | 0.042 | 0.045 |
| TCRBV052_10 | 0.020 | 0.055 |
| TCRBV052_11 | -0.012 | -0.030 |
| TCRBV052_12 | -0.036 | -0.015 |
| TCRBV052_13 | -0.024 | 0.016 |
| TCRBV06_5 | -0.025 | -0.013 |
| TCRBV06_6 | -0.014 | -0.034 |
| TCRBV06_7 | -0.060 | -0.039 |
| TCRBV06_8 | 0.084 | 0.001 |
| TCRBV06_9 | -0.054 | -0.049 |
| TCRBV06_10 | 0.011 | 0.063 |
| TCRBV06_11 | 0.015 | -0.009 |
| TCRBV06_12 | -0.003 | 0.021 |
| TCRBV06_13 | 0.036 | 0.039 |
| TCRBV07_5 | 0.001 | -0.032 |
| TCRBV07_6 | 0.007 | -0.050 |
| TCRBV07_7 | -0.025 | -0.006 |
| TCRBV07_8 | 0.023 | 0.044 |
| TCRBV07_9 | -0.038 | -0.054 |
| TCRBV07_10 | 0.073 | 0.054 |
| TCRBV07_11 | -0.008 | 0.067 |
| TCRBV07_12 | -0.029 | -0.046 |
| TCRBV07_13 | -0.014 | 0.003 |
| TCRBV081_5 | 0.020 | 0.006 |

*FIG. 116A*

| | | |
|---|---|---|
| TCRBV081_6 | -0.014 | 0.043 |
| TCRBV081_7 | 0.006 | 0.034 |
| TCRBV081_8 | -0.028 | -0.034 |
| TCRBV081_9 | -0.008 | -0.039 |
| TCRBV081_10 | 0.004 | 0.040 |
| TCRBV081_11 | -0.013 | 0.012 |
| TCRBV081_12 | 0.033 | -0.062 |
| TCRBV082_4 | 0.103 | -0.021 |
| TCRBV082_5 | -0.054 | -0.020 |
| TCRBV082_6 | 0.101 | -0.007 |
| TCRBV082_7 | -0.086 | 0.107 |
| TCRBV082_8 | 0.013 | -0.019 |
| TCRBV082_9 | -0.050 | 0.023 |
| TCRBV082_10 | -0.033 | -0.055 |
| TCRBV082_11 | 0.006 | -0.009 |
| TCRBV083_4 | -0.001 | 0.004 |
| TCRBV083_5 | -0.020 | -0.000 |
| TCRBV083_6 | -0.047 | -0.001 |
| TCRBV083_7 | 0.059 | 0.043 |
| TCRBV083_8 | -0.098 | 0.001 |
| TCRBV083_9 | 0.052 | 0.013 |
| TCRBV083_10 | 0.062 | -0.018 |
| TCRBV083_11 | -0.052 | 0.017 |
| TCRBV083_12 | 0.044 | -0.058 |
| TCRBV09_5 | 0.011 | 0.003 |
| TCRBV09_6 | 0.022 | 0.052 |
| TCRBV09_7 | -0.055 | 0.091 |
| TCRBV09_8 | 0.050 | -0.010 |
| TCRBV09_9 | 0.001 | -0.032 |
| TCRBV09_10 | 0.025 | -0.007 |
| TCRBV09_11 | 0.043 | 0.004 |
| TCRBV09_12 | 0.004 | -0.125 |
| TCRBV09_13 | -0.083 | -0.060 |
| TCRBV09_14 | -0.079 | 0.009 |
| TCRBV09_15 | -0.009 | -0.023 |
| TCRBV10_6 | -0.004 | -0.022 |
| TCRBV10_7 | -0.026 | -0.011 |
| TCRBV10_8 | 0.002 | -0.074 |
| TCRBV10_9 | 0.008 | 0.041 |
| TCRBV10_10 | -0.045 | 0.092 |
| TCRBV10_11 | 0.028 | -0.027 |
| TCRBV10_12 | 0.035 | -0.001 |
| TCRBV10_13 | 0.002 | 0.002 |
| TCRBV11_5 | 0.012 | 0.022 |
| TCRBV11_6 | 0.032 | 0.015 |
| TCRBV11_7 | -0.045 | 0.092 |
| TCRBV11_8 | -0.087 | -0.067 |
| TCRBV11_9 | 0.058 | -0.057 |
| TCRBV11_10 | -0.034 | 0.013 |
| TCRBV11_11 | 0.028 | -0.071 |
| TCRBV11_12 | 0.006 | 0.022 |
| TCRBV11_13 | 0.008 | -0.000 |
| TCRBV11_14 | 0.009 | 0.008 |
| TCRBV11_15 | 0.003 | 0.003 |
| TCRBV12_4 | -0.047 | -0.033 |
| TCRBV12_5 | 0.023 | 0.054 |
| TCRBV12_6 | -0.034 | -0.007 |
| TCRBV12_7 | -0.007 | 0.118 |
| TCRBV12_8 | 0.045 | 0.008 |
| TCRBV12_9 | 0.039 | -0.101 |
| TCRBV12_10 | 0.000 | -0.021 |
| TCRBV12_11 | -0.041 | -0.037 |
| TCRBV12_12 | 0.021 | 0.021 |
| TCRBV13_5 | 0.022 | -0.015 |

*FIG. 116B*

| | | |
|---|---:|---:|
| TCRBV13_6 | -0.092 | -0.029 |
| TCRBV13_7 | 0.026 | -0.025 |
| TCRBV13_8 | -0.000 | 0.059 |
| TCRBV13_9 | 0.018 | -0.032 |
| TCRBV13_10 | 0.052 | -0.005 |
| TCRBV13_11 | 0.019 | 0.095 |
| TCRBV13_12 | 0.004 | 0.015 |
| TCRBV13_13 | -0.049 | -0.062 |
| TCRBV14_5 | -0.001 | 0.008 |
| TCRBV14_6 | -0.057 | -0.008 |
| TCRBV14_7 | 0.025 | -0.026 |
| TCRBV14_8 | 0.031 | -0.010 |
| TCRBV14_9 | 0.008 | 0.011 |
| TCRBV14_10 | 0.024 | -0.017 |
| TCRBV14_11 | -0.078 | 0.052 |
| TCRBV14_12 | 0.044 | -0.011 |
| TCRBV14_13 | 0.002 | 0.001 |
| TCRBV15_4 | 0.009 | -0.022 |
| TCRBV15_5 | -0.035 | -0.067 |
| TCRBV15_6 | -0.002 | -0.026 |
| TCRBV15_7 | 0.072 | 0.028 |
| TCRBV15_8 | 0.017 | 0.013 |
| TCRBV15_9 | 0.023 | 0.006 |
| TCRBV15_10 | -0.028 | 0.080 |
| TCRBV15_11 | -0.049 | -0.040 |
| TCRBV15_12 | -0.016 | 0.008 |
| TCRBV16_5 | 0.079 | 0.016 |
| TCRBV16_6 | 0.007 | 0.014 |
| TCRBV16_7 | -0.070 | 0.070 |
| TCRBV16_8 | -0.002 | -0.030 |
| TCRBV16_9 | 0.030 | 0.025 |
| TCRBV16_10 | -0.079 | -0.041 |
| TCRBV16_11 | -0.016 | 0.044 |
| TCRBV16_12 | 0.034 | -0.070 |
| TCRBV16_13 | 0.002 | 0.001 |
| TCRBV18_3 | 0.003 | 0.009 |
| TCRBV18_4 | -0.018 | 0.015 |
| TCRBV18_5 | -0.019 | 0.010 |
| TCRBV18_6 | 0.012 | -0.028 |
| TCRBV18_7 | 0.036 | -0.045 |
| TCRBV18_8 | 0.011 | -0.001 |
| TCRBV18_9 | -0.069 | -0.013 |
| TCRBV18_10 | -0.003 | -0.006 |
| TCRBV18_11 | 0.023 | 0.099 |
| TCRBV18_12 | 0.002 | 0.001 |
| TCRBV18_13 | 0.009 | 0.002 |
| TCRBV20_5 | 0.028 | 0.033 |
| TCRBV20_6 | -0.063 | 0.010 |
| TCRBV20_7 | -0.062 | -0.056 |
| TCRBV20_8 | 0.022 | 0.084 |
| TCRBV20_9 | 0.041 | 0.027 |
| TCRBV20_10 | -0.008 | 0.044 |
| TCRBV20_11 | -0.018 | 0.003 |
| TCRBV20_12 | 0.051 | -0.065 |
| TCRBV20_13 | -0.008 | -0.083 |
| TCRBV20_14 | 0.007 | -0.018 |

Standardized scores have been saved.

*FIG. 116C*

53 cases and 56 variables processed.

53 cases and 56 variables processed and saved.

SYSTAT Rectangular file C:\Utilisateurs\OGp8586\Pr81OG290802F.SYD,
created Fri Aug 30, 2002 at 10:39:56, contains variables:

| CASE$ | GROUPS$ | FACTOR(1..52) | TSQUARE | PROB |
|---|---|---|---|---|

Group frequencies

| F3* | F3*S | FS | FT | R3* | R3*6 |
|---|---|---|---|---|---|
| 5 | 10 | 5 | 9 | 5 | 5 |

| RS | RT |
|---|---|
| 5 | 9 |

Group means

*FIG. 116D*

|  | F3* | F3*S | FS | FT | R3* |
|---|---|---|---|---|---|
| FACTOR(1) | -0.029 | 0.701 | 0.789 | -0.582 | -0.556 |
| FACTOR(2) | -0.652 | -0.065 | 0.584 | 0.647 | -0.976 |
| FACTOR(3) | 0.667 | 1.285 | 0.110 | -1.234 | -0.470 |
| FACTOR(4) | 0.561 | -0.170 | 0.972 | -0.038 | -0.367 |
| FACTOR(5) | 0.448 | -0.469 | 0.382 | -0.026 | 0.202 |
| FACTOR(6) | 0.282 | 0.126 | 0.420 | 0.215 | -0.546 |
| FACTOR(7) | 1.267 | 0.083 | -1.236 | 0.401 | 0.114 |
| FACTOR(8) | -0.530 | 0.072 | -0.258 | -0.292 | 0.206 |
| FACTOR(9) | -0.147 | 0.371 | 0.124 | 0.115 | -0.221 |
| FACTOR(10) | -0.446 | 0.130 | 0.019 | 0.225 | -0.179 |
| FACTOR(11) | 0.434 | -0.536 | 0.076 | 0.120 | 0.001 |
| FACTOR(12) | 0.838 | 0.514 | -0.022 | 0.420 | 0.207 |
| FACTOR(13) | -0.646 | 0.161 | 0.450 | 0.386 | -0.429 |
| FACTOR(14) | 0.638 | 0.370 | 0.210 | 0.257 | 0.209 |
| FACTOR(15) | 0.285 | 0.143 | 0.430 | -0.321 | 0.217 |
| FACTOR(16) | -0.020 | -0.127 | -0.144 | 0.214 | -0.111 |
| FACTOR(17) | -0.458 | 0.427 | -0.945 | -0.293 | -0.113 |
| FACTOR(18) | -0.852 | 0.271 | 0.435 | -0.086 | -0.474 |
| FACTOR(19) | 0.220 | 0.034 | 0.055 | 0.041 | 0.340 |
| FACTOR(20) | 1.027 | 0.179 | -0.153 | 0.135 | -0.054 |
| FACTOR(21) | -0.859 | 0.332 | 0.320 | 0.713 | -0.432 |
| FACTOR(22) | -0.048 | -0.018 | -0.247 | -0.248 | -0.226 |
| FACTOR(23) | -0.449 | -0.240 | 0.032 | 0.287 | 0.081 |
| FACTOR(24) | 0.266 | -0.323 | 0.359 | -0.043 | -0.658 |
| FACTOR(25) | -0.225 | -0.194 | 0.171 | -0.156 | 0.045 |
| FACTOR(26) | -0.255 | 0.234 | 0.829 | -0.240 | 0.231 |
| FACTOR(27) | 0.389 | 0.260 | 1.069 | 0.080 | 0.075 |
| FACTOR(28) | -0.222 | 0.080 | 0.055 | 0.027 | -0.197 |
| FACTOR(29) | -0.112 | 0.030 | 0.050 | 0.070 | 0.004 |
| FACTOR(30) | -0.439 | 0.142 | 0.005 | 0.129 | 0.584 |
| FACTOR(31) | -0.104 | -0.046 | 0.218 | -0.406 | -0.123 |

*FIG. 117A*

| | | | | | |
|---|---|---|---|---|---|
| FACTOR(32) | 0.258 | -0.046 | -0.316 | 0.063 | -1.439 |
| FACTOR(33) | 0.041 | -0.090 | -0.323 | 0.189 | -0.732 |
| FACTOR(34) | 0.160 | -0.126 | -0.199 | 0.061 | -0.107 |
| FACTOR(35) | -0.200 | 0.051 | -0.141 | 0.027 | 0.027 |
| FACTOR(36) | -0.040 | 0.019 | -0.167 | 0.220 | 0.329 |
| FACTOR(37) | 0.266 | -0.042 | 0.087 | -0.328 | 0.063 |
| FACTOR(38) | 0.129 | 0.118 | 0.184 | 0.001 | -0.584 |
| FACTOR(39) | 0.298 | -0.086 | 0.173 | -0.194 | -0.728 |
| FACTOR(40) | -0.189 | 0.049 | -0.152 | 0.209 | -0.352 |
| FACTOR(41) | -0.042 | 0.030 | -0.129 | 0.138 | -0.684 |
| FACTOR(42) | 0.011 | 0.067 | -0.343 | -0.103 | 0.266 |
| FACTOR(43) | 0.153 | -0.138 | -0.118 | 0.038 | -0.640 |
| FACTOR(44) | 0.155 | 0.034 | -0.690 | -0.037 | -0.356 |
| FACTOR(45) | 0.012 | -0.073 | -0.015 | -0.330 | 0.208 |
| FACTOR(46) | -0.062 | 0.018 | 0.155 | 0.159 | -0.302 |
| FACTOR(47) | -0.167 | 0.099 | -0.789 | 0.315 | 0.361 |
| FACTOR(48) | -0.118 | 0.087 | -0.168 | -0.011 | 0.483 |
| FACTOR(49) | -0.089 | 0.106 | -0.313 | 0.013 | -0.045 |
| FACTOR(50) | -0.119 | 0.150 | 0.091 | -0.073 | 0.446 |
| FACTOR(51) | 0.007 | 0.003 | 0.045 | -0.079 | 0.084 |
| FACTOR(52) | -0.029 | 0.052 | -0.016 | -0.018 | -0.047 |

*FIG. 117B*

| | R3*S | RS | RT |
|---|---|---|---|
| FACTOR(1) | 0.148 | 0.985 | 0.001 |
| FACTOR(2) | 1.046 | -0.140 | -0.360 |
| FACTOR(3) | -0.172 | -0.043 | -0.244 |
| FACTOR(4) | -0.615 | -0.068 | -0.042 |
| FACTOR(5) | -0.607 | 0.022 | 0.299 |
| FACTOR(6) | -0.309 | -0.314 | -0.096 |
| FACTOR(7) | -0.164 | -0.524 | -0.192 |
| FACTOR(8) | -0.025 | -0.459 | 0.220 |
| FACTOR(9) | 0.265 | 0.167 | 0.193 |
| FACTOR(10) | -0.314 | 0.271 | 0.280 |
| FACTOR(11) | 0.188 | 0.331 | 0.227 |
| FACTOR(12) | 0.155 | -0.396 | -0.307 |
| FACTOR(13) | -0.476 | -0.237 | -0.084 |
| FACTOR(14) | -0.277 | 0.134 | -0.542 |
| FACTOR(15) | 0.270 | -0.092 | -0.214 |
| FACTOR(16) | -0.023 | 0.052 | 0.064 |
| FACTOR(17) | 0.138 | 0.312 | 0.411 |
| FACTOR(18) | 0.242 | 0.215 | 0.026 |
| FACTOR(19) | -0.009 | -0.225 | -0.291 |
| FACTOR(20) | 0.029 | 0.037 | -0.827 |
| FACTOR(21) | -0.537 | 0.109 | -0.306 |
| FACTOR(22) | 0.789 | -0.804 | 0.070 |
| FACTOR(23) | 0.221 | -0.249 | 0.182 |
| FACTOR(24) | 0.514 | 1.032 | -0.438 |
| FACTOR(25) | 0.736 | 0.117 | -0.097 |
| FACTOR(26) | 0.414 | 0.061 | -0.033 |
| FACTOR(27) | 0.108 | 0.861 | 0.006 |
| FACTOR(28) | -0.339 | -0.197 | 0.384 |
| FACTOR(29) | -0.052 | 0.647 | -0.346 |
| FACTOR(30) | -0.066 | 0.027 | -0.348 |
| FACTOR(31) | 0.411 | 0.428 | -0.004 |

*FIG. 117C*

| | | | |
|---|---|---|---|
| FACTOR(32) | -0.004 | -0.005 | 0.825 |
| FACTOR(33) | 0.536 | 0.789 | -0.262 |
| FACTOR(34) | -0.303 | 0.558 | 0.141 |
| FACTOR(35) | -0.098 | 0.631 | -0.205 |
| FACTOR(36) | 0.504 | 0.050 | 0.190 |
| FACTOR(37) | -0.869 | 0.411 | 0.303 |
| FACTOR(38) | 0.522 | -0.456 | 0.244 |
| FACTOR(39) | 0.200 | -0.491 | 0.594 |
| FACTOR(40) | -0.598 | 0.229 | 0.326 |
| FACTOR(41) | 0.218 | 0.412 | -0.093 |
| FACTOR(42) | -0.426 | 0.774 | -0.128 |
| FACTOR(43) | 0.417 | 0.074 | 0.178 |
| FACTOR(44) | -0.184 | 0.661 | 0.229 |
| FACTOR(45) | -0.159 | 0.031 | 0.367 |
| FACTOR(46) | 0.675 | -0.075 | -0.396 |
| FACTOR(47) | -0.667 | 0.562 | -0.035 |
| FACTOR(48) | -0.257 | -0.406 | 0.174 |
| FACTOR(49) | 0.012 | 0.514 | -0.149 |
| FACTOR(50) | -0.219 | -0.128 | -0.133 |
| FACTOR(51) | -0.963 | 0.123 | 0.466 |
| FACTOR(52) | -0.107 | 0.082 | 0.025 |

*FIG. 117D*

Between groups F-matrix -- df = 45   1

| | F3* | F3*S | FS | FT | R3* |
|---|---|---|---|---|---|
| F3* | 0.000 | | | | |
| F3*S | 52.367 | 0.000 | | | |
| FS | 26.426 | 63.091 | 0.000 | | |
| FT | 29.544 | 34.464 | 10.096 | 0.000 | |
| R3* | 18.757 | 47.604 | 2.030 | 5.205 | 0.000 |
| R3*S | 26.437 | 14.504 | 14.702 | 1.906 | 8.65 |
| RS | 22.784 | 65.376 | 0.588 | 11.754 | 2.046 |
| RT | 41.861 | 13.667 | 27.023 | 6.505 | 18.275 |

|       | R3*S | RS   | RT   |
|-------|------|------|------|
| R3*;  | 0.00 |      |      |
|       | 0    |      |      |
| RS    | 15.9 | 0.00 |      |
|       | 21   | 0    |      |
| RT    | 1.02 | 29.4 | 0.00 |
|       | 4    | 65   | 0    |

Wilks' lambda
Lambda = 0.0000    df = 45    7    45
Approx. F= 5.2756  df = 315   20   prob = 0.0000

Classification functions

|          | F3*      | F3*S     | FS       | FT      | R3*      |
|----------|----------|----------|----------|---------|----------|
| CONSTANT | 7356.799 | 5637.861 | 4201.980 | 306.080 | 2116.499 |

|          | R3*S    | RS       | RT       |
|----------|---------|----------|----------|
| CONSTANT | 427.721 | 4460.284 | 1225.056 |

*FIG. 118A*

| Factor | Col 1 | Col 2 | Col 3 | Col 4 | Col 5 |
|---|---|---|---|---|---|
| FACTOR(1) | 885.325 | 3336.155 | 2832.243 | 379.611 | 1994.506 |
| FACTOR(2) | 1189.608 | 640.078 | 482.200 | 53.800 | 357.182 |
| FACTOR(3) | 733.254 | 2954.265 | 2573.948 | 619.584 | 1742.564 |
| FACTOR(4) | 1103.939 | 1214.829 | 980.686 | 34.868 | 716.431 |
| FACTOR(5) | 910.353 | 1522.227 | 1222.642 | 116.464 | 909.387 |
| FACTOR(6) | 288.258 | 295.952 | 265.061 | 80.595 | 187.563 |
| FACTOR(7) | 1619.786 | 1096.056 | 1193.107 | 387.205 | 625.109 |
| FACTOR(8) | 1140.457 | 907.611 | 691.194 | 33.196 | 544.344 |
| FACTOR(9) | 249.941 | 743.279 | 661.489 | 159.031 | 429.891 |
| FACTOR(10) | 719.913 | 227.624 | 278.814 | 145.837 | 116.473 |
| FACTOR(11) | 790.282 | 1311.675 | 1030.215 | 94.504 | 783.396 |
| FACTOR(12) | 1497.052 | 1420.478 | 1038.720 | 29.468 | 862.841 |
| FACTOR(13) | 895.490 | 47.340 | 181.539 | 141.537 | 0.971 |
| FACTOR(14) | 816.867 | 413.070 | 234.639 | 49.142 | 256.640 |
| FACTOR(15) | 482.076 | 46.884 | 67.783 | 88.142 | 23.844 |
| FACTOR(16) | 81.496 | 130.719 | 110.991 | 39.778 | 71.874 |
| FACTOR(17) | 1191.607 | 2057.059 | 1679.725 | 166.411 | 1231.019 |
| FACTOR(18) | 1417.776 | 616.412 | 343.838 | 96.728 | 391.897 |
| FACTOR(19) | 525.084 | 254.610 | 164.486 | 33.702 | 166.883 |
| FACTOR(20) | 1952.578 | 354.785 | 110.301 | 225.896 | 233.415 |
| FACTOR(21) | 1234.827 | 379.534 | 151.066 | 130.150 | 255.522 |
| FACTOR(22) | 666.088 | 1207.799 | 1022.400 | 80.786 | 720.577 |
| FACTOR(23) | 833.821 | 153.721 | 201.197 | 156.884 | 83.376 |
| FACTOR(24) | 941.573 | 1846.576 | 1537.538 | 145.061 | 1085.487 |
| FACTOR(25) | 242.956 | 560.933 | 508.925 | 117.562 | 334.727 |
| FACTOR(26) | 745.639 | 1398.794 | 1164.052 | 110.083 | 838.579 |
| FACTOR(27) | 778.920 | 569.483 | 372.121 | 23.140 | 345.486 |
| FACTOR(28) | 657.807 | 699.621 | 536.667 | 11.767 | 429.010 |
| FACTOR(29) | 252.459 | 729.338 | 629.608 | 72.267 | 432.399 |
| FACTOR(30) | 329.901 | 254.889 | 267.568 | 86.791 | 162.336 |
| FACTOR(31) | 15.784 | 425.790 | 388.537 | 53.283 | 250.897 |
| FACTOR(32) | - | 15 | - | - | - |

*FIG. 118B*

| | | | |
|---|---|---|---|
| FACTOR(1) | -516.421 | -29 71.510 | -1210.085 |
| FACTOR(2) | -32 2.374 | -595.120 | -51 3.744 |
| FACTOR(3) | -15 9.068 | -2501.821 | -62 9.296 |
| FACTOR(4) | -353.442 | -10 96.718 | -654.132 |
| FACTOR(5) | -328.479 | -13 31.529 | -672.563 |
| FACTOR(6) | -37.733 | -251.033 | -3.499 |
| FACTOR(7) | -152.418 | -1010.654 | -74.246 |
| FACTOR(8) | -30 9.949 | -835.407 | -57 0.266 |
| FACTOR(9) | -28.284 | -64 2.608 | -141.922 |
| FACTOR(10) | -10 0.762 | -19 6.379 | -12 2.348 |
| FACTOR(11) | -267.696 | -11 44.530 | -570.825 |
| FACTOR(12) | -410.379 | -12 11.799 | -784.511 |
| FACTOR(13) | -12 9.889 | -62 .525 | -20 0.266 |
| FACTOR(14) | -174.147 | -34 0.427 | -311.017 |
| FACTOR(15) | -89.587 | -14.115 | -123.256 |
| FACTOR(16) | -3.673 | -10 3.078 | -10.157 |
| FACTOR(17) | -44 8.489 | -1806.603 | -91 4.382 |
| FACTOR(18) | -30 5.935 | -512.894 | -52 9.741 |
| FACTOR(19) | -122.409 | -21 9.704 | -213.257 |
| FACTOR(20) | -397.324 | -33 3.055 | -619.912 |
| FACTOR(21) | -23 1.744 | -320.278 | -40 9.228 |
| FACTOR(22) | -26 7.874 | -1108.931 | -54 4.411 |
| FACTOR(23) | -14 2.105 | -10 2.272 | -18 3.290 |
| FACTOR(24) | -376.504 | -16 72.559 | -793.673 |
| FACTOR(25) | -7.187 | -49 3.777 | -98.351 |
| FACTOR(26) | -29 6.676 | -1247.184 | -61 0.743 |
| FACTOR(27) | -180.161 | -49 4.691 | -350.244 |
| FACTOR(28) | -18 9.587 | -622.211 | -37 6.693 |
| FACTOR(29) | -132.213 | -66 8.456 | -290.064 |
| FACTOR(30) | 27 .545 | 22 4.265 | 0.968 |
| FACTOR(31) | -42.314 | -40 2.739 | -126.892 |
| FACTOR(32) | 27 | - | 63 |

FIG. 118C

| | | | | | |
|---|---|---|---|---|---|
| FACTOR(33) | 569.927 15 1.128 | 89.968 - 325.268 | 1341.629 27 0.719 | 161.012 26 .473 | 986.491 1 5.808 |
| FACTOR(34) | - 39 1.097 | - 532.880 | - 42 3.931 | - 24 .130 | - 3 2.562 |
| FACTOR(35) | - 21 .879 | - 479.666 | - 43 2.451 | - 65 .599 | - 2 2.397 |
| FACTOR(36) | - 357.451 | 63 1.311 | - 521.910 | - 54.706 | - 382.198 |
| FACTOR(37) | 56 9.876 | - 338.182 | 25 6.025 | - 38.478 | 2 1.471 |
| FACTOR(38) | - 297.185 | 59 6.832 | - 503.345 | - 45.380 | - 367.606 |
| FACTOR(39) | - 243.396 | 98 9.287 | - 850.458 | - 117.629 | - 604.867 |
| FACTOR(40) | - 465.488 | 38 1.992 | - 275.887 | 12 .571 | - 246.707 |
| FACTOR(41) | - 14.506 | 15 9.792 | - 128.126 | - 24.143 | - 112.574 |
| FACTOR(42) | 44 1.848 | - 579.365 | 47 0.909 | 17 .485 | 3 0.317 |
| FACTOR(43) | - 83.053 | 28 5.618 | - 253.243 | - 30.550 | - 184.865 |
| FACTOR(44) | 12 2.862 | 39 5.119 | - 367.181 | - 84.781 | - 244.696 |
| FACTOR(45) | 0.000 | 0.000 | 0.000 | 0.000 | 0.000 |
| FACTOR(46) | 0.000 | 0.000 | 0.000 | 0.000 | 0.000 |
| FACTOR(47) | 0.000 | 0.000 | 0.000 | 0.000 | 0.000 |
| FACTOR(48) | - 306.610 | 52 1.311 | - 437.054 | - 34.115 | - 299.483 |
| FACTOR(49) | 0.000 | 0.000 | 0.000 | 0.000 | 0.000 |
| FACTOR(50) | 0.000 | 0.000 | 0.000 | 0.000 | 0.000 |
| FACTOR(51) | 0.000 | 0.000 | 0.000 | 0.000 | 0.000 |
| FACTOR(52) | 0.000 | 0.000 | 0.000 | 0.000 | 0.000 |

*FIG. 118D*

| | | | |
|---|---|---|---|
| FACTOR(33) | 7.822 -61.258 | 1405.922 30 -7.829 | 1.130 -134.079 |
| FACTOR(34) | -128.043 | 48 -2.732 | -255.530 |
| FACTOR(35) | -61.517 | 44 -5.127 | -155.045 |
| FACTOR(36) | 14 1.801 | -553.931 | 28 3.078 |
| FACTOR(37) | -149.909 | 32 -6.269 | -254.505 |
| FACTOR(38) | 12 4.734 | -541.574 | 26 2.776 |
| FACTOR(39) | 15 6.442 | -883.045 | 36 5.823 |
| FACTOR(40) | 11 6.478 | -333.909 | 23 2.723 |
| FACTOR(41) | 15 .342 | -123.246 | 48 .324 |
| FACTOR(42) | -146.187 | 53 -6.520 | -292.306 |
| FACTOR(43) | 52 .637 | -255.160 | 11 5.244 |
| FACTOR(44) | 25 .751 | -335.940 | 89 .762 |
| FACTOR(45) | 0.000 | 0.000 | 0.000 |
| FACTOR(46) | 0.000 | 0.000 | 0.000 |
| FACTOR(47) | 0.000 | 0.000 | 0.000 |
| FACTOR(48) | 11 6.883 | -481.245 | 23 6.830 |
| FACTOR(49) | 0.000 | 0.000 | 0.000 |
| FACTOR(50) | 0.000 | 0.000 | 0.000 |
| FACTOR(51) | 0.000 | 0.000 | 0.000 |
| FACTOR(52) | 0.000 | 0.000 | 0.000 |

| | Variable | F-to-remove | Tolerance | | Variable | F-to-enter | Tolerance |
|---|---|---|---|---|---|---|---|
| 3 | FACTOR(1) | 165.86 | 0.001301 | 47 | FACTOR(45) | 0.00 | 0.000000 |
| 4 | FACTOR(2) | 20.89 | 0.010747 | 48 | FACTOR(46) | 0.00 | 0.000000 |
| 5 | FACTOR(3) | 155.48 | 0.002697 | 49 | FACTOR(47) | 0.00 | 0.000000 |
| 6 | FACTOR(4) | 30.37 | 0.005689 | 51 | FACTOR(49) | 0.00 | 0.000000 |
| 7 | FACTOR(5) | 37.26 | 0.004393 | 52 | FACTOR(50) | 0.00 | 0.000000 |
| 8 | FACTOR(6) | 3.26 | 0.045888 | 53 | FACTOR(51) | 0.00 | 0.000000 |
| 9 | FACTOR(7) | 62.50 | 0.003602 | 54 | FACTOR(52) | 0.00 | 0.000000 |
| 10 | FACTOR(8) | 22.54 | 0.006860 | | | | |
| 11 | FACTOR(9) | 10.46 | 0.014231 | | | | |
| 12 | FACTOR(10) | 8.04 | 0.018656 | | | | |
| 13 | FACTOR(11) | 27.69 | 0.005697 | | | | |
| 14 | FACTOR(12) | 44.93 | 0.003898 | | | | |
| 15 | FACTOR(13) | 10.57 | 0.015446 | | | | |
| 16 | FACTOR(14) | 8.78 | 0.018728 | | | | |
| 17 | FACTOR(15) | 3.21 | 0.045731 | | | | |
| 18 | FACTOR(16) | 0.48 | 0.232616 | | | | |
| 19 | FACTOR(17) | 68.14 | 0.002608 | | | | |
| 20 | FACTOR(18) | 24.62 | 0.006671 | | | | |
| 21 | FACTOR(19) | 3.57 | 0.039938 | | | | |
| 22 | FACTOR(20) | 43.13 | 0.004298 | | | | |

*FIG. 119A*

```
23  FACTOR(21)    18.37   0.010330
24  FACTOR(22)    24.41   0.006799
25  FACTOR(23)     9.65   0.015550
26  FACTOR(24)    54.39   0.003457
27  FACTOR(25)     6.53   0.023139
28  FACTOR(26)    31.22   0.005147
29  FACTOR(27)     9.95   0.017948
30  FACTOR(28)    10.02   0.014805
31  FACTOR(29)     8.36   0.017939
32  FACTOR(30)     3.06   0.048530
33  FACTOR(31)     3.36   0.043854
34  FACTOR(32)    39.28   0.005440
35  FACTOR(33)     2.08   0.077397
36  FACTOR(34)     5.09   0.028857
37  FACTOR(35)     3.83   0.037992
38  FACTOR(36)     6.56   0.022503
39  FACTOR(37)     4.86   0.032875
40  FACTOR(38)     5.88   0.026270
41  FACTOR(39)    15.03   0.011187
42  FACTOR(40)     3.95   0.038036
43  FACTOR(41)     0.65   0.194654
44  FACTOR(42)     6.37   0.024341
45  FACTOR(43)     1.50   0.093363
46  FACTOR(44)     3.21   0.048085
50  FACTOR(48)     4.69   0.031305
```

Classification matrix (cases in row categories classified into columns)

|       | F3* | F3*! | FS | FT | R3* | R3*! |
|-------|-----|------|----|----|-----|------|
| F3*   | 5   | 0    | 0  | 0  | 0   | 0    |
| F3*!  | 0   | 10   | 0  | 0  | 0   | 0    |
| FS    | 0   | 0    | 5  | 0  | 0   | 0    |
| FT    | 0   | 0    | 0  | 9  | 0   | 0    |
| R3*   | 0   | 0    | 0  | 0  | 5   | 0    |
| R3*!  | 0   | 0    | 0  | 0  | 0   | 5    |
| RS    | 0   | 0    | 0  | 0  | 0   | 0    |
| RT    | 0   | 0    | 0  | 0  | 0   | 0    |
| Total | 5   | 10   | 5  | 9  | 5   | 5    |

*FIG. 119B*

|        | RS | RT | %correct |
|--------|----|----|----------|
| F3*    | 0  | 0  | 100      |
| F3*:   | 0  | 0  | 100      |
| FS     | 0  | 0  | 100      |
| FT     | 0  | 0  | 100      |
| R3*    | 0  | 0  | 100      |
| R3*:   | 0  | 0  | 100      |
| RS     | 5  | 0  | 100      |
| RT     | 0  | 9  | 100      |
| Total  | 5  | 9  | 100      |

Jackknifed classification matrix

|        | F3* | F3*: | FS | FT | R3* | R3*: |
|--------|-----|------|----|----|-----|------|
| F3*    | 4   | 0    | 0  | 1  | 0   | 0    |
| F3*:   | 2   | 3    | 3  | 0  | 1   | 0    |
| FS     | 1   | 1    | 0  | 0  | 0   | 0    |
| FT     | 3   | 0    | 4  | 1  | 0   | 0    |
| R3*    | 2   | 0    | 0  | 1  | 0   | 1    |
| R3*:   | 3   | 1    | 1  | 0  | 0   | 0    |
| RS     | 0   | 3    | 1  | 0  | 0   | 0    |
| RT     | 2   | 1    | 2  | 0  | 0   | 1    |
| Total  | 17  | 9    | 11 | 3  | 1   | 2    |

|        | RS | RT | %correct |
|--------|----|----|----------|
| F3*    | 0  | 0  | 80       |
| F3*:   | 1  | 0  | 30       |
| FS     | 1  | 2  | 0        |
| FT     | 0  | 1  | 11       |
| R3*    | 1  | 0  | 0        |
| R3*:   | 0  | 0  | 0        |
| RS     | 1  | 0  | 20       |
| RT     | 1  | 2  | 22       |
| Total  | 5  | 5  | 21       |

*FIG. 119C*

Eigenvalues

| 5277.370 | 1800.188 | 87.172 | 38.636 | 26.920 | 5.759 |
|---|---|---|---|---|---|
| 2.402 | | | | | |

Canonical correlations

| 1.000 | 1.000 | 0.994 | 0.987 | 0.982 | 0.923 |
|---|---|---|---|---|---|
| 0.840 | | | | | |

Cumulative proportion of total dispersion

| 0.729 | 0.978 | 0.990 | 0.995 | 0.999 | 1.000 |
|---|---|---|---|---|---|
| 1.000 | | | | | |

Wilks' lambda=     0.000
    Approx.F=     5.299   df= 315,    20   p-tail= 0.0000

Pillai's trace=     6.485
    Approx.F=     1.959   df= 315,    49   p-tail= 0.0026

Lawley-Hotelling trace=    7238.447
    Approx.F=    -16.414   df= 315,    -5   p-tail=

Canonical discriminant functions

| | 1 | 2 | 3 | 4 | 5 |
|---|---|---|---|---|---|
| Constant | 0.000 | 0.000 | 0.000 | 0.000 | 0.000 |

| | 6 | 7 |
|---|---|---|
| Constant | 0.000 | 0.000 |

*FIG. 119D*

| | | | | | |
|---|---|---|---|---|---|
| FACTOR(1) | 31.378 | 4.071 | 0.964 | 1.632 | 0.309 |
| FACTOR(2) | -7.334 | 7.746 | -1.991 | 2.984 | -0.441 |
| FACTOR(3) | -25.539 | -16.382 | 4.358 | 1.598 | -0.365 |
| FACTOR(4) | 12.422 | -5.058 | 1.504 | -1.287 | 0.059 |
| FACTOR(5) | 14.807 | -2.371 | -0.543 | -0.511 | 0.154 |
| FACTOR(6) | -2.286 | -3.427 | 0.861 | -1.432 | 0.042 |
| FACTOR(7) | -8.310 | -17.352 | -2.845 | -0.636 | -0.059 |
| FACTOR(8) | -9.658 | 6.439 | -1.233 | -0.388 | -0.451 |
| FACTOR(9) | 6.376 | 4.672 | -0.584 | -0.123 | 0.724 |
| FACTOR(10) | 1.220 | 6.832 | 0.108 | -0.530 | 0.487 |
| FACTOR(11) | 12.693 | -2.092 | -1.113 | 0.482 | 0.919 |
| FACTOR(12) | 14.435 | -7.638 | -2.155 | -0.913 | -0.241 |
| FACTOR(13) | -0.462 | 7.678 | 1.776 | -1.334 | 0.010 |
| FACTOR(14) | 4.535 | -5.414 | -1.623 | 0.360 | 0.522 |
| FACTOR(15) | 0.244 | -4.213 | 1.198 | 0.286 | -0.087 |
| FACTOR(16) | 1.031 | 1.143 | -0.552 | -0.376 | 0.310 |
| FACTOR(17) | -20.055 | 2.888 | -0.016 | 1.330 | 0.685 |
| FACTOR(18) | -7.071 | 9.757 | 1.984 | 0.048 | 0.240 |
| FACTOR(19) | 2.921 | -3.531 | -0.248 | -0.048 | -0.755 |
| FACTOR(20) | 5.545 | -15.158 | 0.467 | -0.403 | -0.437 |
| FACTOR(21) | -4.720 | 9.052 | 1.757 | -1.940 | -0.405 |
| FACTOR(22) | -11.909 | 1.432 | -1.953 | -0.315 | 0.021 |
| FACTOR(23) | 0.313 | 7.533 | -1.230 | -0.361 | -0.032 |
| FACTOR(24) | 17.959 | -1.525 | 1.660 | 0.241 | 1.311 |
| FACTOR(25) | 4.791 | 3.968 | -0.176 | 0.842 | 0.160 |
| FACTOR(26) | -13.635 | 1.429 | -0.821 | 0.216 | 0.429 |
| FACTOR(27) | 5.934 | -4.565 | -1.317 | 0.909 | 1.138 |
| FACTOR(28) | -7.117 | 3.111 | 0.071 | -0.492 | 0.192 |
| FACTOR(29) | 7.008 | 0.390 | 1.073 | 0.199 | 0.103 |
| FACTOR(30) | 1.986 | 3.631 | 0.223 | 0.204 | -1.108 |
| FACTOR(31) | 3.927 | 1.592 | 1.020 | 1.068 | 0.483 |
| FACTOR(32) | | | | | |

*FIG. 120A*

|  | | | | | |
|---|---:|---:|---:|---:|---:|
|  | -15.192 | -0.671 | -0.273 | -0.961 | 2.409 |
| FACTOR(33) | 3.145 | -0.139 | 0.605 | 0.076 | 1.399 |
| FACTOR(34) | 5.297 | -1.439 | 0.298 | 0.187 | 0.718 |
| FACTOR(35) | 4.460 | 1.463 | 0.925 | 0.326 | 0.175 |
| FACTOR(36) | -6.171 | 0.821 | -0.119 | 0.662 | 0.723 |
| FACTOR(37) | 3.825 | -3.616 | 1.157 | 0.154 | 0.269 |
| FACTOR(38) | -5.844 | 0.449 | -0.643 | -0.382 | 0.689 |
| FACTOR(39) | -9.343 | -1.352 | -0.496 | -0.381 | 1.064 |
| FACTOR(40) | -3.996 | 2.597 | 0.373 | -0.798 | 0.618 |
| FACTOR(41) | -1.432 | -0.422 | 0.716 | -0.307 | 1.015 |
| FACTOR(42) | 5.851 | -1.719 | 0.850 | 0.639 | 0.111 |
| FACTOR(43) | -2.754 | -0.275 | -0.342 | -0.141 | 1.145 |
| FACTOR(44) | -3.465 | -2.389 | 0.077 | 0.375 | 1.222 |
| FACTOR(45) | . | . | . | . | . |
| FACTOR(46) | . | . | . | . | . |
| FACTOR(47) | . | . | . | . | . |
| FACTOR(48) | -5.143 | 0.770 | -0.884 | 0.091 | -0.735 |
| FACTOR(49) | . | . | . | . | . |
| FACTOR(50) | . | . | . | . | . |
| FACTOR(51) | . | . | . | . | . |
| FACTOR(52) | . | . | . | . | . |

*FIG. 120B*

| | | |
|---|---|---|
| FACTOR(1) | 0.374 | 0.030 |
| FACTOR(2) | 0.148 | -0.102 |
| FACTOR(3) | 0.373 | -0.046 |
| FACTOR(4) | 0.589 | 0.007 |
| FACTOR(5) | 0.523 | 0.335 |
| FACTOR(6) | 0.179 | -0.117 |
| FACTOR(7) | -0.509 | 0.137 |
| FACTOR(8) | -0.042 | 0.105 |
| FACTOR(9) | 0.091 | -0.114 |
| FACTOR(10) | -0.030 | 0.261 |
| FACTOR(11) | 0.179 | 0.022 |
| FACTOR(12) | -0.054 | -0.268 |
| FACTOR(13) | -0.182 | 0.101 |
| FACTOR(14) | 0.555 | 0.345 |
| FACTOR(15) | 0.237 | -0.334 |
| FACTOR(16) | -0.119 | 0.039 |
| FACTOR(17) | -0.276 | 0.317 |
| FACTOR(18) | 0.012 | -0.202 |
| FACTOR(19) | -0.076 | -0.087 |
| FACTOR(20) | -0.539 | -0.292 |
| FACTOR(21) | -0.531 | 0.064 |
| FACTOR(22) | 0.043 | 0.498 |
| FACTOR(23) | 0.043 | -0.085 |
| FACTOR(24) | -0.370 | -0.429 |
| FACTOR(25) | 0.004 | -0.397 |
| FACTOR(26) | -0.610 | -0.078 |
| FACTOR(27) | -0.710 | 0.284 |
| FACTOR(28) | 0.293 | 0.226 |
| FACTOR(29) | -0.498 | 0.031 |
| FACTOR(30) | -0.362 | 0.038 |
| FACTOR(31) | 0.105 | -0.183 |
| FACTOR(32) | 0.39 | 0.07 |

*FIG. 120C*

| | 7 | 1 |
|---|---|---|
| FACTOR(33) | -0.655 | -0.297 |
| FACTOR(34) | -0.101 | 0.300 |
| FACTOR(35) | -0.440 | 0.124 |
| FACTOR(36) | 0.091 | -0.195 |
| FACTOR(37) | 0.314 | 0.594 |
| FACTOR(38) | 0.395 | -0.398 |
| FACTOR(39) | 0.742 | -0.151 |
| FACTOR(40) | -0.032 | 0.410 |
| FACTOR(41) | -0.317 | -0.169 |
| FACTOR(42) | -0.430 | 0.413 |
| FACTOR(43) | 0.040 | -0.235 |
| FACTOR(44) | -0.340 | 0.343 |
| FACTOR(45) | . | . |
| FACTOR(46) | . | . |
| FACTOR(47) | . | . |
| FACTOR(48) | 0.152 | 0.241 |
| FACTOR(49) | . | . |
| FACTOR(50) | . | . |
| FACTOR(51) | . | . |
| FACTOR(52) | . | . |

Canonical discriminant functions -- standardized by within variances

FIG. 120D

|  | 1 | 2 | 3 | 4 | 5 |
|---|---|---|---|---|---|
| FACTOR(1) | 27.438 | 3.560 | 0.843 | 1.427 | 0.270 |
| FACTOR(2) | -6.267 | 6.619 | -1.701 | 2.550 | -0.376 |
| FACTOR(3) | -16.017 | -10.274 | 2.733 | 1.002 | -0.229 |
| FACTOR(4) | 12.113 | -4.932 | 1.466 | -1.255 | 0.058 |
| FACTOR(5) | 14.841 | -2.377 | -0.544 | -0.513 | 0.154 |
| FACTOR(6) | -2.351 | -3.525 | 0.885 | -1.473 | 0.044 |
| FACTOR(7) | -7.108 | -14.842 | -2.433 | -0.544 | -0.051 |
| FACTOR(8) | -9.948 | 6.632 | -1.270 | -0.400 | -0.465 |
| FACTOR(9) | 6.671 | 4.888 | -0.611 | -0.128 | 0.757 |
| FACTOR(10) | 1.268 | 7.105 | 0.112 | -0.551 | 0.506 |
| FACTOR(11) | 12.950 | -2.135 | -1.135 | 0.492 | 0.937 |
| FACTOR(12) | 13.992 | -7.404 | -2.089 | -0.885 | -0.234 |
| FACTOR(13) | -0.462 | 7.670 | 1.774 | -1.332 | 0.010 |
| FACTOR(14) | 4.507 | -5.381 | -1.613 | 0.358 | 0.519 |
| FACTOR(15) | 0.253 | -4.373 | 1.244 | 0.297 | -0.090 |
| FACTOR(16) | 1.100 | 1.219 | -0.588 | -0.401 | 0.330 |
| FACTOR(17) | -19.311 | 2.780 | -0.015 | 1.281 | 0.659 |
| FACTOR(18) | -7.069 | 9.754 | 1.983 | 0.048 | 0.240 |
| FACTOR(19) | 3.083 | -3.727 | -0.262 | -0.050 | -0.797 |
| FACTOR(20) | 5.224 | -14.281 | 0.440 | -0.380 | -0.412 |
| FACTOR(21) | -4.385 | 8.410 | 1.632 | -1.803 | -0.376 |
| FACTOR(22) | -11.841 | 1.424 | -1.942 | -0.313 | 0.021 |
| FACTOR(23) | 0.326 | 7.844 | -1.281 | -0.375 | -0.033 |
| FACTOR(24) | 16.806 | -1.427 | 1.553 | 0.226 | 1.227 |
| FACTOR(25) | 4.955 | 4.104 | -0.182 | 0.870 | 0.165 |
| FACTOR(26) | -13.789 | 1.446 | -0.830 | 0.218 | 0.434 |
| FACTOR(27) | 5.664 | -4.357 | -1.257 | 0.867 | 1.086 |
| FACTOR(28) | -7.455 | 3.259 | 0.074 | -0.516 | 0.201 |
| FACTOR(29) | 7.290 | 0.406 | 1.117 | 0.207 | 0.107 |
| FACTOR(30) | 2.048 | 3.745 | 0.230 | 0.211 | -1.142 |
| FACTOR(31) | 4.071 | 1.650 | 1.058 | 1.107 | 0.501 |

*FIG. 121A*

| | | | | | |
|---|---|---|---|---|---|
| FACTOR(32) | -13.329 | -0.589 | -0.239 | -0.843 | 2.114 |
| FACTOR(33) | 3.082 | -0.136 | 0.593 | 0.075 | 1.371 |
| FACTOR(34) | 5.540 | -1.505 | 0.312 | 0.195 | 0.751 |
| FACTOR(35) | 4.666 | 1.531 | 0.968 | 0.341 | 0.183 |
| FACTOR(36) | -6.457 | 0.859 | -0.125 | 0.693 | 0.757 |
| FACTOR(37) | 3.832 | -3.623 | 1.159 | 0.154 | 0.270 |
| FACTOR(38) | -5.971 | 0.459 | -0.657 | -0.390 | 0.704 |
| FACTOR(39) | -9.213 | -1.333 | -0.489 | -0.376 | 1.049 |
| FACTOR(40) | -4.113 | 2.673 | 0.384 | -0.821 | 0.636 |
| FACTOR(41) | -1.483 | -0.437 | 0.741 | -0.318 | 1.051 |
| FACTOR(42) | 5.971 | -1.754 | 0.867 | 0.652 | 0.113 |
| FACTOR(43) | -2.855 | -0.285 | -0.355 | -0.146 | 1.187 |
| FACTOR(44) | -3.504 | -2.416 | 0.078 | 0.379 | 1.236 |
| FACTOR(45) | . | . | . | . | . |
| FACTOR(46) | . | . | . | . | . |
| FACTOR(47) | . | . | . | . | . |
| FACTOR(48) | -5.373 | 0.804 | -0.924 | 0.095 | -0.768 |
| FACTOR(49) | . | . | . | . | . |
| FACTOR(50) | . | . | . | . | . |
| FACTOR(51) | . | . | . | . | . |
| FACTOR(52) | . | . | . | . | . |

*FIG. 121B*

|  | 6 | 7 |
|---|---|---|
| FACTOR(1) | 0.327 | 0.027 |
| FACTOR(2) | 0.126 | -0.087 |
| FACTOR(3) | 0.234 | -0.029 |
| FACTOR(4) | 0.574 | 0.007 |
| FACTOR(5) | 0.525 | 0.336 |
| FACTOR(6) | 0.185 | -0.120 |
| FACTOR(7) | -0.435 | 0.117 |
| FACTOR(8) | -0.043 | 0.108 |
| FACTOR(9) | 0.095 | -0.119 |
| FACTOR(10) | -0.031 | 0.271 |
| FACTOR(11) | 0.183 | 0.023 |
| FACTOR(12) | -0.053 | 0.260 |
| FACTOR(13) | -0.182 | 0.101 |
| FACTOR(14) | 0.552 | 0.342 |
| FACTOR(15) | 0.247 | -0.346 |
| FACTOR(16) | -0.127 | 0.042 |
| FACTOR(17) | -0.266 | 0.306 |
| FACTOR(18) | 0.012 | -0.202 |
| FACTOR(19) | -0.081 | -0.092 |
| FACTOR(20) | -0.508 | -0.275 |
| FACTOR(21) | -0.494 | 0.059 |
| FACTOR(22) | 0.042 | -0.496 |
| FACTOR(23) | 0.045 | -0.089 |
| FACTOR(24) | -0.346 | -0.402 |
| FACTOR(25) | 0.004 | -0.410 |
| FACTOR(26) | -0.616 | -0.079 |
| FACTOR(27) | -0.678 | 0.271 |
| FACTOR(28) | 0.307 | 0.237 |
| FACTOR(29) | -0.518 | 0.032 |
| FACTOR(30) | -0.373 | 0.040 |
| FACTOR(31) | 0.109 | -0.190 |

*FIG. 121C*

| | | |
|---|---|---|
| FACTOR(32) | 0.348 | 0.062 |
| FACTOR(33) | -0.642 | -0.291 |
| FACTOR(34) | -0.105 | 0.314 |
| FACTOR(35) | -0.460 | 0.130 |
| FACTOR(36) | 0.095 | -0.204 |
| FACTOR(37) | 0.314 | 0.595 |
| FACTOR(38) | 0.404 | -0.406 |
| FACTOR(39) | 0.732 | -0.149 |
| FACTOR(40) | -0.033 | 0.422 |
| FACTOR(41) | -0.329 | -0.175 |
| FACTOR(42) | -0.439 | -0.422 |
| FACTOR(43) | 0.041 | -0.244 |
| FACTOR(44) | -0.344 | -0.346 |
| FACTOR(45) | . | . |
| FACTOR(46) | . | . |
| FACTOR(47) | . | . |
| FACTOR(48) | 0.159 | 0.251 |
| FACTOR(49) | . | . |
| FACTOR(50) | . | . |
| FACTOR(51) | . | . |
| FACTOR(52) | . | . |

*FIG. 121D*

Canonical scores of group means

| | 1 | 2 | 3 | 4 | 5 |
|---|---|---|---|---|---|
| F3* | 43.081 | -113.251 | -4.364 | -1.429 | -2.323 |
| F3*! | -104.714 | -14.520 | 9.260 | 0.616 | -2.977 |
| FS | 86.840 | 25.022 | 13.495 | -4.830 | -3.285 |
| FT | 10.393 | 18.853 | 6.650 | -9.729 | -0.283 |
| R3* | 62.606 | 7.312 | 9.120 | -7.595 | -10.641 |
| R3*! | 19.093 | 18.816 | 7.253 | 7.728 | -2.641 |
| RS | 92.468 | 11.944 | 11.481 | 5.703 | 6.912 |
| RT | 41.768 | -25.145 | 5.995 | 0.841 | 4.729 |

|      | 6      | 7      |
|------|--------|--------|
| F3*  | 1.033  | -0.204 |
| F3*S | -0.842 | 0.157  |
| FS   | 3.792  | -1.371 |
| FT   | -2.362 | -0.091 |
| R3*  | -0.258 | 1.309  |
| R3*S | -0.670 | -3.601 |
| RS   | -3.109 | 1.244  |
| RT   | 2.861  | 1.375  |

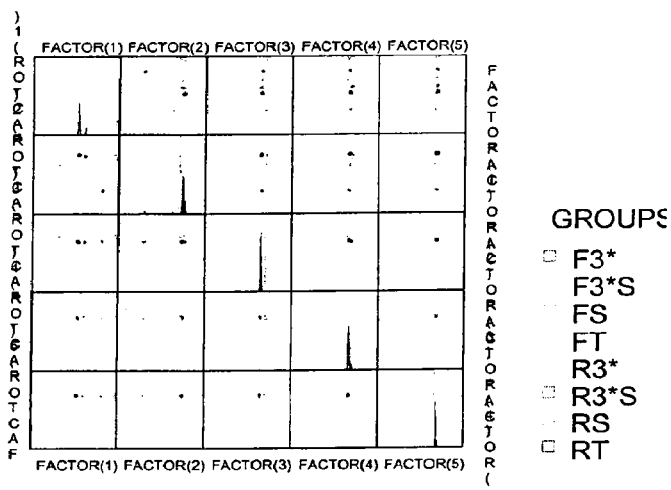

Canonical Scores Plot

GROUPS
- F3*
- F3*S
- FS
- FT
- R3*
- R3*S
- RS
- RT

*FIG. 122A*

```
*WARNING*
The file
      C:\Utilisateurs\OGp8586\Pr81OG290802F.SYD
was read for processing, and its contents have been replaced by saving
the processed data into it.
```

53 cases and 56 variables processed and saved.

```
Distance metric is Euclidean distance k-means splitting cases into 3 groups
Summary statistics for all cases
  Variable       Between SS   df     Within SS   df    F-ratio
  FACTOR(1)          4.310     2        47.690   50      2.259
  FACTOR(2)          2.931     2        49.069   50      1.493
  FACTOR(3)          1.260     2        50.740   50      0.621
  FACTOR(4)          0.450     2        51.550   50      0.218
  FACTOR(5)          0.433     2        51.567   50      0.210
```

| | | | | | |
|---|---|---|---|---|---|
| FACTOR(6) | 0.993 | 2 | 51.007 | 50 | 0.487 |
| FACTOR(7) | 1.371 | 2 | 50.629 | 50 | 0.677 |
| FACTOR(8) | 0.373 | 2 | 51.627 | 50 | 0.181 |
| FACTOR(9) | 1.368 | 2 | 50.632 | 50 | 0.675 |
| FACTOR(10) | 1.309 | 2 | 50.691 | 50 | 0.646 |
| FACTOR(11) | 5.184 | 2 | 46.816 | 50 | 2.768 |
| FACTOR(12) | 4.242 | 2 | 47.758 | 50 | 2.221 |
| FACTOR(13) | 3.361 | 2 | 48.639 | 50 | 1.727 |
| FACTOR(14) | 0.109 | 2 | 51.891 | 50 | 0.052 |
| FACTOR(15) | 0.219 | 2 | 51.781 | 50 | 0.106 |
| FACTOR(16) | 2.089 | 2 | 49.911 | 50 | 1.046 |
| FACTOR(17) | 4.144 | 2 | 47.856 | 50 | 2.165 |
| FACTOR(18) | 3.101 | 2 | 48.899 | 50 | 1.586 |
| FACTOR(19) | 1.107 | 2 | 50.893 | 50 | 0.544 |
| FACTOR(20) | 3.794 | 2 | 48.206 | 50 | 1.968 |
| FACTOR(21) | 2.569 | 2 | 49.431 | 50 | 1.299 |
| FACTOR(22) | 0.117 | 2 | 51.883 | 50 | 0.057 |
| FACTOR(23) | 2.352 | 2 | 49.648 | 50 | 1.184 |
| FACTOR(24) | 4.014 | 2 | 47.986 | 50 | 2.091 |
| FACTOR(25) | 0.662 | 2 | 51.338 | 50 | 0.322 |
| FACTOR(26) | 1.397 | 2 | 50.603 | 50 | 0.690 |
| FACTOR(27) | 0.297 | 2 | 51.703 | 50 | 0.144 |
| FACTOR(28) | 1.058 | 2 | 50.942 | 50 | 0.519 |
| FACTOR(29) | 1.008 | 2 | 50.992 | 50 | 0.494 |
| FACTOR(30) | 0.535 | 2 | 51.465 | 50 | 0.260 |
| FACTOR(31) | 1.603 | 2 | 50.397 | 50 | 0.795 |
| FACTOR(32) | 2.181 | 2 | 49.819 | 50 | 1.095 |
| FACTOR(33) | 0.690 | 2 | 51.310 | 50 | 0.336 |
| FACTOR(34) | 0.029 | 2 | 51.971 | 50 | 0.014 |
| FACTOR(35) | 4.310 | 2 | 47.690 | 50 | 2.260 |
| FACTOR(36) | 2.031 | 2 | 49.969 | 50 | 1.016 |
| FACTOR(37) | 0.522 | 2 | 51.478 | 50 | 0.253 |
| FACTOR(38) | 10.691 | 2 | 41.309 | 50 | 6.470 |
| FACTOR(39) | 1.890 | 2 | 50.110 | 50 | 0.943 |
| FACTOR(40) | 0.161 | 2 | 51.839 | 50 | 0.077 |
| FACTOR(41) | 1.642 | 2 | 50.358 | 50 | 0.815 |
| FACTOR(42) | 1.395 | 2 | 50.605 | 50 | 0.689 |
| FACTOR(43) | 4.625 | 2 | 47.375 | 50 | 2.441 |
| FACTOR(44) | 2.887 | 2 | 49.113 | 50 | 1.469 |
| FACTOR(45) | 0.385 | 2 | 51.615 | 50 | 0.187 |
| FACTOR(46) | 2.941 | 2 | 49.059 | 50 | 1.499 |
| FACTOR(47) | 1.830 | 2 | 50.170 | 50 | 0.912 |
| FACTOR(48) | 0.753 | 2 | 51.247 | 50 | 0.368 |
| FACTOR(49) | 0.026 | 2 | 51.974 | 50 | 0.012 |
| FACTOR(50) | 1.858 | 2 | 50.142 | 50 | 0.927 |
| FACTOR(51) | 1.300 | 2 | 50.700 | 50 | 0.641 |
| FACTOR(52) | 4.092 | 2 | 47.908 | 50 | 2.135 |
| ** TOTAL ** | 104.000 | 104 | 2600.000 | 2600 | |

---

Cluster 1 of 3 contains 18 cases

| Members | | | Statistics | | | |
|---|---|---|---|---|---|---|
| Case | Distance | Variable | Minimum | Mean | Maximum | St.Dev. |
| Case 1 | 0.97 | FACTOR(1) | -0.87 | 0.36 | 1.38 | 0.58 |
| Case 5 | 0.97 | FACTOR(2) | -0.59 | 0.29 | 1.34 | 0.60 |
| Case 6 | 0.97 | FACTOR(3) | -1.65 | -0.19 | 0.69 | 0.50 |
| Case 8 | 0.97 | FACTOR(4) | -1.08 | -0.05 | 1.66 | 0.74 |
| Case 10 | 0.97 | FACTOR(5) | -0.60 | 0.08 | 0.88 | 0.45 |
| Case 11 | 0.97 | FACTOR(6) | -1.30 | -0.09 | 1.61 | 0.74 |
| Case 13 | 0.97 | FACTOR(7) | -1.71 | -0.21 | 1.07 | 0.70 |
| Case 14 | 0.97 | FACTOR(8) | -1.03 | 0.07 | 1.06 | 0.62 |
| Case 16 | 0.97 | FACTOR(9) | -0.52 | 0.11 | 0.58 | 0.34 |
| Case 17 | 0.97 | FACTOR(10) | -2.74 | -0.17 | 1.61 | 0.94 |
| Case 18 | 0.97 | FACTOR(11) | -0.68 | 0.24 | 1.02 | 0.46 |
| Case 19 | 0.97 | FACTOR(12) | -1.61 | -0.01 | 1.21 | 0.68 |

*FIG. 122B*

```
Case  20      0.97  |  FACTOR(13)     -1.30    0.01    0.88    0.55
Case  21      0.97  |  FACTOR(14)     -1.38    0.06    0.94    0.51
Case  28      0.97  |  FACTOR(15)     -0.82    0.06    1.20    0.57
Case  36      0.97  |  FACTOR(16)     -1.60   -0.12    0.65    0.62
Case  38      0.97  |  FACTOR(17)     -1.62    0.07    1.57    0.81
Case  53      0.97  |  FACTOR(18)     -1.10    0.22    2.55    0.94
                    |  FACTOR(19)     -1.25    0.15    3.67    1.00
                    |  FACTOR(20)     -1.48   -0.30    1.47    0.87
                    |  FACTOR(21)     -1.51   -0.15    1.68    0.83
                    |  FACTOR(22)     -2.73   -0.06    2.08    1.12
                    |  FACTOR(23)     -1.86   -0.06    1.44    0.90
                    |  FACTOR(24)     -1.48    0.20    2.00    1.09
                    |  FACTOR(25)     -1.53    0.11    2.06    0.94
                    |  FACTOR(26)     -1.20    0.18    2.67    0.98
                    |  FACTOR(27)     -1.91   -0.08    1.35    1.02
                    |  FACTOR(28)     -2.43    0.09    1.61    0.99
                    |  FACTOR(29)     -1.28    0.04    1.79    0.87
                    |  FACTOR(30)     -2.91    0.05    1.90    1.17
                    |  FACTOR(31)     -1.86    0.20    2.39    1.15
                    |  FACTOR(32)     -2.49   -0.24    1.56    1.25
                    |  FACTOR(33)     -1.58    0.03    1.91    0.99
                    |  FACTOR(34)     -1.55   -0.00    2.96    1.01
                    |  FACTOR(35)     -2.25   -0.31    1.85    1.17
                    |  FACTOR(36)     -2.91    0.07    1.90    1.14
                    |  FACTOR(37)     -2.83    0.13    2.35    1.43
                    |  FACTOR(38)     -2.61   -0.62    2.33    1.15
                    |  FACTOR(39)     -2.80   -0.26    2.23    1.14
                    |  FACTOR(40)     -2.61    0.01    2.51    1.25
                    |  FACTOR(41)     -3.28   -0.24    2.90    1.44
                    |  FACTOR(42)     -2.52    0.05    2.78    1.41
                    |  FACTOR(43)     -2.88    0.31    2.13    1.14
                    |  FACTOR(44)     -1.49   -0.04    1.99    0.96
                    |  FACTOR(45)     -1.42    0.11    1.83    0.91
                    |  FACTOR(46)     -1.62   -0.11    2.10    0.97
                    |  FACTOR(47)     -2.13    0.26    2.79    1.24
                    |  FACTOR(48)     -3.21   -0.15    1.91    1.42
                    |  FACTOR(49)     -1.52   -0.02    2.29    1.03
                    |  FACTOR(50)     -3.70   -0.23    1.37    1.41
                    |  FACTOR(51)     -2.42    0.21    3.70    1.43
                    |  FACTOR(52)     -1.87    0.35    5.52    1.49
-----------------------------------------------------------------------
Cluster 2 of 3 contains 18 cases
       Members                                 Statistics
    Case      Distance  |  Variable   Minimum    Mean   Maximum  St.Dev.
Case  22      0.97  |  FACTOR(1)      -1.96   -0.04    1.50    0.99
Case  23      0.97  |  FACTOR(2)      -1.65   -0.28    1.84    0.91
Case  25      0.97  |  FACTOR(3)      -2.16    0.18    2.85    1.30
Case  26      0.97  |  FACTOR(4)      -3.55    0.13    2.26    1.31
Case  29      0.97  |  FACTOR(5)      -2.04    0.04    2.02    1.17
Case  30      0.97  |  FACTOR(6)      -1.84    0.19    3.40    1.41
Case  31      0.97  |  FACTOR(7)      -2.58    0.18    2.90    1.43
Case  33      0.97  |  FACTOR(8)      -1.79    0.05    3.56    1.31
Case  34      0.97  |  FACTOR(9)      -2.10    0.11    1.92    1.30
Case  35      0.97  |  FACTOR(10)     -2.21    0.20    1.62    1.01
Case  37      0.97  |  FACTOR(11)     -2.89   -0.44    2.63    1.28
Case  39      0.97  |  FACTOR(12)     -0.86    0.34    2.99    0.96
Case  41      0.97  |  FACTOR(13)     -1.25    0.30    1.52    0.81
Case  42      0.97  |  FACTOR(14)     -2.72   -0.05    3.12    1.29
Case  43      0.97  |  FACTOR(15)     -1.89   -0.09    2.38    1.28
Case  45      0.97  |  FACTOR(16)     -1.83   -0.15    1.79    1.02
Case  49      0.97  |  FACTOR(17)     -3.46   -0.36    1.37    1.26
Case  51      0.97  |  FACTOR(18)     -1.87   -0.33    2.39    1.19
                    |  FACTOR(19)     -1.52   -0.19    1.56    0.83
                    |  FACTOR(20)     -1.04    0.34    2.34    0.91
```

*FIG. 122C*

```
                         |  FACTOR(21)    -1.76   -0.15    1.64    0.88
                         |  FACTOR(22)    -2.88    0.05    1.52    1.06
                         |  FACTOR(23)    -1.30    0.28    1.77    0.87
                         |  FACTOR(24)    -1.56    0.18    1.13    0.74
                         |  FACTOR(25)    -2.32   -0.15    1.30    1.13
                         |  FACTOR(26)    -2.06    0.02    2.86    1.08
                         |  FACTOR(27)    -1.84    0.10    1.31    0.96
                         |  FACTOR(28)    -3.30   -0.20    2.60    1.25
                         |  FACTOR(29)    -2.04    0.14    1.94    1.03
                         |  FACTOR(30)    -3.05    0.09    1.97    1.13
                         |  FACTOR(31)    -2.39   -0.22    1.77    1.10
                         |  FACTOR(32)    -1.41    0.00    1.38    0.87
                         |  FACTOR(33)    -1.87    0.12    3.89    1.17
                         |  FACTOR(34)    -1.66   -0.03    2.05    0.98
                         |  FACTOR(35)    -1.30   -0.05    1.39    0.79
                         |  FACTOR(36)    -2.33   -0.26    0.85    0.85
                         |  FACTOR(37)    -1.47   -0.11    0.94    0.67
                         |  FACTOR(38)    -0.69    0.39    2.27    0.72
                         |  FACTOR(39)    -1.65    0.15    2.24    0.95
                         |  FACTOR(40)    -1.99    0.06    2.46    0.98
                         |  FACTOR(41)    -1.96    0.06    1.12    0.73
                         |  FACTOR(42)    -1.48   -0.22    1.04    0.71
                         |  FACTOR(43)    -2.27    0.07    1.99    0.86
                         |  FACTOR(44)    -1.75   -0.26    0.43    0.60
                         |  FACTOR(45)    -2.00   -0.02    1.13    0.75
                         |  FACTOR(46)    -0.59    0.32    2.18    0.77
                         |  FACTOR(47)    -2.07   -0.14    1.24    0.91
                         |  FACTOR(48)    -0.86    0.01    1.02    0.46
                         |  FACTOR(49)    -1.65   -0.01    1.88    0.74
                         |  FACTOR(50)    -1.15    0.01    2.45    0.76
                         |  FACTOR(51)    -1.95   -0.15    0.52    0.59
                         |  FACTOR(52)    -0.85   -0.04    1.08    0.39
--------------------------------------------------------------------------------
Cluster 3 of 3 contains 17 cases
      Members                              Statistics
   Case      Distance  |  Variable     Minimum    Mean   Maximum   St.Dev.
   Case   2    0.97    |  FACTOR(1)     -2.67    -0.34    1.58    1.26
   Case   3    0.97    |  FACTOR(2)     -4.29    -0.01    1.70    1.34
   Case   4    0.97    |  FACTOR(3)     -3.06     0.01    1.49    1.05
   Case   7    0.97    |  FACTOR(4)     -1.44    -0.08    2.65    0.90
   Case   9    0.97    |  FACTOR(5)     -3.05    -0.13    2.34    1.25
   Case  12    0.97    |  FACTOR(6)     -1.95    -0.10    1.24    0.71
   Case  15    0.97    |  FACTOR(7)     -1.12     0.03    1.24    0.69
   Case  24    0.97    |  FACTOR(8)     -2.94    -0.12    1.55    1.00
   Case  27    0.97    |  FACTOR(9)     -2.80    -0.23    1.73    1.12
   Case  32    0.97    |  FACTOR(10)    -1.57    -0.03    1.85    1.07
   Case  40    0.97    |  FACTOR(11)    -1.92     0.20    2.23    0.98
   Case  44    0.97    |  FACTOR(12)    -3.64    -0.35    1.09    1.23
   Case  46    0.97    |  FACTOR(13)    -3.30    -0.32    2.52    1.42
   Case  47    0.97    |  FACTOR(14)    -2.33    -0.00    2.00    1.10
   Case  48    0.97    |  FACTOR(15)    -2.66     0.02    1.87    1.07
   Case  50    0.97    |  FACTOR(16)    -2.14     0.29    2.82    1.27
   Case  52    0.97    |  FACTOR(17)    -0.84     0.31    2.01    0.77
                       |  FACTOR(18)    -1.47     0.12    1.58    0.79
                       |  FACTOR(19)    -2.40     0.05    2.69    1.18
                       |  FACTOR(20)    -1.58    -0.04    2.30    1.15
                       |  FACTOR(21)    -1.10     0.32    3.10    1.24
                       |  FACTOR(22)    -1.15     0.01    1.63    0.85
                       |  FACTOR(23)    -3.20    -0.23    1.17    1.20
                       |  FACTOR(24)    -3.25    -0.40    0.87    1.08
                       |  FACTOR(25)    -1.25     0.04    2.36    0.95
                       |  FACTOR(26)    -2.19    -0.22    0.98    0.94
                       |  FACTOR(27)    -2.32    -0.02    1.60    1.08
                       |  FACTOR(28)    -0.81     0.11    1.39    0.70
```

*FIG. 122D*

| | | | | |
|---|---|---|---|---|
| FACTOR(29) | -2.02 | -0.19 | 1.91 | 1.12 |
| FACTOR(30) | -1.45 | -0.14 | 0.90 | 0.64 |
| FACTOR(31) | -1.32 | 0.01 | 1.44 | 0.68 |
| FACTOR(32) | -1.07 | 0.26 | 2.55 | 0.81 |
| FACTOR(33) | -2.34 | -0.16 | 1.04 | 0.84 |
| FACTOR(34) | -1.63 | 0.03 | 2.15 | 1.07 |
| FACTOR(35) | -0.87 | 0.39 | 3.01 | 0.93 |
| FACTOR(36) | -0.85 | 0.21 | 2.47 | 0.99 |
| FACTOR(37) | -1.42 | -0.02 | 1.98 | 0.75 |
| FACTOR(38) | -0.94 | 0.25 | 2.60 | 0.80 |
| FACTOR(39) | -2.19 | 0.12 | 1.53 | 0.88 |
| FACTOR(40) | -1.06 | -0.07 | 1.56 | 0.74 |
| FACTOR(41) | -0.49 | 0.18 | 1.55 | 0.62 |
| FACTOR(42) | -1.77 | 0.17 | 1.31 | 0.73 |
| FACTOR(43) | -2.28 | -0.40 | 1.13 | 0.88 |
| FACTOR(44) | -2.33 | 0.31 | 2.96 | 1.31 |
| FACTOR(45) | -2.74 | -0.10 | 3.27 | 1.33 |
| FACTOR(46) | -3.40 | -0.23 | 1.73 | 1.20 |
| FACTOR(47) | -1.86 | -0.12 | 1.55 | 0.78 |
| FACTOR(48) | -2.16 | 0.15 | 1.63 | 0.91 |
| FACTOR(49) | -2.51 | 0.03 | 3.14 | 1.24 |
| FACTOR(50) | -1.00 | 0.23 | 1.43 | 0.64 |
| FACTOR(51) | -2.57 | -0.06 | 1.05 | 0.79 |
| FACTOR(52) | -1.99 | -0.33 | 0.44 | 0.68 |

Cluster Profile Plots
1
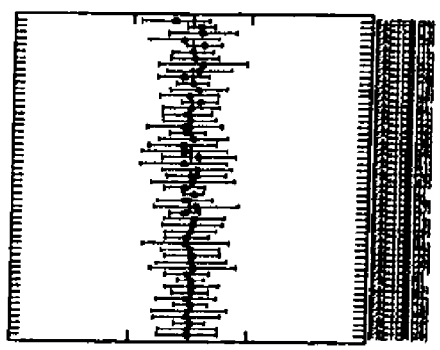
2
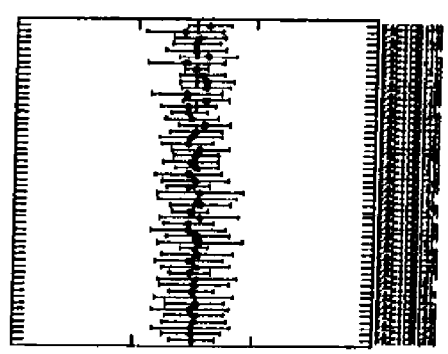
3
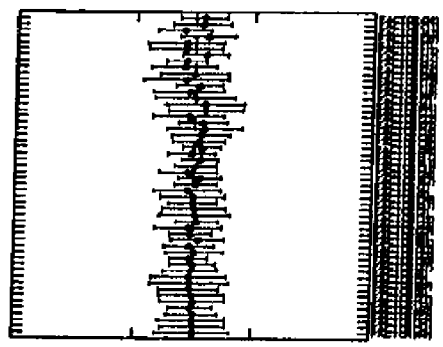
*FIG. 123B*

SEQUENCE LISTING

<160> NUMBER OF SEQ ID NOS: 16

<210> SEQ ID NO 1
<211> LENGTH: 22
<212> TYPE: DNA
<213> ORGANISM: Artificial Sequence
<220> FEATURE:
<223> OTHER INFORMATION: Synthetic DNA

<400> SEQUENCE: 1
tgctggcaac cttcaaatag ga                                              22

<210> SEQ ID NO 2
<211> LENGTH: 23
<212> TYPE: DNA
<213> ORGANISM: Artificial Sequence
<220> FEATURE:
<223> OTHER INFORMATION: Synthetic DNA

<400> SEQUENCE: 2
aggcctaaag gaactaactc cac                                             23

<210> SEQ ID NO 3
<211> LENGTH: 9
<212> TYPE: PRT
<213> ORGANISM: Artificial Sequence
<220> FEATURE:

```
<223> OTHER INFORMATION: Synthetic Peptide
<220> FEATURE:
<221> NAME/KEY: misc_feature
<222> LOCATION: (5)..(6)
<223> OTHER INFORMATION: Xaa can be any naturally occurring amino acid

<400> SEQUENCE: 3

Ser Gly Gly Asp Xaa Xaa Gly Gln Leu
1               5

<210> SEQ ID NO 4
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 4

Ser Val Gly Gly Val Asn Thr Gly Gln Leu
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 5

Ser Val Gly Gln Glu Asn Thr Gly Gln Leu
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (3)..(4)
<223> OTHER INFORMATION: Xaa can be any naturally occurring amino acid

<400> SEQUENCE: 6

Ser Glu Xaa Xaa Asp Asn Gln Ala Pro
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 7

Ser Asp Gly Gln Glu Asp Gln Ala Pro
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 8

Ser Pro Gly Gln Asp Asn Gln Ala Pro
1               5
```

```
<210> SEQ ID NO 9
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 9

Ser Glu Thr Gly Ser Gly Asn Thr Leu
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 10

Ser Val Thr Asp Ser Gly Asn Thr Leu
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 11

Ser Glu Thr Gly Ser Gly Asn Thr Leu
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 12

Ser Xaa Thr Gly Ser Gly Asn Thr Leu
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 13

Ser Gly Asn Thr Leu
1               5

<210> SEQ ID NO 14
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 14

Gly Thr Gly Ala
```

```
<210> SEQ ID NO 15
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 15

Asn Thr Glu Val
1

<210> SEQ ID NO 16
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X = a position that could not be determined
      due to ambiguous reading of the nucleotide sequence

<400> SEQUENCE: 16

Xaa Thr Gly Ala
1
```

SYSTEM, METHOD, DEVICE, AND COMPUTER PROGRAM PRODUCT FOR EXTRACTION, GATHERING, MANIPULATION, AND ANALYSIS OF PEAK DATA FROM AN AUTOMATED SEQUENCER

REFERENCE TO COMPUTER PROGRAM LISTING APPENDIX

Filed herewith in triplicate (labeled Copy 1.1, Copy 1.2, and Copy 1.3, respectively) is a computer program listing appendix on a compact disc read only memory (CD-ROM). The entire contents of the computer program listing appendix is incorporated herein by reference.

Each of the three copies of the computer program listing appendix were created on Jul. 1, 2003, and each includes the following files:

| Name | Size | Type | Modified |
| --- | --- | --- | --- |
| Admin | 49 KB | Text | Jul. 1, 2002 |
| CAppFile.cp | 7 KB | CP file | Feb. 5, 2002 |
| CAppFile.h | 3 KB | H file | Mar. 30, 2001 |
| CAppleScript.cp | 8 KB | CP file | Jan. 29, 2001 |
| CAppleScript.h | 2 KB | H file | Jan. 29, 2001 |
| CGel.cp | 6 KB | CP file | Aug. 16, 2001 |
| CGel.h | 4 KB | H file | Jan. 29, 2001 |
| CISEApeaksApp.cp | 19 KB | CP file | Feb. 7, 2002 |
| CISEApeaksApp.h | 2 KB | H file | Jan. 29, 2001 |
| CISEApeaksApp.ppob | 0 KB | PPOB file | Feb. 4, 2002 |
| CISEApeaksApp.rsrc | 0 KB | RSRC file | Jun. 19, 2001 |
| CISEApp.cp | 11 KB | CP file | Apr. 20, 2001 |
| CISEApp.h | 2 KB | H file | Mar. 27, 2001 |
| Common.ppob | 0 KB | PPOB file | Nov. 10, 2000 |
| Constants.h | 5 KB | H file | Jun. 20, 2002 |
| Constants | 24 B | TEXT | Jul. 1, 2002 |
| COutPutDoc.cp | 5 KB | CP file | Mar. 27, 2001 |
| COutPutDoc.h | 3 KB | H file | Jan. 29, 2001 |
| CPictPlaces.cp | 8 KB | CP file | Aug. 10, 2001 |
| CPictPlaces.h | 3 KB | H file | Jan. 29, 2001 |
| CPrefFile.cp | 4 KB | CP file | Mar. 1, 2001 |
| CPrefFile.h | 1 KB | H file | Jan. 29, 2001 |
| CRun.cp | 34 KB | CP file | Feb. 7, 2002 |
| CRun.h | 3 KB | H file | Jan. 29, 2001 |
| CTextDocument.cp | 9 KB | CP file | Jan. 29, 2001 |
| CTextDocument.h | 1 KB | H file | Jan. 29, 2001 |
| CTextView.cp | 2 KB | CP file | Jan. 29, 2001 |
| CTextView.h | 2 KB | H file | Jan. 29, 2001 |
| DataAnalyser | 237 KB | TEXT | Jul. 1, 2002 |
| DataFormater | 83 KB | TEXT | Jul. 1, 2002 |
| DataParameter | 55 KB | TEXT | Jul. 1, 2002 |
| DataUtility | 66 KB | TEXT | Jul. 1, 2002 |
| DEApp.ppob | 0 KB | PPOB file | Dec. 22, 2000 |
| DEApp.rsrc | 0 KB | RSRC file | Jun. 19, 2001 |
| DSApp.ppob | 0 KB | PPOB file | Oct. 19, 2000 |
| DSApp.rsrc | 0 KB | RSRC file | Jun. 19, 2001 |
| FrmAbout | 22 KB | TEXT | Jul. 1, 2002 |
| FrmDFPref | 22 KB | TEXT | Jul. 1, 2002 |
| FrmfileInfo | 21 KB | TEXT | Jul. 1, 2002 |
| FrmLicence | 23 KB | TEXT | Jul. 1, 2002 |
| FrmMainMenu | 24 KB | TEXT | Jul. 1, 2002 |
| FrmNewFile | 21 KB | TEXT | Jul. 1, 2002 |
| FrmPreferences | 25 KB | TEXT | Jul. 1, 2002 |
| FrmYesNo | 20 KB | TEXT | Jul. 1, 2002 |
| GSExportscript | 25 KB | TEXT | Jul. 1, 2002 |
| GSPeak.h | 2 KB | H file | Jan. 29, 2001 |
| GSProfile.cp | 3 KB | CP file | Jan. 29, 2001 |
| GSProfile.h | 2 KB | H file | Jan. 29, 2001 |
| GUI_Macros | 76 KB | TEXT | Jul. 1, 2002 |
| ISEApp.ppob | 0 KB | PPOB file | Mar. 27, 2001 |
| ISEApp.rsrc | 0 KB | RSRC file | Jun. 19, 2001 |
| ISPeak.h | 2 KB | H file | Jan. 29, 2001 |
| ISProfile.cp | 15 KB | CP file | Jan. 29, 2001 |
| ISProfile.h | 3 KB | H file | Jan. 29, 2001 |
| MyFileUtilities.cp | 18 KB | CP file | Aug. 10, 2001 |
| MyFileUtilities.h | 2 KB | H file | Jan. 29, 2001 |
| MyUtilities.cp | 5 KB | CP file | Feb. 6, 2002 |
| MyUtilities.h | 2 KB | H file | Feb. 5, 2002 |
| Peak.h | 1 KB | H file | Feb. 5, 2002 |
| PictPlace.h | 2 KB | H file | Jan. 29, 2001 |
| PrintingConstants.h | 1 KB | H file | Oct. 5, 2000 |
| Profile.cp | 21 KB | CP file | Feb. 13, 2002 |
| Profile.cp.old | 18 KB | CP file | Mar. 1, 2001 |
| Profile.h | 7 KB | H file | Feb. 5, 2002 |
| Thiswbk | 21 KB | TEXT | Jul. 1, 2002 |
| Utilities | 94 KB | TEXT | Jul. 1, 2002 |
| Well.h | 2 KB | H file | Jan. 29, 2001 |

BACKGROUND OF THE INVENTION

1. Field of the Invention

The present invention relates to a novel computer program product to extract and gather peak information from an automated sequencer or bioinformatics tool into a peak database, and to manipulate and analyze the peak information within the database.

2. Discussion of the Background

The recent conclusion of several genome sequencing projects, including yeast (*Nature* 1997; 387:suppl. 3-105), human (Venter et al, *Science* 2001; 291:1304-1351), *C. elegans* (*Science* 1998; 282:2012-8), and rice (J. Yu et al., *Science* 2002; 296:79 and S. A. Goff et al., *Science* 2002; 296:92), as well as on-going sequencing efforts, have generated a deluge of DNA sequence information. These DNA sequences encode the basic "message of life." However, cataloguing and probing the vast numbers of genes and the proteins, which they encode, can provide novel insights into cell biology, drug design, and therapeutic strategies.

Accordingly, many new analytical methods have been developed to digest the flood of genome sequence data, including analysis of the transcriptome, proteome and metabolites. High-throughput analysis of protein targeting and other methods will ascribe new information to proteins and create important links with other large datasets. To fulfill the potential revealed by this genomic information, many challenges have to be met. Among these are indexing and cataloguing of raw DNA and RNA sequence data, identification of genes and the regulation of their expression, characterization of protein activity and protein-protein, protein-ligand, or protein-DNA/RNA interactions.

One such strategy commonly employed is a DNA automatic sequencer. DNA automatic sequencers are used to determine DNA fragment lengths in a wide array of applications: DNA sequencing, microsatellites, Single Nucleotide Polymorphism, Restriction or Amplified Fragment Length Polymorphism, Single Strand Conformation Polymorphism, gene expression quantification and analyses of the immune receptor diversity. All of these applications require access to raw data (peak area and nucleotide length). Raw data being stored in one file per lane, studies rapidly give rise to hundreds of files. However, with the increasing number of samples analyzed, no tool is currently available to allow the extensive and efficient retrieval of this raw data.

Accordingly, there remains a critical need for a novel program for handling the extensive amounts raw data provided by automated sequencers. In addition, there remains a critical need for a novel program for efficient retrieval of this raw data. Moreover, there remains a critical need for a novel program to analyze the extensive amounts of raw data.

SUMMARY OF THE INVENTION

It is an object of the present invention to provide a method for high throughput analysis of data. One embodiment being a method of using bioinformatic tools to extract and/or smooth peak data sets according to parameter files and store them in data files. In a further embodiment, particular profiles representing peaks may be created and may be analyzed.

Another object of the invention is a method of building a database.

Another object of the invention is a method of analyzing database by statistical tools. One embodiment being a method of determining prognostic or diagnostic criteria. In a further embodiment, the prognostic and diagnostic criteria are used in the field of physiopathology such as immunotherapy, cancer treatment, HIV, infectious disease, and/or autoimmune disease.

Another object of the invention is a high-throughput method for analysis of immune repertoires.

Another object of the invention is a high-throughput method for analysis of immune repertoires comprising purifying polynucleotide fragments from biological samples, which contains polynucleotide fragments, synthesizing polynucleotides from purified polynucleotides, and amplifying polynucleotides. In one embodiment, the polynucleotide is amplified by PCR or SDA methods. A further embodiment is related to labeling polynucleotides for detection. Another embodiment is related separating polynucleotides, identifying peaks by determining their position in a separation matrix and area that correspond to labeled polynucleotides.

Another object of the invention is a method comprising:
a) isolating a biological sample;
b) extracting raw data from the biological sample; and
c) compiling the raw data into a database using ISEApeaks.

The objects above can be obtained and performed according the following further objects of the invention.

Another object of the invention is a computer program product, comprising:
a computer storage medium; and
a computer program code mechanism embedded in the computer storage medium for causing a computer to produce an analysis of raw data produced by a separation technique for biomolecules, the computer program code mechanism having
a first computer code device configured to extract a first set of raw data and a second set of raw data from at least one database,
a second computer code device configured to determine a first value from the first set of raw data corresponding to a first characteristic and a second value from the second set of raw data corresponding to the first characteristic, and
a third computer code device configured to store the first value and the second value in a memory. The above object may be performed in combination with these further embodiments. One embodiment is a computer code device configured to retrieve the first value and the second value from the memory and to order the first value and the second value based on a user preference stored in a second memory. One embodiment is a computer code device configured to produce a graphical representation of the first value and the second value as ordered by the fourth computer code device. One embodiment is a computer code device configured to smooth at least one of the first set of raw data and the second set of raw data produced by the separation technique for biomolecules. One embodiment is a computer code device configured to format at least one of the first value and the second value. One embodiment is a computer code device configured to parameterize at least one of the first set of raw data and the second set of raw data. One embodiment is a computer code device, configured to analyze at least one of the first set of raw data and the second set of raw data. One embodiment is a computer code device, configured to export at least one of the first value and the second value.

Another object of the invention is a device, comprising:
at least one extractor configured to extract raw data produced by a separation technique for biomolecules, the extractor including
a processor, and
a computer readable medium encoded with processor readable instructions that, when executed by the processor implement,
an extraction mechanism configured to extract a first set of raw data and a second set of raw data from at least one database,
a characteristic determining mechanism configured to determine a first value from the first set of raw data corresponding to a first characteristic and a second value from the second set of raw data corresponding to the first characteristic, and
an output mechanism configured to store the first value and the second value in a memory.

Another object of the invention is a system, comprising:
a digital repository populated with entries of raw data produced by a separation technique for biomolecules;
a processor; and
a computer readable medium encoded with processor readable instructions that, when executed by the processor implement,
an extraction mechanism configured to extract a first set of raw data and a second set of raw data from the digital repository,
a characteristic determining mechanism configured to determine a first value from the first set of raw data corresponding to a first characteristic and a second value from the second set of raw data corresponding to the first characteristic, and
an output mechanism configured to store the first value and the second value in a memory.

Another object of the invention is a system, comprising:
a digital repository populated with entries of raw data produced by a separation technique for biomolecules;
a processor; and
a computer readable medium encoded with processor readable instructions that, when executed by the processor implement,
an extraction mechanism configured to extract a first set of raw data and a second set of raw data from the digital repository via a network,
a characteristic determining mechanism configured to determine a first value from the first set of raw data corresponding to a first characteristic and a second value from the second set of raw data corresponding to the first characteristic, and
an output mechanism configured to store the first value and the second value in a memory.

Another object of the invention is a computer data signal embodied in a carrier wave, said computer data signal comprising extracted raw data produced by a separation technique for biomolecules.

Another object of the invention is a computer data signal embodied in a carrier wave, said computer data signal comprising smoothed raw data, wherein the raw data includes data produced by a separation technique for biomolecules.

Another object of the invention is a computer data signal embodied in a carrier wave, said computer data signal comprising formatted raw data, wherein the raw data includes data produced by a separation technique for biomolecules.

Another object of the invention is a computer data signal embodied in a carrier wave, said computer data signal comprising parameterized raw data, wherein the raw data includes data produced by a separation technique for biomolecules.

Another object of the invention is a computer data signal embodied in a carrier wave, said computer data signal comprising analyzed raw data, wherein the raw data includes data produced by a separation technique for biomolecules.

Another object of the invention is a computer data signal embodied in a carrier wave, said computer data signal comprising exported raw data, wherein the raw data includes data produced by a separation technique for biomolecules.

Another object of the invention is a software package, wherein said software package is embodied by the ISEApeaks package 2.0.1.

The above objects highlight certain aspects of the invention. Additional objects, aspects and embodiments of the invention are found in the following detailed description of the invention.

BRIEF DESCRIPTION OF THE FIGURES

A more complete appreciation of the invention and many of the attendant advantages thereof will be readily obtained as the same becomes better understood by reference to the following Figures in conjunction with the detailed description below.

FIG. 7: ISEApeaks peak smoothing and quality checks. (A) A CDR3 profile of human BV4-BC amplification as provided by the Immunoscope product. Nine peaks are visible by eye. (B) Histograms of peaks as obtained after extraction with DataExtractor (raw Immunoscope peak data) and after application of the three filters of DataSmoother. After filtering, peaks correspond to what is seen on the Immunoscope profile. (C) Table of peak data of this BV4-BC profile after each filter as it appears in the DataFormatter file. DataFormatter highlights adjacent peaks in light grey, ambiguous peaks in dark grey, the main peak in medium grey and the first peak that can be attributed to the mTheoreticLength (here 192 nt) in bold. Note that ISEApeaks uses color. In this example, DataSmoother finally solved all problems: each peak can be attributed to a theoretical length without conflicts.

FIG. 10: Perturbation of TCRB repertoires induced by *P. berghei* ANKA. (A) BV-BC repertoire perturbations (DBV-BC) during hyperparasitemia. DBV-BC were computed with ISEApeaks using the CTR spleen group as control. Mean sample DBV-BC (µDBV-BC) with their standard error are shown for HP and CTR mice in the PBL and spleen. DBV-BC range from 0, identical to the reference repertoire, to 100, completely perturbed. Sample numbers are identical to FIG. 8. (B) Schematic representation of sample clusters obtained with k-mean clustering on DBV-BC with k=2.

FIG. 11: DBV-BJ perturbation during hyperparasitemia. The BV-BJ repertoires of eleven PBL samples (6 CTR and 5 HP) were correctly grouped by k-mean clustering with k=2 on DBV-BJ data.

FIG. 17: A DataParameter CGEL worksheet.
FIG. 18: A DataParameter CPICTPLACES worksheet.
FIG. 19: A DataFormatter file.
FIG. 20: DataAnalyser 'para' worksheet is used to parameterise the different macros of DataAnalyser.
FIG. 21: A DataAnalyser 'Peaks' worksheet.
FIG. 22: A DataAnalyser worksheet showing the result of the 'PercentImport' macro.
FIG. 23: the 'Perturbation1' macro.
FIG. 24: the 'Perturbation2' macro.
FIG. 25: the 'RIS' macro.
FIG. 26: the 'OligoScore' macro.
FIG. 28 B. Depiction of overall disturbance.
FIG. 28 C. Depiction of overall disturbance vs. oligoclonality.
FIG. 28 D. Depiction of overall disturbance vs. oligoclonality.
FIG. 29. Parameters of File to Use.
FIG. 30 B. Depiction of overall disturbance
FIG. 31. Parameters of File to Use.
FIG. 32 A. Depiction of overall disturbance vs. oligoclonality.
FIG. 32 B. Depiction of overall disturbance.
FIG. 33. Parameters of File to Use.
FIG. 34 B. Depiction of overall disturbance.
FIG. 35. Parameters of File to Use.
FIG. 36. Parameters of File to Use.
FIG. 39. Oligoclonality score.
FIG. 40 B. Draw array/parameters.
FIG. 41. Parameters of file to use.
FIG. 45 B. Draw array/parameters.
FIG. 46. Parameters of File to Use.
FIG. 49. Oligoclonality score.
FIG. 50 B. Draw array/parameters.
FIG. 51. Parameters of File to Use.
FIG. 53 B. Draw array/parameters.
FIG. 54. Oligoclonality score.
FIG. 55 B. Draw array/parameters.
FIG. 56. Parameters of File to Use.
FIG. 57 B. *Plasmodium berghei* infection of B120D2mice.
FIG. 57 C. *Plasmodium berghei* infection of B120D2mice.
FIG. 57 D. *Plasmodium berghei* infection of B120D2mice.
FIG. 58 B. *Plasmodium berghei* infection of B120D2mice.
FIG. 58 C. *Plasmodium berghei* infection of B120D2mice.
FIG. 58 D. *Plasmodium berghei* infection of B120D2mice.
FIG. 59 B. Means Table for TCRBV01.
FIG. 59 C. Chart of Interactions for TCRBV01.
FIG. 59 D(1). PLSD Fisher's Test for TCRBV01.
FIG. 59 D(2). PLSD Fisher's Test for TCRBV01.
FIG. 59 E. ANOVA (Analysis of Variance) Table for TCRBV02.
FIG. 59 F. Means Table for TCRBV02.
FIG. 59 G. Chart of Interactions for TCRBV02.
FIG. 59 H(1). PLSD Fisher's Test for TCRBV02.
FIG. 59 H(2). PLSD Fisher's Test for TCRBV02.
FIG. 60 B. Means Table for TCRBV03.
FIG. 60 C. Chart of Interactions for TCRBV03.
FIG. 60 D(1). PLSD Fisher's Test.
FIG. 60 D(2). PLSD Fisher's Test.
FIG. 60 E. ANOVA (Analysis of Variance) Table for TCRBV04.
FIG. 60 F. Means Table for TCRBV04.
FIG. 60 G. Chart of Interactions for TCRBV04.
FIG. 60 H(1). PLSD Fisher's Test.
FIG. 60 H(2). PLSD Fisher's Test.
FIG. 61 B. Means Table for TCRBV05.1.
FIG. 61 C. Chart of Interactions for TCRBV05.1.
FIG. 61 D(1). PLSD Fisher's Test.
FIG. 61 D(2). PLSD Fisher's Test.
FIG. 61 E. ANOVA Table.
FIG. 61 F. Means Table for TCRBV05.2.
FIG. 61 G. Chart of Interactions for TCRBV05.2.
FIG. 61 H(1). PLSD Fisher's Test.
FIG. 61 H(2). PLSD Fisher's Test.
FIG. 62 B. Means Table for TCRBV06.
FIG. 62 C. Chart of Interactions for TCRBV06.

FIG. 62 D(1). PLSD Fisher's Test.
FIG. 62 D(2). PLSD Fisher's Test.
FIG. 62 E. ANOVA Table.
FIG. 62 F. Means Table for TCRBV07.
FIG. 62 G. Chart of Interactions for TCRBV07.
FIG. 62 H(1). PLSD Fisher's Test.
FIG. 62 H(2). PLSD Fisher's Test.
FIG. 63 B. Means Table for TCRBV08.1.
FIG. 63 C. Chart of Interactions for TCRBV08.1.
FIG. 63 D(1). PLSD Fisher's Test.
FIG. 63 D(2). PLSD Fisher's Test.
FIG. 63 E. ANOVA Table.
FIG. 63 F. Means Table for TCRBV08.2.
FIG. 63 G. Chart of Interactions for TCRBV08.2.
FIG. 63 H(1). PLSD Fisher's Test.
FIG. 63 H(2). PLSD Fisher's Test.
FIG. 64 B. Means Table for TCRBV08.3.
FIG. 64 C. Chart of Interactions for TCRBV08.3.
FIG. 64 D(1). PLSD Fisher's Test.
FIG. 64 D(2). PLSD Fisher's Test.
FIG. 64 E. ANOVA Table.
FIG. 64 F. Means Table for TCRBV09.
FIG. 64 G. Chart of Interactions for TCRBV09.
FIG. 64 H(1). PLSD Fisher's Test.
FIG. 64 H(2). PLSD Fisher's Test.
FIG. 65 B. Means Table for TCRBV10.
FIG. 65 B. Chart of Interactions for TCRBV10.
FIG. 65 D(1). PLSD Fisher's Test.
FIG. 65 D(2). PLSD Fisher's Test.
FIG. 65 E. ANOVA Table.
FIG. 65 F. Means Table for TCRBV11.
FIG. 65 G. Chart of Interactions for TCRBV11.
FIG. 65 H(1). PLSD Fisher's Test.
FIG. 65 H(2). PLSD Fisher's Test.
FIG. 66 B. Means Table for TCRBV12.
FIG. 66 C. Chart of Interactions for TCRBV12.
FIG. 66 D(1). PLSD Fisher's Test.
FIG. 66 D(2). PLSD Fisher's Test.
FIG. 66 E. ANOVA Table.
FIG. 66 F. Means Table for TCRBV13.
FIG. 66 G. Chart of Interactions for TCRBV13.
FIG. 66 H(1). PLSD Fisher's Test.
FIG. 66 H(2). PLSD Fisher's Test.
FIG. 67 B. Means Table for TCRBV14.
FIG. 67 C. Chart of Interactions for TCRBV14.
FIG. 67 D(1). PLSD Fisher's Test.
FIG. 67 D(2). PLSD Fisher's Test.
FIG. 67 E. ANOVA Table.
FIG. 67 F. Means Table for TCRBV15.
FIG. 67 G. Chart of Interactions for TCRB15.
FIG. 67 H(1). PLSD Fisher's Test.
FIG. 67 H(2). PLSD Fisher's Test.
FIG. 68 B. Means Table for TCRBV16.
FIG. 68 C. Chart of Interactions for TCRBV16.
FIG. 68 D(1). PLSD Fisher's Test.
FIG. 68 D(2). PLSD Fisher's Test.
FIG. 68 E. ANOVA Table.
FIG. 68 F. Means Table for TCRBV18.
FIG. 68 G. Chart of Interactions for TCRBV18.
FIG. 68 H(1). PLSD Fisher's Test.
FIG. 68 H(2). PLSD Fisher's Test.
FIG. 69 B. Means Table for TCRBV20.
FIG. 69 C. Chart of Interactions for TCRBV20.
FIG. 69 D(1). PLSD Fisher's Test.
FIG. 69 D(2). PLSD Fisher's Test.
FIG. 70 B. Means Table for TCRBV01.
FIG. 70 C. Chart of Interactions for TCRBV01.
FIG. 70 D. PLSD Fisher's Test.
FIG. 70 E. ANOVA (Analysis of Variance) Table for TCRBV02.
FIG. 70 F. Means Table for TCRBV02.
FIG. 70 G. Chart of Interactions for TCRBV02.
FIG. 70 H. PLSD Fisher's Test for TCRBV02.
FIG. 71 B. Means Table for TCRBV03.
FIG. 71 C. Chart of Interactions for TCRBV03.
FIG. 71 D. PLSD Fisher's Test.
FIG. 71 E. ANOVA Table.
FIG. 71 F. Means Table.
FIG. 71 G. Chart of Interactions for TCRBV04.
FIG. 71 H. PLSD Fisher's Test.
FIG. 72 B. Means Table.
FIG. 72 C. Chart of Interactions.
FIG. 72 D. PLSD Fisher's Test.
FIG. 72 E. ANOVA Table.
FIG. 72 F. Mean Table.
FIG. 72 G. Chart of Interactions.
FIG. 72 H. PLSD Fisher's Test.
FIG. 73 B. Mean Table.
FIG. 73 C. Chart of Interactions.
FIG. 73 D. PLSD Fisher's Test.
FIG. 73 E. ANOVA Table.
FIG. 73 F. Mean Table.
FIG. 73 G. Chart of Interactions.
FIG. 73 H. PLSD Fisher's Test.
FIG. 74 B. Mean Table.
FIG. 74 C. Chart of Interactions.
FIG. 74 D. PLSD Fisher's Test.
FIG. 74 E. ANOVA (Analysis of Variance) Table for TCRBV08.2.
FIG. 74 F. Mean Table for TCRBV08.2.
FIG. 74 G. Chart of Interactions for TCRBV08.2.
FIG. 74 H. PLSD Fisher's Test for TCRBV08.2.
FIG. 75 B. Mean Table.
FIG. 75 C. Chart of Interactions.
FIG. 75 D. PLSD Fisher's Test.
FIG. 75 E. ANOVA Table.
FIG. 75 F. Mean Table.
FIG. 75 G. Chart of Interactions.
FIG. 75 H. PLSD Fisher's Test.
FIG. 76 B. Mean Table.
FIG. 76 C. Chart of Interactions.
FIG. 76 D. PLSD Fisher's Test.
FIG. 76 E. ANOVA Table.
FIG. 76 F. Mean Table.
FIG. 76 G. Chart of Interactions.
FIG. 76 H. PLSD Fisher's Test.
FIG. 77 B. Mean Table.
FIG. 77 C. Chart of Interactions.
FIG. 77 D. PLSD Fisher's Test.

FIG. 77 E. ANOVA Table.
FIG. 77 F. Mean Table.
FIG. 77 G. Chart of Interactions.
FIG. 77 H. PLSD Fisher's Test.
FIG. 78 B. Mean Table.
FIG. 78 C. Chart of Interactions.
FIG. 78 D. PLSD Fisher's Test.
FIG. 78 E. ANOVA Table.
FIG. 78 F. Mean Table.
FIG. 78 G. Chart of Interactions.
FIG. 78 H. PLSD Fisher's Test.
FIG. 79 B. Mean Table.
FIG. 79 C. Chart of Interactions.
FIG. 79 D. PLSD Fisher's Test.
FIG. 79 E. ANOVA Table.
FIG. 79 F. Mean Table.
FIG. 79 G. Chart of Interactions.
FIG. 79 H. PLSD Fisher's Test.
FIG. 80 B. Mean Table & Graph of Interactions for TCRBV20.
FIG. 81. Peak Parameters to be recovered.
FIG. 82 A. Oligoclonality Score.
FIG. 82 B. µDVb.
FIG. 83. Peak Parameters to be recovered.
FIG. 84 A. Ranging according to oligoclonality score.
FIG. 84 B. Ranging according to oligoclonality score.
FIG. 85 A. Groups RT3-FT14.
FIG. 85 B. Groups FT15-F3*S10.
FIG. 89 B. Means Table for TCRBV01.
FIG. 89 C. PLSD Fisher's Test for TCRBV02.
FIG. 89 D. PLSD Fisher's Test for TCRBV01 & Curve of Interactions for TCRBV01.
FIG. 89 E. ANOVA Table for TCRBV02.
FIG. 89 F. Means Table for TCRBV02.
FIG. 89 G. PLSD Fisher's Test or TCRBV02.
FIG. 89 H. PLSD Fisher's Test for TCRBV02 & Curve of Interactions for TCRBV02.
FIG. 90 B. Means Table for TCRBV05.1.
FIG. 90 C. PLSD Fisher's Test for TCRBV05.1.
FIG. 90 D. PLSD Fisher's Test for TCRBV05.1 & Curve of Interactions for TCRBV05.1.
FIG. 90 E. ANOVA Table for TCRBV05.2.
FIG. 90 F. Means Table for TCRBV05.2.
FIG. 90 G. PLSD Fisher's Test or TCRBV05.1.
FIG. 90 H. PLSD Fisher's Test for TCRBV05.2 & Curve of Interactions for TCRBV05.2.
FIG. 91 B. Means Table for TCRBV06.1.
FIG. 91 C. PLSD Fisher's Test for TCRBV06.1.
FIG. 91 D. PLSD Fisher's Test for TCRBV06.1 & Curve of Interactions for TCRBV06.1.
FIG. 91 E. ANOVA Table for TCRBV06.2.
FIG. 91 F. Means Table for TCRBV06.2.
FIG. 91 G. PLSD Fisher's Test or TCRBV06.2.
FIG. 91 H. PLSD Fisher's Test for TCRBV06.2 & Curve of Interactions for TCRBV06.2.
FIG. 92 B. Means Table for TCRBV10.
FIG. 92 C. PLSD Fisher's Test for TCRBV10.
FIG. 92 D. PLSD Fisher's Test for TCRBV10 & Curve of Interactions for TCRBV010.
FIG. 92 E. ANOVA Table for TCRBV11.
FIG. 92 F. Means Table for TCRBV11.
FIG. 92 G. PLSD Fisher's Test or TCRBV11.
FIG. 92 H. PLSD Fisher's Test for TCRBV11 & Curve of Interactions for TCRBV11.
FIG. 93 B. Means Table for TCRBV14.
FIG. 93 C. PLSD Fisher's Test for TCRBV14.
FIG. 93 D. PLSD Fisher's Test for TCRBV14 & Curve of Interactions for TCRBV14.
FIG. 93 E. ANOVA Table for TCRBV15.
FIG. 93 F. Means Table for TCRBV15.
FIG. 93 G. PLSD Fisher's Test or TCRBV15.
FIG. 93 H. PLSD Fisher's Test for TCRBV15 & Curve of Interactions for TCRBV11.
FIG. 94 B. Means Table for TCRBV20.
FIG. 94 C. PLSD Fisher's Test for TCRBV20.
FIG. 94 D. PLSD Fisher's Test for TCRBV20.
FIG. 95 C. Curve of Interactions for TCRBV0.3.
FIG. 95 D. Curve of Interactions for TCRBV13.
FIG. 95 E. Curve of Interactions for TCRBV14.
FIG. 95 F. Curve of Interactions for TCRBV20.
FIG. 95 G. Curve of Interactions for TCRBV12.
FIG. 96 B. Flowchart.
FIG. 98 A. Systat Rectangular File & Latent Roots.
FIG. 98 B. Latent Roots, cont.
FIG. 98 C. Latent Roots, cont.
FIG. 98 D. Latent Roots, cont. & Component Loadings
FIG. 99 A. Entries TCRVB018_7 to TCRVB0_12.
FIG. 99 B. Entries TCRVB010_12 to TCRVB18_17.
FIG. 99 C. Entries TCRVB18_8 to TCRVB051_12.
FIG. 99 D. Entries TCRVB51_13 to TCRVB010_6.
FIG. 100 A. Entries TCRVB10_7 to TCRVB016_13.
FIG. 100 B. Entries TCRVB18_13 to TCRVB051_7.
FIG. 100 C. Entries TCRVB51_8 to TCRVB009_11.
FIG. 100 D. Entries TCRVB09_12 to TCRVB16_8.
FIG. 101 A. Entries TCRVB16_9 to TCRVB04_13.
FIG. 100 B. Entries TCRVB18_13 to TCRVB051_7.
FIG. 100 C. Entries TCRVB51_8 to TCRVB009_11.
FIG. 100 D. Entries TCRVB09_12 to TCRVB16_8.
FIG. 101 A. Entries TCRVB16_9 to TCRVB04_13.
FIG. 100 B. Entries TCRVB18_13 to TCRVB051_7.
FIG. 100 C. Entries TCRVB51_8 to TCRVB009_11.
FIG. 100 D. Entries TCRVB09_12 to TCRVB16_8.
FIG. 101 A. Entries TCRVB16_9 to TCRVB04_13.
FIG. 101 B. Entries TCRVB04_14 to TCRVB09_6.
FIG. 101 C. Entries TCRVB09_7 to TCRVB15_11.
FIG. 101 D. Entries TCRVB15_12 to TCRVB04_8.
FIG. 102 A. Entries TCRVB04_9 to TCRVB083_9.
FIG. 102 B. Entries TCRVB082_10 to TCRVB15_7.
FIG. 102 C. Entries TCRVB15_8 to TCRVB03_11.
FIG. 102 D. Entries TCRVB03_12 to TCRVB083_4.
FIG. 103 A. Entries TCRVB083_5 to TCRVB14_12.
FIG. 103 B. Entries TCRVB14_13 to TCRVB03_6.
FIG. 103 C. Entries TCRVB03_7 to TCRVB82_7.
FIG. 103 D. Entries TCRVB082_8 to TCRVB14_7.
FIG. 104 A. Entries TCRVB14_8 to TCRVB02_11.
FIG. 104 B. Entries TCRVB02_12 to TCRVB81_11.
FIG. 104 C. Entries TCRVB081_12 to TCRVB13_11.

FIG. 104 D. Entries TCRVB013__12 to TCRVB02__7.
FIG. 105 A. Entries TCRVB02__8 to TCRVB081__6.
FIG. 105 B. Entries TCRVB081__7 to TCRVB13__6.
FIG. 105 C. Entries TCRVB013__7 to TCRVB01__11.
FIG. 105 D. Entries TCRVB01__12 to TCRVB07__10.
FIG. 106 A. Entries TCRVB07__11 to TCRVB012__9.
FIG. 106 B. Entries TCRVB012__10 to TCRVB20__14.
FIG. 106 C. Entries TCRVB01__7 to TCRVB07__7.
FIG. 106 D. Entries TCRVB07__7 to TCRVB12__4.
FIG. 107 B. Entries TCRVB20__14 Variance Explained by Components.
FIG. 107 C. Scree Plot.
FIG. 108 A. Coefficients for Standardized Factor Scores.
FIG. 108 B. Coefficients for Standardized Factor Scores (cont.)
FIG. 108 C. Coefficients for Standardized Factor Scores (cont.)
FIG. 109 A. Coefficients for Standardized Factor Scores (cont.)
FIG. 109 B. Coefficients for Standardized Factor Scores (cont.)
FIG. 108 C. Coefficients for Standardized Factor Scores (cont.)
FIG. 109 D. Coefficients for Standardized Factor Scores (cont.)
FIG. 110 A. Coefficients for Standardized Factor Scores (cont.)
FIG. 110 B. Coefficients for Standardized Factor Scores (cont.)
FIG. 110 C. Coefficients for Standardized Factor Scores (cont.)
FIG. 110 D. Coefficients for Standardized Factor Scores (cont.)
FIG. 111 A. Coefficients for Standardized Factor Scores (cont.)
FIG. 111 B. Coefficients for Standardized Factor Scores (cont.)
FIG. 111 C. Coefficients for Standardized Factor Scores (cont.)
FIG. 111 D. Coefficients for Standardized Factor Scores (cont.)
FIG. 112 A. Coefficients for Standardized Factor Scores (cont.)
FIG. 112 B. Coefficients for Standardized Factor Scores (cont.)
FIG. 112 C. Coefficients for Standardized Factor Scores (cont.)
FIG. 112 D. Coefficients for Standardized Factor Scores (cont.)
FIG. 113 A. Coefficients for Standardized Factor Scores (cont.)
FIG. 113 B. Coefficients for Standardized Factor Scores (cont.)
FIG. 113 C. Coefficients for Standardized Factor Scores (cont.)
FIG. 113 D. Coefficients for Standardized Factor Scores (cont.)
FIG. 114 A. Coefficients for Standardized Factor Scores (cont.)
FIG. 114 B. Coefficients for Standardized Factor Scores (cont.)
FIG. 114 C. Coefficients for Standardized Factor Scores (cont.)
FIG. 114 D. Coefficients for Standardized Factor Scores (cont.)
FIG. 115 A. Coefficients for Standardized Factor Scores (cont.)
FIG. 115 B. Coefficients for Standardized Factor Scores (cont.)
FIG. 115 C. Coefficients for Standardized Factor Scores (cont.)
FIG. 115 D. Coefficients for Standardized Factor Scores (cont.)
FIG. 116 A. Coefficients for Standardized Factor Scores (cont.)
FIG. 116 B. Coefficients for Standardized Factor Scores (cont.)
FIG. 116 C. Coefficients for Standardized Factor Scores (cont.)
FIG. 116 D. Systat Rectangular File
FIG. 117 A. Entries Factor (1) to Factor (31)
FIG. 117 B. Entries Factor (32) to Factor (52)
FIG. 117 C. Entries Factor (1) to Factor (31)
FIG. 117 D. Entries Factor (32) to Factor (52)
FIG. 118 A. Classification Functions
FIG. 118 B. Entries Factor (1) to Factor (32)
FIG. 118 C. Entries Factor (1) to Factor (32)
FIG. 118 D. Entries Factor (33) to Factor (52)
FIG. 119 A. Entries Factor (33) to Factor (52)
FIG. 119 B. Classification Matrix
FIG. 119 C. Jack-knifed Classification Matrix
FIG. 119 D. Canonical Discriminant Functions
FIG. 120 A. Entries Factors (1) to Factor (32)
FIG. 120 B. Entries Factors (33) to Factor (52)
FIG. 120 C. Entries Factors (1) to Factor (32)
FIG. 120 D. Canonical Discriminant Functions
FIG. 121A. Entries Factors (1) to Factor (31)
FIG. 121B. Entries Factors (32) to Factor (52)
FIG. 121C. Entries Factors (1) to Factor (31)
FIG. 121D. Canonical Score of Group Means
FIG. 122A. Canonical Scores Plot
FIG. 122 B. Entries Factors (6) to Factor (52)
FIG. 122 C. Entries Factors (13) to Factor (52)
FIG. 122 D. Entries Factors (21) to Factor (52)
FIG. 123 A. Cluster Coordinate Plots
FIG. 123 B. Cluster Profile Plots

DETAILED DESCRIPTION OF THE INVENTION

Figure 1:
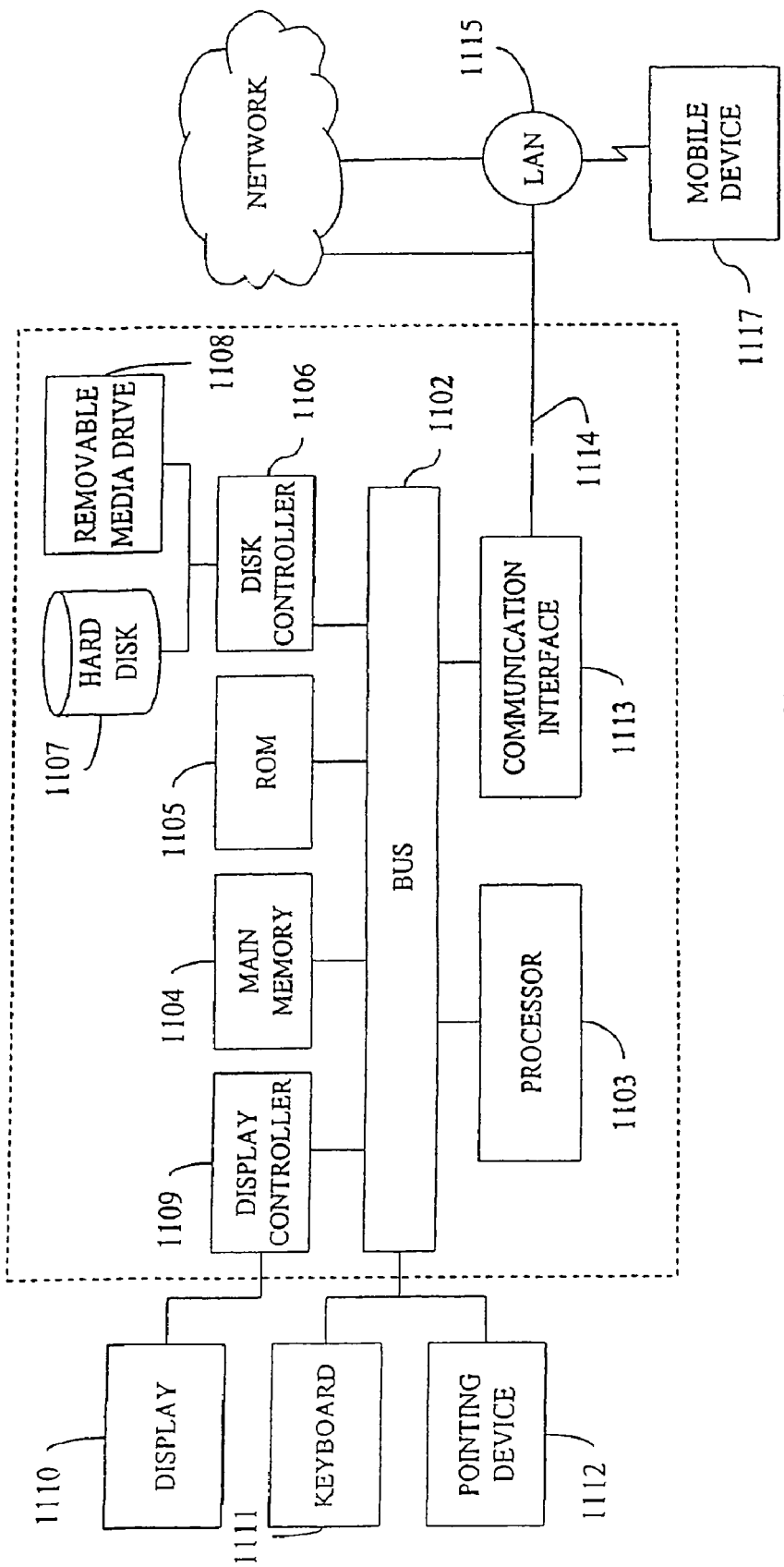
FIG. 1: a computer system 1101.

Unless specifically defined, all technical and scientific terms used herein have the same meaning as commonly understood by a skilled artisan in computers, software/program design, biochemistry, cellular biology, molecular biology, and the medical sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

In the central paradigm of modern molecular biology, biological information flows from DNA to RNA to protein. This general scheme gives rise to a powerful template-driven precision, in which the experimenter has the ability to manipulate any one of these classes of biomolecules based on the knowledge of another. Moreover, patterns of sequence homology and relatedness are tools to predict function and reveal evolutionary relationships. With the recent completion of the genomic sequences of humans and several other commonly studied model organisms, researchers are in the unprecedented position to probe the intricate interrelationship of biomolecules, not just in the context of this paradigm, but also in the context of gene identification, protein expression, characterization of protein activity, and characterization of protein-protein interactions, protein-ligand interactions, protein-drug interactions, and protein-DNA/RNA. Accordingly, researchers have devised a dynamic array of techniques to probe the structure, activity, and relationship of DNA, RNA, and proteins.

The present invention provides, in part, a program for handling the extensive amounts raw data made available by automated sequencers and raw data extraction programs. The automated sequencers and raw data extraction programs have been designed to digitize the results of growth culturing, electrophoresis, chromatography, blotting techniques, centrifugation, DNA microarrays, or protein microarrays or sugar residue arrays of biological samples. The nature of position and area of peaks will depend on the nature of the new data produced by these techniques, either periodical or ordered. For example, in the case of microarrays, peak position will correspond to its coordinate (column×row) on the array; the peak area will correspond to the intensity of the signal detected.

In addition, the present invention provides a novel program for efficient retrieval of this raw data which has been extracted by automated sequencers and raw data extraction programs.

Moreover, the present invention provides a novel program to analyze the extensive amounts of raw data extracted by automated sequencers and raw data extraction programs.

In particular, raw data extraction programs and DNA automatic sequencers are used to determine DNA fragment lengths in a wide array of applications: DNA sequencing, microsatellites, Single Nucleotide Polymorphism, Restriction or Amplified Fragment Length Polymorphism, Single Strand Conformation Polymorphism, gene expression quantification and analyses of the immune receptor diversity. All of these applications require access to raw data (peak area and nucleotidic length). Raw data being stored in one file per lane, studies rapidly give rise to hundreds of files. However, with the increasing number of samples analyzed, no tool is currently available to allow the extensive and efficient retrieval of this raw data. The Applicants have developed the ISEApeaks software package in order to satisfy these needs.

In general, ISEApeaks extracts raw data and transfers it into one Excel file per sequencing gel. Then, data of different samples can be gathered in a peak database. Raw data extraction is currently possible with data generated from bioinformatics tools including the programs IMMUNOSCOPE™ (Pannetier et al, Proc Natl Acad Sci USA 1993; 90:4319-4323, available from INSERM, Paris, France), GENESCAN™ (PE Applied Biosystems, Foster City, Calif., USA), and GENOTESTER™ (Amersham, Uppsala, Sweden), the most popular packages used to determine peak area and size. Programs which are used for raw data acquisition from growth cultures, electrophoretic samples, chromatographic columns, blotting membranes, centrifugation tubes, or microarray chips, also include IMAGEQUANT™ (Molecular Dynamics, Piscataway, N.J., USA), EAGLESIGHT™ (Stratagene, La Jolla, Calif., USA), QUANTITYONE™ (BioRad, Hercules, Calif., USA), and MICROARRAY SUITE (Affymetrix, Santa Clara, Calif., USA).

Accordingly, within the purview of the prevent invention, the primary source of the raw data is not limiting. Exemplary primary sources include growth cultures, electrophoretic samples, chromatographic columns, blotting membranes, centrifugation tubes, or microarray chips.

The means of extraction of raw data from the primary source varies with the technique or reporting system, as well as the automated sequencer and bioinformatics tool employed. These techniques are well known in the art. The biomolecules may be labeled or unlabeled. Extraction of raw DNA and RNA data may be accomplished, for example, by fluorescence by way of a fluorophore coupled to a DNA molecule, fluorescence using a DNA intercalation agent, or autoradiography in which the DNA is end-labeled with a radioisotope. Similarly, raw protein data extraction may be accomplished, for example, by using reporters such as fluorescence labeling, autoradiography, immunography, chemiluminescence.

In one embodiment of the present invention is a method for high throughput analysis of data sets generally described by sets of peaks having a defined position and area. In this embodiment, the data may be extracted from a primary source by a bioinformatics tool (i.e. raw data extraction program or DNA automatic sequencer) and the resultant peaks are subsequently smoothed according to a user-defined parameter file. Each smooth peak data set is then stored in a data file.

In another embodiment, the particular profiles (data files), representing peaks, can be recreated for further analysis.

In a further embodiment, the peaks present in the individual data files can be assimilated into a single peak database using ISEApeaks.

In yet another embodiment, the peak database is analyzed by statistical tools contained within the ISEApeaks program.

In another embodiment of the present invention is a method for determining prognostic and diagnostic criteria by high throughput analysis of data sets generally described by sets of peaks having a defined position and area by extracting the data from a primary source by a bioinformatics tool (i.e. raw data extraction program or DNA automatic sequencer) and subsequently smoothing the resultant peaks according to a user-defined parameter file. Each smooth peak data set is then stored in a data file, which contains a particular profiles (data files), representing peaks, that is recreated for further analysis. The peaks present in the individual data files can then be assimilated into a single peak database using ISEApeaks and analyzed by statistical tools contained within this program.

The prognostic and diagnostic criteria that are established by this method can be used in field of physiopathology such as immunotherapy, cancer treatment, HIV, infectious disease, and autoimmune disease.

The methods of the present invention may be used as a high throughput method for analysis of immune repertoires.

Immune repertoires of T or B cells are very often studied by CDR3 spectratyping. However, data obtained with this method is usually subject to a biased eye analysis. Accordingly, the ISEApeaks software package provided herein has been employed to retrieve and handle peak data from automated sequencers, from which CDR3 spectratype data is obtained. In a general strategy two new specific modules and multivariate statistics analyses are used to analyze the CDR3 spectratype. The first module addresses the crucial problem of peak smoothing. The second is a toolbox for the analysis of CDR3 spectratypes, which includes perturbation computation, recurrent peak finding, expansion assessment and datamining. To illustrate this approach, the complex TCRB repertoire modifications induced by *Plasmodium berghei* ANKA infection were assessed and are presented in Example 2. This global and exhaustive repertoire analysis approach is of general interest for T and B lymphocyte repertoire studies and is currently used in human cohorts in various pathologies and during clinical trials.

Roles of B or T cells in abnormal situations, such as infectious diseases (Louis et al, *Curr. Opin. Immunol.* 1998; 10:459 and Boubou et al, *Int. Immunol.* 1999; 11:1553), autoimmunity (Wagner et al, Proc. Natl. Acad. Sci. USA 1998; 95:14447) or cancers (Pannetier et al, The Immunoscope technique for analysis of TCR repertoire. In: The human antigen T cell receptor: selected protocols and applications. 1995 J R Oksenberg, Austin, Tex., p. 287), are widely studied by examining their repertoire of antigen-specific receptors. During lymphocyte differentiation, the diversity of these heterodimeric receptors is produced by random somatic DNA rearrangements of V, (D) and J segments later spliced to C segments (Davis and Bjorkman, *Nature* 1988; 334:395). The product of the V(D)J joining, called the Complementary Determining Region 3 (CDR3), is in contact with the antigen. This region is imprecise in the number and the nature of nucleotides that are removed or added and is therefore variable in amino-acid length and composition.

Several approaches have been used to describe a repertoire. One of the most widely used is CDR3 spectratyping that describe the diversity of a T cell population repertoire by the analysis of the CDR3 length distribution (Pannetier et al, *Proc. Natl. Acad. Sci. USA* 1993; 90:4319). Briefly, sets of PCR amplification are performed with V-specific and C- or J-specific primers. These PCR products are then labeled in run-off experiment with C- or J-specific primers coupled with a fluorophore and loaded on an automated DNA sequencer to separate the different CDR3 lengths in each V-C or V-J combination. GENESCAN™ (Applied Biosystems, Foster City), IMMUNOSCOPE™ (INSERM, Paris) and GENOTESTER™ (Amersham, Uppsala) are three popular software packages used to determine nucleotide sizes and areas of the observed CDR3 peaks. This CDR3 spectratyping technique, by far the more exhaustive one, can for instance describe the human TCRB repertoire with up to 2400 measurements (Pannetier et al, *Immunol Today* 1995; 16:176). In the past, CDR3 spectratype data has mainly been analyzed qualitatively by eye, which can introduce biases in analysis and possibly lead to loss of relevant information. With the help of recent automated sequencers (96 well- and/or capillary-based sequencers), it is now possible to analyze cohorts of individuals. Research teams performing such high throughput acquisition are rapidly overwhelmed by the amount of data. A complete use of the CDR3 spectratype method thus requires the development of appropriate software tools for retrieving, handling, organizing and objectively analyzing data scattered through dozens of sample files on different gels.

Accordingly, the present Inventors have developed the ISEAPEAKS™ software package to retrieve, handle and organize raw data generated by bioinformatics tools, such as GENESCAN™, IMMUNOSCOPE™ (Collette and Six, *Bioinformatics* 2002; 18:329) and GENOTESTER™ software. Data of different samples can be gathered in an EXCEL™ (Microsoft, Seattle, Wash., USA) peak database. According to the present invention, the EXCEL™ peak database was used to set up an original strategy based on multivariate statistics to achieve a global description of CDR3 repertoires.

To illustrate this strategy, TCRB repertoire data from *Plasmodium berghei* ANKA (PbA) infected B10.D2 mice were analyzed to characterize modifications during malaria (Example 2). In this model, PbA induces either fatal cerebral malaria between day 7 to 10 after infection or severe anemia due to hyperparasitemia (HP) leading to death three weeks after infection (Boubou et al, *Int. Immunol.* 1999; 11:1553). In Example 2, only mice presenting HP were considered. Mice developing the cerebral syndrome were not included in Example 2, but are described in Example 1.

In another object of the present invention is a high throughput method for analysis of immune repertoires by starting with biological samples, which contain DNA or RNA fragments. The DNA or RNA fragments are then purified. If the source is purified RNA, cDNA is then transcribed by using reverse transcription PCR (Sambrook et al, Molecular Cloning: A Laboratory Manual, $3^{rd}$ Edition, 2001, Cold Spring Harbor Laboratory Press). The purified DNA or cDNA, obtained by transcribing the RNA, are then amplified by PCR or strand displacement amplification (SDA, Walker et al, *Clin Chem* 1996; 42:9-13 and Little et al, *Clin Chem* 1999; 45:777-784) methods using oligonucleotides specific for antigen specific receptor genes, for example Immunoglobulin and T-cell receptor, variable (V), Junctional (J) and Constant (C) regions. The amplified DNA are labeled for detection. Suitable DNA labels include radiolabels (available from ICN Biomedicals, Costa Mesa, Calif., USA) chemiluminescent probes, and fluorophores (a broad range are available from Molecular Probes, Eugene, Oreg., USA), for example performing a runoff extension step with J or C specific oligonucleotide labeled with a fluorescent drug. Each labeled amplified DNA is then electrophoretically separated in an automatic sequencer and the electrophoregram is analyzed, identifying peaks by determining their position and area that correspond to labeled amplified DNA.

The sets of peaks having a defined position and area may be extracted from the electrophoregram by a bioinformatics tool (i.e. raw data extraction program or DNA automatic sequencer) and subsequently smoothing the resultant peaks according to a user-defined parameter file. Each smooth peak data set is then stored in a data file, which contains a particular profiles (data files), representing peaks, that is recreated for further analysis. The peaks present in the individual data files can then be assimilated into a single peak database using ISEApeaks and analyzed by statistical tools contained within this program.

As is evident from the central paradigm of modern molecular biology, the samples that are amenable to the present invention are the fundamental biomolecules include DNA, RNA, and proteins.

The proteins embraced by the present invention encompass a vast spectrum of protein classes, all of which are within the purview of the present invention. Some examples of protein-types include, but by no means are limited to, antigenic proteins, antibodies, DNA-binding proteins, RNA-binding proteins, kinases, methylases, proteases, proteins involved in replication, proteins involved cell division, and proteins involved in regulation of cellular processes and homeostasis.

As used herein the term "biological sample" refers to a solution, mixture, or suspension that contains one or more biomolecule. The term "biomolecule" refers to any matter of biological origin, which includes intact cells, cellular material, DNA, RNA and proteins. These biomolecules may be naturally occurring or may be obtained by synthetic methods. In addition, a biomolecule obtained from either means may be modified or unmodified and may be a member of an extract or may be isolated or purified.

The term "naturally occurring" refers to a DNA, RNA, or protein that has is found in or expressed from a living host organism. This term includes genomically, chromosomally, plasmid, and cosmid expressed proteins, as well as genomic DNA, chromosomal DNA, plasmid DNA and cosmid DNA. Accordingly, this term also embraces the RNA the is transcribed from genomic DNA, chromosomal DNA, plasmid DNA and cosmid DNA.

The term "synthetic methods" in relation to DNA or RNA refers to solid-phase or liquid-phase synthesis. Examples of suitable synthetic methods for DNA or RNA are provided by Rayner et al (*Genome Res.* 1998; 8:741-747), Lashkari et at (*Proc Natl Acad Sci* 1995; 92:7912-7915), and Andrus et al (*Nucleic Acids Symp Ser* 1995; 34:183-184). In relation to proteins the term "synthetic methods" refers to in vitro transcription and translation of target DNA to protein in a single tube. Two common commercially available kits to for in vitro protein system are the EXPRESSWAY™ System (Invitrogen Life Technologies, Carlsbad, Calif., USA) and TNT™ Quick Coupled Transcription/Translation System (Promega, Madison, Wis., USA).

As used herein, the term "unmodified" relates to DNA, RNA, or protein molecules that exist in their nascent state, i.e. does not have any post-replication, post-transcription, or post-translation alterations (deletions, mutations, additions).

As used herein, the term "modified" relates to DNA, RNA, or proteins molecules, which have been altered post-replicationally, post-transcriptionally, or post-translationally. These modifications may occur within the host source or by experimental manipulation. Common modifications of DNA and RNA include methylation, acetylation, nucleoside excision, fluorophore labeling, and radiolabeling. Similarly, common protein modifications include methylation, acetylation, nucleoside excision, fluorophore labeling, radiolabeling, carbohydrates, glycoconjugates, and lipids. A detailed description and understanding can be readily obtained for carbohydrate, glycoconjugate, and lipid protein modification can be obtained by reference to, inter alia, Essentials of Glycobiology (1999), Edited By Ajit Varki, Cold Spring Harbor Laboratory Press, Cold Spring Harbor, N.Y. Suitable fluorophores for DNA, RNA, and proteins, and detailed descriptions thereof, are available in the Handbook of Fluorescent Probes and Research Products from Molecular Probes (Eugene, Oreg., USA).

Within the context of the present invention "isolated" or "purified" means separated out of its natural environment, which is also substantially free of other contaminating proteins, polynucleotides, and/or other biological materials often found in cell extracts. Techniques for obtaining cell extracts are described in Roe et al (DNA isolation and Sequencing, 1996, John Wiley & Sons, New York), Sambrook et al (Molecular Cloning: A Laboratory Manual, $3^{rd}$ Edition, 2001, Cold Spring Harbor Laboratory Press), and Scopes (Protein Purification, Principles and Practice, 1994, Springer-Verlag New York, Inc). Common methods of isolation and/or purification of DNA, RNA, and/or proteins include: centrifugation, precipitation, batch adsorption, chromatography, and electrophoresis (Scopes, Protein Purification, Principles and Practice, 1994, Springer-Verlag New York, Inc).

Chromatographic techniques that are routinely used to isolate and/or purify DNA, RNA, and/or proteins include, liquid chromatography and column chromatography.

"Liquid Chromatography" in the context of this invention includes, High-Performance Liquid Chromatography (HPLC), Reverse Phase-HPLC, Fast Performance Liquid Chromatography (FPLC). The artisan is directed to *Scopes* (Protein Purification, Principles and Practice (1994), Springer-Verlag New York, Inc.) for a more detailed description of these techniques.

"Column Chromatography" in the context of this invention includes, ion-exchange chromatography, inorganic adsorbents, hydrophobic adsorbents, immobilized metal affinity chromatography (IMAC), cationic polymer-nucleic acid complexes, thiophilic adsorbents, mixed-function adsorbents, affinity chromatography, immunoadsorbent chromatography, dye-ligand chromatography, and gel filtration chromatography. The artisan is directed to *Scopes* (Protein Purification, Principles and Practice (1994), Springer-Verlag New York, Inc.) for a more detailed description of these techniques.

Electrophoretic techniques that routinely used to isolate and/or purify DNA, RNA, and/or proteins include, native gel electrophoresis, urea gel electrophoresis, sodium dodecyl sulfate polyacrylamide gel electrophoresis (SDS-PAGE), gradient gel electrophoresis, isoelectric focusing, two-dimensional gel electrophoresis, and capillary electrophoresis. Additional electrophoretic techniques may include coupled gel-membrane techniques for isolating, separating, and/or probing DNA, RNA, or proteins, such as Southern Blotting, Northern Blotting, and Western Blotting. The artisan is directed to *Scopes* (Protein Purification, Principles and Practice, 1994, Springer-Verlag New York, Inc.) and Ausubel et al (Current Protocols in Molecular Biology, 1994, New York: Greene Publishing Assoc. and Wiley-Interscience) for a more detailed description of these techniques.

The term "growth culture" as used herein refers to bacterial, phage, viral, and eukaryotic growth in solid, liquid, or gaseous medium.

FIG. 1 illustrates a computer system 1101 upon which an embodiment of the present invention may be implemented. The computer system 1101 includes a bus 1102 or other communication mechanism for communicating information, and a processor 1103 coupled with the bus 1102 for processing the information. The computer system 1101 also includes a main memory 1104, such as a random access memory (RAM) or other dynamic storage device (e.g., dynamic RAM (DRAM), static RAM (SRAM), and synchronous DRAM (SDRAM)), coupled to the bus 1102 for storing information and instructions to be executed by processor 1103. In addition, the main memory 1104 may be used for storing temporary variables or other intermediate information during the execution of instructions by the processor 1103. The computer system 1101 further includes a read only memory (ROM) 1105 or other static storage device (e.g., programmable ROM (PROM), erasable PROM (EPROM), and electrically erasable PROM (EEPROM)) coupled to the bus 1102 for storing static information and instructions for the processor 1103.

The computer system 1101 also includes a disk controller 1106 coupled to the bus 1102 to control one or more storage devices for storing information and instructions, such as a magnetic hard disk 1107, and a removable media drive 1108 (e.g., floppy disk drive, read-only compact disc drive, read/write compact disc drive, compact disc jukebox, tape drive, and removable magneto-optical drive). The storage devices may be added to the computer system 1101 using an appropriate device interface (e.g., small computer system interface (SCSI), integrated device electronics (IDE), enhanced-IDE (E-IDE), direct memory access (DMA), or ultra-DMA).

The computer system 1101 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1101 may also include a display controller 1109 coupled to the bus 1102 to control a display 1110, such as a cathode ray tube (CRT), for displaying information to a computer user. The computer system includes input devices, such as a keyboard 1111 and a pointing device 1112, for interacting with a computer user and providing information to the processor 1103. The pointing device 1112, for example, may be a mouse, a trackball, or a pointing stick for communicating direction information and command selections to the processor 1103 and for controlling cursor movement on the display 1110. In addition, a printer may provide printed listings of data stored and/or generated by the computer system 1101.

The computer system 1101 performs a portion or all of the processing steps of the invention in response to the processor 1103 executing one or more sequences of one or more instructions contained in a memory, such as the main memory 1104. Such instructions may be read into the main memory 1104 from another computer readable medium, such as a hard disk 1107 or a removable media drive 1108. One or more processors in a multi-processing arrangement may also be employed to execute the sequences of instructions contained in main memory 1104. In alternative embodiments, hard-wired circuitry may be used in place of or in combination with software instructions. Thus, embodiments are not limited to any specific combination of hardware circuitry and software.

As stated above, the computer system 1101 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the present invention includes software for controlling the computer system 1101, for driving a device or devices for implementing the invention, and for enabling the computer system 1101 to interact with a human user. Such software may include, but is not limited to, device drivers, operating systems, development tools, and applications software. Such computer readable media further includes the computer program product of the present invention for performing all or a portion (if processing is distributed) of the processing performed in implementing the invention.

The computer code devices of the present invention may be any interpretable or executable code mechanism, including but not limited to scripts, interpretable programs, dynamic link libraries (DLLs), Java classes, and complete executable programs. Moreover, parts of the processing of the present invention may be distributed for better performance, reliability, and/or cost.

The term "computer readable medium" as used herein refers to any medium that participates in providing instructions to the processor 1103 for execution. A computer readable medium may take many forms, including but not limited to, non-volatile media, volatile media, and transmission media. Non-volatile media includes, for example, optical, magnetic disks, and magneto-optical disks, such as the hard disk 1107 or the removable media drive 1108. Volatile media includes dynamic memory, such as the main memory 1104. Transmission media includes coaxial cables, copper wire and fiber optics, including the wires that make up the bus 1102. Transmission media also may also take the form of acoustic or light waves, such as those generated during radio wave and infrared data communications.

Various forms of computer readable media may be involved in carrying out one or more sequences of one or more instructions to processor 1103 for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to the computer system 1101 may receive the data on the telephone line and use an infrared transmitter to convert the data to an infrared signal. An infrared detector coupled to the bus 1102 can receive the data carried in the infrared signal and place the data on the bus 1102. The bus 1102 carries the data to the main memory 1104, from which the processor 1103 retrieves and executes the instructions. The instructions received by the main memory 1104 may optionally be stored on storage device 1107 or 1108 either before or after execution by processor 1103.

The computer system 1101 also includes a communication interface 1113 coupled to the bus 1102. The communication interface 1113 provides a two-way data communication coupling to a network link 1114 that is connected to, for example, a local area network (LAN) 1115, or to another communications network 1116 such as the Internet. For example, the communication interface 1113 may be a network interface card to attach to any packet switched LAN. As another example, the communication interface 1113 may be an asymmetrical digital subscriber line (ADSL) card, an integrated services digital network (ISDN) card or a modem to provide a data communication connection to a corresponding type of communications line. Wireless links may also be implemented. In any such to implementation, the communication interface 1113 sends and receives electrical, electromagnetic or optical signals that carry digital data streams representing various types of information.

The network link 1114 typically provides data communication through one or more networks to other data devices. For example, the network link 1114 may provide a connection to a another computer through a local network 1115 (e.g., a LAN) or through equipment operated by a service provider, which provides communication services through a communications network 1116. In preferred embodiments, the local network 1114 and the communications network 1116 preferably use electrical, electromagnetic, or optical signals that carry digital data streams. The signals through the various networks and the signals on the network link 1114 and through the communication interface 1113, which carry the digital data to and from the computer system 1101, are exemplary forms of carrier waves transporting the information. The computer system 1101 can transmit and receive data, including program code, through the network(s) 1115 and 1116, the network link 1114 and the communication interface 1113. Moreover, the network link 1114 may provide a connection through a LAN 1115 to a mobile device 1117 such as a personal digital assistant (PDA) laptop computer, or cellular telephone. The LAN communications network 1115 and the communications network 1116 both use electrical, electromagnetic or optical signals that carry digital data streams. The signals through the various networks and the signals on the network link 1114 and through the communication interface 1113, which carry the digital data to and from the system 1101, are exemplary forms of carrier waves transporting the information. The processor system 1101 can transmit notifications and receive data, including program code, through the network(s), the network link 1114 and the communication interface 1113.

Having generally described this invention, a further understanding can be obtained by reference to certain specific examples, which are provided herein for purposes of illustration only, and are not intended to be limiting unless otherwise specified.

EXAMPLES

Example 1.1

Mice and Parasites

Eight-week old B10.D2 mice were purchased from Harlan UK Limited. The clone 1.49 L of *Plasmodium berghei* ANKA (Amani, V., M. I. Boubou, S. Pied, M. Marussig, D. Walliker, D. Mazier, and L. Renia. 1998. Cloned lines of Plasmodium berghei ANKA differ in their abilities to induce Experimental Cerebral Malaria. Infect. Immun 66:4093-4099) was kindly given by Dr. Walliker (Institute of Genetics, Edinburg, UK) and is maintained in the laboratory on C57BL/6J female mice. This clone induced in mice a neurological syndrome partly mimicking the one of human CM. Erythrocytic stages of the parasite were cryopreserved in liquid nitrogen as stabilates in Alserver's solution containing 10% glycerol. Infection was induced by intraperitoneal injection of $10^6$ parasitized red blood cells. Between day 7 to day 10 after infection, 90% of the mice developed cerebral malaria characterized by ataxia, paralysis, deviation of the head and convulsions followed by deep coma and death. These mice constituted the $CM^+$ group. $CM^-$ mice were sacrificed between day 11 to 16 after infection because they did not shown signs of CM during the critical period, however, they did exhibit a parasitemia above 20%.

Example 1.2

Cell Preparation

Blood was obtained on heparin by retroorbital punction. Mononuclear cells were isolated on ficoll-Hypaque gradient (Pharmacia, France). Spleen was removed and cells suspended in 3% FCS-PBS. Red blood cells were lysed with ammonium chloride buffer (ACK) for five minutes at room temperature. Cell preparations were then washed twice with PBS. Lymphoid cells were counted using Malassez cell in presence of eosin to exclude dead cells.

Example 1.3

TCRB Repertoire

Total RNA was extracted from more than 90,000 mononuclear cells for each sample using the TRI REAGENT kit (Molecular Research Center, Cincinnati, Ohio). 20 µg of glycogen (Roche, Meylan, France) was used to ensure optimal precipitation of RNA and pellet visualization. Protocols for TCR BV-BC and BV-BJ CDR3 spectratyping have been described previously, which were utilized in the present example (Pannetier, C., M. Cochet, S. Darche, A. Casrouge, M. Zöller, and P. Kourilsky. 1993. The sizes of the CDR3 hypervariable regions of the murine T-cell receptor b chains vary as a function of the recombined germ-line segments. Proc. Natl. Acad. Sci. USA 90:4319-4323; Pannetier, C., J. Even, and P. Kourilsky. 1995. The Immunoscope technique for analysis of TCR repertoire. In The human antigen T cell receptor: Selected protocols and applications. J. R. Oksenberg, Austin, Tex. 287-325). BC, BV and BJ primer sequences were those described previously (Pannetier, C., M. Cochet, S. Darche, A. Casrouge, M. Zöller, and P. Kourilsky. 1993. The sizes of the CDR3 hypervariable regions of the murine T-cell receptor b chains vary as a function of the recombined germ-line segments. Proc. Natl. Acad. Sci. USA 90:4319-4323), except BV8.3 (5'-TGCTGGCAACCT-TCAAATAGGA-3') (SEQ ID NO: 1) and BV13 (5'-AGGCCTAAAGGAACTAACTCCAC-3') (SEQ ID NO: 2). Because BV5.3 (Chou, H. S., S. J. Anderson, M. C. Louie, S. A. Godambe, M. R. Pozzi, M. A. Behlke, K. Huppi, and D. Y. Loh. 1987. Tandem linkage and unusual RNA splicing of the T-cell receptor beta-chain variable-region genes. Proc. Natl. Acad. Sci. USA 84:1992-1996), BV17 (Wade, T., J. Bill, P. C. Marrack, E. Palmer, and J. W. Kappler. 1988. Molecular basis for the nonexpression of Vb 17 in some strains of mice. J. Immunol. 141:2165-2167), and BV19 (Louie, M. C., C. A. Nelson, and D. Y. Loh. 1989. Identification and characterization of new murine T cell receptor b chain variable region (Vb) genes. J. Exp. Med. 170:1987-1998) are not functional in B10.D2 mice, they were not amplified. For BV-BJ repertoires, BV2, BV3, BV4, BV5.1, BV6, BV7, BV8.1-3, BV9, BV14 and BV16 genes were analyzed. PCR products were loaded on a 36-well ABI373 automated sequencer (Applied Biosystems, Foster city, CA) and separated according to their nucleotide length forming a profile of peaks for each primer combination, spaced by 3 nucleotides as expected for in-frame transcripts. Each peak corresponded to a CDR3 length. The Immunoscope product (Pannetier, C., M. Cochet, S. Darche, A. Casrouge, M. Zöller, and P. Kourilsky. 1993. The sizes of the CDR3 hypervariable regions of the murine T-cell receptor b chains vary as a function of the recombined germ-line segments. Proc. Natl. Acad. Sci. USA 90:4319-4323) was used to obtain peak area and nucleotide length and CDR3 profile displays from sequencer raw data.

Example 1.4

BV-BJ Direct Sequencing

Direct sequencing was performed with BV and BJ primers for peaks representing between 65% and 100% of the BV-BJ profile following the recommendations of the ABI Prism Dye Terminator Cycle Sequencing Ready Reaction kit (Applied Biosystems). BV-BJ PCR products were first reamplified. PCR products were then incubated with 0.5 units of Shrimp Alkaline Phosphatase (USB) and 5 units of Exonuclease I (USB) at 37° C. for 40 min followed by 20 min at 80° C. DNA alignments were performed using the GCG product.

Example 1.5

Methods and Tools for CDR3 Spectratype Analyses

The present inventors developed the ISEApeaks® product (©2000-2002 Institut Pasteur, France, Paris) to extract, smooth, manage and analyze the large amount of data obtained in this study (Collette, A., and A. Six. 2002. ISEApeaks: an Excel platform for GeneScan and Immunoscope data retrieval, management and analysis. Bioinformatics 18:329-330. and Example 2). As the intensity of CDR3 peaks is not comparable between different amplifications, the percentage of use of each CDR3 length was obtained by dividing the area of CDR3 peaks by the total area of all peaks within the profile.

Perturbation of BV-BC repertoire were compared to a control group as explained previously (Gorochov, G., A. U. Neumann, A. Kereveur, C. Parizot, T. S. Li, C. Katlama, M. Karmochkine, G. Raguin, B. Autran, and P. Debre. 1998. Perturbation of CD4+ and CD8+ T-Cell repertoires during progression to AIDS and regulation of the CD4+ repertoire during antiviral therapy. Nat. Med 4:215-221; Han, M., L. Harrison, P. Kelm, K. Stevenson, J. Currier, and M. A. Robinson. 1999. Invariant or highly conserved TCRα are expressed on double-negative (CD3+ CD4−CD8−) and CD8+ T cells. J. Immunol. 163:301-311). Sample perturbation (μDBV-BC) is the mean of perturbations of each BV segment (DBV-BC). The perturbation index was expanded to BV-BJ repertoires by computing μμDBV-BJ, the mean of the DBV-BJ for all BV and BJ segments. BV-BC and BV-BJ perturbations range from 0, identical profiles, to 100, completely different profiles. For sake of reference, TCRα, TCRb, TCRg, and TCRd refer to TCRα, TCRβ, TCRγ, and TCRΔ, respectively. In addition TCRab refers to TCRαβ and TCRgd refers to TCRγΔ.

Recurrence of CDR3 expansions was assessed quantitatively with OligoScore (Collette, A., and A. Six. 2002. ISEA-peaks: an Excel platform for GeneScan and Immunoscope data retrieval, management and analysis. Bioinformatics 18:329-330), which scored each peak in each group of samples. The maximum score of the control group was used as a threshold for other groups. Peaks with a score above this threshold were considered recurrently expanded.

Example 1.6

Statistics

Multivariate statistics were used to analyze repertoire data. In a first approach, each repertoire was considered as a vector in n-dimensional space, where n is the number of variables that describe the repertoires. Missing values were replaced by the overall mean of the variable (Rencher, A. C. 1995. Methods of multivariate analysis. J Wiley, New York. 627 pp). The number of variables (230 peaks for BV-BC repertoires) was too high for theoretical constraints of Discriminant Analysis and was thus reduced using Principal Components Analysis (PCA). PCA extracts new variables from the data set that retains the variability contained in the original data set. Linear Discriminant Analysis (DA) was performed on the new data set to compare the different groups. DA computes discriminant functions that maximize inter-group variation and minimize intra-group variation. Significance of each discriminant function was tested using $\chi^2$ approximation of Wilks' statistics (Rencher, A. C. 1995. Methods of multivariate analysis. J Wiley, New York. 627 pp).

Univariate one-way or two-way Analysis of Variance (ANOVA) was used to analyze sample perturbation data (μDBV-BC or μμDBV-BJ). When significant, comparison between two categories was performed with Fischer's Protected Least Significant Difference. One-way Multiple Analysis of Variance (MANOVA) was used to compare DBV-BJ. MANOVA F-statistics approximation of Wilk's lambda, Roy's greatest root, Pillai trace and Hotelling-Lawley trace multivariate statistics were calculated. As the power of these four statistics are not equivalent (Rencher, A. C. 1995. Methods of multivariate analysis. J Wiley, New York. 627 pp), MANOVA was considered significant when all four statistics were significant. Indicated p value corresponds to the maximum value of the p value obtained for these four statistics (Spanakis, E., and D. Brouty-Boye. 1997. Discrimination of fibroblast subtypes by multivariate analysis of gene expression. Int. J. Cancer 71:402-409). When significant, a one-way ANOVA was carried out on each variable (BV-BC perturbation) to assess for differences in the considered groups. This enables minimization of global error rate of the univariate tests (Rencher, A. C. 1995. Methods of multivariate analysis. J Wiley, New York. 627 pp).

To further assess similarity between samples, k-mean clustering with Euclidean distance was used. Significance of the clusters were assessed by computing the probability of observing by chance the number of samples of a particular group within the cluster (Tavazoie, S., J. D. Hughes, M. J. Campbell, R. J. Cho, and G. M. Church. 1999. Systematic determination of genetic network architecture. Nat. Genet 22:281-285).

PCA, DA and k-mean clustering were performed with SYSTAT 10 (SPSS). ANOVA and MANOVA were performed with StatView 5.0 (SAS Institute Inc). Statistics were considered significant when $p<0.01$.

Example 1.7

Analysis of TCRB Repertoire During Cerebral Malaria by the Immunoscope Method

Figure 2A:
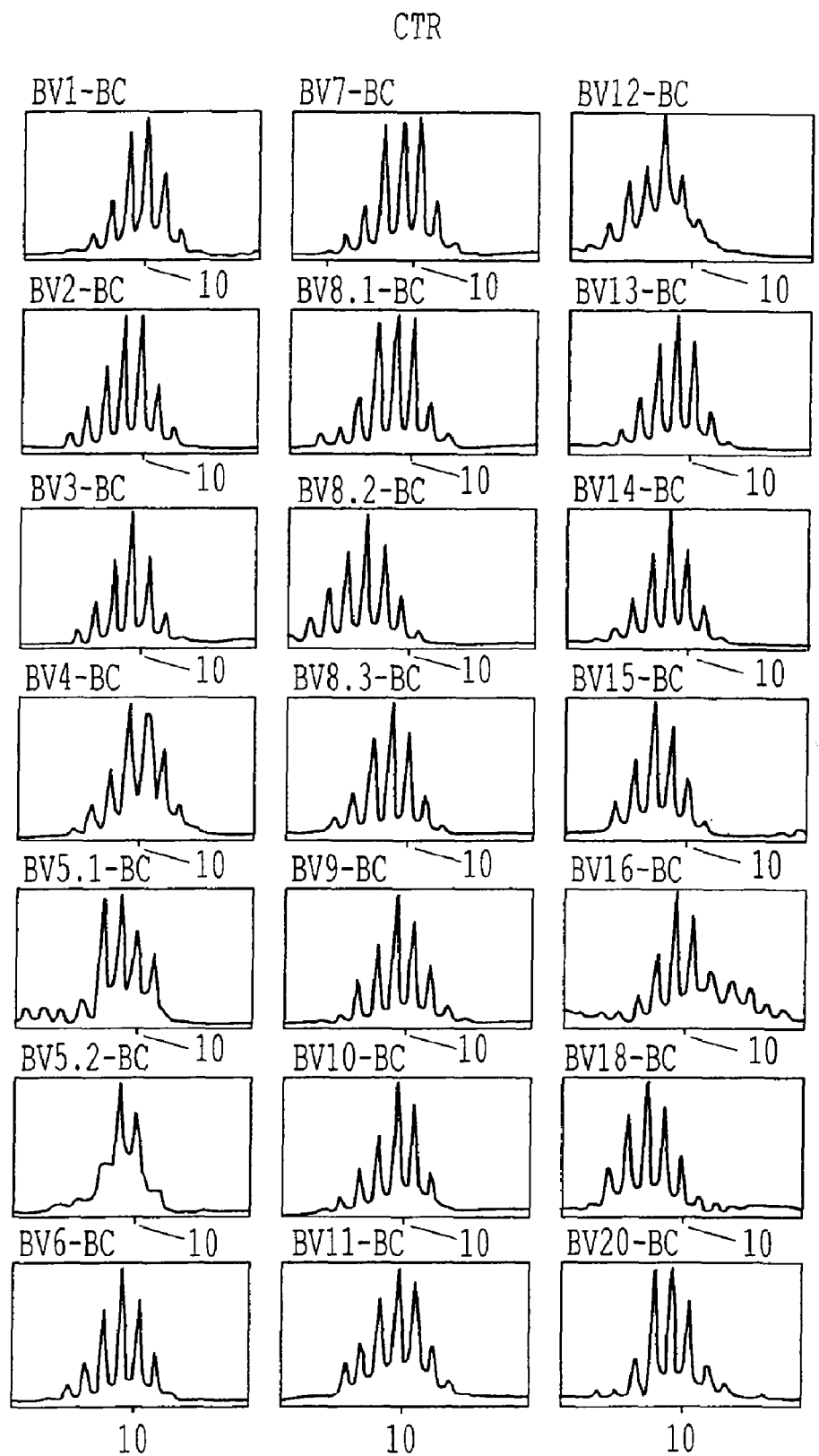
FIG. 2: Typical PBL repertoires of CTR, CM$^-$ and CM$^+$ mice. cDNA were obtained from PBL of control (CTR), infected without neurological signs (CM) and infected with CM (CM$^+$) mice. BV-BC CDR3 spectratyping was performed by PCR amplification of cDNA with combinations of BV-specific primers and a BC-specific primer. After run-off with a fluorescent BC-specific primer, PCR products were size separated on an automated DNA sequencer. Sequencing gels were analyzed with the Immunoscope product. Typical samples are represented. Horizontal axis represents the nucleotide size, centered on a 10 amino acid CDR3 fragment, and vertical axis the fluorescence intensity, in arbitrary units.

The TCRB repertoire during Cerebral Malaria (CM) induced in B10.D2 mice by *Plasmodium berghei* ANKA was analyzed using the exhaustive CDR3 length spectratyping approach (Pannetier, C., M. Cochet, S. Darche, A. Casrouge, M. Zöller, and P. Kourilsky. 1993. The sizes of the CDR3 hypervariable regions of the murine T-cell receptor b chains vary as a function of the recombined germ-line segments. Proc. Natl. Acad. Sci. USA 90:4319-4323). BV-BC repertoires were studied with total cDNA, prepared from non-infected control (CTR) mice and infected mice that did ($CM^+$) or did not (CM) develop CM. In PBL and spleen of naive mice, CDR3 profile for each BV-BC combination was bell-shaped, indicative of a diverse polyclonal repertoire ( FIG. 2 and data not shown). The TCRB repertoires of the $CM^+$ and $CM^-$ mice were profoundly altered: almost all CDR3 profiles were different from a bell-shaped profile and multiple expansions were evidenced ( FIG. 2). Among these complex repertoire modifications, some could contribute to the protective response against *P. berghei* ANKA infection while others may be involved in pathology. The comparison between CDR3 profiles from $CM^+$ and $CM^-$ mice enabled the identification of potentially pathogenic clones associated with CM that would be present in $CM^+$ mice but absent in $CM^-$ mice.

Example 1.8

Specific Alterations of TCRB Repertoire During Cerebral Malaria

Figure 3:
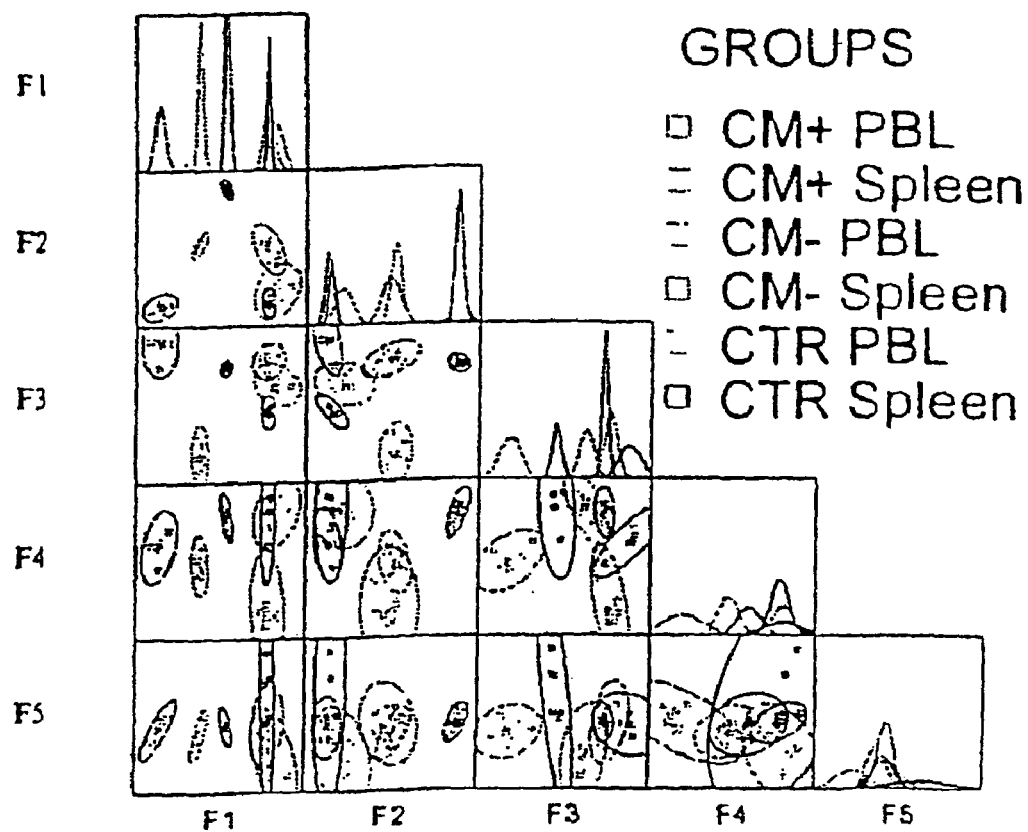
FIG. 3: Descriminant Analysis separates CM$^+$ PBL from CM$^+$ spleen, CM$^-$ PBL and CM$^-$ spleen BV-BC repertoires. Discriminant Analysis was performed on the new set of variables obtained with Principal Components Analysis. Bivariate graphics represent the value of two discriminant functions. Discriminant functions are linear combination of the variables that try to separate groups. F1 to F5 stands for each discriminant function, sorted decreasingly by the associated eigenvalue. Samples (8 CTR PBL, 6 CTR spleen, 10 CM$^-$ PBL, 8 CM$^-$ spleen, 13 CM$^+$ PBL and 10 CM$^+$ spleen) are represented on the bivariate plots, but are scarcely visible since DA groups samples very well. Confidence (0.95) ellipses, centered on group centroid, are overlaid. The density normal curve of each group is shown on the diagonal. Vertical and horizontal axes represent canonical scores for each function. The density normal curves of F4 and F5 show that groups are not well separated, consistent with the non-significance of these functions.

To identify CM-associated alterations, ex vivo PBL and splenocyte TCRB repertoires of several individuals for CTR, $CM^-$ and $CM^+$ groups were analyzed. A total of 1150 BV-BC CDR3 profiles was obtained for 55 samples. The analysis of this set of BV-BC profiles each including 6-8 peaks required the use of an original approach that combined bioinformatic tools and multivariate statistics. All peak data of TCRB repertoire was extracted, formatted and edited with the ISEA-peaks product to construct the peak database. Principal Components Analysis was used to reduce the initial number of variables. The new data set retained 97% of the original information. Linear Discriminant Analysis (DA) was used to evidence global modifications due to infection in $CM^+$ and $CM^-$ mice. DA determined if multivariate observations of different groups were samples of the same statistical population. All members of a given group were closely clustered together (FIG. 3). Moreover, sample groups were separated in four statistically significant clusters, as only the first three discriminant functions were significant: $CM^+$ PBL, $CM^-$ PBL, $CM^-$ spleen and a group containing $CM^+$ spleen, CTR PBL and CTR spleen.

Figure 4A:
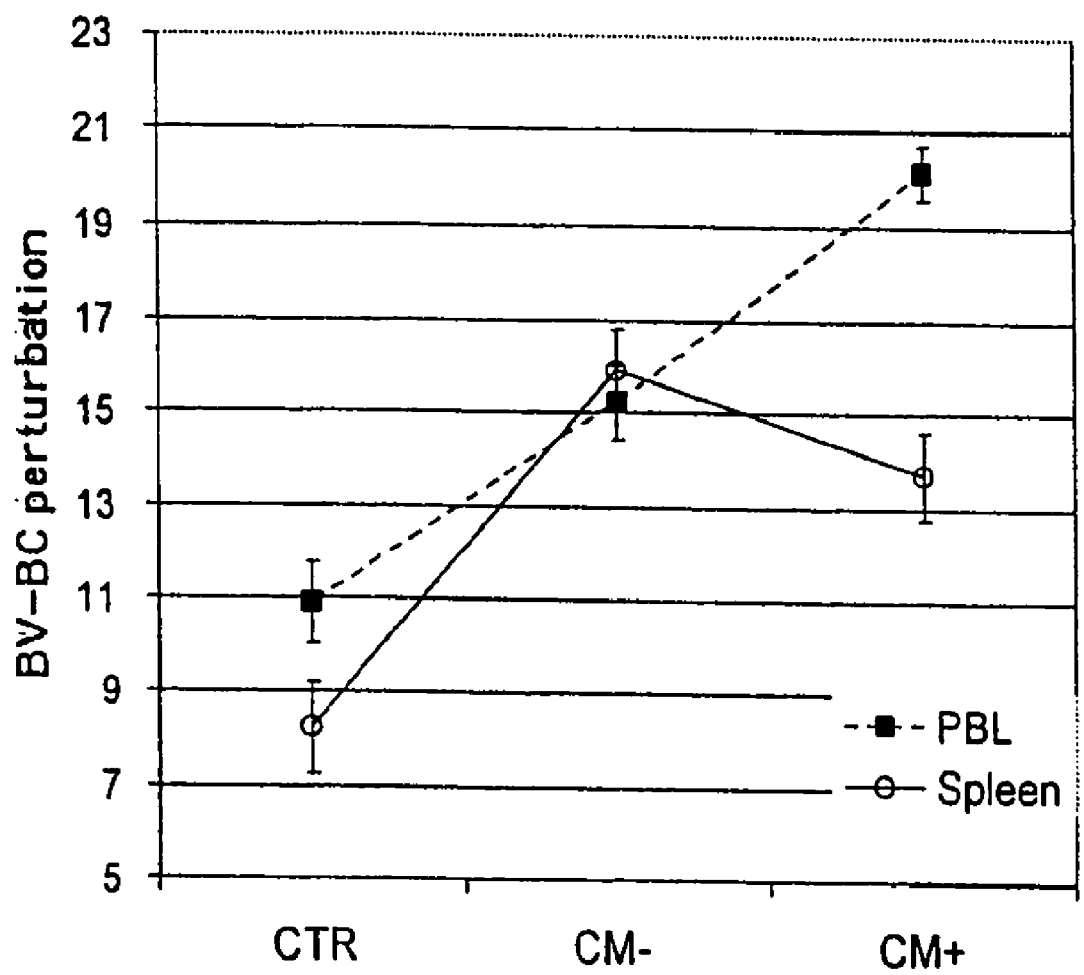
FIG. 4: PBL CM$^+$ repertoire are significantly more perturbed than CM$^-$ PBL or spleen repertoires and can be clustered separately. (a) BV-BC perturbations (DBV-BC) were computed with ISEApeaks using the CTR spleen group as control. Mean sample DBV-BC (ADBV-BC) with their standard error are shown for CM$^+$, CM$^-$ and CTR mice in the PBL and spleen. DBV-BC range from 0, identical to the reference repertoire, to 100, completely perturbed. (b) Schematic representation of sample clusters obtained with k-mean clustering on DBV-BC with k=4 and 3. BV-BC perturbation of each sample was analyzed without prior knowledge of group composition. For k=5 or 6, PBL CM$^+$ samples were split in two clusters. (c) The BV-BJ repertoires of PBL samples (6 CTR, 5 CM$^-$ and 6 CM$^+$) were correctly grouped by k-mean clustering with k=3 on DBV-BJ data.
Figure 4B:
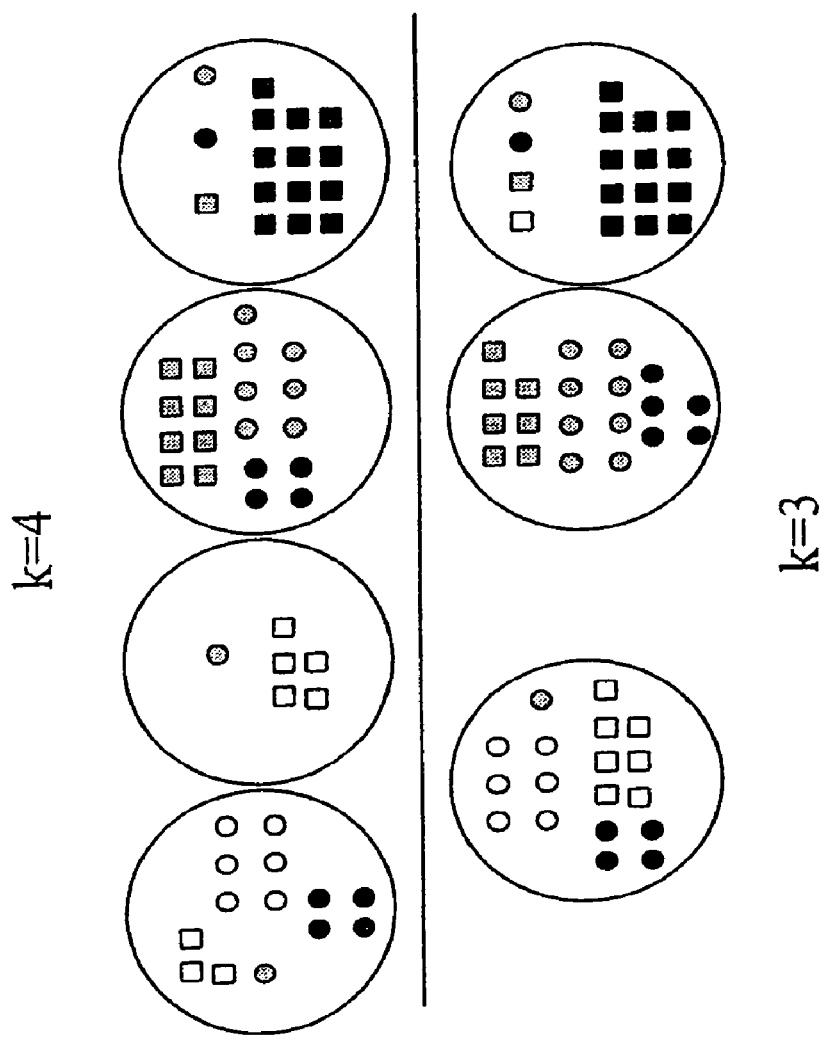

To further characterize the repertoires, another previously-known method was used which computed CDR3 spectratype perturbation index for each sample (Gorochov, G., A. U. Neumann, A. Kereveur, C. Parizot, T. S. Li, C. Katlama, M. Karmochkine, G. Raguin, B. Autran, and P. Debre. 1998. Perturbation of CD4+ and CD8+ T-Cell repertoires during progression to AIDS and regulation of the CD4+ repertoire during antiviral therapy. Nat. Med 4:215-221). All repertoires were compared to the spleen CTR repertoires to obtain a perturbation index for each BV-BC combination (DBV-BC). pDBV-BC, the average of BV-BC perturbations, were compared by two-way Analysis of Variance (ANOVA) between compartments (PBL and spleen) and the different groups of mice (CTR, CM⁻ and CM⁺) (FIG. 4a). ANOVA compared the effect of qualitative factors on a quantitative dependent variable. Infection by *P. berghei* ANKA led to significant alteration of the TCRB perturbation both due to the groups of mice ($p<0.0001$) and to the lymphoid compartment ($p=0.0002$). PBL repertoires of CM⁺ mice (mean=20.2) were more perturbed than in CM⁻ mice (mean=15.2; t-test, df=21, $p<0.0001$). To strengthen this observation, the k-mean clustering was used to see if groups could be separated on the basis of BV-BC perturbations without knowledge of group composition, which was the case of DA and ANOVA. For k=3 (or k=4), all 13 CM⁺ PBL samples clustered together in a group containing 17 samples (or 16) which had the probability $p=1.64E-9$ ($p=3.86E-10$) to occur by (FIG. 4b). Since PBL BV-BC repertoires appeared to be specifically altered in CM⁺ as compared to CM⁻ mice, further analyses were performed on PBL only.

Example 1.9

BV-BC Perturbation of PBL Repertoires Allows Prediction of CM

An investigation to see if the alteration of PBL BV-BC repertoire could be used to classify samples was performed. Since the sample number is not large enough to divide it in training set and testing sets, the jackknife method was used where: each sample is left out in turn and DA is performed on the remaining samples to obtain classification functions. These functions were then used to determine to which group the left-out sample belongs.

Table 1 shows that 85% of CM⁺ PBL samples were correctly classified, indicating that perturbation of PBL repertoire can be used to discriminate between CM⁺ and CM⁻ mice.

Example 1.10

BV-BJ PBL Repertoire Analysis During Infection

Figure 4C:
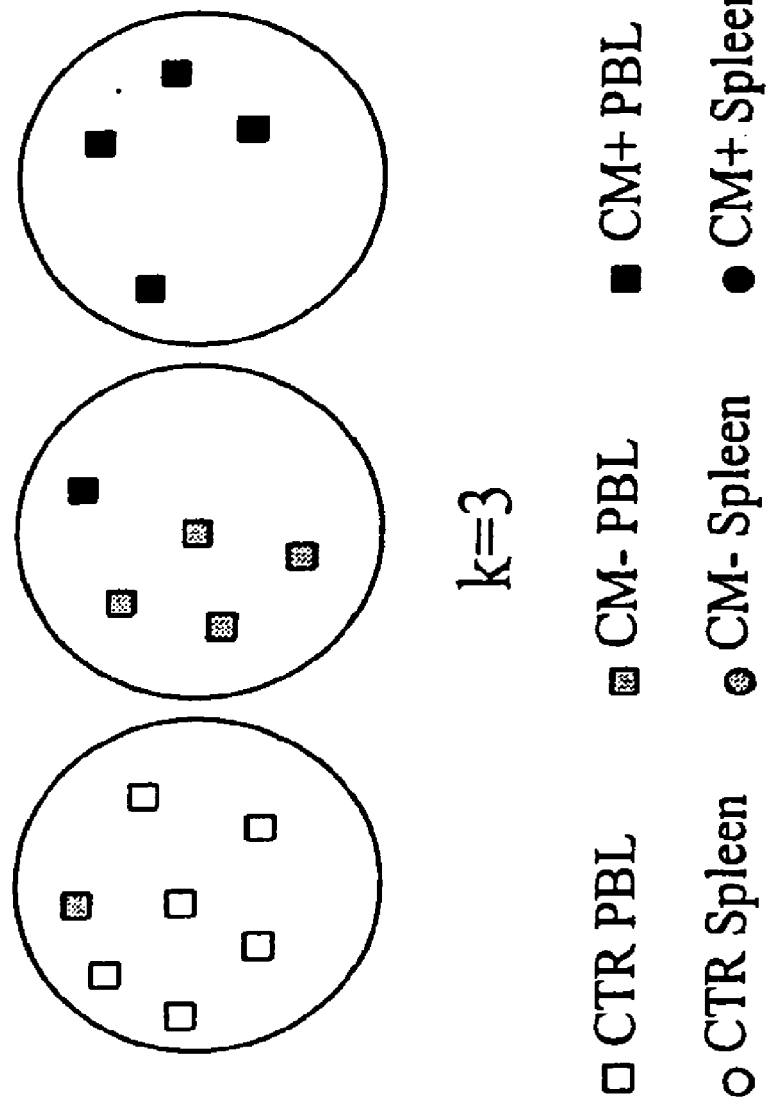

To describe more precisely the TCRB repertoire during CM, BV-BJ repertoire analysis for 9 BV genes out of 21, which represented more than two thirds of the total TCRB repertoire, was performed. A total number of 2300 BV-BJ profiles were generated. To compare perturbation results obtained from BV-BC and BV-BJ repertoire analysis, the average DBV-BJ for all BV and BJ genes for each sample (μμDBV-BJ) was first computed. The three PBL groups (CTR, CM⁻ and CM⁺) were significantly different (ANOVA, $p<0.0001$). Again, CM⁺ PBL repertoires (mean=32.3) were more altered than those of CM⁻ PBL (mean=24.5; $p=0.0035$). By using k-mean clustering with DBV-BJ data, all three groups could also be reconstituted without prior knowledge of group composition (FIG. 4c). 5 out of 6 CM⁺ PBL samples ($p=0.0001$) clustered together apart from CTR and CM⁻ samples.

To determine which BV gene(s) contributed to this difference, the perturbation of BV genes on the basis of BV-BJ repertoires (μDBV-BJ perturbation) was computed. MANOVA analysis showed that the three groups are statistically different ($p=0.01$). However, only μBV8.1-BJ (ANOVA, $p=0.01$) was significantly more altered in CM⁺ mice compared to CM⁻ mice. Finally, analysis of the contribution of BJ segments in BV8.1-positive T cells by MANOVA followed by ANOVA implicated only DBV8.1-BJ1.1, DBV8.1-BJ1.6, DBV8.1-BJ2.1 and DBV8.1-BJ2.2.

ISEApeaks was used to compute BJ percentages for each BV gene in PBL samples. These percentages were compared by MANOVA. BJ use was not significantly different between the CTR, CM⁻ and CM⁺ groups (data not shown). Thus, perturbations of BV-BJ CDR3 spectratypes are not correlated with modifications of the BJ use.

Example 1-11

Identification of Pathogenic Recurrent Clones

The PBL BV-BC and BV-BJ repertoire data was searched for pathogenic T cell clones associated with CM. Focus was given to the identification of pathogenic clones that are recurrently present in CM⁺ but not in CM⁻ mice. OligoScore was then used, which scores peaks for their recurrence in each group (Collette, A., and A. Six. 2002. ISEApeaks: an Excel platform for GeneScan and Immunoscope data retrieval,

TABLE 1

Perturbation of BV-BC repertoires allows prediction of CM[A]

| | | | CM⁺ | | CM⁻ | | CTR | | % correct |
|---|---|---|---|---|---|---|---|---|---|
| | | n | PBL | Spleen | PBL | Spleen | PBL | Spleen | Prediction[B] |
| CM⁺ | PBL | 13 | 11 | 1 | 0 | 1 | 0 | 0 | 85 |
| | Spleen | 10 | 2 | 4 | 1 | 1 | 2 | 0 | 40 |
| CM⁻ | PBL | 10 | 1 | 0 | 5 | 3 | 0 | 1 | 50 |
| | Spleen | 8 | 1 | 2 | 0 | 5 | 0 | 0 | 63 |
| CTR | PBL | 8 | 1 | 1 | 0 | 0 | 5 | 1 | 63 |
| | Spleen | 6 | 0 | 2 | 1 | 0 | 0 | 3 | 50 |
| Total | | | 16 | 10 | 7 | 10 | 7 | 5 | 60 |

[A]BV-BC perturbation data was analyzed by Discriminant Analysis with the jackknife method. Each sample had been left-out in turn while classification functions were computed on the remaining samples. These functions were used to predict the class membership for this sample. Left-out cases are in row and attributed categories in columns.
[B]The percentage of correct prediction was obtained by dividing the correctly classified samples by the total number of samples.

management and analysis. Bioinformatics 18:329-330). For BV-BC repertoires, no peak in CM⁻ or CM⁺ groups has a score higher than the threshold of CTR groups (data not shown). Hence, no BV-BC peak is found recurrently expanded. The same scoring approach was used to identify recurrent clones in BV-BJ repertoires. 122 peaks in the PBL CM⁺ mice have a score above the corresponding threshold defined with the CTR PBL group. They were compared to those of the CM⁻ group by subtracting the corresponding peak scores. Peaks were sorted decreasingly to identify the most recurrent in CM⁺ but absent in CM⁻. The three most differentially expressed recurrent peaks belong to BV8.1-BJ1.5 and BV8.1-BJ2.2 profiles (Table 2 and FIG. 5). BV2-BJ1.3 peak is given as an example of a peak that was recurrently expanded both in CM⁺ and CM⁻ mice and thus low ranked in Table 2 (this point will be discussed later). BV8.1 peaks were directly sequenced. For each of the two BV8.1-BJ combinations, similar amino-acid sequences were found in several CM⁺ individuals (Table 3). On the contrary, direct sequencing for the PCR products in CM⁻ samples yielded no readable CDR3 sequence (data not shown).

TABLE 2

Identification of recurrent expansions in CM⁺ mice in BV-BJ CDR3 profiles by OligoScore[A]

| Rank | BV | BJ | CDR3 (aa) | OS CM⁺ | OS CM⁻ | ΔCM+/− |
|---|---|---|---|---|---|---|
| 1 | 8.1 | 2.2 | 10 | 10.25 | 0.25 | 10.01 |
| 2 | 8.1 | 1.5 | 9 | 7.51 | 0.44 | 7.07 |
| 3 | 8.1 | 2.2 | 9 | 7.03 | 0.18 | 6.85 |
| 4 | 2 | 1.1 | 9 | 7.07 | 1.37 | 5.70 |
| 5 | 8.1 | 1.3 | 9 | 5.86 | 0.30 | 5.56 |
| 6 | 7 | 1.6 | 9 | 6.07 | 1.58 | 4.49[B] |
| 7 | 8.1 | 1.4 | 9 | 3.27 | 0.13 | 3.14 |
| 8 | 9 | 1.5 | 9 | 3.54 | 0.53 | 3.01[B] |
| 9 | 8.3 | 2.2 | 10 | 3.30 | 0.30 | 3.00 |
| 10 | 6 | 1.5 | 9 | 3.90 | 0.91 | 2.99 |
| 59 | 2 | 1.3 | 9 | 7.01 | 6.12 | 0.53 |

[A]Differences (ΔCM+/−) between the OligoScore of the CM⁺ PBL (OS CM⁺) and the CM⁻ (OS CM⁻) groups were sorted decreasingly to identify recurrent CDR3 peaks differently expressed in CM⁺ PBL but not in CM⁻ PBL. All OligoScores can be obtained on the supplemental data web page.
[B]Only one or two CM⁻ PBL samples were analyzable for these peaks whereas four or more were for the other peaks and groups.

TABLE 3

CDR3 sequences of BV-BJ expansions in CM⁺ mice.

| BV | BJ | CDR3 Length (aa) | Mice | BV | <- CDR3[A] -> | BJ |
|---|---|---|---|---|---|---|
| 8.1 | 2.2 | 9/10 | CM+ #1 | CAS | SGGDXXGQL | YFG |
|  |  |  | #2 | CAS | SVGGVNTGQL | YFG |
|  |  |  | #3 | CAS | SVGQENTGQL | YFG |
| 8.1 | 1.5 | 9 | CM+ #1 | CAS | SEXXDNQAP | LFG |
|  |  |  | #2 | CAS | SDGQEDQAP | LFG |
|  |  |  | #3 | CAS | SPGQDNQAP | LFG |
| 2 | 1.3 | 9 | CM+ #1 | CTC | SETGSGNTL | YFG |
|  |  |  | #7 | CTC | SVTDSGNTL | YFG |
|  |  |  | #9 | CTC | SETGSGNTL | YFG |
|  |  |  | CM− #1 | CTC | SXTGSGNTL | YFG |

BV-BJ PCR products were directly sequenced for indicated PBL samples using both a BV- and a BJ-specific primers.
[A]X stands for a position that could not be determined. Following Kabat et al (31), the CDR3 region was taken as encompassing amino-acids 95 to 106.

Example 1-12

Discussion

The aim of the above study was to exhaustively characterize the TCRB repertoire during cerebral malaria (CM) in B10.D2 mice infected with *Plasmodium berghei* ANKA clone 1.4. To this end, new global methods and tools were devised, based on a large-scale use of the CDR3 spectatyping approach. The results showed that the TCRB repertoire is specifically altered in the PBL of CM⁺ mice as compared to PBL of CM⁻ mice whereas no difference was evidenced in the spleen. This perturbation of the TCRB repertoire was partly explained by recurrent clones that are present in CM⁺ and absent in CM⁻ mice.

Analysis of the repertoire using the CDR3 spectatyping described the entire ex vivo TCRB repertoire of a sample by up to 2400 measurements. As a high number of parameters were measured, it was ensured that the cell quantity used is sufficient. In particular, paucity of material tends to favor stochastic PCR amplifications. Therefore, a set of cell dilutions were carefully determined by repertoire analysis so that the cell numbers used were sufficient to guarantee the quality of the repertoire data (A. Six et al, unpublished data). Furthermore, the identification of recurrent BV-BJ CDR3 expansions shows that the repertoire modifications documented herein are not artifacts (Table 3).

The original bioinformatic tools devised enabled to analyze the 3450 CDR3 profiles generated in this study. All three independent multivariate statistics were consistently gather in a similar manner the 6 experimental groups into 3 to 4 clusters. Moreover, as expected, the CTR PBL and CTR spleen groups were not separated for DA, ANOVA and k-mean clustering (with k=3). For the first time, it has been demonstrated that T cell repertoire data can give diagnostic/prognostic information when analyzed by class prediction. The alteration of the BV-BC repertoire enabled the group classification of 85% of the PBL samples of CM⁺ mice. PBL samples of CM⁻ mice are less correctly classified (50%). However, only one out of 10 CM⁻ PBL samples was erroneously classified as a CM⁺ PBL indicating that the risk to predict falsely that an infected individual is developing CM is small.

An original quantitative scoring method, OligoScore (Collette, A., and A. Six. 2002. ISEApeaks: an Excel platform for GeneScan and Immunoscope data retrieval, management and analysis. Bioinformatics 18:329-330), was used to identify recurrent expansion of T cell clones among the 1040 BV-BJ CDR3 peaks. It should be noted that existence of perturbation in a particular BV-BC or BV-BJ profile did not imply existence of recurrent expansion within this profile since private expansions can also distort it. Surprisingly, no recurrent peaks were found at the level of BV-BC. Two explanations can be given. Recurrent peaks in the BV-BC repertoires might have been below the detection limit of the scoring method. This is unlikely since OligoScore enabled detection of recurrence that were not visible by eye, even with a small number of samples (Collette, A., and A. Six. 2002. ISEApeaks: an Excel platform for GeneScan and Immunoscope data retrieval, management and analysis. Bioinformatics 18:329-330). More likely, it might have been the consequence of a "buffer effect" between BV-BC and BV-BJ data (Boudinot, P., S. Boubekeur, and A. Benmansour. 2001. Rhabdovirus infection induces public and private T cell responses in teleost fish. J. Immunol. 167:6202-6209). Variation at the more precise level of BV-BJ repertoires could have been averaged in the corresponding BV-BC repertoires since these repertoires were the addition of all BV-BJ repertoires. An example of this "buffer effect" can be visualized on FIG. 5 for BV8.1+ cells where modifications seen at the BV8.1BJ1.5 and BV8.1BJ2.2 levels were smoothed at the BV8.1-BC level. This effect was also seen on PBL sample perturbation of CM+ mice, which was 20.2 when estimated on BV-BC repertoires and 32.3 on BV-BJ repertoires. It is because BV-BJ repertoires were twelve times more precise than BV-BC and therefore gave a more accurate description of the repertoire. Finally, as BV-BJ repertoires are quantitative inside a given BV gene (Musette, P., A. Galelli, P. Truffa-Bachi, W. Peumans, P. Kourilsky, and G. Gachelin. 1996. The Jb segment of the T cell receptor contributes to the Vb-specific T cell expansion caused by staphylococcal enterotoxin 13 and *Urtica dioica* superantigens. Eur. J. Immunol 26:618-622; Pannetier, C., S. Delassus, S. Darche, C. Saucier, and P. Kourilsky. 1993. Quantitative titration of nucleic acids by enzymatic amplification reactions run to saturation. Nucleic Acids Res 21:577-583), it was possible to test this "buffer effect" by calculus. BV-BC profiles were, indeed, constructed with the BV-BJ data (data not shown).

The implication of Tαβ cells in the neuropathogenesis of malaria has been demonstrated with depletion by antibodies (Curfs, J. H., T. P. Schetters, C. C. Hermsen, C. R. Jerusalem, A. A. van Zon, and W. M. Eling. 1989. Immunological aspects of cerebral lesions in murine malaria. Clin. Exp. Immunol 75:136-140., Grau, G. E., P. F. Piguet, H. D. Engers, J. A. Louis, P. Vassalli, and P. H. Lambert. 1986. L3T4+ T lymphocytes play a major role in the pathogenesis of murine cerebral malaria. J. Immunol. 137:2348-2354; Hermsen, C., T. Vandewiel, E. Mommers, R. Sauerwein, and W. Eling. 1997. Depletion Of CD4+ or CD8+ T-cells prevents Plasmodium berghei induced cerebral malaria in end-stage disease. Parasitology 114:7-12; Yanez, D. M., J. Batchelder, H. C. van der Heyde, D. D. Manning, and W. P. Weidanz. 1999. gd T-cell function in pathogenesis of cerebral malaria in mice infected with Plasmodium berghei ANKA. Infect. Immun 67:446-448) and use of nude (Finley, R. W., L. J. Mackey, and P. H. Lambert. 1982. Virulent *P. berghei* malaria: prolonged survival and decreased cerebral pathology in cell-dependent nude mice. J. Immunol. 129:2213-2218) or knockout mice (Yanez, D. M., J. Batchelder, H. C. van der Heyde, D. D. Manning, and W. P. Weidanz. 1999. gd T-cell function in pathogenesis of cerebral malaria in mice infected with Plasmodium berghei ANKA. Infect. Immun 67:446-448; Boubou, M. I., A. Collette, D. Voegtlé, D. Mazier, P.-A. Cazenave, and S. Pied. 1999. T cell response in malaria pathogenesis: selective increase in T cells carrying the TCR Vb8 during experimental cerebral malaria. Int. Immunol 11:1553-1562). The results added to these previous studies and demonstrated, ex vivo, a profound perturbation and the existence of recurrent CDR3 peaks in TCRB PBL repertoires during CM despite the numerous *P. berghei* molecules that stimulated the immune system during infection. By contrast with recurrent responses against single antigens (Levraud, J. P., C. Pannetier, P. Langlade-Demoyen, V. Brichard, and P. Kourilsky. 1996. Recurrent T cell receptor rearrangements in the cytotoxic T lymphocyte response in vivo against the p815 murine tumor. J. Exp. Med. 183:439-449; Faure, M., S. Calbo, J. Kanellopoulos, A. M. Drapier, P. A. Cazenave, and D. Rueff-Juy. 1999. Tolerance to maternal immunoglobulins: resilience of the specific T cell repertoire in spite of long-lasting perturbations. J. Immunol. 163:6511-6519), the recurrent response against *P. berghei* was modest since it was not found at the BV-BC level. This could have been related to a general activation of T cells, possibly due to Plasmodium mitogens (Ballet, J. J., P. Druilhe, M. A. Querleux, C. Schmitt, and M. Agrapart. 1981. Parasite-derived mitogenic activity for human T cells in Plasmodium falciparum continuous cultures. Infect. Immun 33:758-762; Riley, E. M., G. Anderson, L. N. Otoo, S. Jepsen, and B. M. Greenwood. 1988. Cellular immune responses to Plasmodium falciparum antigens in Gambian children during and after acute attack of falciparum malaria. Clin. Exp. Immunol 73:17-22; Ho, M., H. K. Webster, B. Green, S. Looareesuwan, S. Kongchareon, and N. J. White. 1988. Defective production of and response to IL-2 in acute human falciparum malaria. J. Immunol. 141:2755-2759) that prevented the expansion of antigen-specific clones. The stability of BJ use observed between groups was consistent with this observation (data not shown).

Modification of the TCRB repertoire was evidenced only in the PBL of CM+ mice in contrast with the usually well-accepted idea that PBL reflects spleen. This is also in contrast with spleen being necessary for the occurrence of CM (Curfs, J. H., T. P. Schetters, C. C. Hermsen, C. R. Jerusalem, A. A. van Zon, and W. M. Eling. 1989. Immunological aspects of cerebral lesions in murine malaria. Clin. Exp. Immunol 75:136-140, Mercado, T. I. 1973. *Plasmodium berghei*. Inhibition by splenectomy of a paralyzing syndrome in infected rats. Exp. Parasitol 34:142-144; Hermsen, C. C., E. Mommers, T. van de Wiel, R. W. Sauerwein, and W. M. Eling. 1998. Convulsions due to increased permeability of the blood-brain barrier in experimental cerebral malaria can be prevented by splenectomy or anti-T cell treatment. J. Infect. Dis 178:1225-1227). Absence of specific alteration in the spleen of CM+ mice could be explained by the dilution of stimulated cells in the bulk of T cells present in this organ and the fact that they leave to recirculate when they were activated (Mackay, C. R., and U. H. von Andrian. 2001. Memory T cells: local heroes in the struggle for immunity. Science 291:2323-2324).

T cell clones associated with neuropathogenesis can be of different types. First, they can be private, specific to one individual, or recurrent, present in different individuals and sometimes designated as public clones. Secondly, their function might be pathogenic, protective or regulatory. Recurrent clones associated to neuropathogenesis were identified by assessing their presence in CM+ mice and absence in CM− mice. Five out of the ten most recurrent and differentially expressed peaks use the BV8.1 segment. Observations that supported their having a pathogenic role is that depletion of BV8.1/2+ cells diminished the incidence of CM from 90% to 40% (Boubou, M. I., A. Collette, D. Voegtlé, D. Mazier, P.-A. Cazenave, and S. Pied. 1999. T cell response in malaria pathogenesis: selective increase in T cells carrying the TCR Vb8 during experimental cerebral malaria. Int. Immunol 11:1553-1562). Others peaks including the ones using BV6, BV7 and BV9 segments have been identified in CM+ mice (Table 2). This relates to the absence of CM in mice treated with a superantigen that deleted BV6, 7, 8.1 and 9 using T cells (Boubou, M. I., A. Collette, D. Voegtlé, D. Mazier, P.-A. Cazenave, and S. Pied. 1999. T cell response in malaria pathogenesis: selective increase in T cells carrying the TCR Vb8 during experimental cerebral malaria. Int. Immunol 11:1553-1562., Gorgette, O., A. Existe, M. Idrissa-Boubou, S. Bagot, J.-L. Guénet, D. Mazier, P.-A. Cazenave, and S. Pied. 2002. Deletion of T cells bearing Vb8.1 TCR following MTV-7 integration confers resistance to murine cerebral malaria. Infect. Immun In press).

Figure 5A:
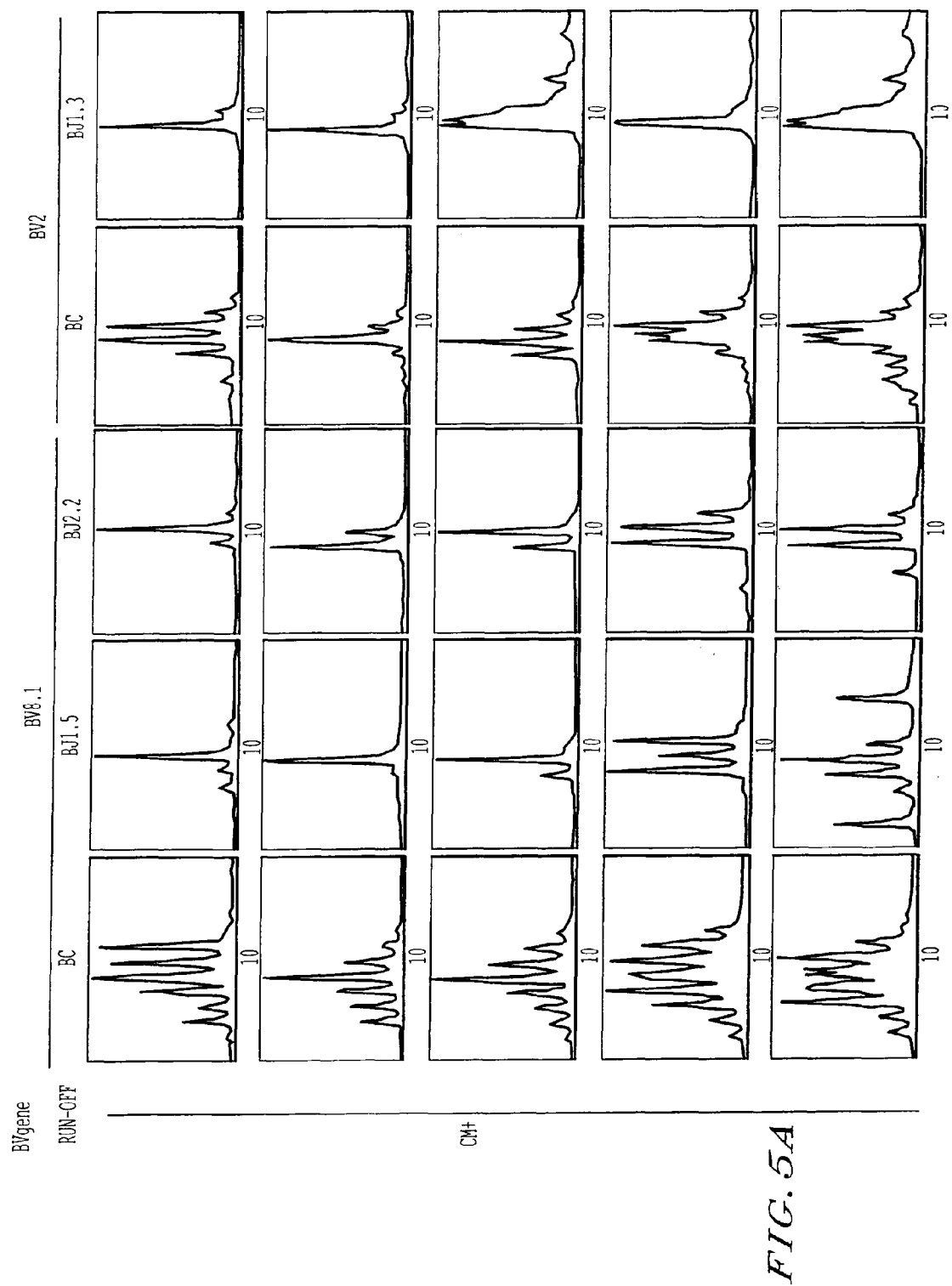
FIG. 5: BV-BJ CDR3 profiles of recurrent expansions identified by OligoScore and perturbation analysis. PBL cDNA were amplified with BV8.1- or BV2-specific primers with a BC-specific primer. PCR products were then subjected to run-off with appropriate BJ-specific primers. Products were separated on an automated sequencer and analyzed with Immunoscope and ISEApeaks. All PBL samples for which those combinations were analyzed are represented. Horizontal axis represents the nucleotide size and vertical axis the fluorescence intensity, in arbitrary units.
Figure 5B:
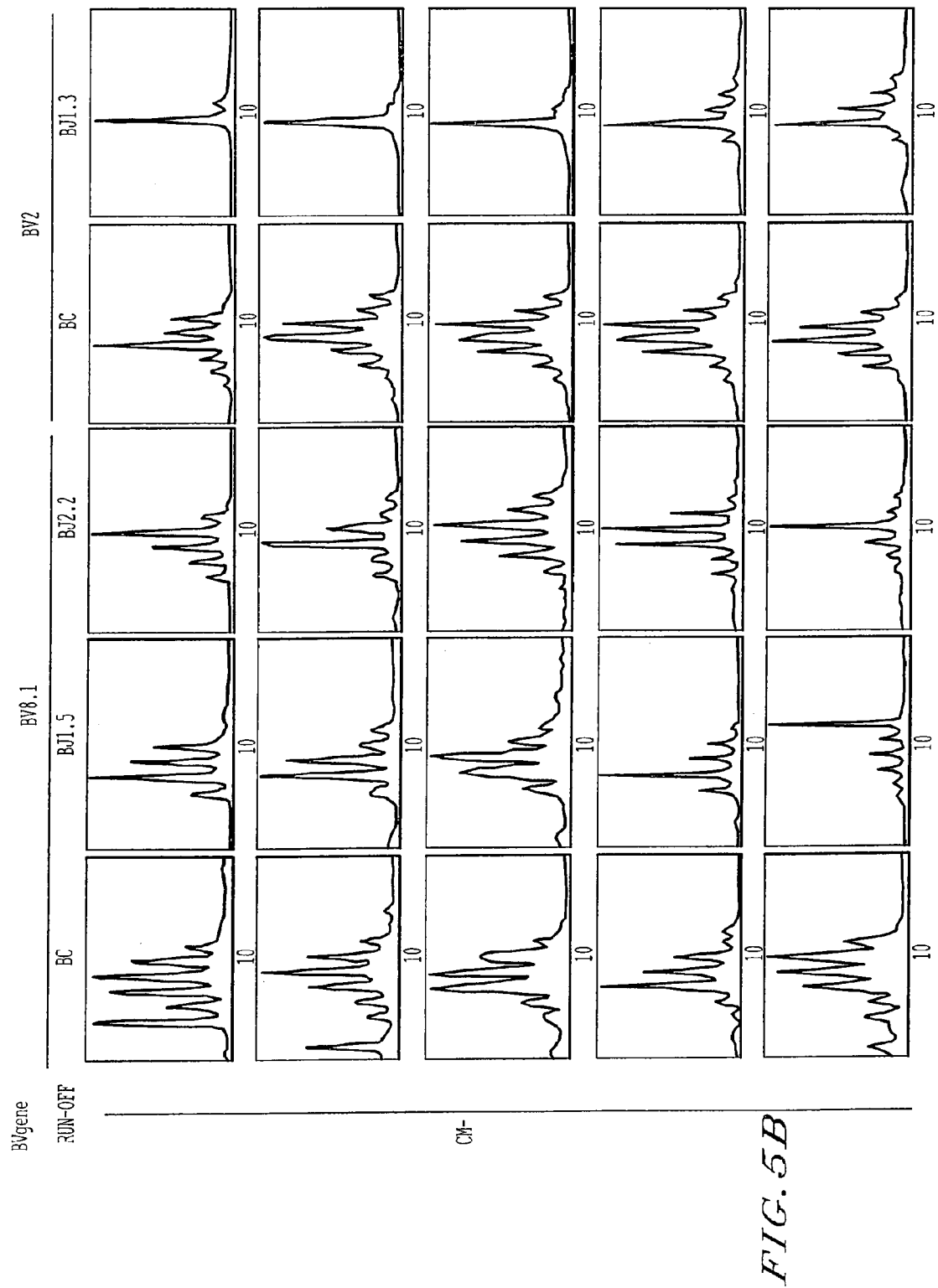
Figure 5C:
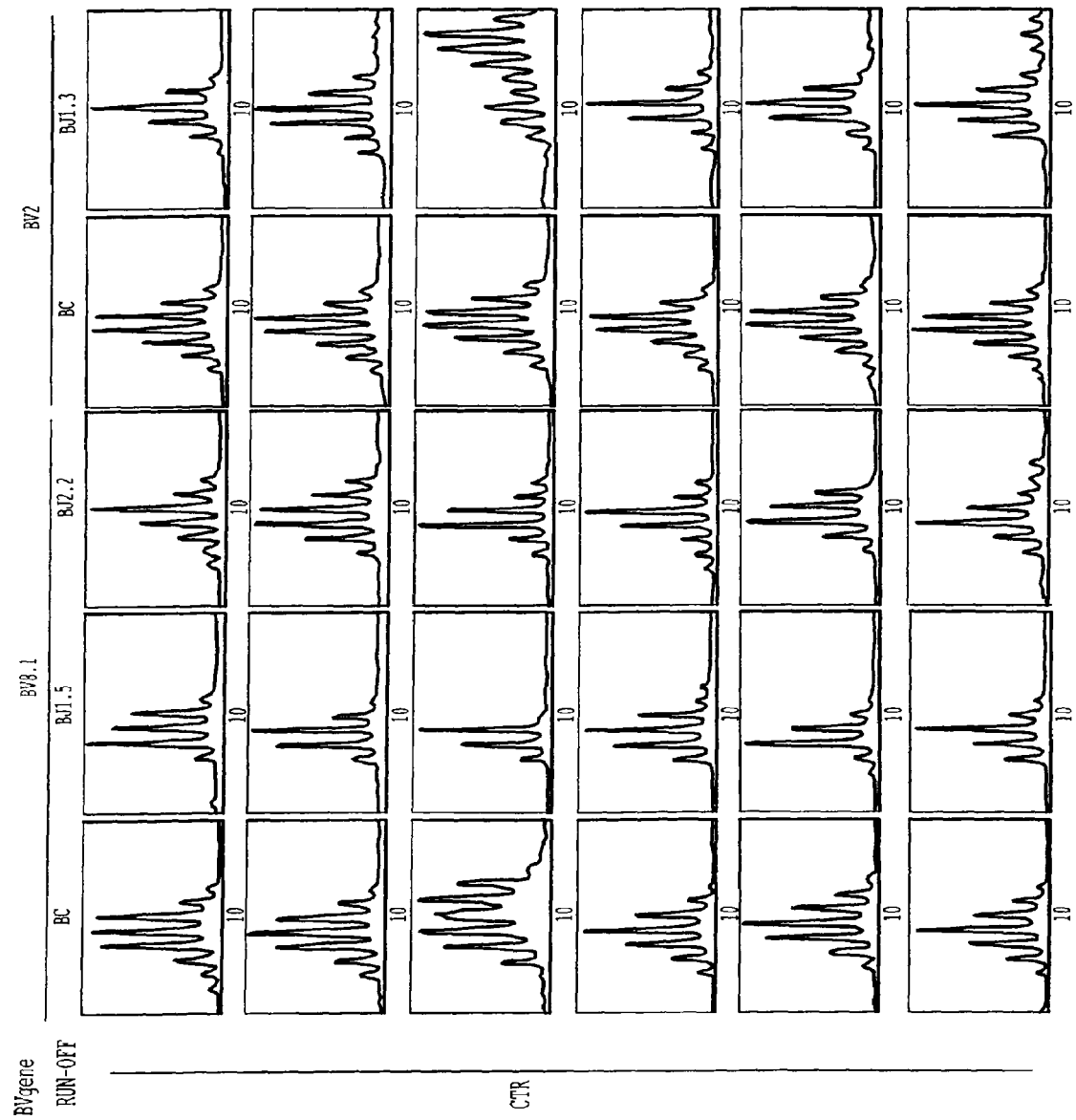

No CM−-specific recurrent peak (data not shown) were identified, which could be involved in protection, but a BV2-BJ1.3 peak was recurrently present both in CM+ and CM− mice as judged by the high score obtained for the two groups (Table 2 and FIG. 5). This peak was by far the most expanded peak in CM⁻ mice (data not shown). Mechanisms contributing to neuropathogenesis could thus be the result of a regulatory pathway between BV2 and BV8.1-expanded clones leading to alteration of their cytokine profiles (de Kossodo, S., and G. E. Grau. 1993. Profiles of cytokine production in relation with susceptibility to cerebral malaria. J. Immunol. 151:4811-4820).

Altogether, these results may suggest that few T cell clones were implicated in the development of CM. The immunological history for each individual shapes the emergent repertoire differentially between inbred individuals (Bousso, P., A. Casrouge, J. D. Altman, M. Haury, J. Kanellopoulos, J. P. Abastado, and P. Kourilsky. 1998. Individual variations in the murine T Cell response to a specific peptide reflect variability in naive repertoires. Immunity 9:169-178). These variations could explain why, among a group of genetically identical mice infected with the same stabilate of parasites, only some developed CM.

In a previous study, it was observed by flow cytometry an increase of BV8.1/2+ T cells in the PBL of CM⁺ mice while no expansion was seen in the spleen of CM⁺ mice nor in the PBL and spleen of CM⁻ mice ((Boubou, M. I., A. Collette, D. Voegtlé, D. Mazier, P.-A. Cazenave, and S. Pied. 1999. T cell response in malaria pathogenesis: selective increase in T cells carrying the TCR Vb8 during experimental cerebral malaria. Int. Immunol 11:1553-1562); data not shown). This increase, if caused by the expansion of few T cell clones, should distort the bell-shaped CDR3 length distribution of BV8.1/2-BC profiles. However, the PBL BV8.1/2-BC repertoire of CM⁺ mice was not perturbed by comparison with CTR mice (ANOVA, p=0.71) or CM⁻ mice (ANOVA, p=0.29). In addition, no modification of the BJ segment used was observed in the CM⁺ mice. The increase of the representation of BV8.1/2 cells in the PBL of CM⁺ mice thus cannot be attributed to a mono- or oligo-clonal increase and is therefore polyclonal. BV8.1/2 could be stimulated by a superantigen-like molecule, as observed in *P. yoelii* infection (Pied, S., D. Voegtlé, M. Marussig, L. Rénia, F. Miltgen, D. Mazier, and P.-A. Cazenave. 1997. Evidence for a superantigenic activity during murine malaria infection. Int. Immunol 9:17-25). Implications of such molecules in pathogenesis have been reported for infections by *Toxoplasma gondii* (Subauste, C. S., F. Fuh, R. D. Malefyt, and J. S. Remington. 1998. ab T cell response to *Toxoplasma gondii* in previously unexposed Individuals. J. Immunol. 160:3403-3411) and *Leishmania infantum* (A. Sassi, A. Collette et al, unpublished results).

The original method presented in this report allowed the exhaustive analysis of immune repertoires. Applied to a mouse model of malaria, it demonstrated that the neuropathology induced by *P. berghei* ANKA was associated with a global perturbation of TCRB repertoires specifically found in PBL together with the recurrent expansion of few T cell clones.

This method can easily be transposed to human malaria since PBL are easily accessible to experiment. It is intriguing to know if the same association between PBL perturbation and neuropathology can be found in *P. falciparum* malaria. Furthermore, classification experiments allowed separation of the CM⁺ and CM⁻ mice and thus provide new tools for a better understanding of the immune response during malaria in humans. These hypotheses are being tested by studying cohorts of malaria patients. Finally, the original approach for deciphering lymphocyte repertoires can be transposed to various pathological conditions. For instance, this methodology is used in clinical follow-ups of patients after bone marrow transplantation or vaccination. The results and approach presented provide a promising basis for the bioinformatics revolution in the field of immunology.

Example 2-1

TCRB Repertoire Data

Parasite, mice and TCR BV-BC and BV-BJ CDR3 spectratype raw data, used in the present study, are described in Example 1.1 above. Briefly, eight-week old B10.D2 mice were infected by intraperitoneal injection of $10^6$ red blood cells parasitized by PbA. Between day 7 to 10 after infection, PbA induces in some mice a cerebral syndrome, which is used as a model for cerebral malaria. Mice that do not show any cerebral signs die of severe anemia due to hyperparasitemia three weeks after infection. These mice, designated HP⁺ in this report, were sacrificed between day 11 to 16 after infection when exhibiting a parasitemia above 20%, indicating that they had survived the critical cerebral malaria period. The PBL and spleen TCRB repertoires of these mice were analyzed. Percentages of use of each CDR3 peak inside its profile were computed and assembled into a peak database with ISEApeaks DataAnalyser module.

Example 2-2

Data Smoothing Algorithm

A series of data filters were implemented in the DataSmoother module of the ISEApeaks product to obtain a CDR3 spectratype, which is composed of several peaks. The $i^{th}$ peak of the $j^{th}$ profile of the $k^{th}$ sample can be described by its area $A_{i,j,k}$ in arbitrary unit and its nucleotide length $L_{i,j,k}$. The peaks are ordered by increasing length. For each profile, $\lambda_j$ will represent the theoretical PCR product length for a CDR3 of 10 amino acids.

The first filter removed background noise and peaks inferior to a defined cut-off according to user-defined parameters. In addition, peaks with identical length are summed. The second filter corrected peaks for which $L_{i+1,j,k}-L_{i,j,k}=1$, designated as adjacent peaks, and, thus, do not respect the three nucleotide spacing expected for in-frame V(D)J rearrangements. Accordingly, each pair of adjacent peaks were tested to determine whether $L_{i,j,k}-\lambda_j$ or $L_{i+1,j,k}-\lambda_j$ are a multiple of 3. When this criteria was met, the corresponding peak is attributed to the biologically expected peak and the adjacent peak is summed. Otherwise, it is not possible to decide since the peaks are between two consecutive expected peaks. Hence, they are left unmodified for manually corrected by the DataFormatter module of the ISEApeaks product.

The final filter solved more subtle problems.

Following the peak processing by the aforementioned filters, some peaks remained (designated as ambiguous peaks), which can be attributed to the same theoretical length; however, these ambiguous peaks, in fact, corresponded to two distinct theoretical peaks. To estimate a possible shift which causes this problem in a profile (j, k), the Euclidean division of $L_{i,j,k}-\lambda_j$ by 3 was calculated with the remainder being assigned to an element of $\{-1, 0, 1\}$. If the mean of remainders was superior to 0.5 (respectively inferior to −0.5), all profile's lengths were shifted by −1 nucleotide length (respectively 1). Afterwards, the profile was analyzed again to warn the user of remaining ambiguous peaks.

Example 2-3

Methods for CDR3 Spectratype Analyses and Statistics

Three different methods were implemented in the MacOS ISEApeaks product to analyze the peak database.

In a first approach, multivariate statistics were used to give a global description of the peak database using the percentage of use of each CDR3 length directly. Each repertoire was considered as a vector in n-dimensional space, where n is the number of variables that describe the repertoires. Missing values were replaced by the overall mean of the variable as recommended in Rencher (Methods of multivariate analysis. 1995, J. Wiley, New York). The resulting number of variables (230 peaks for BV-BC repertoires) was too high for theoretical constraints of Discriminant Analysis. The Principal Component Analysis (PCA) was first used to reduce the number of variables. PCA extracts new variables from the data set that retains the variability contained in the original data set. Linear Discriminant Analysis (DA) was then performed on the new data set to compare the different groups. DA computes discriminant functions that maximize inter-group variation and minimize intra-group variation. Significance of each discriminant function was tested using $\chi^2$ approximation of Wilks' statistics Rencher (Methods of multivariate analysis. 1995, J. Wiley, New York).

The second method estimated the perturbation of a BV-BC repertoire by comparison to a control group (Gorochov et al. Nat. Med 1998, 4; 215 and Han et al., J. Immunol. 1999, 163; 301). μDBV-BC was defined as the mean of BV-BC perturbations, which corresponds to the overall sample perturbation. Similarly, DBV-BJ was defined as the BV-BJ perturbations. μμDBV-BJ was defined as the overall BV-BJ perturbation for all BV-BJ combinations analyzed. All BV-BC and BV-BJ perturbations ranged from 0 (identical profiles) to 100 (completely different profiles). Two-way Analysis of Variance (ANOVA) and t-test were used to analyze sample μμDBV-BC and μDBV-BJ, respectively. When ANOVA was significant, comparisons between two categories were performed with Fischer's Protected Least Significant Difference. To further assess similarity between samples, k-mean clustering with the Euclidian distance and hierarchical clustering with Ward minimum variance criteria were used. Significance of the clusters obtained from k-mean clustering were assessed by computing the probability of observing by chance the number of samples of a particular group within the cluster (Tavazoie et al. Nat. Genet. 1999, 22; 281).

In the third method, recurrent expansions in a group of samples were scored by OligoScore computed by ISEApeaks (Collette and Six, Bioinformatics 2002, 18; 329). A score was computed for each peak in each group of samples. OligoScore of the control group was then subtracted to remove background noise.

PCA, DA and k-mean clustering were performed with SYSTAT 10 (SPSS). ANOVA were performed with StatView 5.0 (SAS Institute Inc). Theoretical considerations on multivariate statistics used here can be found in Rencher (Methods of multivariate analysis. 1995, J. Wiley, New York). Statistics were considered significant when p<0.01.

Example 2-4

ISEApeaks Modules for CDR3 Spectratyping Analysis

Figure 6:
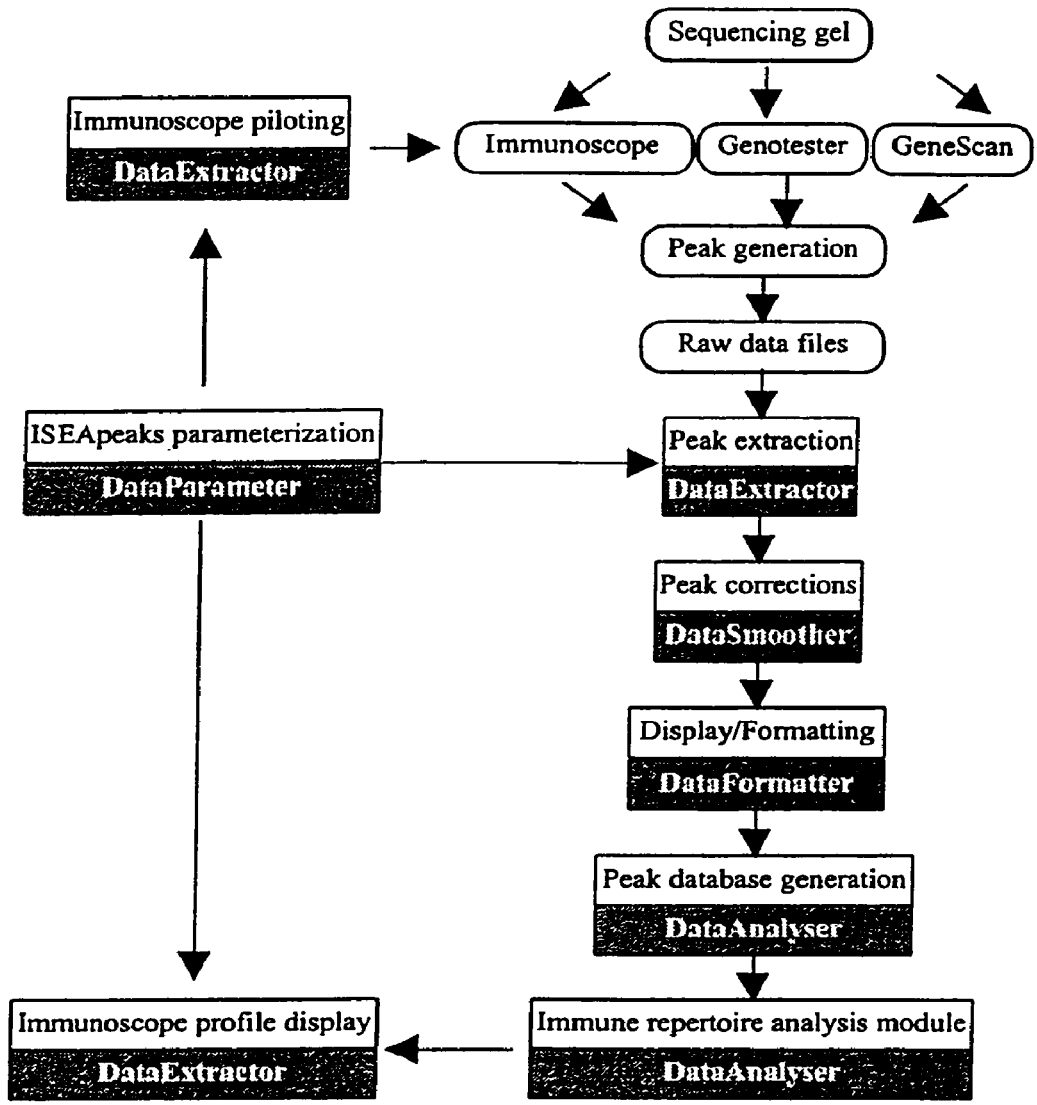
FIG. 6: ISEApeaks architecture and data flowchart. ISEApeaks modules and specific files are indicated in shaded rectangles.

To enable the analysis of large amount of CDR3 spectratype data, ISEApeaks product was employed to extract, format, and gather data from the automated sequencers GeneScan, Immunoscope or Genotester into an Excel peak database as already described (Collette and Six, Bioinformatics 2002, 18; 329). Two modules were specifically designed for CDR3 spectratype data, addressing the problem of data smoothing and data analysis (FIG. 6).

Figure 2B:
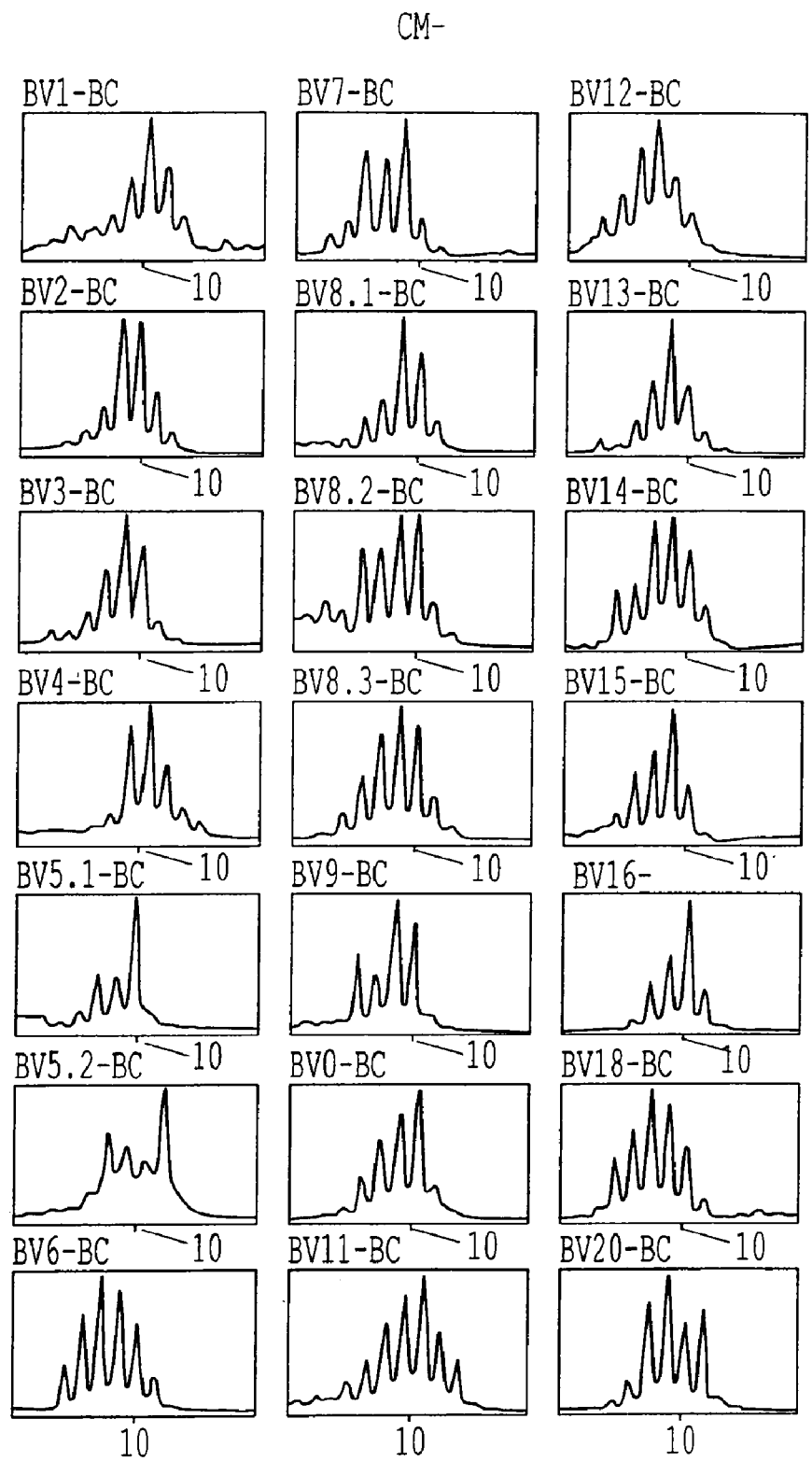
Figure 2C:
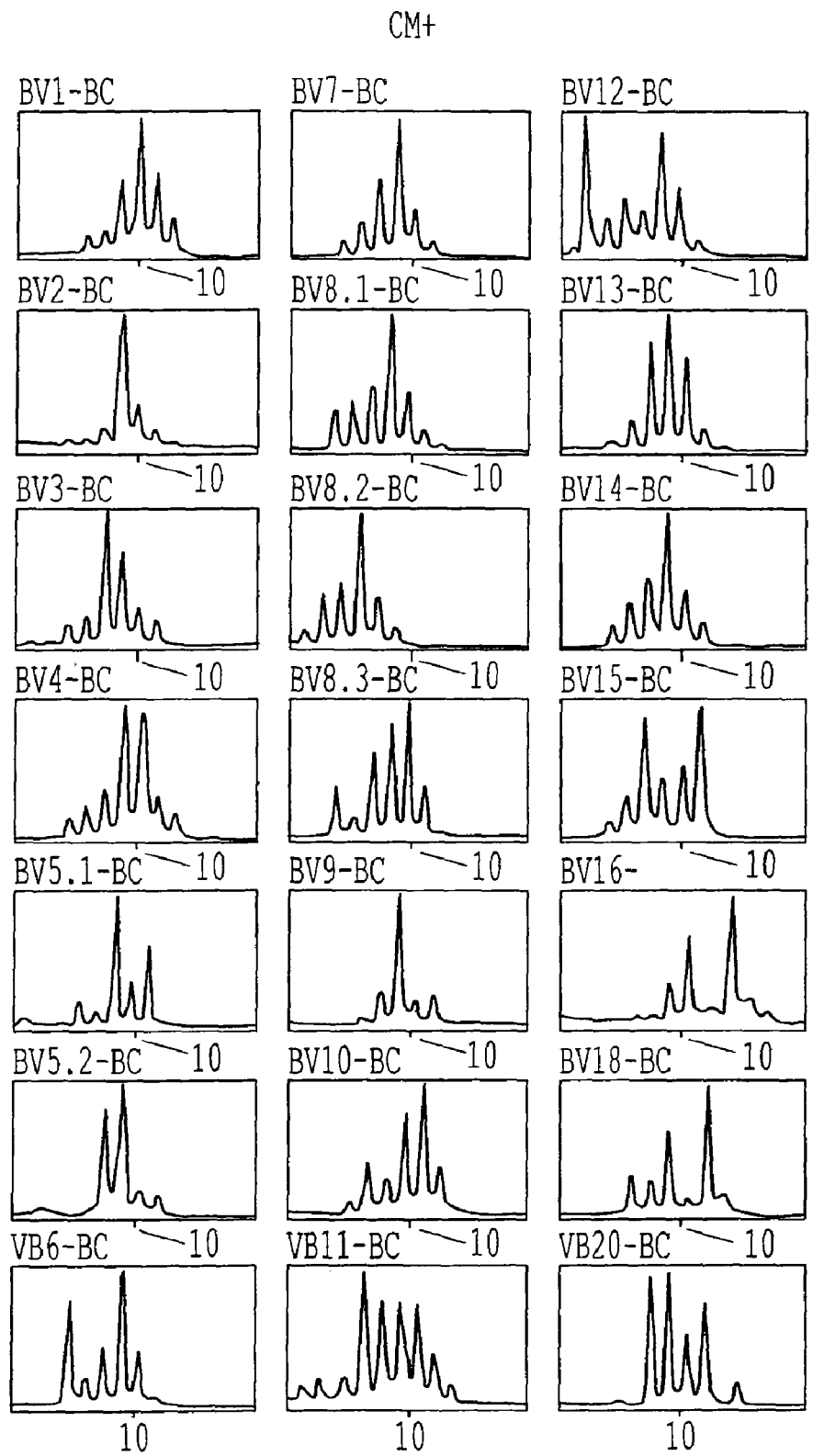

Differences in lane migration and peak finding algorithm of GeneScan, Immunoscope or Genotester automated sequencers results in divergence between what one observes on a gel and the figures given by these softwares (FIGS. 7A and 2B). This problem is of paramount importance since it is not possible to build the peak database when two experimental peaks are found where only one is theoretically expected. An automatic analysis thus requires that this problem be first solved. CDR3 peaks should be separated by three nucleotides as expected for in-frame rearrangements found in peripheral lymphocytes. On this basis, filters were designed and implemented in the DataSmoothing module to smooth peak data (FIG. 7C).

The resolution of peak data problems were assessed with 9 mouse BV-BC repertoires. Raw data presented 141 problems of which one third were solved by the first filter consisting in background noise removal and addition of peaks with identical length. 82% of the 45 adjacent peaks and 60% of the 50 ambiguous peaks were resolved with the last two filters, thereby considerably reducing the amount of time necessary for manual data correction. Altogether, 80% of peak problems were solved. The remaining inconsistencies, highlighted in ISEApeaks DataFormatter sheets, needed to be corrected by the user by comparing two CDR3 profiles of the same BV-BC or BV-BJ combination for two different samples.

The second module, DataAnalyser, module was then used to build and analyze the CDR3 peak database. ISEApeaks enabled the assessment of repertoire perturbations (Gorochov et al. Nat. Med 1998, 4; 215 and Dechanet et al. J. Clin. Invest. 1999, 103, 1437), oligoclonal expansions (Cochet et al., Eur. J. Immunol. 1992, 22; 2639) or recurrent clones defined as rearrangements that were used by different individuals in response to a particular infection or immunization (Collette and Six, Bioinformatics 2002, 18; 329). The average CDR3 length of each profile, the average repertoire for each group and the peak number per profile were also be computed. In addition, a summary table representing the different samples in which diversity of each BV-BC or BV-BJ profiles was plotted, which was color-coded. Altogether, DataAnalyser module enabled a global and objective analysis of immune repertoire data.

In a third module, tools were devised to facilitate the use of the Immunoscope products. For example, a first tool created Immunoscope 3.1α analysis macros using DataParameter files. A second tool tackled the problem of data representation. Typically, experimenters need to gather CDR3 spectratypes of different samples, which resulted in files containing CDR3 profiles being scattered in different folders with abstruse names. ISEApeaks solves this problem by assigning a file, which describes each load of a run. DataExtractor then uses this parameter file to find, copy and rename all needed files before assembling them in a template provided in the product of up to 16 12 profiles.

Example 2-5

Analysis of BV-BC Repertoire Modifications During Mouse Malaria

The TCRB repertoire in a group of PbA-infected mice, developing severe anemia due to hyperparasitemia (HP), was analyzed to study repertoire modifications induced by PbA infection by comparing HP mice to control (CTR) non-infected mice. Multivariate statistics were required to apprehend the complex changes induced by this parasite.

Figure 8:
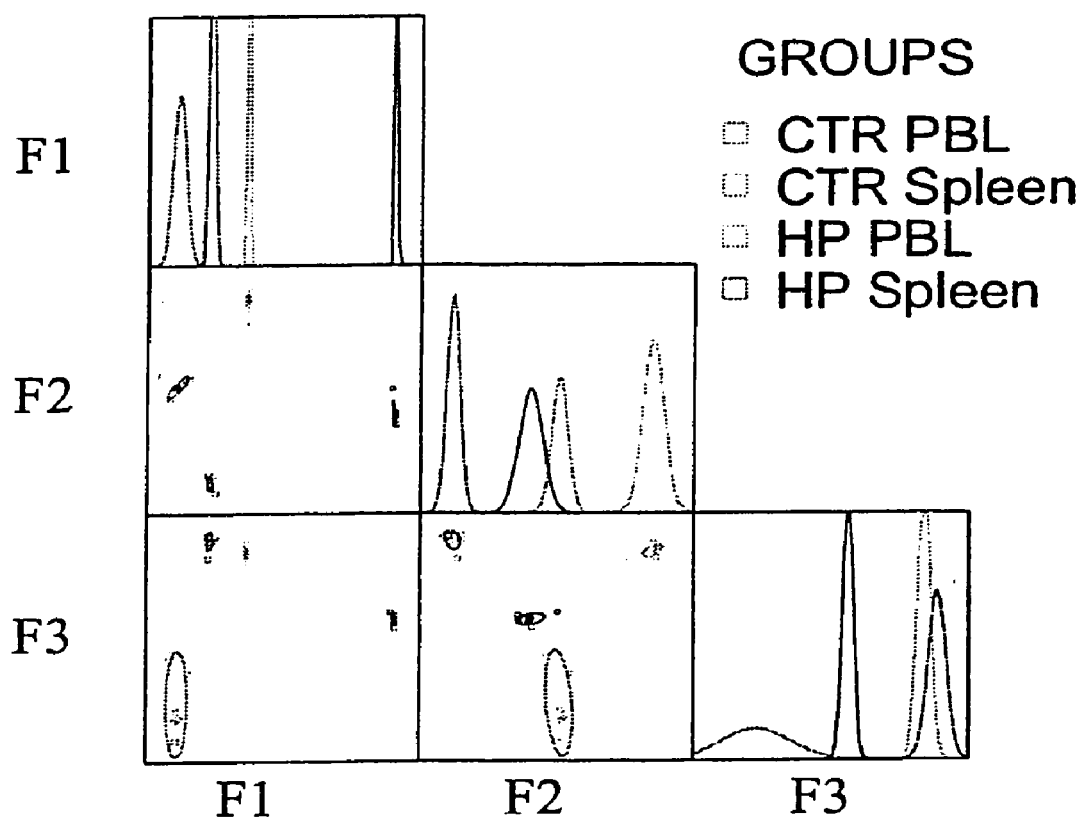
FIG. 8: Separation of samples according to BV-BC repertoire. Discriminant Analysis was performed on the new set of variables obtained with Principal Components Analysis. Bivariate graphics represent the sample value in two discriminant functions. Discriminant functions are linear combination of the variables that endeavor to separate groups. F1 to F3 stands for each discriminant function, sorted decreasingly by the associated eigenvalue. The first two functions are statistically significant, indicating that only three groups can be separated (p<0.01). Each sample is represented on the bivariate plots, but are scarcely visible since DA groups the samples very well. 0.95 confidence ellipses, centered on group centroid, are overlaid. The density normal curve of each group is shown on the diagonal. Vertical and horizontal axes represent canonical scores for each function. The density normal curve of F3 shows that groups are not well separated, consistent with the non-significance of this function. Sample numbers are as follows: 8 CTR PBL, 6 CTR spleen, 10 HP PBL and 8 HP spleen.

BV-BC repertoire was analyzed both in the PBL and spleen compartments, representing 32 samples. ISEApeaks was used to retrieve raw data from the 672 CDR3 profiles. After smoothing, the peak database was formed. In a first approach, the differences between the four groups of samples (CTR PBL, CTR spleen, HP PBL and HP spleen) was assessed by Discriminant Analysis (DA) after reduction of the number of CDR3 peak variables by Principal Components Analysis (PCA). Results of DA performed on this new data set, which retained 99% of the original data information, are displayed in FIG. 8. Only the first two discriminant functions are statistically significant indicating that only three groups could be separated: HP PBL, HP spleen and CTR samples. Thus, infection by PbA globally induced alteration of the BV-BC repertoires.

Figure 9:
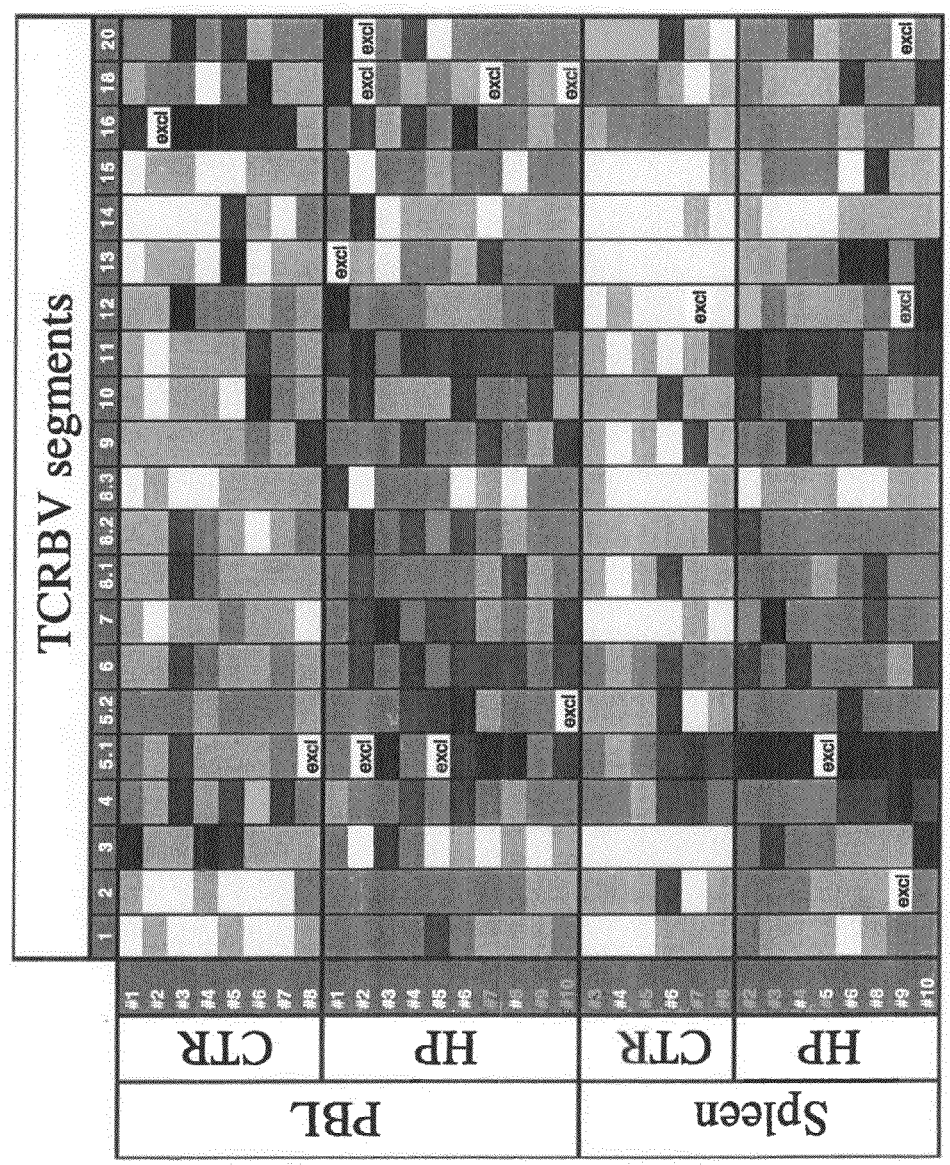
FIG. 9: Representation of BV-BC perturbations. BV-BC perturbations for each BV segments (horizontal axis) and each sample (vertical axis) have been color-coded. Mice ID are indicated in the third column. TCRB perturbations were computed and displayed with ISEApeaks product. Coding is as follows: light grey (DBV-BC<5), mid grey (<10), dark grey (<20), pink (<25), red (<30), dark red (<50), black (<100). "excl" denotes excluded combinations for which the recovered signal was too poor.

To get insights into the nature of this alteration, indexes of perturbation (DBV-BC) between samples and the CTR spleen group were computed. DBV-BC data was visualized in an objectively color-coded array (FIG. 9). Globally, perturbation in HP samples seemed greater. To test this observation, sample perturbations (μDBV-BC), the mean of the DBV-BC, were compared by Analysis of Variance (ANOVA) using the organ (PBL or spleen) and clinical status (CTR or HP) factors (FIG. 10A). Only the clinical status factor was significant (p<0.0001), confirming that the infection induces an alteration of the TCRB repertoire without distinction of blood versus spleen compartments.

Typically, both DA on peak data and ANOVA on perturbation data are used to assess the difference between known groups of samples. However, k-mean clustering, another multivariate statistical method, can be used to cluster related samples without a priori knowledge of group composition. This method was applied on BV-BC repertoire data (FIG. 10B). Cluster analysis allowed separation of all CTR samples and infected samples but one (p=2.8×10$^{-8}$). Thus, three independent statistical methods showed that infection by PbA induced an alteration of the BV-BC repertoire both in the blood and the spleen compartments.

Example 2-6

Analysis of Blood BV-BJ Repertoire Modifications During Mouse Malaria

The precision of the repertoire description by BV-BC CDR3 spectratypes was assessed by studying BV-BJ repertoires. The BV-BJ spectratypes of 9 (out 21) BV genes, representing more than two third of the TCRB repertoire, were studied in the PBL compartment. Likewise, the repertoire alteration of each sample as compared to the CTR PBL reference group was studied. ISEApeaks computed the perturbation for each BV and BJ segments (DBV-BJ). The average of DBV-BJ among BV and BJ segments (μμDBV-BJ) quantitatively measured the alteration for each sample. PBL BV-BJ repertoires of HP mice (mean=24.5) were also more altered than in CTR mice (mean=11.9; t-test, df=9, p=0.0001).

To assess whether this alteration of BV-BJ repertoires could also enable the clustering of samples without a priori knowledge of group composition, hierarchical and k-mean clustering were used. Both methods achieved a complete separation of groups (p=0.002), confirming a strong dissimilarity between these samples (FIG. 11).

Example 2-7

Identification of Recurrent Clones During Malaria

Another interesting feature of CDR3 repertoire analyzed was the finding of recurrent CDR3 expansions of similar clones responding to challenge. The PbA parasite contained a very large number of antigens and induced a profound alteration of the TCRB repertoire. OligoScore, which objectively scores each of the 1056 peaks for their recurrence (Collette and Six, *Bioinformatics* 2002, 18; 329) was employed. No peak was found recurrently expanded in the BV-BC repertoires. Analysis of BV-BJ data enabled the finding of recurrent peaks, particularly of BV2-BJ1.3 and BV2-BJ1.1 peak with a CDR3 length of nine amino-acids (Table 4).

TABLE 4

Identification of BV-BJ recurrent peaks during experimental malaria.

| Rank | Description | CDR3 (aa)[1] | OligoScores HP | OligoScores CTR | Number[2] HP | Number[2] CTR | □HP/CTR |
|---|---|---|---|---|---|---|---|
| 1 | BV2-BJ1.3 | 9 | 6.12 | 0.25 | 4 | 5 | 5.87 |
| 2 | BV9-BJ1.5 | 10 | 3.46 | 0.01 | 1 | 1 | 3.45 |
| 3 | BV2-BJ1.1 | 9 | 1.37 | 0.25 | 4 | 6 | 1.12 |
| 4 | BV8.2-BJ2.2 | 10 | 1.24 | 0.19 | 5 | 6 | 1.05 |
| 5 | BV7-BJ1.2 | 7 | 1.17 | 0.13 | 4 | 6 | 1.04 |
| 6 | BV6-BJ1.3 | 10 | 1.09 | 0.19 | 3 | 6 | 0.90 |
| 7 | BV7-BJ1.6 | 9 | 1.58 | 0.68 | 2 | 5 | 0.90 |
| 8 | BV4-BJ1.3 | 10 | 1.48 | 0.59 | 4 | 6 | 0.89 |
| 9 | BV6-BJ2.1 | 9 | 0.89 | 0.07 | 5 | 6 | 0.82 |
| 10 | BV2-BJ1.3 | 10 | 1.19 | 0.37 | 4 | 5 | 0.82 |

The 1056 peaks of BV-BJ repertoires were scored for recurrent expansion in the CTR and HP group by OligoScore (Collette and Six, *Bioinformatics* 2002, 18; 329). Peaks were then sorted decreasingly according to the difference (□HT/CTR) between the score of the HP group and the one of the CTR group. All OligoScores can be obtained on the supplemental data web page.

[1]CDR3 lengths are indicated in amino-acids.

[2]Number of samples for which the given profile data was analyzable is indicated. A total of 4 CTR and 6 HP mice were studied.

Figure 12:
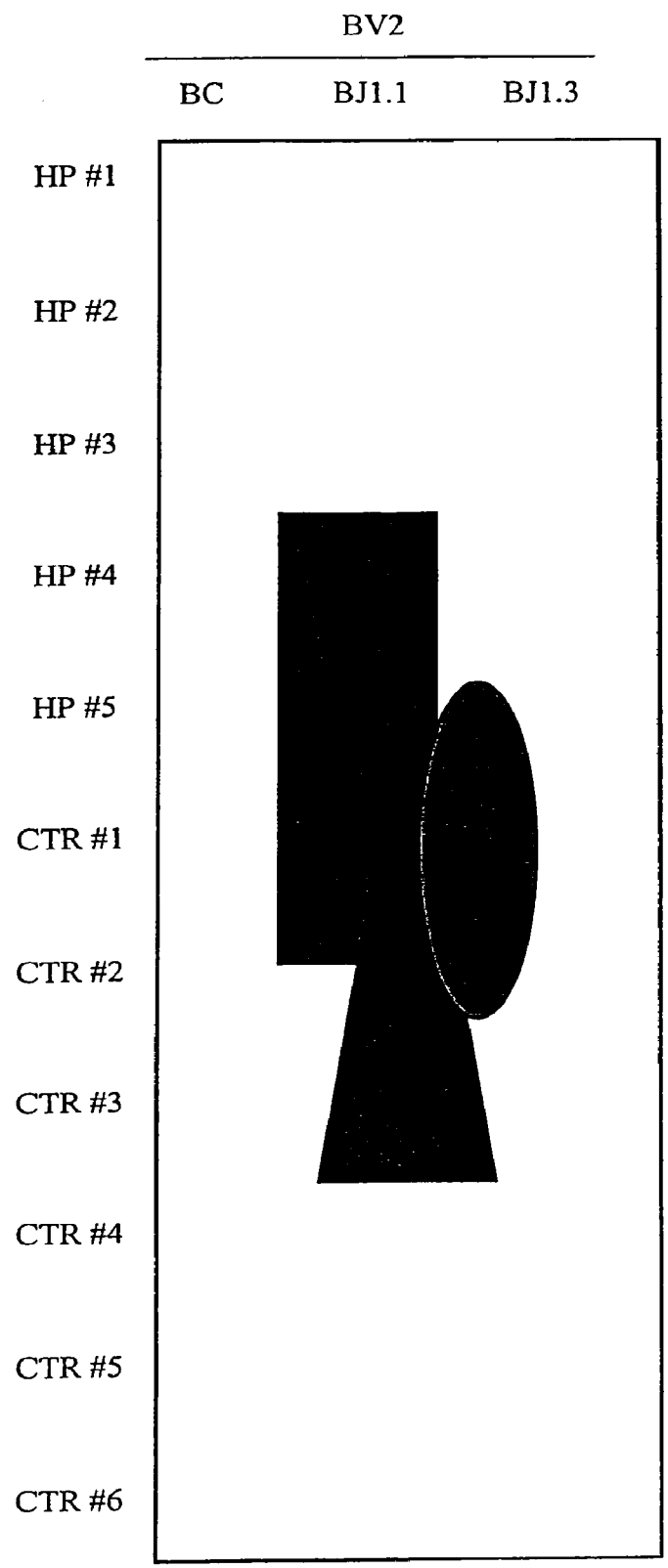
FIG. 12: CDR3 profiles of BV2-BJ1.3 and BV2 BJ1.1 in PBL of HP and CTR mice. PBL cDNA were amplified with BV2- and a BC-specific primer. PCR products were then subject to run-off with appropriate BJ-specific primers. Products were separated on an automated sequencer and analyzed with the Immunoscope and ISEApeaks packages. Horizontal axis represents the nucleotide size and vertical axis the fluorescence intensity in arbitrary units.

FIG. 12 shows the corresponding BV2-BJ1.3 and BV2-BJ1.1 CDR3 profiles. BV9-BJ1.5 cannot be considered recurrently expanded since sufficient signal was only obtained for one sample in each group. Direct sequencing confirmed that these expansions represented public clones since very similar CDR3 sequences were found (Table 5).

TABLE 5

CDR3 direct sequencing of identified PBL expansions in infected mice.

| TCRBJ | CDR3 (aa) | Mice | TCRBV2 -> | | <- CDR3[1] Sequences -> | | <- TCRBJ |
|---|---|---|---|---|---|---|---|
| 1.3 | 9 | #1 | CTC | S | XTG | SGNTL | YFG |
|  |  | #2 | CTC | S | SAK | SGNTL | YFG |
|  |  | #3 | CTC | S | SGT | SGNTL | YFG |
| 1.1 | 9 | #1 | CTC | S | GTGA | NTEV | FFG |
|  |  | #2 | CTC | S | GTGA | NTEV | FFG |
|  |  | #3 | CTC | S | XTGA | NTEV | FFG |
|  |  | #4 | CTC | S | GTGA | NTEV | FFG |

BV2-BJ PCR products were directly sequenced using both BV- and BJ-specific primers.
[1]X stands for a position that could not be determined due to ambiguous reading of the nucleotide sequence. Following (Kabat et al, *Sequences of proteins of immunological interest* 1991, Bethesda, MD) the CDR3 region was taken as encompassing amino-acids 95 to 106.

Example 3.1

ISEApeaks package 2.0.1 and its Interface with GeneScan and Immunoscope to Analyze Immune Repertoires—Overview The ISEApeaks 2.0.1α product can be used with all versions of the immunoscope products (Pannetier, C., M. Cochet, S. Darche, A. Casrouge, M. Zöller, and P. Kourilsky. 1993. The sizes of the CDR3 hypervariable regions of the murine T-cell receptor b chains vary as a function of the recombined germ-line segments. Proc. Natl. Acad. Sci. USA 90:4319-4323). However, using the latest one, Immunoscope 3.1α, will allow the use of all ISEApeaks utilities devised for this product (see below). Hence, fluorescent signal from any Sequencing Automate of PE Biosystems (370A, 373, 310 or 377) can be analysed after Immunoscope or GeneScan 2.2.1 analysis. Similar results can be achieved by using other automated sequencers with the appropriate software, such as MEGABACE sequencer AND GENOTESTER™ software. The Immunoscope technique (Pannetier, C., M. Cochet, S. Darche, A. Casrouge, M. Zöller, and P. Kourilsky. 1993. The sizes of the CDR3 hypervariable regions of the murine T-cell receptor b chains vary as a function of the recombined germ-line segments. Proc. Natl. Acad. Sci. USA 90:4319-4323) with or without utilizing Excel, Immunoscope and GeneScan softwares can be used with the ISEApeaks 2.0.1α product.

Figure 13:
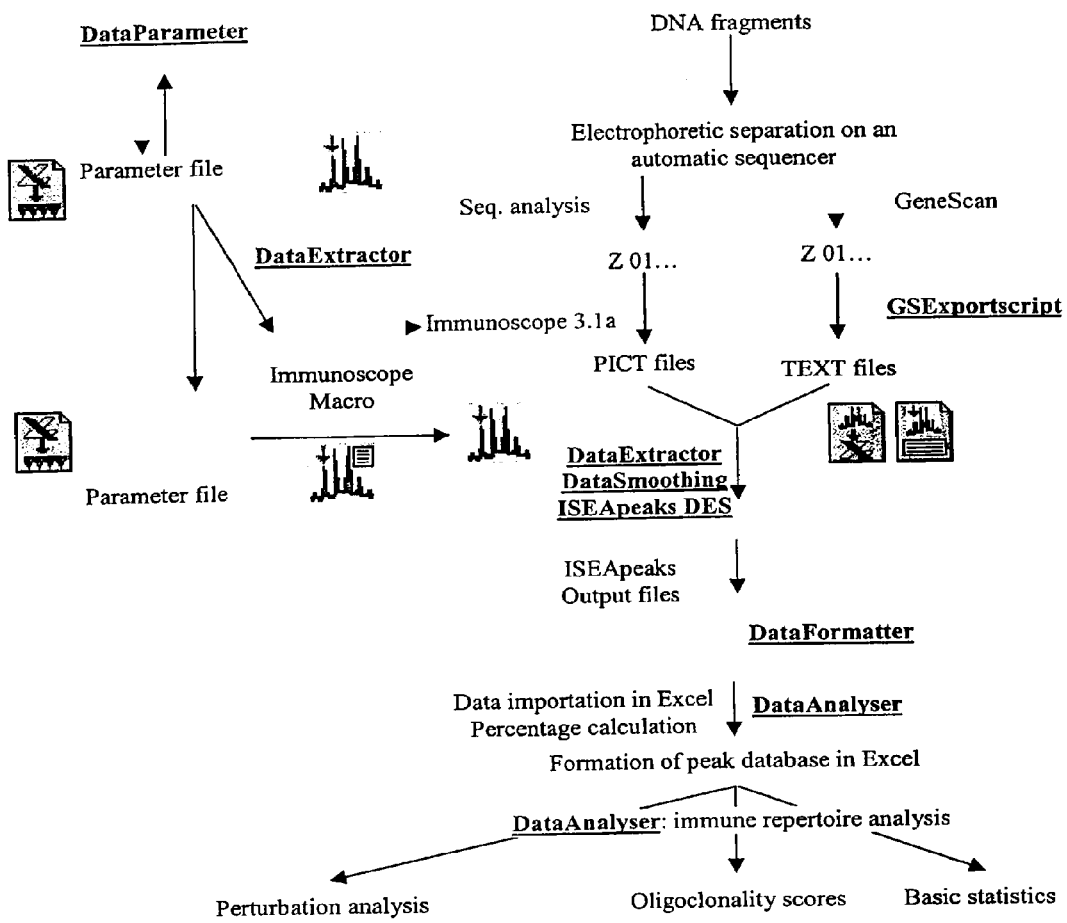
FIG. 13: Organisation scheme of the ISEApeaks package.

Preceding the use of the ISEApeaks product, the different steps of the analysis are summarized in FIG. 13. Samples are amplified using V to C or V to J primer combinations and PCR products are labelled by run-off amplifications with fluorescent primers. Labelled PCR products are loaded on an automatic sequencer to be separated according to their nucleotidic length. PE Biosystems product, Sequencing Analysis, is used to generate raw data files, one per well. Immunoscope and GeneScan use these files to analyse the fluorescent signal: they both generate files containing nucleotidic sizes and areas of identified peaks. Through Immunoscope macros, it is possible to automatically analyse the whole gel, generating as many PICT files as the number of well and the number of loads per well. These PICT files contain the profile of the analysed fluorescent signal as well as the length and area of the peaks. They can be assembled to form the image of a whole repertoire using template files. A "profile" will designate either the analysed fluorescent signal stored in a PICT file or the description of the CDR3 peaks by their nucleotidic size and peak area.

The ISEApeaks product has been developed to solve the following example of problems that may arise (Collette, A. et al. 2002. High throughput screening and analysis for CDR3 spectratypes during malaria with the ISEApeaks software package. manuscript in preparation; Collette, A., and A. Six. 2002. ISEApeaks: an Excel platform for GeneScan and Immunoscope data retrieval, management and analysis. Bioinformatics 18:329-330). First, no tool is available in Immunoscope or GeneScan to retrieve peak data. Secondly, there is a discrepancy between the number of peaks as seen by eye and the number of peaks given in the Immunoscope PICT or GeneScan files. Thirdly, there is no product to address the problem of data analysis while the amount of data generated is increasing with the use of high throughput sequencers. ISEApeaks gives answers to these problems. FIG. 13 shows the overall architecture of the ISEApeaks product. Data generated by Immunoscope or GeneScan can be extracted using DataExtractor. DataSmoother is suited for immune repertoire application. DataExtractor and DataSmoother are parameterised with files created with DataParameter. Data obtained can then be imported into Excel files using DataFormatter Excel templates and the ISEApeaks Excel Add-in. After using DataAnalyser and the add-in, the data peaks of a whole experiment with different organs, individuals and groups, can be gathered. Several tests are implemented to perform repertoire perturbation analyses.

ISEApeaks package helps the experimenter to extract and gather peaks in an Excel database. This database is used to analyse immune repertoires. Further, specific modules have been implemented (i.e. DataSmoother and the analysis part of DataAnalyser). DataParameter enables the user to parameterize the extraction and smoothing of data using DataExtractor and DataSmoother.

DataFormatter displays the data in Excel. DataAnalyser performs both the gathering of peaks scattered in different DataFormatter files and the analysis of this peak database for immune repertoires. Useful utilities have been incorporated in the package such as automatic construction of Immunoscope macros or assembling of Immunoscope PICT files in a unique sheet. ISEApeaks softwares are displayed in underlined red.

DataFormatter is used to display the data in Excel. DataAnalyser performs both the gathering of peaks scattered in different DataFormatter files and the analysis of this peak database for immune repertoires. Useful utilities have been incorporated in the package such as automatic construction of Immunoscope macros or assembling of Immunoscope PICT files in a unique sheet. ISEApeaks softwares are displayed in underlined red.

Figure 14:
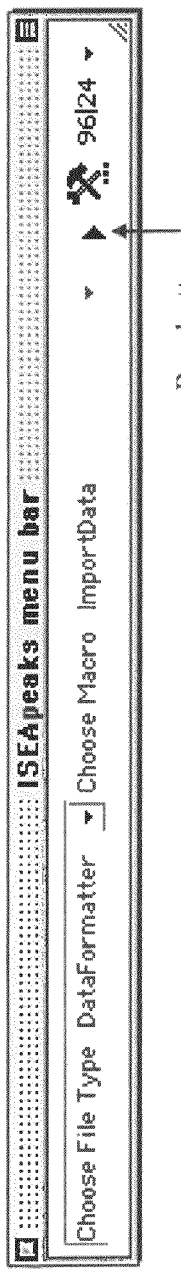
FIG. 14: ISEApeaks main menu.

ISEApeaks Excel add-in displays a menu bar from which one can launch macros after selecting the proper file type one is using. Clicking the right icon will launch the ISEApeaks Excel main menu, or use the shortcut (alt+option+m) (FIG. 14) where one can access Preferences menu (FIG. 15), create new files, get preferences or information about the Excel active file or reset the ISEApeaks menu bar.

ISEApeaks Excel add-in preferences are displayed in

Figure 15:
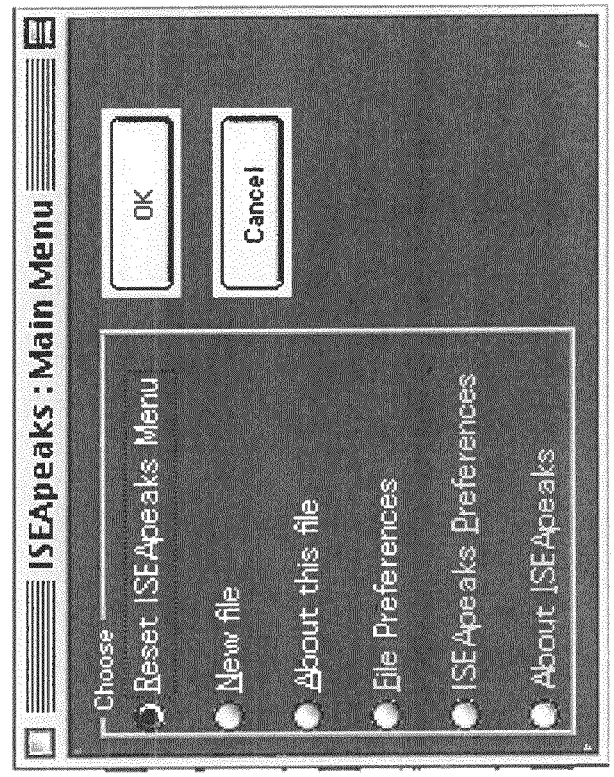
FIG. 15: ISEApeaks Preferences menu.
Figure 16:
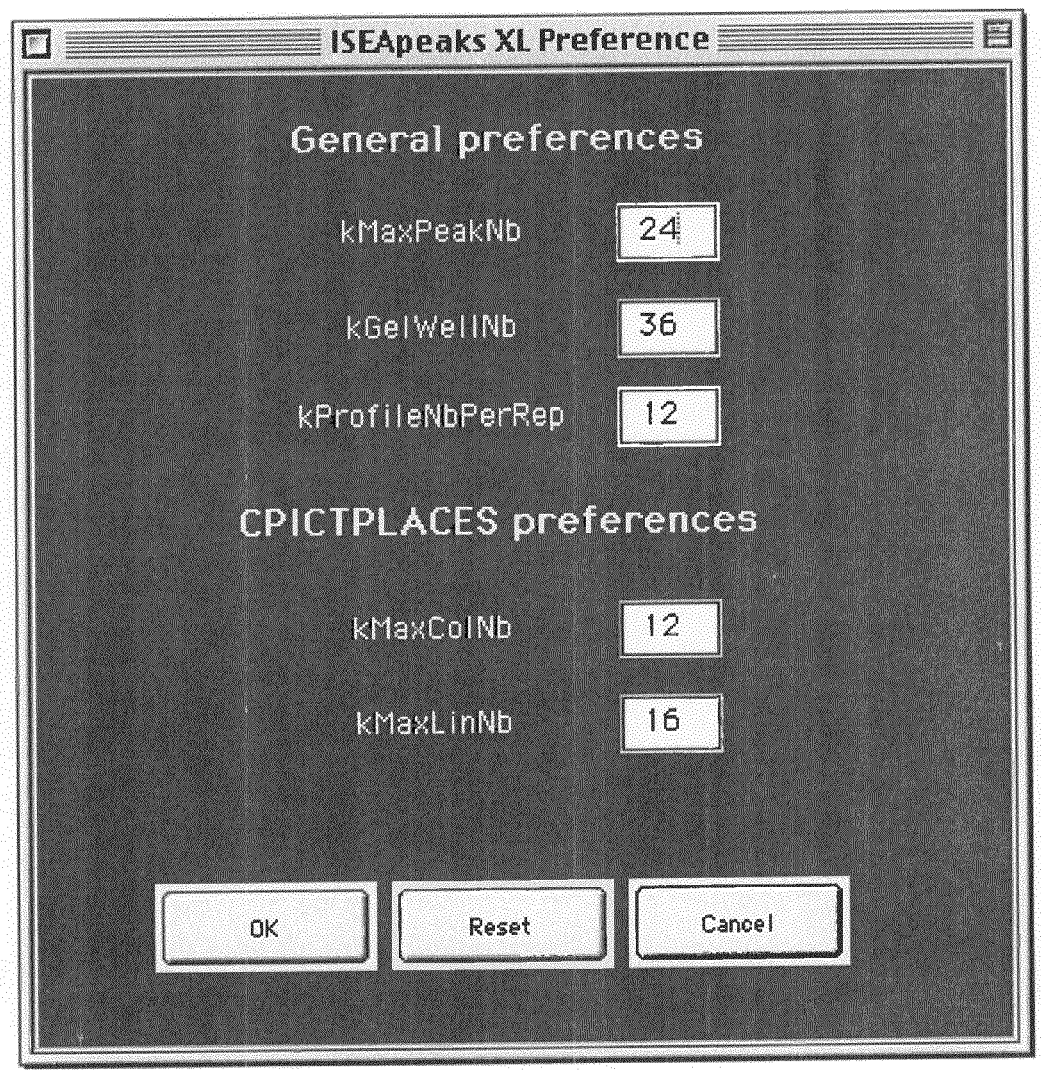
FIG. 16: ISEApeaks menu bar.

FIG. 15. When screen updating is off, some long ISEApeaks macros will not update the screen so that computations are more rapid. Excel status bar (bottom of the screen) will indicate to user the status of the execution. kMaxPeakNb is the maximum number of peaks per profile that will be displayed (see DataFormatter section). kGelWellNb is the number of well of the sequencing gel one uses. For a 36-well automatic sequencer this preference value should be set to 36. kProfileNbPerRep is the number of profiles in a repertoire. This value is used to separate data in a gel. For instance, a common human Vβ-Cβ repertoire analyses 24 different combinations; hence this preference value should be set to 24; 36-well gel data will be displayed in 3 sheets, one per repertoire (double loading is assumed). Note that kGelWellNb and kProfileNbPerRep parameters can be modified from the ISEApeaks menu bar (see FIG. 16) using the last button command: the first figure is the kGelWellNb and the second kProfileNbPerRep. kMaxColNb and kMaxLinNb is used by ISEApeaks in the assembling of Immunoscope profiles (see below) to determine how many files are to be assembled.

The ISEApeaks preferences menu enables the user to modify preference values used by the ISEApeaks XL add-in.

DataExtractor and DataSmoother are standard Macintosh applications. A menu indicates the different functionalities available. Dialog boxes prompt the user to chose parameter files or folders where data to be extracted are stored.

Different files are used by the ISEApeaks package. To help the user distinguish between files, they have been assigned different file types which are described below.

'APPL' files are ISEApeaks application file.

'CGEL' file are parameter files used by DataExtractor and DataSmoother to extract and smooth Immunoscope or GeneScan data of a whole gel. A CGEL file is also needed to create an Immunoscope 3.1α macro using the Utilities menu of DataExtractor. CGEL files are created with DataParameter.

'CPIC' file (CPICTPLACES files) are parameter files to use with DataExtractor to prepare the assembling of Immunoscope PICT files using Immunoscope. When having loaded different gels to analyse different samples one might want to gather a particular profile for all the analysed samples. To assist one with this tedious work, DataExtractor will automatically copy and rename the files corresponding to this particular profile as indicated by a CPICTPLACES parameter file. CPICTPLACES files are created with DataParameter. After DataExtractor has copied the desired PICT files, one can use the Immunoscope software to assemble the profile saved in the PICT files in the template provided by the ISEApeaks package. This template contains an array of empty profiles of 16 lines by 12 columns.

'DATA' file are output files of DataExtractor and DataSmoother containing peak data. These files will be used by DataFormatter to import the peaks in Excel.

'COUP' file are output log files of DataExtractor and DataSmoother that can be saved.

'TEXT' file are usual TEXT files that contain the Immunoscope 3.1α macros created with DataExtractor.

'PREF' files are ISEApeaks preferences files.

Example 3.2

DataParameter a) CGEL Parameter Files

Figure 17:
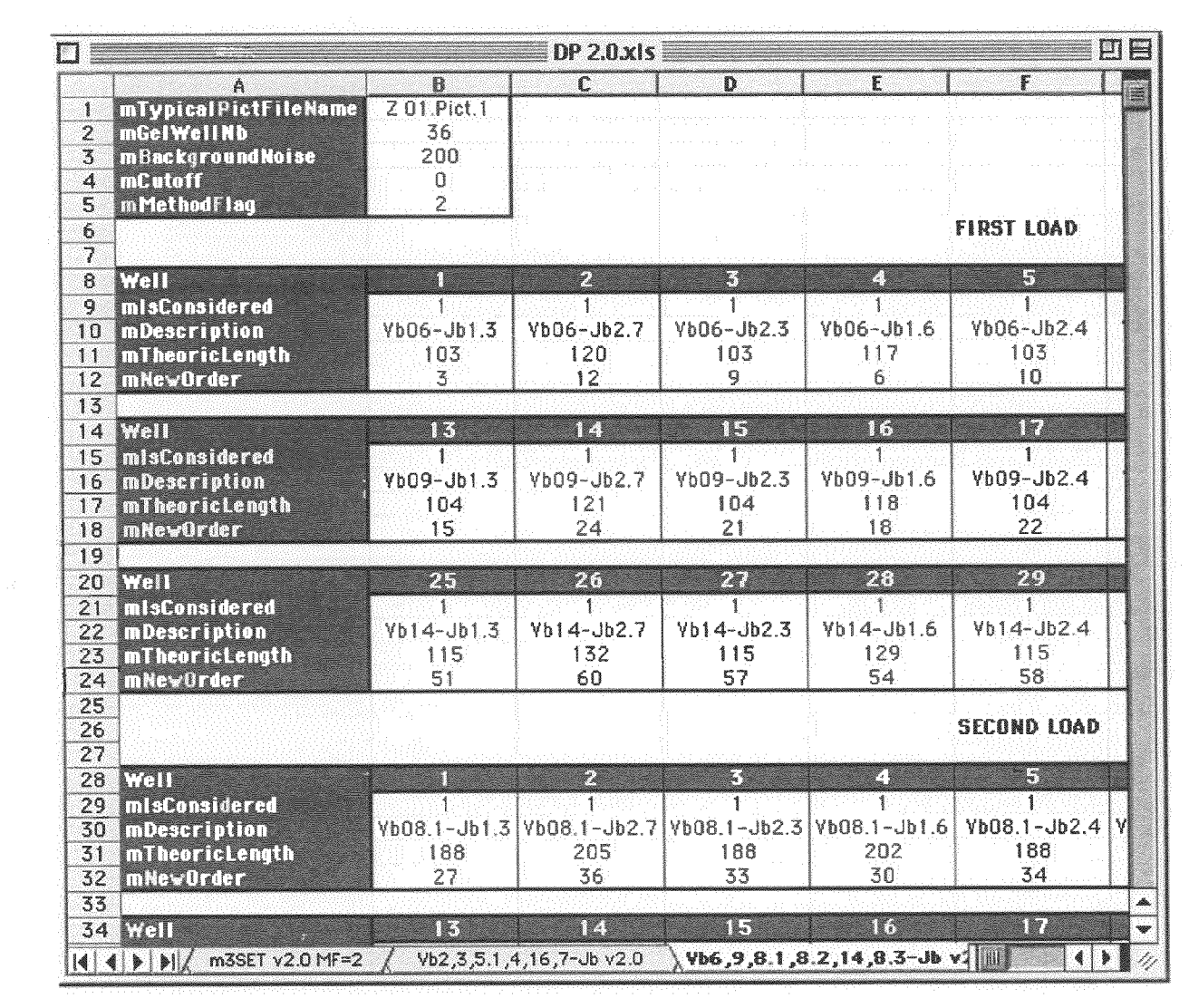

DataParameter will help one to create the CGEL parameter file needed for DataExtractor and DataSmoother. In this file, one will give information concerning the nature of what one wants to extract and analyse and how one wants to get it done (FIG. 17). In this example, the selected Excel worksheet shows a part of CGEL parameter file data.

Open a DataParameter file using Excel® 98.

FIG. 17 shows an example of a DataParameter file. For each well of the sequencing gel, one can specify at least one of the following different parameters.

The 'mIsConsidered' parameter: setting the parameter to 0 means one does not want to analyse this well, for instance because no sample has been loaded in the well. Setting it to 1 indicates that this well will be extracted and smoothed.

The 'mDescription' parameter: in this box, one can put a string of characters that depicts the nature of the sample one loaded in this well. This string must not contain the ';' character.

The 'mLength' parameter: put in this box the size of one's expected fragment. For instance in a repertoire analysis, put the value expected for a PCR fragment with a 10 aminoacids CDR3.

The 'mNewOrder' parameter: this parameter sets the new order of appearance of the different wells. This function enables automatic sorting of the different wells. This new order will be used for extraction and in the 3e) paragraph.

Double loading is a widespread way to extend the loading capacity of a sequencing gel. That's why double loading is possible in DataParameter. If one doesn't double load, just set to 0 the mIsConsidered parameter of all the wells of the second load. The other parameters in the left corner of the worksheet are the general parameters for the analysis of the run. They are as follows.

The 'mTypicalPictFileName' parameter is the name of one of the data files. Note that the 'mTypicalPictFileName' parameter must contain no other figures than the two figures automatically attributed by the Immunoscope software or created by ISEApeaks from GeneScan data. This restriction makes impossible the use of name such as 'Z 24/2/98 24.1: use instead 'Z 24.1'. This string must not contain the ';' character.

The 'mGelWellNb' parameter: the well number of the sequencing gel one loaded. This value can be for instance 36, 48 or 96.

The 'mBackgroundNoise' value is the threshold under which signal is considered to be background and will be ignored.

The 'mCutoff' value is used by DataSmoother: it is the percentage of the maximal area under which one wants to ignore the signal.

The 'mMethodFlag' value will be discussed in the DataSmoother paragraph. Set this value to 2 to use a correction based on the value of mTheoricLength. Set this value to 3 to use a correction based on the length of the peak of maximal area of the profile.

In the ISEApeaks menu bar, one can access the different macros of DataParameter. The 'ImportCGelFile' macro can be used to import a parameter file in the Excel file where parameters can be easily modified. A dialog box will prompt the user to choose a file. The 'CreateCGelFile' macro can be used to create a parameter file. Note that if one is doing the same experiments (loading each time one's gels in the same manner), one will need only once to create a CGEL parameter file. The 'CGELPageSetUp' macro will create an empty sheet containing a page set up that can be used to enter new values for a CGEL file. To find about the use of the CGEL parameter files, please see the DataExtractor or DataSmoother sections.

Finally, executing the ImportCGelFile or CreateCGelFile macro will update automatically the Excel preferences with the values used in the file imported or created. When using the CreateCGelFile macro, it might happen that Excel seems to be frozen. To solve this problem, see the Pitfalls section below.

b) CPICTPLACES Parameter Files

The ISEApeaks package provides a useful utility to solve the tedious problem of Immunoscope PICT files assembling. Let's take an example: say one has analysed the Vβ-Cβ repertoire (24 profiles per sample) of 6 mice and the Vβ8.1-Jβ repertoires (12 profiles per sample) of 6 mice. One surely wants to compare the Vβ8.1-Cβ and the 12 Vβ8.1-Jβ profiles of these 6 mice, but all these profiles are stored in 13*6=78 different files scattered in different folders. To put these 78 profiles on a unique image, one will have to open each of these files and copy their profile to a unique document. The ISEApeaks package provides an easy solution. With CPICTPLACES parameter files, one can specify the PICT files one wants to assemble. These files are copied by DataExtractor utility. Finally, the copied files are assembled by Immunoscope software using a template provided in the ISEApeaks package or one that one customised.

Figure 18:
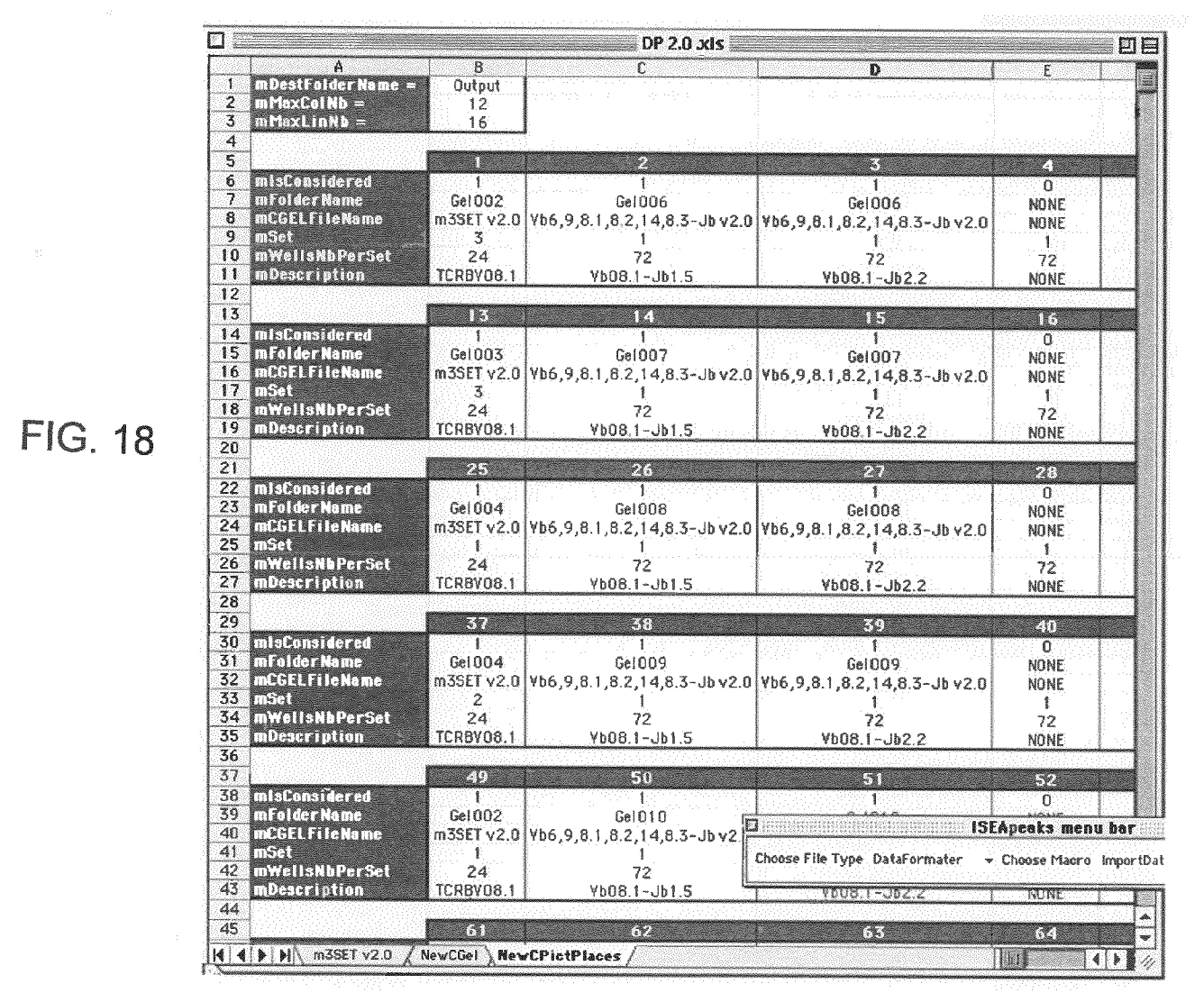

DataParameter helps one to create the CPICTPLACES parameter files needed for preparing the assembling of PICT files scattered in different folders. In this file, one will provide information concerning the PICT files one wants to gather on a same paper sheet to compare them. The DataExtractor section will describe the use of CPICTPLACES parameter files to prepare the assembling of PICT files. FIG. 18 shows an example of a DataParameter file. On the top left part of the sheet, the general parameters needed for all of the assembling procedure are displayed. There parameters are explained below.

The 'mDestFolderName' parameter specifies the name of the folder where duplicated PICT files will be stored.

The 'mMaxColNb' parameter specifies the number of rows used in one's repertoire template file.

The 'mMaxLinNb' parameter specifies the number of lines used in one's repertoire template file.

In this example, one can see a portion of a CPICTPLACES worksheet. For each file, different parameters are listed that will enable DataExtractor utility to process through the different gel folders and select the PICT files indicated in the CPICTPLACES parameter file. This example corresponds to the case envisaged in the text (assembly of Vβ8.1-Cβ and Vβ8.1-Jβ for 6 mice, see also the example folder).

For each file, one can specify different parameters. These parameters are described below.

The 'mIsConsidered' parameter: setting the parameter to 0 means one does not want to use this profile position. Setting it to 1 implies that this profile position will be considered.

The 'mFolderName' parameter is the name of the folder where the PICT file one wants to put in the corresponding profile is located. This string must not contain the ';' character.

The 'mCGELFileName' parameter is the name of the CGEL parameter file of the corresponding mFolderName. This CGEL file describes how the gel whose data are stored in this folder was loaded and must be in the same folder as the PICT files. Note that this requires that the CGEL parameter is systematically left in the folder. This string must not contain the ';' character.

The 'mSet' parameter is the repertoire set number (each set has as defined mWellsNbPerSet wells). For instance, three mice Vβ-Cβ repertoires can be loaded on a same gel, while one can load the Vβ-Jβ repertoires of 6 different VP on a gel. In the first example, mSet should be set to 3 if one wants to take profiles of the third repertoire while in the second one mSet should be set to 1 as there is only one occurrence of a particular Vβ-JP combination since the 6 Vβ are different. This parameter should never be set to 0.

The 'mWellsNbPerSet' parameter is the number of profiles per repertoire. For a double-loaded 36-well gel used to analyse 3 Vβ-Cβ repertoires, this parameter should be set to 24. For a double-loaded 36-well gel used to analyse the Vβ-Jβ repertoires of 6 different Vβ, this parameter should be set to 72 as all profile description will be different. This parameter should never be set to 0.

The 'mDescription' parameter is the description of the nature of the analysed profile one wants DataExtractor to pick among all the Pict files of this gel. This string must not contain the ';' character.

Note that these parameters should be set in accordance with the parameters given in the corresponding CGEL parameter files, especially for the mDescription and that each set should contain only one occurrence of each mDescription! Using the ISEApeaks menu bar one can access to the 2 macros proposed to deal with CPICTPLACES parameter files. The 'ImportCPictPlacesFile' macro allows one to import a CPICTPLACES parameter file. A dialog box will prompt the user to choose the file. The 'CreateCPictPlacesFile' macro will use the data of the active Excel sheet to create a new CPICTPLACES parameter file. The CPICTPLACESPageSetUp macro enables the user to build an empty formatted sheet to be filled with new parameters. Finally, importation or creation of CPICPLACES files will update the Excel Preferences of the add-in with the values used in the file.

The use of CPICTPLACES parameter files is described in detail in the DataExtractor section. The provided template allows the assembly of up to 192 profiles organised in 16 lines by 12 rows.

Example 3.3

DataExtractor

DataExtractor extracts the data from Immunoscope, GeneScan, and Genotester files using the information provided by a CGEL parameter file (FIG. 13). GeneScan data must first be exported by the use of the GSExportscript of the ISEApeaks package. After detailing the extraction process for both Immunoscope and GeneScan data, 3 Immunoscope-related utilities are described: renaming of the PICT files, creation of Immunoscope 3.1α macros using CGEL parameter file and assembling of PICT files in a repertoire template to gather profiles analysed on different gels.

a) GeneScan Export Script

Gel data are stored in GeneScan files, one per well. The first task to perform is to export data peaks to text files readable by ISEApeaks. To assist one, ISEApeaks provides an applescript to automate the exportation process. Use DataParameter to generate the list of GS Filename: names should be entered just below the mNewOrder parameter (see FIG. 18). Launch the GSCreateFileList macro using the ISEApeaks Excel menu bar. The provided apple script will use this file.

Then open GeneScan to set the current folder of GeneScan to the folder where one's GeneScan files are stored: a common way to do this is to open one of the sample files and cancel the action when in the proper folder. Launch the apple script GSExportscript, choose the data-containing folder, select the file names list and, finally, indicate the first number to use in exported files. The script will open each GeneScan files and export the data. The subsequent step of data extraction is described in the next section.

b) Data Extraction

DataExtractor reads the data files and extracts the length and area of the peaks either of Immunoscope PICT files or exported GeneScan data files or Genotester exported data (see previous section). Launch the DataExtractor program by double clicking on the file icon (for Immunoscope data only). Choose the appropriate function in the menu. DataExtractor can extract data for all well formats and ensures the reordering of the samples (indicated in the CGEL parameter file).

To Launch the extraction of Immunoscope data, select the 'For Immunoscope Data' item in the 'Extraction' menu (shortcut—I). To Launch the extraction of GeneScan data files exported with ISEApeaks (see GeneScan export script section), select the 'For GeneScan Data' item in the 'Extraction' menu (shortcut—G). To Launch the extraction of MegaBACE data file, i.e. Genotester datafile, exported in tab-delimited TEXT with Excel, select the 'For MegaBACE Data' item in the 'Extraction' menu (shortcut—M). The user is then asked by a dialog box to select a 'CGEL' parameter file. This file must be in the same folder as the data files: it is very convenient to leave the parameter file used to extract the data in the gel folder, in case one wants to look back to what has been done or use PICT file assembling utility. During the execution, the status of the program is shown in a window. This output file can be saved as a text file and lists extracted files. Extracted files are listed as well as adjacent and ambiguous peaks, which could not be resolved by smoothing filters. The program generates a 'data.0' file. This file contains all the data stored in data files, without any computing which can also be imported in DataFormatter (see below page 75). At the moment, DataExtractor only keeps peaks whose lengths are +/−20 nt of the mTheoriclength value.

c) Immunoscope Utilities: Renaming ".Pict" Files.

Some useful utilities for Immunoscope© have been incorporated in the DataExtractor program: one can access them through the 'Utilities' menu. Use the 'rename .Pict files' utility to modify the names of one's Immunoscope PICT of exported GeneScan files: one will be asked to select the old first well file, to indicate the desired new name and the gel well number. This can be useful when the files one has generated are named 'Z XX.Pict.3' by Immunoscope: one surely wants them to be renamed 'Z XX.Pict.1' to be able to assemble them in one's own template repertoire!

d) Immunoscope Utilities: Creating Immunoscope 3.1α Macros.

The second utility enables one to create Immunoscope© 3.1α macro using the parameter file created with DataParameter. This utility is not compatible with older versions of Immunoscope. One will be asked to select a CGEL parameter file, to indicate the range, a template Immunoscope macro that will be used to create the new macro and, finally, the location and name of the new macro to create. The Immunoscope template macro can be the one provided with the package (named 'Macrotemplate' for 36-well gels) or any Immunoscope 3.1α macro.

This useful utility will spare one the tedious work of modifying the macros by selecting each of the 72 (for a double-loaded 36-well gel) macro instructions to change the length between which Immunoscope should analyse the fluorescent signal. These operations are often a source of errors.

e) Immunoscope Utilities: Preparing the Assembling of .Pict File Profiles

The DataParameter section has dealt with the creation and importation of CPICTPLACES parameter files as well as its usefulness for Immunoscope data. Choose the 'Preparing .Pict file assembling' in the 'Utilities' menu. A dialog box will first ask for a CPICTPLACES parameter file, and then to select a folder containing all the data, that is the common root folder for all the data-containing folders. Finally, indicate a default PICT file to use. This default file will be used when mIsConsidered is set to 0 (see page 69): Immunoscope needs to find a PICT file for each profile of the template repertoire. The process status of the operation is shown: DataExtractor reads the parameter file, locates the proper files and renames them to the output folder. The output folder is created in the selected folder. Note that, when renaming, existing files are overwritten.

Now, form the image with created file set using Immunoscope and the '16×12 RepIS template' template file provided with the ISEApeaks package. Open Immunoscope, open the template file using the 'Open repertoire' option and choose the 'Construct Rep.' option. Select one of the files created by DataExtractor in the output folder. Immunoscope then puts each profile in the proper location.

Example 3.4

DataSmoother

DataSmoother does the smoothing of the peaks: suppression of background noise and of double peaks and other problem solving.

Open DataSmoother. Choose the 'To import and analyse the data' option, select the CGEL parameter file and a 'data.0' file created by DataExtractor. A window will describe the operations performed. Let's describe what one sees. DataSmoother first imports the data: for each profile 'mDescription' and 'mTheoricLength' parameters as well as the number of peaks imported are listed. Then the analysis starts: background is removed using the value one specified in the CGEL parameter file. Peaks which areas are less that mCutoff percent of the maximal area of the profile are deleted. After this step, the file 'data.1' is saved containing all gel peaks.

The two other filters have been specifically designed for immune repertoire data whose peaks should be spaced by 3 nt at the periphery, as required for in-frame rearrangements. Two different algorithms are possible for "adjacent" peaks correction. One of the adjacent peaks is summed to the other one according to the method chosen with the mMethodFlag. If the parameter mMethodFlag is set to 2, the reference will be the theoretical length calculated using mTheoricLength. When set to 3, the reference will be the length of the maximal area peak. After this step, the file 'data.2' is generated.

Then, DataSmoother tries to solve another problem: two consecutive peaks can sometimes be attributed to the same theoretical length. Let's call them "ambiguous" peaks. This problem arises because of a too imprecise length analysis by GeneScan or Immunoscope. This problem is crucial as one of the two peaks will be erased when trying to gather all the peaks of different samples using DataAnalyser. For each profile, different parameters are listed. Just track the profile for which one of this problem is found, one can see that DataSmoother tries to resolve it. After this try, DataSmoother searches again for ambiguous peaks: if some are still detected, the user will be prompted to solve the problem in DataFormatter. Finally, the file 'data.3' is generated. Don't forget to save the log of the DataSmoother program.

Example 3.5

ISEApeaks DES

ISEApeaks DES gathers DataExtractor and DataSmoother functions: one just runs one application instead of two and the 'data.0' file is automatically used to do the smoothing.

Example 3.6

DataFormatter

Figure 19:
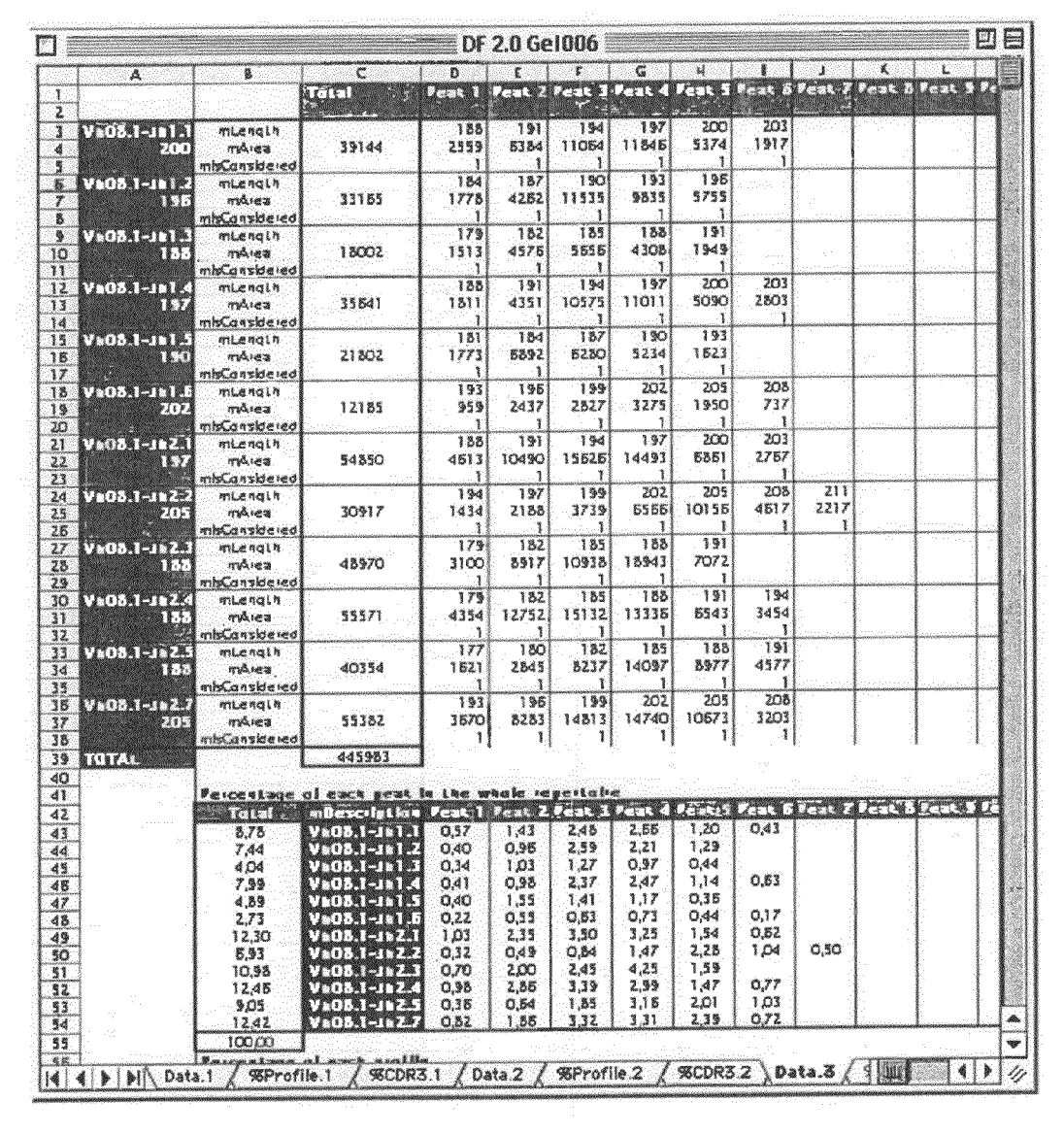

DataFormatter is used to display in Excel the data extracted and smoothed by DataExtractor and DataSmoother. In Excel, corrections can be easily done if needed. It is also a good start to perform custom analysis. Data of a sequencing gel is stored in a unique DataFormatter file. Data will be displayed according to the preferences values: data will be separated in kGelWellNb/kProfileNbPerRep different sheets (See CGEL parameter files section). If the DataFormatter file used does not contain enough data sheets (FIG. 19), ISEApeaks will create missing sheets. For instance, human and mice Vβ-Cβ repertoires are usually composed of 24 profiles (Pannetier, C., M. Cochet, S. Darche, A. Casrouge, M. Zöller, and P. Kourilsky. 1993. The sizes of the CDR3 hypervariable regions of the murine T-cell receptor b chains vary as a function of the recombined germ-line segments. Proc. Natl. Acad. Sci. USA 90:4319-4323., Even, J., A. Lim, I. Puisieux, L. Ferradini, P. Y. Dietrich, A. Toubert, T. Hercend, F. Triebel, C. Pannetier, and P. Kourilsky. 1995. T-cell repertoires in healthy and diseased human tissues analysed by T-cell receptor beta-chain CDR3 size determination: evidence for oligoclonal expansions in tumours and inflammatory diseases. Res. Immunol 146:65-80). So one may have up to 3 different sets of 24 profiles per gel. The way these 3 sets will be filled depends on the CGEL parameter file one gave to extract the gel data To import the data, use the 'ImportData' macro of the ISEApeaks menu bar. Select the 'data' file one wants to import. The 'Calculation' (alt+option+c) macro is automatically launched: it calculates different percentages based on the imported data. Two graphical displays represent the obtained percentages. The 'LengthCheck' (alt+option+l) macro is also launched automatically: consecutive peaks are highlighted in yellow, "ambiguous" peaks are highlighted in red, maximum peak in green and the first peak that can be attributed to the mTheoricLength in bold. Importation is dependent of the way mNewOrder orders were set in the CGEL parameter and also of the Preferences values. In particular, the number of different data sheets will be determined by the values of kGelWellNb and kProfileNbPerRep.

Maximal peaks are highlighted in green. On this examples, ISEApeaks preferences have been set to, a 36-well gel and 12 profiles per repertoire (6 data sheets for 6 mouse V□ complete Vβ-Jβ repertoires).

One can use the 'mIsConsidered' parameter to sum a given peak to the previous one (mIsConsidered=2), or to the next one (mIsConsidered=3), or to exclude it (mIsConsidered=0). Cell background can be set to blue to keep track of modifications of original data (alt+option+b) or to blank (alt+option+e). Use these features to correct the adjacent or ambiguous peaks reported in yellow or in red. After finishing these modifications, run again the 'Calculation' macro to update calculations. Rerun the 'LengthCheck' macro which will warn the user if some lengths have not been corrected. Note that Calculation/LengthCheck applies only to the active worksheet. The 'PeakPageSetUp' and 'PercentPageSetUp' macros allow one to draw the display using preferences values of the peaks array and percentage, respectively.

Calculations are the percentage of use of each fragment for each combination (for instance, V to C or V to J) in the whole sample, percentage of use of each profile (mDescription) and percentage of use of each fragment length in each profile. These percentages are displayed in histograms ("% Profile" and "% CDR3" sheets).

Example 3.7

DataAnalyser

DataAnalyser has two functions: gathering the data stored in the different DataFormatter files and analysis of this large amount of data for immune repertoires. DataAnalyser macros can be accessed using the ISEApeaks menu bar. First will be described the parameterisation of DataAnalyser and the retrieval of data scattered in different DataFormatter files to form the peak database. Finally, all implemented perturbation and oligoclonality tests as well as some useful utilities will be detailed. Of course, DataAnalyser will use the preferences values of the ISEApeaks Excel Add-in.

a) Parameterisation

Figure 20:
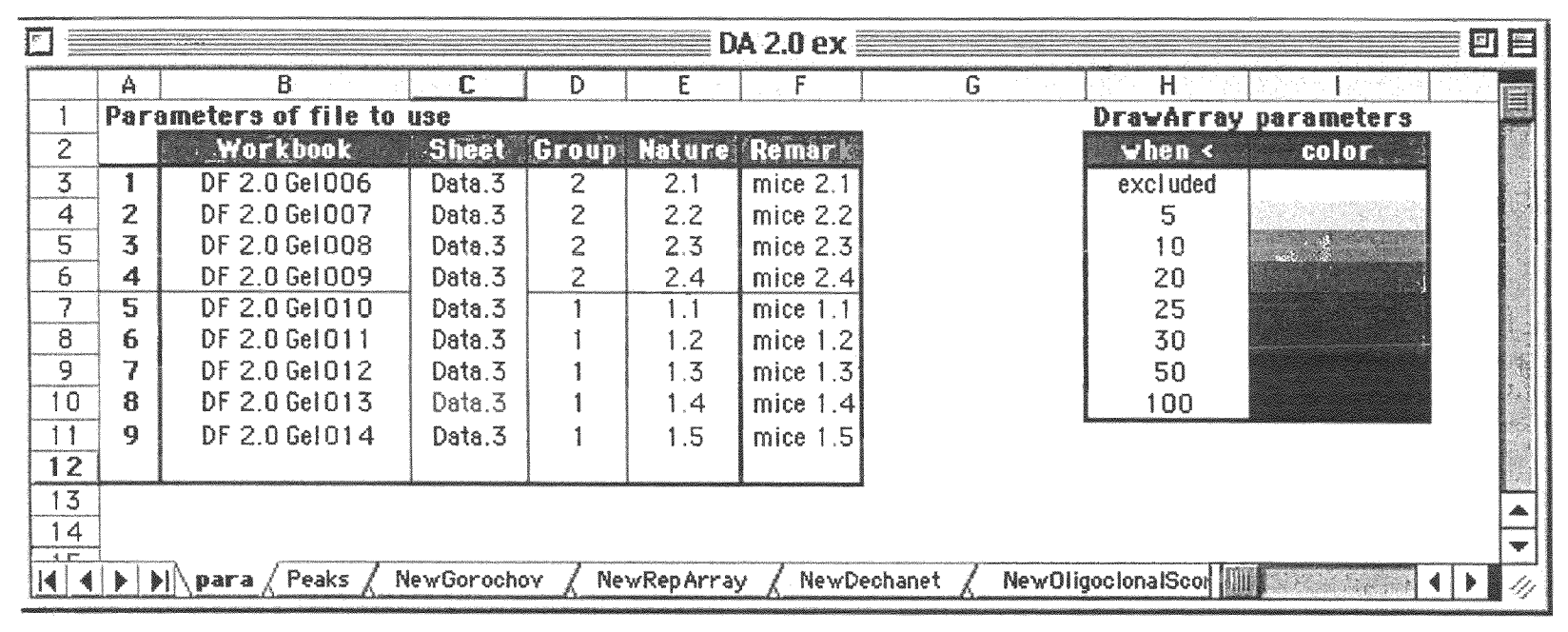

Open a DataAnalyser file. First one will need to specify the different files one wants to import. Choose the 'para' worksheet. Specify the name of the DataFormatter files where each set of data is to be found, the name of the worksheet, the group it belongs to and finally characters to depict what this sample is (FIG. 20). Note that all the DataFormatter files must be in the same folder.

Here is described an experiment where 9 mice were analysed in a Vβ-Cβ repertoire. Two groups have been created to compare the repertoire in the two analysed mice groups (cf. the 'Group' column). Note that the group numbers must be consecutive integer values starting with 1.

b) The 'TakePeaks' Macro

Figure 21:
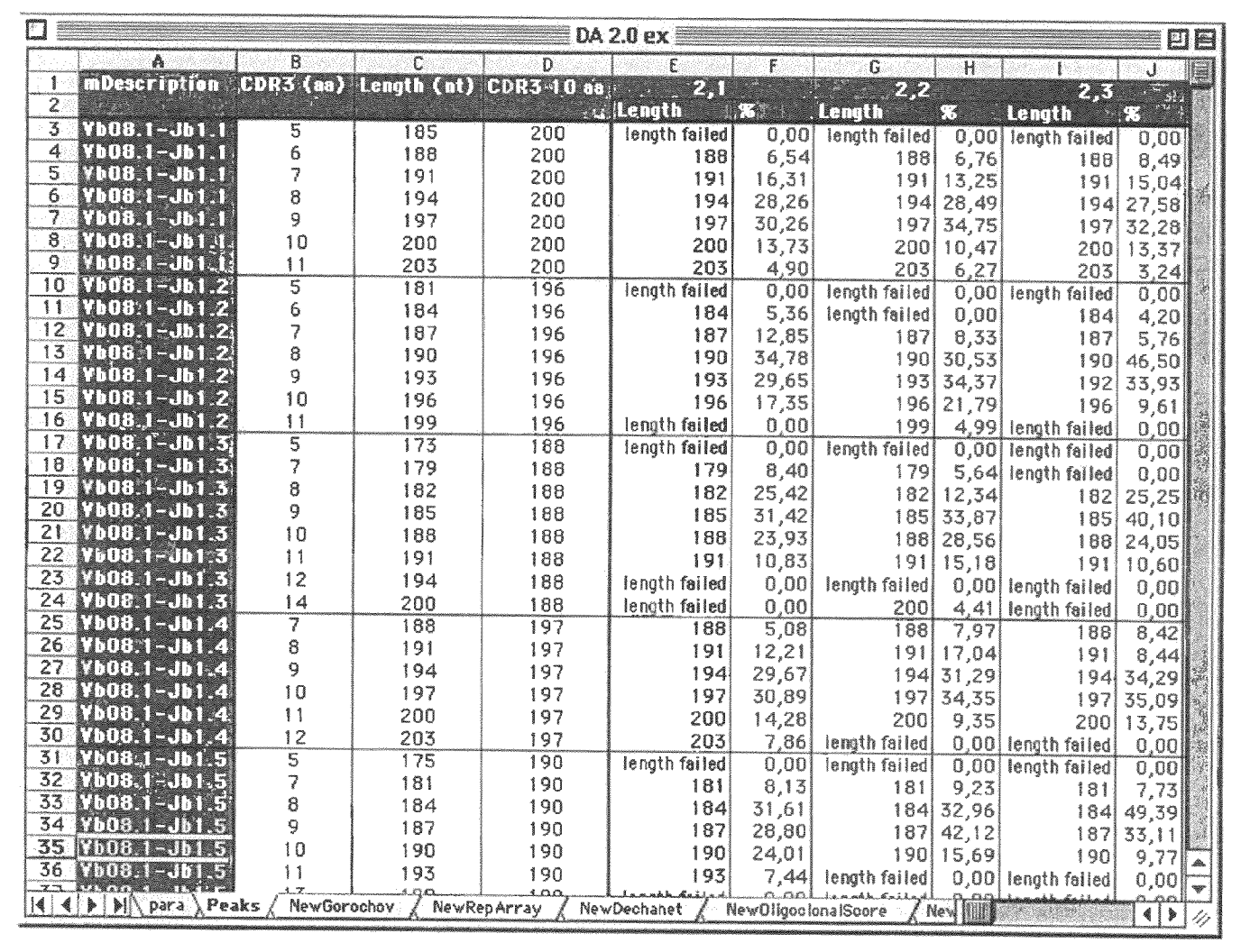

After parameterisation has been done, begin the retrieving and alignment of peaks by selecting the 'TakePeaks' item of the ISEApeaks menu bar. First choose if one wants to retrieve peaks' areas or percentage of use of peaks. Each DataFormatter file is opened and DataAnalyser gathers the data of same nature and length in the 'Peaks' sheet. For instance, in a repertoire analysis, all the percentage of use concerning the peak using TCRBV8.1 with a certain CDR3 length will be gathered (FIG. 21). Peaks are sorted in order of appearance. 'length failed' means this particular length is not present in the sample. 'excluded' means that this profile is not considered for this particular repertoire. The 'LengthCheck' procedure (see below) is automatically launched to check that the lengths are correct. Status of the execution is indicated in the Excel status bar (bottom of the screen).

The parameters shown in FIG. 20 have been used to import the corresponding data. For each peak, the mDescription, the length in amino-acids of the CDR3 region, the length of the PCR product in nucleotides and the length of the 10 amino-acids CDR3 PCR product in nucleotides are indicated. Followed for each sample by the length of the peak and the percentage of use of this peak among this profile.

c) The 'LengthCheck' Macro

The procedure 'LengthCheck' is automatically launched after 'TakePeaks' macro to check that the lengths are correct. Especially, if all the ambiguous peaks reported by DataSmoother were not corrected in DataFormatter, some peaks will be missing and the sum of the areas of the different peaks for the profile will not be 100%! Consecutive peak lengths are highlighted in yellow. These problems need to be solved before going further, usually it implies to go back to the corresponding DataFormatter file. Status of the execution is indicated in the Excel status bar (bottom of the screen).

d) The 'ImportPercent' Macro

The procedure 'ImportPercent' can be used to retrieve the percentage of use and the fluorescent signal of the profile. FIG. 22 shows an example of the gathering of the percentage of use and signal, using 'ImportPercent'. The 'ImportPercent' procedure uses the parameters entered in the 'para' sheet, as for the 'TakePeaks' macro. Status of the execution is indicated in the Excel status bar (bottom of the screen).

This example shows the retrieval of the Vβ-Jβ repertoire of 9 mice using parameters of FIG. 20. The upper array displays the percentage of use of the 12 different profiles (here Vβ-Jβ) and in the lower array the fluorescence signal.

e) The 'Perturbation1' Macro

This 'Perturbation1' macro is the first type of programmed analysis one can use to analyse perturbation of repertoires. This method implies the use of n=1 dimension distance. The method is based on an absolute value distance to compare each repertoire to an average control group (Gorochov, G., A. U. Neumann, A. Kereveur, C. Parizot, T. S. Li, C. Katlama, M. Karmochkine, G. Raguin, B. Autran, and P. Debre. 1998. Perturbation of CD4+ and CD8+ T-Cell repertoires during progression to AIDS and regulation of the CD4+ repertoire during antiviral therapy. Nat. Med 4:215-221; Han, M., L. Harrison, P. Kelm, K. Stevenson, J. Currier, and M. A. Robinson. 1999. Invariant or highly conserved TCRα are expressed on double-negative (CD3+ CD4−CD8−) and CD8+ T cells. J. Immunol. 163:301-311). This distance is computed using the percentage of use of each CDR3 length in each profile.

Figure 23:
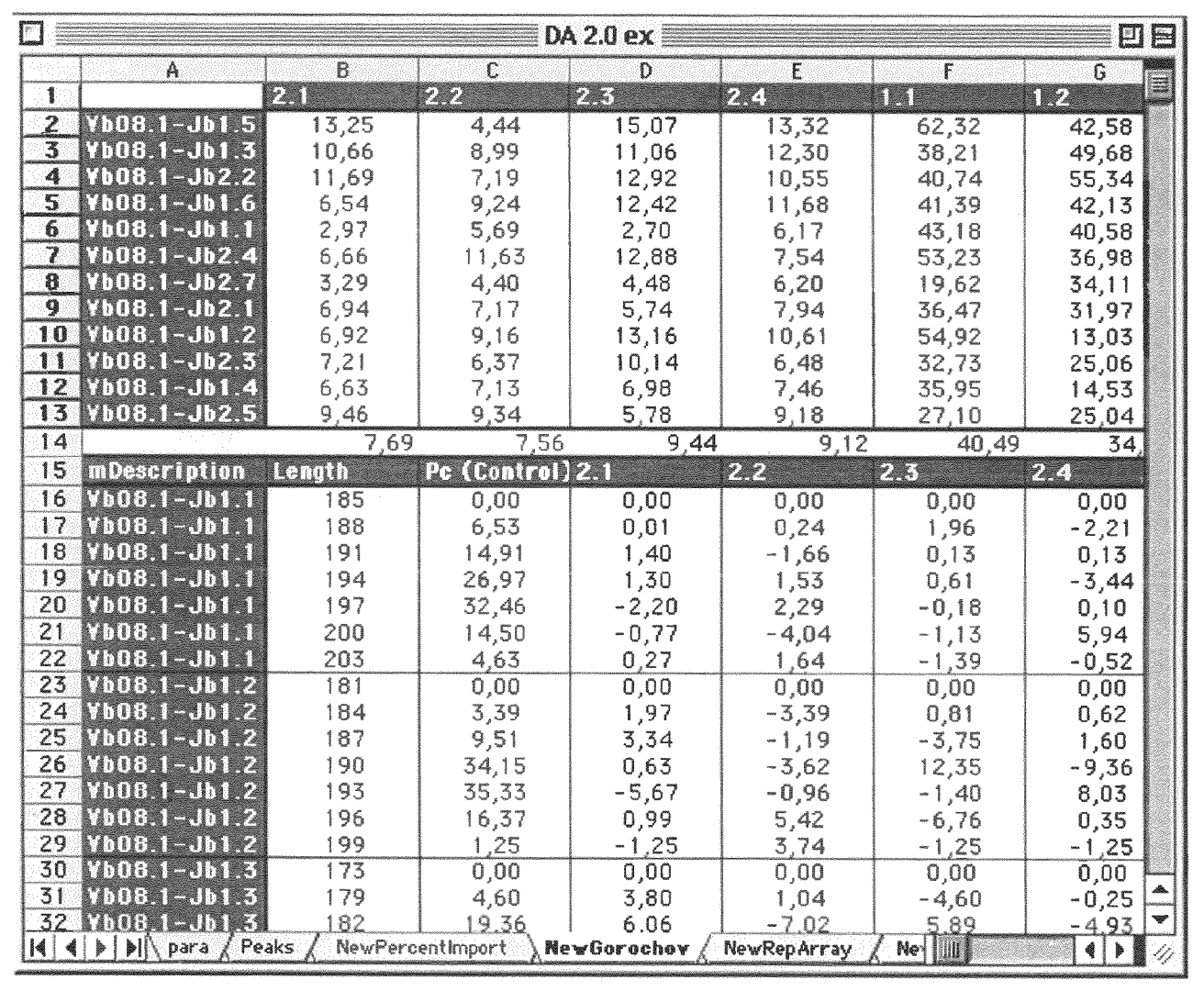

Check that one has specified for each sample's group by its group number (FIG. 20, column D). Select the 'Perturbation1' macro using the ISEApeaks menu bar. The user is asked to give the number of the control group. The control average repertoire is computed and checked: the sum of the usage of the peaks of each profile should be 100%. Then DataAnalyser calculates the distance between each repertoire and this average repertoire for each peak (FIG. 23). Finally, the distance between a repertoire and the control average repertoire is calculated for each profile. ISEApeaks calculates the mean perturbation of a profile by averaging the perturbation of each profile. Status of the execution is indicated in the Excel status bar (bottom of the screen). Using the facilities of Excel® one can now plot and sort results. One can use the 'FillExcluded' macro to replace all occurrence of "nb_CTR=0" or "excluded" by the mean perturbation of the same profile for its group. This can be useful for subsequent statistical analyses such as MANOVA (Collette, A., S. Bagot, P.-A. Cazenave, A. Six, and S. Pied. 2002. A profound alteration of blood TCRB repertoire allows prediction of cerebral malaria. submitted).

The upper array shows perturbation of each profile of each sample, lower array the perturbation of each peak compared to the average control repertoire ('Pc(Control)', column C].

f) The 'Perturbation2' Macro

The 'Perturbation2' macro is another proposed method to assess the perturbation of repertoires that was described by C. Pannetier (Déchanet, J., P. Merville, A. Lim, C. Retiere, V. Pitard, X. Lafarge, S. Michelson, C. Meric, M. M. Hallet, P. Kourilsky, L. Potaux, M. Bonneville, and J. F. Moreau. 1999. Implication of gd T cells in the human immune response to cytomegalovirus. J. Clin. Invest. 103:1437-1449). This method also computes the distance between a repertoire and a computed average control repertoire but is different from the precedent one: the n-dimension distance used is the standard quadratic distance (n=2). Secondly, the data used is quantitative: CDR3 length analysis is performed but the percentage of use of each profile is also estimated (for instance Vα, to follow the example). This method can be extended to other quantitative data: the percentage of use of each profile can be estimated by FACS analysis (Déchanet, J., P. Merville, A. Lim, C. Retiere, V. Pitard, X. Lafarge, S. Michelson, C. Meric, M. M. Hallet, P. Kourilsky, L. Potaux, M. Bonneville, and J. F. Moreau. 1999. Implication of gd T cells in the human immune response to cytomegalovirus. J. Clin. Invest. 103: 1437-1449), by semi-quantitative CDR3 length analysis (Even, J., A. Lim, I. Puisieux, L. Ferradini, P. Y. Dietrich, A. Toubert, T. Hercend, F. Triebel, C. Pannetier, and P. Kourilsky. 1995. T-cell repertoires in healthy and diseased human tissues analysed by T-cell receptor beta-chain CDR3 size determination: evidence for oligoclonal expansions in tumours and inflammatory diseases. Res. Immunol 146:65-80; David-Ameline, J., A. Lim, F. Davodeau, M. A. Peyrat, J. M. Berthelot, G. Semana, C. Pannetier, J. Gaschet, H. Vie, J. Even, and M. Bonneville. 1996. Selection of T cells reactive against autologous B lymphoblastoid cells during chronic rheumatoid arthritis. J. Immunol. 157:4697-4706; Caignard, A., P. Y. Dietrich, V. Morand, A. Lim, C. Pannetier, A. M. Leridant, T. Hercend, J. Even, P. Kourilsky, and F. Triebel. 1994. Evidence for T-cell clonal expansion in a patient with squamous cell carcinoma of the head and neck. Cancer Res. 54:1292-1297) or with Taqman (Lang, R., K. Pfeffer, H. Wagner, and K. Heeg. 1997. A rapid method for semiquantitative analysis of the human Vb-repertoire using TaqManR PCR. J. Immunol. Methods 203:181-192). For semi-quantitative CDR3 length analysis, DataFormatter will automatically calculate the percentage of use. For FACS analysis, the percentage should be put in the DataFormatter file, replacing the percentage calculated by DataFormatter.

Figure 24:
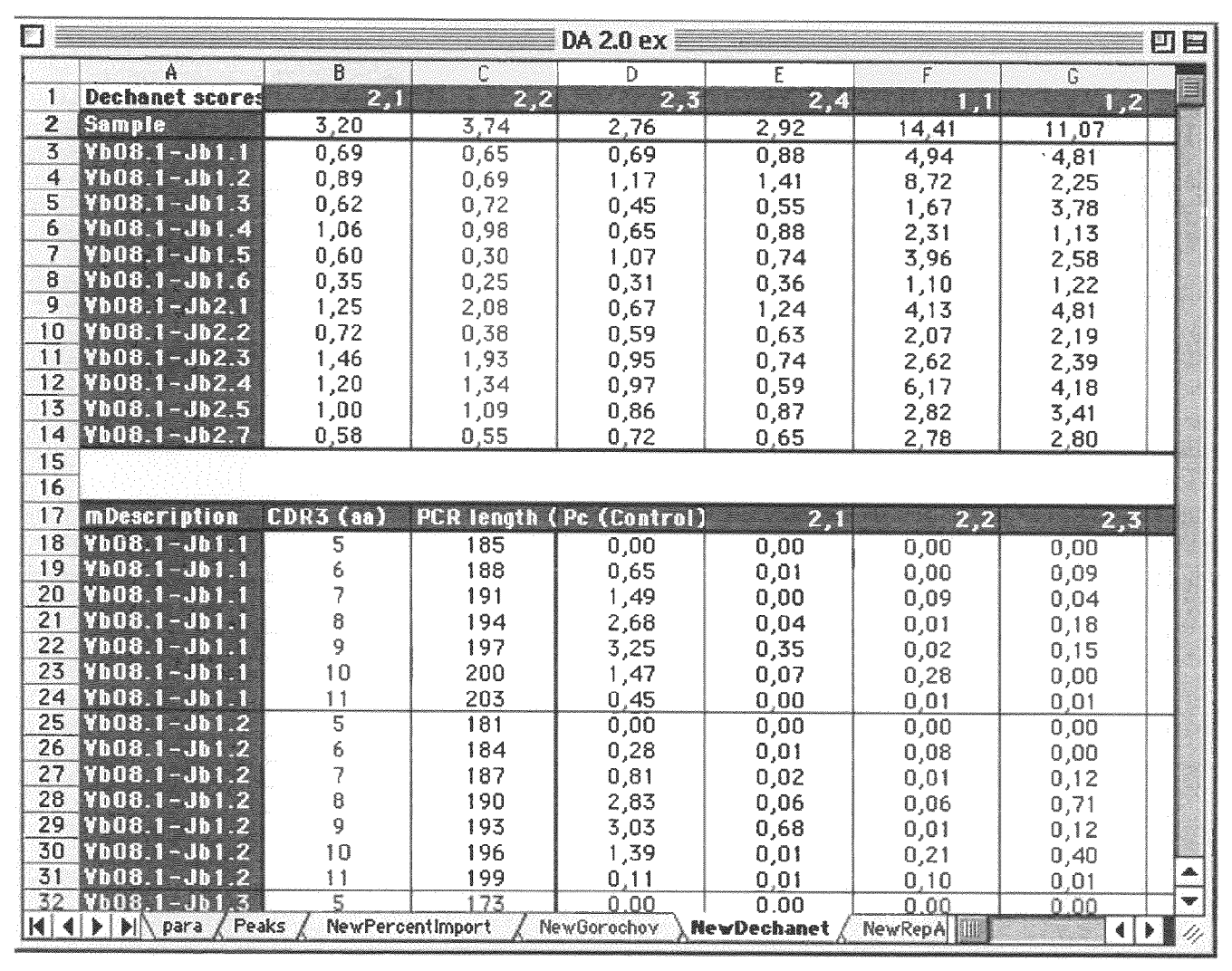

The group numbers must be filled in the 'para' sheet file (FIG. 20). Select the 'Perturbation2' macro using the ISEApeaks menu bar. The user is asked to give the number of the control group. Each DataFormatter file will be opened to retrieve the percentage of use of each profile. The control average repertoire is computed and checked: the sum of the usage of the peaks of each profile should be 100%. Then, DataAnalyser calculates the distance between a repertoire and this mean repertoire for each peak (FIG. 24). Finally, the distance between a repertoire and the control average repertoire is calculated for each profile. Status of the execution is indicated in the Excel status bar (bottom of the screen).

The upper array shows perturbation of each profile and of the sample (row 2), the lower array shows the perturbation of each peak.

g) The 'RIS' Macro

Another calculation has been used to described oligoclonality: the Relative Index of Stimulation (Cochet, M., C. Pannetier, A. Régnault, S. Darche, C. Leclerc, and P. Kourilsky. 1992. Molecular detection and in vivo analysis of the specific T cell response to a protein antigen. Eur. J. Immunol 22:2639-2647; Cibotti, R., J. P. Cabaniols, C. Pannetier, C. Delarbre, I. Vergnon, J. M. Kanellopoulos, and P. Kourilsky. 1994. Public and private V beta T cell receptor repertoires against hen egg white lysozyme (HEL) in nontransgenic versus HEL transgenic mice. J. Exp. Med. 180:861-872). This analysis has been implemented in the ISEApeaks package.

Figure 25:
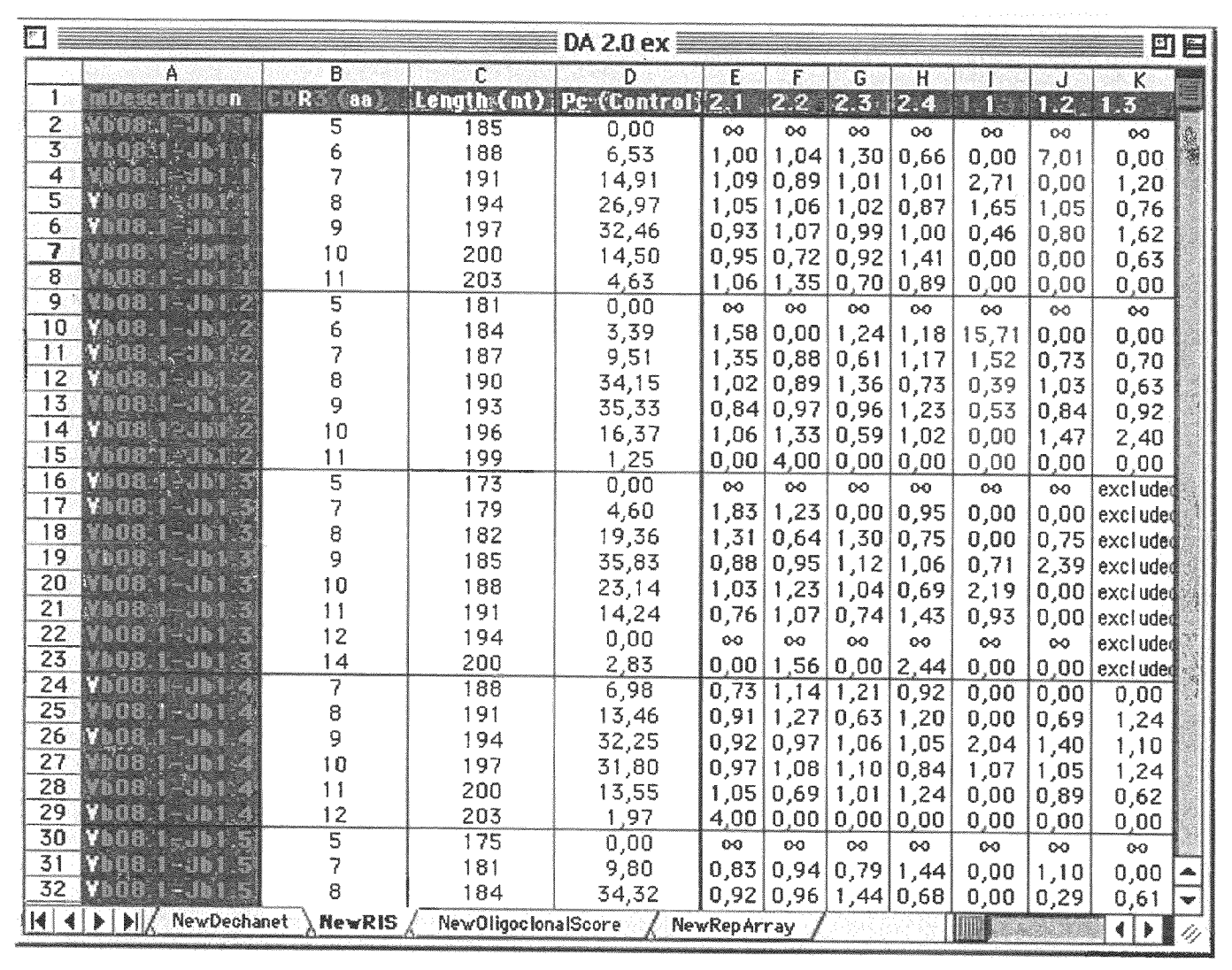

Select the 'RIS' macro in the ISEApeaks menu bar. Indicate the group of samples to use as the control. To specify a particular sample, just give a new group identification to this sample. The average control repertoire is computed. RIS is calculated for each peak of each sample (FIG. 25). The average RIS of each group is computed for each peak. Status of the execution is indicated in the Excel status bar (bottom of the screen).

The Relative Index of Stimulation (RIS) is calculated for each peak. Pc(Control) is the average computed repertoire. 'excluded' signals a profile that could not be analysed in this sample while '∞' signals a peak not present in the average control repertoire.

h) The 'OligoScore' Macro

Figure 26:
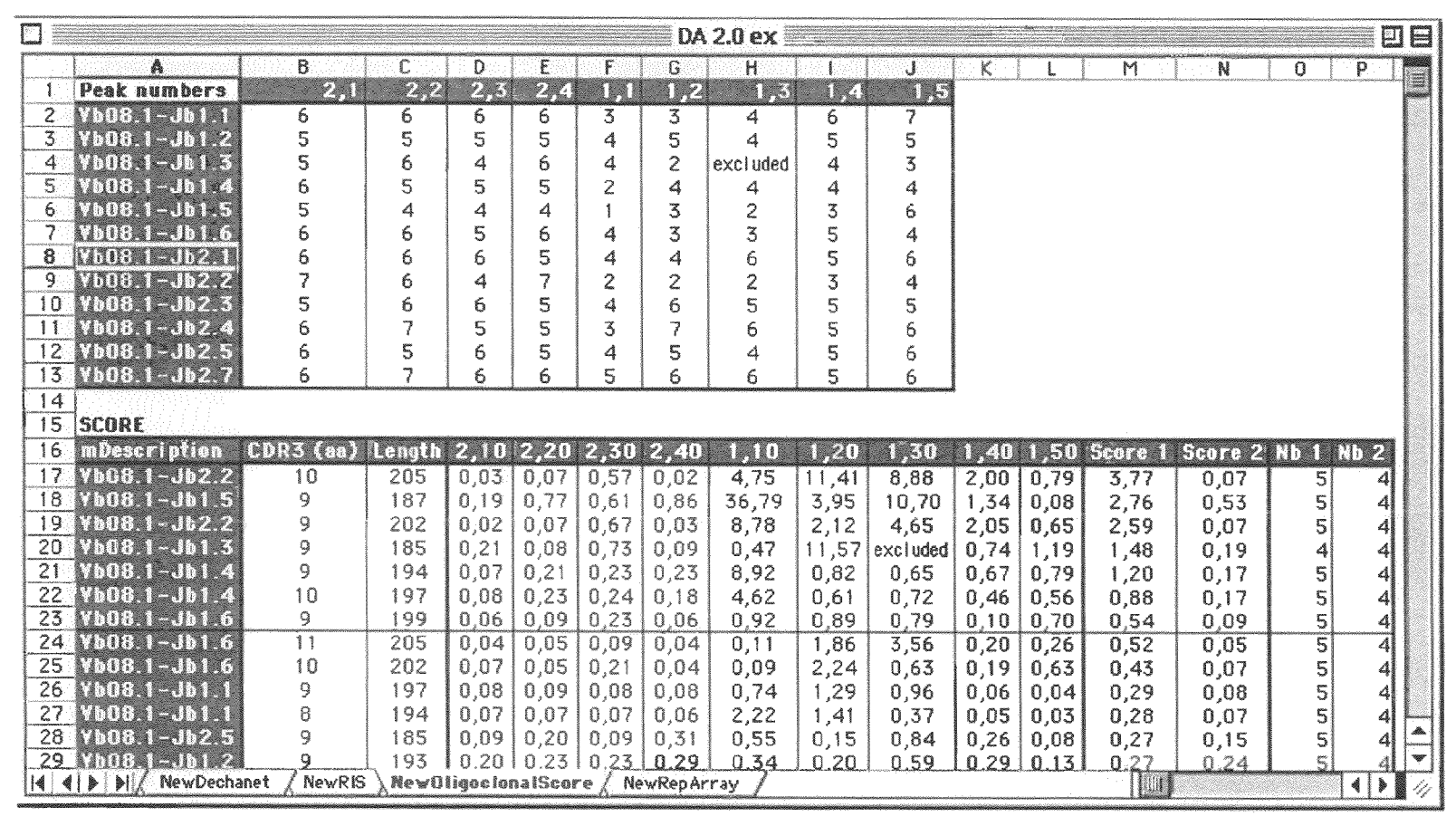

To assess the oligoclonality of a set of repertoires or to find recurrent peaks, a score was devised to quantify oligoclonality for each peak (Collette, A., S. Bagot, P.-A. Cazenave, A. Six, and S. Pied. 2002. A profound alteration of blood TCRB repertoire allows prediction of cerebral malaria. submitted, Collette, A., and A. Six. 2002. ISEApeaks: an Excel platform for GeneScan and Immunoscope data retrieval, management and analysis. Bioinformatics 18:329-330). Launch the macro by choosing the 'OligoScore' item in the ISEApeaks menu bar. A score is first calculated for each peak, afterwards a global score is computed for each group (FIG. 26, column M). One will find the recurrent peaks by sorting peaks using the scores of a particular group of samples compared to other groups (Collette, A., and A. Six. 2002. ISEApeaks: an Excel platform for GeneScan and Immunoscope data retrieval, management and analysis. Bioinformatics 18:329-330). Status of the execution is indicated in the Excel status bar (bottom of the screen).

The upper array summarises peak numbers per profile for each sample. The lower array first shows the score per individual and the score per group (columns M and N). Peaks have been sorted according to the oligoclonal score of the first group, the second being the control (see FIG. 20).

i) The 'Shohei' Macro

Another useful utility has been implemented in DataAnalyser: One can import the peaks obtained for a quantification of a particular set of cells using a given Vβ, Jβ and CDR3 length (Hori, S. and al., manuscript in preparation). To do that, use DataParameter to make a parameter file that will order the n repetition of the same amplification in the position 1 to n. Then use DataExtractor and DataSmoother to extract and smooth the peaks. DataFormatter will then enable one to import the peaks into Excel. Check the peaks obtained and make the necessary correction.

Open DataAnalyser. Click the 'Shohei' macro in the ISEApeaks menu bar to start the analysis. Select the DataFormatter file where peak data are stored and indicate the correct worksheet. DataAnalyser then imports the peaks area and makes the calculations to estimate the number of cells using these particular Vβ, Jβ and CDR3 length.

j) The 'DrawArray' Macro

Visualisation of repertoire diversity is not handy when analysing several repertoires. Colour-coding of diversity is a common way to visualise diversity (Pannetier, C., M. Cochet, S. Darche, A. Casrouge, M. Zöller, and P. Kourilsky. 1993. The sizes of the CDR3 hypervariable regions of the murine T-cell receptor b chains vary as a function of the recombined germ-line segments. Proc. Natl. Acad. Sci. USA 90:4319-4323., Lim, A., A. Toubert, C. Pannetier, M. Dougados, D. Charron, P. Kourilsky, and J. Even. 1996. Spread Of Clonal T-Cell Expansions In Rheumatoid Arthritis Patients. Human Immunology 48:77-83; Mempel, M., B. Flageul, F. Suarez, C. Ronet, L. Dubertret, P. Kourilsky, G. Gachelin, and P. Musette. 2000. Comparison of the T cell patterns in leprous and cutaneous sarcoid granulomas—Presence of V alpha 24-invariant natural killer T cells in T-cell-reactive leprosy together with a highly biased T cell receptor V alpha repertoire. American Journal of Pathology 157:509-523; Musette, P., H. Bachelez, B. Flageul, C. Delarbre, P. Kourilsky, L. Dubertret, and G. Gachelin. 1999. Immune-mediated destruction of melanocytes in halo nevi is associated with the local expansion of a limited number of T cell clones. J. Immunol. 162:1789-1794). ISEApeaks can automatically generate this representation. This macro is very useful as it is now possible to use this representation with objective classification of diversity as the Gorochov or Déchanet scores.

Figure 27:
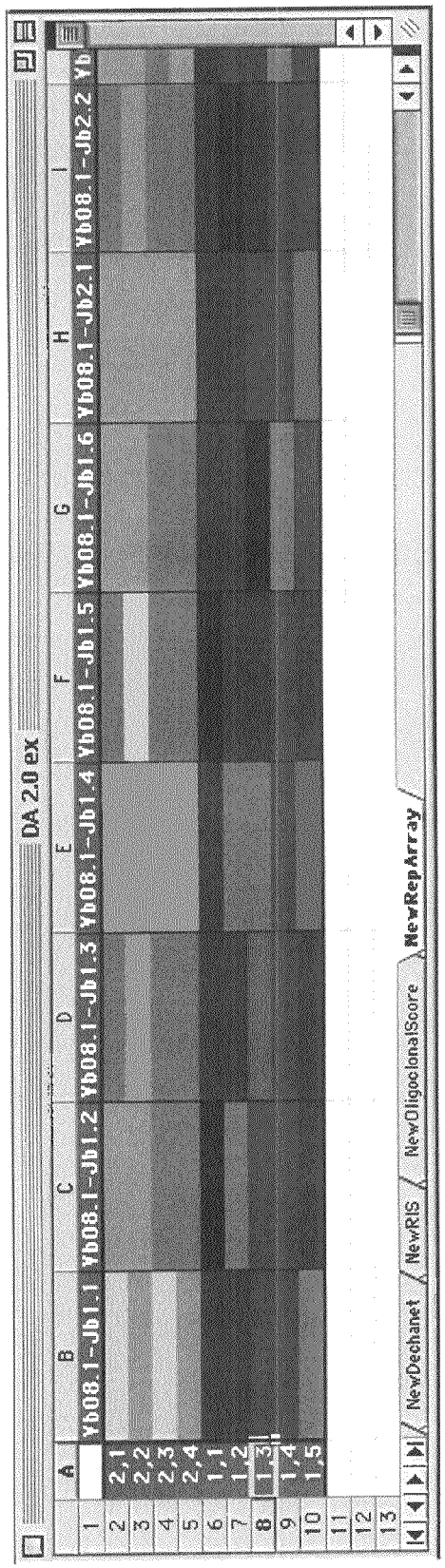
FIG. 27: the 'DrawArray' procedure creates a representation of diversity in the repertoires.
Figure 28A:
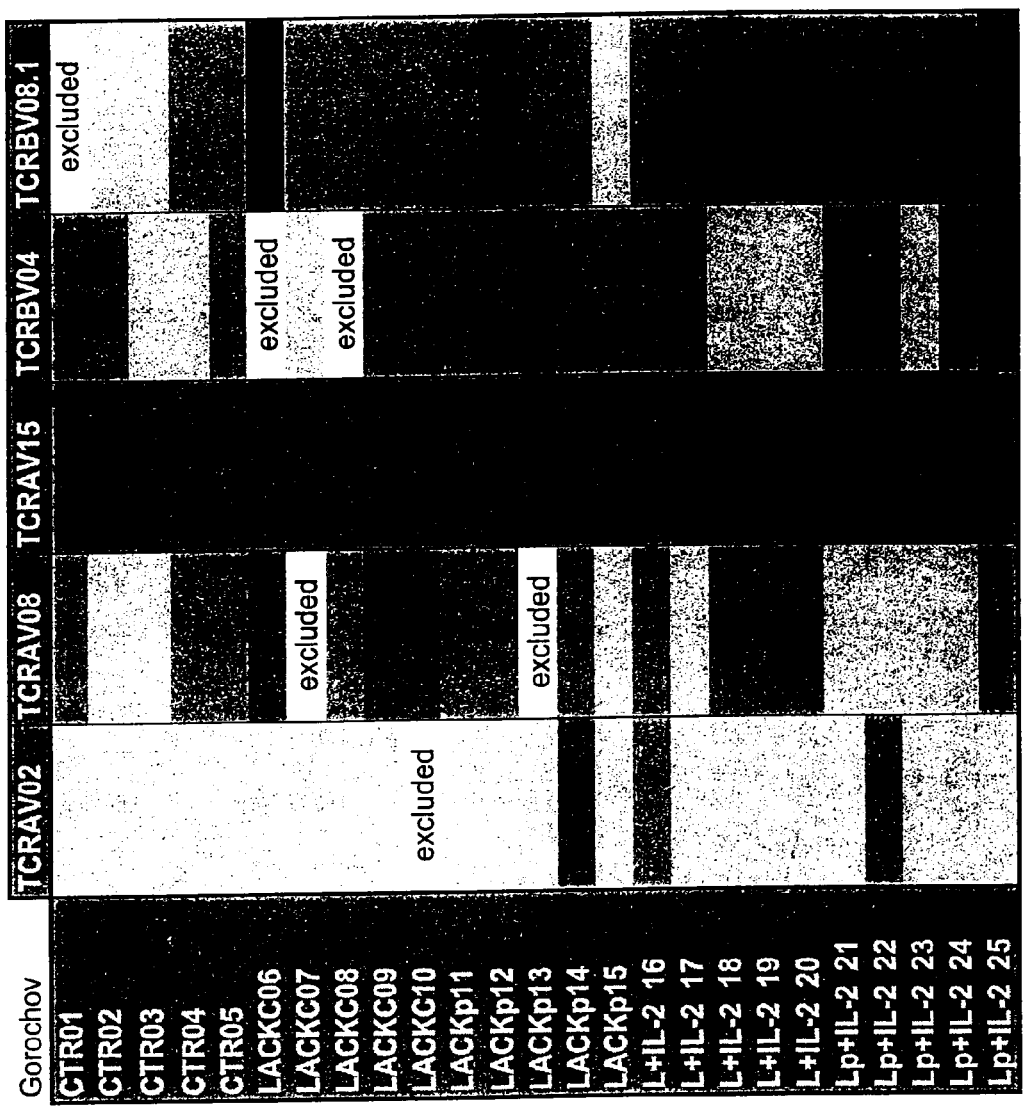
FIG. 28 A. Depiction of overall disturbance.
Figure 28:
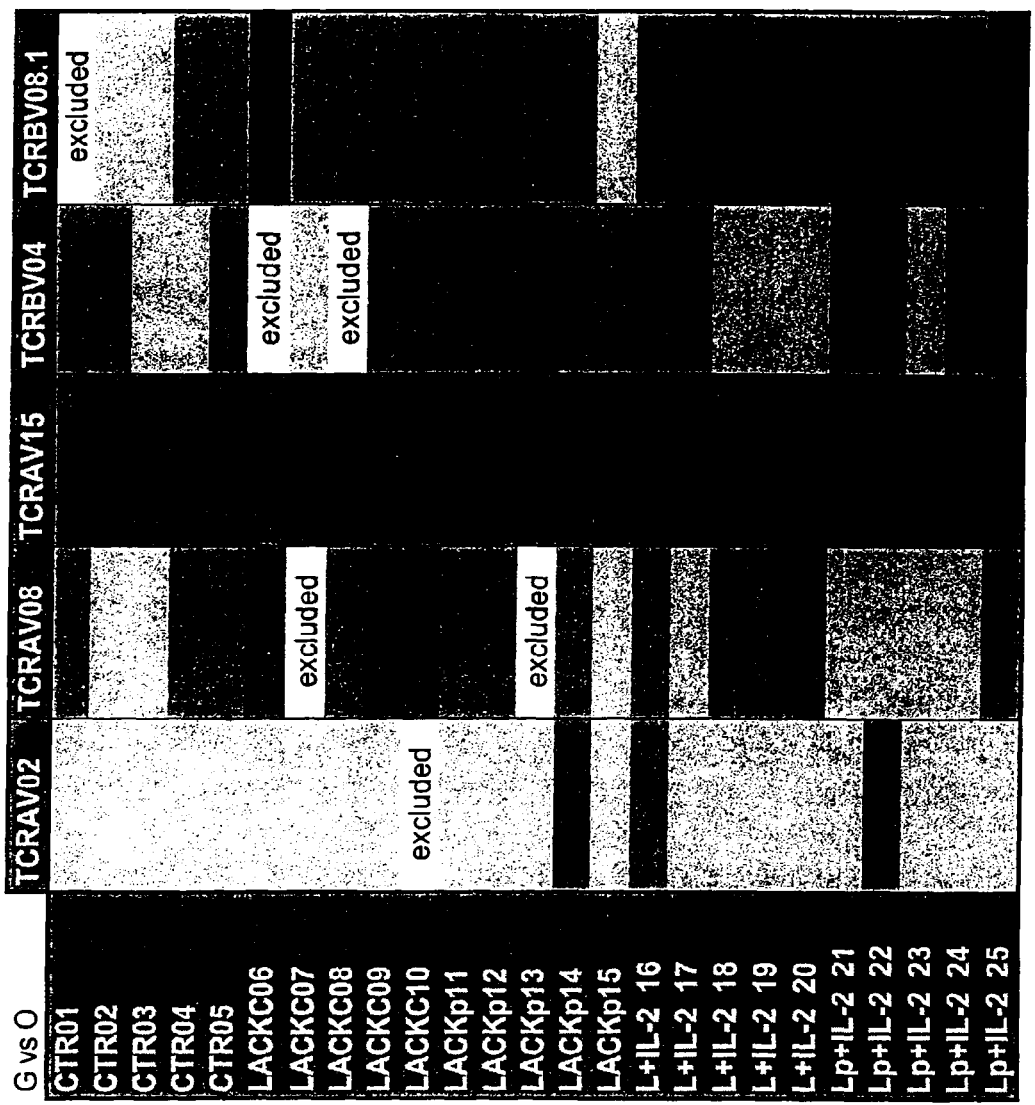
Figure 30A:
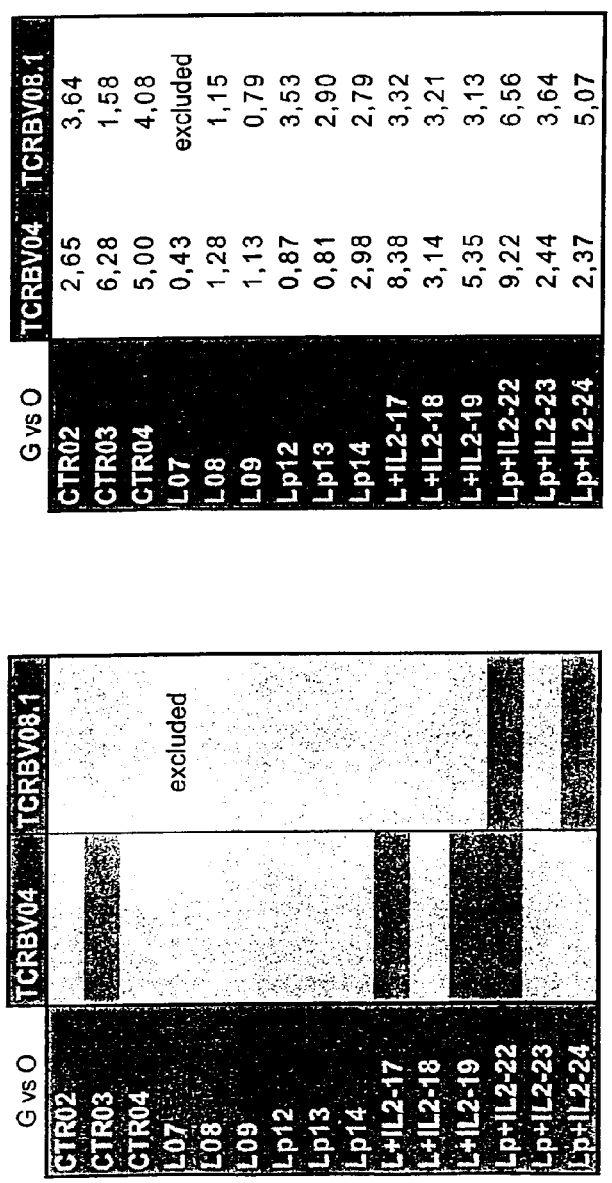
FIG. 30 A. Depiction of overall disturbance vs. oligoclonality.
Figure 30B:
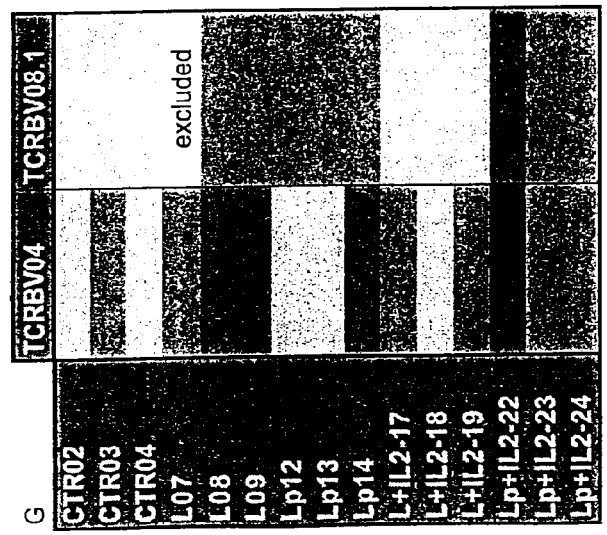
Figure 34A:
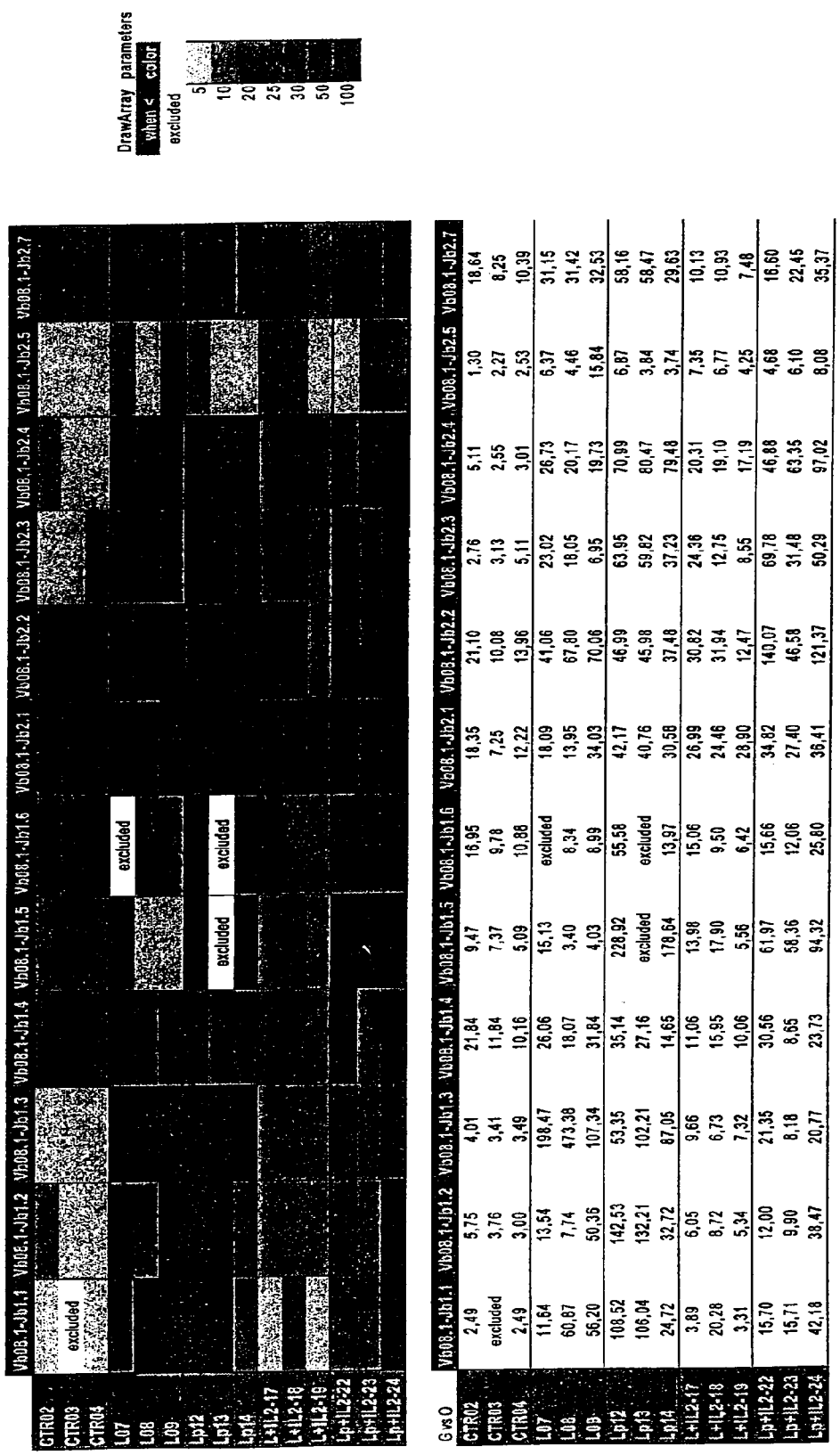
FIG. 34 A. Depiction of overall disturbance vs. oligoclonality.
Figure 34B:
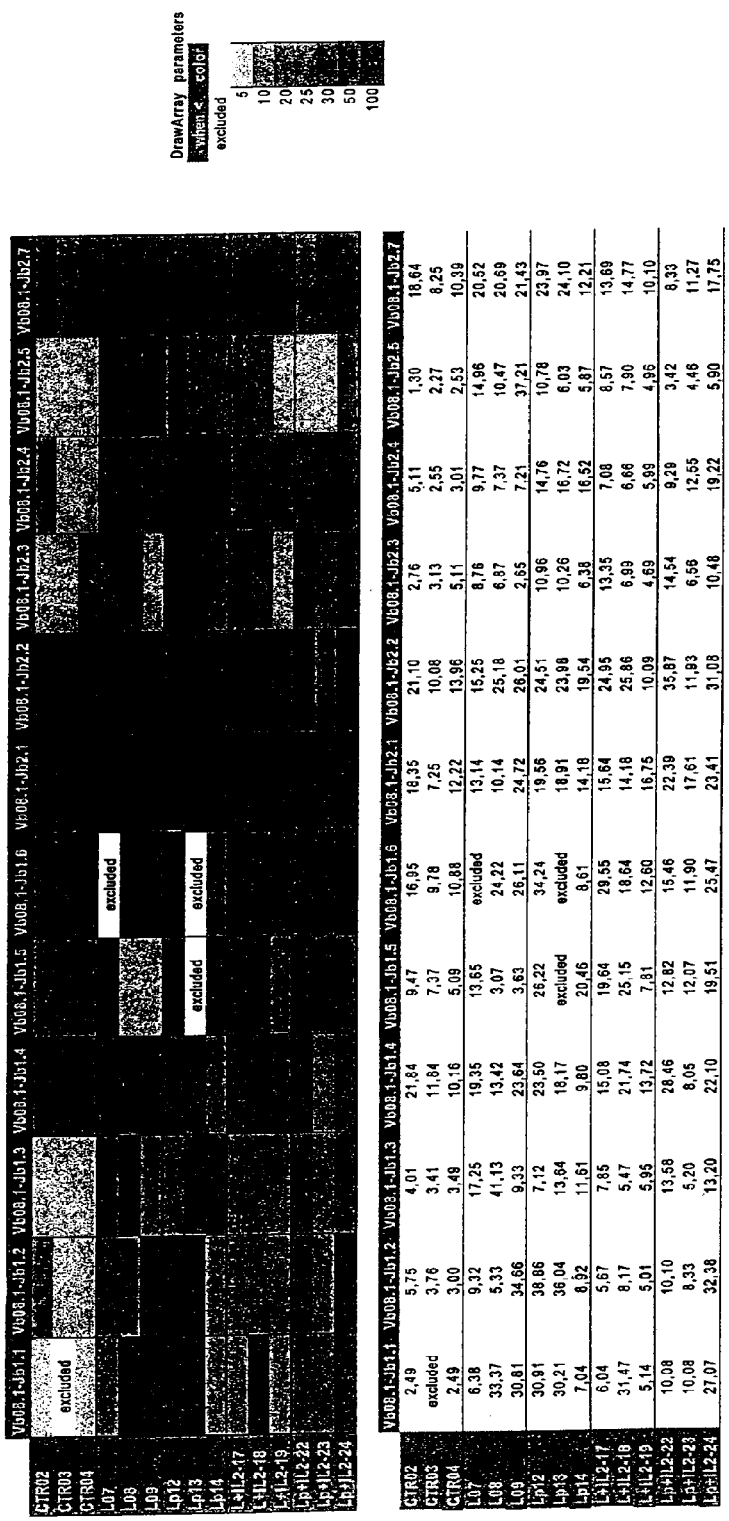
Figure 37:
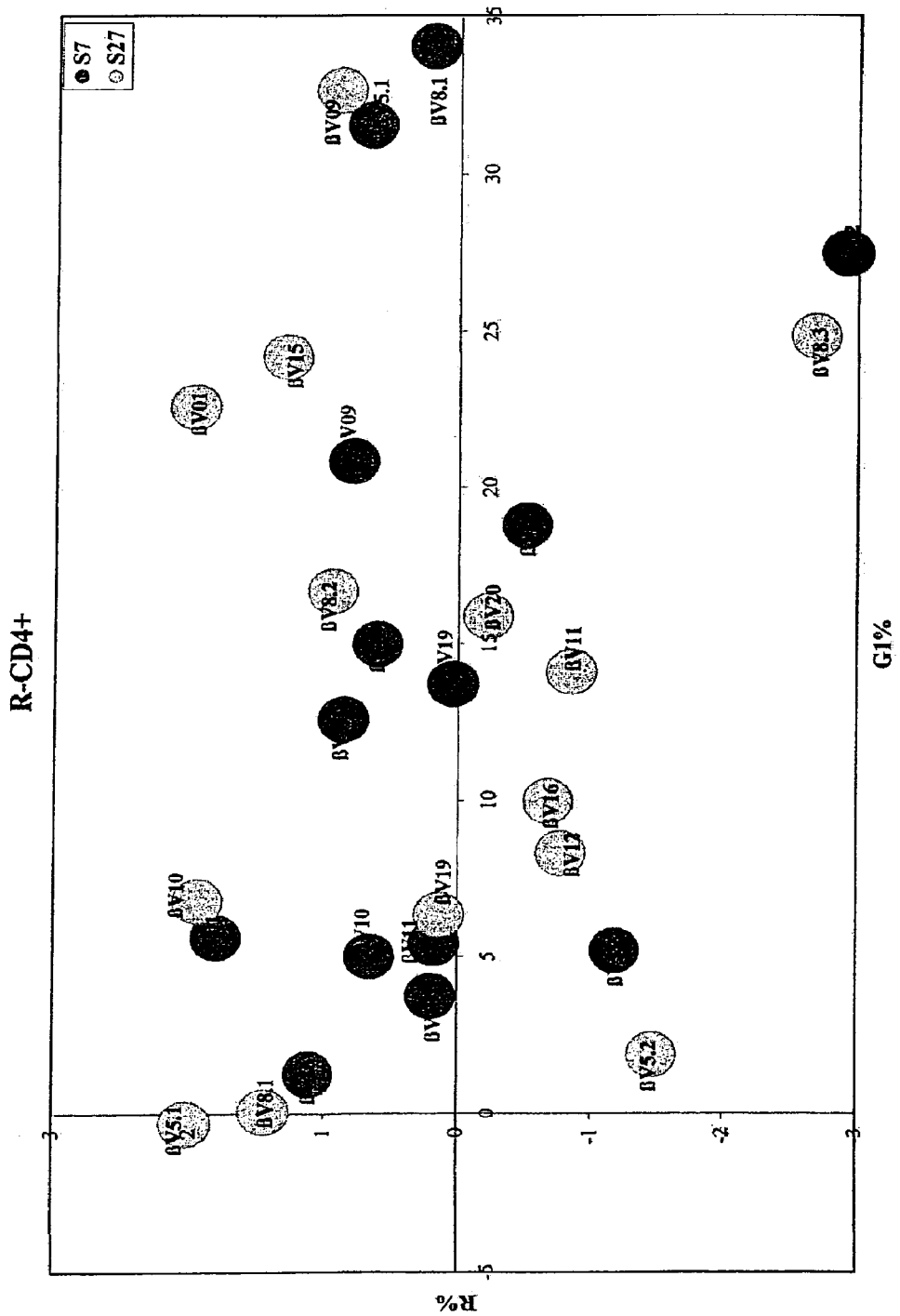
FIG. 37. R-CD4+
FIG. 38 A. Draw array/parameters.
Figure 38A:
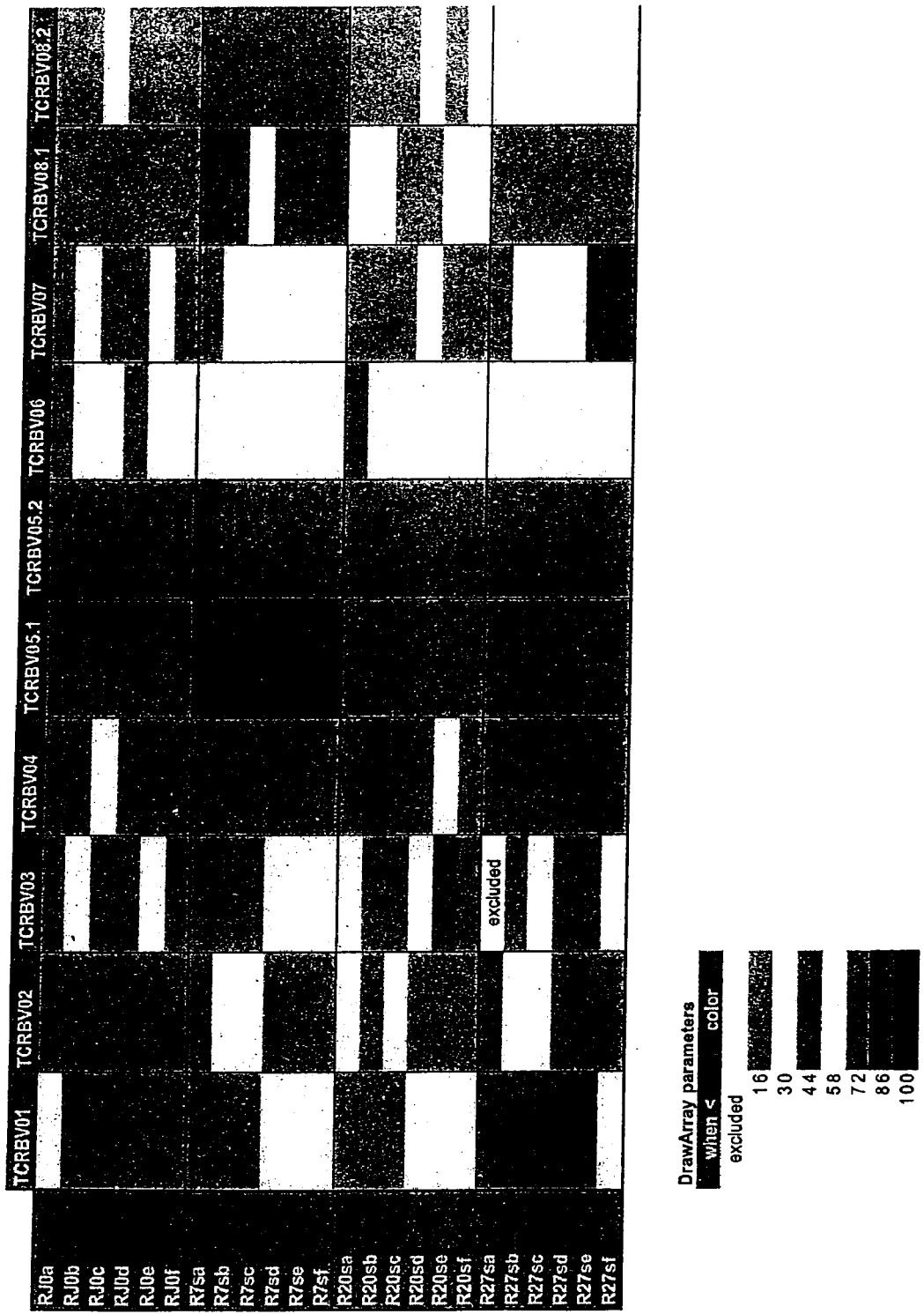
FIG. 38 B. Draw array/parameters.
Figure 40A:
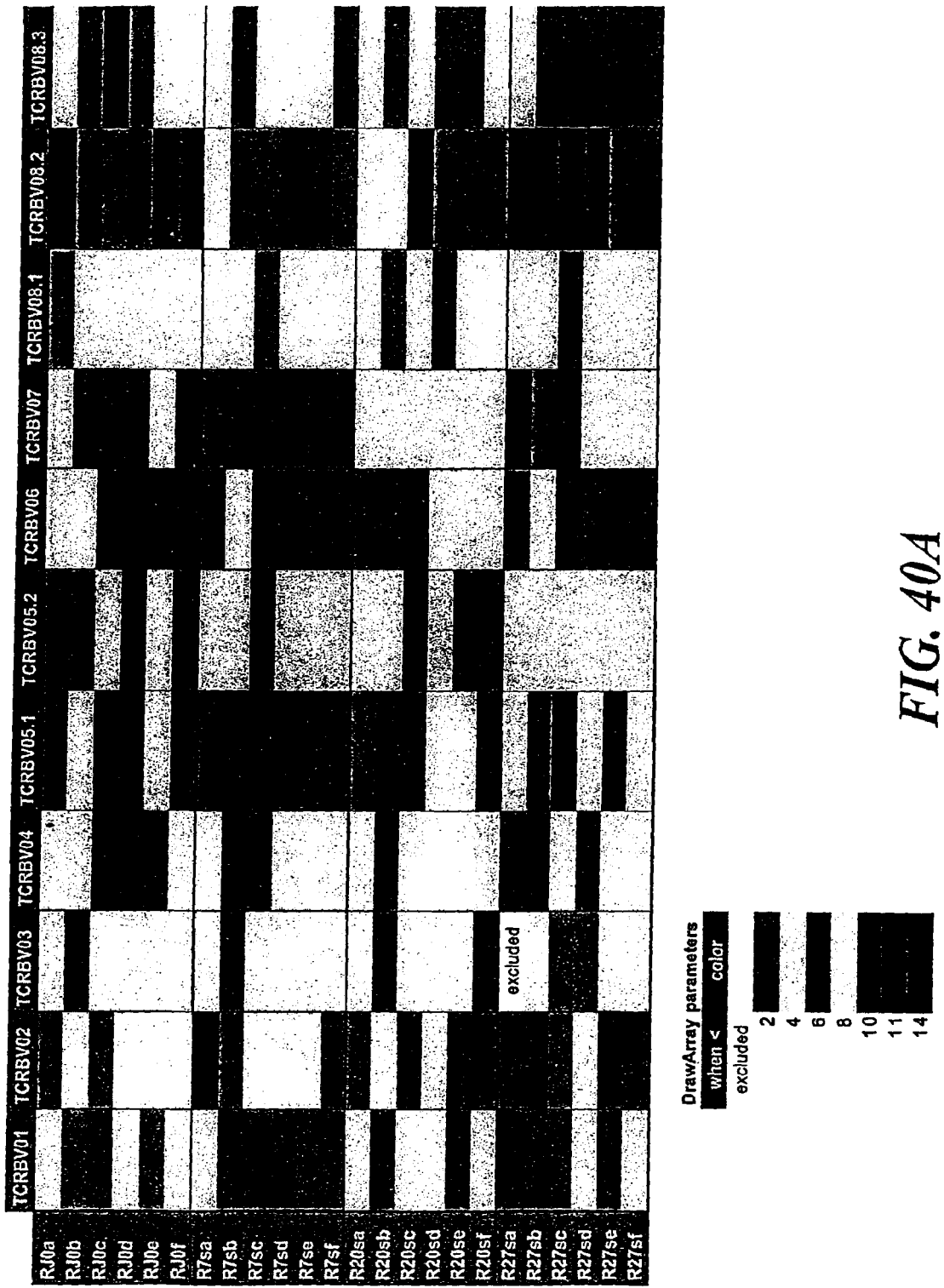
FIG. 40 A. Draw array/parameters.
Figure 40B:
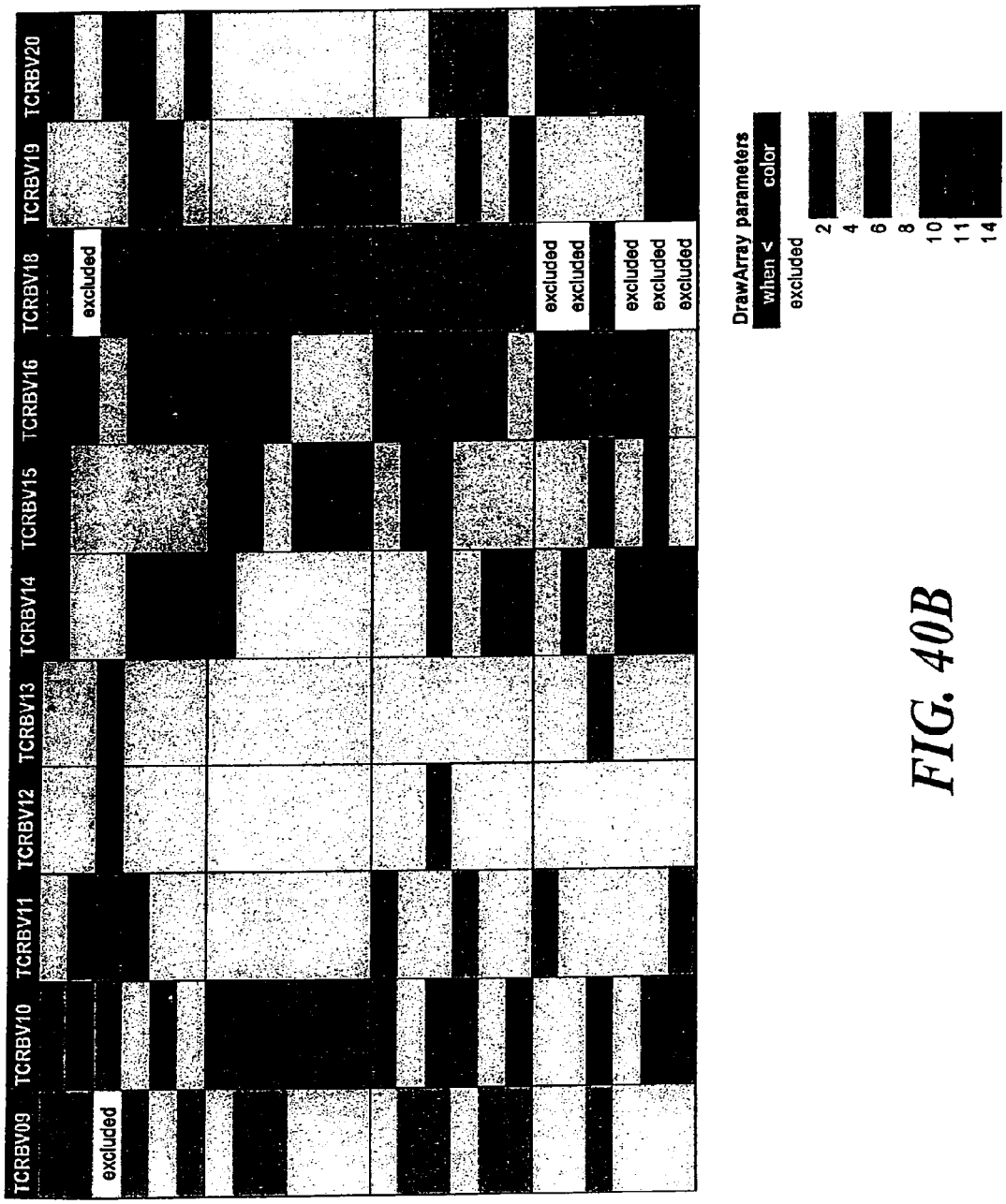
Figure 42:
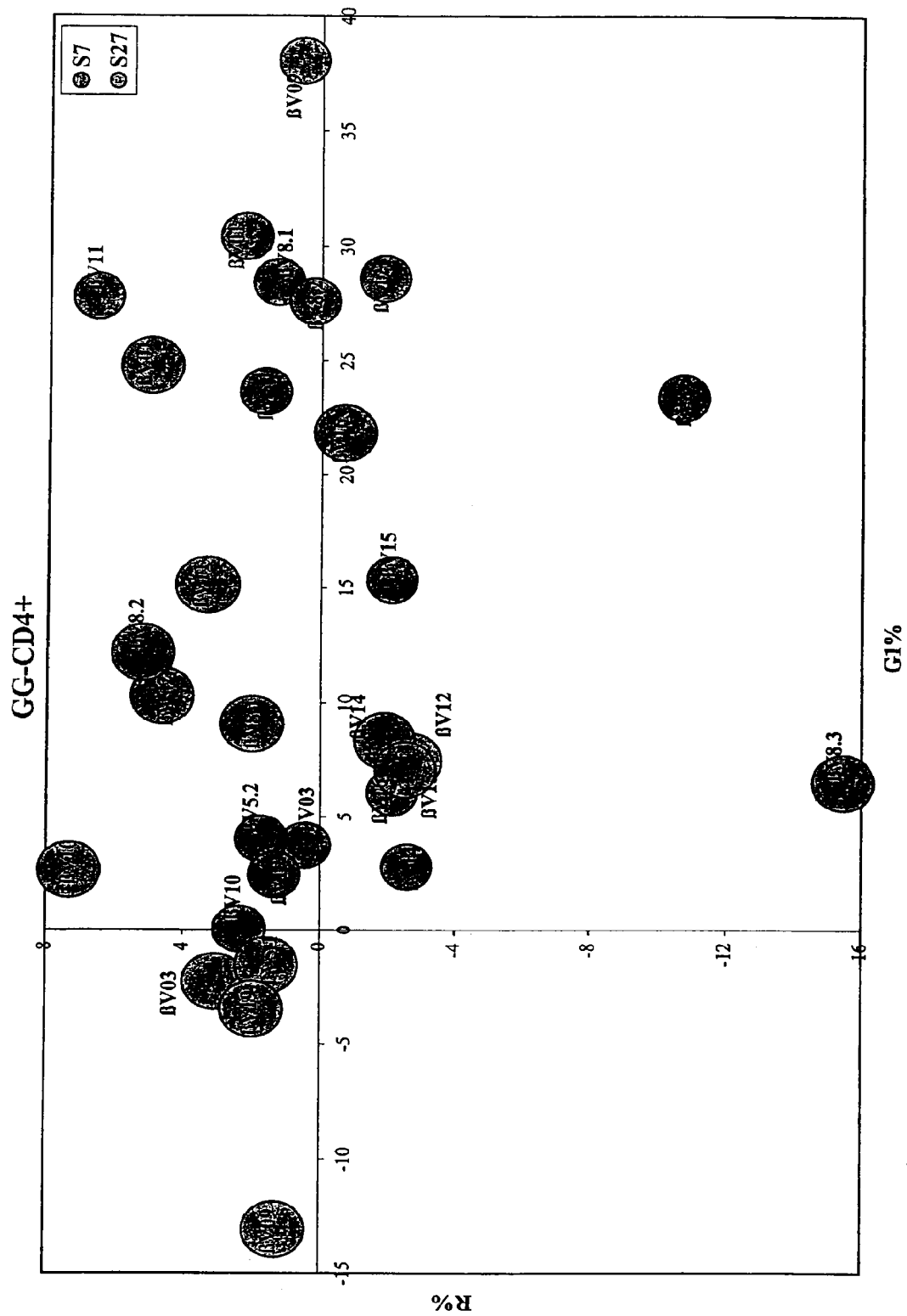
FIG. 42. GG CD4+
FIG. 43 A. Draw array/parameters.
Figure 43A:
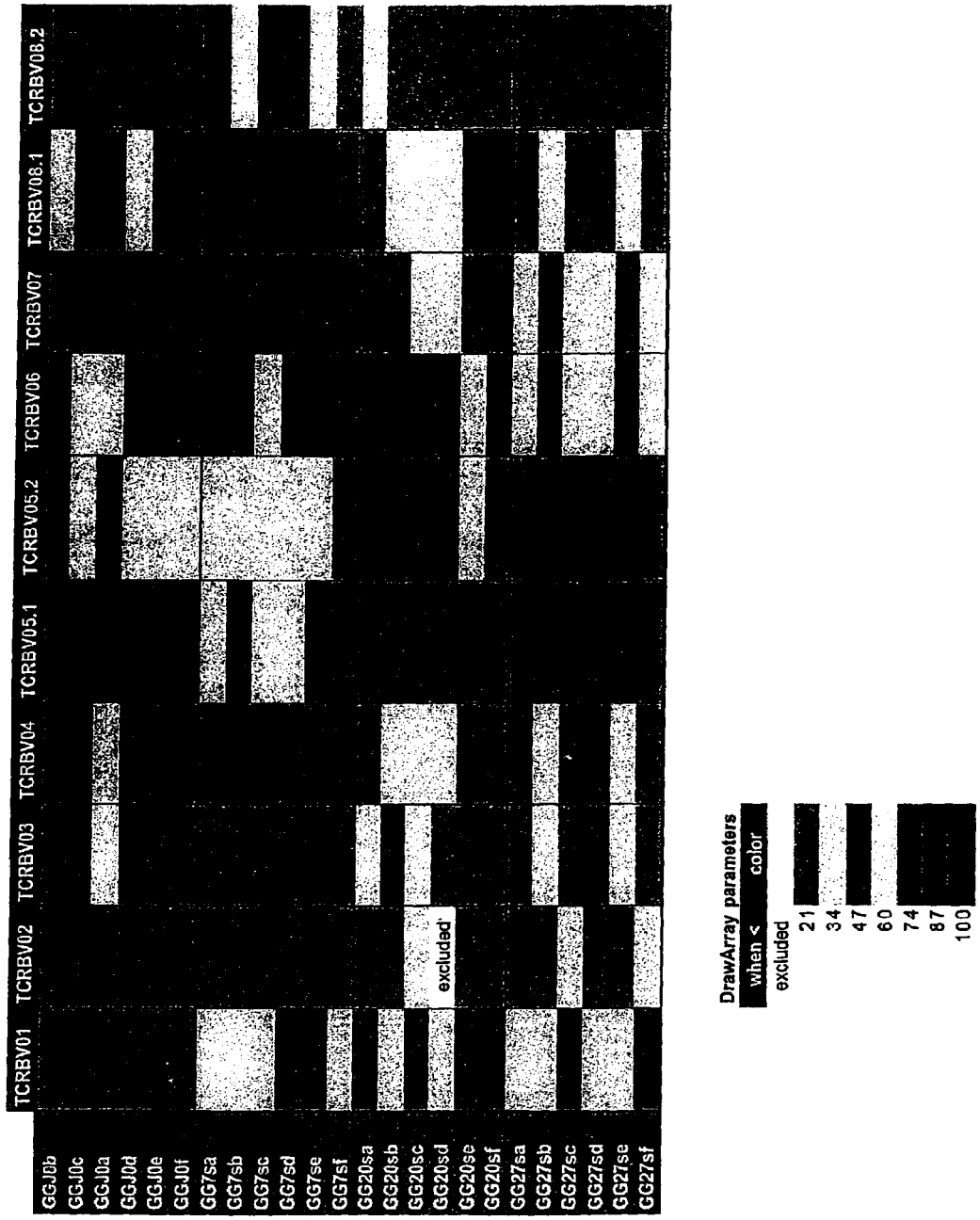
FIG. 43 B. Draw array/parameters
FIG. 44. Oligoclonality score.
Figure 43B:
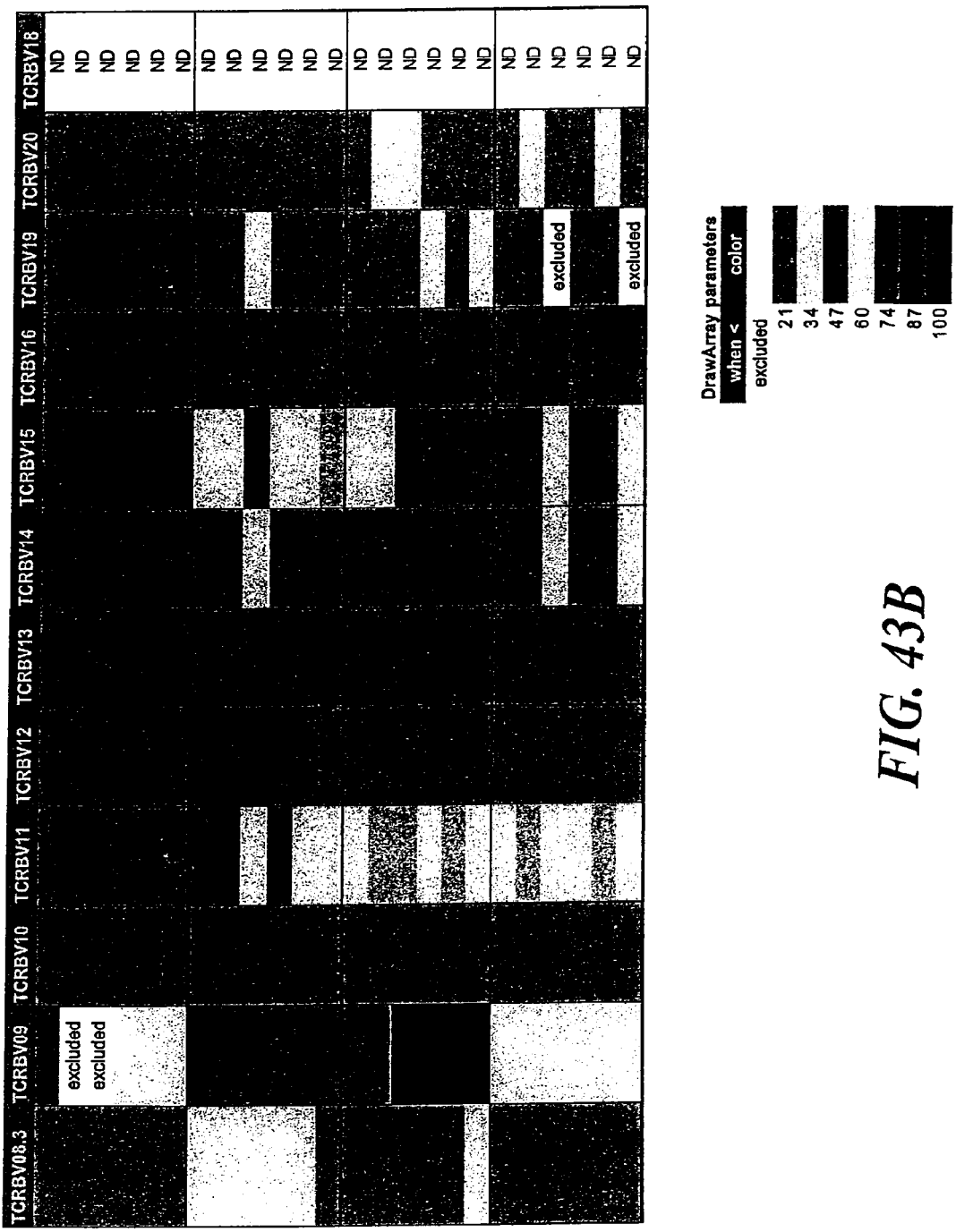
Figure 45A:
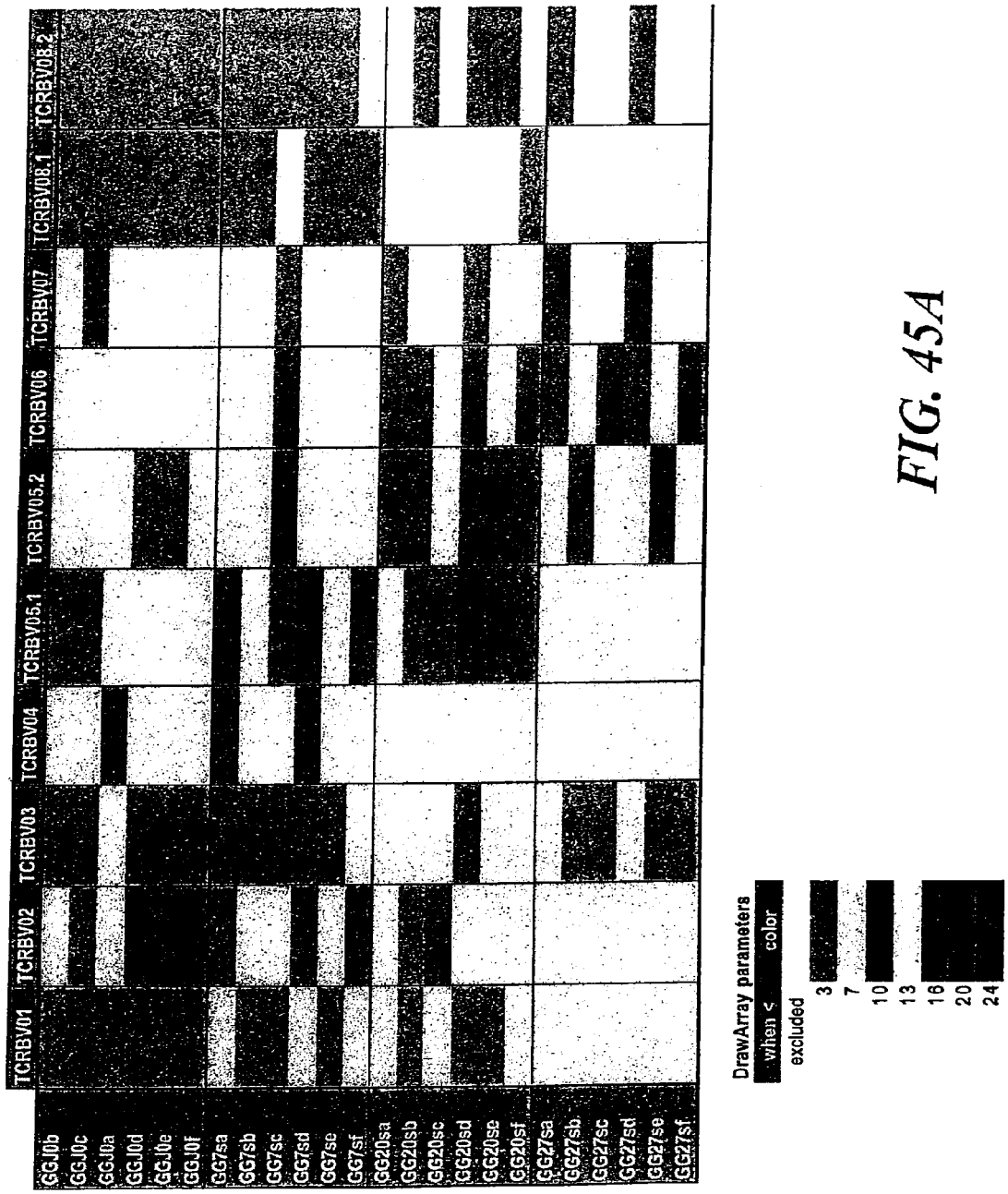
FIG. 45 A. Draw array/parameters.
Figure 45B:
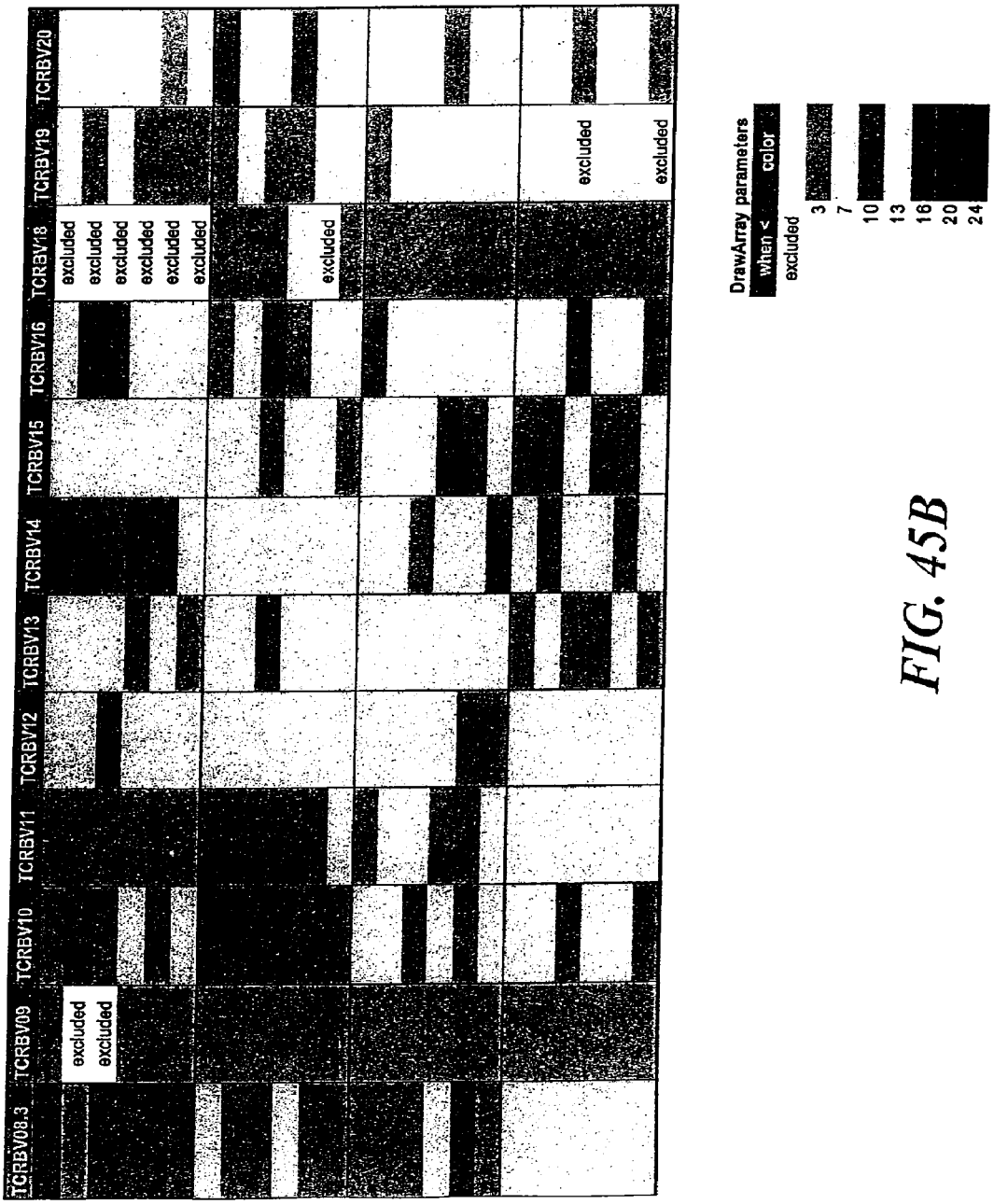
Figure 47:
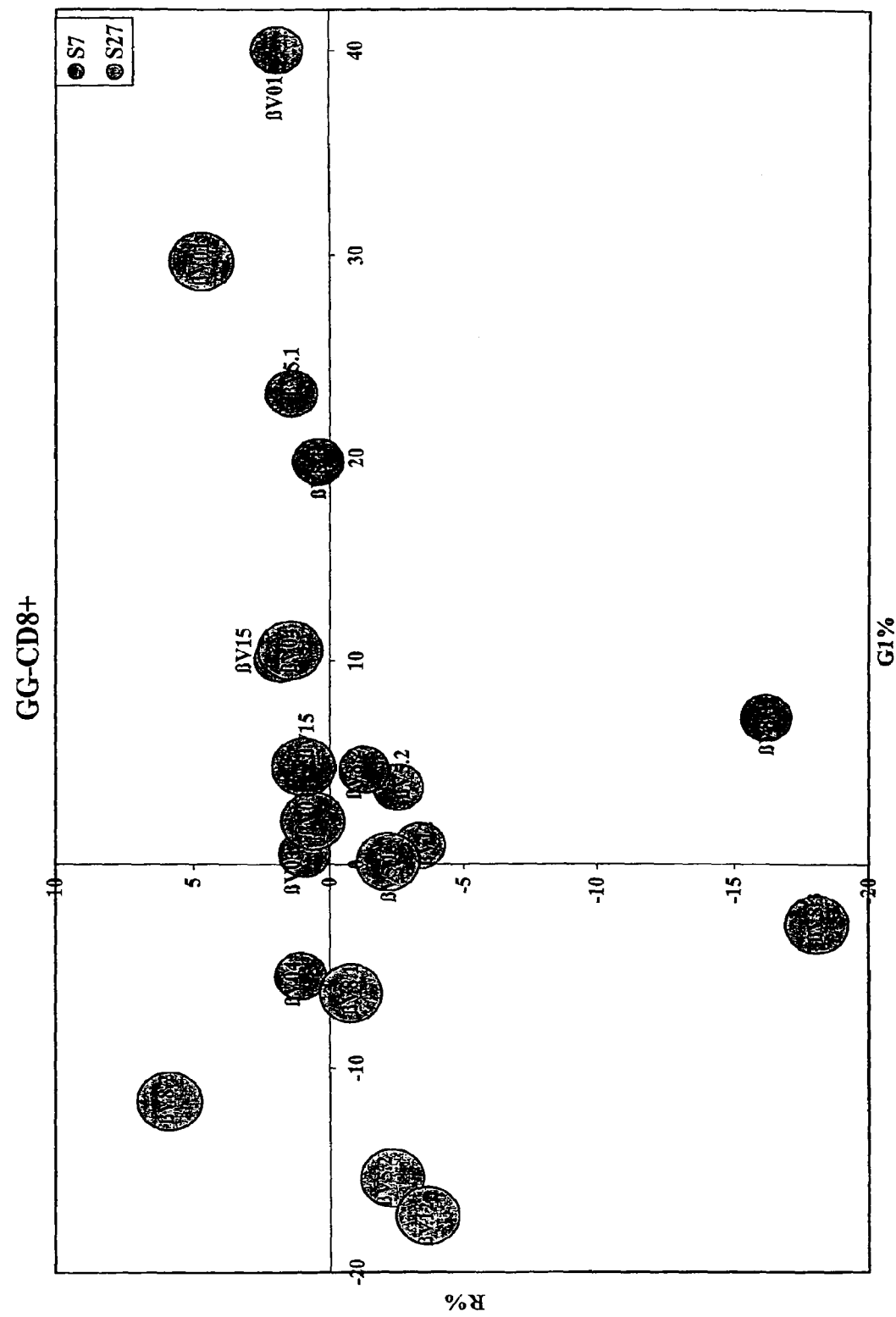
FIG. 47. GG-CD8+
FIG. 48 A. Draw array/parameters.
Figure 48A:
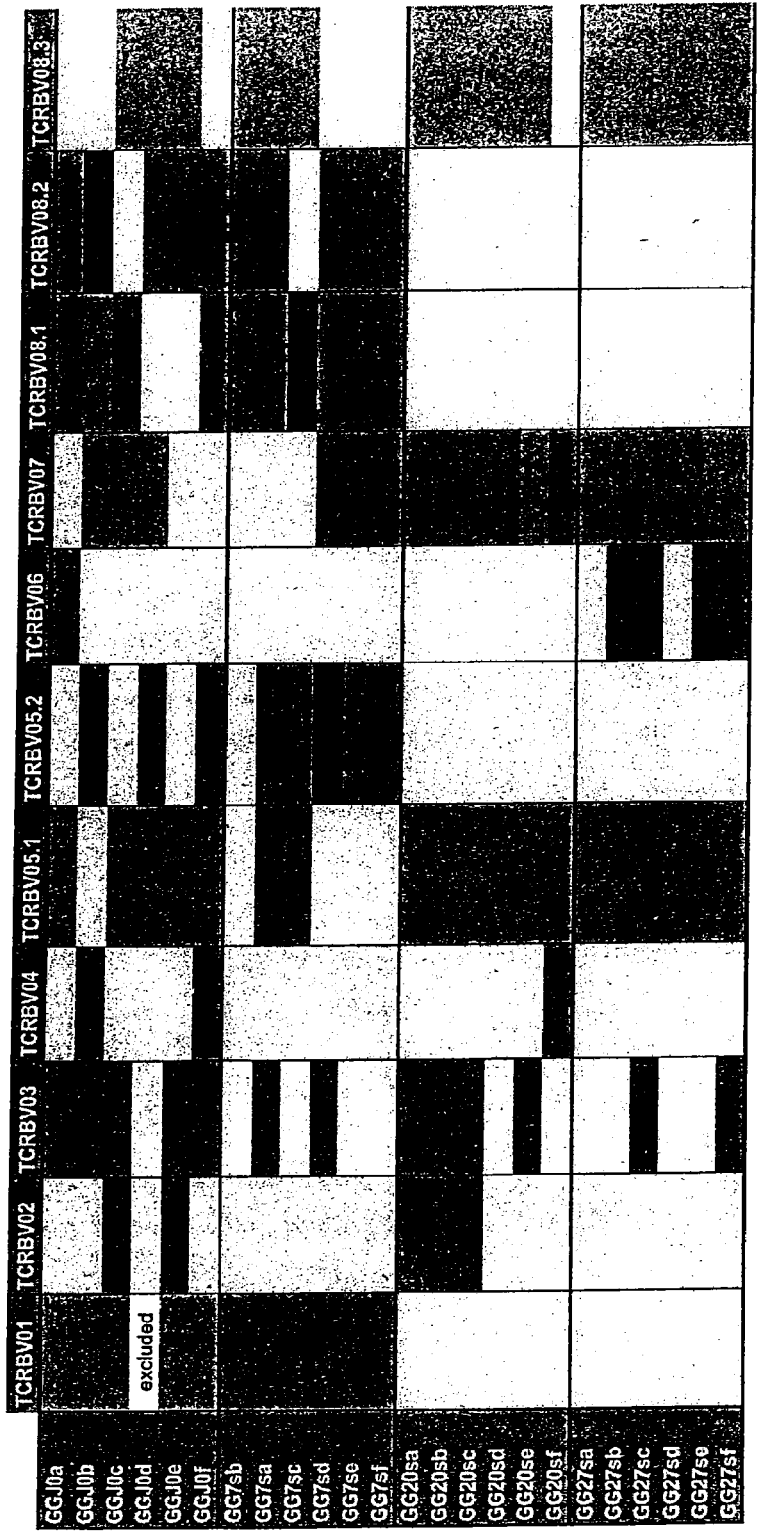
FIG. 48 B. Draw array/parameters.
Figure 48B:
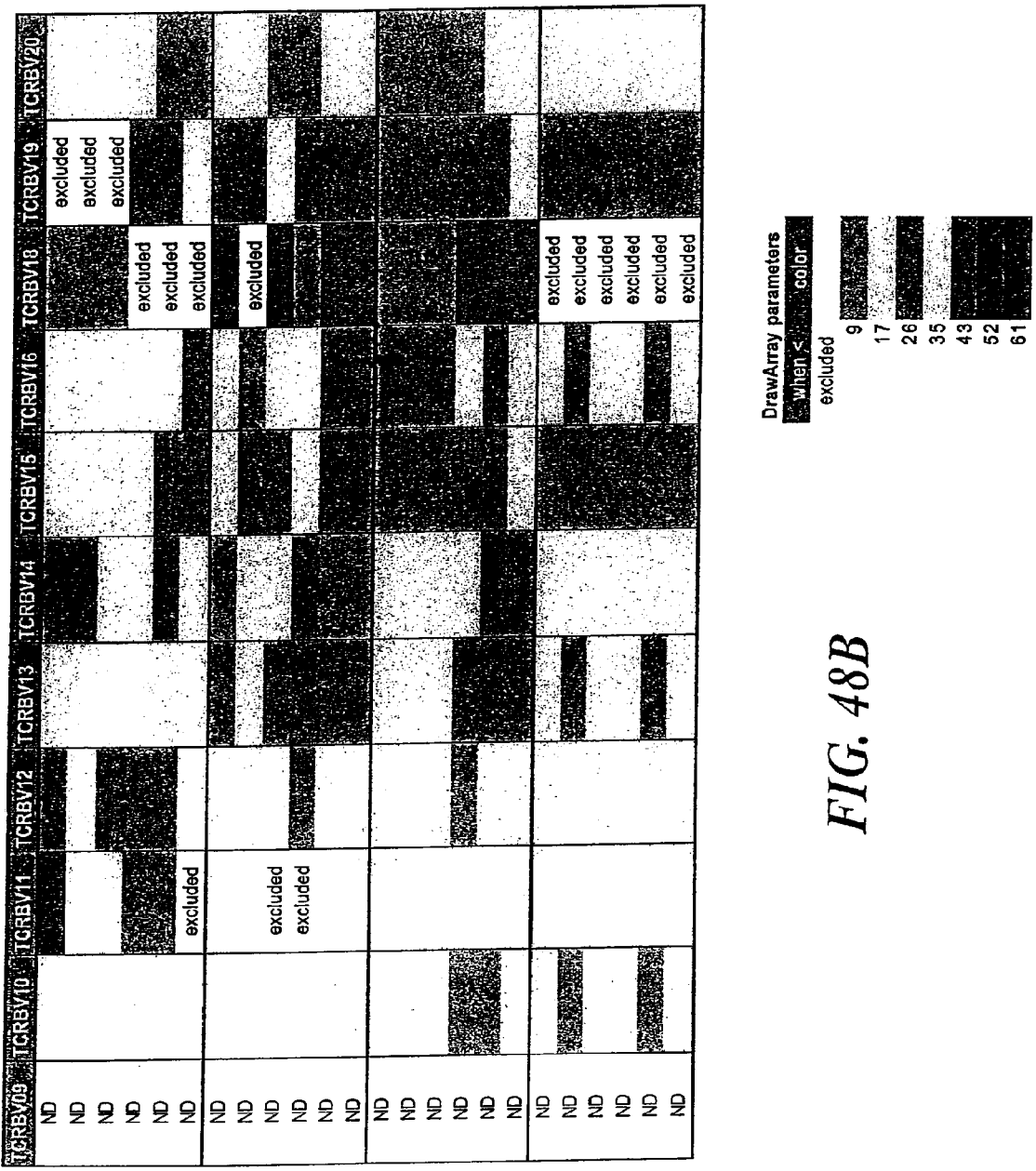
Figure 50A:
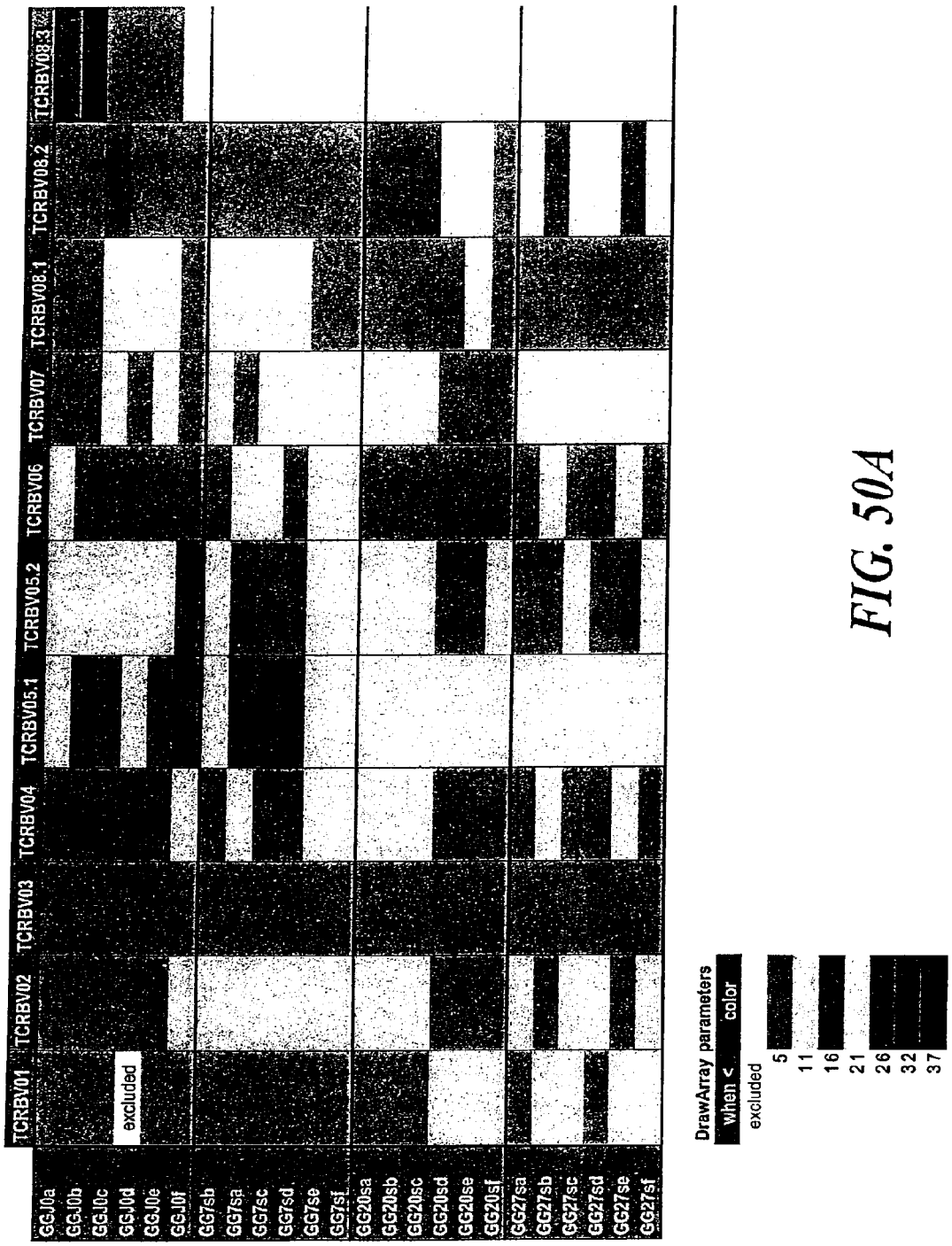
FIG. 50 A. Draw array/parameters.
Figure 50B:
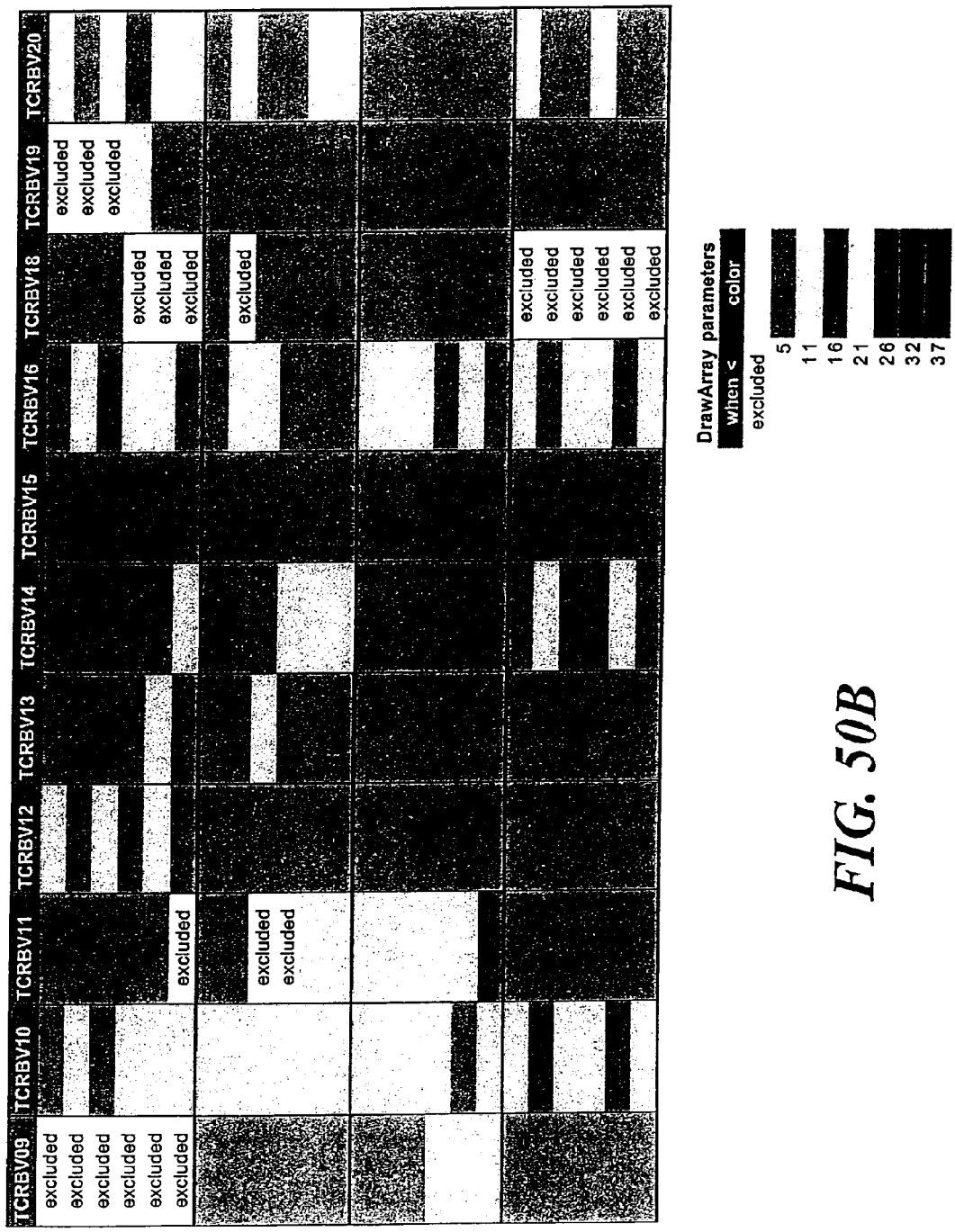
Figure 52:
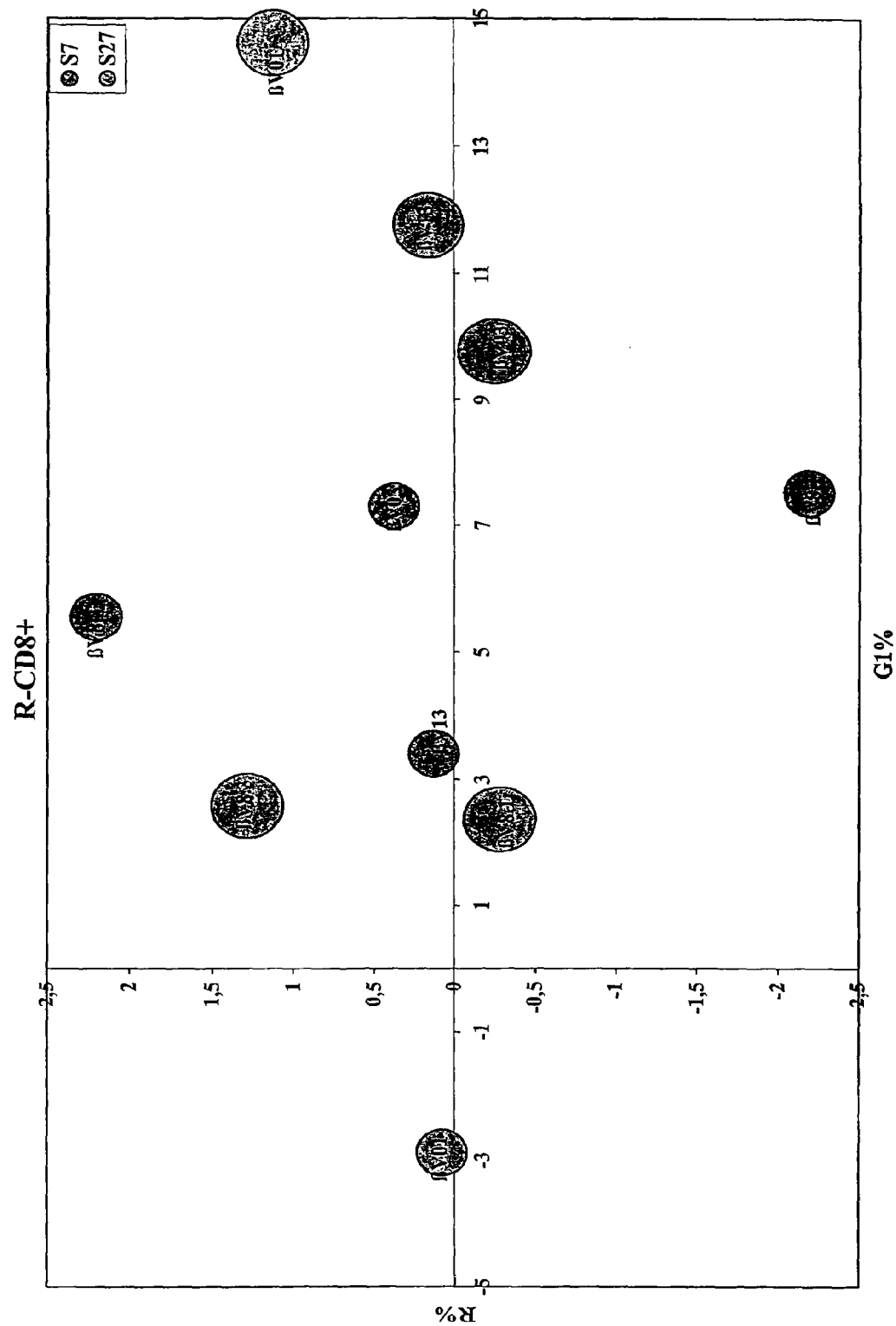
FIG. 52. R-CD8+.
Figure 53A:
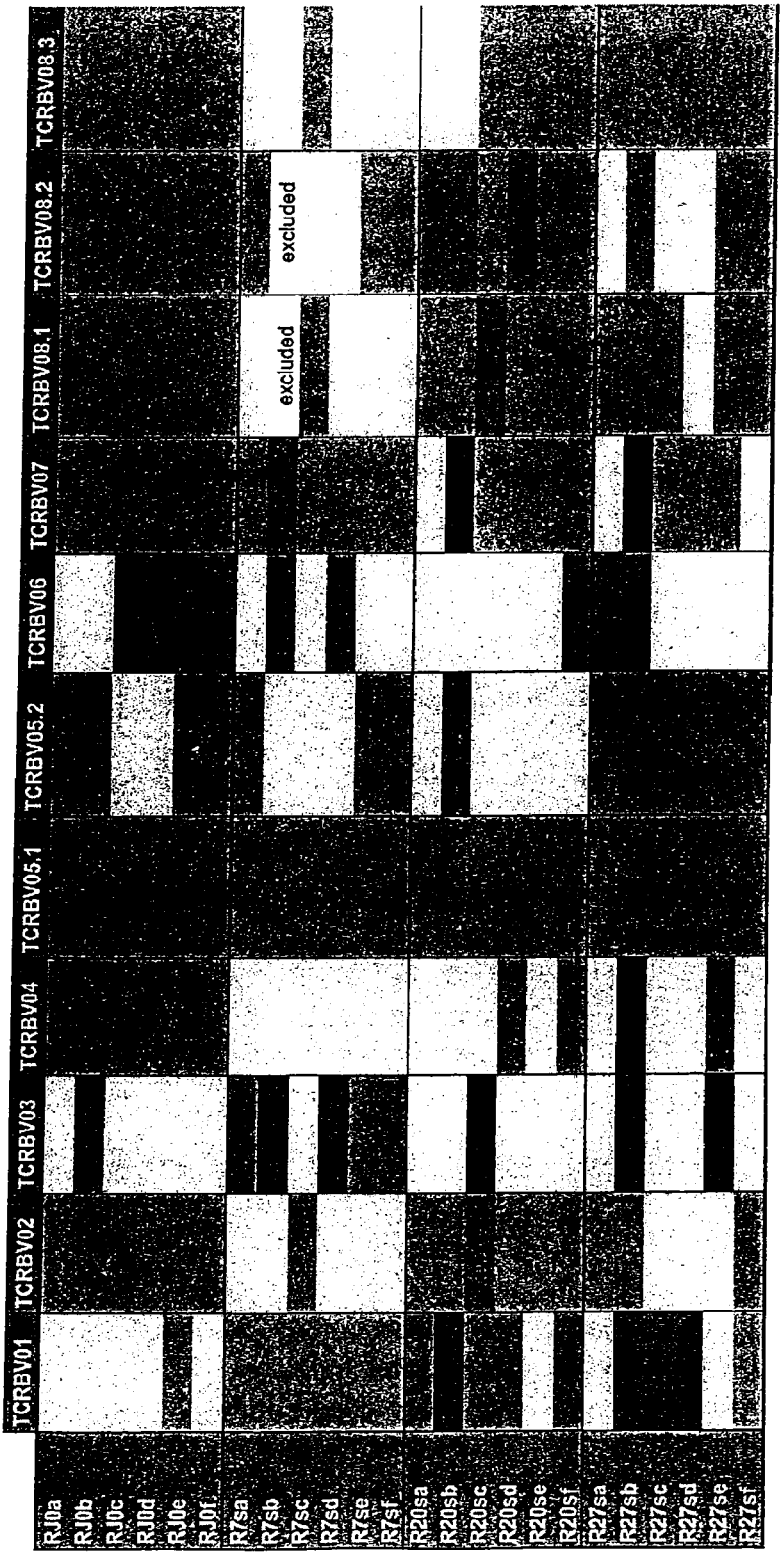
FIG. 53 A. Draw array/parameters.
Figure 53B:
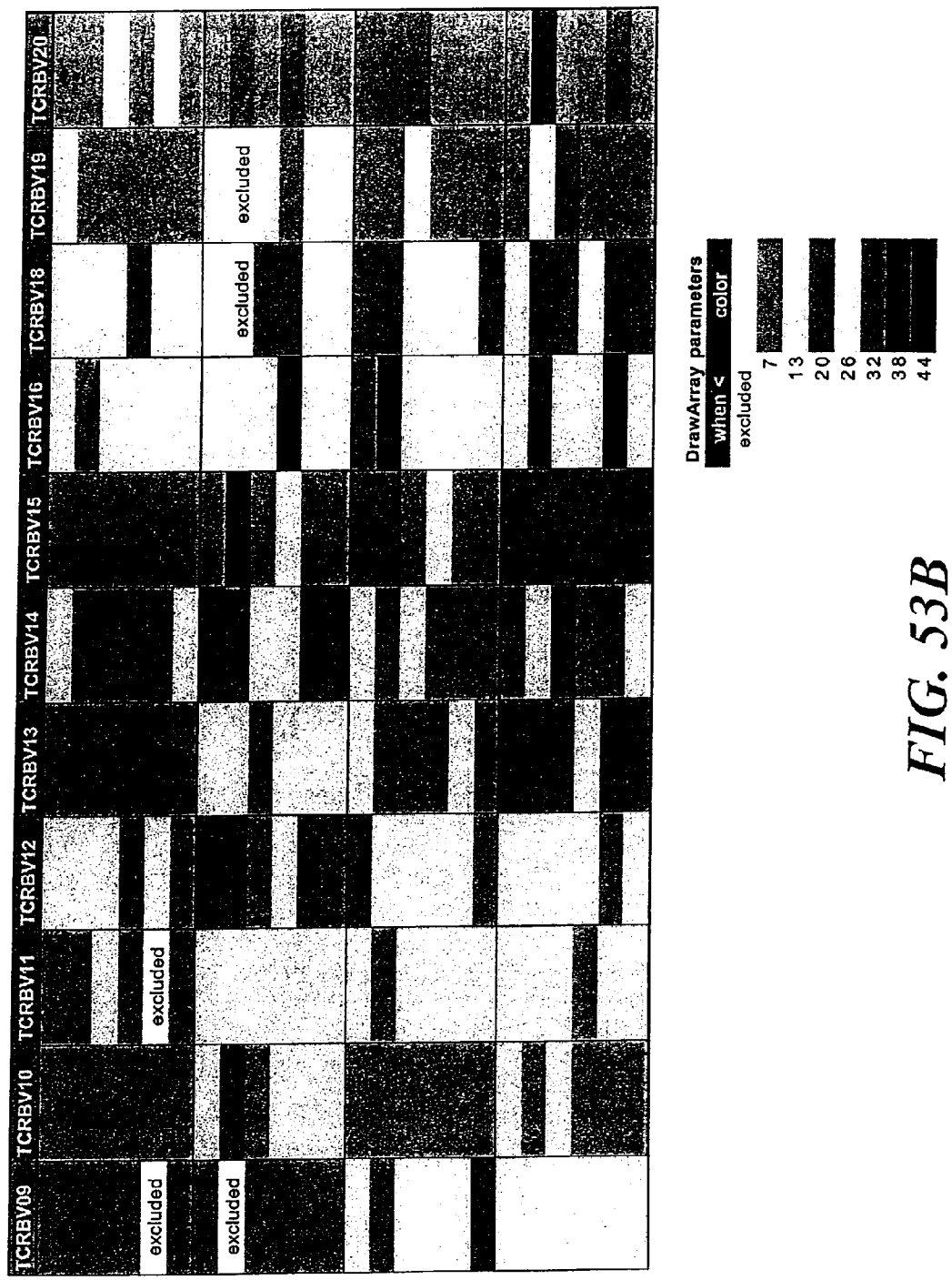
Figure 55A:
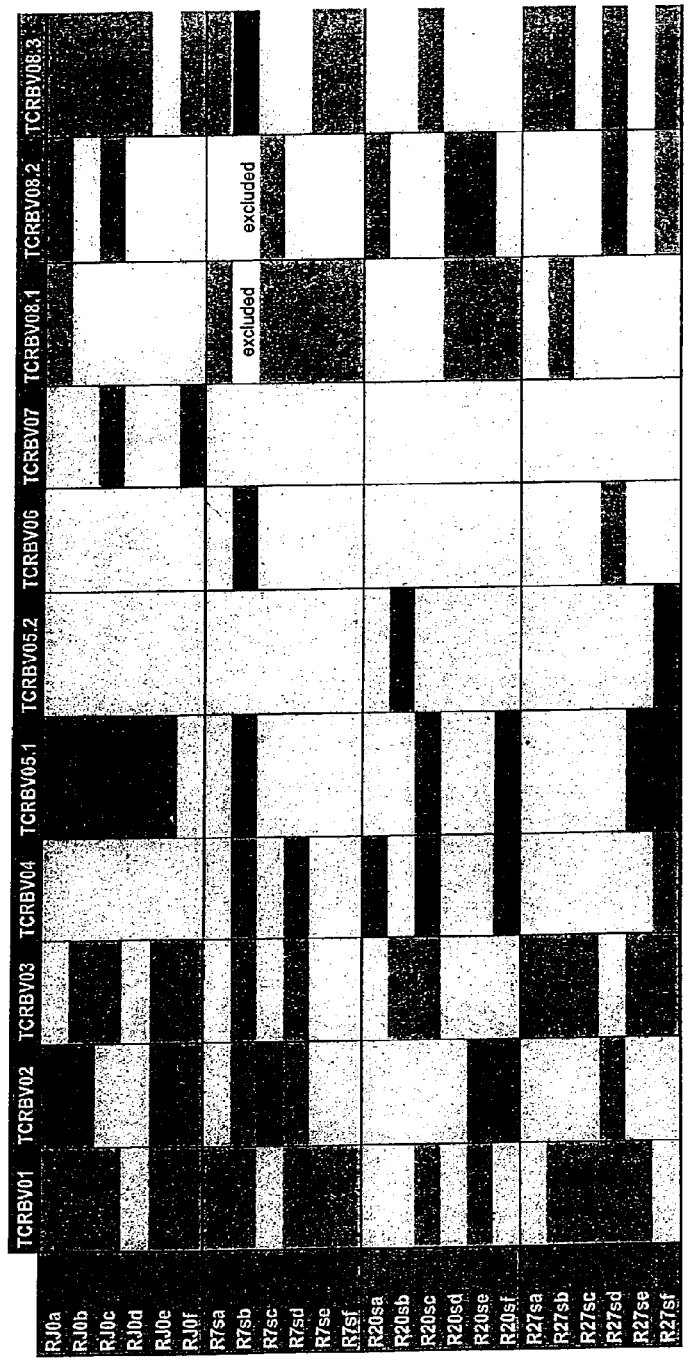
FIG. 55 A. Draw array/parameters.
Figure 57A:
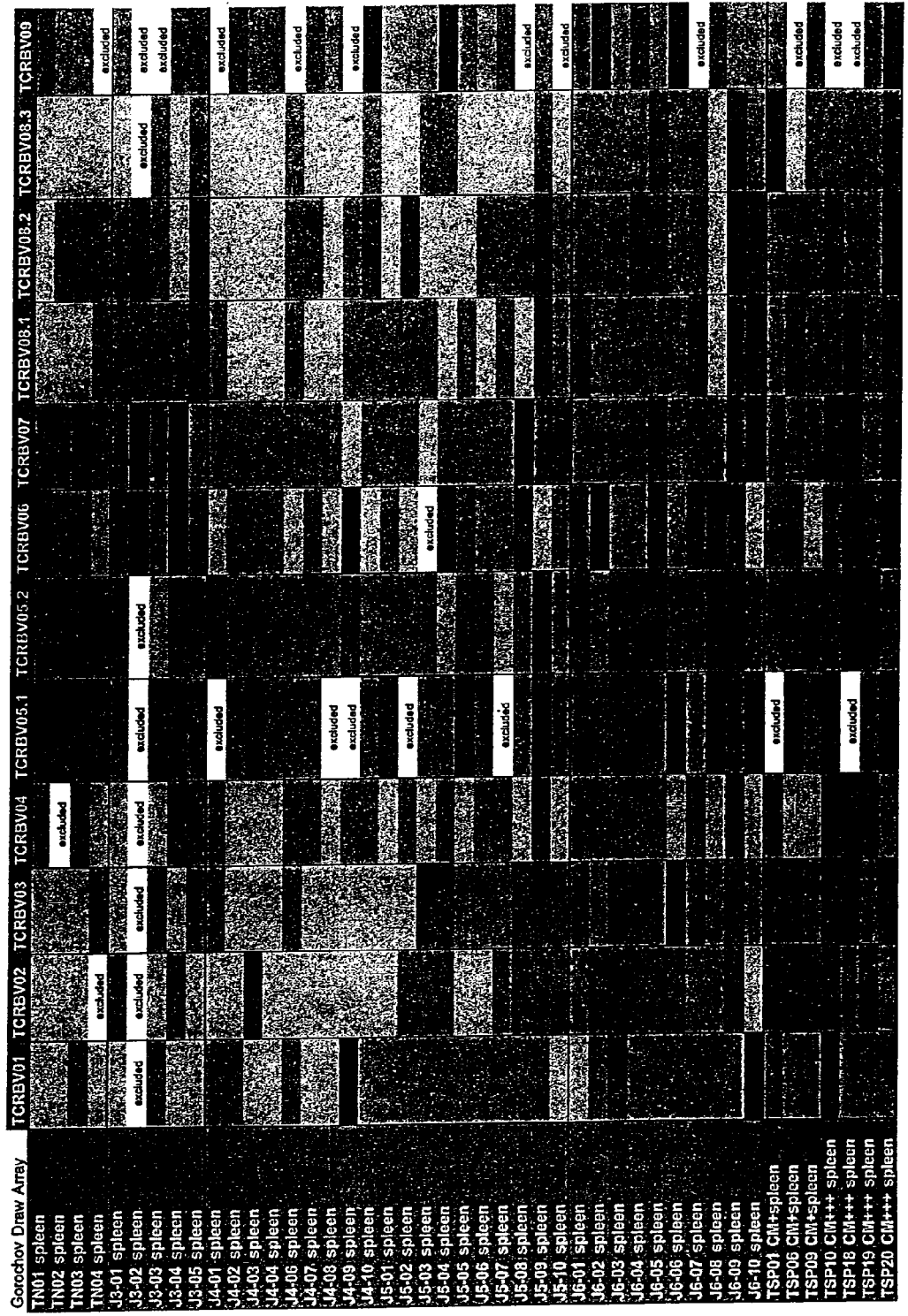
FIG. 57 A. *Plasmodium berghei* infection of B120D2mice.
Figure 57C:
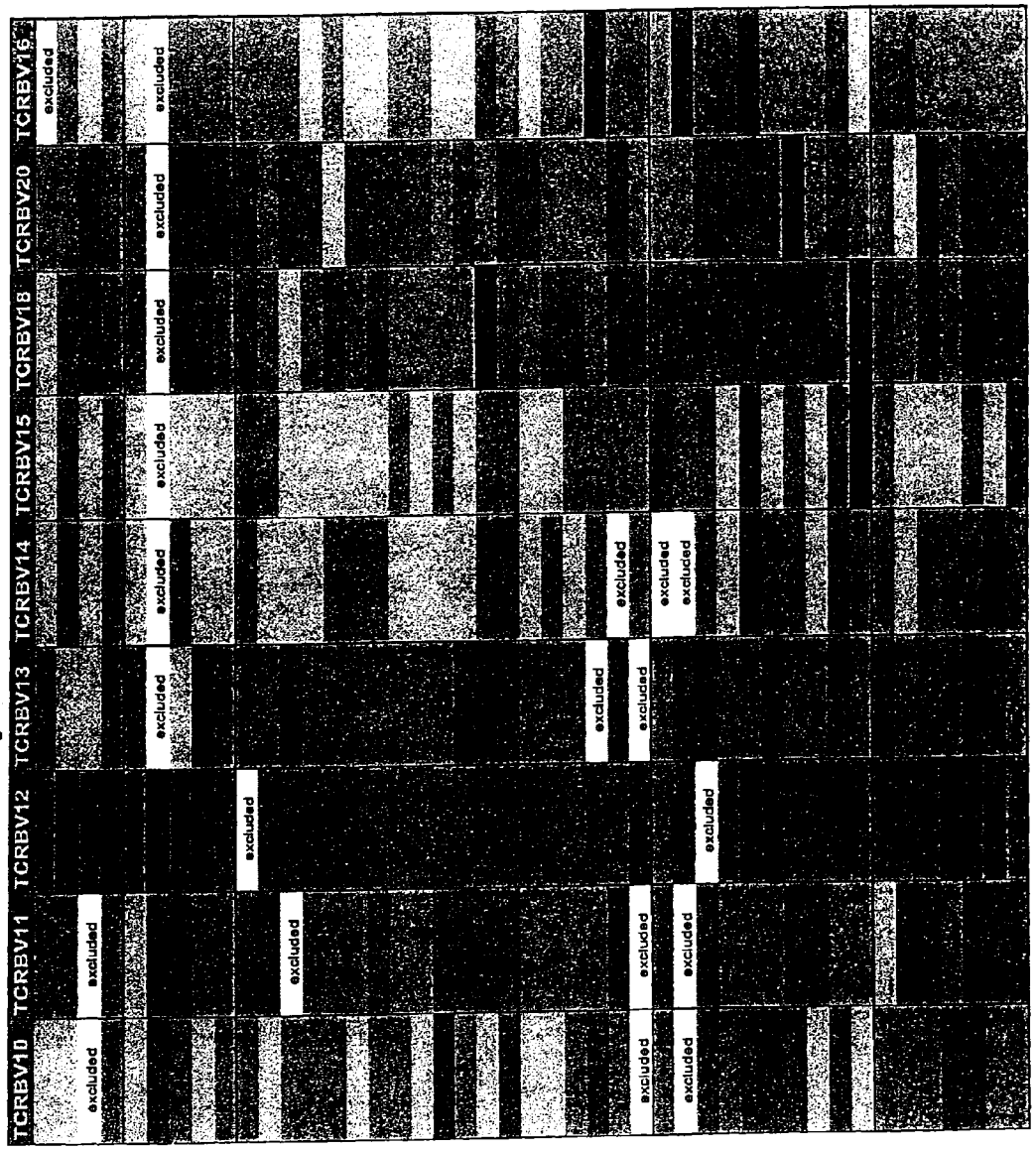
Figure 57D:
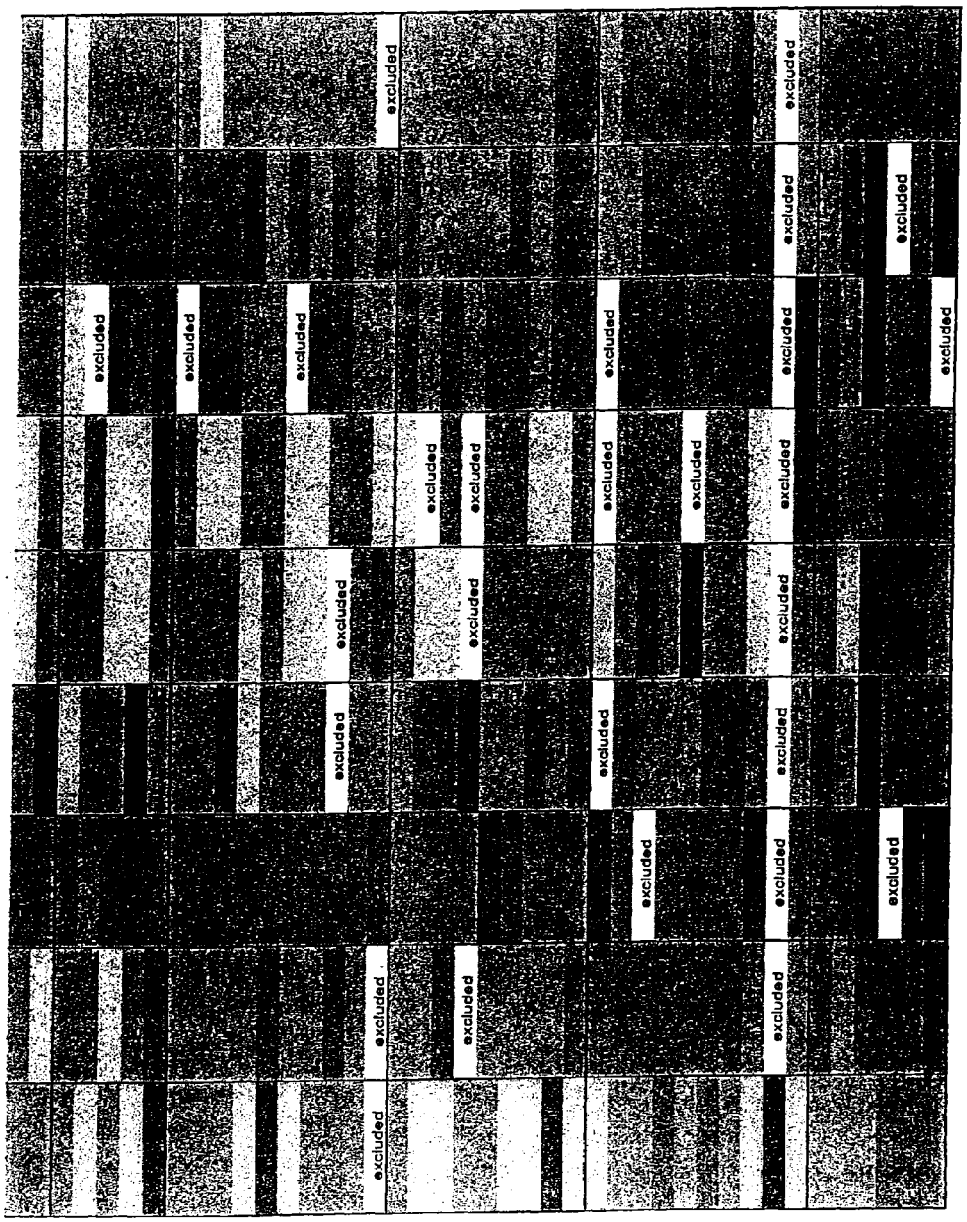
Figure 58C:
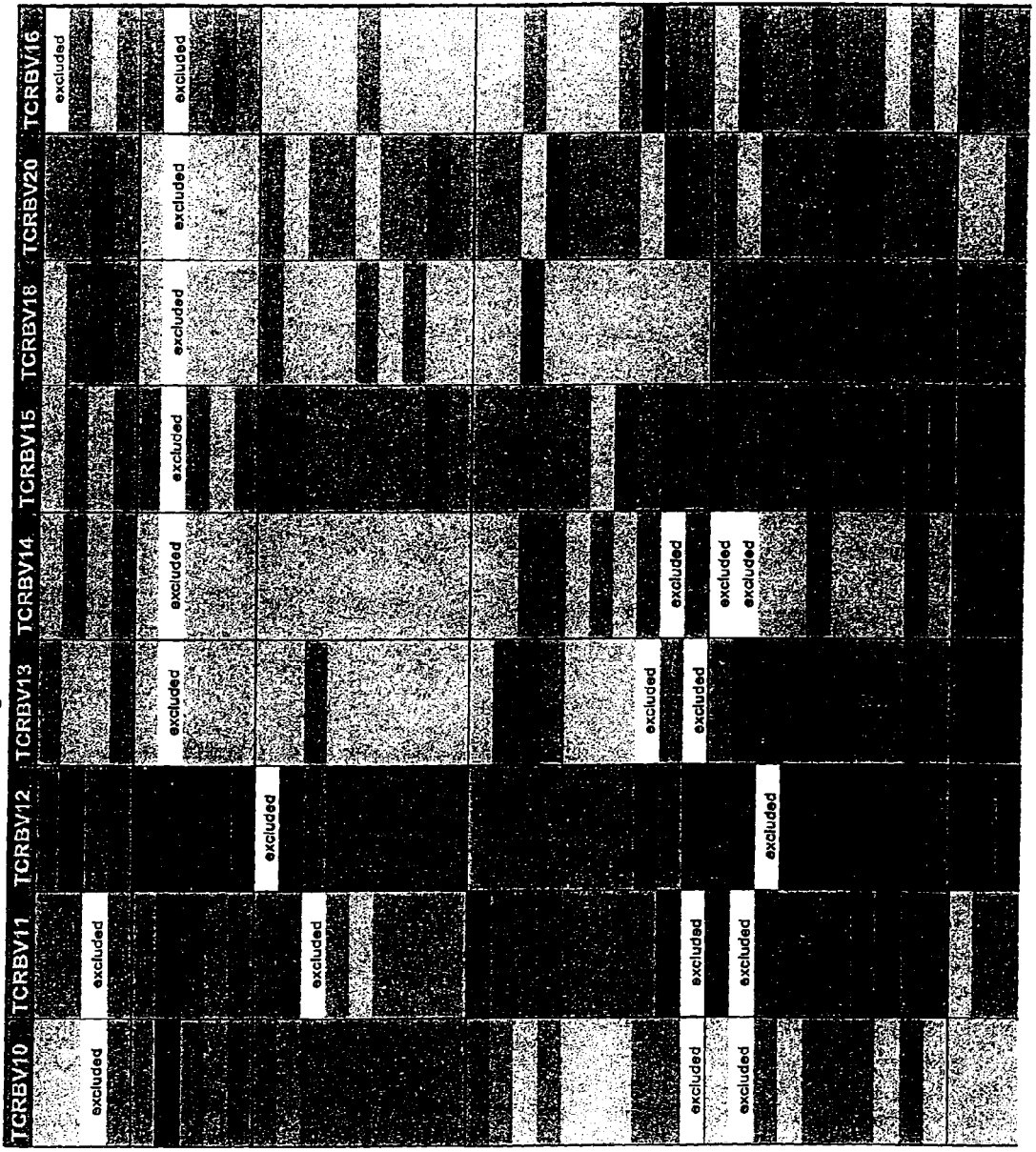
FIG. 58 A. *Plasmodium berghei* infection of B120D2mice.
Figure 58D:
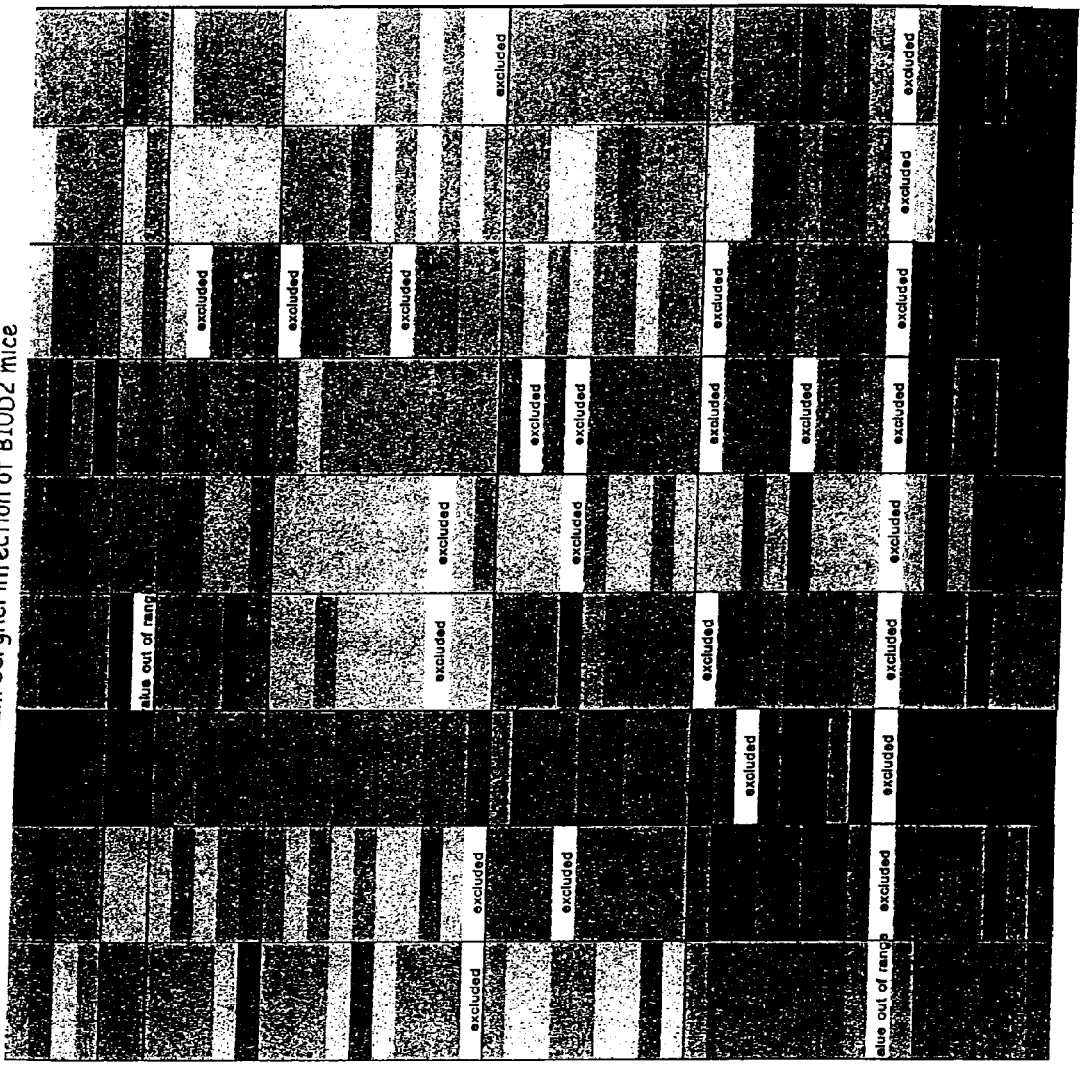
Figures 59B, 59C:
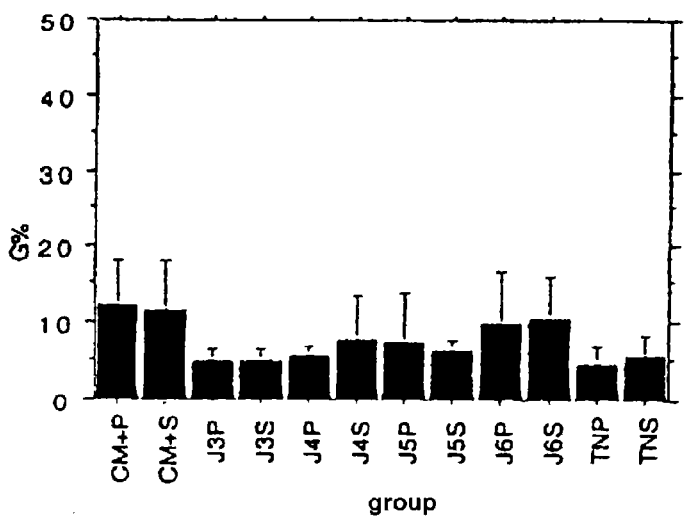
FIG. 59 A. ANOVA (Analysis of Variance) Table for TCRBV01.
Figures 59F, 59G:
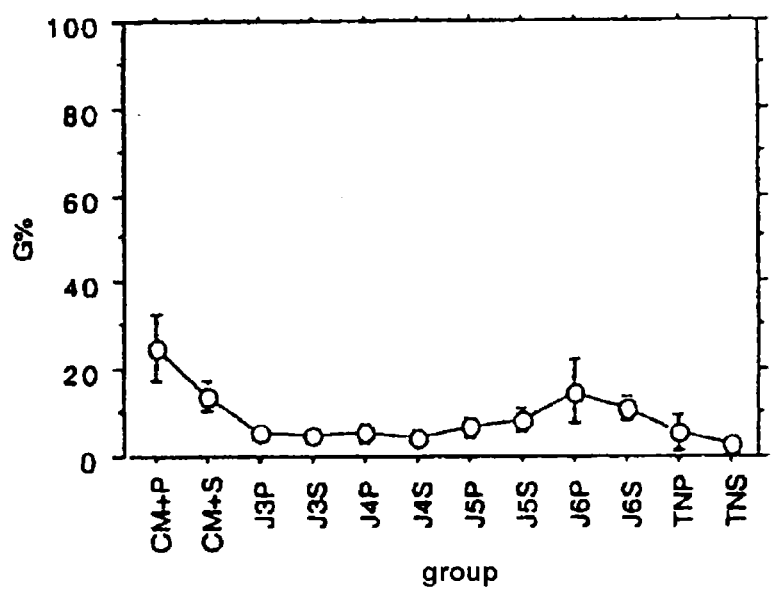
Figures 60B, 60C:
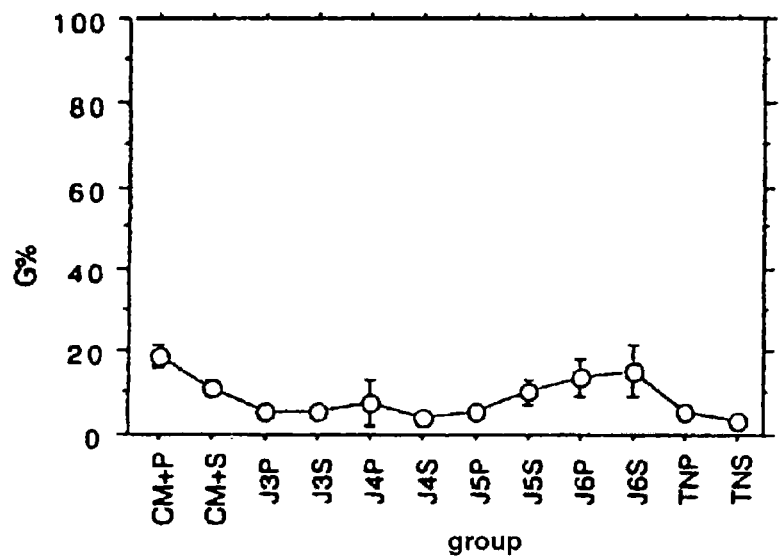
FIG. 60 A. ANOVA Table.
Figures 60F, 60G:
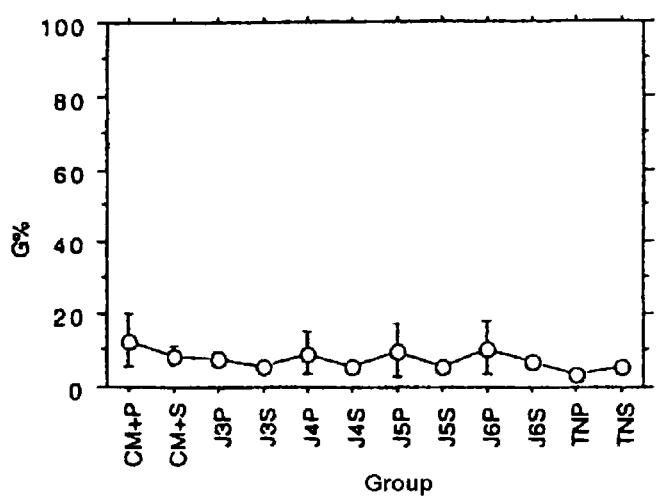
Figures 61B, 61C:
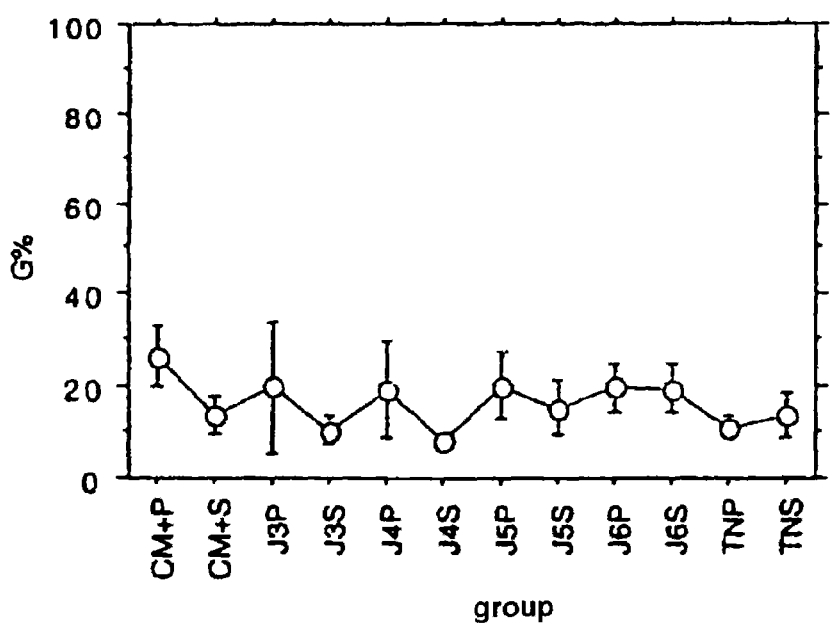
FIG. 61 A. ANOVA Table.
Figures 61F, 61G:
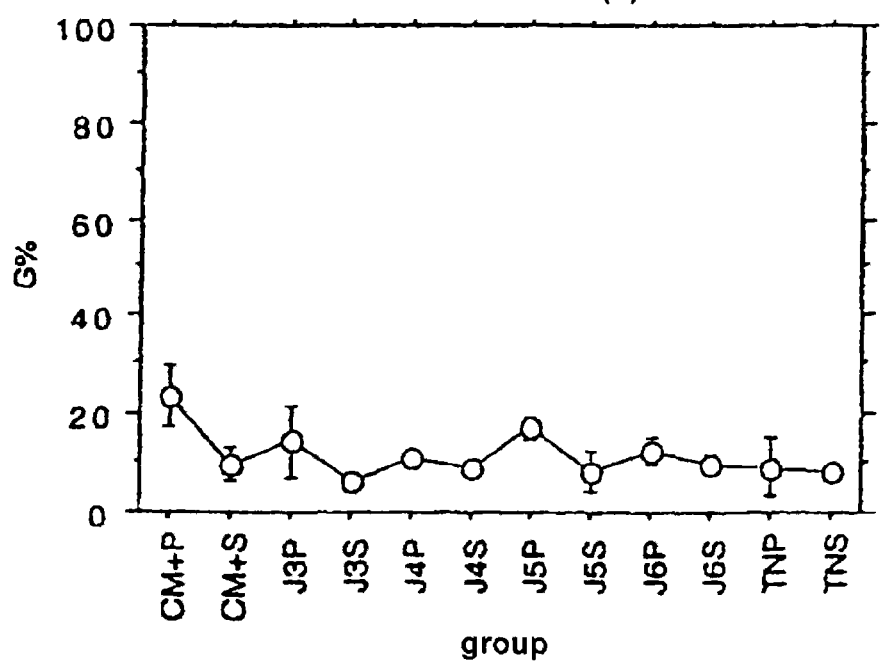
Figures 62B, 62C:
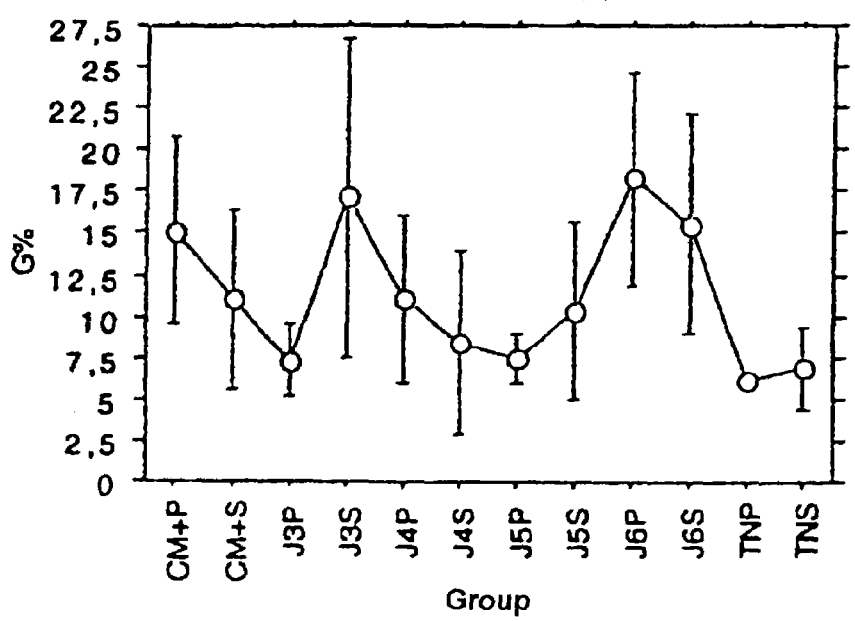
FIG. 62 A. ANOVA Table.
Figures 62F, 62G:
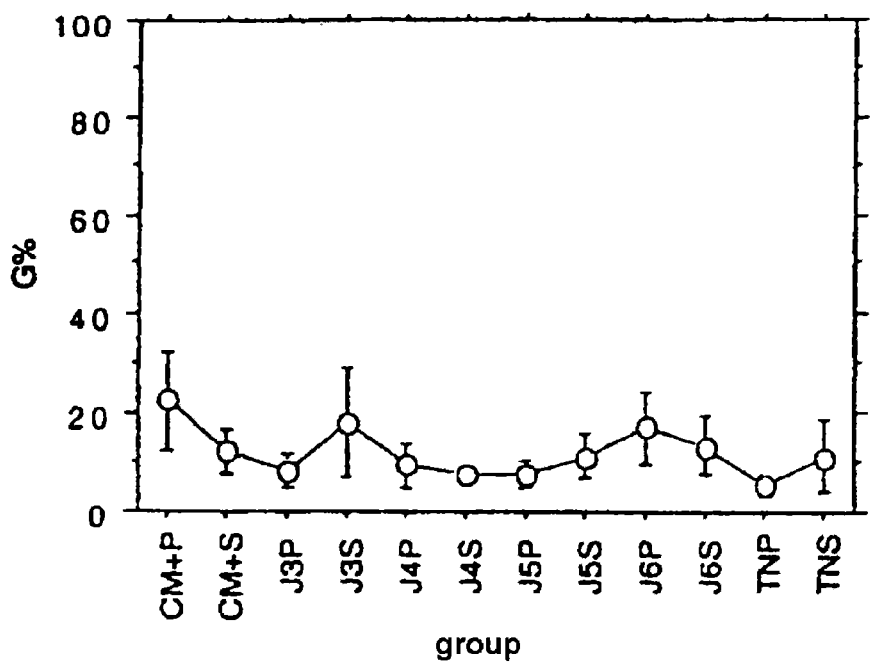
Figures 63B, 63C:
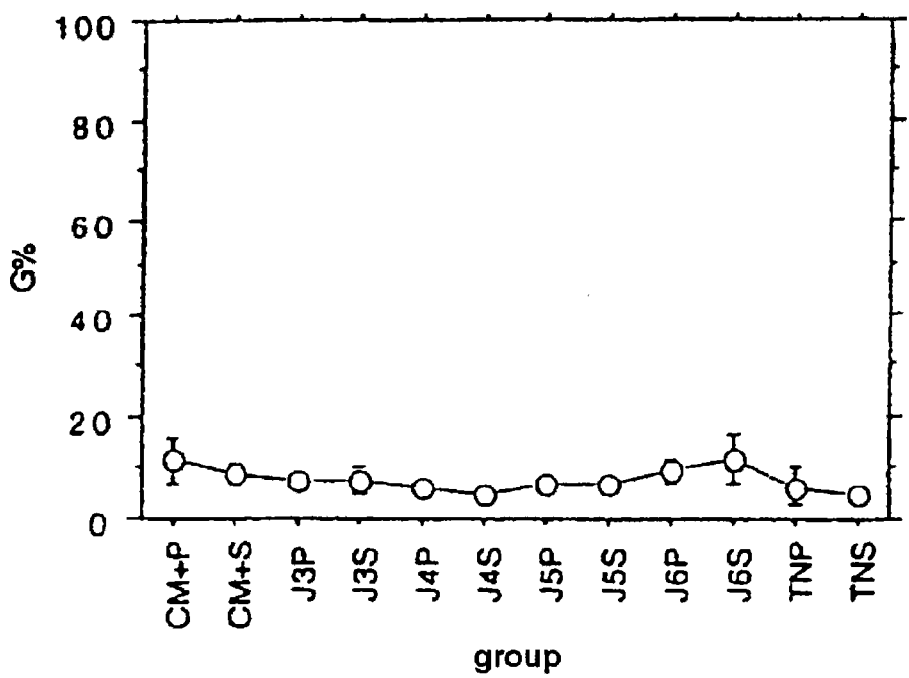
FIG. 63 A. ANOVA Table.
Figures 63F, 63G:
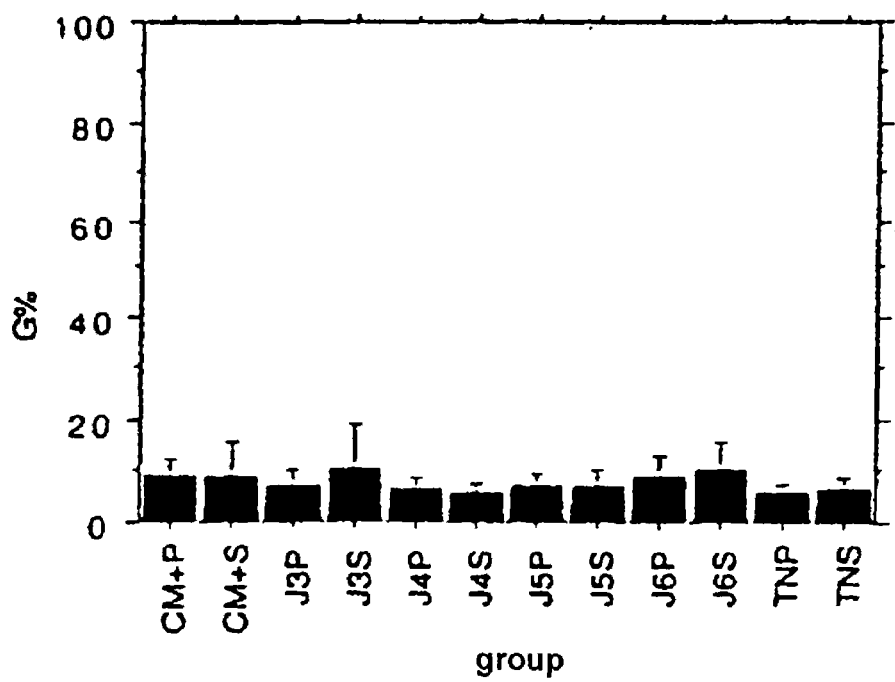
Figures 64B, 64C:
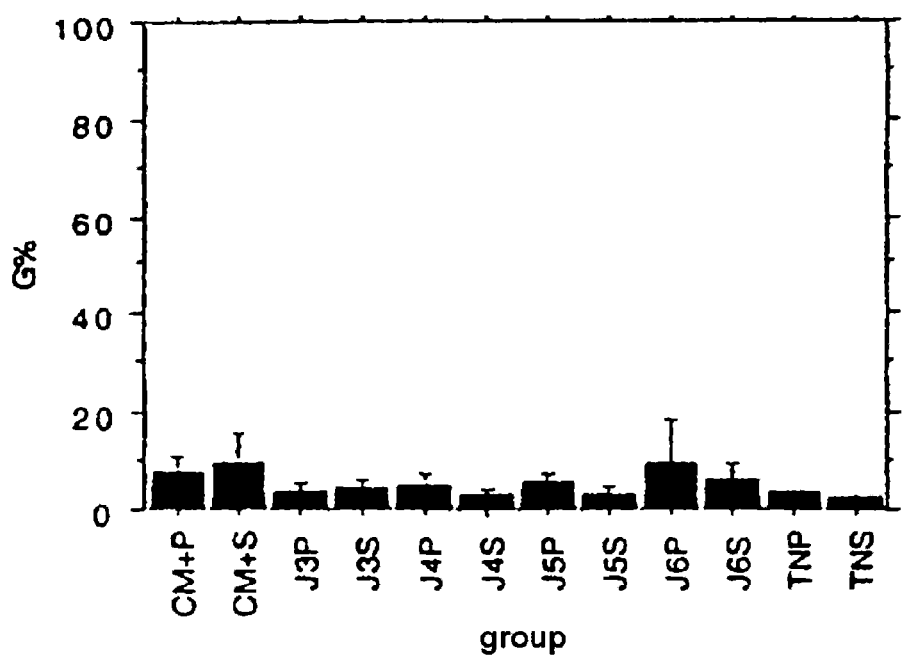
FIG. 64 A. ANOVA Table.
Figures 64F, 64G:
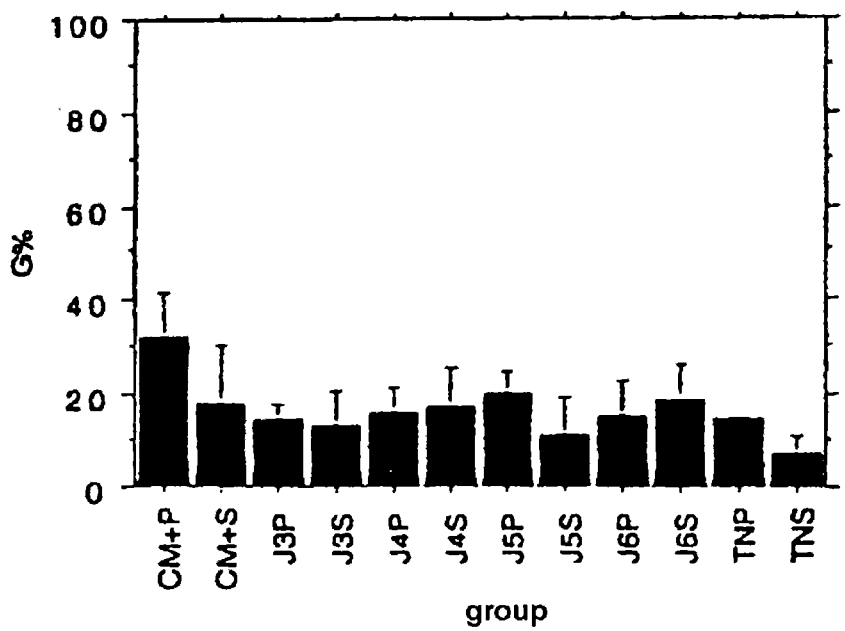
Figures 65B, 65C:
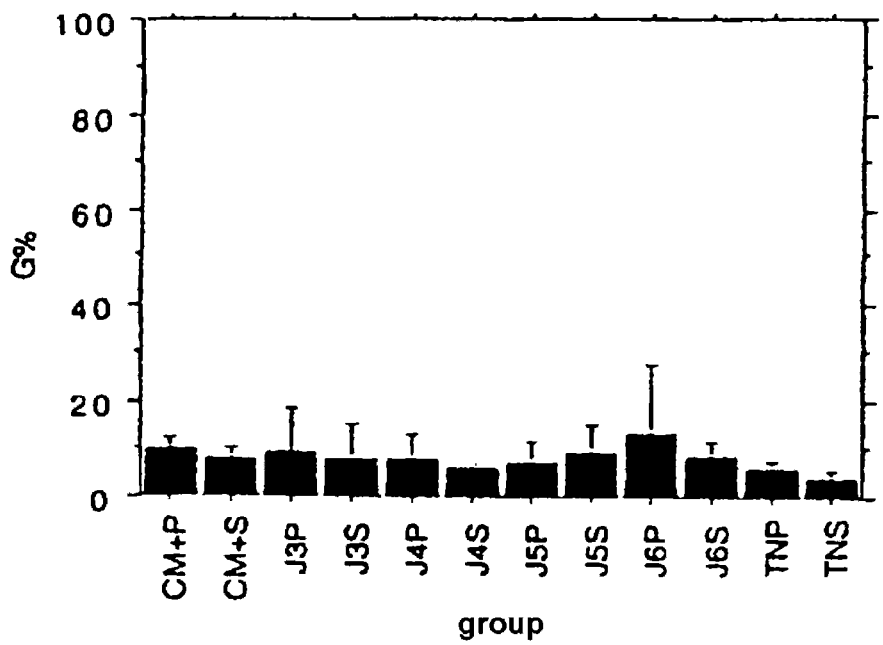
FIG. 65 A. ANOVA Table.
Figures 65F, 65G:
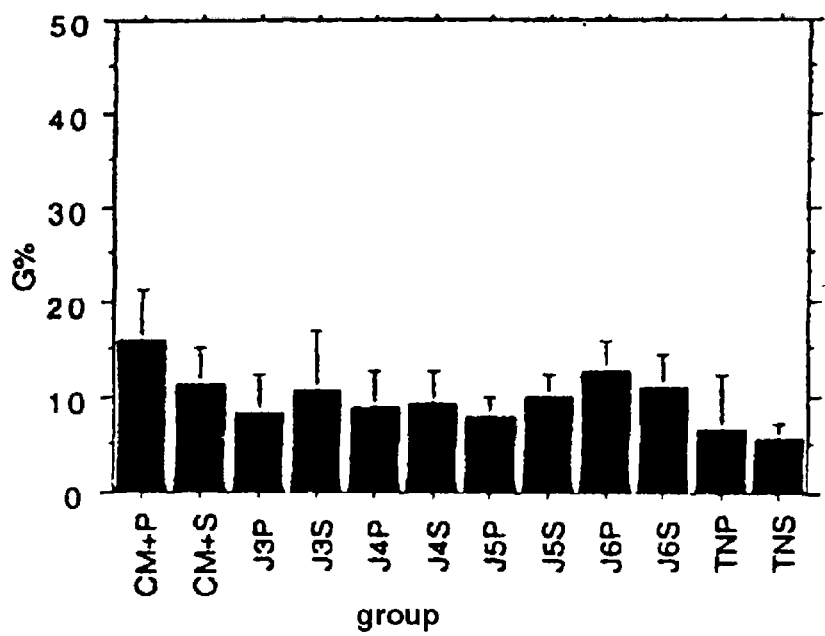
Figures 66B, 66C:
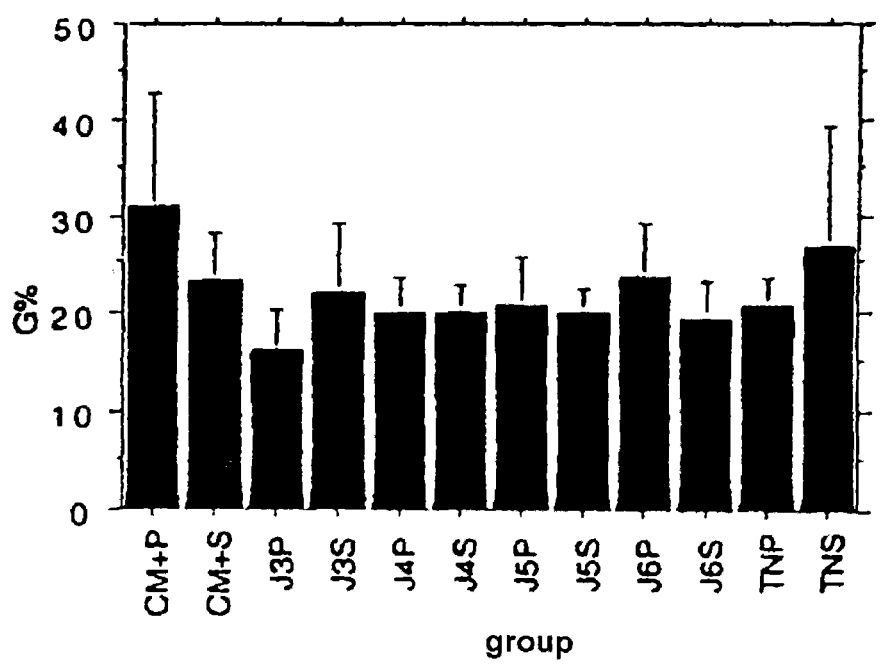
FIG. 66 A. ANOVA Table.
Figures 66F, 66G:
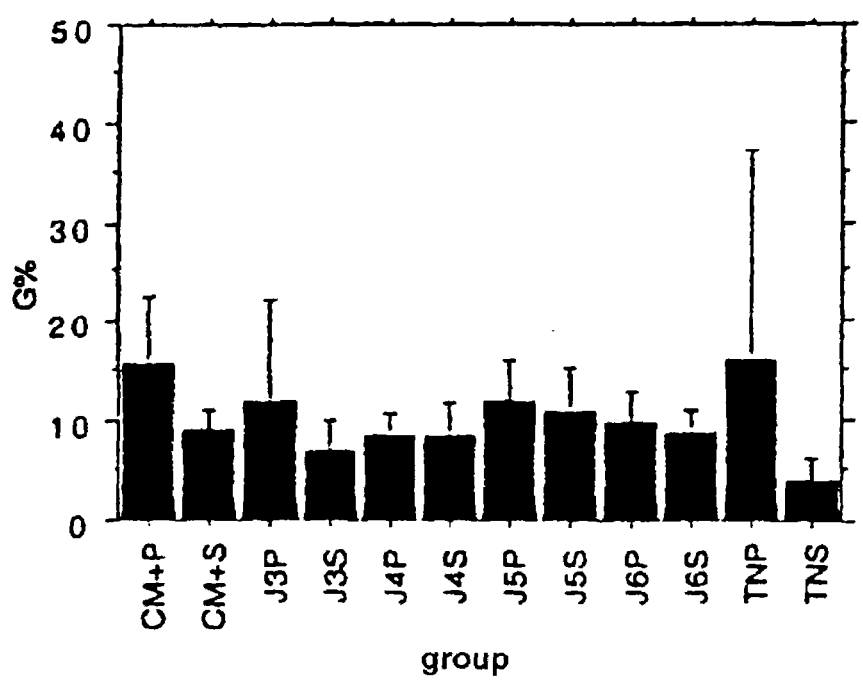
Figures 67B, 67C:
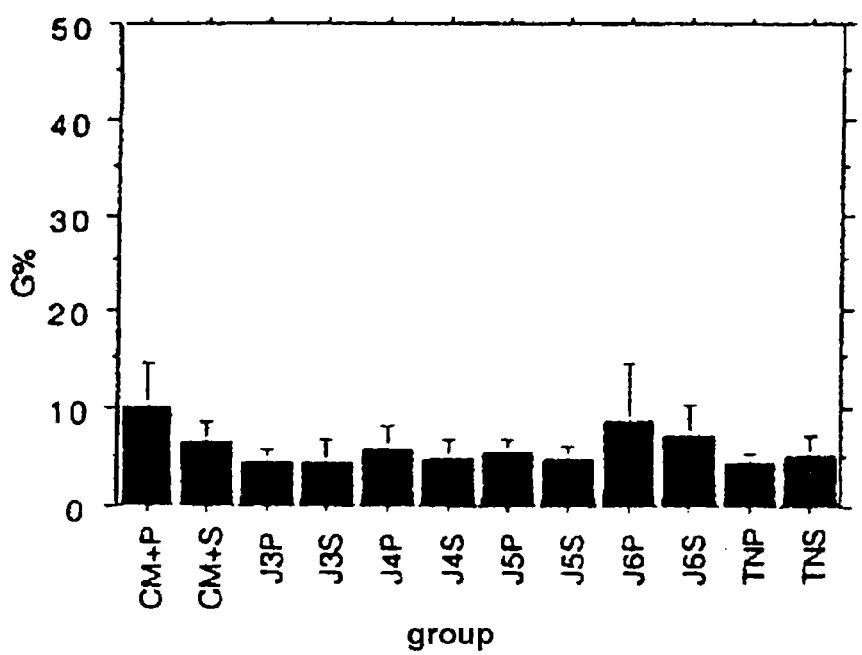
FIG. 67 A. ANOVA Table.
Figures 67F, 67G:
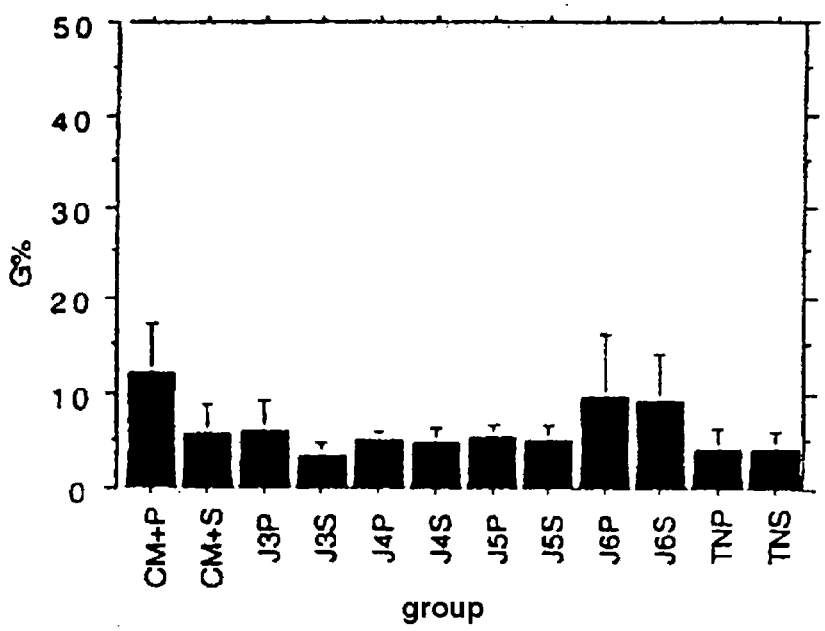
Figures 68B, 68C:
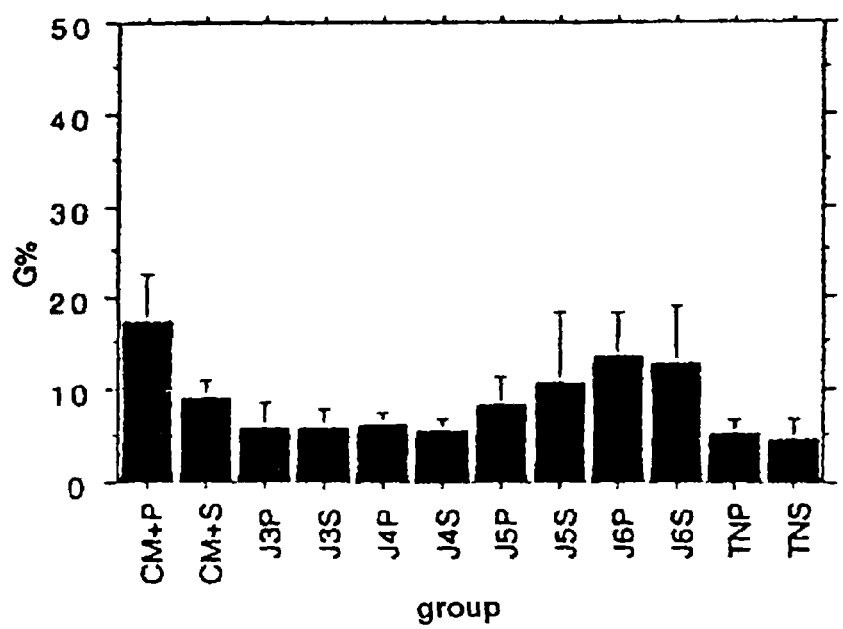
FIG. 68 A. ANOVA Table.
Figures 68F, 68G:
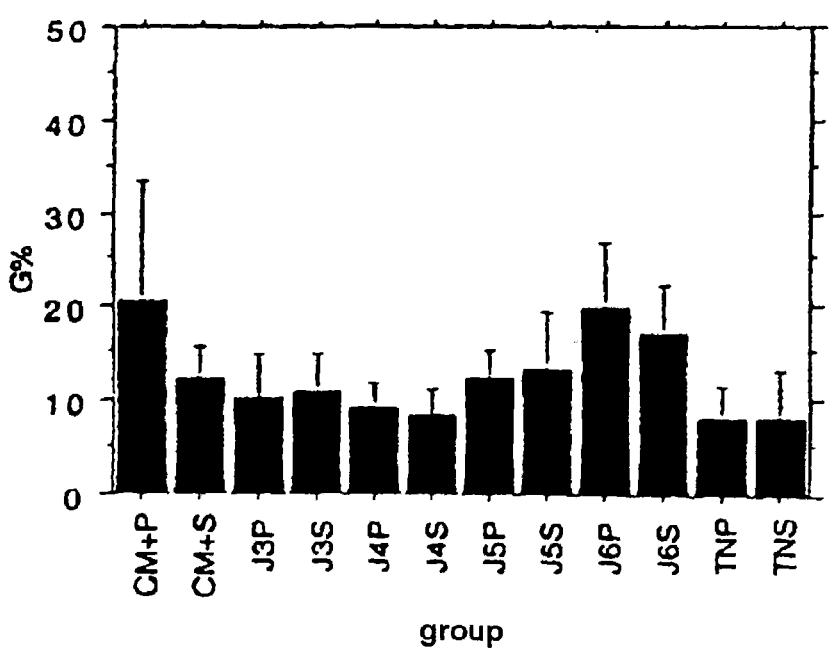
Figures 69B, 69C:
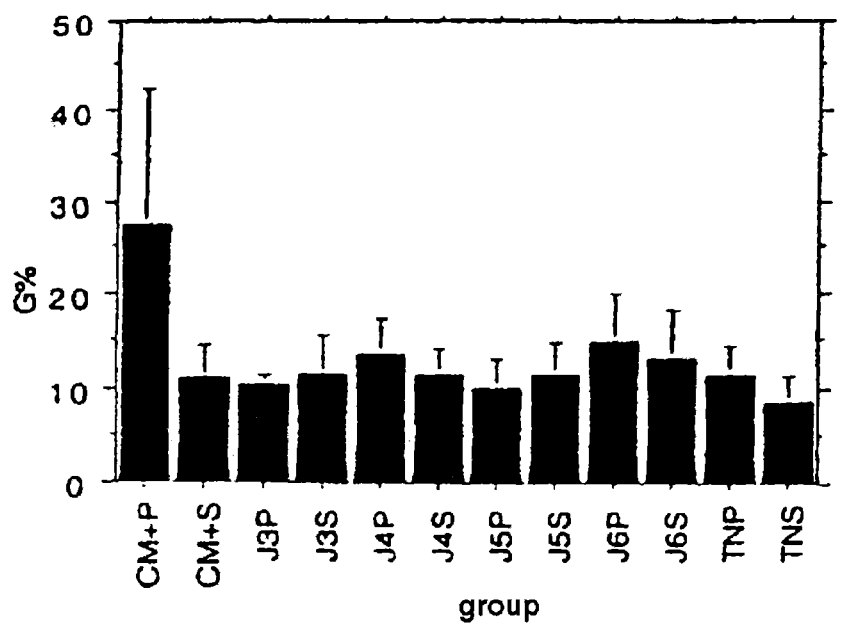
FIG. 69 A. ANOVA Table.
Figures 70B, 70C:
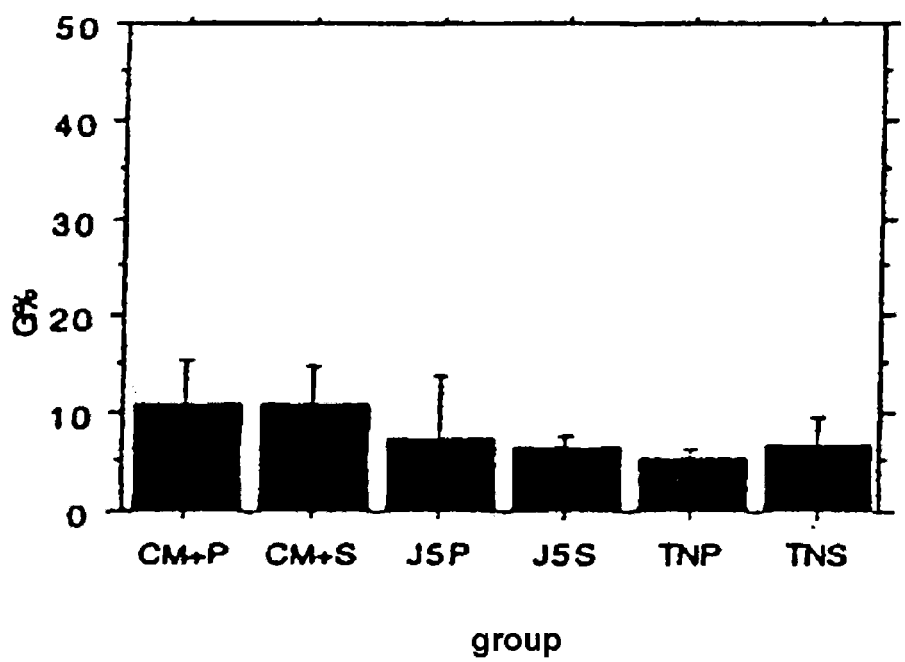
FIG. 70 A. ANOVA Table.
Figures 70F, 70G:
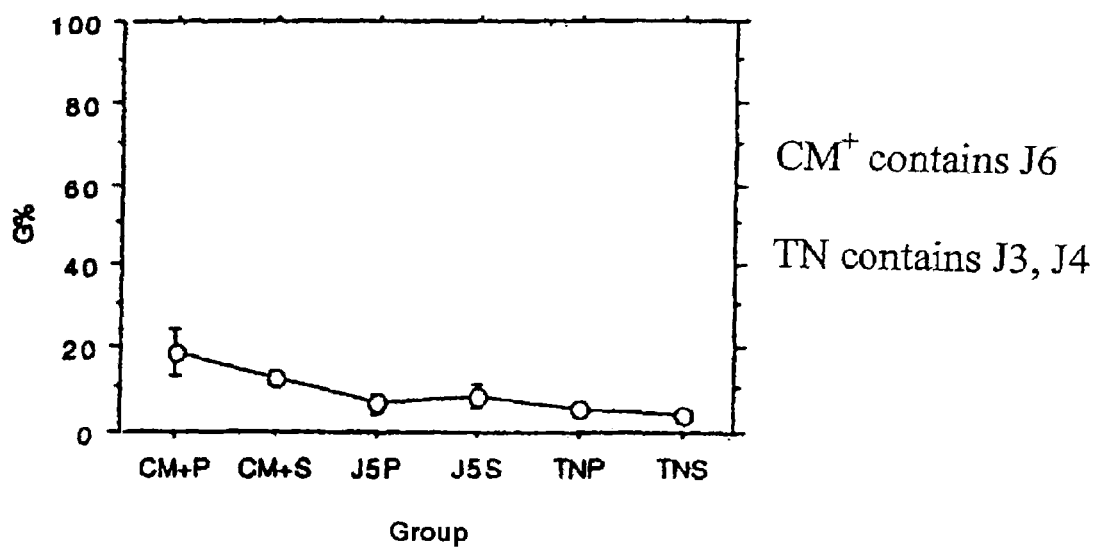
Figures 71B, 71C:
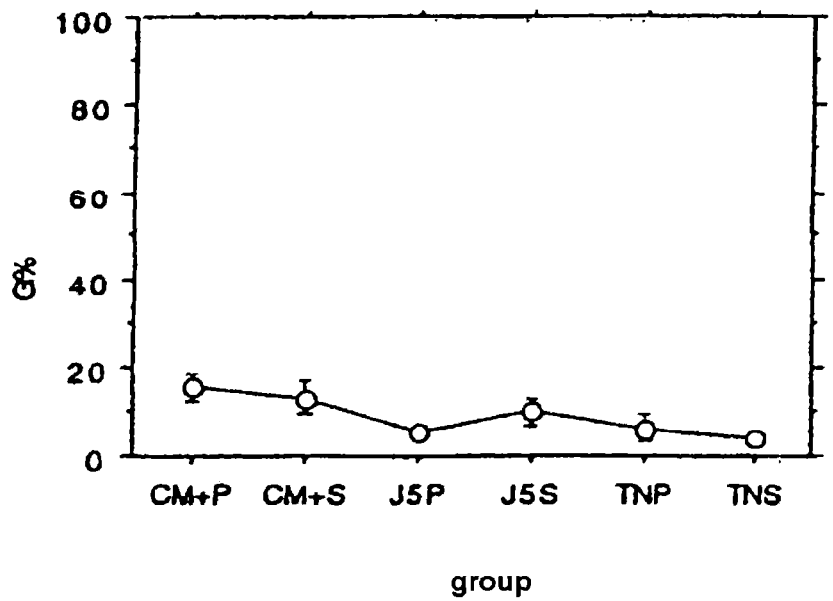
FIG. 71 A. ANOVA Table.
Figures 71F, 71G:
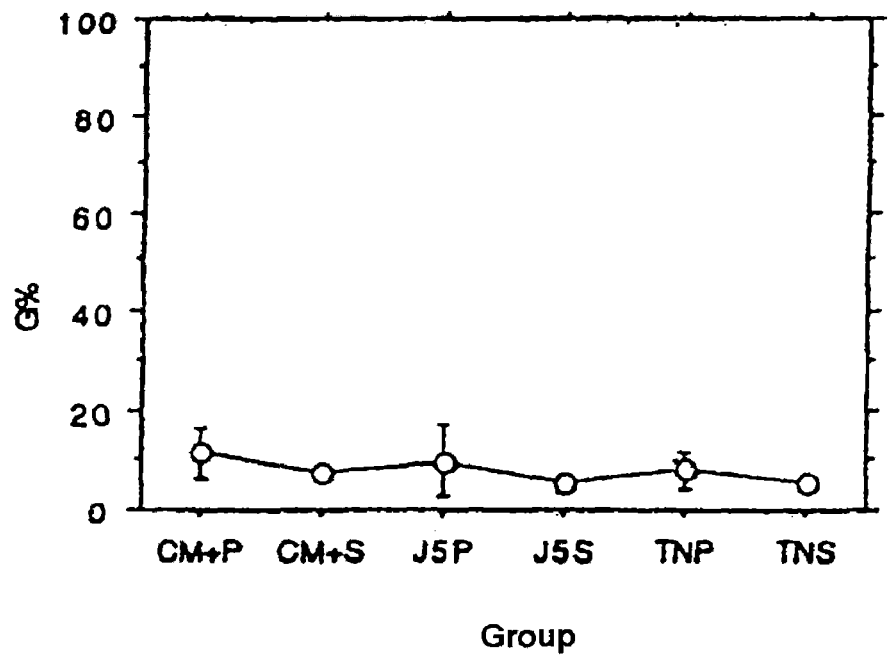
Figures 72B, 72C:
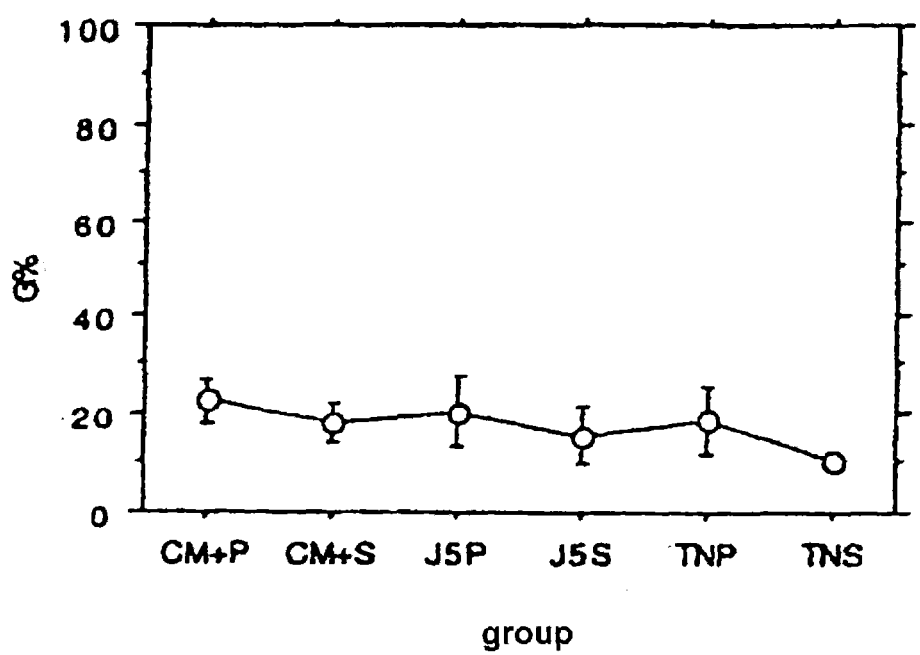
FIG. 72 A. ANOVA Table.
Figures 72F, 72G:
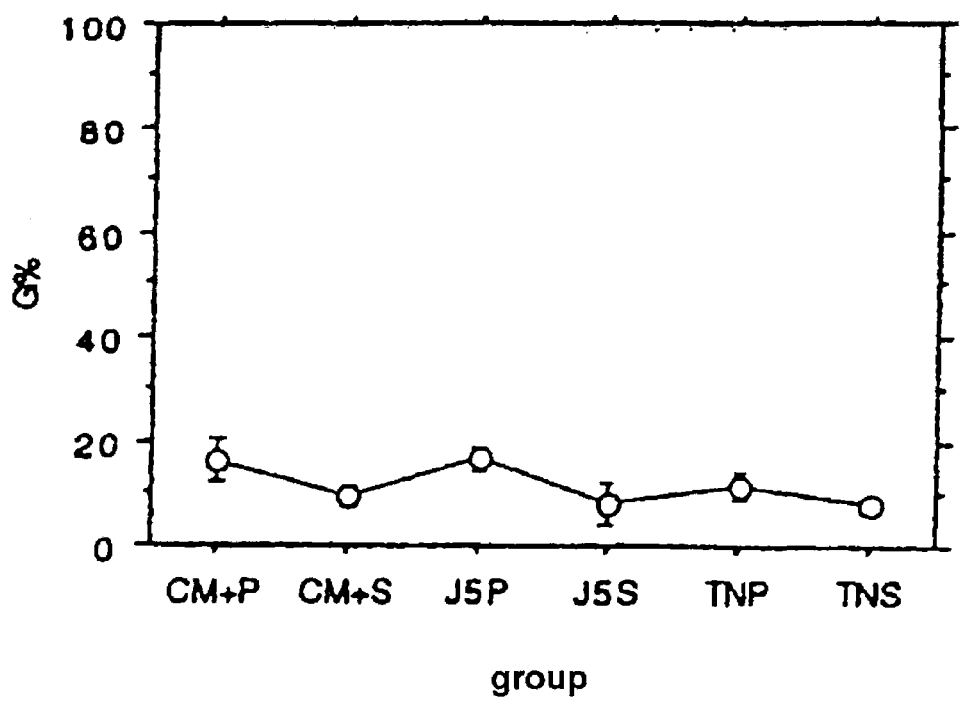
Figures 73B, 73C:
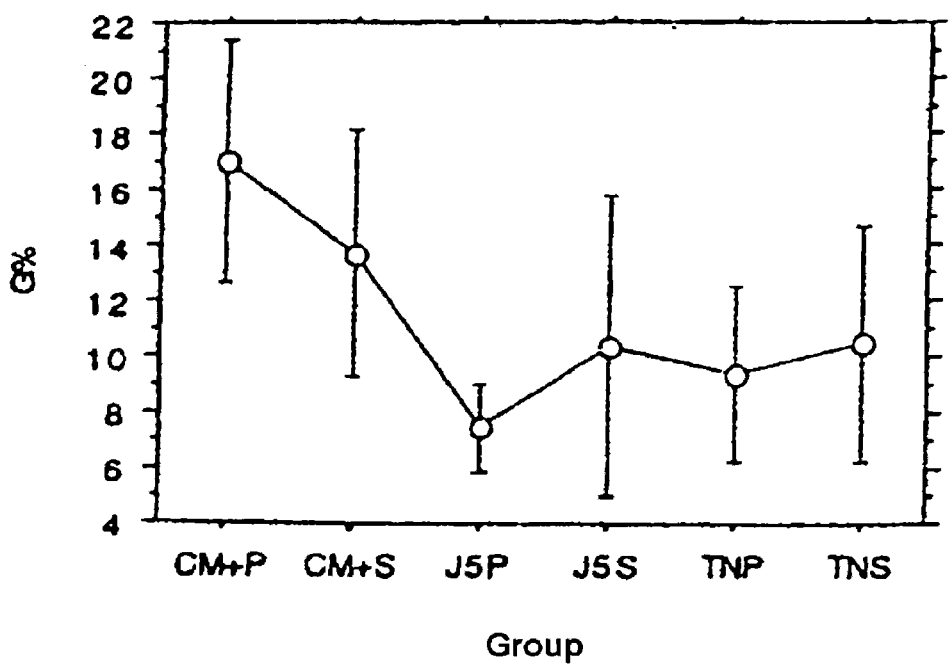
FIG. 73 A. ANOVA Table.
Figures 73F, 73G:
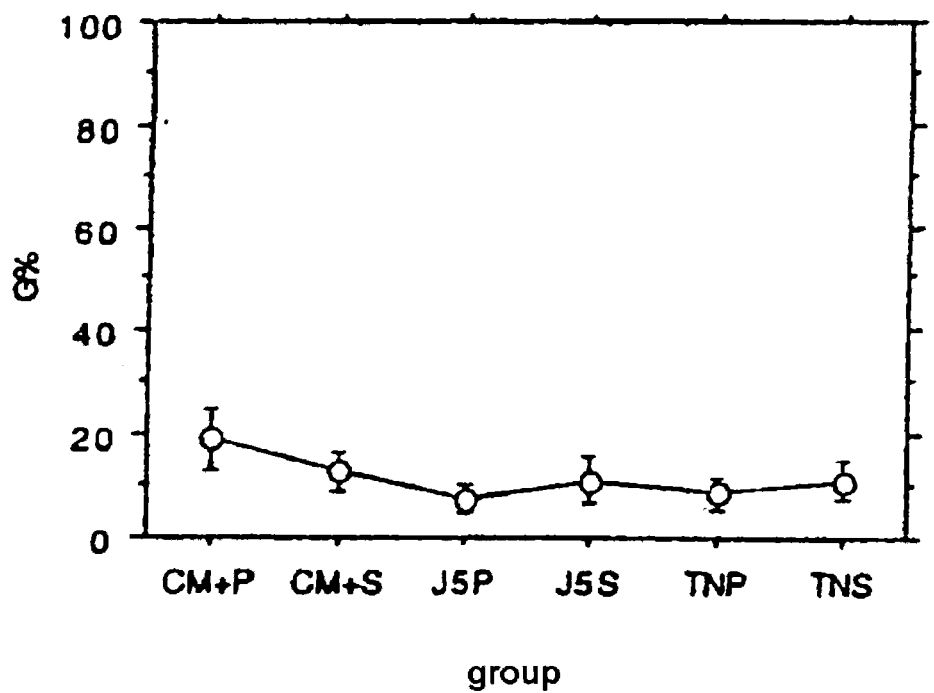
Figures 74B, 74C:
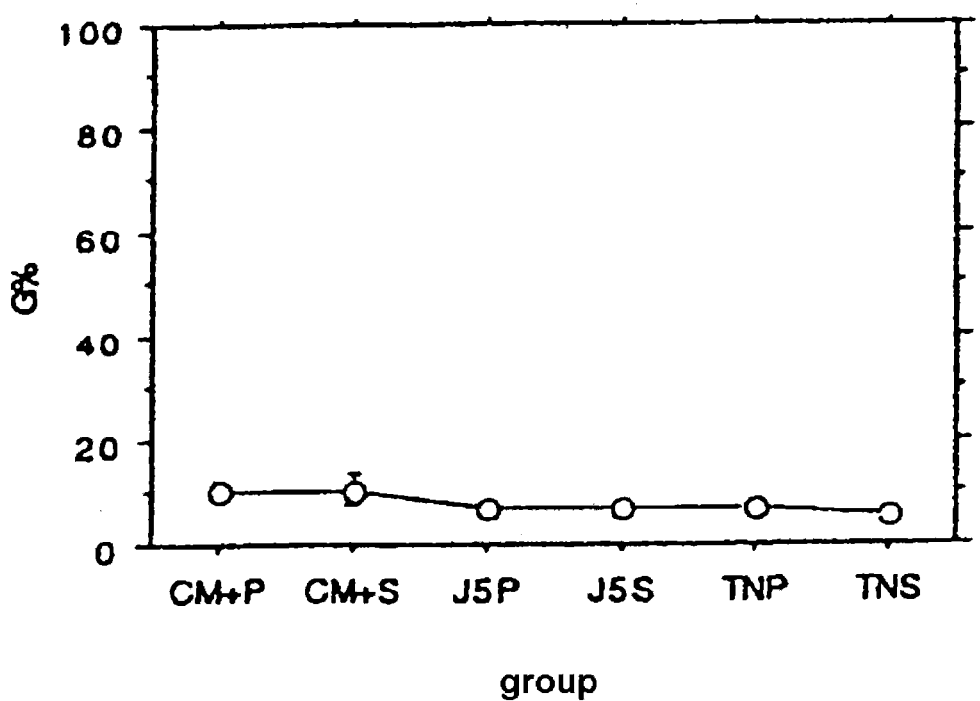
FIG. 74 A. ANOVA Table.
Figures 74F, 74G:
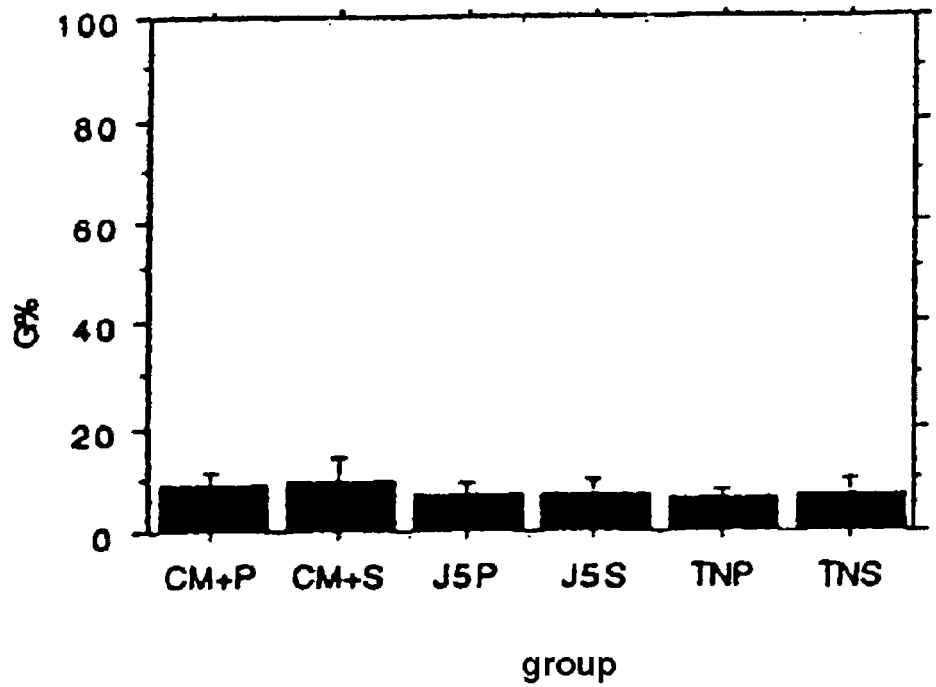
Figures 75B, 75C:
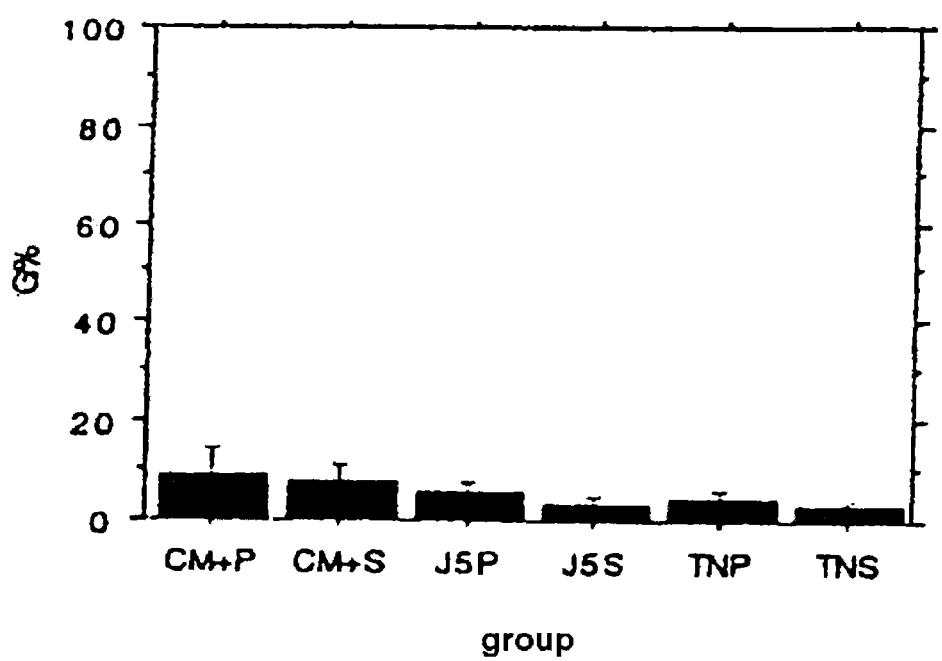
FIG. 75 A. ANOVA Table.
Figures 75F, 75G:
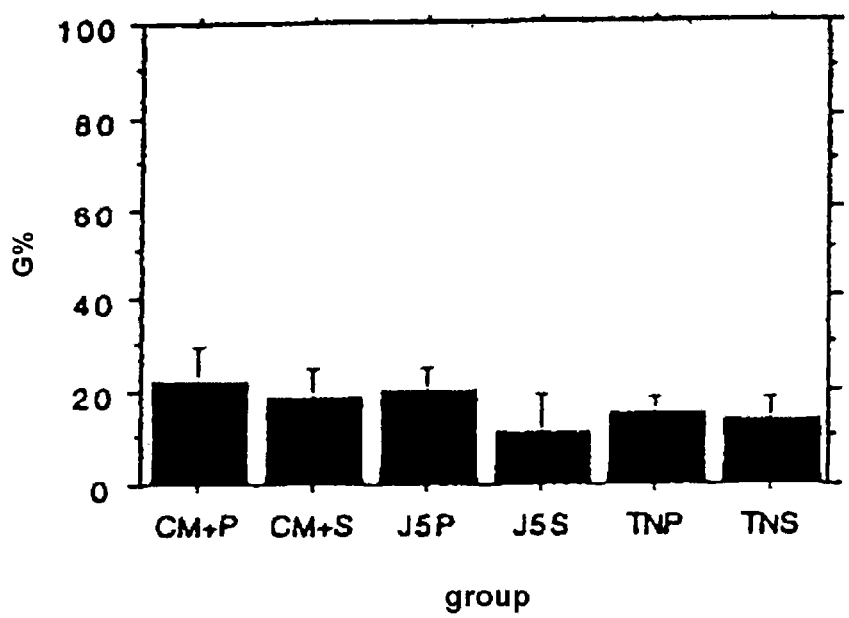
Figures 76B, 76C:
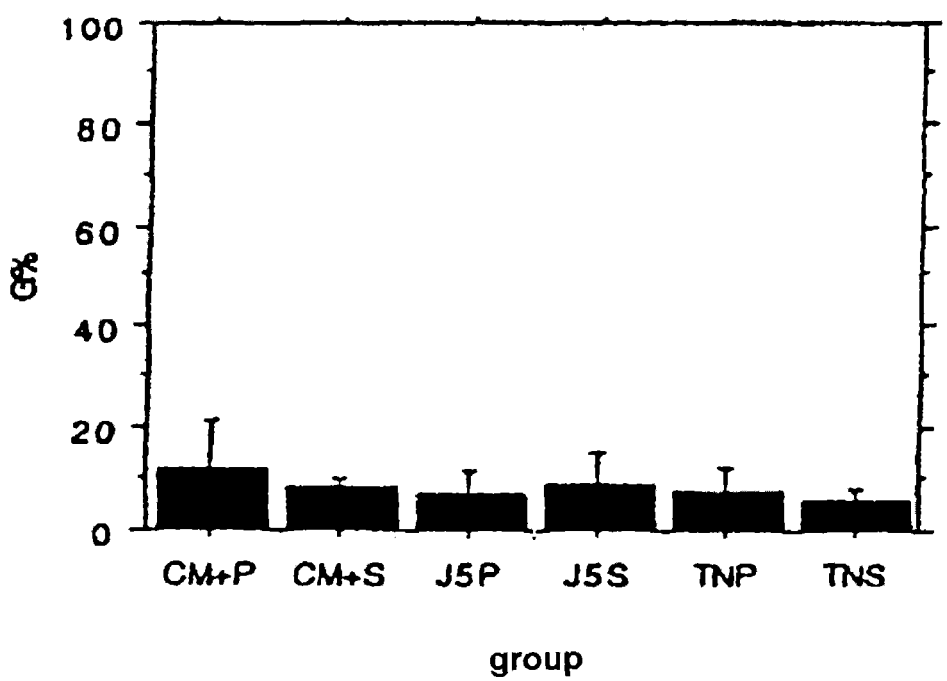
FIG. 76 A. ANOVA Table.
Figures 76F, 76G:
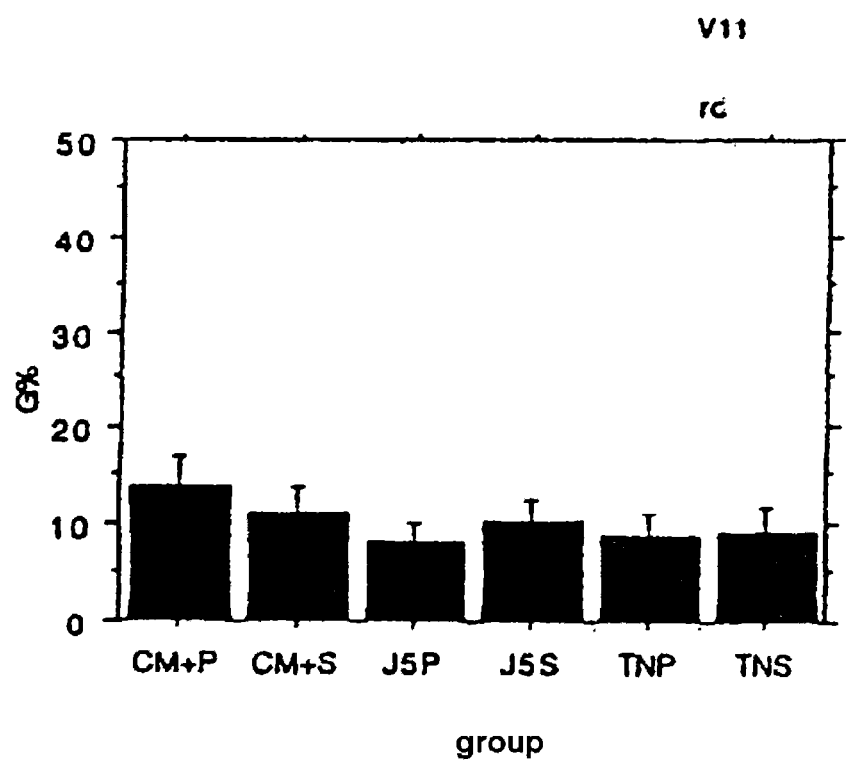
Figures 77B, 77C:
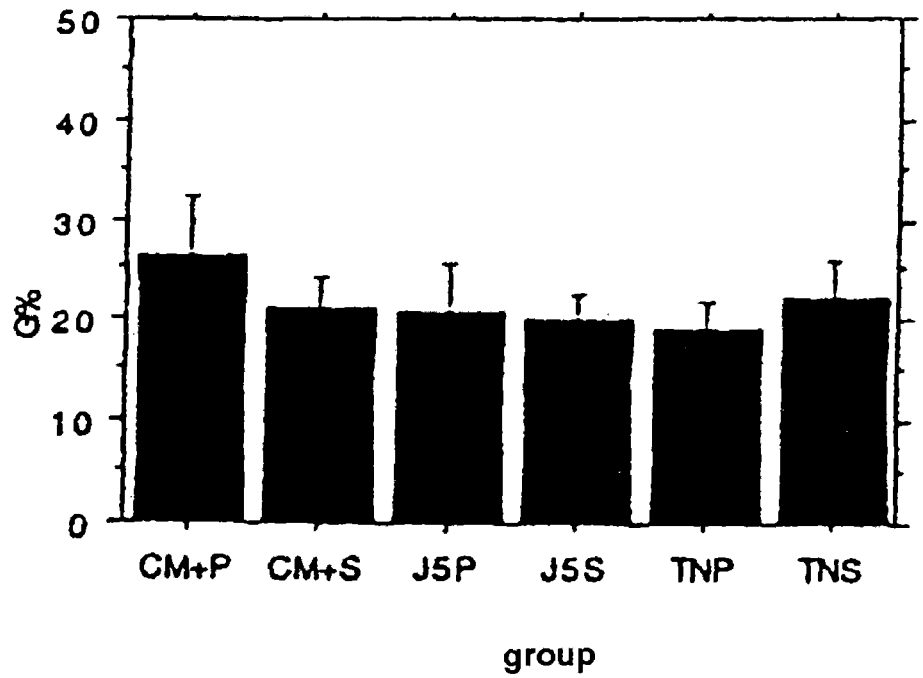
FIG. 77 A. ANOVA Table.
Figures 77F, 77G:
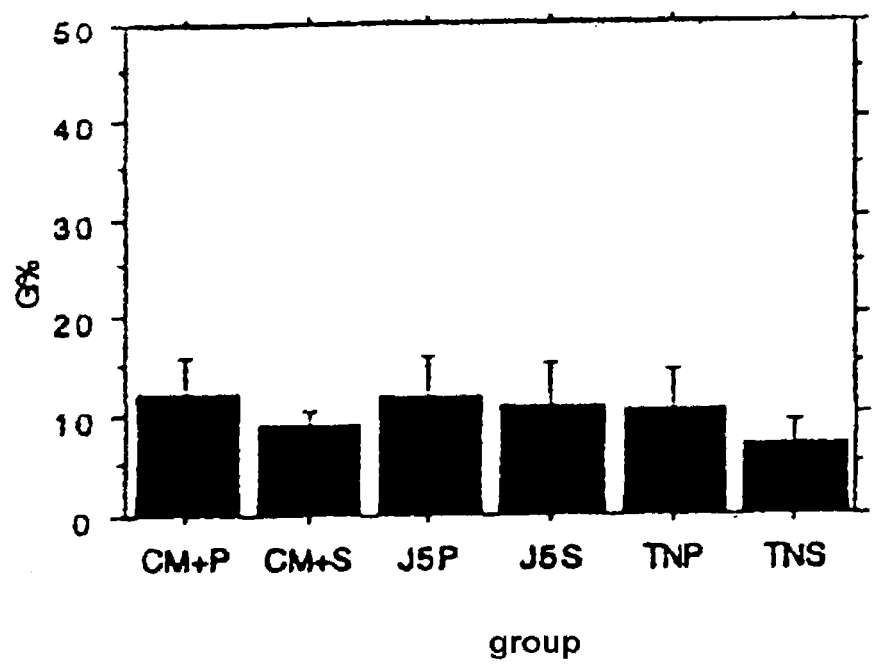
Figures 78B, 78C:
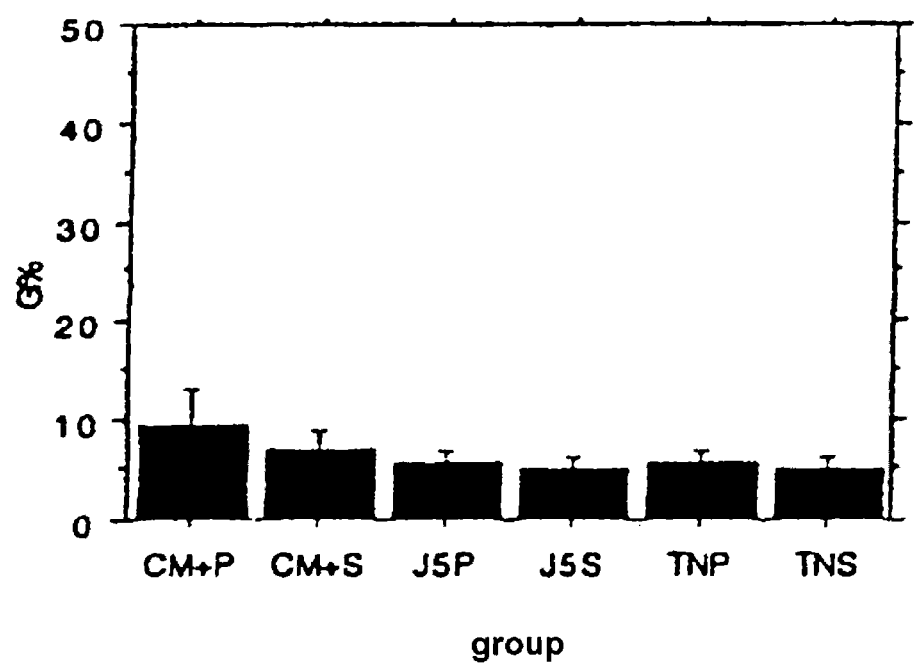
FIG. 78 A. ANOVA Table.
Figures 78F, 78G:
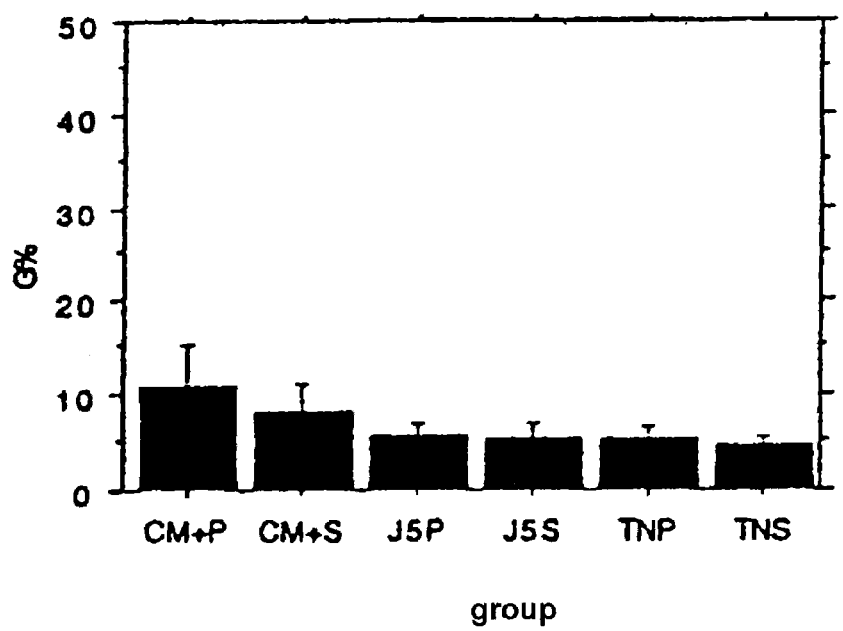
Figures 79B, 79C:
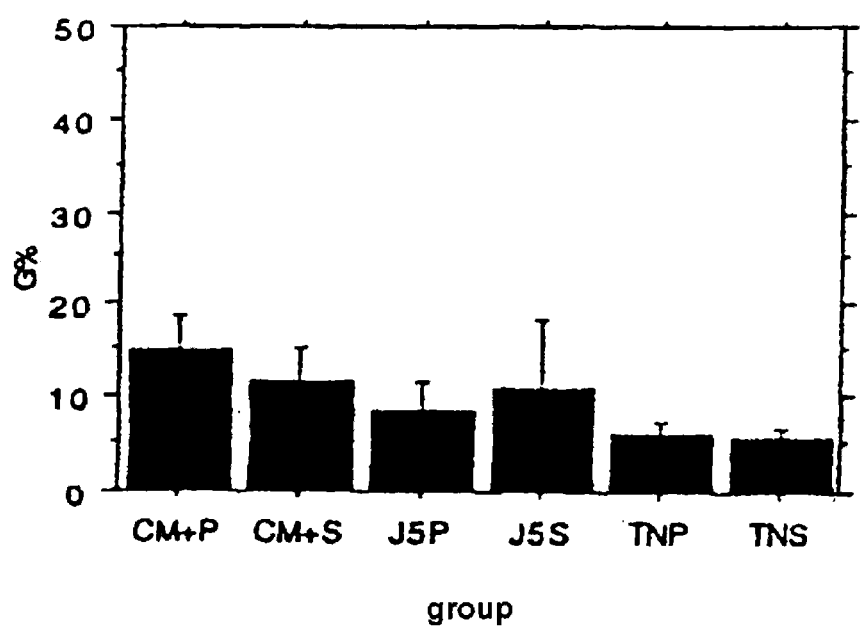
FIG. 79 A. ANOVA Table.
Figures 79F, 79G:
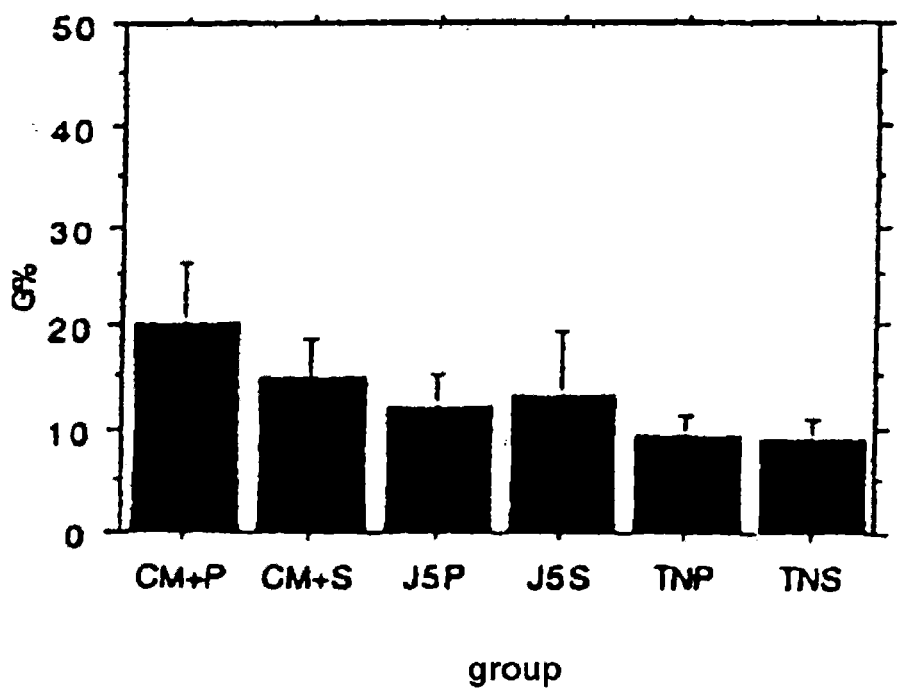
Figure 80B:
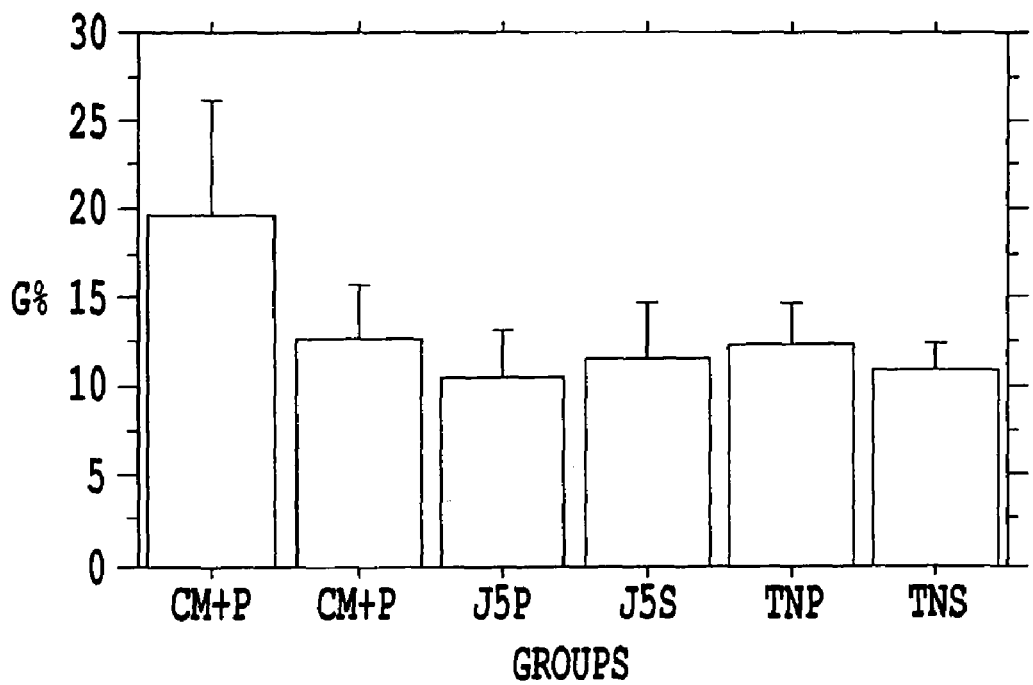
FIG. 80 A. ANOVA Table & Fisher's PLSD Test for TCRBV20.
Figure 86:
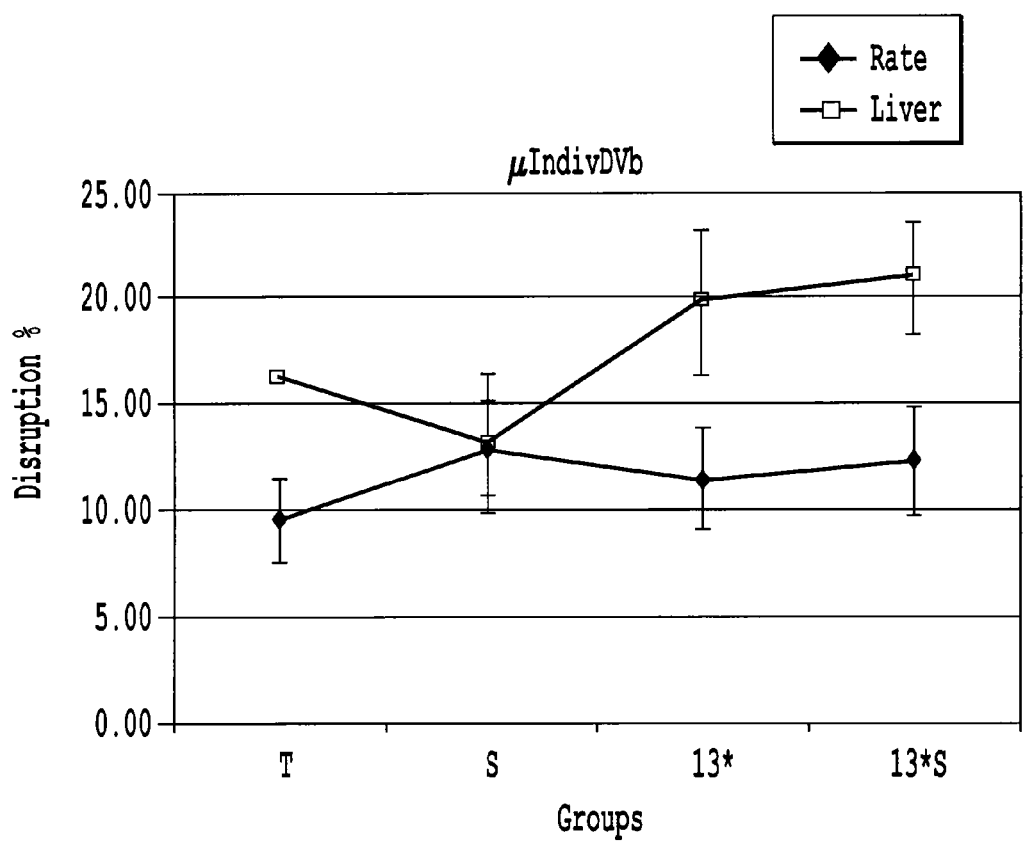
FIG. 86. µIndivDVb.
Figure 87:
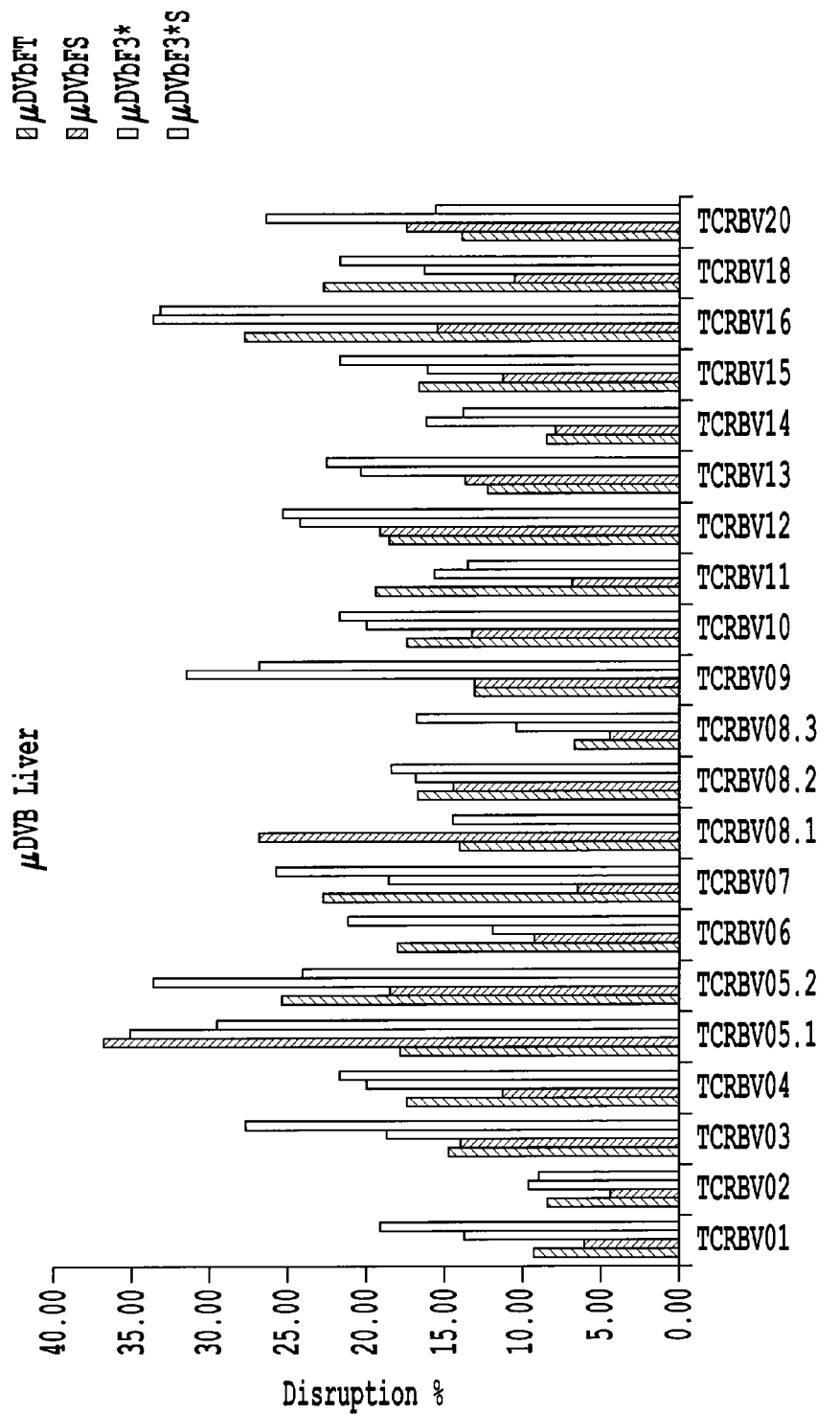
FIG. 87. µDVB Liver.
Figure 88:
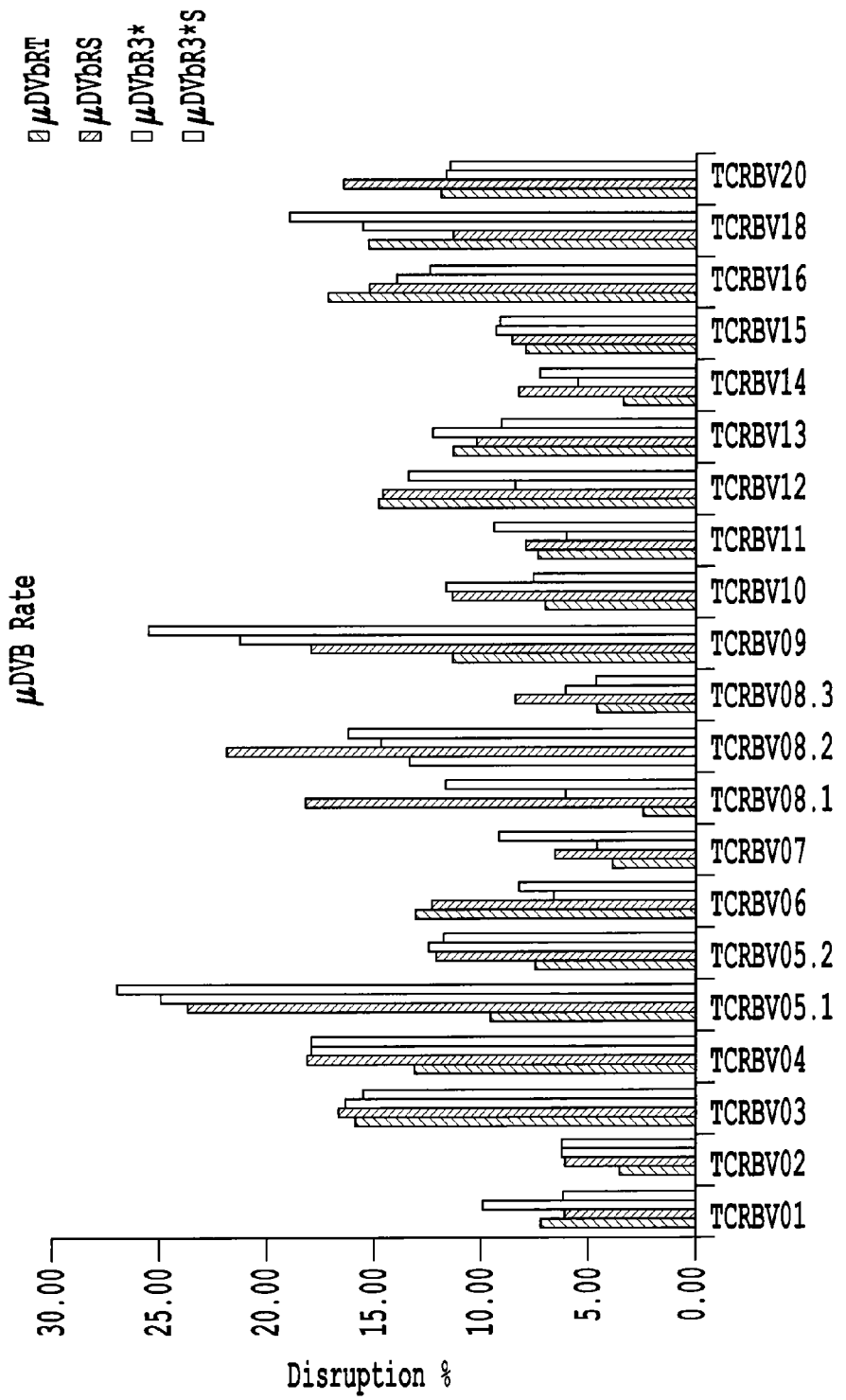
FIG. 88. µDVB Rate.
Figure 89D:
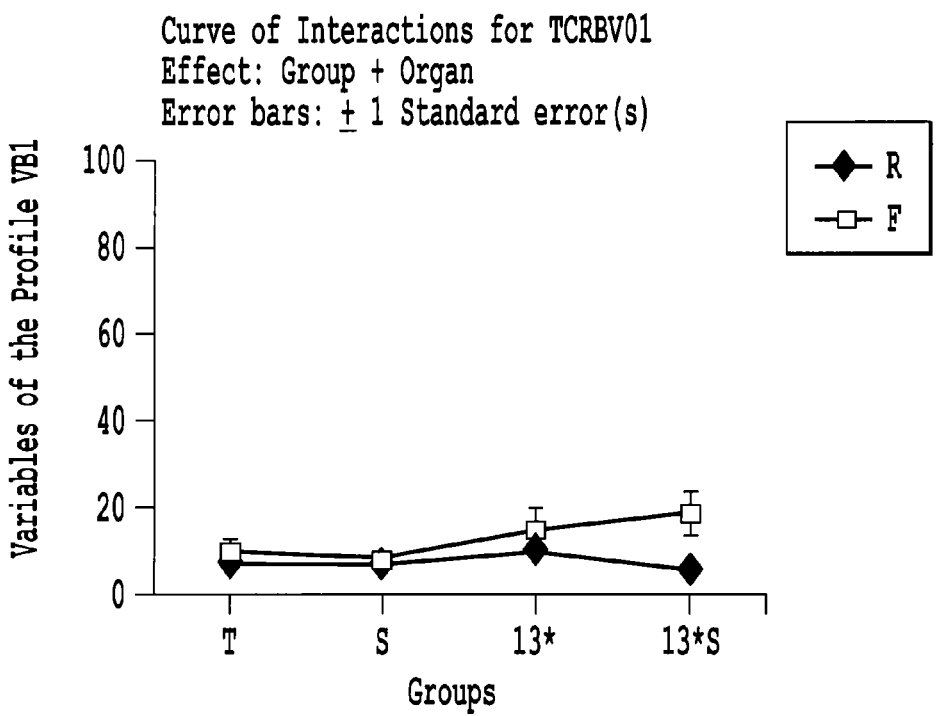
FIG. 89 A. ANOVA Table for TCRBV10.
Figure 89H:
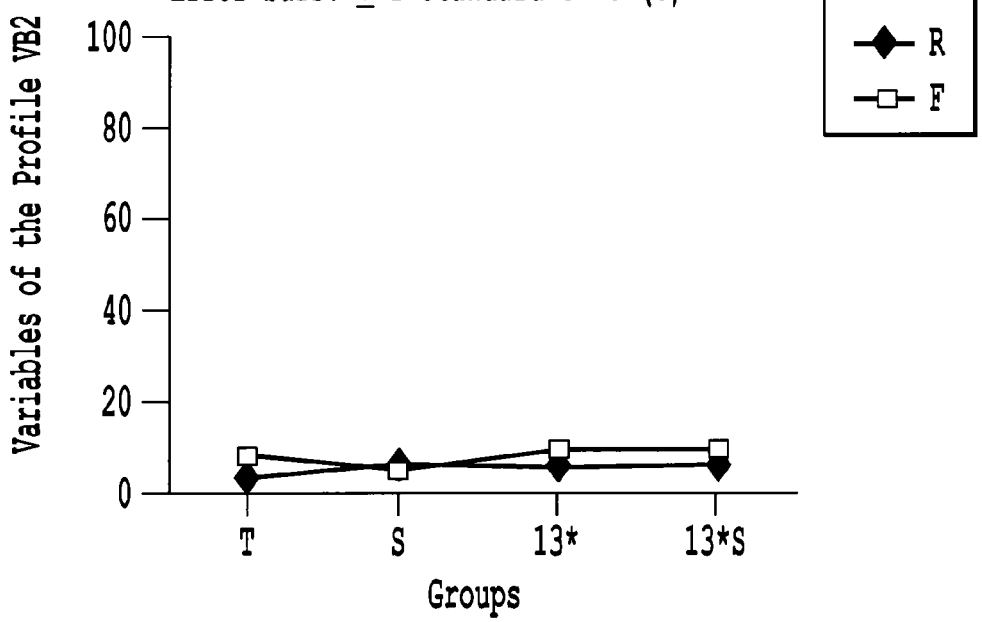
Figure 90D:
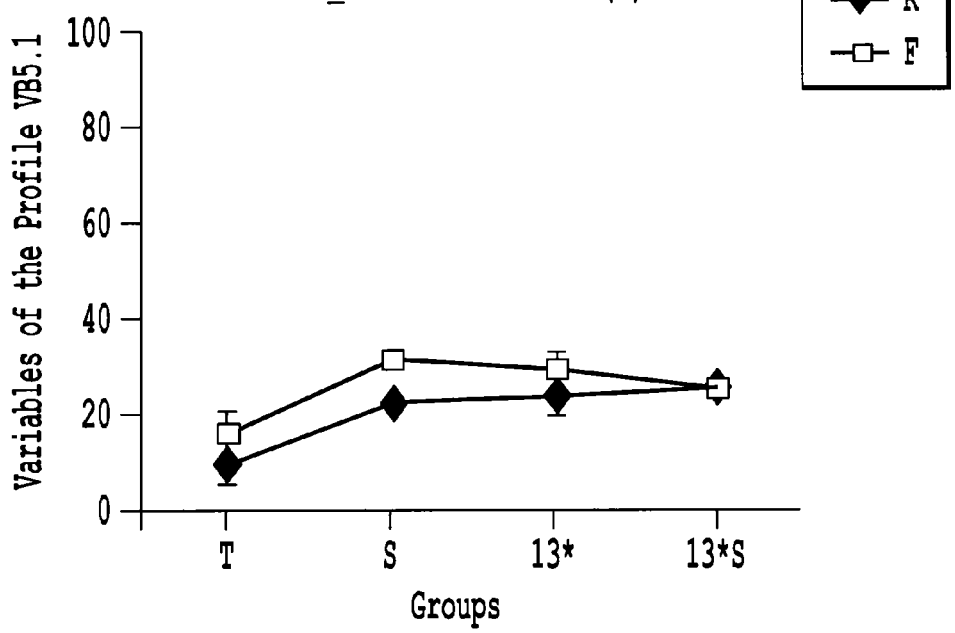
FIG. 90 A. ANOVA Table for TCRBV5.1.
Figure 90H:
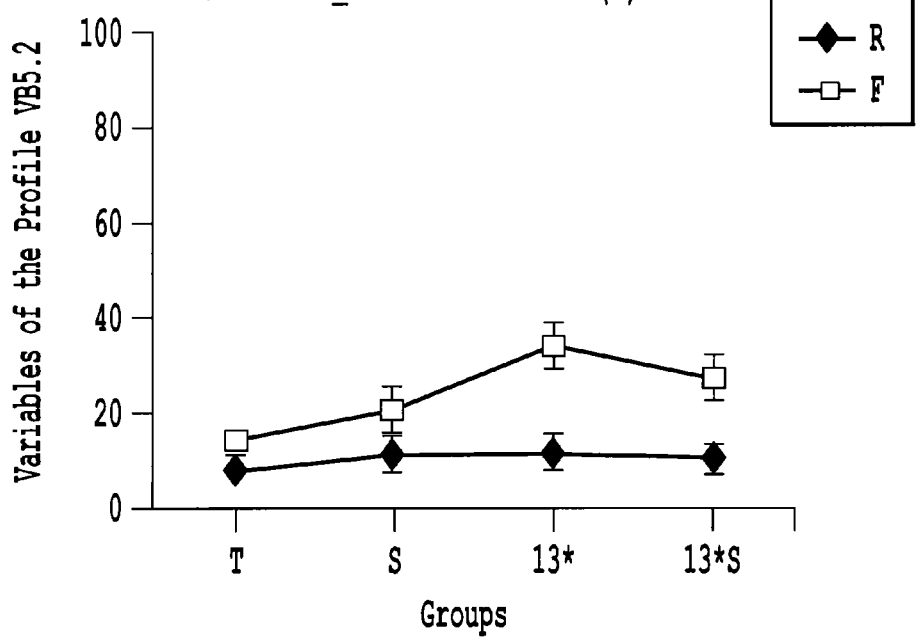
Figure 91D:
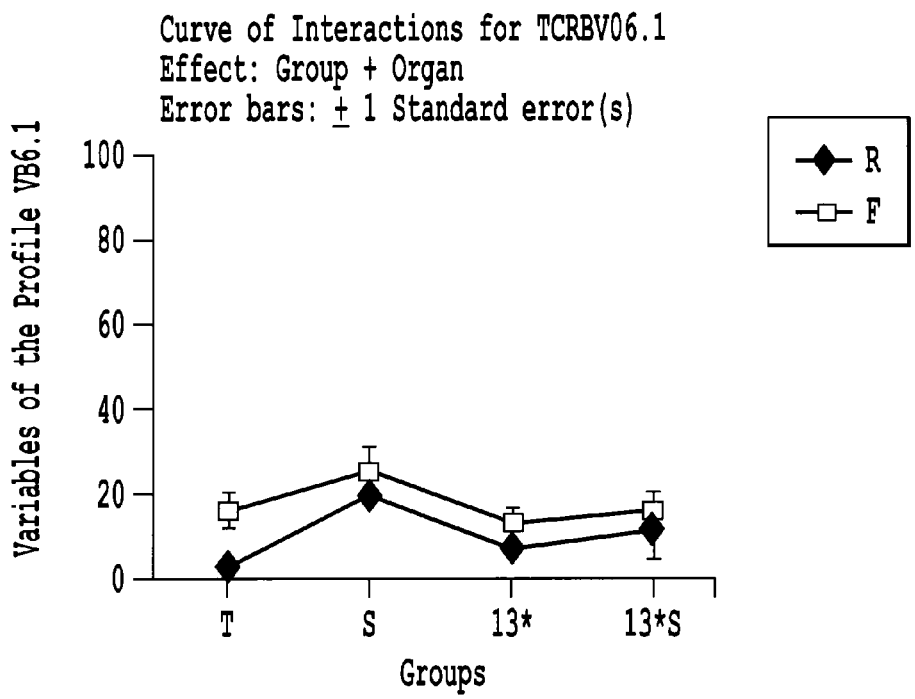
FIG. 91 A. ANOVA Table for TCRBV06.1.
Figure 91H:
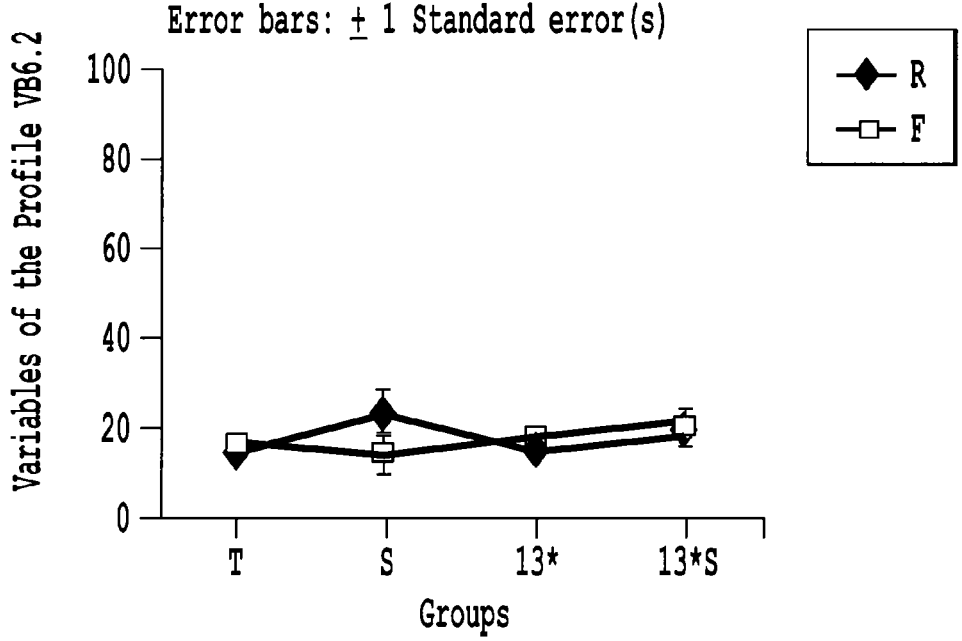
Figure 92D:
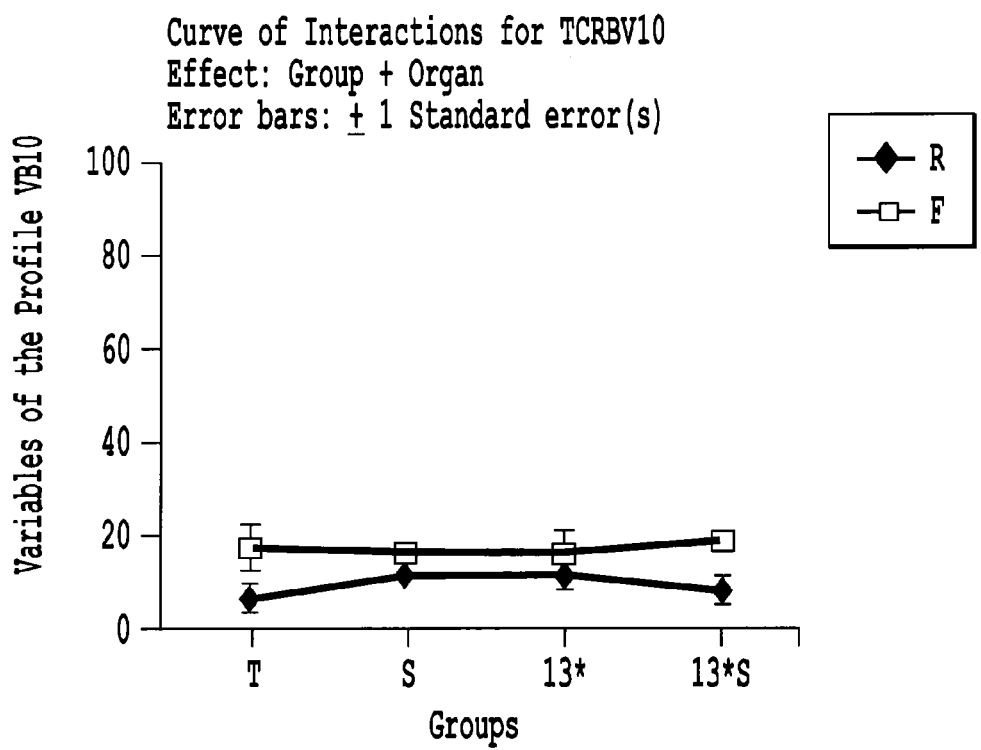
FIG. 92 A. ANOVA Table for TCRBV10.
Figure 92H:
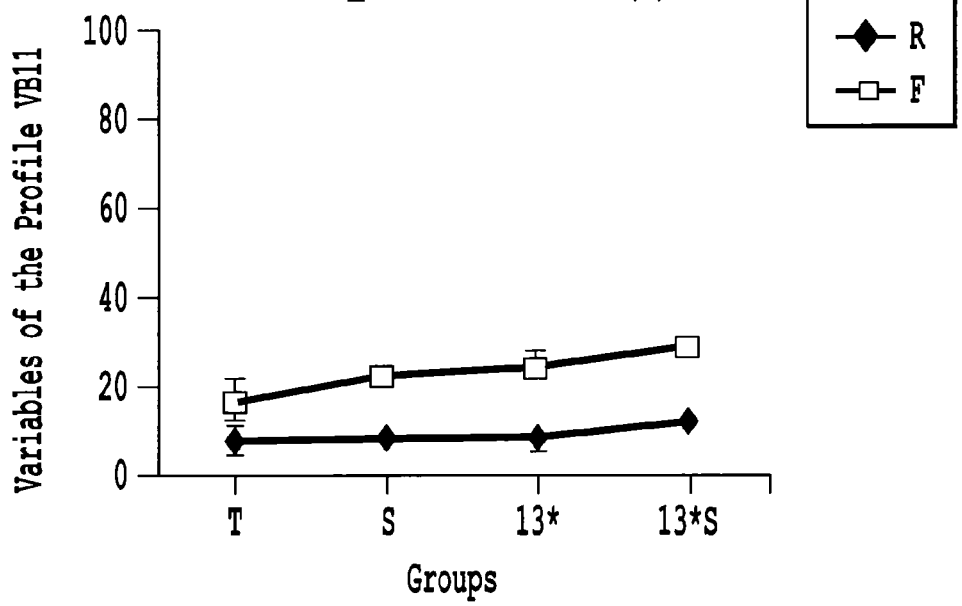
Figure 93D:
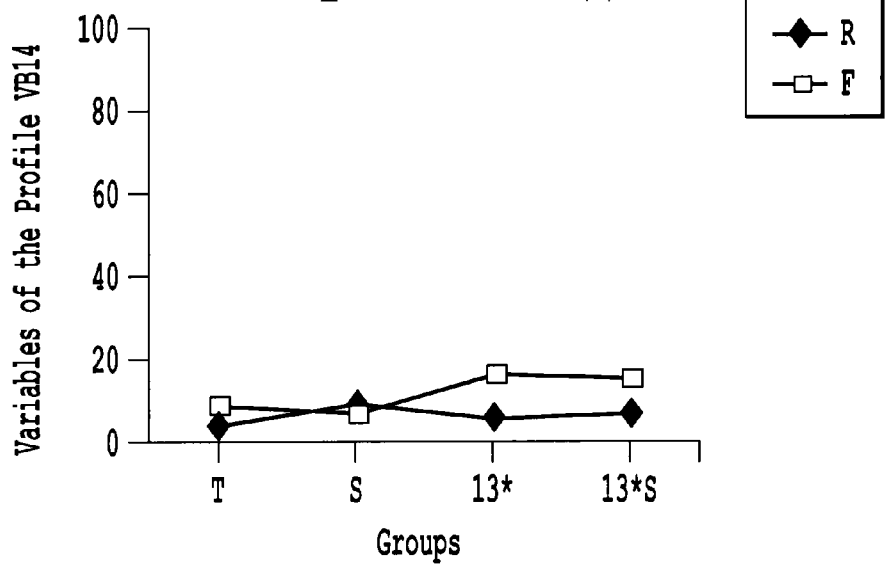
FIG. 93 A. ANOVA Table for TCRBV14.
Figure 93H:
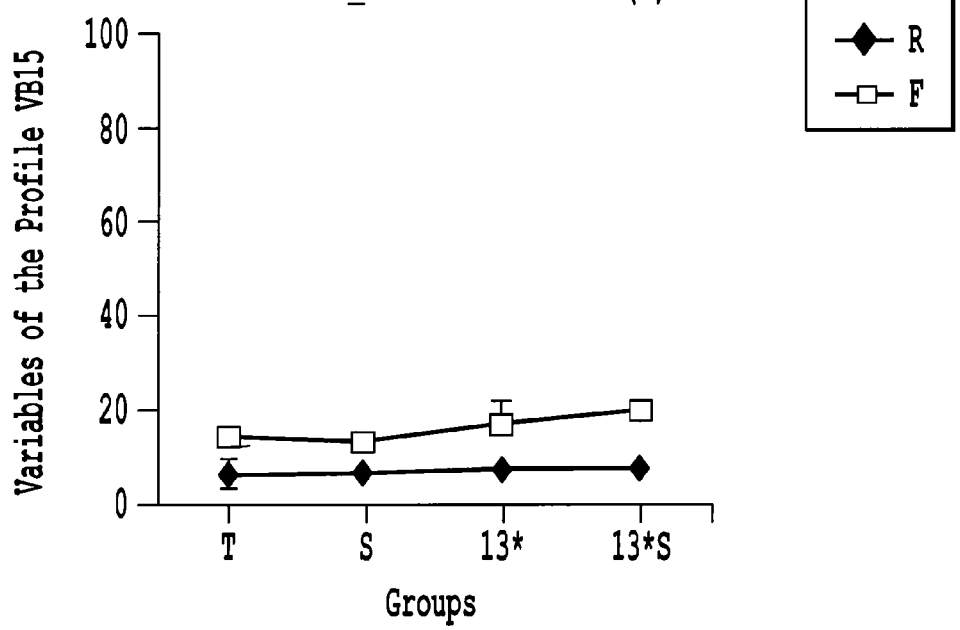
Figure 94D:
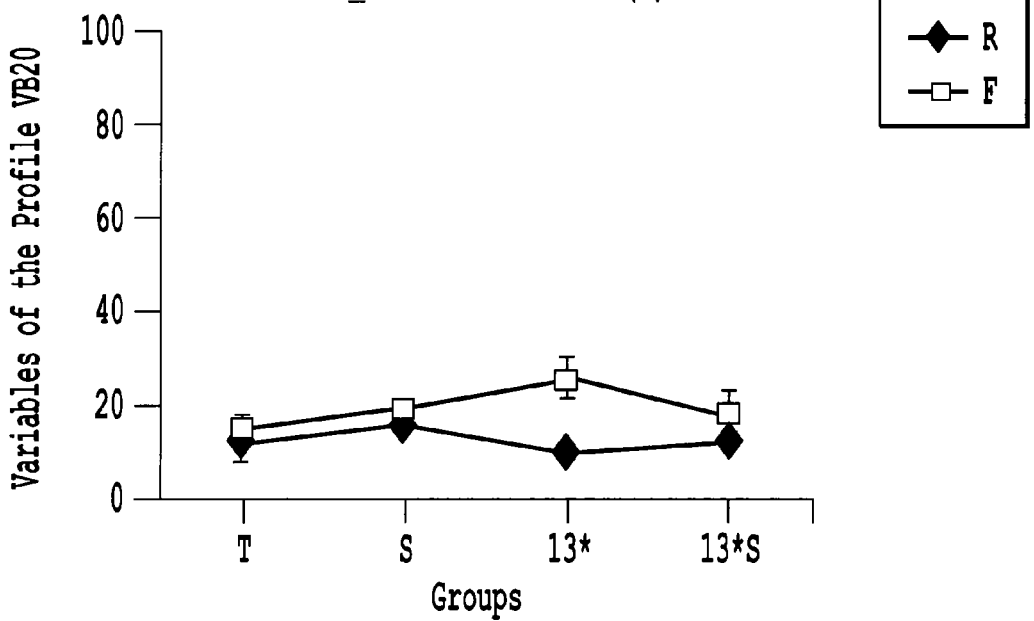
FIG. 94 A. ANOVA Table for TCRBV20.
Figure 95B:
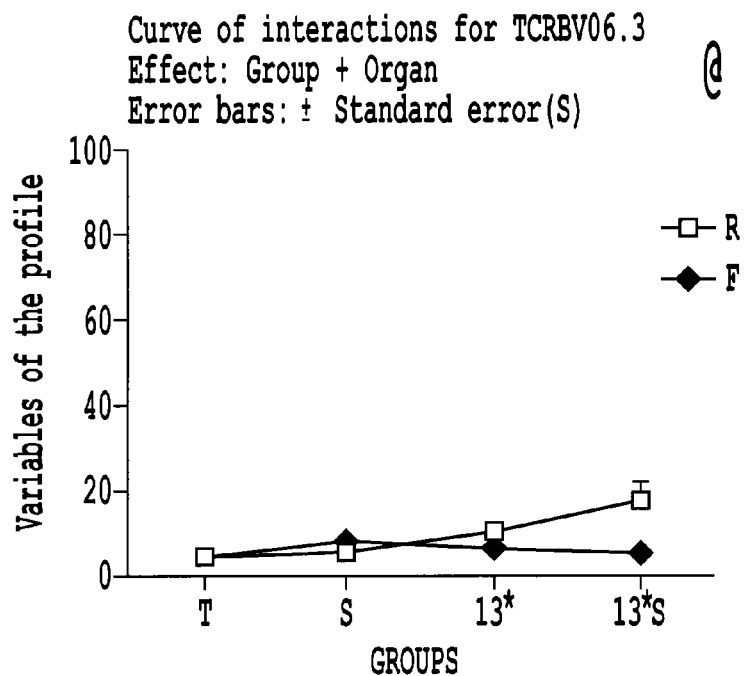
FIG. 95A. Results of the corresponding ANOVA.
FIG. 95 B. Curve of Interactions for TCRBV06.3.
Figure 95C:
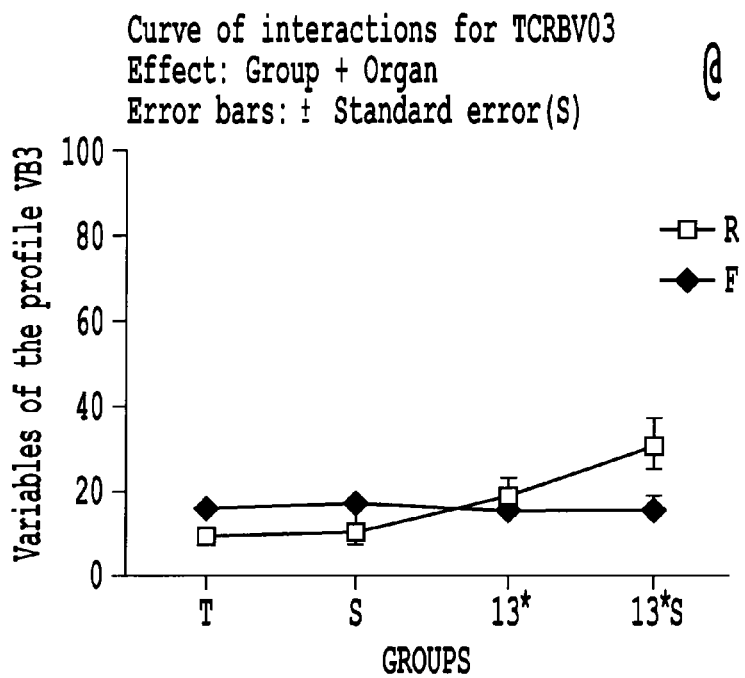
Figure 95D:
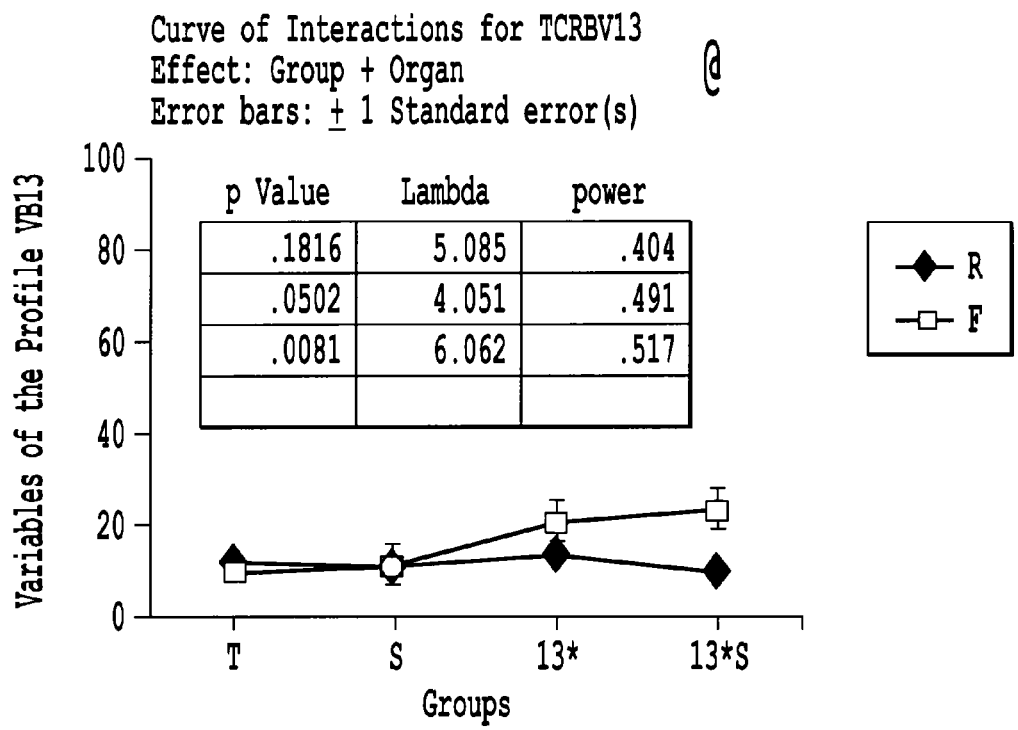
Figure 95E:
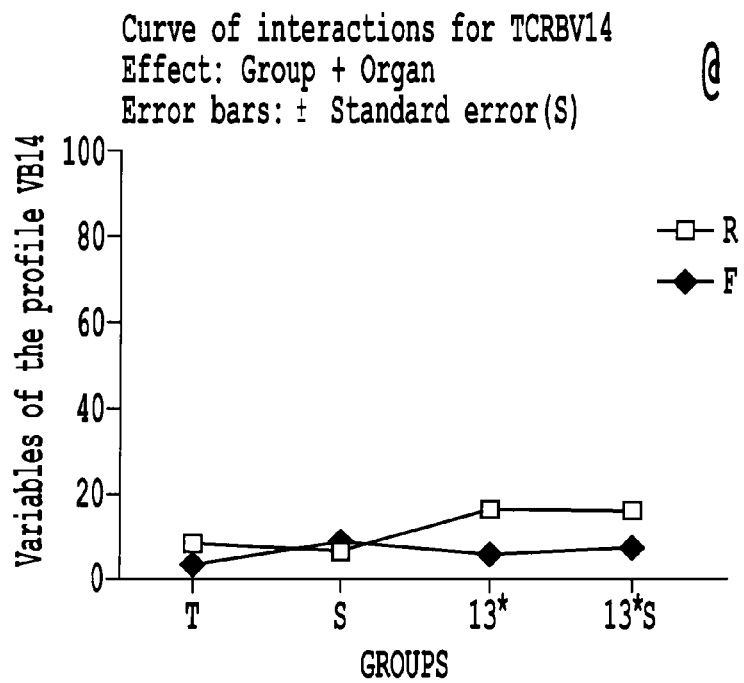
Figure 95F:
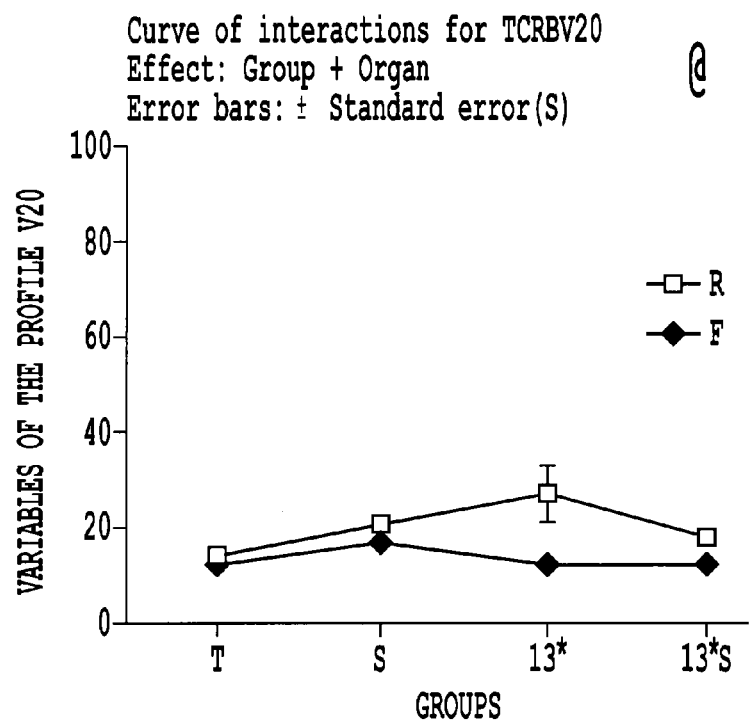
Figure 95G:
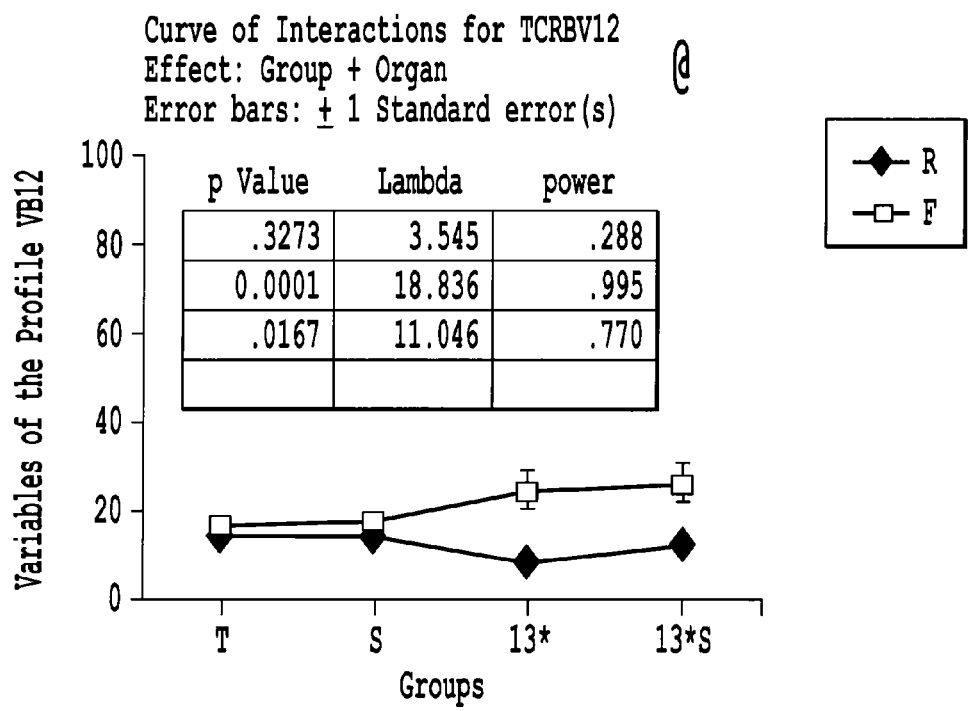
Figure 96A:
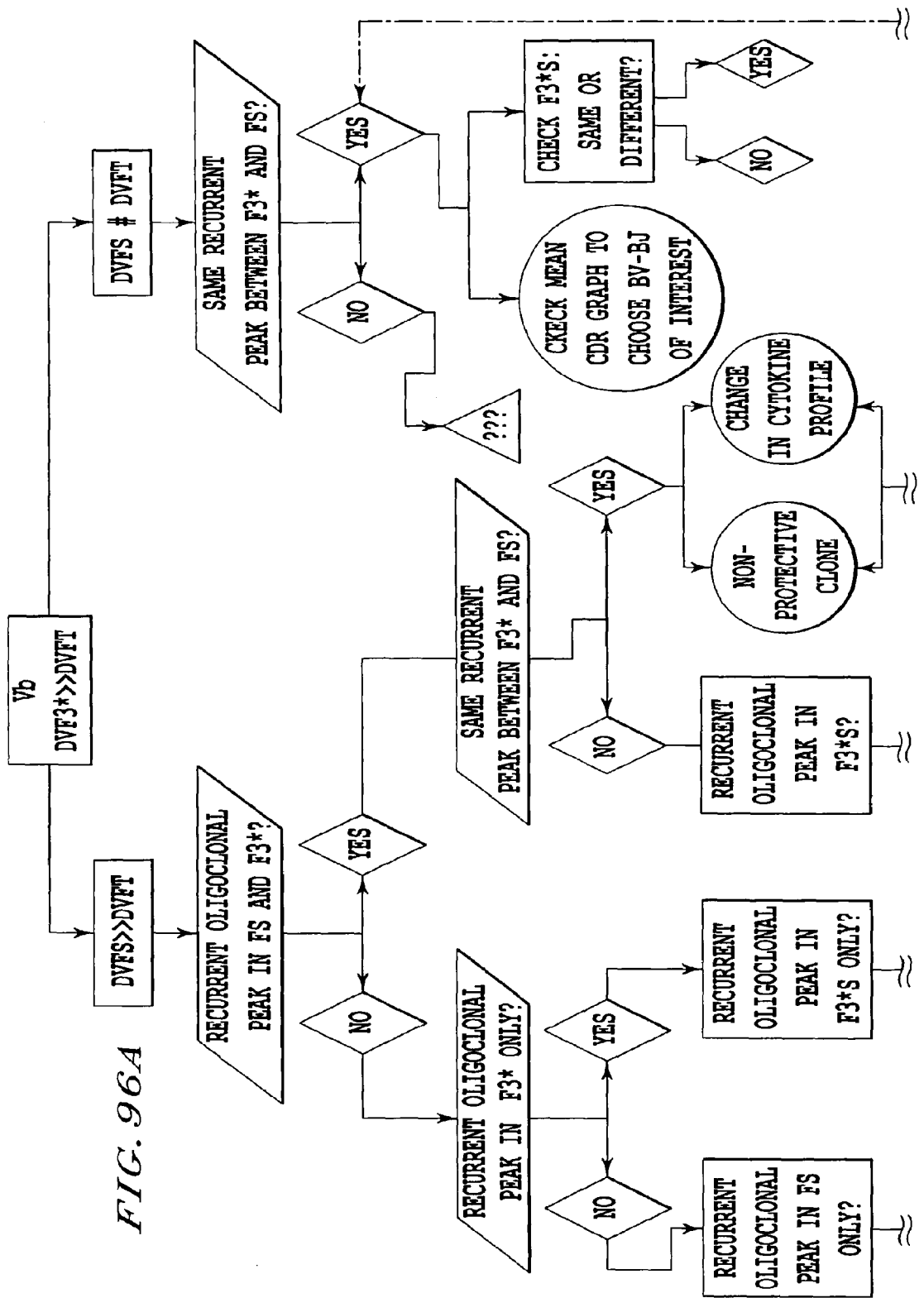
FIG. 96 A. Flowchart.
Figure 96B:
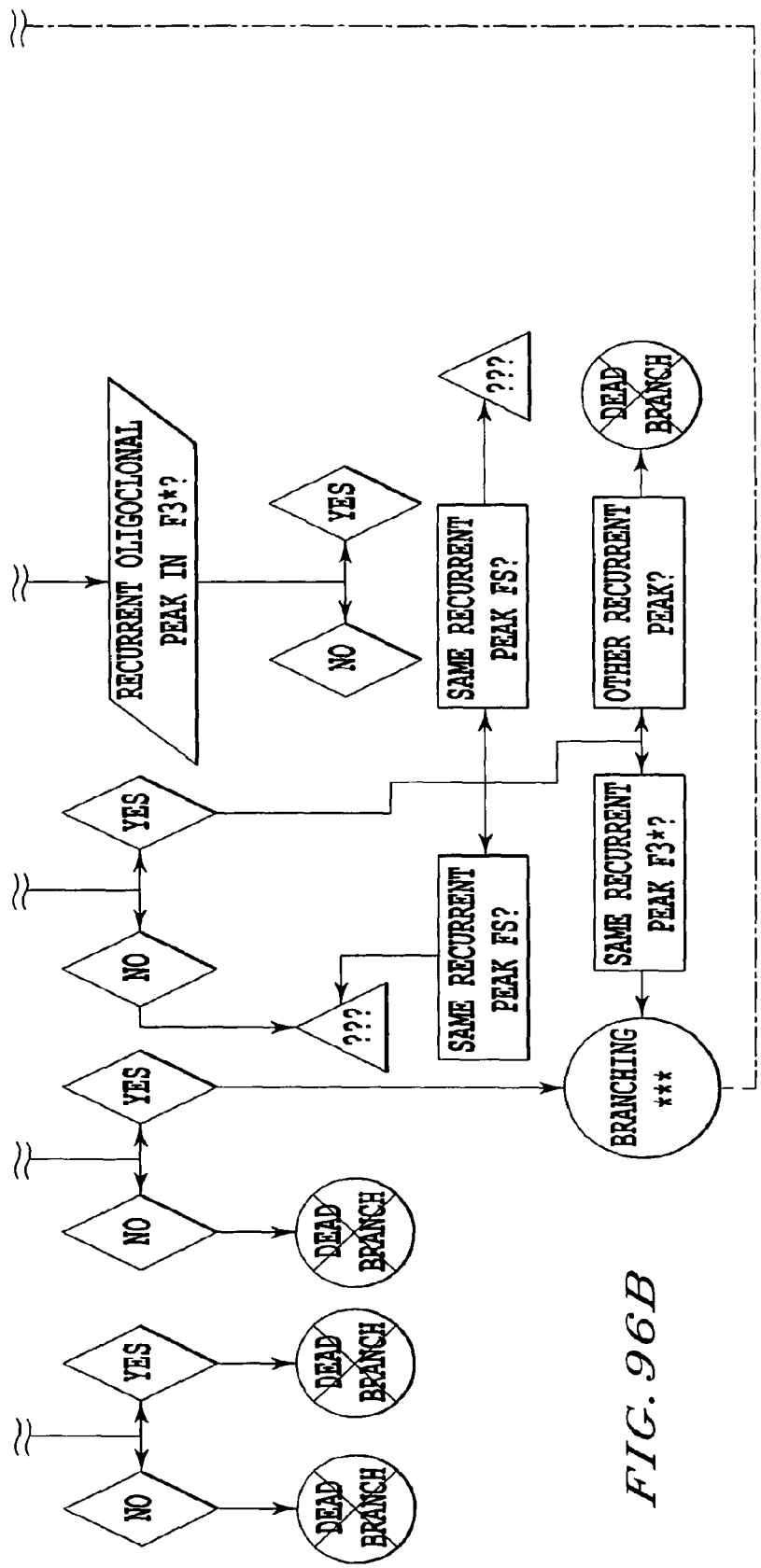
Figure 97:
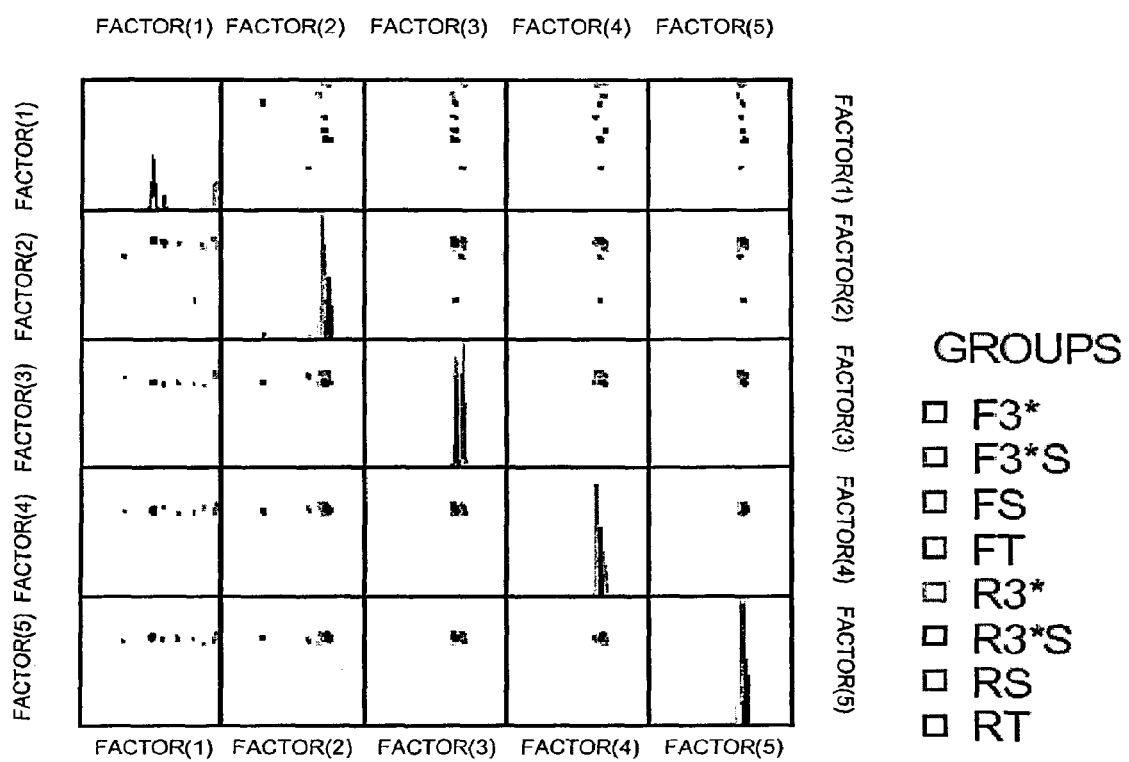
FIG. 97. Canonical Scores Plot.
Figure 107C:
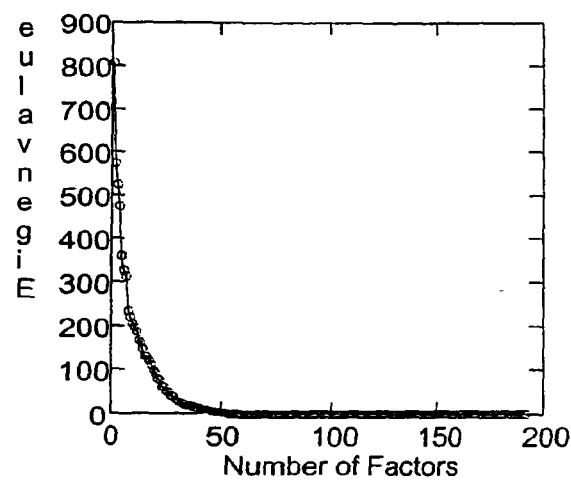
FIG. 107 A. Entries TCRVB12__5 to TCRVB020__13.
Figure 123A:
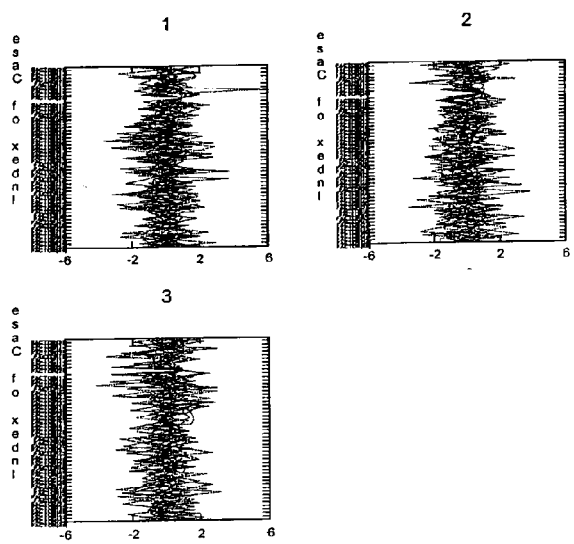

First parameterise the colour coding in the 'para' sheet (FIG. 20). Select an array of cells where the values (for instance Gorochov values) have been entered: the array selected must contain the profile description but not the sample description. Launch the 'DrawArray' procedure with the ISEApeaks menu bar to create the new graphic (FIG. 27).

For each profile, the diversity/perturbation is coded by a colour. The difference between the samples of each group is obvious.

k) The 'PeakNb' Macro

One can obtain the number of peaks in each profile by using the 'PeakNb' macro. This number can be indicative of the oligoclonality of a repertoire.

l) The 'RepertoireMean' Macro

The 'RepertoireMean' macro calculates the average repertoire for each group as determined in the 'para' sheet. The number of sample considered is also mentioned. This method can be used to identify public expansions (Han, M., L. Harrison, P. Kehn, K. Stevenson, J. Currier, and M. A. Robinson. 1999. Invariant or highly conserved TCRα are expressed on double-negative (CD3+ CD4−CD8−) and CD8+ T cells. J. Immunol. 163:301-311).

m) The 'CDR3Mean' Macro

The 'CDR3Mean' macro calculates the average CDR3 length for each profile and for each sample. This can be useful as shown in Mugnaini et al. (Mugnaini, E. N., T. Egeland, A. M. Syversen, A. Spurkland, and J. E. Brinchmann. 1999. Molecular analysis of the complementarity determining region 3 of the human T cell receptor beta chain. Establishment of a reference panel of CDR3 lengths from phytohaemagglutinin activated lymphocytes. J. Immunol. Methods 223:207-216).

n) The 'SeparatemDescription' Macro

The 'SeparatemDescription' macro achieves the visual separation of peaks by grouping them according to their mDescription. This macro will be useful if one has reordered the peaks to fit one's own criteria. Just select the zone in which one wants to separate the peaks, select the 'SeparatemDescription' in the ISEApeaks menu bar. One will be asked to indicate the column number of the column containing the mDescription (or other informations . . . ).

o) The 'Export_Peaks' Macro

The 'Export_Peaks' macro generates an array containing the percentage of use for each peak in its profile. This array is more convenient to export the data from Excel to other software (including statistics software such as StatView).

p) The 'Inverse_Array' Macro

The 'Inverse_Array' macro is a utility to inverse any Excel array. The macro should be called when the data containing worksheet is active, then just indicate the array one wants to transpose. The result will be put in a separate worksheet. Alternatively, one can use the copy special of Excel to transpose an array.

q) Conclusion

By combining these tests and utilities, one can gain a good view of the repertoires that one would not be possible by eye. Additional scoring methods are currently in development and will be implemented in future versions.

Example 3.8

DataUtilities

DataUtilities proposes utility to deal with DataFormatter file.

a) The 'RenameNature' Macro

This utility is used to modify the designation of each well. One must specify the different files to be modified in the 'para' sheet while in the 'correspondence' sheet one will put, in the 'in' raw, the string of character to search for and, in the 'replace by' raw, the string of character one wants to use instead. Note that the 'NewName' raw is not used in this macro. After choosing 'RenameNature' in the ISEApeaks menu bar, select one of the DataFormatter files to process (all must be in the same folder). Then, in all the specified files, each occurrence of a 'in' character string will be replaced automatically by the corresponding 'replace by' character string.

In the DataUtilities Excel template, one can find worksheets with examples of parameterisation that have been used in the laboratory.

b) The 'ChangeOnemTheoricLength' Macro

This macro will replace the mTheoricLength parameter in all sheets and all DataFormatter files indicated in the para sheet of a profile according to the mDescription and the new mTheoricLength values the user gave.

c) The 'ShiftmLengths' Macro

This macro will shift the mLength value of all peaks in all sheets and all DataFormatter files indicated in the para sheet of a profile according to the mDescription and the new mTheoricLength values the user gave.

d) The 'DFConverter' Macro

The 'DFConverter' macro allows the conversion of old DataFormatter files to the latest version of DataFormatter. Open DataUtilities, and fill the 'para' sheet: put the names of files to convert as well as the new name under which one wants ISEApeaks to save one's converted data (the sheet row is not used in this macro; therefore, a DataFormatter should appear only once). The use of 'para' sheet will allow one to convert a big set of files. Choose the 'DFConverter' item in the ISEApeaks menu bar.

Indicate the folder where one's old DataFormatter files are stored (the new DataFormatter files will be also saved in this folder). The conversion starts: each old file is open, data are transferred and percentage calculations are done, copying also the page set up.

e) The 'DFSpliter' Macro

This macro allows one to separate data stored in DataFormatter files in separate data sheets of newly created DataFormatter files. For instance, imagine that one analyses the Vβ08.1-Jβ and Vβ08.2-Jβ repertoires and set the ISEApeaks add-in preferences in a way that these two groups of profiles are gathered in a common data sheet (12+12=24 profiles). DFSpliter will enable one to split the data in different data sheets in all the workbooks one precises in the 'para' sheet, like for the other DataUtilities macros. Fill the 'para' sheet, with the names of the workbook to split, indicate a template DataFormatter file (that should contain a data.1 sheet) and how many time a data sheet should be split (2 for the example). The macro will open each workbook and split the data. The macro checks that the number of profiles is dividable by the split number and that the preferences are suitable for the created workbooks (for the example, it should be 12).

Example 3.9

Examples

For each example, a 'Readme.txt' file will give one more detail of what to do to have a complete tour of the example.

DP & Parameter Files

Files in the 'DP & Parameter files' folder provide CGEL parameter files and the corresponding Excel DataParameter sheets for 3SETCP v2.0 and 3SET2.1 v2.0: 36-well gel, 3 human Vβ-Cβ repertoires, m3SET v2.0: 36-well gel, 3 mouse Vβ-Cβ repertoires; Vb2, 3, 5.1, 4, 16, 7-Jb v2.0; and Vb6, 9, 8.1, 8.2, 14, 8.3-Jb v2.0: analysis of 12 mouse Vβ-Jβ repertoire on two 36-well gels. These files can be used with DataParameter related macros.

DE, DS, DES & DF: Immunoscope Data

Files in the 'IS Example' folder provide an example of a gel analysis from CGEL parameter file to the formatting of the extracted data in DataFormatter files.

DE, DS, DES & DF: GeneScan Data

Files in the 'GExample' folder provide an example of analysis of 2 gels from CGEL parameter file to the formatting of the extracted data in DataFormatter files. See the Readme.txt in this 'GExample'.

DA

The 'DA' folder gathers DataFormatter files used in the DataAnalyser file 'DA 2.0 ex' where the result of all DataAnalyser macros is stored.

Utilities

The '.Pict files assembling' folder gathers data and results of an assembling of different PICT files according to a CPIC file parameter ('CPictPlaces para v2.0').

Example 3.10

Pitfalls

Some errors are quite usual when manipulating the programs. Remember that string in ISEApeaks must not contain the ';' character. DataExtractor opens none of the '.pict' files. Check the value of 'mTypicalPictFileName (FIG. 17): is it correct? The name of the data files can be anything provided that it does not contain anymore figures than the 2 automatically assigned by the Immunoscope© software. The program will warn one if it is not the case. Also check that the '.pict' files CGEL parameter file one selected are in the same folder. Be careful not to confuse the different types of file used in the ISEApeaks package. Types and corresponding icons have been created to limit possibility of confusions. A good way to differentiate the different file types is to add a prefix to file names: 'Is m3SET' will be the Immunoscope macro created using the CGEL parameter file 'm3SET'. When using the CreateCGelFile macro, it might happen that Excel seems to be frozen. this is because other applications with whom the ISEApeaks Add-in is talking to do not signal to Excel that the job is finished. To avoid this, just after running CreateCGelFile, click on the desk of one's Mac (or any window not related to Excel). When Excel has finished, the Finder application becomes active. Just go back to Excel.

The following Examples are provided as analyses using ISEApeaks software in order to confirm the good working thereof.

Example 4.1

Perturbation of the CD4+ and CD8+ T Lymphocyte Repertoires During Leishmania Infection in a Murine Experimental Model

Example 4.2

Experimental Model

This study was carried out with wild-derived PWK inbred mice which was selected as a new promising model for human *Leishmania major* infection since the clinical and biological features of PWK mice parallels those observed in humans. PWK mice were infected by Leishmania major in footpads. 7, 20 and 27 weeks after infection groups of 6 mice were sacrificed. Lymphocyte cell suspensions were prepared from draining lymph nodes (G) and spleen (R) and sorted into CD4+ and CD8+ sub-populations. Six additional mice were sacrificed just after infection and serve as controls.

Total ARN was extracted and reverse-transcribed into cDNA. The Immunoscope technique was applied to describe the diversity of Vβ Cβ repertoires.

Example 4.3

Question

What is the perturbation of T lymphocyte repertoires during infection?
Is the perturbation different earlier (7 weeks) or later (27 weeks) after infection?
Is the perturbation different depending on the organ?
Is the perturbation different depending on the CD4+ or CD8+ sub-population?

Example 4.4

Results

Results are presented in the following pages and FIGS. 29-125 recapitulating this analysis:
  ISEApeaks data were collected from Immunoscope TCRBV-BC repertoire data and assembled into four "DataAnalyser Peaks" databases:
  i. Spleen CD8+ samples 0, 7, 20 and 27 weeks after infection
  ii. Spleen CD4+ samples 0, 7, 20 and 27 weeks after infection
  iii. Lymph node CDC samples 0, 7, 20 and 27 weeks after infection
  iv. Lymph node CD4+ samples 0, 7, 20 and 27 weeks after infection
  "Gorochov perturbation" (G1%) tables were generated to represent the global variability for each Vβ-Cβ profile of every sample with regard to the average variability measured for the control group. "Gorochov perturbation" were then computed by ANOVA for determining whether groups are statistically different based on their repertoire diversity.
  "Oligoscore" tables were generated for each group indicating the possible presence of recurrent oligoclonal peaks indicative of recurrent clonal lymphocyte expansions within a group. Heuristically, the threshold value corresponds to the maximal "Oligoscore" value of the control group for which no significant expansion is expected. Only significant expansion are shown here.
  "Expression level" tables (R %) were generated to indicate the level of expression each Vβ-Cβ profile of every sample. Note that the experimental condition used here are not quantitative so that this value is only indicative when a major change is observed.
  Synthetic graphs for 7 and 27 weeks were drawn to represent the "Gorochov perturbation" of Vβ-Cβ combinations for which the "Gorochov perturbation" is statistically than control mice.

Example 4.5

Conclusions

On the basis of the elements of analysis obtained by the implementation of the ISEApeaks strategy described in the statements of invention DI99-92 and DI02-48 and the corresponding patent filed, we can support the following conclusions:
  CD8+ repertoires appear to be less perturbed than CD4+ repertoire especially in the spleen.
  The few Vβ-Cβ combinations which are perturbed among R CD8+ are found among 7 and 27 week groups. On the contrary, the Vβ-Cβ combinations which are perturbed among G CD8+ are mostly found among the 7 week group when the perturbation is close to control groups in the 27 week group.
  For CD4+ repertoire, many Vβ-Cβ combinations are perturbed in the spleen and the lymph nodes. Again and more strikingly, the Vβ-Cβ combinations which are perturbed among G CD4+ are almost always higher among the 7 week group than the perturbation of the 27 week group.

In another murine experimental model of parasite infection (PWK mice infected by *Leishmania major*), these results thus show the power of the ISEApeaks strategy to discriminate between subtle lymphocyte repertoire perturbations which would not otherwise be detected by eye.

Example 5.1

Effect of the LACK Protein on the Repertoire of αβ T Lymphocytes in a Murine Experimental Model

Example 5.2

Experimental Model

This study was carried out with seven-week-old female BALB/C mice. They received an injection at the level of footpads of the LACK protein, or the LACKp (156-173) peptide, with or without treatment by an anti-IL-2 antibody. Every group of mice includes 5 individuals. Five additional mice received an injection of DMEM buffer and serve as controls.

The draining lymph nodes were taken 16 hours after injection. Total ARN was extracted and reverse-transcribed into cDNA.

First, the Immunoscope technique was applied to describe the diversity of VαCα and VβCβ repertoire, for Vβ4, Vβ8.1, Vβ3, Vα2, Vα8 and Vα15 TCRBV-BC combinations. Second, the diversity of Vβ4-Jβ and Vβ8.1-Jβ was analyzed.

Example 5.3

Question

Is it possible to detect a perturbation of the αβ T lymphocyte diversity following immunization by LACK protein or LACKp$_{156-173}$ peptide?

Example 5.4

Results

Immunoscope data was analyzed implementing the ISEApeaks strategy (data extraction, data smoothing, data formatting, peak database construction, data analysis). Results are presented in the following pages and FIGS. 29-125 recapitulating this analysis:

Tables "DataAnalyser DA" created with ISEApeaks to prepare the extraction of the data through the various gels. It is at this level that the distribution of samples in groups is indicated.

"DataAnalyser Peaks" tables corresponding to the database of peaks obtained for all individuals of all groups.

"Gorochov perturbation" tables representing the global variability for each Vα-Cα, Vβ-Cβ or Vβ-Jβ profile of every sample with regard to the average variability measured for the control group (group n°1—DMEM injection).

"Oligoscore" tables for each group indicating the possible presence of recurrent oligoclonal peaks indicative of recurrent clonal lymphocyte expansions within a group. Heuristically, the threshold value corresponds to the maximal "Oligoscore" value of the control group for which no significant expansion is expected.

"Gorochov perturbation" tables normalized by the "Oligoscore" values: for each individual and each Vα-Cα/Vβ-Cβ/Vβ-Jβ combination, the value of "Gorochov perturbation" of the individual was normalized by the ratio of the maximum Oligoscore for the Vα-Cα/Vβ-Cβ/Vβ-Jβ combination of the group considered by the maximum Oligoscore for the Vα-Cα/Vβ-Cβ/Vβ-Jβ combination measured for the control group.

"DrawArray" tables for the "Gorochov perturbation" values.

"DrawArray" tables for the "Gorochov perturbation" values normalized by "Oligoscore".

Example 5.5

Conclusions

On the basis of the elements of analysis obtained by the implementation of the ISEApeaks strategy described in the statements of invention DI99-92 and DI02-48 and the corresponding patent filed, we can support the following conclusions:

Whereas neither Vα-Cα repertoire nor Vβ4-Cβ repertoires show any perturbation by comparison to the control group, Vβ8.1-Cβ repertoires show a tendency to perturbation.

The comparison of the perturbation of the Vβ4-Jβ, combinations to the average perturbation of Vβ4-Jβ combinations within the control group shows no difference. It's the same for the representativeness of every peak.

Concerning Vβ8.1-Jβ combinations, perturbations superior to those of the control group are observed for Vβ8.1-Jβ1.1, Vβ8.1-Jβ1.2, Vβ8.1-Jβ2.2, Vβ8.1-Jβ2.7 combinations and to a lesser extent for Vβ8.1J1.3 combination, and this for the four experimental groups. This perturbation is not correlated to the representativeness. On the other hand, when we normalize the Gorochov perturbation by Oligoscore, it appears an increase of the perturbation correlated to the appearance of oligoclonal peak expansion for the following combinations:

Vβ8.1-Jβ1.1, Vβ8.1-Jβ1.2, Vβ8.1-J1.3, Vβ8.1-Jβ1.4 within the LACK and LACKp groups Vβ8.1-Jβ2.1, Vβ8.1-Jβ2.2, Vβ8.1-Jβ2.3, Vβ8.1-Jβ2.4 and Vβ8.1-Jβ2.7 within four experimental groups.

Vβ8.1-Jβ1.5 within the LACKp peptide groups, with or without treatment by the anti-IL-2 antibody.

In another murine experimental model, these results thus show the power of the ISEApeaks strategy to discriminate between subtle lymphocyte repertoire perturbations which would not otherwise be detected by eye.

Example 6.1

Kinetic of Perturbation of αβ T Lymphocyte Repertoires in a Murine Experimental Model of Cerebral Malaria

Example 6.2

Experimental Model

This study was carried out with 2-month-old B10.D2 mice. They were infected by intraperitoneal injection of $10^6$ *Plasmodium berghei* ANKA clone 1.49 L parasitized red blood cells. We constituted six groups of mice: J3, J4, J5 and J6 groups (3, 4, 5 and 6 days after infection, respectively). J3 group included 5 mice when J4, J5 and J6 groups included 10 mice. The TSP group included 20 infected individuals and was used to follow the onset of cerebral malaria (CM). Parasitemia was systematically assessed before sacrificing the mice to confirm infection. Five additional mice were not infected and served as controls (TN group). Blood, spleen and brain were collected for each individual. For the TSP group, collection was done on the onset of CM clinical signs as assessed by paralysis, deviation of the head, respiratory troubles. For the TN group, collection was done on day 14 of the experiment. Total RNA was extracted and reverse-transcribed into cDNA.

The Immunoscope technique was applied to describe the diversity of Vβ-Cβ repertoire, for all the 23 Vβ TCRBV-BC combinations.

Example 6.3

Question

What is the kinetic of Vβ-Cβ repertoire perturbation during *P. berghei* infection?

Example 6.4

Results

Immunoscope data was analyzed implementing the ISEApeaks strategy (data extraction, data smoothing, data formatting, peak database construction, data analysis). Results are presented in the following pages and FIGS. 29-125 recapitulating this analysis:

"DataAnalyser DA" table created with ISEApeaks to prepare the extraction of the data through the various gels. It is at this level that the distribution of samples in groups is indicated.

"DataAnalyser Peaks" table corresponding to the database of peaks obtained for all individuals of all groups (not printed).

"Gorochov perturbation" table representing the global variability for each Vβ-Cβ profile of every sample with regard to the average variability measured for the control group (non-infected TN group) (not printed).

"Oligoscore" tables for each group indicating the possible presence of recurrent oligoclonal peaks indicative of recurrent clonal lymphocyte expansions within a group. Heuristically, the threshold value corresponds to the maximal "Oligoscore" value of the control group for which no significant expansion is expected (not printed).

"Gorochov perturbation" tables normalized by the "Oligoscore" values: for each individual and each Vβ-Cβ combination, the value of "Gorochov perturbation" of the individual was normalized by the ratio of the maximum Oligoscore for the Vβ-Cβ combination of the group considered by the maximum Oligoscore for the Vβ-Cβ combination measured for the control group (not printed).

"DrawArray" tables for the "Gorochov perturbation" values.

"DrawArray" tables for the "Gorochov perturbation" values normalized by "Oligoscore".

Despite the small size of some experimental groups, Gorochov perturbation data was analyzed for each Vβ-Cβ combination by analysis of variance in order to identify statistically significant differences between groups. In order to confirm the preliminary observations, another analysis of variance was performed based on three sets of individuals only: one set comprising controls, J3 and J4 groups; a second set corresponding to J5 group; a third set comprising J6 and TSP groups.

Example 6.5

Conclusions

On the basis of the elements of analysis obtained by the implementation of the ISEApeaks strategy described in the statements of invention DI99-92 and DI02-48 and the corresponding patent filed, we can support the following conclusions:

The overall results of this experiment confirms our previous observation that repertoire perturbation can be observed during CM as compared to non-infected controls.

From this study it can be seen that the repertoire perturbation is progressive during infection. The repertoires are globally not different between TN, J3 and J4 groups, on the one hand, and between J6 and TSP on the other hand. J5 group appears intermediate.

For some Vβ-Cβ combinations the shift of perturbation happens between J4 and J5; for others, it happens between J5 and J6. This is confirmed when looking at the data obtained from the analysis of variance of the three sets [TN, J3, J4], [J5] and [J6, TSP].

These results suggest the predictive/diagnostic value Vβ-Cβ repertoire perturbation data. They show the power of the ISEApeaks strategy to discriminate between subtle lymphocyte repertoire perturbations which would not otherwise be detected by eye.

Example 7.1

Effect of Vaccination with Irradiated *Plamodium yoelii* Sporozoites on the Repertoire of αβ T Lymphocytes in a Murine Model of Malaria Example 7.2

Experimental Model

This study was carried out with C57BL/6 mice. Mice were constituted into groups as follows:

A group of mice was immunized three times with irradiated *Plasmodium yoelii* sporozoites in order to induce protection to *P. yoelii* infection (I3*).

A group of mice was immunized three times with irradiated *Plasmodium yoelii* sporozoites in order to induce protection to *P. yoelii* infection and later challenged with infectious *Plasmodium yoelii* sporozoites (I3*S).

A group of mice was challenged with infectious *Plasmodium yoelii* sporozoites (S).

An additional group of unmanipulated mice served as controls (T).

One week after challenge, spleen (R) and liver (F) were collected and lymphocyte suspensions were prepared. Total ARN was extracted and reverse-transcribed into cDNA.

The Immunoscope technique was applied to describe the diversity of Vβ-Cβ repertoire, for all the 23 Vβ TCRBV-BC combinations.

Example 7.3

Question

Is it possible to detect differences between repertoire diversity perturbation between groups?

In particular, is there a difference during challenge when mice have immunized or not with irradiated sporozoites (S vs. I3*S groups)?

Is there a difference between organs (liver vs. spleen)?

Example 7.4

Results

Immunoscope data was analyzed implementing the ISEApeaks strategy (data extraction, data smoothing, data formatting, peak database construction, data analysis). Results are presented in the following pages and FIGS. 29-125 recapitulating this analysis:

"DataAnalyser DA" table created with ISEApeaks to prepare the extraction of the data through the various gels. It is at this level that the distribution of samples in groups is indicated.

"DataAnalyser Peaks" table corresponding to the database of peaks obtained for all individuals of all groups (not printed).

"Gorochov perturbation" table representing the global variability for each Vβ-Cβ profile of every sample with regard to the average variability measured for the control group (non-infected TN group) (not printed).

Average "Gorochov perturbation" graph comparing the perturbation between organs (R & F) and experimental groups (T, S, I3* & I3*S) for each Vβ-Cβ combination and on average.

"Oligoscore" tables for each group indicating the possible presence of recurrent oligoclonal peaks indicative of recurrent clonal lymphocyte expansions within a group. Heuristically, the threshold value corresponds to the maximal "Oligoscore" value of the control group for which no significant expansion is expected.

"DrawArray" tables for the "Gorochov perturbation" values (not printed).

Gorochov perturbation data was analyzed for each Vβ-Cβ combination by analysis of variance (ANOVA) in order to identify statistically significant differences between groups.

Principle Component Analysis followed by Discriminant Analysis was performed in order to determine how many groups can be distinguished based on peak percentage information. The plot of data according to the first five factors is shown.

Example 7.7

Conclusions

On the basis of the elements of analysis obtained by the implementation of the ISEApeaks strategy described in the statements of invention DI99-92 and DI02-48 and the corresponding patent filed, we can support the following conclusions:

As summarized in the attached table, statistical analysis of data shows differences of perturbation repertoire between organs (R vs. F) or between experimental groups (in particular I3*S vs. S). This study brought us to design decisional trees to help decision in analyzing the data (see attached document). PCA/DA analysis also provides evidence that experimental group+organ combinations can be distinguished on the basis of the Vβ-Cβ repertoire diversity information. It can be seen that factors 1, 2 & 3 can discriminate between experimental groups F3* vs. F3*S vs. FT/RT/R3*S vs. FS/R3*/RS. This analysis will help determining the protective components of the immune response following vaccination by irradiated sporozoites.

In another murine experimental model, these results thus show the power of the ISEApeaks strategy to discriminate between subtle lymphocyte repertoire perturbations which would not otherwise be detected by eye.

Reference to Computer Listing of Raw Data and ISEApeaks Software Appendices

Filed herewith in triplicate (labeled Copy 2.1, Copy 2.2, Copy 2.3, Copy 3.1, Copy 3.2, and Copy 3.3 respectively) are computer listings of raw data on two separate compact discs read only memory (CD-ROM). The entire contents of the raw data appendix is incorporated herein by reference.

Each of the three copies of the computer listings of raw data appendix were created on Jul. 1, 2003.

Filed herewith in triplicate (labeled Copy 4.1, Copy 4.2, and 4.3 respectively) is a computer listing of the software program ISEApeaks 2.0.1A on separate compact discs read only memory (CD-ROM). The entire contents of the computer listings of the software program ISEApeaks is incorporated herein by reference.

Each of the three copies of the computer listings of raw data appendix were created on Jul. 1, 2003.

Numerous modifications and variations on the present invention are possible in light of the above teachings. It is, therefore, to be understood that within the scope of the accompanying claims, the invention may be practiced otherwise than as specifically described herein.

The invention claimed is:

1. A method for high throuphput analysis of data sets generally described by sets of peaks, each set of peaks having been extracted from an electrophoregram profile j of a biological sample k which has been amplified for a particular sequence of nucleotide, and in each set of peaks, the $i^{th}$ peak is characterized by a nucleotide length $L_{i,j,k}$ and an area $A_{i,j,k}$, the method comprising using bioinformatics tools comprising a computer to extract and smooth peak data sets according to parameter files and store them in data files, wherein smoothing comprises steps of:
for each peak of a set of peaks, calculating an Euclidian division using the integer 3 of $L_{i,j,k}\lambda_j$ with the remainder being assigned to an element of $\{-1\ 0\ 1\}$ wherein $\lambda_j$ is a theoretical length of the amplified sequence of nucleotide, and
if the mean of reminders is superior to a first predefined threshold, shifting all peaks of the set of peaks by −1 nucleotide length, and if the mean of reminders is inferior to a second predefined threshold, shifting all peaks of the set of peaks +1 nucleotide length.

2. The method according to claim 1 comprising a step of creating particular profiles representing peaks to be analyzed.

3. The method according to claim 1, comprising a step of building a peak database.

4. The method according to claim 1 comprising a step of building peak database by statistical tools.

5. The method according to claim 1 comprising a step of using analysis of peak database to determine prognostic or diagnostic criteria.

6. The method according to claim 1 comprising a step of using the prognostic and diagnostic criteria in the field of physiopathology such as immunotherapy, cancer treatment, HIV, infectious disease, autoimmune disease.

7. The method according to claim 1 that is a high throughput method for analysis of immune repertoires.

8. The method according to claim 7 comprising steps of starting with biological samples, which contains DNA or RNA fragments purifying DNA or RNA fragments.

9. The method according to claim 8, further comprising the steps of:
providing purified DNA or synthesizing cDNA from purified RNA,
amplifying purified DNA or cDNA by a PCR or SDA method by using oligonucleotides specific for antigen specific receptor genes, e.g., Immunoglobulin and T-cell receptor, variable (V), Junctional (J) and Constant (c) regions,
labeling the amplified DNA for detection e.g. by performing a runoff extension step with J or C specific oligonucleotide labeled with a fluorescent drug,
electrophoretically separating the labeled amplified DNA using an automatic sequencer for each electrophoregram, and
identifying peaks that characterize the separated labeled and amplified by determining their nucleotide length and area that correspond to labeled amplified DNA.

10. The method according to claim 8, comprising reading the labeled amplified DNA to analyze it.

11. The method according to claim 1, wherein the first predefined threshold is 0.5.

12. The method according to claim 1, wherein the second predefined threshold is −0.5.

13. The method according to claim 1, wherein smoothing comprises a step of removing background noise and peaks inferior to a defined cut-off from the set of peaks.

14. The method according to claim 1, wherein smoothing comprises a step of summing peaks having an identical nucleotide length.

15. The method according to claim 1, wherein smoothing comprises a step of:
detecting in the set of peaks adjacent peaks for which $L_{i,j,k}=1$, determining for adjacent peaks whether $L_{i,j,k}\lambda_j$ or $L_{i+1,j,k}\lambda_j$ is a multiple of 3, shifting the i+1$^{th}$ peak −1 nucleotide length when $L_{i,j,k}\lambda_j$ is a multiple of 3;

or shifting the i$^{th}$ peak by +1 nucleotide length, when $L_{i+1,j,k}\lambda_j$ is a multiple of 3.

16. The method according to claim 15, wherein smoothing comprises a step of summing adjacent peaks.

17. A method for high throughput analysis of data sets generally described by sets of peaks, each set of peaks having been extracted from an electrophoregram profile j of a DNA sample k which has been amplified for a particular sequence of nucleotide, and in each set of peaks, the i$^{th}$ peak is characterized by a nucleotide length $L_{i,j,k}$ and an area $A_{i,j,k}$, wherein said method comprises using bioinformatics tools comprising a computer to extract and smooth peak data sets according to parameter files and store them in data files, wherein extracting comprises the steps of:

for a plurality of data files (PICTfiles), each data file storing one set of peaks, generating an associated parameter file (CGEL parameter file) storing, for each data file, an order parameter (mNewOrder), reading successively the data files following the order parameters (mNewOrder) stored in the parameter file (CGEL parameter file), for each data file being read, extracting the nucleotide length $L_{i,j,k}$ and area $A_{i,j,k}$ of the peaks of the set of peaks stored in the data file, and generating a raw data file (data 0) gathering all sets of peaks ordered according to the order parameters (mNewOrder).

18. A method according to claim 17, wherein the parameter file (CGEL parameter file) also stores, for each data file, a consideration parameter (misConsidered) indicating whether the parameter file must be read or not.

19. A method according to claim 17, wherein the parameter file (CGEL parameter file) also stores for each data file, a description parameter (mDescription) which is a string of characters that depicts the Particular sequence of nucleotide which has been amplified.

20. A method according to claim 17, wherein the parameter file (CGEL parameter file) also stores, for each data file, a length parameter (mLength) which is a value of a theoretical length of the amplified sequence of nucleotide.

21. A method according to claim 17, comprising a step of—displaying extracted and smoothed peak data sets.

22. A method for high throughput analysis of data sets characterized by sets of peaks extracted from an electrophoregram profile comprising:

extracting and smoothing peak data sets using a computer according to parameter files and storing them in data files, wherein smoothing comprises:

for each peak of a set of peaks, calculating an Euclidian division using the integer 3 of $L_{i,j,k}\lambda_j$ with the remainder being assigned to an element of {−1 0 1} wherein $\lambda_j$ is a theoretical length of the amplified sequence of nucleotide, and if the mean of reminders is superior to a first predefined threshold, shifting all peaks of the set of peaks by −1 nucleotide length, and if the mean of reminders is inferior to a second predefined threshold, shifting all peaks of the set of peaks +1 nucleotide length;

wherein said data sets characterized by sets of peaks extracted from an electrophoregram profile j of a biological sample k which has been amplified for a particular sequence of nucleotide, and in each set of peaks, the i$^{th}$ peak is characterized by a nucleotide length $L_{i,j,k}$ and an area $A_{i,j,k}$.

23. The method of claim 22, further comprising extracting peak data sets from an electrophoregram.

24. The method of claim 23, further comprising amplifying a polynucleotide in biological sample k and producing an electropherogram j from said amplified polynucleotide.

* * * * *